(12) United States Patent
Doudna et al.

(10) Patent No.: US 11,739,309 B2
(45) Date of Patent: Aug. 29, 2023

(54) CRISPR-CAS12J EFFECTOR POLYPEPTIDES AND METHODS OF USE THEREOF

(71) Applicant: The Regents of the University of California, Oakland, CA (US)

(72) Inventors: Jennifer A. Doudna, Berkeley, CA (US); Basem Al-Shayeb, Berkeley, CA (US); Jillian F. Banfield, Berkeley, CA (US); Patrick Pausch, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/403,245

(22) Filed: Aug. 16, 2021

(65) Prior Publication Data

US 2021/0403888 A1    Dec. 30, 2021

Related U.S. Application Data

(63) Continuation of application No. 17/225,866, filed on Apr. 8, 2021, which is a continuation of application No. PCT/US2020/021213, filed on Mar. 5, 2020.

(60) Provisional application No. 62/948,470, filed on Dec. 16, 2019, provisional application No. 62/907,422, filed on Sep. 27, 2019, provisional application No. 62/855,739, filed on May 31, 2019, provisional application No. 62/815,173, filed on Mar. 7, 2019.

(51) Int. Cl.
| | |
|---|---|
| *C12N 9/22* | (2006.01) |
| *C12N 15/11* | (2006.01) |
| *C12N 15/90* | (2006.01) |
| *C12N 15/10* | (2006.01) |
| *C12Q 1/6818* | (2018.01) |
| *A61K 31/7088* | (2006.01) |
| *A61K 38/46* | (2006.01) |
| *A61K 38/00* | (2006.01) |
| *A61K 48/00* | (2006.01) |

(52) U.S. Cl.
CPC ............ *C12N 9/22* (2013.01); *A61K 31/7088* (2013.01); *A61K 38/465* (2013.01); *C12N 15/102* (2013.01); *C12N 15/11* (2013.01); *C12N 15/111* (2013.01); *C12N 15/907* (2013.01); *C12Q 1/6818* (2013.01); *A61K 38/00* (2013.01); *A61K 48/00* (2013.01); *C07K 2319/02* (2013.01); *C07K 2319/09* (2013.01); *C12N 2310/20* (2017.05); *C12N 2800/80* (2013.01)

(58) Field of Classification Search
CPC ..... C12N 15/907; C12N 9/22; C07K 2319/09
See application file for complete search history.

(56) References Cited

U.S. PATENT DOCUMENTS

| | | | |
|---|---|---|---|
| 10,253,365 B1 | 4/2019 | Doudna et al. | |
| 10,337,051 B2 | 7/2019 | Doudna et al. | |
| 10,494,664 B2 | 12/2019 | Doudna et al. | |
| 10,570,415 B2 | 2/2020 | Doudna et al. | |
| 2016/0251410 A1 | 9/2016 | Tirosh et al. | |
| 2016/0298134 A1* | 10/2016 | Chen .................. | C12N 15/85 |
| 2017/0362644 A1 | 12/2017 | Doudna et al. | |
| 2018/0208976 A1 | 7/2018 | Doudna et al. | |
| 2018/0208977 A1 | 7/2018 | Doudna et al. | |
| 2018/0250339 A1 | 9/2018 | Gill et al. | |
| 2018/0346927 A1 | 12/2018 | Doudna et al. | |
| 2019/0177775 A1 | 6/2019 | Doudna et al. | |
| 2019/0241954 A1 | 8/2019 | Doudna et al. | |
| 2019/0249200 A1* | 8/2019 | Seebeck ................ | C12N 15/85 |
| 2019/0276842 A1 | 9/2019 | Doudna et al. | |
| 2019/0300908 A1 | 10/2019 | Doudna et al. | |
| 2020/0010878 A1 | 1/2020 | Doudna et al. | |
| 2020/0010879 A1 | 1/2020 | Doudna et al. | |
| 2020/0017879 A1 | 1/2020 | Doudna et al. | |
| 2020/0087640 A1 | 3/2020 | Doudna et al. | |
| 2020/0172886 A1 | 6/2020 | Doudna et al. | |
| 2020/0190487 A1 | 6/2020 | Zhang et al. | |
| 2020/0299659 A1 | 9/2020 | Cheng et al. | |
| 2020/0299660 A1 | 9/2020 | Doudna et al. | |
| 2020/0299768 A1 | 9/2020 | Doudna et al. | |
| 2020/0370028 A1 | 11/2020 | Doudna et al. | |
| 2020/0399697 A1 | 12/2020 | Doudna et al. | |
| 2021/0017508 A1 | 1/2021 | Doudna et al. | |
| 2021/0317447 A1 | 10/2021 | Doudna et al. | |

FOREIGN PATENT DOCUMENTS

| | | | |
|---|---|---|---|
| CA | 3120432 | 5/2020 | |
| WO | WO-2017053312 A1 * | 3/2017 | ............... B82Y 5/00 |
| WO | WO 2017/083722 | 5/2017 | |
| WO | WO 2017/218573 | 12/2017 | |
| WO | WO 2018/064352 | 4/2018 | |
| WO | WO 2018/064371 | 4/2018 | |
| WO | WO 2018/172556 | 9/2018 | |

(Continued)

OTHER PUBLICATIONS

Machine translation of Lai et al. WO 2019/214604 A1, printed as pp. 1-64 on Feb. 17, 2022. (Year: 2022).*

(Continued)

*Primary Examiner* — Jennifer Dunston
(74) *Attorney, Agent, or Firm* — Bozicevic, Field & Francis LLP; Shweta Chandra

(57) ABSTRACT

The present disclosure provides RNA-guided CRISPR-Cas effector proteins, nucleic acids encoding same, and compositions comprising same. The present disclosure provides ribonucleoprotein complexes comprising: an RNA-guided CRISPR-Cas effector protein of the present disclosure; and a guide RNA. The present disclosure provides methods of modifying a target nucleic acid, using an RNA-guided CRISPR-Cas effector protein of the present disclosure and a guide RNA. The present disclosure provides methods of modulating transcription of a target nucleic acid.

25 Claims, 108 Drawing Sheets

Specification includes a Sequence Listing.

(56) References Cited

FOREIGN PATENT DOCUMENTS

| WO | WO 2019/036185 | 2/2019 |
|----|----|----|
| WO | WO 2019/089820 | 5/2019 |
| WO | WO 2019/104058 | 5/2019 |
| WO | WO 2019/214604 | 11/2019 |
| WO | WO 2019/222555 | 11/2019 |
| WO | WO 2020/098772 | 11/2019 |
| WO | WO 2021/007563 | 1/2021 |
| WO | WO 2021/081200 | 4/2021 |

OTHER PUBLICATIONS

Priority document for Lai et al. WO 2019/214604 A1, which is Application No. CN 2018104266661, filed May 17, 2018, pp. 1-117, printed on Feb. 17, 2022. (Year: 2022).*
Karvelis et al. Methods for decoding Cas9 protospacer adjacent motif (PAM) sequences: A brief overview. Methods, vol. 121-122, pp. 3-8, Mar. 24, 2017. (Year: 2017).*
Carabias et al. Structure of the mini-RNA-guided endonuclease CRISPR-Cas12j3. Nature Communications, vol. 12, 4476, printed as pp. 1-12, and Jan. 17-17 2017 of Supplementary Information, Jul. 2021. (Year: 2021).*
Fonfara et al. Phylogeny of Cas9 determines functional exchangeability of dual-RNA and Cas9 among orthologous type II CRISPR-Cas systems. Nucleic Acids Research, vol. 42, No. 4, pp. 2577-2590, and p. 1/67-67/67 of Supplementary Information, 2014, published online Nov. 22, 2013. (Year: 2013).*
GenBank Accession No. AAK33936.1, printed as pp. 1/2-2/2, publicly available Apr. 2014. (Year: 2014).*
GenBank Accession No. NP_721764.1, printed as pp. 1/2-2/2, publicly available May 2017. (Year: 2017).*
GenBank Accession No. YP_820832.1, printed as pp. 1/2-2/2, publicly available Dec. 2014. (Year: 2014).*
Song, M. The CRISPR/Cas9 system: Their delivery, in vivo and ex vivo applications and clinical development by startups. Biotechnology Progress, vol. 33, No. 4, pp. 1035-1045, May 14, 2017. (Year: 2017).*
Fonfara et al. Phylogeny of Cas9 determines functional exchangeability of dual-RNA and Cas9 among orthologous type II CRISPR-Cas systems. Nucleic Acids Research, vol. 42, No. 4, pp. 2577-2590, and pp. 1/67-67/67 of Supplementary Information, 2014. (Year: 2014).*
U.S. Appl. No. 17/225,874 Non-Final Office Action dated Oct. 21, 2021.
U.S. Appl. No. 17/225,878 Non-Final Office Action dated Oct. 4, 2021.
U.S. Appl. No. 17/229,272 Non-Final Office Action dated Sep. 15, 2021.
Al-Shayeb, et al.; "Clades of huge phages from across Earth's ecosystems"; Nature; vol. 578, 23 pages (Feb. 20, 2020).
Branden, et al.; "Introduction to Protein Structure"; Garland Publishing Inc.; New York; pp. 247 (1991).
JGI Accession No. (Taxon ID:Gene ID) 3300027908.a:Ga0209006_1000028662; 2 pages (Jun. 2021).
Sadowski, et al.; "The sequence-structure relationship and protein function prediction"; Current Opinion in Structural Biology; vol. 19, pp. 357-362 (May 4, 2009).
Seffernick, et al.; "Melamine Deaminase and Atrazine Chlorohydrolase: 98 Percent Identical but Functionally Different"; Journal of Bacteriology; vol. 183, No. 8, pp. 2405-2410 (Apr. 2001).
Tang, et al.; "Identification of *Dehalobacter* reductive dehalogenases that catalyse dechlorination of chloroform, 1,1,1-trichloroethane and 1,1-dichloroethane"; Phil. Trans. R. Soc. B.; vol. 368, 10 pages (Apr. 13, 2019).
Witkowski, et al.; "Conversion of a β-Ketoacyl Synthase to a Malonyl Decarboxylase by Replacement of the Active-Site Cysteine with Glutamine"; Biochemistry; vol. 38, pp. 11643-11650 (Aug. 18, 1999).
Pausch, et al.; "DNA interference states of the hypercompact CRISPR-CasΦ effector"; Nature Structural & Molecular Biology; vol. 28, pp. 652-661 (Aug. 2021).
U.S. Appl. No. 62/672,489, filed Nov. 21, 2019, Arbor.
Pausch, et al.; "CRISPR-CasΦ from huge phages is a hypercompact genome editor"; Science; vol. 369, 5 pages (Jul. 17, 2020).
Yan, et al.; "Cas13d is a compact RNA-targeting type VI CRISPR effector positively modulated by a WYL domain-containing accessory protein"; Mol Cell; vol. 70, No. 2, pp. 327-339 (Apr. 19, 2018).
U.S. Appl. No. 62/642,919, filed Mar. 14, 2018, Arbor Biotechnologies, Inc.
U.S. Appl. No. 62/666,397, filed May 3, 2018, Arbor Biotechnologies, Inc.
Chen, et al.; "CRISPR-Cas12a target binding unleashes indiscriminate single-stranded DNase activity"; Science; vol. 360, No. 6387, pp. 436-439 (Feb. 15, 2018), printed as pp. 1-12.

* cited by examiner

FIG. 5

| | | | |
|---|---|---|---|
| HUMAN | Adult fecal samples, Bangladesh | 393-209 kbp | ① |
| | Hadza fecal samples, Tanzania | 255-216 kbp | ② |
| | Human fecal, Peru | 280-201 kbp | ③ |
| | Premature infant gut, Pittsburgh, PA | 266 kbp | ④ |
| | Saliva from pregnant woman, preterm, CA | 371-206 kbp | ⑤ |
| | Saliva from pregnant woman, term, CA | 341-201 kbp | ⑥ |
| | Stool from pregnant woman, CA | 225-206 kbp | ⑦ |
| OTHER ANIMAL | Baboon fecal samples, Kenya | 396-200 kbp | ⑧ |
| | Moose | 420-207 kbp | ⑨ |
| | Pig fecal material, Denmark | 286-206 kbp | ⑩ |
| SOIL | Riparian zone soil, East River, CO | 213 kbp | ⑪ |
| | Grassland soil, Northern CA | 636 kbp | ⑫ |
| | Prairie Potholes | 223 kbp | ⑬ |
| | Soil, East River, Colorado | 404-251 kbp | ⑭ |
| | Vernal pool mud, Lake County, CA | 595-210 kbp | ⑮ |
| SUB-SOIL | Sapolite, East River, CO | 350-299 kbp | ⑯ |
| RIVER | Eel River mats, CA | 356-209 kbp | ⑰ |
| | River, Wrighton | 383 kbp | ⑱ |
| | Amazon River | 203 kbp | ⑲ |
| LAKE | Anderson Lake, Canada | 368-209 kbp | ⑳ |
| | Moose Lake, Ontario | 207-227 kbp | ㉑ |
| | Mining impact water, Newfoundland | 339 kbp | ㉒ |
| | Mining-associated Lake, Manitoba | 271-204 kbp | ㉓ |

FIG. 5 (Cont.)

| | | | |
|---|---|---|---|
| GROUNDWATER | Stratified Lake, Alberta | 395-206 kbp | ㉔ |
| | Lac Pavin, France | 716-210 kbp | ㉕ |
| | Sewerage pond, Modesto, CA | 349 kbp | ㉖ |
| | Groundwater enrichment, Modesto, CA | 438-215 kbp | ㉗ |
| | Groundwater, Modesto, CA | 402-208 kbp | ㉘ |
| | Groundwater, Rifle, CO | 485-206 kbp | ㉙ |
| | Crystal Geyser, UT | 415-235 kbp | ㉚ |
| | Sulfide Spring, OK | 214 kbp | ㉛ |
| SUBSURFACE | Deep subsurface, Horonobe, Japan | 635-231 kbp | ㉜ |
| | Giant Mine, Canada | 343 kbp | ㉝ |
| | Sediment, Rifle, CO | 503-420 kbp | ㉞ |
| | Hydraulically Fractured Shale | 299-232 kbp | ㉟ |
| MARINE | Landsort Deep, Baltic Sea | 444-437 kbp | ㊱ |
| | Marine, global ocean virome | 318 kbp | ㊲ |
| | Marine, Tara ocean study | 499 kbp | ㊳ |
| | Bay mud, Berkeley, CA | 438-401 kbp | ㊴ |
| | Oil Seep, Santa Barbara, CA | 347 kbp | ㊵ |
| HYPERSALINE | Atacama salt, Chile | 484-322 kbp | ㊶ |
| | Salt Pond, CA | 322-201 kbp | ㊷ |
| HOT SPRINGS | Tibet/Yunan Hot Springs | 326-213 kbp | ㊸ |
| BIOTECHNOLOGY | Thiocyanate bioreactor, South Africa | 338-209 kbp | ㊹ |
| ROOM | NICU, Pittsburgh, PA | 1235-234 kbp | ㊺ |

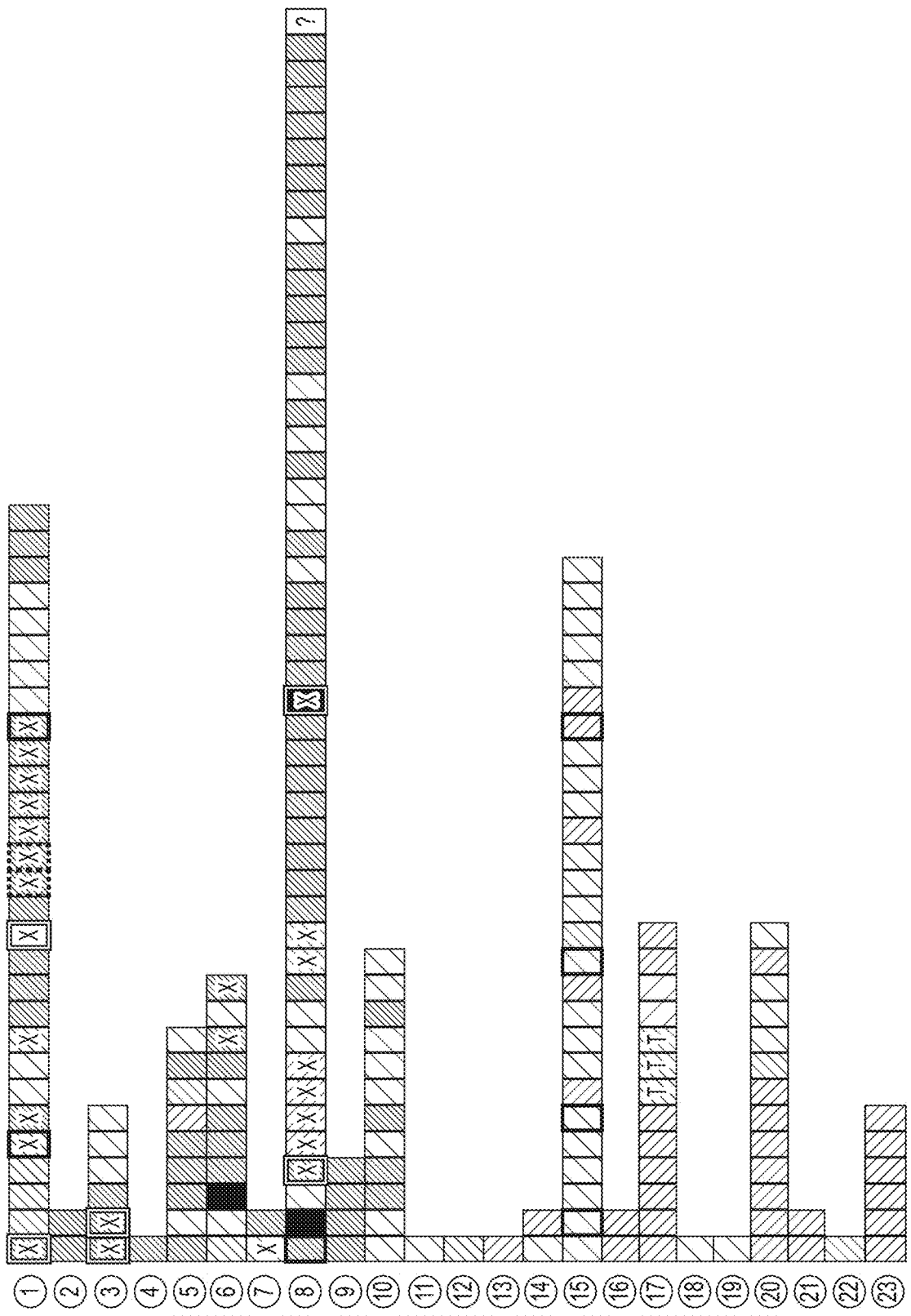

FIG. 6A

Cas12J_1947455 (SEQ ID NO: 109)

MADTPTLFTQFLRHHLPGQRFRKDILKQAGRILANKGEDATIAFLRGKSEESPPDFQPP
VKCPIIACSRPLTEWPIYQASVAIQGYVYGQSLAEFEASDPGCSKDGLLGWFDKTGVCTDYFSV
QGLNLIFQNARKRYIGVQTKVTNRNEKRHKKLKRINAKRIAEGLPELTSDEPESALDETGHLIDP
PGLNTNIYCYQQVSPKPLALSEVNQLPTAYAGYSTSGDDPIQPMVTKDRLSISKGQPGYIPEHQ
RALLSQKKHRRMRGYGLKARALLVIVRIQDDWAVIDLRSLLRNAYWRRIVQTKEPSTITKLLKLV
TGDPVLDATRMVATFTYKPGIVQVRSAKCLKNKQGSKLFSERYLNETVSVTSDLGSNNLVAVA
TYRLVNGNTPELLQRFTLPSHLVKDFERYKQAHDTLEDSIQKTAVASLPQGQQTEIRMWSMYG
FREAQERVCQELGLADGSIPWNVMTATSTILTDLFLARGGDPKKCMFTSEPKKKKNSKQVLYKI
RDRAWAKMYRTLLSKETREAWNKALWGLKRGSPDYARLSKRKEELARRCVNYTISTAEKRAQ
CGRTIVALEDLNIGFFHGRGKQEPGWVGLFTRKKENRWLMQALHKAFLELAHHRGYHVIEVNP
AYTSQTCPVCRHCDPDNRDQHNREAFHCIGCGFRGNADLDVATHNIAMVAITGESLKRARGS
VASKTPQPLAAE*

FIG. 6B

Cas12J_2071242 (SEQ ID NO: 110)

MPKPAVESEFSKVLKKHFPGERFRSSYMKRGGKILAAQGEEAVVAYLQGKSEEEPPNF
QPPAKCHVVTKSRDFAEWPIMKASEAIQRYIYALSTTERAACKPGKSSESHAAWFAATGVSNH
GYSHVQGLNLIFDHTLGRYDGVLKKVQLRNEKARARLESINASRADEGLPEIKAEEEEVATNET
GHLLQPPGINPSFYVYQTISPQAYRPRDEIVLPPEYAGYVRDPNAPIPLGVVRNCDIQKGCPG
YIPEWQREAGTAISPKTGKAVTVPGLSPKKNKRMRRYWRSEKEKAQDALLVTVRIGTDWVVID
VRGLLRNARWRTIAPKDISLNALLDLFTGDPVIDVRRNIVTFTYTLDACGTYARKWTLKGKQTKA
TLDKLTATQTVALVAIDGQTNPISAGISRVTQENGALQCEPLDRFTLPDDLLKDISAYRIAWDRN
EEELRARSVEALPEAQQAEVRALDGVSKETARTQLCADFGLDPKRLPWDKMSSNTTFISEALL
SNSVSRDQVFFTPAPKKGAKKKAPVEVMRKDRTWARAYKPRLSVEAQKLKNEALWALKRTSP
EYLKLSRRKEELCRRSINYVIEKTRRRTQCQIVIPVIEDLNVRFFHGSGKRLPGWDNFFTAKKEN
RWFIQGLHKAFSDLRTHRSFYVFEVRPERTSITCPKCGHCEVGNRDGEAFQCLSCGKTCNADL
DVATHNLTQVALTGKTMPKREEPRDAQGTAPARKTKKASKSKAPPAEREDQTPAQEPSQTS

FIG. 6C

Cas12J_1973640 (SEQ ID NO: 111)

MYILEMADLKSEPSLLAKLLRDRFPGKYWLPKYWKLAEKKRLTGGEEAACEYMADKQL
DSPPPNFRPPARCVILAKSRPFEDWPVHRVASKAQSFVIGLSEQGFAALRAAPPSTADARRDW
LRSHGASEDDLMALEAQLLETIMGNAISLHGGVLKKIDNANVKAAKRLSGRNEARLNKGLQELP
PEQEGSAYGADGLLVNPPGLNLNIYCRKSCCPKPVKNTARFVGHYPGYLRDSDSILISGTMDRL
TIIEGMPGHIPAWQREQGLVKPGGRRRRLSGSESNMRQKVDPSTGPRRSTRSGTVNRSNQRT
GRNGDPLLVEIRMKEDWVLLDARGLLRNLRWRESKRGLSCDHEDLSLSGLLALFSGDPVIDPV
RNEVVFLYGEGIIPVRSTKPVGTRQSKKLLERQASMGPLTLISCDLGQTNLIAGRASAISLTHGS
LGVRSSVRIELDPEIIKSFERLRKDADRLETEILTAAKETLSDEQRGEVNSHEKDSPQTAKASLC
RELGLHPPSLPWGQMGPSTTFIADMLISHGRDDDAFLSHGEFPTLEKRKKFDKRFCLESRPLLS
SETRKALNESLWEVKRTSSEYARLSQRKKEMARRAVNFVVEISRRKTGLSNVIVNIEDLNVRIFH
GGGKQAPGWDGFFRPKSENRWFIQAIHKAFSDLAAHHGIPVIESDPQRTSMTCPECGHCDSK
NRNGVRFLCKGCGASMDADFDAACRNLERVALTGKPMPKPSTSCERLLSATTGKVCSDHSLS
HDAIEKAS*

FIG. 6D

Cas12J_3339380 (SEQ ID NO: 112)

MEKEITELTKIRREFPNKKFSSTDMKKAGKLLKAEGPDAVRDFLNSCQEIIGDFKPPVKT
NIVSISRPFEEWPVSMVGRAIQEYYFSLTKEELESVHPGTSSEDHKSFFNITGLSNYNYTSVQGL
NLIFKNAKAIYDGTLVKANNKNKKLEKKFNEINHKRSLEGLPIITPDFEEPFDENGHLNNPPGINR
NIYGYQGCAAKVFVPSKHKMVSLPKEYEGYNRDPNLSLAGFRNRLEIPEGEPGHVPWFQRMDI
PEGQIGHVNKIQRFNFVHGKNSGKVKFSDKTGRVKRYHHSKYKDATKPYKFLEESKKVSALDSI
LAIITIGDDWVVFDIRGLYRNVFYRELAQKGLTAVQLLDLFTGDPVIDPKKGVVTFSYKEGVVPVF
SQKIVPRFKSRDTLEKLTSQGPVALLSVDLGQNEPVAARVCSLKNINDKITLDNSCRISFLDDYK
KQIKDYRDSLDELEIKIRLEAINSLETNQQVEIRDLDVFSADRAKANTVDMFDIDPNLISWDSMSD
ARVSTQISDLYLKNGGDESRVYFEINNKRIKRSDYNISQLVRPKLSDSTRKNLNDSIWKLKRTSE
EYLKLSKRKLELSRAVVNYTIRQSKLLSGINDIVIILEDLDVKKKFNGRGIRDIGWDNFFSSRKEN
RWFIPAFHKAFSELSSNRGLCVIEVNPAWTSATCPDCGFCSKENRDGINFTCRKCGVSYHADI
DVATLNIARVAVLGKPMSGPADRERLGDTKKPRVARSRKTMKRKDISNSTVEAMVTA*

FIG. 6E

Cas12J_10037042_3 (SEQ ID NO: 113)

MDMLDTETNYATETPAQQQDYSPKPPKKAQRAPKGFSKKARPEKKPPKPITLFTQKHF
SGVRFLKRVIRDASKILKLSESRTITFLEQAIERDGSAPPDVTPPVHNTIMAVTRPFEEWPEVILS
KALQKHCYALTKKIKIKTWPKKGPGKKCLAAWSARTKIPLIPGQVQATNGLFDRIGSIYDGVEKK
VTNRNANKKLEYDEAIKEGRNPAVPEYETAYNIDGTLINKPGYNPNLYITQSRTPRLITEADRPLV
EKILWQMVEKKTQSRNQARRARLEKAAHLQGLPVPKFVPEKVDRSQKIEIRIIDPLDKIEPYMPQ
DRMAIKASQDGHVPYWQRPFLSKRRNRRVRAGWGKQVSSIQAWLTGALLVIVRLGNEAFLADI
RGALRNAQWRKLLKPDATYQSLFNLFTGDPVVNTRTNHLTMAYREGVVNIVKSRSFKGRQTR
EHLLTLLGQGKTVAGVSFDLGQKHAAGLLAAHFGLGEDGNPVFTPIQACFLPQRYLDSLTNYR
NRYDALTLDMRRQSLLALTPAQQQEFADAQRDPGGQAKRACCLKLNLNPDEIRWDLVSGIST
MISDLYIERGGDPRDVHQQVETKPKGKRKSEIRILKIRDGKWAYDFRPKIADETRKAQREQLWK
LQKASSEFERLSRYKINIARAIANWALQWGRELSGCDIVIPVLEDLNVGSKFFDGKGKWLLGWD
NRFTPKKENRWFIKVLHKAVAELAPHRGVPVYEVMPHRTSMTCPACHYCHPTNREGDRFECQ
SCHVVKNTDRDVAPYNILRVAVEGKTLDRWQAEKKPQAEPDRPMILIDNQES*

FIG. 6F

Cas12J_10020921_9 (SEQ ID NO: 114)

MDMLDTETNYATETPAQQQDYSPKPPKKAQRAPKGFSKKARPEKKPPKPITLFTQKHF
SGVRFLKRVIRDASKILKLSESRTITFLEQAIERDGSAPPDVTPPVHNTIMAVTRPFEEWPEVILS
KALQKHCYALTKKIKIKTWPKKGPGKKCLAAWSARTKIPLIPGQVQATNGLFDRIGSIYDGVEKK
VTNRNANKKLEYDEAIKEGRNPAVPEYETAYNIDGTLINKPGYNPNLYITQSRTPRLITEADRPLV
EKILWQMVEKKTQSRNQARRARLEKAAHLQGLPVPKFVPEKVDRSQKIEIRIIDPLDKIEPYMPQ
DRMAIKASQDGHVPYWQRPFLSKRRNRRVRAGWGKQVSSIQAWLTGALLVIVRLGNEAFLADI
RGALRNAQWRKLLKPDATYQSLFNLFTGDPVVNTRTNHLTMAYREGVVDIVKSRSFKGRQTR
EHLLTLLGQGKTVAGVSFDLGQKHAAGLLAAHFGLGEDGNPVFTPIQACFLPQRYLDSLTNYR
NRYDALTLDMRRQSLLALTPAQQQEFADAQRDPGGQAKRACCLKLNLNPDEIRWDLVSGIST
MISDLYIERGGDPRDVHQQVETKPKGKRKSEIRILKIRDGKWAYDFRPKIADETRKAQREQLWK
LQKASSEFERLSRYKINIARAIANWALQWGRELSGCDIVIPVLEDLNVGSKFFDGKGKWLLGWD
NRFTPKKENRWFIKVLHKAVAELAPHKGVPVYEVMPHRTSMTCPACHYCHPTNREGDRFECQ
SCHVVKNTDRDVAPYNILRVAVEGKTLDRWQAEKKPQAEPDRPMILIDNQES*

FIG. 6G

Cas12J_10000002_47 (SEQ ID NO: 115)
MSSLPTPLELLKQKHADLFKGLQFSSKDNKMAGKVLKKDGEEAALAFLSERGVSRGEL
PNFRPPAKTLVVAQSRPFEEFPIYRVSEAIQLYVYSLSVKELETVPSGSSTKKEHQRFFQDSSV
PDFGYTSVQGLNKIFGLARGIYLGVITRGENQLQKAKSKHEALNKKRRASGEAETEFDPTPYEY
MTPERKLAKPPGVNHSIMCYVDISVDEFDFRNPDGIVLPSEYAGYCREINTAIEKGTVDRLGHLK
GGPGYIPGHQRKESTTEGPKINFRKGRIRRSYTALYAKRDSRRVRQGKLALPSYRHHMMRLNS
NAESAILAVIFFGKDWVVFDLRGLLRNVRWRNLFVDGSTPSTLLGMFGDPVIDPKRGVVAFCYK
EQIVPVVSKSITKMVKAPELLNKLYLKSEDPLVLVAIDLGQTNPVGVGVYRVMNASLDYEVVTRF
ALESELLREIESYRQRTNAFEAQIRAETFDAMTSEEQEEITRVRAFSASKAKENVCHRFGMPVD
AVDWATMGSNTIHIAKWVMRHGDPSLVEVLEYRKDNEIKLDKNGVPKKVKLTDKRIANLTSIRL
RFSQETSKHYNDTMWELRRKHPVYQKLSKSKADFSRRVVNSIIRRVNHLVPRARIVFIIEDLKNL
GKVFHGSGKRELGWDSYFEPKSENRWFIQVLHKAFSETGKHKGYYIECWPNWTSCTCPKCS
CCDSENRHGEVFRCLACGYTCNTDFGTAPDNLVKIATTGKGLPGPKKRCKGSSKGKNPKIARS
SETGVSVTESGAPKVKKSSPTQTSQSSSQSAP*

FIG. 6H

Cas12J_10100763_4 (SEQ ID NO: 116)
MNKIEKEKTPLAKLMNENFAGLRFPFAIIKQAGKKLLKEGELKTIEYMTGKGSIEPLPNFK
PPVKCLIVAKRRDLKYFPICKASCEIQSYVYSLNYKDFMDYFSTPMTSQKQHEEFFKKSGLNIEY
QNVAGLNLIFNNVKNTYNGVILKVKNRNEKLKKKAIKNNYEFEEIKTFNDDGCLINKPGINNVIYC
FQSISPKILKNITHLPKEYNDYDCSVDRNIIQKYVSRLDIPESQPGHVPEWQRKLPEFNNTNNPR
RRRKWYSNGRNISKGYSVDQVNQAKIEDSLLAQIKIGEDWIILDIRGLLRDLNRRELISYKNKLTI
KDVLGFFSDYPIIDIKKNLVTFCYKEGVIQVVSQKSIGNKKSKQLLEKLIENKPIALVSIDLGQTNP
VSVKISKLNKINNKISIESFTYRFLNEEILKEIEKYRKDYDKLELKLINEA

FIG. 6I

Cas12J_10004149_10 (SEQ ID NO: 117)

MDMLDTETNYATETPSQQQDYSPKPPKKDRRAPKGFSKKARPEKKPPKPITLFTQKHF
SGVRFLKRVIRDASKILKLSESRTITFLEQAIERDGSAPPDVTPPVHNTIMAVTRPFEEWPEVILS
KALQKHCYALTKKIKIKTWPKKGPGKKCLAAWSARTKIPLIPGQVQATNGLFDRIGSIYDGVEKK
VTNRNANKKLEYDEAIKEGRNPAVPEYETAYNIDGTLINKPGYNPNLYITQSRTPRLITEADRPLV
EKILWQMVEKKTQSRNQARRARLEKAAHLQGLPVPKFVPEKVDRSQKIEIRIIDPLDKIEPYMPQ
DRMAIKASQDGHVPYWQRPFLSKRRNRRVRAGWGKQVSSIQAWLTGALLVIVRLGNEAFLADI
RGALRNAQWRKLLKPDATYQSLFNLFTGDPVVNTRTNHLTMAYREGVVDIVKSRSFKGRQTR
EHLLTLLGQGKTVAGVSFDLGQKHAAGLLAAHFGLGEDGNPVFTPIQACFLPQRYLDSLTNYR
NRYDALTLDMRRQSLLALTPAQQQEFADAQRDPGGQAKRACCLKLNLNPDEIRWDLVSGIST
MISDLYIERGGDPRDVHQQVETKPKGKRKSEIRILKIRDGKWAYDFRPKIADETRKAQREQLWK
LQKASSEFERLSRYKINIARAIANWALQWGRELSGCDIVIPVLEDLNVGSKFFDGKGKWLLGWD
NRFTPKKENRWFIKVLHKAVAELAPHRGVPVYEVMPHRTSMTCPACHYCHPTNREGDRFECQ
SCHVVKNTDRDVAPYNILRVAVEGKTLDRWQAEKKPQAEPDRPMILIDNQES*

FIG. 6J

Cas12J_10000724_71 (SEQ ID NO: 118)

MDMLDTETNYATETPSQQQDYSPKPPKKDRRAPKGFSKKARPEKKPPKPITLFTQKHF
SGVRFLKRVIRDASKILKLSESRTITFLEQAIERDGSAPPDVTPPVHNTIMAVTRPFEEWPEVILS
KALQKHCYALTKKIKIKTWPKKGPGKKCLAAWSARTKIPLIPGQVQATNGLFDRIGSIYDGVEKK
VTNRNANKKLEYDEAIKEGRNPAVPEYETAYNIDGTLINKPGYNPNLYITQSRTPRLITEADRPLV
EKILWQMVEKKTQSRNQARRARLEKAAHLQGLPVPKFVPEKVDRSQKIEIRIIDPLDKIEPYMPQ
DRMAIKASQDGHVPYWQRPFLSKRRNRRVRAGWGKQVSSIQAWLTGALLVIVRLGNEAFLADI
RGALRNAQWRKLLKPDATYQSLFNLFTGDPVVNTRTNHLTMAYREGVVNIVKSRSFKGRQTR
EHLLTLLGQGKTVAGVSFDLGQKHAAGLLAAHFGLGEDGNPVFTPIQACFLPQRYLDSLTNYR
NRYDALTLDMRRQSLLALTPAQQQEFADAQRDPGGQAKRACCLKLNLNPDEIRWDLVSGIST
MISDLYIERGGDPRDVHQQVETKPKGKRKSEIRILKIRDGKWAYDFRPKIADETRKAQREQLWK
LQKASSEFERLSRYKINIARAIANWALQWGRELSGCDIVIPVLEDLNVGSKFFDGKGKWLLGWD
NRFTPKKENRWFIKVLHKAVAELAPHRGVPVYEVMPHRTSMTCPACHYCHPTNREGDRFECQ
SCHVVKNTDRDVAPYNILRVAVEGKTLDRWQAEKKPQAEPDRPMILIDNQES*

FIG. 6K

Cas12J_1000001_267 (SEQ ID NO: 119)

MSNTAVSTREHMSNKTTPPSPLSLLLRAHFPGLKFESQDYKIAGKKLRDGGPEAVISYL
TGKGQAKLKDVKPPAKAFVIAQSRPFIEWDLVRVSRQIQEKIFGIPATKGRPKQDGLSETAFNEA
VASLEVDGKSKLNEETRAAFYEVLGLDAPSLHAQAQNALIKSAISIREGVLKKVENRNEKNLSKT
KRRKEAGEEATFVEEKAHDERGYLIHPPGVNQTIPGYQAVVIKSCPSDFIGLPSGCLAKESAEA
LTDYLPHDRMTIPKGQPGYVPEWQHPLLNRRKNRRRRDWYSASLNKPKATCSKRSGTPNRK
NSRTDQIQSGRFKGAIPVLMRFQDEWVIIDIRGLLRNARYRKLLKEKSTIPDLLSLFTGDPSIDMR
QGVCTFIYKAGQACSAKMVKTKNAPEILSELTKSGPVVLVSIDLGQTNPIAAKVSRVTQLSDGQL
SHETLLRELLSNDSSDGKEIARYRVASDRLRDKLANLAVERLSPEHKSEILRAKNDTPALCKARV
CAALGLNPEMIAWDKMTPYTEFLATAYLEKGGDRKVATLKPKNRPEMLRRDIKFKGTEGVRIEV
SPEAAEAYREAQWDLQRTSPEYLRLSTWKQELTKRILNQLRHKAAKSSQCEVVVMAFEDLNIK
MMHGNGKWADGGWDAFFIKKRENRWFMQAFHKSLTELGAHKGVPTIEVTPHRTSITCTKCGH
CDKANRDGERFACQKCGFVAHADLEIATDNIERVALTGKPMPKPESERSGDAKKSVGARKAAF
KPEEDAEAAE*

FIG. 6L

Cas12J_10000286_53 (SEQ ID NO: 120)

MIKPTVSQFLTPGFKLIRNHSRTAGLKLKNEGEEACKKFVRENEIPKDECPNFQGGPAIA
NIIAKSREFTEWEIYQSSLAIQEVIFTLPKDKLPEPILKEEWRAQWLSEHGLDTVPYKEAAGLNLII
KNAVNTYKGVQVKVDNKNKNNLAKINRKNEIAKLNGEQEISFEEIKAFDDKGYLLQKPSPNKSIY
CYQSVSPKPFITSKYHNVNLPEEYIGYYRKSNEPIVSPYQFDRLRIPIGEPGYVPKWQYTFLSKK
ENKRRKLSKRIKNVSPILGIICIKKDWCVFDMRGLLRTNHWKKYHKPTDSINDLFDYFTGDPVIDT
KANVVRFRYKMENGIVNYKPVREKKGKELLENICDQNGSCKLATVDVGQNNPVAIGLFELKKV
NGELTKTLISRHPTPIDFCNKITAYRERYDKLESSIKLDAIKQLTSEQKIEVDNYNNNFTPQNTKQI
VCSKLNINPNDLPWDKMISGTHFISEKAQVSNKSEIYFTSTDKGKTKDVMKSDYKWFQDYKPKL
SKEVRDALSDIEWRLRRESLEFNKLSKSREQDARQLANWISSMCDVIGIENLVKKNNFFGGSG
KREPGWDNFYKPKKENRWWINAIHKALTELSQNKGKRVILLPAMRTSITCPKCKYCDSKNRNG
EKFNCLKCGIELNADIDVATENLATVAITAQSMPKPTCERSGDAKKPVRARKAKAPEFHDKLAP
SYTVVLREAV*

FIG. 6M

Cas12J_10001283_7 (SEQ ID NO: 121)

MRSSREIGDKILMRQPAEKTAFQVFRQEVIGTQKLSGGDAKTAGRLYKQGKMEAAARE
WLLKGARDDVPPNFQPPAKCLVVAVSHPFEEWDISKTNHDVQAYIYAQPLQAEGHLNGLSEK
WEDTSADQHKLWFEKTGVPDRGLPVQAINKIAKAAVNRAFGVVRKVENRNEKRRSRDNRIAE
HNRENGLTEVVREAPEVATNADGFLLHPPGIDPSILSYASVSPVPYNSSKHSFVRLPEEYQAYN
VEPDAPIPQFVVEDRFAIPPGQPGYVPEWQRLKCSTNKHRRMRQWSNQDYKPKAGRRAKPL
EFQAHLTRERAKGALLVVMRIKEDWVVFDVRGLLRNVEWRKVLSEEAREKLTLKGLLDLFTGD
PVIDTKRGIVTFLYKAEITKILSKRTVKTKNARDLLLRLTEPGEDGLRREVGLVAVDLGQTHPIAA
AIYRIGRTSAGALESTVLHRQGLREDQKEKLKEYRKRHTALDSRLRKEAFETLSVEQQKEIVTVS
GSGAQITKDKVCNYLGVDPSTLPWEKMGSYTHFISDDFLRRGGDPNIVHFDRQPKKGKVSKKS
QRIKRSDSQWVGRMRPRLSQETAKARMEADWAAQNENEEYKRLARSKQELARWCVNTLLQN
TRCITQCDEIVVVIEDLNVKSLHGKAREPGWDNFFTPKTENRWFIQILHKTFSELPKHRGEHVI
EGCPLRTSITCPACSYCDKNSRNGEKFVCVACGATFHADFEVATYNLVRLATTGMPMPKSLER
QGGGEKAGGARKARKKAKQVEKIVVQANANVTMNGASLHSP*

FIG. 6N

Cas12J_1000002_112 (SEQ ID NO: 115)

MSSLPTPLELLKQKHADLFKGLQFSSKDNKMAGKVLKKDGEEAALAFLSERGVSRGEL
PNFRPPAKTLVVAQSRPFEEFPIYRVSEAIQLYVYSLSVKELETVPSGSSTKKEHQRFFQDSSV
PDFGYTSVQGLNKIFGLARGIYLGVITRGENQLQKAKSKHEALNKKRRASGEAETEFDPTPYEY
MTPERKLAKPPGVNHSIMCYVDISVDEFDFRNPDGIVLPSEYAGYCREINTAIEKGTVDRLGHLK
GGPGYIPGHQRKESTTEGPKINFRKGRIRRSYTALYAKRDSRRVRQGKLALPSYRHHMMRLNS
NAESAILAVIFFGKDWVVFDLRGLLRNVRWRNLFVDGSTPSTLLGMFGDVIDPKRGVVAFCYK
EQIVPVVSKSITKMVKAPELLNKLYLKSEDPLVLVAIDLGQTNPVGVGVYRVMNASLDYEVVTRF
ALESELLREIESYRQRTNAFEAQIRAETFDAMTSEEQEEITRVRAFSASKAKENVCHRFGMPVD
AVDWATMGSNTIHIAKWVMRHGDPSLVEVLEYRKDNEIKLDKNGVPKKVKLTDKRIANLTSIRL
RFSQETSKHYNDTMWELRRKHPVYQKLSKSKADFSRRVVNSIIRRVNHLVPRARIVFIIEDLKNL
GKVFHGSGKRELGWDSYFEPKSENRWFIQVLHKAFSETGKHHKGYYIECWPNWTSCTCPKCS
CCDSENRHGEVFRCLACGYTCNTDFGTAPDNLVKIATTGKGLPGPKKRCKGSSKGKNPKIARS
SETGVSVTESGAPKVKKSSPTQTSQSSSQSAP*

FIG. 6O

Cas12J_10000506_8 (SEQ ID NO: 120)

MIKPTVSQFLTPGFKLIRNHSRTAGLKLKNEGEEACKKFVRENEIPKDECPNFQGGPAIA
NIIAKSREFTEWEIYQSSLAIQEVIFTLPKDKLPEPILKEEWRAQWLSEHGLDTVPYKEAAGLNLII
KNAVNTYKGVQVKVDNKNKNNLAKINRKNEIAKLNGEQEISFEEIKAFDDKGYLLQKPSPNKSIY
CYQSVSPKPFITSKYHNVNLPEEYIGYYRKSNEPIVSPYQFDRLRIPIGEPGYVPKWQYTFLSKK
ENKRRKLSKRIKNVSPILGIICIKKDWCVFDMRGLLRTNHWKKYHKPTDSINDLFDYFTGDPVIDT
KANVVRFRYKMENGIVNYKPVREKKGKELLENICDQNGSCKLATVDVGQNNPVAIGLFELKKV
NGELTKTLISRHPTPIDFCNKITAYRERYDKLESSIKLDAIKQLTSEQKIEVDNYNNNFTPQNTKQI
VCSKLNINPNDLPWDKMISGTHFISEKAQVSNKSEIYFTSTDKGKTKDVMKSDYKWFQDYKPKL
SKEVRDALSDIEWRLRRESLEFNKLSKSREQDARQLANWISSMCDVIGIENLVKKNNFFGGSG
KREPGWDNFYKPKKENRWWINAIHKALTELSQNKGKRVILLPAMRTSITCPKCKYCDSKNRNG
EKFNCLKCGIELNADIDVATENLATVAITAQSMPKPTCERSGDAKKPVRARKAKAPEFHDKLAP
SYTVVLREAV*

FIG. 6P

Cas12J_1000007_143 (SEQ ID NO: 119)

MSNTAVSTREHMSNKTTPPSPLSLLLRAHFPGLKFESQDYKIAGKKLRDGGPEAVISYL
TGKGQAKLKDVKPPAKAFVIAQSRPFIEWDLVRVSRQIQEKIFGIPATKGRPKQDGLSETAFNEA
VASLEVDGKSKLNEETRAAFYEVLGLDAPSLHAQAQNALIKSAISIREGVLKKVENRNEKNLSKT
KRRKEAGEEATFVEEKAHDERGYLIHPPGVNQTIPGYQAVVIKSCPSDFIGLPSGCLAKESAEA
LTDYLPHDRMTIPKGQPGYVPEWQHPLLNRRKNRRRRDWYSASLNKPKATCSKRSGTPNRK
NSRTDQIQSGRFKGAIPVLMRFQDEWVIIDIRGLLRNARYRKLLKEKSTIPDLLSLFTGDPSIDMR
QGVCTFIYKAGQACSAKMVKTKNAPEILSELTKSGPVVLVSIDLGQTNPIAAKVSRVTQLSDGQL
SHETLLRELLSNDSSDGKEIARYRVASDRLRDKLANLAVERLSPEHKSEILRAKNDTPALCKARV
CAALGLNPEMIAWDKMTPYTEFLATAYLEKGGDRKVATLKPKNRPEMLRRDIKFKGTEGVRIEV
SPEAAEAYREAQWDLQRTSPEYLRLSTWKQELTKRILNQLRHKAAKSSQCEVVVMAFEDLNIK
MMHGNGKWADGGWDAFFIKKRENRWFMQAFHKSLTELGAHKGVPTIEVTPHRTSITCTKCGH
CDKANRDGERFACQKCGFVAHADLEIATDNIERVALTGKPMPKPESERSGDAKKSVGARKAAF
KPEEDAEAAE*

FIG. 6Q

Cas12J_3877103_16 (SEQ ID NO: 125)

MYSLEMADLKSEPSLLAKLLRDRFPGKYWLPKYWKLAEKKRLTGGEEAACEYMADKQ
LDSPPPNFRPPARCVILAKSRPFEDWPVHRVASKAQSFVIGLSEQGFAALRAAPPSTADARRD
WLRSHGASEDDLMALEAQLLETIMGNAISLHGGVLKKIDNANVKAAKRLSGRNEARLNKGLQEL
PPEQEGSAYGADGLLVNPPGLNLNIYCRKSCCPKPVKNTARFVGHYPGYLRDSDSILISGTMD
RLTIIEGMPGHIPAWQREQGLVKPGGRRRLSGSESNMRQKVDPSTGPRRSTRSGTVNRSNQ
RTGRNGDPLLVEIRMKEDWVLLDARGLLRNLRWRESKRGLSCDHEDLSLSGLLALFSGDPVID
PVRNEVVFLYGEGIIPVRSTKPVGTRQSKKLLERQASMGPLTLISCDLGQTNLIAGRASAISLTH
GSLGVRSSVRIELDPEIIKSFERLRKDADRLETEILTAAKETLSDEQRGEVNSHEKDSPQTAKAS
LCRELGLHPPSLPWGQMGPSTTFIADMLISHGRDDDAFLSHGEFPTLEKRKKFDKRFCLESRP
LLSSETRKALNESLWEVKRTSSEYARLSQRKKEMARRAVNFVVEISRRKTGLSNVIVNIEDLNV
RIFHGGGKQAPGWDGFFRPKSENRWFIQAIHKAFSDLAAHHGIPVIESDPQRTSMTCPECGHC
DSKNRNGVRFLCKGCGASMDADFDAACRNLERVALTGKPMPKPSTSCERLLSATTGKVCSDH
SLSHDAIEKAS*

FIG. 6R

Cas12J_877636_12 (SEQ ID NO: 126)

MEKEITELTKIRREFPNKKFSSTDMKKAGKLLKAEGPDAVRDFLNSCQEIIGDFKPPVKT
NIVSISRPFEEWPVSMVGRAIQEYYFSLTKEELESVHPGTSSEDHKSFFNITGLSNYNYTSVQGL
NLIFKNAKAIYDGTLVKANNKNKKLEKKFNEINHKRSLEGLPIITPDFEEPFDENGHLNNPPGINR
NIYGYQGCAAKVFVPSKHKMVSLPKEYEGYNRDPNLSLAGFRNRLEIPEGEPGHVPWFQRMDI
PEGQIGHVNKIQRFNFVHGKNSGKVKFSDKTGRVKRYHHSKYKDATKPYKFLEESKKVSALDSI
LAIITIGDDWVVFDIRGLYRNVFYRELAQKGLTAVQLLDLFTGDPVIDPKKGVVTFSYKEGVVPVF
SQKIVPRFKSRDTLEKLTSQGPVALLSVDLGQNEPVAARVCSLKNINDKITLDNSCRISFLDDYK
KQIKDYRDSLDELEIKIRLEAINSLETNQQVEIRDLDVFSADRAKANTVDMFDIDPNLISWDSMSD
ARVSTQISDLYLKNGGDESRVYFEINNKRIKRSDYNISQLVRPKLSDSTRKNLNDSIWKLKRTSE
EYLKLSKRKLELSRAVVNYTIRQSKLLSGINDIVIILEDLDVKKKFNGRGIRDIGWDNFFSSRKEN
RWFIPAFHKTFSELSSNRGLCVIEVNPAWTSATCPDCGFCSKENRDGINFTCRKCGVSYHADID
VATLNIARVAVLGKPMSGPADRERLGDTKKPRVARSRKTMKRKDISNSTVEAMVTA*

FIG. 7

>Cas12J_1947455
GTCTCGACTAATCGAGCAATCGTTTGAGATCTCTCC (SEQ ID NO: 1)
or
GGAGAGATCTCAAACGATTGCTCGATTAGTCGAGAC (SEQ ID NO: 128)

> Cas12J_2071242
GTCGGAACGCTCAACGATTGCCCCTCACGAGGGGAC (SEQ ID NO: 3)
or
GTCCCCTCGTGAGGGGCAATCGTTGAGCGTTCCGAC (SEQ ID NO: 130)

>Cas12J_3339380
GTCCCAGCGTACTGGGCAATCAATAGTCGTTTTGGT (SEQ ID NO: 5)
or
ACCAAAACGACTATTGATTGCCCAGTACGCTGGGAC (SEQ ID NO: 23)

>Cas12J_10000002_47
GGATCCAATCCTTTTGATTGCCCAATTCGTTGGGAC (SEQ ID NO: 7)

>Cas12J_10000724_71
GGATCTGAGGATCATTATTGCTCGTTACGACGAGAC (SEQ ID NO: 9)
or
GTCTCGTCGTAACGAGCAATAATGATCCTCAGATCC (SEQ ID NO: 11)

>Cas12J_1000001_267
GTCTCAGCGTACTGAGCAATCAAAAGGTTTCGCAGG (SEQ ID NO: 13)
or
CCTGCGAAACCTTTTGATTGCTCAGTACGCTGAGAC (SEQ ID NO: 137)

>Cas12J_10000286_53
GTCTCCTCGTAAGGAGCAATCTATTAGTCTTGAAAG (SEQ ID NO: 15)
or
CTTTCAAGACTAATAGATTGCTCCTTACGAGGAGAC

>Cas12J_10001283_7
GTCTCGGCGCACCGAGCAATCAGCGAGGTCTTCTAC (SEQ ID NO: 17)
or
GTAGAAGACCTCGCTGATTGCTCGGTGCGCCGAGAC

>Cas12J_10000506_8
GTCTCCTCGTAAGGAGCAATCTATTAGTCTTGAAAG (SEQ ID NO: 15)
or
CTTTCAAGACTAATAGATTGCTCCTTACGAGGAGAC (SEQ ID NO: 139)

FIG. 7 (Cont.)

>Cas12J_1000007_143
GTCTCAGCGTACTGAGCAATCAAAAGGTTTCGCAGG (SEQ ID NO: 13)
or
CCTGCGAAACCTTTTGATTGCTCAGTACGCTGAGAC (SEQ ID NO: 137)

>Cas12J_877636_12
ACCAAAACGACTATTGATTGCCCAGTACGCTGGGAC (SEQ ID NO: 23)

>Cas12J_1000002
GTCCCAACGAATTGGGCAATCAAAAGGATTGGATCC (SEQ ID NO: 19)
or
GGATCCAATCCTTTTGATTGCCCAATTCGTTGGGAC (SEQ ID NO: 7)

>Cas12J_1000007
GTCTCAGCGTACTGAGCAATCAAAAGGTTTCGCAGG (SEQ ID NO: 13)
or
CCTGCGAAACCTTTTGATTGCTCAGTACGCTGAGAC (SEQ ID NO: 137)

>Cas12J_1947455
GTCTCGACTAATCGAGCAATCGTTTGAGATCTCTCC (SEQ ID NO: 1)
or
GGAGAGATCTCAAACGATTGCTCGATTAGTCGAGAC (SEQ ID NO: 128)

>Cas12J_2071242
GTCGGAACGCTCAACGATTGCCCCTCACGAGGGAC (SEQ ID NO: 3)
or
GTCCCCTCGTGAGGGGCAATCGTTGAGCGTTCCGAC (SEQ ID NO: 130)

>Cas12J_3877103
GTCGCGGCGTACCGCGCAATGAGAGTCTGTTGCCAT (SEQ ID NO: 21)
or
ATGGCAACAGACTCTCATTGCGCGGTACGCCGCGAC (SEQ ID NO: 156)

>Cas12J_10000286
GTCTCCTCGTAAGGAGCAATCTATTAGTCTTGAAAG (SEQ ID NO: 15)
or
CTTTCAAGACTAATAGATTGCTCCTTACGAGGAGAC (SEQ ID NO: 139)

>Cas12J_10001283
GTCTCGGCGCACCGAGCAATCAGCGAGGTCTTCTAC (SEQ ID NO: 17)
or
GTAGAAGACCTCGCTGATTGCTCGGTGCGCCGAGAC (SEQ ID NO: 141)

FIG. 9

| Protein | RuvC-I amino acid | Position | RuvC-II amino acid | Position | RuvC-III amino acid | Position |
|---|---|---|---|---|---|---|
| Cas12J_10037042_3 | Aspartic Acid | 464 | Glutamic Acid | 678 | Aspartic Acid | 769 |
| Cas12J_10020921_9 | Aspartic Acid | 464 | Glutamic Acid | 678 | Aspartic Acid | 769 |
| Cas12J_10000002_47 | Aspartic Acid | 416 | Glutamic Acid | 631 | Aspartic Acid | 722 |
| Cas12J_10100763_4 | Aspartic Acid | 384 | - | - | Aspartic Acid | - |
| Cas12J_10004149_10 | Aspartic Acid | 464 | Glutamic Acid | 678 | Aspartic Acid | 769 |
| Cas12J_10000724_71 | Aspartic Acid | 464 | Glutamic Acid | 678 | Aspartic Acid | 769 |
| Cas12J_10000001_267 | Aspartic Acid | 423 | Glutamic Acid | 632 | Aspartic Acid | 722 |
| Cas12J_10000286_53 | Aspartic Acid | 369 | Glutamic Acid | 567 | Aspartic Acid | 658 |
| Cas12J_10001283_7 | Aspartic Acid | 426 | Glutamic Acid | 639 | Aspartic Acid | 728 |
| Cas12J_1000002_112 | Aspartic Acid | 416 | Glutamic Acid | 631 | Aspartic Acid | 722 |
| Cas12J_10000506_8 | Aspartic Acid | 369 | Glutamic Acid | 567 | Aspartic Acid | 658 |
| Cas12J_1000007_143 | Aspartic Acid | 423 | Glutamic Acid | 632 | Aspartic Acid | 722 |
| Cas12J_3339380_12 | Aspartic Acid | 413 | Glutamic Acid | 618 | Aspartic Acid | 708 |
| Cas12J_877636_12 | Aspartic Acid | 413 | Glutamic Acid | 618 | Aspartic Acid | 708 |
| Cas12J_1947455_11 | Aspartic Acid | 371 | Glutamic Acid | 579 | Aspartic Acid | 671 |
| Cas12J_2071242 | Aspartic Acid | 394 | Glutamic Acid | 606 | Aspartic Acid | 695 |
| Cas12J_3877103_16 | Aspartic Acid | 419 | Glutamic Acid | 625 | Aspartic Acid | 714 |
| Cas12J_559231_218 | Aspartic Acid | 394 | Glutamic Acid | 606 | Aspartic Acid | 695 |
| Cas12J_1973640_1 | Aspartic Acid | 419 | Glutamic Acid | 625 | Aspartic Acid | 714 |

FIG. 11C
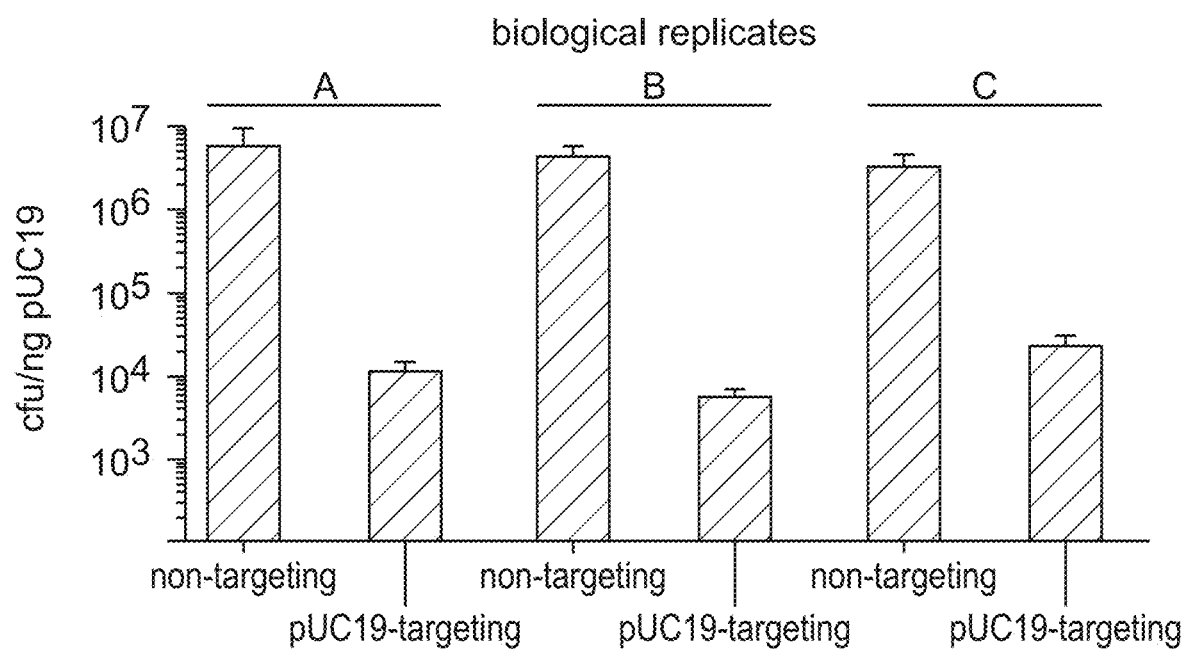
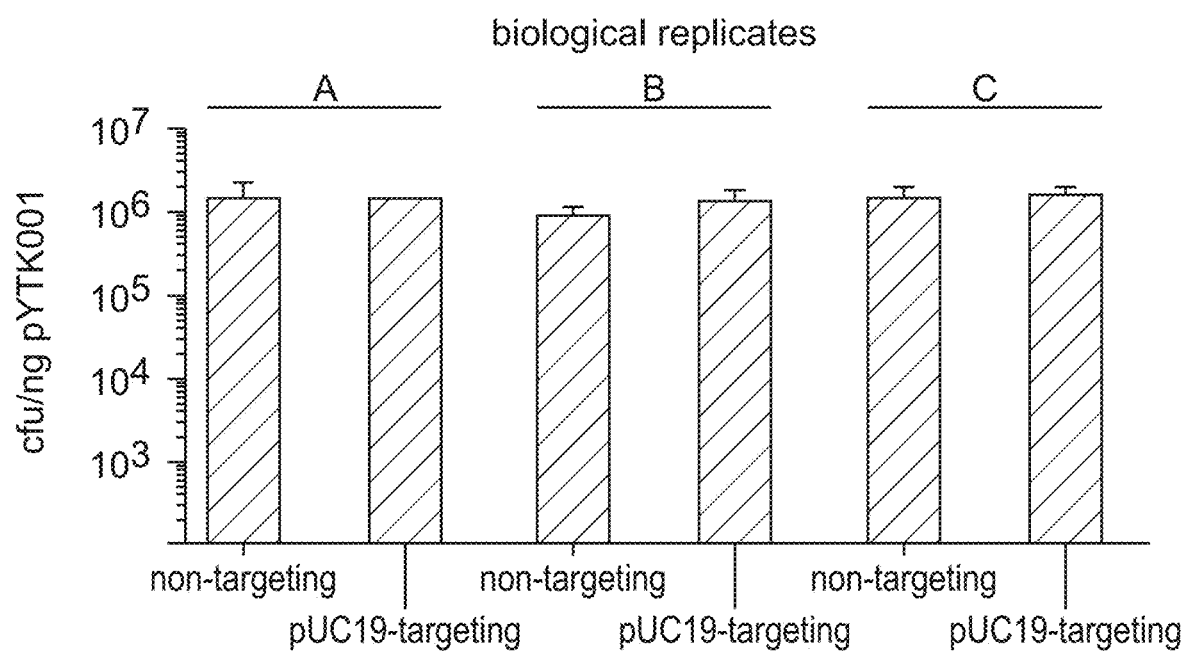

FIG. 17A (Table 1)

| Vector | Sequence (circular) |
|---|---|
| pCas12J-2-hs (bold: *cas12J-2*; bold and underlined: repeat; bold and italicized: stuffer spacer) | ATGCCAAAGCCAGCCGTGGAGTCTGAGTTTTCTAAGGTACTCAAGAAGCACTTTCCGGGCGAGCGATTTAGGTCTAGCTACATGAAGCGGGGTGGTAAAATCTTGGCAGCCCAGGGTGAAGAAGCGGTCGTCGCGTATCTGCAAGGCAAGTCCGAGGAGGAACCCCGAATTTTCAGCCGCCGGCGAAATGTCATGTTGTTACGAAATCACGAGATTTCGCCGAGTGGCCAATTATGAAGGCCTCGAAGCAATCCAAGGTATATCTATGCGCTCTCTACGACGGAACGGGCAGCTTGCAAGCCTGGCAAATCTTCAGAGTCCCACGCGGCCTGGTTCGCGGCAACTGGCGTGTCAAACCACGGTTATAGCCATGTTCAAGGCCTCAATCTTATCTTCGACCACACGCTGGGAAGATACGATGGTGTTCTGAAAAGGTGCAGCTGAGAAATGAGAAGCCCGCGCCGGCTGGAAAGTATCAACGCCTCGAGCCGACGAAGGACTTCCAGAAATAAAGGCAGAGGAGGAAGAGGTCGCTACAAATGAAACCGGACACCTTTTGCAGCCTCCGGGGATCAACCCAAGTTTCTACGTTTACCAGACTATTTCTCCGCAGGCTTACAGGCCGCGAGATGAGATTGTACTGCCGCCCGAGTATGCCGGCTACGTCCGAGATCCGAACGCCCTATCCCCCTTGGCGTGGTTCGGAATCGGTGCGATATTCAGAAGGGATGCCCTGGATACATCCCCGAATGGCAAAGAGAGGCAGGTACTGCAATTTCCCCTAAGACGGGTAAAGCCGTCACCGTTCCGGCCTCAGTCCAAAAAAAAATAAACGAATGCGACGATACTGGAGGTCCGAGAAAGAGAAGGCCCAAGATGCACTGCTCGTTACTGTGAGAATCGGCACTGACTGGGTCGTAATCGACGTTCGAGGTTTGCTGCGGAATGCGCGGTGGCGCACCATTGCGCCCAAGGATATATCCTTGAATGCCCTCTTGGATCTCTTTACAGGCGACCCGGTCATAGATGTTCGGAGAAACATTGTGACTTTCACCTACACTCTGGACGCTTGCGGTACATATGCTCGCAAATGGACTCTCAAAGGGAAACAGACTAAGGCAACCCTCGATAAGTTGACCGCAACCCAGACCGTGGCCCTGGTAGCAATAGACCTTGGACAAACCAATCCCATAAGTGCGGGTATCAGTAGGGTCACGCAAGAAAACGGGGCACTTCAATGTGAACCTCTGGATCGGTTCACTCTCCCTGATGATCTGCTCAAGGATATCTCCGCGTACCGAATCGCTTGGGATCGCAACGAGGAGGAACTGAGGGCTAGGTCCGTCGAAGCGCTCCCAGAAGCTCAACAAGCTGAAGTGAGGGCTCTGGACGGCGTTTCTAAAGAAACCGCCAGGACCCAGCTCTGCGCGGACTTCGGCCTTGATCCCAAACGGCTGCCTTGGGATAAAATGAGCAGCAACACCACTTTCATCAGTGAAGCGTTGCTTAGTAATTCTGTGTCTAGAGATCAGGTTTTTTTTACTCCTGCGCCTAAAAAGGGAGCAAAGAAAAAAGCCCCGTTGAAGTTATGCGGAAGGATAGGACCTGGGCGAGGGCCTATAAACCACGGCTCAGTGTGGAAGCCCAAAAGCTGAAAAATGAGGCCTTGTGGGCTCTCAAGCGCACTTCTCCAGAATACCTCAAGCTGAGTCGGAGAAAGAGGAGCTTTGTAGGCGAAGTATTAACTACGTCATTGAAAAACAAGACGGAGGACACAATGTCAGATCGTGATACCTGTCATAGAGGACTTGAATGTGCGATTCTTTCACGGTTCAGGGAAGCGCCTGCCTGGCTGGGATAATTTTTTCACTGCGAAGAAGGAGAACAGGTGGTTTATACAGGGCCTCCACAAAGCATTCAGCGACTTGCGAACTCATCGCTCCTTCTACGTATTCGAAGTCCGCCCGGAGCGGACTTCAATAACGTGCCCAAAATGCGGGCACTGCGAGGTTGGGAACCGGGATGGGGAGGCTTTTCAGTGCCTTAGTTGCGGCAA |

FIG. 17B (Table 1 Continued)

AACGTGCAATGCCGACCTTGACGTGGCTACCCATAATCTGACTC
AAGTCGCCCTTACAGGAAAAACAATGCCGAAACGCGAGGAACCT
AGAGATGCCCAGGGCACAGCTCCAGCCCGAAAAACAAAGAAGG
CGTCAAAGAGCAAGGCTCCGCCAGCCGAACGAGAGGACCAAAC
TCCAGCACAGGAACCGTCCCAGACTTCCGGAAGCGGACCCAAGA
AAAAACGCAAGGTGGAAGATCCTAAGAAAAAGCGGAAAGTGAGCC
TGGGCAGCGGCTCCGATTACAAAGATGACGATGACAAGACTACA
AGGATGATGATGATAAGGGATCCGGCGCAACAAACTTCTCTCTGC
TGAAACAAGCCGGAGATGTCGAAGAGAATCCTGGACCGACCGAGT
ACAAGCCCACGGTGCGCCTCGCCACCCGCGACGACGTCCCCAGG
GCCGTACGCACCCTCGCCGCCGCGTTCGCCGACTACCCCGCCAC
GCGCCACACCGTCGATCCGGACCGCCACATCGAGCGGGTCACCG
AGCTGCAAGAACTCTTCCTCACGCGCGTCGGGCTCGACATCGGCA
AGGTGTGGGTCGCGGACGACGGCGCCGCGGTGGCGGTCTGGAC
CACGCCGGAGAGCGTCGAAGCGGGGGCGGTGTTCGCCGAGATC
GGCCCGCGCATGGCCGAGTTGAGCGGTTCCCGGCTGGCCGCGC
AGCAACAGATGGAAGGCCTCCTGGCGCCGCACCGGCCCAAGGAG
CCCGCGTGGTTCCTGGCCACCGTCGGAGTCTCGCCCGACCACCA
GGGCAAGGGTCTGGGCAGCGCCGTCGTGCTCCCGGAGTGGAG
GCGGCCGAGCGCGCCGGGGTGCCCGCCTTCCTGGAGACCTCCG
CGCCCCGCAACCTCCCCTTCTACGAGCGGCTCGGCTTCACCGTCA
CCGCCGACGTCGAGGTGCCCGAAGGACCGCGCACCTGGTGCATG
ACCCGCAAGCCCGGTGCCTGAACGCGTTAAGAATTCCTAGAGCTC
GCTGATCAGCCTCGACTGTGCCTTCTAGTTGCCAGCCATCTGTTG
TTTGCCCCTCCCCGTGCCTTCCTTGACCCTGGAAGGTGCCACTC
CCACTGTCCTTTCCTAATAAAATGAGGAAATTGCATCGCATTGTCT
GAGTAGGTGTCATTCTATTCTGGGGGGTGGGGTGGGCAGGACA
GCAAGGGGGAGGATTGGGAAGAGAATAGCAGGCATGCTGGGGAG
CGGCCGCAGGAACCCCTAGTGATGGAGTTGGCCACTCCCTCTCT
GCGCGCTCGCTCGCTCACTGAGGCCGGGCGACCAAAGGTCGCCC
GACGCCCGGGCTTTGCCCGGGCGGCCTCAGTGAGCGAGCGAGC
GCGCAGCTGCCTGCAGGGCGCCTGATGCGGTATTTCTCCTTAC
GCATCTGTGCGGTATTTCACACCGCATACGTCAAAGCAACCATAGT
ACGCGCCCTGTAGCGGCGCATTAAGCGCGGCGGGTGTGGTGGTT
ACGCGCAGCGTGACCGCTACACTTGCCAGCGCCTTAGCGCCCGC
TCCTTTCGCTTTCTTCCCTTCCTTTCTCGCCACGTTCGCCGGCTTT
CCCCGTCAAGCTCTAAATCGGGGGCTCCCTTTAGGGTTCCGATTT
AGTGCTTTACGGCACCTCGACCCCAAAAAACTTGATTTGGGTGAT
GGTTCACGTAGTGGGCCATCGCCCTGATAGACGGTTTTCGCCCT
TTGACGTTGGAGTCCACGTTCTTTAATAGTGGACTCTTGTTCCAAA
CTGGAACAACACTCAACTCTATCTCGGGCTATTCTTTTGATTTATAA
GGGATTTTGCCGATTTCGGTCTATTGGTTAAAAAATGAGCTGATTT
AACAAAAATTTAACGCGAATTTTAACAAAATATTAACGTTTACAATTT
TATGGTGCACTCTCAGTACAATCTGCTCTGATGCCGCATAGTTAAG
CCAGCCCCGACACCCGCCAACACCCGCTGACGCGCCCTGACGGG
CTTGTCTGCTCCCGGCATCCGCTTACAGACAAGCTGTGACCGTCT
CCGGGAGCTGCATGTGTCAGAGGTTTTCACCGTCATCACCGAAAC
GCGCGAGACGAAAGGGCCTCGTGATACGCCTATTTTTATAGGTTA
ATGTCATGATAATAATGGTTTCTTAGACGTCAGGTGGCACTTTTCG
GGGAAATGTGCGCGGAACCCCTATTTGTTTATTTTTCTAAATACATT
CAAATATGTATCCGCTCATGAGACAATAACCCTGATAAATGCTTCA

FIG. 17C (Table 1 Continued)

```
ATAATATTGAAAAAGGAAGAGTATGAGTATTCAACATTTCCGTGTC
GCCCTTATTCCCTTTTTTGCGGCATTTTGCCTTCCTGTTTTTGCTCA
CCCAGAAACGCTGGTGAAAGTAAAAGATGCTGAAGATCAGTTGGG
TGCACGAGTGGGTTACATCGAACTGGATCTCAACAGCGGTAAGAT
CCTTGAGAGTTTTCGCCCCGAAGAACGTTTTCCAATGATGAGCACT
TTTAAAGTTCTGCTATGTGGCGCGGTATTATCCCGTATTGACGCCG
GGCAAGAGCAACTCGGTCGCCGCATACACTATTCTCAGAATGACT
TGGTTGAGTACTCACCAGTCACAGAAAGCATCTTACGGATGGCA
TGACAGTAAGAGAATTATGCAGTGCTGCCATAACCATGAGTGATAA
CACTGCGGCCAACTTACTTCTGACAACGATCGGAGGACCGAAGGA
GCTAACCGCTTTTTGCACAACATGGGGGATCATGTAACTCGCCTT
GATCGTTGGGAACCGGAGCTGAATGAAGCCATACCAAACGACGAG
CGTGACACCACGATGCCTGTAGCAATGGCAACAACGTTGCGCAAA
CTATTAACTGGCGAACTACTTACTCTAGCTTCCCGGCAACAATTAA
TAGACTGGATGGAGGCGGATAAAGTTGCAGGACCACTTCTGCGCT
CGGCCCTTCCGGCTGGCTGGTTTATTGCTGATAAATCTGGAGCCG
GTGAGCGTGGAAGCCGCGGTATCATTGCAGCACTGGGGCCAGAT
GGTAAGCCCTCCCGTATCGTAGTTATCTACACGACGGGGAGTCAG
GCAACTATGGATGAACGAAATAGACAGATCGCTGAGATAGGTGCC
TCACTGATTAAGCATTGGTAACTGTCAGACCAAGTTTACTCATATAT
ACTTTAGATTGATTTAAAACTTCATTTTAATTTAAAAGGATCTAGGT
GAAGATCCTTTTTGATAATCTCATGACCAAAATCCCTTAACGTGAG
TTTTCGTTCCACTGAGCGTCAGACCCCGTAGAAAAGATCAAAGGAT
CTTCTTGAGATCCTTTTTTTCTGCGCGTAATCTGCTGCTTGCAAAC
AAAAAAACCACCGCTACCAGCGGTGGTTTGTTTGCCGGATCAAGA
GCTACCAACTCTTTTTCCGAAGGTAACTGGCTTCAGCAGAGCGCA
GATACCAAATACTGTTCTTCTAGTGTAGCCGTAGTTAGGCCACCAC
TTCAAGAACTCTGTAGCACCGCCTACATACCTCGCTCTGCTAATCC
TGTTACCAGTGGCTGCTGCCAGTGGCGATAAGTCGTGTCTTACCG
GGTTGGACTCAAGACGATAGTTACCGGATAAGGCGCAGCGGTCG
GGCTGAACGGGGGGTTCGTGCACACAGCCCAGCTTGGAGCGAAC
GACCTACACCGAACTGAGATACCTACAGCGTGAGCTATGAGAAAG
CGCCACGCTTCCCGAAGGGAGAAAGGCGGACAGGTATCCGGTAA
GCGGCAGGGTCGGAACAGGAGAGCGCACGAGGGAGCTTCCAGG
GGGAAACGCCTGGTATCTTTATAGTCCTGTCGGGTTTCGCCACCT
CTGACTTGAGCGTCGATTTTGTGATGCTCGTCAGGGGGGCGGAG
CCTATGGAAAAACGCCAGCAACGCGGCCTTTTTACGGTTCCTGGC
CTTTTGCTGGCCTTTTGCTCACATGTGAGGGCCTATTTCCCATGAT
TCCTTCATATTTGCATATACGATACAAGGCTGTTAGAGAGATAATT
GGAATTAATTTGACTGTAAACACAAAGATATTAGTACAAAATACGTG
ACGTAGAAAGTAATAATTTCTTGGGTAGTTTGCAGTTTTAAAATTAT
GTTTTAAAATGGACTATCATATGCTTACCGTAACTTGAAAGTATTTC
GATTTCTTGGCTTTATATATCTTGTGGAAAGGACGAAACACCGGTC
GGAACGCTCAACGATTGCCCCTCACGAGGGGACAGAAGAGCTA
*ATGCTCTTCA**TTTTTTTTGGTACCCGTTACATAACTTACGGTAAATG
GCCCGCCTGGCTGACCGCCCAACGACCCCGCCCATTGACGTCA
ATAGTAACGCCAATAGGGACTTTCCATTGACGTCAATGGGTGGAG
TATTTACGGTAAACTGCCCACTTGGCAGTACATCAAGTGTATCATA
TGCCAAGTACGCCCCCTATTGACGTCAATGACGGTAAATGGCCCG
CCTGGCATTGTGCCCAGTACATGACCTTATGGGACTTTCCTACTTG
GCAGTACATCTACGTATTAGTCATCGCTATTACCATGGTCGAGGTG
```

FIG. 17D (Table 1 Continued)

| | |
|---|---|
| | AGCCCCACGTTCTGCTTCACTCTCCCCATCTCCCCCCCCTCCCCA CCCCCAATTTTGTATTTATTTATTTTTAATTATTTTGTGCAGCGATG GGGGCGGGGGGGGGGGGGGCGCGCGCCAGGCGGGGCGGG GSGGGGSGRGGGGSGGGGSGGGGSGRGGCGGAGAGGTGCGGC GGCAGCCAATCAGAGCGGCGCGCTCCGAAAGTTTCCTTTTATGGC GAGGCGGCGGCGGCGGCGGCCCTATAAAAGCGAAGCGCGCGG CGGGCGGGAGTCGCTGCGCGCTGCCTTCGCCCCGTGCCCCGCT CCGCCGCCGCCTCGCGCCGCCCGCCCCGGCTCTGACTGACCGC GTTACTCCCACAGGTGAGCGGGCGGGACGGCCCTTCTCCTCCGG GCTGTAATTAGCTGAGCAAGAGGTAAGGGTTTAAGGGATGGTTGG TTGGTGGGGTATTAATGTTTAATTACCTGGAGCACCTGCCTGAAAT CACTTTTTTTCAGGTTGGACCGGTGCCACC |
| pCas12J-3-hs (bold: *cas12J-3*; bold and underlined: repeat; bold and italicized: stuffer spacer) | ATGGAAAAGAAATAACTGAGCTCACCAAGATTAGGCGCGAGTT TCCGAATAAAAAGTTCAGCAGCACTGATATGAAGAAGGCAGGTA AGTTGTTGAAGGCAGAAGGTCCTGATGCTGTTAGAGACTTCCTG AACTCCTGCCAGGAGATTATCGGGGATTTTAAGCCGCCTGTAAA GACAAACATAGTCAGCATATCACGACCCTTTGAGGAGTGGCCTG TTAGTATGGTGGGGCGCGCCATCCAGGAATATTACTTTAGTTTGA CAAAAGAGGAATTGGAGTCCGTCCATCCCGGAACTTCCAGCGAG GATCACAAGTCCTTCTTTAACATAACTGGCCTGAGCAATTACAAT TATACGTCAGTCCAAGGCTTGAATCTCATCTTCAAAAATGCGAAG GCCATATCGACGGGACTCTGGTTAAAGCAAACAATAAAAATAA GAAGTTGGAAAAAAGTTCAATGAGATTAACCACAAGCGAAGCC TTGAGGGGCTTCCTATAATTACGCCGGATTTCGAGGAACCCTTTG ATGAGAATGGCCATCTGAATAATCGCCAGGTATTAATCGAAATA TTTACGGCTACCAAGGATGTGCCGCTAAAGTATTCGTTCCTTCCA AGCATAAAATGGTATCCCTCCCTAAAGAATACGAAGGGTACAAC CGGGATCCGAACCTGTCCTTGGCGGGCTTCCGAAATCGGCTCGA GATACCGGAGGGGGAGCCCGGTCACGTGCCATGGTTTCAGCGC ATGGATATCCCGGAAGGCCAGATCGGGCACGTAAATAAGATTCA ACGATTCAATTTCGTTCATGGCAAGAATTCAGGAAAAGTCAAATT CAGCGATAAGACAGGACGGGTAAAACGCTACCATCATTCCAAGT ATAAAGATGCCACTAAGCCTTACAAATTTCTTGAAGAATCCAAGA AAGTCAGTGCTCTGGACTCCATCCTTGCCATTATCACAATCGGTG ATGACTGGGTAGTGTTTGACATTCGCGGTCTGTATAGAAATGTTT TTTATCGCGAACTGGCACAGAAGGGCCTGACAGCAGTGCAGCTG CTGGATCTGTTTACGGGGATCCGGTGATTGACCCGAAGAAGGG CGTTGTGACATTCAGCTATAAGGAAGGCGTGGTTCCAGTATTTTC ACAGAAGATCGTTCCAAGGTTCAAGAGTCGAGACACGCTCGAGA AATTGACCAGTCAAGGACCTGTGGCGCTGCTCTCAGTCGACCTC GGCCAAAATGAACCAGTGGCGGCAAGGGTTTGTAGCTTGAAGAA CATAAATGATAAGATCACATTGGATAATTCTTGCAGAATCTCCTT CCTGGATGACTACAAAAAACAAATCAAAGACTACAGAGATTCCC TGGACGAACTTGAAATCAAGATACGACTGGAAGCAATCAATTCT CTGGAAACTAACCAACAAGTAGAAATTCGCGACCTGGATGTATT CAGTGCTGATCGGGCAAGGCAAACACTGTAGATATGTTCGACA TCGACCCAAATTTGATATCCTGGGATTCAATGAGCGACGCGAGG GTGAGCACGCAAATAAGCGATCTTTATCTGAAGAATGGGGGTGA CGAATCTCGAGTATATTTCGAAATTAACAACAAACGGATAAAGC GATCTGATTATAACATTAGTCAGCTGGTGAGGCCAAAGCTTTCCG ACAGCACTCGGAAGAATCTGAACGATTCTATATGGAAGTTGAAA|

FIG. 17E
(Table 1 Continued)

AGAACTAGTGAAGAATATTTGAAATTGTCCAAACGAAAGTTGGA
ACTGAGCAGAGCTGTTGTGAACTACACTATCCGCCAGAGCAAGC
TCCTCTCCGGAATTAACGACATTGTTATAATACTTGAGGACCTGG
ATGTAAAAAAAAATTCAATGGCAGGGGCATTCGAGATATCGGA
TGGGACAACTTCTTCAGCTCCAGGAAAGAGAACAGGTGGTTCAT
TCCGGCATTCCATAAGGCTTTCTCAGAGCTTTCAAGCAACCGGG
GCCTCTGTGTCATCGAAGTCAACCCGGCATGGACATCTGCCACC
TGTCCCGACTGCGGGTTCGTAGTAAAGAGAACAGAGATGGCAT
TAATTTTACCTGTCGCAAGTGCGGTGTCTCTTACCACGCGGACAT
AGATGTTGCCACTCTTAATATAGCCCGGGTGGCCGTTCTCGGCA
AGCCTATGTCCGGACCCGCCGACCGCGAGAGACTGGGCGATAC
TAAGAAACCCCGGGTAGCAAGGAGCCGAAAGACTATGAAACGG
AAAGATATTAGCAATAGCACCGTTGAGGCTATGGTTACAGCCGG
AAGCGGACCCAAGAAAAACGCAAGGTGGAAGATCCTAAGAAAAA
GCGGAAAGTGAGCCTGGGCAGCGGCTCCGATTACAAAGATGACG
ATGACAAAGACTACAAGGATGATGATGATAAGGGATCCGGCGCAA
CAAACTTCTCTCTGCTGAAACAAGCCGGAGATGTCGAAGAGAATC
CTGGACCGACCGAGTACAAGCCCACGGTGCGCCTCGCCACCCGC
GACGACGTCCCCAGGGCCGTACGCACCCTCGCCGCCGCGTTCGC
CGACTACCCCGCCACGCGCCACACCGTCGATCCGGACCGCCACA
TCGAGCGGGTCACCGAGCTGCAAGAACTCTTCCTCACGCGCGTC
GGGCTCGACATCGGCAAGGTGTGGGTCGCGGACGACGGCGCCG
CGGTGGCGGTCTGGACCACGCCGGAGAGCGTCGAAGCGGGGGC
GGTGTTCGCCGAGATCGGCCCGCGCATGGCCGAGTTGAGCGGTT
CCCGGCTGGCCGCGCAGCAACAGATGGAAGGCCTCCTGGCGCC
GCACCGGCCCAAGGAGCCCGCGTGGTTCCTGGCCACCGTCGGAG
TCTCGCCCGACCACCAGGGCAAGGGTCTGGGCAGCGCCGTCGTG
CTCCCCGGAGTGGAGGCGGCCGAGCGCGCCGGGGTGCCCGCCT
TCCTGGAGACCTCCGCGCCCCGCAACCTCCCCTTCTACGAGCGG
CTCGGCTTCACCGTCACCGCCGACGTCGAGGTGCCCGAAGGACC
GCGCACCTGGTGCATGACCCGCAAGCCCGGTGCCTGAACGCGTT
AAGAATTCCTAGAGCTCGCTGATCAGCCTCGACTGTGCCTTCTAGT
TGCCAGCCATCTGTTGTTTGCCCCTCCCCGTGCCTTCCTTGACC
CTGGAAGGTGCCACTCCCACTGTCCTTTCCTAATAAAATGAGGAAA
TTGCATCGCATTGTCTGAGTAGGTGTCATTCTATTCTGGGGGGTG
GGGTGGGGCAGGACAGCAAGGGGGAGGATTGGGAAGAGAATAG
CAGGCATGCTGGGGAGCGGCCGCAGGAACCCCTAGTGATGGAGT
TGGCCACTCCCTCTCTGCGCGCTCGCTCGCTCACTGAGGCCGGG
CGACCAAAGGTCGCCCGACGCCCGGGCTTTGCCCGGGCGGCCTC
AGTGAGCGAGCGAGCGCGCAGCTGCCTGCAGGGGCGCCTGATG
CGGTATTTTCTCCTTACGCATCTGTGCGGTATTTCACACCGCATAC
GTCAAAGCAACCATAGTACGCGCCCTGTAGCGGCGCATTAAGCGC
GGCGGGTGTGGTGGTTACGCGCAGCGTGACCGCTACACTTGCCA
GCGCCTTAGCGCCCGCTCCTTTCGCTTTCTTCCCTTCCTTTCTCGC
CACGTTCGCCGGCTTTCCCCGTCAAGCTCTAAATCGGGGGCTCCC
TTTAGGGTTCCGATTTAGTGCTTTACGGCACCTCGACCCCAAAAAA
CTTGATTTGGGTGATGGTTCACGTAGTGGGCCATCGCCCTGATAG
ACGGTTTTTCGCCCTTTGACGTTGGAGTCCACGTTCTTTAATAGTG
GACTCTTGTTCCAAACTGGAACAACACTCAACTCTATCTCGGGCTA
TTCTTTTGATTTATAAGGGATTTTGCCGATTTCGGTCTATTGGTTAA
AAAATGAGCTGATTTAACAAAAATTTAACGCGAATTTTAACAAAATA

FIG. 17F
(Table 1 Continued)

```
TTAACGTTTACAATTTTATGGTGCACTCTCAGTACAATCTGCTCTGA
TGCCGCATAGTTAAGCCAGCCCCGACACCCGCCAACACCCGCTG
ACGCGCCCTGACGGGCTTGTCTGCTCCCGGCATCCGCTTACAGA
CAAGCTGTGACCGTCTCCGGGAGCTGCATGTGTCAGAGGTTTTCA
CCGTCATCACCGAAACGCGCGAGACGAAAGGGCCTCGTGATACG
CCTATTTTTATAGGTTAATGTCATGATAATAATGGTTTCTTAGACGT
CAGGTGGCACTTTTCGGGGAAATGTGCGCGGAACCCCTATTTGTT
TATTTTTCTAAATACATTCAAATATGTATCCGCTCATGAGACAATAA
CCCTGATAAATGCTTCAATAATATTGAAAAGGAAGAGTATGAGTA
TTCAACATTTCCGTGTCGCCCTTATTCCCTTTTTTGCGGCATTTTGC
CTTCCTGTTTTTGCTCACCCAGAAACGCTGGTGAAAGTAAAAGATG
CTGAAGATCAGTTGGGTGCACGAGTGGGTTACATCGAACTGGATC
TCAACAGCGGTAAGATCCTTGAGAGTTTTCGCCCCGAAGAACGTT
TTCCAATGATGAGCACTTTTAAAGTTCTGCTATGTGGCGCGGTATT
ATCCCGTATTGACGCCGGGCAAGAGCAACTCGGTCGCCGCATACA
CTATTCTCAGAATGACTTGGTTGAGTACTCACCAGTCACAGAAAAG
CATCTTACGGATGGCATGACAGTAAGAGAATTATGCAGTGCTGCC
ATAACCATGAGTGATAACACTGCGGCCAACTTACTTCTGACAACGA
TCGGAGGACCGAAGGAGCTAACCGCTTTTTGCACAACATGGGGG
ATCATGTAACTCGCCTTGATCGTTGGGAACCGGAGCTGAATGAAG
CCATACCAAACGACGAGCGTGACACCACGATGCCTGTAGCAATGG
CAACAACGTTGCGCAAACTATTAACTGGCGAACTACTTACTCTAGC
TTCCCGGCAACAATTAATAGACTGGATGGAGGCGGATAAAGTTGC
AGGACCACTTCTGCGCTCGGCCCTTCCGGCTGGCTGGTTTATTGC
TGATAAATCTGGAGCCGGTGAGCGTGGAAGCCGCGGTATCATTGC
AGCACTGGGGCCAGATGGTAAGCCCTCCCGTATCGTAGTTATCTA
CACGACGGGGAGTCAGGCAACTATGGATGAACGAAATAGACAGAT
CGCTGAGATAGGTGCCTCACTGATTAAGCATTGGTAACTGTCAGA
CCAAGTTTACTCATATATACTTTAGATTGATTTAAAACTTCATTTTTA
ATTTAAAAGGATCTAGGTGAAGATCCTTTTTGATAATCTCATGACCA
AAATCCCTTAACGTGAGTTTTCGTTCCACTGAGCGTCAGACCCCGT
AGAAAAGATCAAAGGATCTTCTTGAGATCCTTTTTTTCTGCGCGTA
ATCTGCTGCTTGCAAACAAAAAAACCACCGCTACCAGCGGTGGTT
TGTTTGCCGGATCAAGAGCTACCAACTCTTTTTCCGAAGGTAACTG
GCTTCAGCAGAGCGCAGATACCAAATACTGTTCTTCTAGTGTAGCC
GTAGTTAGGCCACCACTTCAAGAACTCTGTAGCACCGCCTACATA
CCTCGCTCTGCTAATCCTGTTACCAGTGGCTGCTGCCAGTGGCGA
TAAGTCGTGTCTTACCGGGTTGGACTCAAGACGATAGTTACCGGA
TAAGGCGCAGCGGTCGGGCTGAACGGGGGGTTCGTGCACACAGC
CCAGCTTGGAGCGAACGACCTACACCGAACTGAGATACCTACAGC
GTGAGCTATGAGAAAGCGCCACGCTTCCCGAAGGGAGAAAGGCG
GACAGGTATCCGGTAAGCGGCAGGGTCGGAACAGGAGAGCGCAC
GAGGGAGCTTCCAGGGGGAAACGCCTGGTATCTTTATAGTCCTGT
CGGGTTTCGCCACCTCTGACTTGAGCGTCGATTTTGTGATGCTC
GTCAGGGGGCGGAGCCTATGGAAAAACGCCAGCAACGCGGCCT
TTTTACGGTTCCTGGCCTTTTGCTGGCCTTTTGCTCACATGTGAGG
GCCTATTTCCCATGATTCCTTCATATTTGCATATACGATACAAGGCT
GTTAGAGAGATAATTGGAATTAATTTGACTGTAAACACAAAGATATT
AGTACAAATACGTGACGTAGAAAGTAATAATTTCTTGGGTAGTTT
GCAGTTTTAAAATTATGTTTTAAAATGGACTATCATATGCTTACCGT
AACTTGAAAGTATTTCGATTTCTTGGCTTTATATATCTTGTGGAAAG
```

FIG. 17G (Table 1 Continued)

| |GACGAAACACCGACCAAAACGACTATTGATTGCCCAGTACGCTG GGAC*AGAAGAGCTAATGCTCTTCA*TTTTTTTTGGTACCCGTTACAT AACTTACGGTAAATGGCCCGCCTGGCTGACCGCCCAACGACCCC CGCCCATTGACGTCAATAGTAACGCCAATAGGGACTTTCCATTGAC GTCAATGGGTGGAGTATTTACGGTAAACTGCCCACTTGGCAGTAC ATCAAGTGTATCATATGCCAAGTACGCCCCTATTGACGTCAATGA CGGTAAATGGCCCGCCTGGCATTGTGCCCAGTACATGACCTTATG GGACTTTCCTACTTGGCAGTACATCTACGTATTAGTCATCGCTATT ACCATGGTCGAGGTGAGCCCCACGTTCTGCTTCACTCTCCCCATC TCCCCCCCTCCCCACCCCCAATTTTGTATTTATTTATTTTTTAATT ATTTTGTGCAGCGATGGGGGCGGGGGGGGGGGGGGCGCGCG CCAGGCGGGGCGGGGSGGGGSGRGGGGSGGGGSGGGGSGRGG CGGAGAGGTGCGGCGGCAGCCAATCAGAGCGGCGCGCTCCGAA AGTTTCCTTTTATGGCGAGGCGGCGGCGGCGGCGGCCCTATAAA AAGCGAAGCGCGCGGCGGGCGGGAGTCGCTGCGCGCTGCCTTC GCCCCGTGCCCCGCTCCGCCGCCGCCTCGCGCCGCCCGCCCCG GCTCTGACTGACCGCGTTACTCCCACAGGTGAGCGGGCGGGACG GCCCTTCTCCTCCGGGCTGTAATTAGCTGAGCAAGAGGTAAGGGT TTAAGGGATGGTTGGTTGGTGGGGTATTAATGTTTAATTACCTGGA GCACCTGCCTGAAATCACTTTTTTTCAGGTTGGACCGGTGCCACC|
|---|---|

FIG. 31A
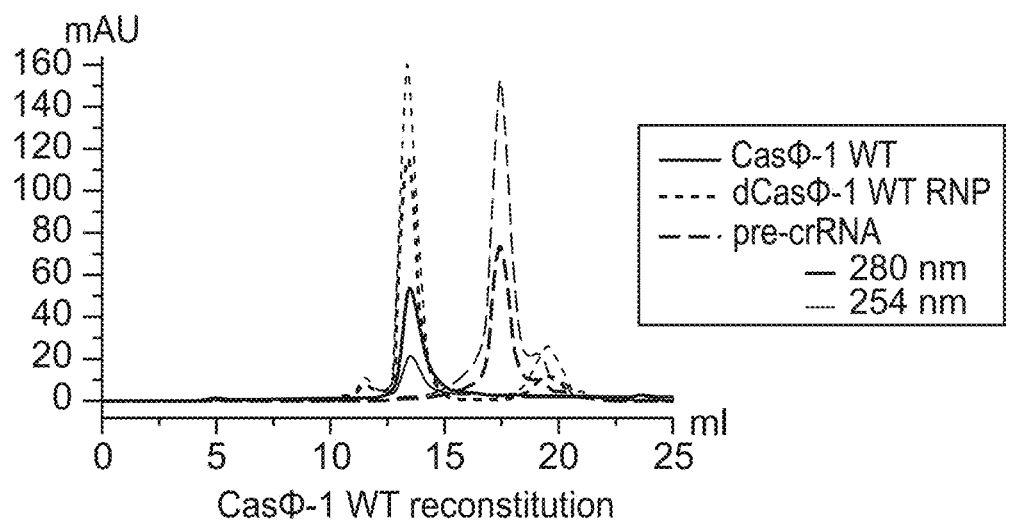
CasΦ-1 WT reconstitution
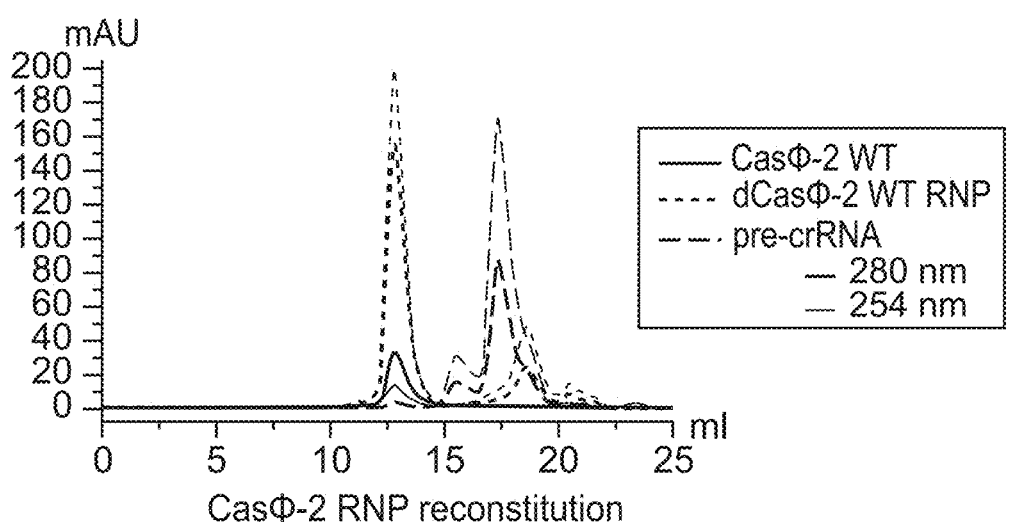
CasΦ-2 RNP reconstitution
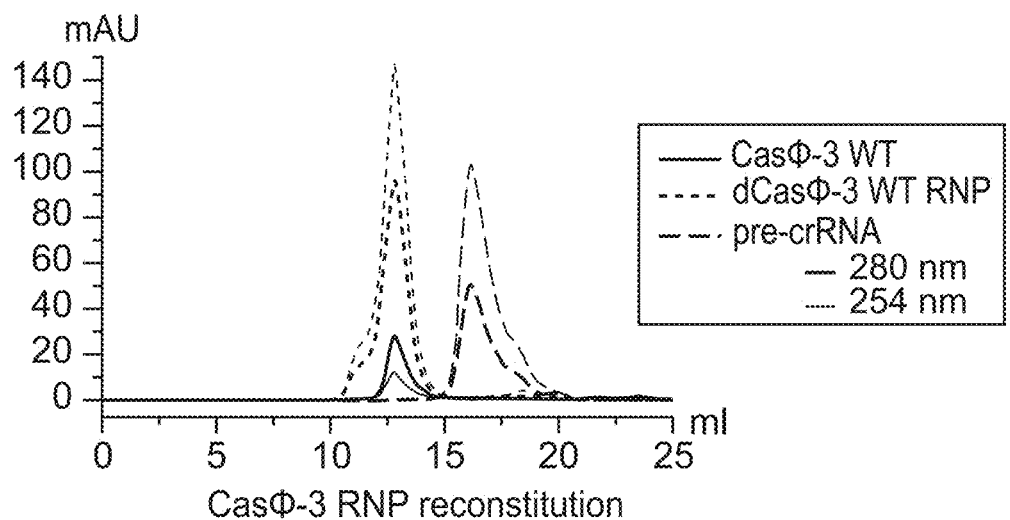
CasΦ-3 RNP reconstitution FIG. 32A
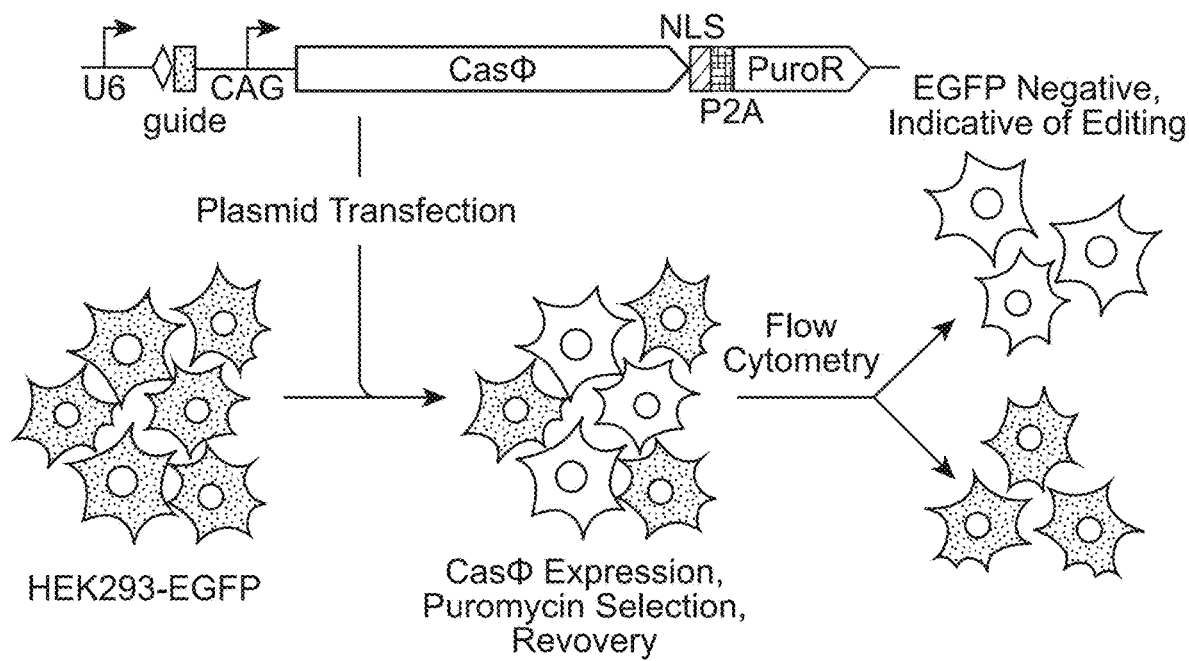
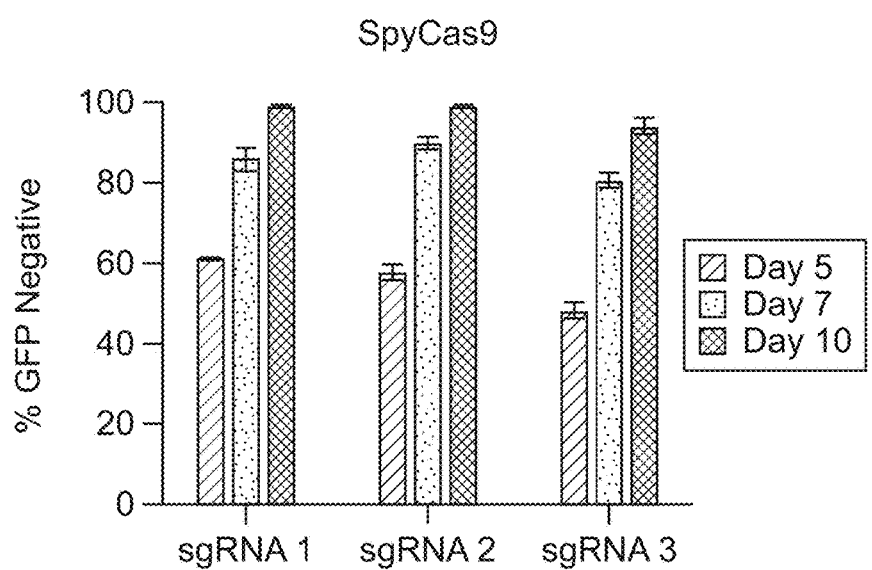

FIG. 32B
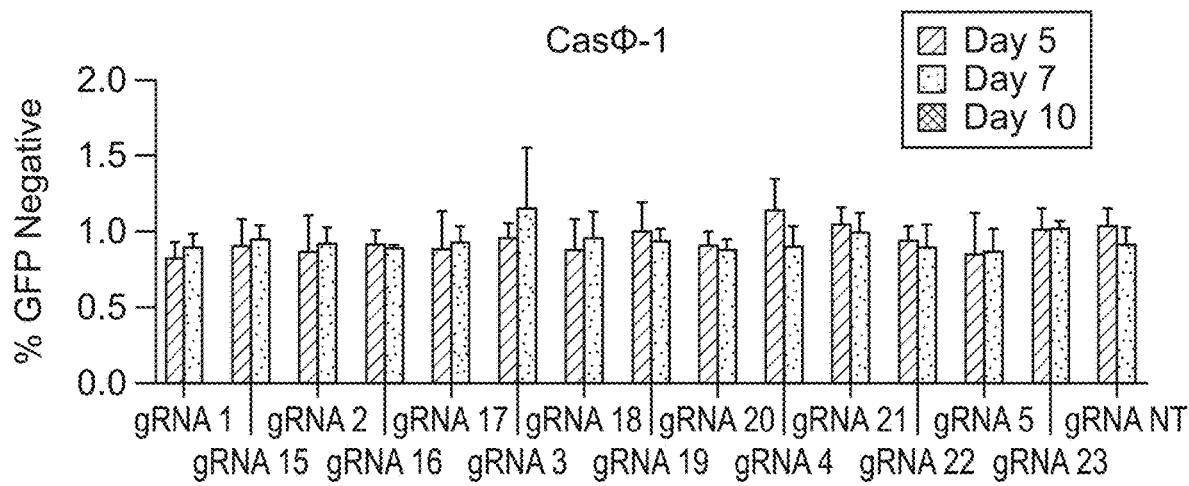
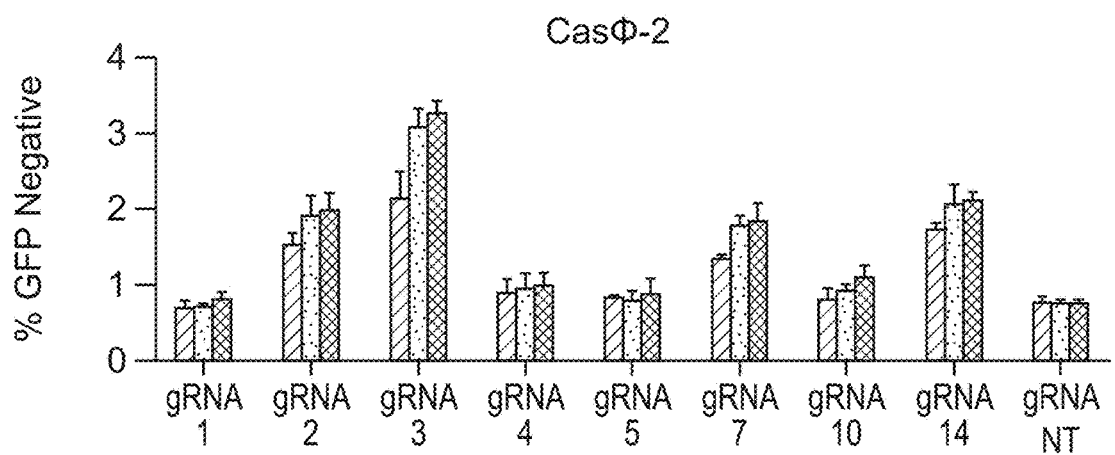
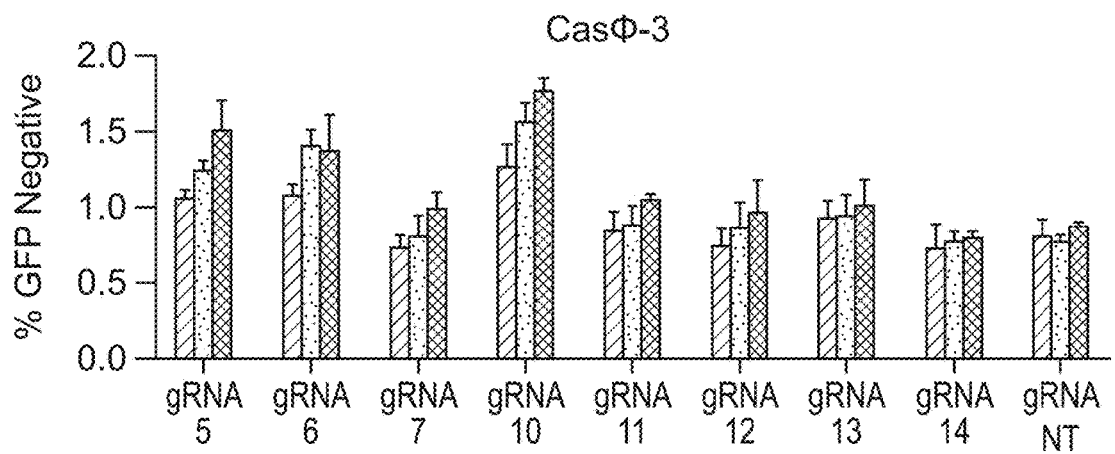

FIG. 34

(Table 3)

| ID # | Assay | Features | Selection marker |
|---|---|---|---|
| pPP048 | PAM-depletion, RNA-seq | pBLO1-backbone derived plasmid containing CasΦ-1 locus under control of tetracycline inducible promoter. Contains mini-CRISPR non-targeting AarI-GG stuffer spacer. | Chloramphenicol |
| pPP053 | PAM-depletion, RNA-seq | pBLO1-backbone derived plasmid containing CasΦ-2 locus under control of tetracycline inducible promoter. Contains mini-CRISPR non-targeting AarI-GG stuffer spacer. CasΦ gene was codon optimized for expression in *E. coli*. | Chloramphenicol |
| pPP060 | PAM-depletion, RNA-seq | pBLO1-backbone derived plasmid containing CasΦ-3 locus under control of tetracycline inducible promoter. Contains mini-CRISPR non-targeting AarI-GG stuffer spacer. | Chloramphenicol |
| pPP049 | PAM-depletion | pBLO1-backbone derived plasmid containing CasΦ-1 locus under control of tetracycline inducible promoter. Contains mini-CRISPR with PAM-library targeting spacer. | Chloramphenicol |
| pPP056 | PAM-depletion | pBLO1-backbone derived plasmid containing CasΦ-2 locus under control of tetracycline inducible promoter. Contains mini-CRISPR with PAM-library targeting spacer. CasΦ gene was codon optimized for expression in *E. coli*. | Chloramphenicol |
| pPP062 | PAM-depletion | pBLO1-backbone derived plasmid containing CasΦ-3 locus under control of tetracycline inducible promoter. Contains mini-CRISPR with PAM-library targeting spacer. | Chloramphenicol |
| pPP094 | PAM-depletion | pRSF-Duet1 derived plasmid containing CasΦ-1 in MCS1 and a mini CRISPR (repeat-spacer-repeat) in MCS2. Contains non-targeting AarI-GG stuffer spacer. | Kanamycin |

FIG. 34 (Cont.)

(Table 3 Continued)

| ID # | Assay | Features | Selection marker |
|---|---|---|---|
| pPP100 | PAM-depletion | pRSF-Duet1 derived plasmid containing CasΦ-2 in MCS1 and a mini CRISPR (repeat-spacer-repeat) in MCS2. Contains non-targeting AarI-GG stuffer spacer. | Kanamycin |
| pPP106 | PAM-depletion | pRSF-Duet1 derived plasmid containing CasΦ-3 in MCS1 and a mini CRISPR (repeat-spacer-repeat) in MCS2. Contains non-targeting AarI-GG stuffer spacer. | Kanamycin |
| pPP097 | PAM-depletion | pRSF-Duet1 derived plasmid containing CasΦ-1 in MCS1 and a mini CRISPR (repeat-spacer-repeat) in MCS2. Contains mini-CRISPR with PAM-library targeting spacer. | Kanamycin |
| pPP102 | PAM-depletion | pRSF-Duet1 derived plasmid containing CasΦ-2 in MCS1 and a mini CRISPR (repeat-spacer-repeat) in MCS2. Contains mini-CRISPR with PAM-library targeting spacer. | Kanamycin |
| pPP107 | PAM-depletion | pRSF-Duet1 derived plasmid containing CasΦ-3 in MCS1 and a mini CRISPR (repeat-spacer-repeat) in MCS2.Contains mini-CRISPR with PAM-library targeting spacer. | Kanamycin |
| pPP190 | Efficiency of transformation | pRSF-Duet1 derived plasmid containing CasΦ-3 in MCS1 and a mini CRISPR (repeat-spacer-HDVrz) in MCS2. Contains non-targeting AarI-GG stuffer spacer. | Kanamycin |
| pPP192 | Efficiency of transformation | pRSF-Duet1 derived plasmid containing CasΦ-3 in MCS1 and a mini CRISPR (repeat-spacer-HDVrz) in MCS2. Contains bla gene targeting spacer. | Kanamycin |
| pPP240 | Efficiency of transformation | pRSF-Duet1 derived plasmid containing dCasΦ-3 (D413A) in MCS1 and a mini CRISPR (repeat-spacer-HDVrz) in MCS2. Contains bla gene targeting spacer. | Kanamycin |

FIG. 34 (Cont.) (Table 3 Continued)

| ID # | Assay | Features | Selection marker |
|---|---|---|---|
| pPP242 | Efficiency of transformation | pRSF-Duet1 derived plasmid containing dCasɸ-3 (E618A) in MCS1 and a mini CRISPR (repeat-spacer-HDVrz) in MCS2. Contains bla gene targeting spacer. | Kanamycin |
| pPP244 | Efficiency of transformation | pRSF-Duet1 derived plasmid containing dCasɸ-3 (D708A) in MCS1 and a mini CRISPR (repeat-spacer-HDVrz) in MCS2. Contains bla gene targeting spacer. | Kanamycin |
| pPP076 | Protein purification | pRSF-Duet1 derived plasmid containing C-terminally hexa-histidine tagged Casɸ-1 in MCS1. | Kanamycin |
| pPP085 | Protein purification | pRSF-Duet1 derived plasmid containing C-terminally hexa-histidine tagged Casɸ-2 in MCS1. | Kanamycin |
| pPP089 | Protein purification | pRSF-Duet1 derived plasmid containing C-terminally hexa-histidine tagged Casɸ-3 in MCS1. | Kanamycin |
| pPP378 | Protein purification | pRSF-Duet1 derived plasmid containing C-terminally hexa-histidine tagged dCasɸ-1 (D371A) in MCS1. | Kanamycin |
| pPP381 | Protein purification | pRSF-Duet1 derived plasmid containing C-terminally hexa-histidine tagged dCasɸ-2 (D394A) in MCS1. | Kanamycin |
| pPP384 | Protein purification | pRSF-Duet1 derived plasmid containing C-terminally hexa-histidine tagged dCasɸ-3 (D431A) in MCS1. | Kanamycin |
| pPP338 | Cleavage assay | pYTK095 derived plasmid containing a protospacer corresponding to position 1-24 of spacer 2 from the Casɸ-1 CRISPR-array, as derived from metagenomic analysis. PAM: 5-TTA (cognate) | Ampicillin |

FIG. 34 (Cont.)  (Table 3 Continued)

| ID # | Assay | Features | Selection marker |
|---|---|---|---|
| pPP341 | Cleavage assay | pYTK095 derived plasmid containing a protospacer corresponding to position 1-24 of spacer 2 from the CasΦ-1 CRISPR-array, as derived from metagenomic analysis. PAM: 5-CCA (non-cognate) | Ampicilin |
| pPP394 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. SapI-GG stuffer spacer. | Ampicilin (*E. coli*) Puromycin (*H. sapiens*) |
| pPP441 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. SapI-GG stuffer spacer. | Ampicilin (*E. coli*) Puromycin (*H. sapiens*) |
| pPP444 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. SapI-GG stuffer spacer. | Ampicilin (*E. coli*) Puromycin (*H. sapiens*) |

FIG. 34 (Cont.)

(Table 3 Continued)

| ID # | Assay | Features | Selection marker |
|---|---|---|---|
| pPP400 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #1 -change number- spacer. | Ampicillin (*E. coli*) Puromycin (*H. sapiens*) |
| pPP403 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #15 -change number- spacer. | Ampicillin (*E. coli*) Puromycin (*H. sapiens*) |
| pPP406 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #2 -change number- spacer. | Ampicillin (*E. coli*) Puromycin (*H. sapiens*) |
| pPP409 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #16 -change number- spacer. | Ampicillin (*E. coli*) Puromycin (*H. sapiens*) |

FIG. 34 (Cont.)   (Table 3 Continued)

| ID # | Assay | Features | Selection marker |
|---|---|---|---|
| pPP412 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #17 -change number- spacer. | Ampicillin (*E. coli*) Puromycin (*H. sapiens*) |
| pPP415 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #3 -change number- spacer. | Ampicillin (*E. coli*) Puromycin (*H. sapiens*) |
| pPP417 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #18 -change number- spacer. | Ampicillin (*E. coli*) Puromycin (*H. sapiens*) |
| pPP420 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #19 -change number- spacer. | Ampicillin (*E. coli*) Puromycin (*H. sapiens*) |

FIG. 34 (Cont.)

(Table 3 Continued)

| ID # | Assay | Features | Selection marker |
|---|---|---|---|
| pPP423 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #20 -change number- spacer. | Ampicillin (*E. coli*) Puromycin (*H. sapiens*) |
| pPP426 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #4 -change number- spacer. | Ampicillin (*E. coli*) Puromycin (*H. sapiens*) |
| pPP428 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #21 -change number- spacer. | Ampicillin (*E. coli*) Puromycin (*H. sapiens*) |
| pPP429 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #22 -change number- spacer. | Ampicillin (*E. coli*) Puromycin (*H. sapiens*) |

FIG. 34 (Cont.) (Table 3 Continued)

| ID # | Assay | Features | Selection marker |
|---|---|---|---|
| pPP432 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #5 -change number- spacer. | Ampicillin (*E. coli*) Puromycin (*H. sapiens*) |
| pPP435 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #23 -change number- spacer. | Ampicillin (*E. coli*) Puromycin (*H. sapiens*) |
| pPP438 | Genome editing | Plasmid contains *Homo sapiens* codon optimized CasΦ-1 under the control of CMV-CAG promoter. CasΦ-1 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. Non-targeting scrambled guide spacer. | Ampicillin (*E. coli*) Puromycin (*H. sapiens*) |
| pPP447 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #1 -change number- spacer. | Ampicillin (*E. coli*) Puromycin (*H. sapiens*) |

FIG. 34 (Cont.) (Table 3 Continued)

| ID # | Assay | Features | Selection marker |
|---|---|---|---|
| pPP449 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #2 -change number- spacer. | Ampicillin (*E. coli*) Puromycin (*H. sapiens*) |
| pPP452 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #3 -change number- spacer. | Ampicillin (*E. coli*) Puromycin (*H. sapiens*) |
| pPP455 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #4 -change number- spacer. | Ampicillin (*E. coli*) Puromycin (*H. Sapiens*) |
| pPP458 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #5 -change number- spacer. | Ampicillin (*E. coli*) Puromycin (*H. sapiens*) |

FIG. 34 (Cont.)   (Table 3 Continued)

| ID # | Assay | Features | Selection marker |
|---|---|---|---|
| pPP460 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #6 -change number- spacer. | Ampicilin (*E. coli*) Puromycin (*H. sapiens*) |
| pPP463 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #9 -change number- spacer. | Ampicilin (*E. coli*) Puromycin (*H. sapiens*) |
| pPP466 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #10 -change number- spacer. | Ampicilin (*E. coli*) Puromycin (*H. sapiens*) |
| pPP468 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #7 -change number- spacer. | Ampicilin (*E. coli*) Puromycin (*H. sapiens*) |

FIG. 34 (Cont.) (Table 3 Continued)

| ID # | Assay | Features | Selection marker |
|---|---|---|---|
| pPP471 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #8 -change number- spacer. | Ampicillin (*E. coli*) Puromycin (*H. sapiens*) |
| pPP473 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #14 -change number- spacer. | Ampicillin (*E. coli*) Puromycin (*H. sapiens*) |
| pPP475 | Genome editing | Plasmid contains *Homo sapiens* codon optimized CasΦ-2 under the control of CMV-CAG promoter. CasΦ-2 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. Non-targeting scrambled guide spacer. | Ampicillin (*E. coli*) Puromycin (*H. sapiens*) |
| pPP478 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #5 -change number- spacer. | Ampicillin (*E. coli*) Puromycin (*H. sapiens*) |

FIG. 34 (Cont.) (Table 3 Continued)

| ID # | Assay | Features | Selection marker |
|---|---|---|---|
| pPP481 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #6 -change number- spacer. | Ampicillin (*E. coli*) Puromycin (*H. Sapiens*) |
| pPP484 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #7 -change number- spacer. | Ampicillin (*E. coli*) Puromycin (*H. sapiens*) |
| pPP487 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #8 -change number- spacer. | Ampicillin (*E. coli*) Puromycin (*H. sapiens*) |
| pPP490 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #9 -change number- spacer. | Ampicillin (*E. coli*) Puromycin (*H. sapiens*) |

FIG. 34 (Cont.) (Table 3 Continued)

| ID # | Assay | Features | Selection marker |
|---|---|---|---|
| pPP493 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #10 -change number- spacer. | Ampicillin (*E. coli*) Puromycin (*H. sapiens*) |
| pPP495 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #11 -change number- spacer. | Ampicillin (*E. coli*) Puromycin (*H. sapiens*) |
| pPP498 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #12 -change number- spacer. | Ampicillin (*E. coli*) Puromycin (*H. sapiens*) |
| pPP501 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #13 -change number- spacer. | Ampicillin (*E. coli*) Puromycin (*H. sapiens*) |

FIG. 34 (Cont.)  (Table 3 Continued)

| ID # | Assay | Features | Selection marker |
|---|---|---|---|
| pPP504 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. EGFP targeting guide #14 -change number- spacer. | Ampicillin (*E. coli*) Puromycin (*H. sapiens*) |
| pPP506 | Genome editing | Plasmid contains *Homo sapiens* codon optimized CasΦ-3 under the control of CMV-CAG promoter. CasΦ-3 is C-terminally fused to two SV40 NLS sequences, a FLAG tag and linked to PuroR via the P2A peptide sequence. Locus for guide expression is controlled by U6-promoter and constitutes a repeat-spacer unit terminated by a poly-T sequence. Non-targeting scrambled guide spacer. | Ampicillin (*E. coli*) Puromycin (*H. sapiens*) |
| pBFC545 | Genome editing | Plasmid contains SpyCas9 under the control of CMV-CAG promoter. SpyCas9 is N-terminally and C-terminally fused to SV40 NLS sequences, a FLAG tag and C-terminally linked to PuroR via the P2A peptide sequence. Locus for guide expression is controlled by U6-promoter and constitutes a spacer-repeat-tracr unit terminated by a poly-T sequence. EGFP targeting single-guide (sg) #1 | Ampicillin (*E. coli*) Puromycin (*H. sapiens*) |
| pBFC546 | Genome editing | Plasmid contains SpyCas9 under the control of CMV-CAG promoter. SpyCas9 is N-terminally and C-terminally fused to SV40 NLS sequences, a FLAG tag and C-terminally linked to PuroR via the P2A peptide sequence. Locus for guide expression is controlled by U6-promoter and constitutes a spacer-repeat-tracr unit terminated by a poly-T sequence. EGFP targeting single-guide (sg) #2 | Ampicillin (*E. coli*) Puromycin (*H. sapiens*) |

FIG. 34 (Cont.)     (Table 3 Continued)

| ID # | Assay | Features | Selection marker |
|---|---|---|---|
| pBFC547 | Genome editing | Plasmid contains SpyCas9 under the control of CMV-CAG promoter. SpyCas9 is N-terminally and C-terminally fused to SV40 NLS sequences, a FLAG tag and C-terminally linked to PuroR via the P2A peptide sequence. Locus for guide expression is controlled by U6-promoter and constitutes a spacer-repeat-tracr unit terminated by a poly-T sequence. EGFP targeting single-guide (sg) #3 | Ampicillin (*E. coli*) Puromycin (*H. sapiens*) |

FIG. 35 (Table 4)

| ID # | Assay | Description | Spacer sequence |
|---|---|---|---|
| g_Lib | PAM-depletion | CasΦ guide targeting the PAM depletion library plasmid next to the randomized PAM sequence | CTGGAGTTGTCCCAATTCTTGTTGAA TTAGATGGT (SEQ ID NO: 198) |
| g_bla | Efficiency of transformation | CasΦ guide targeting the beta lactamase gene (*bla*) of pUC19 | AACATTTCCGTGTCGCCCTTATTCCC TTTTTTGCG (SEQ ID NO: 199) |
| sg_1 | Genome editing | SpyCas9 single-guide targeting the EGFP gene | GGCGAGGGCGATGCCACCTA (SEQ ID NO: 200) |
| sg_2 | Genome editing | SpyCas9 single-guide targeting the EGFP gene | TTCAAGTCCGCCATGCCCGA (SEQ ID NO: 201) |
| sg_3 | Genome editing | SpyCas9 single-guide targeting the EGFP gene | GGTGAACCGCATCGAGCTGA (SEQ ID NO: 202) |
| g_1 | Genome editing | CasΦ guide targeting the EGFP gene | CTTGTACAGCTCGTCCATGC (SEQ ID NO: 203) |
| g_2 | Genome editing | CasΦ guide targeting the EGFP gene | TCGGGCAGCAGCACGGGGCC (SEQ ID NO: 204) |
| g_3 | Genome editing | CasΦ guide targeting the EGFP gene | TAGTTGTACTCCAGCTTGTG (SEQ ID NO: 205) |
| g_4 | Genome editing | CasΦ guide targeting the EGFP gene | TGGCCGTTTACGTCGCCGTC (SEQ ID NO: 206) |
| g_5 | Genome editing | CasΦ guide targeting the EGFP gene | AAGAAGTCGTGCTGCTTCAT (SEQ ID NO: 207) |

FIG. 35 (Cont.)  (Table 4 Continued)

| ID # | Assay | Description | Spacer sequence |
|---|---|---|---|
| g_6 | Genome editing | CasΦ guide targeting the EGFP gene | ACCGGGGTGGTGCCCATCCT (SEQ ID NO: 106) |
| g_7 | Genome editing | CasΦ guide targeting the EGFP gene | AGCGTGTCCGGCGAGGGCGA (SEQ ID NO: 209) |
| g_8 | Genome editing | CasΦ guide targeting the EGFP gene | ATCTGCACCACCGGCAAGCT (SEQ ID NO: 107) |
| g_9 | Genome editing | CasΦ guide targeting the EGFP gene | GAGGGCGACACCCTGGTGAA (SEQ ID NO: 108) |
| g_10 | Genome editing | CasΦ guide targeting the EGFP gene | ACCAGGGTGTCGCCCTCGAA (SEQ ID NO: 212) |
| g_11 | Genome editing | CasΦ guide targeting the EGFP gene | TTCTGCTTGTCGGCCATGAT (SEQ ID NO: 213) |
| g_12 | Genome editing | CasΦ guide targeting the EGFP gene | ACCTTGATGCCGTTCTTCTG (SEQ ID NO: 214) |
| g_13 | Genome editing | CasΦ guide targeting the EGFP gene | TGCTGGTAGTGGTCGGCGAG (SEQ ID NO: 215) |
| g_14 | Genome editing | CasΦ guide targeting the EGFP gene | GTGACCGCCGCCGGGATCAC (SEQ ID NO: 216) |

FIG. 35 (Cont.)      (Table 4 Continued)

| ID # | Assay | Description | Spacer sequence |
|---|---|---|---|
| g_15 | Genome editing | CasΦ guide targeting the EGFP gene | GGGTCTTTGCTCAGCTTGGA (SEQ ID NO: 217) |
| g_16 | Genome editing | CasΦ guide targeting the EGFP gene | TGGCGGATCTTGAAGTTCAC (SEQ ID NO: 218) |
| g_17 | Genome editing | CasΦ guide targeting the EGFP gene | TGGCTGTTGTAGTTGTACTC (SEQ ID NO: 219) |
| g_18 | Genome editing | CasΦ guide targeting the EGFP gene | TACTCCAGCTTGTGCCCCAG (SEQ ID NO: 220) |
| g_19 | Genome editing | CasΦ guide targeting the EGFP gene | CCGTCCTCCTTGAAGTCGAT (SEQ ID NO: 221) |
| g_20 | Genome editing | CasΦ guide targeting the EGFP gene | CCGTCGTCCTTGAAGAAGAT (SEQ ID NO: 222) |
| g_21 | Genome editing | CasΦ guide targeting the EGFP gene | CCGTAGGTGGCATCGCCCTC (SEQ ID NO: 223) |
| g_22 | Genome editing | CasΦ guide targeting the EGFP gene | CCGGTGGTGCAGATGAACTT (SEQ ID NO: 224) |
| g_23 | Genome editing | CasΦ guide targeting the EGFP gene | AAGAAGATGGTGCGCTCCTG (SEQ ID NO: 225) |
| g_NT | Genome editing | Non-targeting scrambled CasΦ guide | CGTGATGGTCTCGATTGAGT (SEQ ID NO: 105) |

FIG. 36 (Table 5)

| ID # | Assay | Description | Sequence (5'->3') |
|---|---|---|---|
| rPP001 | pre-crRNA processing | Contains from 5'->3': 4 nt of spacer #1, 36 nt repeat #2 (underlined), 20 nt of spacer #2 from the genomic CasΦ-1 CRISPR array | HO-CACAGGAGAGAUCUCAAACGAUUGCUCGAUUAGUCGAGACAGCUGGUAAUGGGAUACCUU (SEQ ID NO: 99) |
| rPP002 | pre-crRNA processing | Contains from 5'->3': 4 nt of spacer #2, 36 nt repeat #3 (underlined), 20 nt of spacer #3 from the genomic CasΦ-2 CRISPR array | HO-UAAUGUCGGAACGCUCAACGAUUGCCCCUCACGAGGGGACUGCCGCCUCCGCGACGCCCA (SEQ ID NO: 100) |
| rPP003 | pre-crRNA processing | Contains from 5'->3': 4 nt of leader, 36 nt repeat #1 (underlined), 20 nt of spacer #1 from the genomic CasΦ-3 CRISPR array | HO-AUUAACCAAAACGACUAUUGAUUGCCCAGUACGCUGGGACUAUGAGCUUAUGUACAUCAA (SEQ ID NO: 101) |
| rGJK008 | pre-crRNA processing | AsCas12a pre-crRNA substrate | HO-GACCUUUUUAAUUUCUACUCUUGUAGAUAAAGUGCUCAUCAUUGGAAAACGU (SEQ ID NO: 230) |
| pPP338 | Spacer tiling cleavage assay | pYTK095 derived plasmid containing a protospacer corresponding to position 1-24 of spacer 2 from the CasΦ-1 CRISPR-array (underlined sequence), as derived from metagenomic analysis. Cognate PAM: 5-TTA (italicized sequence) | circular dsDNA CCAATGCTTAATCAGTGAGGCACCTATCTCAGCGATCTGTCTATTTCGTTCATCCATAGTTGCCTGACTCCCCGTCGTGTAGATAACTACGATACGGGAGGGCTTACCATCTGGCCCCAGTGCTGCAATGATACCGCGGGACCCACGCTCACCGGCTCCAGATTTATCAGCAATAAACCAGCCAGCCGGAAGGGCCGAGCGCAGAAGTGGTCCTGCAACTTTATCCGCCTCCATCCAGTCTATTAATTGTTGCCGGGAAGCTAGAGTAAGTAGTTCGCCAGTTAATAGTTTGCGCA |

FIG. 36 (Cont.) (Table 5 Continued)

| ID # | Assay | Description | Sequence (5'->3') |
|---|---|---|---|
| | | | ACGTTGTTGCCATTGCTACAGGCATCGTGGTGT<br>CACGCTCGTCGTTTGGTATGGCTTCATTCAGCT<br>CCGGTTCCCAACGATCAAGGCGAGTTACATGAT<br>CCCCCATGTTGTGCAAAAAAGCGGTTAGCTCCT<br>TCGGTCCTCCGATCGTTGTCAGAAGTAAGTTGG<br>CCGCAGTGTTATCACTCATGGTTATGGCAGCAC<br>TGCATAATTCTCTTACTGTCATGCCATCCGTAAG<br>ATGCTTTTCTGTGACTGGTGAGTACTCAACCAA<br>GTCATTCTGAGAATAGTGTATGCGGCGACCGAG<br>TTGCTCTTGCCCGGCGTCAATACGGGATAATAC<br>CGCGCCACATAGCAGAACTTTAAAAGTGCTCAT<br>CATTGGAAAACGTTCTTCGGGGCGAAAACTCTC<br>AAGGATCTTACCGCTGTTGAGATCCAGTTCGAT<br>GTAACCCACTCGTGCACCCAACTGATCTTCAGC<br>ATCTTTTACTTTCACCAGCGTTTCTGGGTGAGCA<br>AAAACAGGAAGGCAAAATGCCGCAAAAAAGGGA<br>ATAAGGGCGACACGGAAATGTTGAATACTCATA<br>CTCTTCCTTTTTCAATATTATTGAAGCATTTATCA<br>GGGTTATTGTCTCATGAGCGGATACATATTTGAA<br>TGTATTTAGAAAAATAAACAAATAGGGGTTCCGC<br>GCACATTTCCCCGAAAAGTGCCACCTGTCATGA<br>CCAAAATCCCTTAACGTGAGTTTTCGTTCCACTG<br>AGCGTCAGACCCCGTAGAAAAGATCAAAGGATC<br>TTCTTGAGATCCTTTTTTTCTGCGCGTAATCTGC<br>TGCTTGCAAACAAAAAAACCACCGCTACCAGCG<br>GTGGTTTGTTTGCCGGATCAAGAGCTACCAACT<br>CTTTTTCCGAAGGTAACTGGCTTCAGCAGAGCG<br>CAGATACCAAATACTGTTCTTCTAGTGTAGCCGT<br>AGTTAGGCCACCACTTCAAGAACTCTGTAGCAC<br>CGCCTACATACCTCGCTCTGCTAATCCTGTTAC<br>CAGTGGCTGCTGCCAGTGGCGATAAGTCGTGT<br>CTTACCGGGTTGGACTCAAGACGATAGTTACCG |

FIG. 36 (Cont.)

(Table 5 Continued)

| ID # | Assay | Description | Sequence (5'->3') |
|---|---|---|---|
| | | | GATAAGGCGCAGCGGTCGGGCTGAACGGGGG GTTCGTGCACACAGCCCAGCTTGGAGCGAACG ACCTACACCGAACTGAGATACCTACAGCGTGAG CTATGAGAAAGCGCCACGCTTCCCGAAGGGAG AAAGGCGGACAGGTATCCGGTAAGCGGCAGGG TCGGAACAGGAGAGCGCACGAGGGAGCTTCCA GGGGGAAACGCCTGGTATCTTTATAGTCCTGTC GGGTTTCGCCACCTCTGACTTGAGCGTCGATTT TTGTGATGCTCGTCAGGGGGGCGGAGCCTATG GAAAAACGCCAGCAACGCGGCCTTTTTACGGTT CCTGGCCTTTTGCTGGCCTTTTGCTCACATGTT CTTTCCTGCGTTATCCCCTGATTCTGTGGATAAC CGTGCGGCCGCCCCTTGTAG*TTAAGCTGGTAA* <u>*TGGGATACCTTGTGC*</u>TACAGCGGCCGCGATTAT CAAAAAGGATCTTCACCTAGATCCTTTTAAATTA AAAATGAAGTTTTAAATCAATCTAAAGTATATATG AGTAAACTTGGTCTGACAGTTA (SEQ ID NO: 231) |
| PCR-pPP338 | Spacer tiling cleavage assay | PCR fragment of pYTK095 derived plasmid containing a protospacer corresponding to position 1-24 of spacer 2 from the CasΦ-1 CRISPR-array (underlined sequence), as derived from metagenomic analysis. Cognate PAM: 5-TTA (italicized sequence) | linear dsDNA GCTCTTGCCCGGCGTCAATACGGGATAATACCG CGCCACATAGCAGAACTTTAAAAGTGCTCATCA TTGGAAAACGTTCTTCGGGGCGAAAACTCTCAA GGATCTTACCGCTGTTGAGATCCAGTTCGATGT AACCCACTCGTGCACCCAACTGATCTTCAGCAT CTTTTACTTTCACCAGCGTTTCTGGGTGAGCAAA AACAGGAAGGCAAAATGCCGCAAAAAAGGGAAT AAGGGCGACACGGAAATGTTGAATACTCATACT CTTCCTTTTTCAATATTATTGAAGCATTTATCAGG GTTATTGTCTCATGAGCGGATACATATTTGAATG TATTTAGAAAAATAAACAAATAGGGGTTCCGCG CACATTTCCCCGAAAAGTGCCACCTGTCATGAC |

FIG. 36 (Cont.) (Table 5 Continued)

| ID # | Assay | Description | Sequence (5'->3') |
|---|---|---|---|
| | | | CAAAATCCCTTAACGTGAGTTTTCGTTCCACTGA<br>GCGTCAGACCCCGTAGAAAAGATCAAAGGATCT<br>TCTTGAGATCCTTTTTTTTCTGCGCGTAATCTGCT<br>GCTTGCAAACAAAAAAACCACCGCTACCAGCGG<br>TGGTTTGTTTGCCGGATCAAGAGCTACCAACTC<br>TTTTTCCGAAGGTAACTGGCTTCAGCAGAGCGC<br>AGATACCAAATACTGTTCTTCTAGTGTAGCCGTA<br>GTTAGGCCACCACTTCAAGAACTCTGTAGCACC<br>GCCTACATACCTCGCTCTGCTAATCCTGTTACC<br>AGTGGCTGCTGCCAGTGGCGATAAGTCGTGTCT<br>TACCGGGTTGGACTCAAGACGATAGTTACCGGA<br>TAAGGCGCAGCGGTCGGGCTGAACGGGGGGTT<br>CGTGCACACAGCCCAGCTTGGAGCGAACGACC<br>TACACCGAACTGAGATACCTACAGCGTGAGCTA<br>TGAGAAAGCGCCACGCTTCCCGAAGGGAGAAA<br>GGCGGACAGGTATCCGGTAAGCGGCAGGGTCG<br>GAACAGGAGAGCGCACGAGGGAGCTTCCAGGG<br>GGAAACGCCTGGTATCTTTATAGTCCTGTCGGG<br>TTTCGCCACCTCTGACTTGAGCGTCGATTTTTGT<br>GATGCTCGTCAGGGGGGCGGAGCCTATGGAAA<br>AACGCCAGCAACGCGGCCTTTTTACGGTTCCTG<br>GCCTTTTGCTGGCCTTTTGCTCACATGTTCTTTC<br>CTGCGTTATCCCCTGATTCTGTGGATAACCGTG<br>CGGCCGCCCCTTGTAGTTAAGCTGGTAATGGG<br>ATACCTTGTGCTACAGCGGCCGCGATTATCAAA<br>AAGGATCTTCACCTAGATCCTTTTAAATTAAAAA<br>TGAAGTTTTAAATCAATCTAAAGTATATATGAGT<br>AAACTTGGTCTGACAGTTACCAATGCTTAATCAG<br>TGAGGCACCTATCTCAGCGATCTGTCTATTTCG<br>TTCATCCATAGTTGCCTGACTCCCCGTCGTGTA<br>GATAACTACGATACGGGAGGGCTTACCATCTGG<br>CCCCAGTGCTGCAATGATACCGCGGGACCCAC |

FIG. 36 (Cont.)                                        (Table 5 Continued)

| ID # | Assay | Description | Sequence (5'->3') |
|---|---|---|---|
| | | | GCTCACCGGCTCCAGATTTATCAGCAATAAACC<br>AGCCAGCCGGAAGGGCCGAGCGCAGAAGTGGT<br>CCTGCAACTTTATCCGCCTCCATCCAGTCTATTA<br>ATTGTTGCCGGGAAGCTAGAGTAAGTAGTTCGC<br>CAGTTAATAGTTTGCGCAACGTTGTTGCCATTG<br>CTACAGGCATCGTGGTGTCACGCTCGTCGTTTG<br>GTATGGCTTCATTCAGCTCCGGTTCCCAACGAT<br>CAAGGCGAGTTACATGATCCCCCATGTTGTGCA<br>AAAAAGCGGTTAGCTCCTTCGGTCCTCCGATCG<br>TTGTCAGAAGTAAGTTGGCCGCAGTGTTATCAC<br>TCATGGTTATGGCAGCACTGCATAATTCTCTTAC<br>TGTCATGCCATCCGTAAGATGCTTTTCTGTGACT<br>GGTGAGTACTCAACCAAGTCATTCTGAGAATAG<br>TGTATGCGGCG (SEQ ID NO: 232) |
| PCR-pPP341 | Spacer tiling cleavage assay | PCR fragment of pYTK095 derived plasmid containing a protospacer corresponding to position 1-24 of spacer 2 from the CasΦ-1 CRISPR-array (underlined sequence), as derived from metagenomic analysis. Non-cognate PAM: 5'-CCA (italicized sequence) | linear dsDNA<br>GCTCTTGCCCGGCGTCAATACGGGATAATACCG<br>CGCCACATAGCAGAACTTTAAAAGTGCTCATCA<br>TTGGAAAACGTTCTTCGGGGCGAAAACTCTCAA<br>GGATCTTACCGCTGTTGAGATCCAGTTCGATGT<br>AACCCACTCGTGCACCCAACTGATCTTCAGCAT<br>CTTTTACTTTCACCAGCGTTTCTGGGTGAGCAAA<br>AACAGGAAGGCAAAATGCCGCAAAAAAGGGAAT<br>AAGGGCGACACGGAAATGTTGAATACTCATACT<br>CTTCCTTTTTCAATATTATTGAAGCATTTATCAGG<br>GTTATTGTCTCATGAGCGGATACATATTTGAATG<br>TATTTAGAAAAATAAACAAATAGGGGTTCCGCG<br>CACATTTCCCCGAAAAGTGCCACCTGTCATGAC<br>CAAAATCCCTTAACGTGAGTTTTCGTTCCACTGA<br>GCGTCAGACCCCGTAGAAAAGATCAAAGGATCT<br>TCTTGAGATCCTTTTTTTCTGCGCGTAATCTGCT<br>GCTTGCAAACAAAAAAACCACCGCTACCAGCGG |

FIG. 36 (Cont.) (Table 5 Continued)

| ID # | Assay | Description | Sequence (5'→3') |
|---|---|---|---|
| | | | TGGTTTGTTTGCCGGATCAAGAGCTACCAACTC<br>TTTTTCCGAAGGTAACTGGCTTCAGCAGAGCGC<br>AGATACCAAATACTGTTCTTCTAGTGTAGCCGTA<br>GTTAGGCCACCACTTCAAGAACTCTGTAGCACC<br>GCCTACATACCTCGCTCTGCTAATCCTGTTACC<br>AGTGGCTGCTGCCAGTGGCGATAAGTCGTGTCT<br>TACCGGGTTGGACTCAAGACGATAGTTACCGGA<br>TAAGGCGCAGCGGTCGGGCTGAACGGGGGGTT<br>CGTGCACACAGCCCAGCTTGGAGCGAACGACC<br>TACACCGAACTGAGATACCTACAGCGTGAGCTA<br>TGAGAAAGCGCCACGCTTCCCGAAGGGAGAAA<br>GGCGGACAGGTATCCGGTAAGCGGCAGGGTCG<br>GAACAGGAGAGCGCACGAGGGAGCTTCCAGGG<br>GGAAACGCCTGGTATCTTTATAGTCCTGTCGGG<br>TTTCGCCACCTCTGACTTGAGCGTCGATTTTTGT<br>GATGCTCGTCAGGGGGGCGGAGCCTATGGAAA<br>AACGCCAGCAACGCGGCCTTTTTACGGTTCCTG<br>GCCTTTTGCTGGCCTTTTGCTCACATGTTCTTTC<br>CTGCGTTATCCCCTGATTCTGTGGATAACCGTG<br>CGGCCGCCCCTTGTAG<u>CCAAGCTGGTAATGGG</u><br><u>ATACCTTGTGC</u>TACAGCGGCCGCGATTATCAAA<br>AAGGATCTTCACCTAGATCCTTTTAAATTAAAAA<br>TGAAGTTTTAAATCAATCTAAAGTATATATGAGT<br>AAACTTGGTCTGACAGTTACCAATGCTTAATCAG<br>TGAGGCACCTATCTCAGCGATCTGTCTATTTCG<br>TTCATCCATAGTTGCCTGACTCCCCGTCGTGTA<br>GATAACTACGATACGGGAGGGCTTACCATCTGG<br>CCCCAGTGCTGCAATGATACCGCGGGACCCAC<br>GCTCACCGGCTCCAGATTTATCAGCAATAAACC<br>AGCCAGCCGGAAGGGCCGAGCGCAGAAGTGGT<br>CCTGCAACTTTATCCGCCTCCATCCAGTCTATTA<br>ATTGTTGCCGGGAAGCTAGAGTAAGTAGTTCGC |

FIG. 36 (Cont.) (Table 5 Continued)

| ID # | Assay | Description | Sequence (5'->3') |
|---|---|---|---|
| | | | CAGTTAATAGTTTGCGCAACGTTGTTGCCATTGCTACAGGCATCGTGGTGTCACGCTCGTCGTTTGGTATGGCTTCATTCAGCTCCGGTTCCCAACGATCAAGGCGAGTTACATGATCCCCCATGTTGTGCAAAAAGCGGTTAGCTCCTTCGGTCCTCCGATCGTTGTCAGAAGTAAGTTGGCCGCAGTGTTATCACTCATGGTTATGGCAGCACTGCATAATTCTCTTACTGTCATGCCATCCGTAAGATGCTTTTCTGTGACTGGTGAGTACTCAACCAAGTCATTCTGAGAATAGTGTATGCGGCG (SEQ ID NO: 233) |
| oPP510 | radiolabeled cleavage assay | DNA non-target strand for CasΦ-1 and CasΦ-2 cleavage assays | HO-CGGCCGCCCCTTGTAGTTAAGCTGGTAATGGGATACCTTGTGCTACAGCGGCCGCG (SEQ ID NO: 234) |
| oPP511 | radiolabeled cleavage assay | DNA target strand for CasΦ-1 and CasΦ-2 cleavage assays | HO-CGCGGCCGCTGTAGCACAAGGTATCCCATTACCAGCTTAACTACAAGGGGCGGCCG (SEQ ID NO: 235) |
| oPP596 | radiolabeled cleavage assay | DNA non-target strand for CasΦ-3 cleavage assays | HO-CGGCCGCCCCTTGTAATTCAGCTGGTAATGGGATACCTTGTGCTACAGCGGCCGCG (SEQ ID NO: 236) |
| oPP597 | radiolabeled cleavage assay | DNA target strand for CasΦ-3 cleavage assays | HO-CGCGGCCGCTGTAGCACAAGGTATCCCATTACCAGCTGAATTACAAGGGGCGGCCG (SEQ ID NO: 237) |

FIG. 36 (Cont.)   (Table 5 Continued)

| ID # | Assay | Description | Sequence (5'→3') |
|---|---|---|---|
| rPP015 | radiolabeled cleavage assay | RNA target strand for cleavage assays | HO-CGCUGUAGCACAAGGUAUCCCAUUACCAGCUUAACUACAAG (SEQ ID NO: 238) |
| dGJK001 | radiolabeled cleavage assay | Trans cleavage DNA substrate | HO-GTGGCCGTTTAAAAGTGCTCATCATTGGAAAACGTAGGATGGGCACCA (SEQ ID NO: 239) |
| rGJK118 | radiolabeled cleavage assay | Trans cleavage RNA substrate | HO-AGUAUUUAAUCGUUGCAAGAGGCGCUGCGUUU (SEQ ID NO: 240) |

FIG. 37 (Table 6)

| ID # | Assay | Description | Sequence (5'->3') |
|---|---|---|---|
| rPP007 | Spacer tiling cleavage assay | Contains from 5'->3': 25 nt of 3'-repeat fraction (underlined) from the genomic CasΦ-2 CRISPR array. | HO-<u>CAACGAUUGCCCCUCACGAGGGGAC</u> |
| rPP008 | Spacer tiling cleavage assay | Contains from 5'->3': 25 nt of 3'-repeat fraction (underlined) from the genomic CasΦ-2 CRISPR array. 12 nt of spacer #2 from the genomic CasΦ-1 CRISPR array | HO-<u>CAACGAUUGCCCCUCACGAGGGGAC</u>AGCUGGUAAUGG |
| rPP009 | Spacer tiling cleavage assay | Contains from 5'->3': 25 nt of 3'-repeat fraction (underlined) from the genomic CasΦ-2 CRISPR array. 14 nt of spacer #2 from the genomic CasΦ-1 CRISPR array | HO-<u>CAACGAUUGCCCCUCACGAGGGGAC</u>AGCUGGUAAUGGGA |
| rPP010 | Spacer tiling cleavage assay | Contains from 5'->3': 25 nt of 3'-repeat fraction (underlined) from the genomic CasΦ-2 CRISPR array. 16 nt of spacer #2 from the genomic CasΦ-1 CRISPR array | HO-<u>CAACGAUUGCCCCUCACGAGGGGAC</u>AGCUGGUAAUGGGAUA |
| rPP011 | Spacer tiling and radiolabeled cleavage assay | Contains from 5'->3': 25 nt of 3'-repeat fraction (underlined) from the genomic CasΦ-2 CRISPR array. 18 nt of spacer #2 from the genomic CasΦ-1 CRISPR array | HO-<u>CAACGAUUGCCCCUCACGAGGGGAC</u>AGCUGGUAAUGGGAUACC |
| rPP012 | Spacer tiling cleavage assay | Contains from 5'->3': 25 nt of 3'-repeat fraction (underlined) from the genomic CasΦ-2 CRISPR array. 20 nt of spacer #2 from the genomic CasΦ-1 CRISPR array | HO-<u>CAACGAUUGCCCCUCACGAGGGGAC</u>AGCUGGUAAUGGGAUACCUU |

FIG. 37 (Cont.) (Table 6 Continued)

| ID # | Assay | Description | Sequence (5'->3') |
|---|---|---|---|
| rPP013 | Spacer tiling cleavage assay | Contains from 5'->3': 25 nt of 3'-repeat fraction (underlined) from the genomic CasΦ-2 CRISPR array. 22 nt of spacer #2 from the genomic CasΦ-1 CRISPR array | HO-<u>CAACGAUUGCCCCUCACGAGGGGAC</u>AGCUGGUAAUGGGAUACCUUGU |
| rPP014 | Spacer tiling cleavage assay | Contains from 5'->3': 25 nt of 3'-repeat fraction (underlined) from the genomic CasΦ-2 CRISPR array. 24 nt of spacer #2 from the genomic CasΦ-1 CRISPR array | HO-<u>CAACGAUUGCCCCUCACGAGGGGAC</u>AGCUGGUAAUGGGAUACCUUGUGC |
| rPP016 | radiolabeled cleavage assay | Contains from 5'->3': 25 nt of 3'-repeat fraction (underlined) from the genomic CasΦ-1 CRISPR array. 18 nt of spacer #2 from the genomic CasΦ-1 CRISPR array | HO-<u>AAACGAUUGCUCGAUUAGUCGAGAC</u>AGCUGGUAAUGGGAUACC |
| rPP017 | radiolabeled cleavage assay | Contains from 5'->3': 25 nt of 3'-repeat fraction (underlined) from the genomic CasΦ-3 CRISPR array. 18 nt of spacer #2 from the genomic CasΦ-1 CRISPR array | HO-<u>UAUUGAUUGCCCAGUACGCUGGGAC</u>AGCUGGUAAUGGGAUACC |

SEQUENCE LISTING

```
<160> NUMBER OF SEQ ID NOS: 250

<210> SEQ ID NO 1
<211> LENGTH: 36
<212> TYPE: DNA
<213> ORGANISM: Artificial Sequence
<220> FEATURE:
<223> OTHER INFORMATION: Synthetic sequence

<400> SEQUENCE: 1
gtctcgacta atcgagcaat cgtttgagat ctctcc                              36

<210> SEQ ID NO 2
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 2
nnnnnnnnnn nnnnnnnnnn nnnnnnnnnn gtctcgacta atcgagcaat cgtttgagat    60
ctctcc                                                               66

<210> SEQ ID NO 3
<211> LENGTH: 36
<212> TYPE: DNA
<213> ORGANISM: Artificial Sequence
<220> FEATURE:
<223> OTHER INFORMATION: Synthetic sequence
```

```
<400> SEQUENCE: 3
gtcggaacgc tcaacgattg cccctcacga ggggac                                 36

<210> SEQ ID NO 4
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 4
nnnnnnnnnn nnnnnnnnnn nnnnnnnnnn gtcggaacgc tcaacgattg cccctcacga       60
ggggac                                                                  66

<210> SEQ ID NO 5
<211> LENGTH: 36
<212> TYPE: DNA
<213> ORGANISM: Artificial Sequence
<220> FEATURE:
<223> OTHER INFORMATION: Synthetic sequence

<400> SEQUENCE: 5
gtcccagcgt actgggcaat caatagtcgt tttggt                                 36

<210> SEQ ID NO 6
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 6
nnnnnnnnnn nnnnnnnnnn nnnnnnnnnn gtcccagcgt actgggcaat caatagtcgt       60
tttggt                                                                  66

<210> SEQ ID NO 7
<211> LENGTH: 37
<212> TYPE: DNA
<213> ORGANISM: Artificial Sequence
<220> FEATURE:
<223> OTHER INFORMATION: Synthetic sequence

<400> SEQUENCE: 7
ggatccaatc cttttttgatt gcccaattcg ttgggac                                37

<210> SEQ ID NO 8
<211> LENGTH: 67
<212> TYPE: DNA
<213> ORGANISM: Artificial Sequence
<220> FEATURE:
<223> OTHER INFORMATION: Synthetic sequence
```

```
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 8
nnnnnnnnnn nnnnnnnnnn nnnnnnnnnn ggatccaatc cttttttgatt gcccaattcg    60 ttgggac                                                               67

<210> SEQ ID NO 9
<211> LENGTH: 36
<212> TYPE: DNA
<213> ORGANISM: Artificial Sequence
<220> FEATURE:
<223> OTHER INFORMATION: Synthetic sequence

<400> SEQUENCE: 9
ggatctgagg atcattattg ctcgttacga cgagac                               36

<210> SEQ ID NO 10
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 10
nnnnnnnnnn nnnnnnnnnn nnnnnnnnnn ggatctgagg atcattattg ctcgttacga    60
cgagac                                                                66

<210> SEQ ID NO 11
<211> LENGTH: 36
<212> TYPE: DNA
<213> ORGANISM: Artificial Sequence
<220> FEATURE:
<223> OTHER INFORMATION: Synthetic sequence

<400> SEQUENCE: 11
gtctcgtcgt aacgagcaat aatgatcctc agatcc                               36

<210> SEQ ID NO 12
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 12
nnnnnnnnnn nnnnnnnnnn nnnnnnnnnn gtctcgtcgt aacgagcaat aatgatcctc    60
agatcc                                                                66
```

-continued

```
<210> SEQ ID NO 13
<211> LENGTH: 36
<212> TYPE: DNA
<213> ORGANISM: Artificial Sequence
<220> FEATURE:
<223> OTHER INFORMATION: Synthetic sequence

<400> SEQUENCE: 13
gtctcagcgt actgagcaat caaaaggttt cgcagg                                36

<210> SEQ ID NO 14
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 14
nnnnnnnnnn nnnnnnnnnn nnnnnnnnnn gtctcagcgt actgagcaat caaaaggttt     60
cgcagg                                                                 66

<210> SEQ ID NO 15
<211> LENGTH: 36
<212> TYPE: DNA
<213> ORGANISM: Artificial Sequence
<220> FEATURE:
<223> OTHER INFORMATION: Synthetic sequence

<400> SEQUENCE: 15
gtctcctcgt aaggagcaat ctattagtct tgaaag                                36

<210> SEQ ID NO 16
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 16
nnnnnnnnnn nnnnnnnnnn nnnnnnnnnn gtctcctcgt aaggagcaat ctattagtct     60
tgaaag                                                                 66

<210> SEQ ID NO 17
<211> LENGTH: 36
<212> TYPE: DNA
<213> ORGANISM: Artificial Sequence
<220> FEATURE:
<223> OTHER INFORMATION: Synthetic sequence

<400> SEQUENCE: 17
gtctcggcgc accgagcaat cagcgaggtc ttctac                                36
```

```
<210> SEQ ID NO 18
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 18
nnnnnnnnnn nnnnnnnnnn nnnnnnnnnn gtctcggcgc accgagcaat cagcgaggtc    60
ttctac                                                                66

<210> SEQ ID NO 19
<211> LENGTH: 37
<212> TYPE: DNA
<213> ORGANISM: Artificial Sequence
<220> FEATURE:
<223> OTHER INFORMATION: Synthetic sequence

<400> SEQUENCE: 19
gtcccaacga attgggcaat caaaaaggat tggatcc                              37

<210> SEQ ID NO 20
<211> LENGTH: 67
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 20
nnnnnnnnnn nnnnnnnnnn nnnnnnnnnn gtcccaacga attgggcaat caaaaaggat    60
tggatcc                                                               67

<210> SEQ ID NO 21
<211> LENGTH: 36
<212> TYPE: DNA
<213> ORGANISM: Artificial Sequence
<220> FEATURE:
<223> OTHER INFORMATION: Synthetic sequence

<400> SEQUENCE: 21
gtcgcggcgt accgcgcaat gagagtctgt tgccat                               36

<210> SEQ ID NO 22
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.
```

```
<400> SEQUENCE: 22
nnnnnnnnnn nnnnnnnnnn nnnnnnnnnn gtcgcggcgt accgcgcaat gagagtctgt      60
tgccat                                                                 66

<210> SEQ ID NO 23
<211> LENGTH: 36
<212> TYPE: DNA
<213> ORGANISM: Artificial Sequence
<220> FEATURE:
<223> OTHER INFORMATION: Synthetic sequence

<400> SEQUENCE: 23
accaaaacga ctattgattg cccagtacgc tgggac                                36

<210> SEQ ID NO 24
<211> LENGTH: 66
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(30)
<223> OTHER INFORMATION: The nucleotides at positions 1 to 30 may either
      be present or absent such that the number of nucleotides ranges
      from 15 to 30, and each n is a, c, t, or g.

<400> SEQUENCE: 24
nnnnnnnnnn nnnnnnnnnn nnnnnnnnnn accaaaacga ctattgattg cccagtacgc      60
tgggac                                                                 66

<210> SEQ ID NO 25
<211> LENGTH: 84
<212> TYPE: PRT
<213> ORGANISM: Artificial Sequence
<220> FEATURE:
<223> OTHER INFORMATION: Synthetic sequence

<400> SEQUENCE: 25

Met Ala Ser Met Ile Ser Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Ser Arg Ala

<210> SEQ ID NO 26
<211> LENGTH: 57
<212> TYPE: PRT
<213> ORGANISM: Artificial Sequence
<220> FEATURE:
<223> OTHER INFORMATION: Synthetic sequence
```

<400> SEQUENCE: 26

Met Ala Ser Met Ile Ser Ser Ala Val Thr Thr Val Ser Arg Ala
1               5                   10                  15

Ser Arg Gly Gln Ser Ala Ala Met Ala Pro Phe Gly Gly Leu Lys Ser
            20                  25                  30

Met Thr Gly Phe Pro Val Arg Lys Val Asn Thr Asp Ile Thr Ser Ile
        35                  40                  45

Thr Ser Asn Gly Gly Arg Val Lys Ser
    50                  55

<210> SEQ ID NO 27
<211> LENGTH: 85
<212> TYPE: PRT
<213> ORGANISM: Artificial Sequence
<220> FEATURE:
<223> OTHER INFORMATION: Synthetic sequence

<400> SEQUENCE: 27

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
    50                  55                  60

Lys Lys Phe Glu Thr Leu Ser Tyr Leu Pro Asp Leu Thr Asp Ser Gly
65                  70                  75                  80

Gly Arg Val Asn Cys
                85

<210> SEQ ID NO 28
<211> LENGTH: 76
<212> TYPE: PRT
<213> ORGANISM: Artificial Sequence
<220> FEATURE:
<223> OTHER INFORMATION: Synthetic sequence

<400> SEQUENCE: 28

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 29
<211> LENGTH: 76
<212> TYPE: PRT
<213> ORGANISM: Artificial Sequence
<220> FEATURE:
<223> OTHER INFORMATION: Synthetic sequence

```
<400> SEQUENCE: 29

Met Ala Gln Val Ser Arg Ile Cys Asn Gly Val Trp Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 30
<211> LENGTH: 72
<212> TYPE: PRT
<213> ORGANISM: Artificial Sequence
<220> FEATURE:
<223> OTHER INFORMATION: Synthetic sequence

<400> SEQUENCE: 30

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Phe Leu
                20                  25                  30

Val Phe Gly Ser Lys Lys Leu Lys Asn Ser Ala Asn Ser Met Leu Val
            35                  40                  45

Leu Lys Lys Asp Ser Ile Phe Met Gln Leu Phe Cys Ser Phe Arg Ile
    50                  55                  60

Ser Ala Ser Val Ala Thr Ala Cys
65                  70

<210> SEQ ID NO 31
<211> LENGTH: 69
<212> TYPE: PRT
<213> ORGANISM: Artificial Sequence
<220> FEATURE:
<223> OTHER INFORMATION: Synthetic sequence

<400> SEQUENCE: 31

Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
                20                  25                  30

Arg Asn Pro Ala Asp Ala Ala Leu Gly Met Arg Thr Val Gly Ala Ser
            35                  40                  45

Ala Ala Pro Lys Gln Ser Arg Lys Pro His Arg Phe Asp Arg Arg Cys
    50                  55                  60

Leu Ser Met Val Val
65

<210> SEQ ID NO 32
<211> LENGTH: 77
<212> TYPE: PRT
<213> ORGANISM: Artificial Sequence
<220> FEATURE:
<223> OTHER INFORMATION: Synthetic sequence
```

```
<400> SEQUENCE: 32

Met Ala Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Val Cys
65                  70                  75

<210> SEQ ID NO 33
<211> LENGTH: 57
<212> TYPE: PRT
<213> ORGANISM: Artificial Sequence
<220> FEATURE:
<223> OTHER INFORMATION: Synthetic sequence

<400> SEQUENCE: 33

Met Ala Ser Ser Val Leu Ser Ser Ala Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 34
<211> LENGTH: 65
<212> TYPE: PRT
<213> ORGANISM: Artificial Sequence
<220> FEATURE:
<223> OTHER INFORMATION: Synthetic sequence

<400> SEQUENCE: 34

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Thr Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala
65

<210> SEQ ID NO 35
<211> LENGTH: 72
<212> TYPE: PRT
<213> ORGANISM: Artificial Sequence
<220> FEATURE:
<223> OTHER INFORMATION: Synthetic sequence

<400> SEQUENCE: 35

Met Gly Ala Ala Ala Thr Ser Met Gln Ser Leu Lys Phe Ser Asn Arg
1               5                   10                  15

Leu Val Pro Pro Ser Arg Arg Leu Ser Pro Val Pro Asn Asn Val Thr
            20                  25                  30
```

```
Cys Asn Asn Leu Pro Lys Ser Ala Ala Pro Val Arg Thr Val Lys Cys
        35                  40                  45

Cys Ala Ser Ser Trp Asn Ser Thr Ile Asn Gly Ala Ala Ala Thr Thr
    50                  55                  60

Asn Gly Ala Ser Ala Ala Ser Ser
65                  70

<210> SEQ ID NO 36
<211> LENGTH: 20
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (4)..(4)
<223> OTHER INFORMATION: The amino acid at position 4 is selected from
      lysine, histidine and arginine.
<220> FEATURE:
<221> NAME/KEY: MISC_FEATURE
<222> LOCATION: (8)..(8)
<223> OTHER INFORMATION: The amino acid at position 8 is selected from
      lysine, histidine and arginine.
<220> FEATURE:
<221> NAME/KEY: MISC_FEATURE
<222> LOCATION: (11)..(11)
<223> OTHER INFORMATION: The amino acid at position 11 is selected from
      lysine, histidine and arginine.
<220> FEATURE:
<221> NAME/KEY: MISC_FEATURE
<222> LOCATION: (15)..(15)
<223> OTHER INFORMATION: The amino acid at position 15 is selected from
      lysine, histidine and arginine.
<220> FEATURE:
<221> NAME/KEY: MISC_FEATURE
<222> LOCATION: (19)..(19)
<223> OTHER INFORMATION: The amino acid at position 19 is selected from
      lysine, histidine and arginine.

<400> SEQUENCE: 36

Gly Leu Phe Xaa Ala Leu Leu Xaa Leu Leu Xaa Ser Leu Trp Xaa Leu
1               5                   10                  15

Leu Leu Xaa Ala
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic sequence

<400> SEQUENCE: 37

Gly Leu Phe His Ala Leu Leu His Leu Leu His Ser Leu Trp His Leu
1               5                   10                  15

Leu Leu His Ala
            20

<210> SEQ ID NO 38
<211> LENGTH: 167
<212> TYPE: PRT
<213> ORGANISM: Artificial Sequence
<220> FEATURE:
<223> OTHER INFORMATION: Synthetic sequence
```

<400> SEQUENCE: 38

Met Ser Glu Val Glu Phe Ser His Glu Tyr Trp Met Arg His Ala Leu
1               5                   10                  15

Thr Leu Ala Lys Arg Ala Trp Asp Glu Arg Glu Val Pro Val Gly Ala
            20                  25                  30

Val Leu Val His Asn Asn Arg Val Ile Gly Glu Gly Trp Asn Arg Pro
        35                  40                  45

Ile Gly Arg His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Leu Glu Pro Cys Val Met Cys Ala Gly Ala Met Ile His
                85                  90                  95

Ser Arg Ile Gly Arg Val Val Phe Gly Ala Arg Asp Ala Lys Thr Gly
            100                 105                 110

Ala Ala Gly Ser Leu Met Asp Val Leu His His Pro Gly Met Asn His
        115                 120                 125

Arg Val Glu Ile Thr Glu Gly Ile Leu Ala Asp Glu Cys Ala Ala Leu
    130                 135                 140

Leu Ser Asp Phe Phe Arg Met Arg Gln Glu Ile Lys Ala Gln Lys
145                 150                 155                 160

Lys Ala Gln Ser Ser Thr Asp
                165

<210> SEQ ID NO 39
<211> LENGTH: 178
<212> TYPE: PRT
<213> ORGANISM: Artificial Sequence
<220> FEATURE:
<223> OTHER INFORMATION: Synthetic sequence

<400> SEQUENCE: 39

Met Arg Arg Ala Phe Ile Thr Gly Val Phe Leu Ser Glu Val Glu
1               5                   10                  15

Phe Ser His Glu Tyr Trp Met Arg His Ala Leu Thr Leu Ala Lys Arg
            20                  25                  30

Ala Trp Asp Glu Arg Glu Val Pro Val Gly Ala Val Leu Val His Asn
        35                  40                  45

Asn Arg Val Ile Gly Glu Gly Trp Asn Arg Pro Ile Gly Arg His Asp
    50                  55                  60

Pro Thr Ala His Ala Glu Ile Met Ala Leu Arg Gln Gly Gly Leu Val
65                  70                  75                  80

Met Gln Asn Tyr Arg Leu Ile Asp Ala Thr Leu Tyr Val Thr Leu Glu
                85                  90                  95

Pro Cys Val Met Cys Ala Gly Ala Met Ile His Ser Arg Ile Gly Arg
            100                 105                 110

Val Val Phe Gly Ala Arg Asp Ala Lys Thr Gly Ala Ala Gly Ser Leu
        115                 120                 125

Met Asp Val Leu His His Pro Gly Met Asn His Arg Val Glu Ile Thr
    130                 135                 140

Glu Gly Ile Leu Ala Asp Glu Cys Ala Ala Leu Leu Ser Asp Phe Phe
145                 150                 155                 160

Arg Met Arg Arg Gln Glu Ile Lys Ala Gln Lys Lys Ala Gln Ser Ser
                165                 170                 175

Thr Asp

```
<210> SEQ ID NO 40
<211> LENGTH: 160
<212> TYPE: PRT
<213> ORGANISM: Artificial Sequence
<220> FEATURE:
<223> OTHER INFORMATION: Synthetic sequence

<400> SEQUENCE: 40

Met Gly Ser His Met Thr Asn Asp Ile Tyr Phe Met Thr Leu Ala Ile
1               5                   10                  15

Glu Glu Ala Lys Lys Ala Ala Gln Leu Gly Glu Val Pro Ile Gly Ala
                20                  25                  30

Ile Ile Thr Lys Asp Asp Glu Val Ile Ala Arg Ala His Asn Leu Arg
            35                  40                  45

Glu Thr Leu Gln Gln Pro Thr Ala His Ala Glu His Ile Ala Ile Glu
        50                  55                  60

Arg Ala Ala Lys Val Leu Gly Ser Trp Arg Leu Glu Gly Cys Thr Leu
65                  70                  75                  80

Tyr Val Thr Leu Glu Pro Cys Val Met Cys Ala Gly Thr Ile Val Met
                85                  90                  95

Ser Arg Ile Pro Arg Val Val Tyr Gly Ala Asp Asp Pro Lys Gly Gly
                100                 105                 110

Cys Ser Gly Ser Leu Met Asn Leu Leu Gln Gln Ser Asn Phe Asn His
            115                 120                 125

Arg Ala Ile Val Asp Lys Gly Val Leu Lys Glu Ala Cys Ser Thr Leu
        130                 135                 140

Leu Thr Thr Phe Phe Lys Asn Leu Arg Ala Asn Lys Lys Ser Thr Asn
145                 150                 155                 160

<210> SEQ ID NO 41
<211> LENGTH: 161
<212> TYPE: PRT
<213> ORGANISM: Artificial Sequence
<220> FEATURE:
<223> OTHER INFORMATION: Synthetic sequence

<400> SEQUENCE: 41

Met Thr Gln Asp Glu Leu Tyr Met Lys Glu Ala Ile Lys Glu Ala Lys
1               5                   10                  15

Lys Ala Glu Glu Lys Gly Glu Val Pro Ile Gly Ala Val Leu Val Ile
                20                  25                  30

Asn Gly Glu Ile Ile Ala Arg Ala His Asn Leu Arg Glu Thr Glu Gln
            35                  40                  45

Arg Ser Ile Ala His Ala Glu Met Leu Val Ile Asp Glu Ala Cys Lys
        50                  55                  60

Ala Leu Gly Thr Trp Arg Leu Glu Gly Ala Thr Leu Tyr Val Thr Leu
65                  70                  75                  80

Glu Pro Cys Pro Met Cys Ala Gly Ala Val Leu Ser Arg Val Glu
                85                  90                  95

Lys Val Val Phe Gly Ala Phe Asp Pro Lys Gly Cys Ser Gly Thr
                100                 105                 110

Leu Met Asn Leu Leu Gln Glu Glu Arg Phe Asn His Gln Ala Glu Val
            115                 120                 125

Val Ser Gly Val Leu Glu Glu Glu Cys Gly Gly Met Leu Ser Ala Phe
        130                 135                 140
```

```
Phe Arg Glu Leu Arg Lys Lys Lys Ala Ala Arg Lys Asn Leu Ser
145                 150                 155                 160

Glu
```

<210> SEQ ID NO 42
<211> LENGTH: 183
<212> TYPE: PRT
<213> ORGANISM: Artificial Sequence
<220> FEATURE:
<223> OTHER INFORMATION: Synthetic sequence

<400> SEQUENCE: 42

```
Met Pro Pro Ala Phe Ile Thr Gly Val Thr Ser Leu Ser Asp Val Glu
1               5                   10                  15

Leu Asp His Glu Tyr Trp Met Arg His Ala Leu Thr Leu Ala Lys Arg
                20                  25                  30

Ala Trp Asp Glu Arg Glu Val Pro Val Gly Ala Val Leu Val His Asn
            35                  40                  45

His Arg Val Ile Gly Glu Gly Trp Asn Arg Pro Ile Gly Arg His Asp
    50                  55                  60

Pro Thr Ala His Ala Glu Ile Met Ala Leu Arg Gln Gly Gly Leu Val
65                  70                  75                  80

Leu Gln Asn Tyr Arg Leu Leu Asp Thr Thr Leu Tyr Val Thr Leu Glu
                85                  90                  95

Pro Cys Val Met Cys Ala Gly Ala Met Val His Ser Arg Ile Gly Arg
            100                 105                 110

Val Val Phe Gly Ala Arg Asp Ala Lys Thr Gly Ala Ala Gly Ser Leu
        115                 120                 125

Ile Asp Val Leu His His Pro Gly Met Asn His Arg Val Glu Ile Ile
130                 135                 140

Glu Gly Val Leu Arg Asp Glu Cys Ala Thr Leu Leu Ser Asp Phe Phe
145                 150                 155                 160

Arg Met Arg Arg Gln Glu Ile Lys Ala Leu Lys Lys Ala Asp Arg Ala
                165                 170                 175

Glu Gly Ala Gly Pro Ala Val
            180
```

<210> SEQ ID NO 43
<211> LENGTH: 164
<212> TYPE: PRT
<213> ORGANISM: Artificial Sequence
<220> FEATURE:
<223> OTHER INFORMATION: Synthetic sequence

<400> SEQUENCE: 43

```
Met Asp Glu Tyr Trp Met Gln Val Ala Met Gln Met Ala Glu Lys Ala
1               5                   10                  15

Glu Ala Ala Gly Glu Val Pro Val Gly Ala Val Leu Val Lys Asp Gly
                20                  25                  30

Gln Gln Ile Ala Thr Gly Tyr Asn Leu Ser Ile Ser Gln His Asp Pro
            35                  40                  45

Thr Ala His Ala Glu Ile Leu Cys Leu Arg Ser Ala Gly Lys Lys Leu
    50                  55                  60

Glu Asn Tyr Arg Leu Leu Asp Ala Thr Leu Tyr Ile Thr Leu Glu Pro
65                  70                  75                  80

Cys Ala Met Cys Ala Gly Ala Met Val His Ser Arg Ile Ala Arg Val
                85                  90                  95
```

```
Val Tyr Gly Ala Arg Asp Glu Lys Thr Gly Ala Ala Gly Thr Val Val
            100                 105                 110

Asn Leu Leu Gln His Pro Ala Phe Asn His Gln Val Glu Val Thr Ser
        115                 120                 125

Gly Val Leu Ala Glu Ala Cys Ser Ala Gln Leu Ser Arg Phe Phe Lys
    130                 135                 140

Arg Arg Arg Asp Glu Lys Lys Ala Leu Lys Leu Ala Gln Arg Ala Gln
145                 150                 155                 160

Gln Gly Ile Glu

<210> SEQ ID NO 44
<211> LENGTH: 173
<212> TYPE: PRT
<213> ORGANISM: Artificial Sequence
<220> FEATURE:
<223> OTHER INFORMATION: Synthetic sequence

<400> SEQUENCE: 44

Met Asp Ala Ala Lys Val Arg Ser Glu Phe Asp Glu Lys Met Met Arg
1               5                   10                  15

Tyr Ala Leu Glu Leu Ala Asp Lys Ala Glu Ala Leu Gly Glu Ile Pro
            20                  25                  30

Val Gly Ala Val Leu Val Asp Asp Ala Arg Asn Ile Ile Gly Glu Gly
        35                  40                  45

Trp Asn Leu Ser Ile Val Gln Ser Asp Pro Thr Ala His Ala Glu Ile
    50                  55                  60

Ile Ala Leu Arg Asn Gly Ala Lys Asn Ile Gln Asn Tyr Arg Leu Leu
65                  70                  75                  80

Asn Ser Thr Leu Tyr Val Thr Leu Glu Pro Cys Thr Met Cys Ala Gly
            85                  90                  95

Ala Ile Leu His Ser Arg Ile Lys Arg Leu Val Phe Gly Ala Ser Asp
            100                 105                 110

Tyr Lys Thr Gly Ala Ile Gly Ser Arg Phe His Phe Asp Asp Tyr
        115                 120                 125

Lys Met Asn His Thr Leu Glu Ile Thr Ser Gly Val Leu Ala Glu Glu
    130                 135                 140

Cys Ser Gln Lys Leu Ser Thr Phe Phe Gln Lys Arg Arg Glu Glu Lys
145                 150                 155                 160

Lys Ile Glu Lys Ala Leu Leu Lys Ser Leu Ser Asp Lys
                165                 170

<210> SEQ ID NO 45
<211> LENGTH: 161
<212> TYPE: PRT
<213> ORGANISM: Artificial Sequence
<220> FEATURE:
<223> OTHER INFORMATION: Synthetic sequence

<400> SEQUENCE: 45

Met Arg Thr Asp Glu Ser Glu Asp Gln Asp His Arg Met Met Arg Leu
1               5                   10                  15

Ala Leu Asp Ala Ala Arg Ala Ala Ala Glu Ala Gly Glu Thr Pro Val
            20                  25                  30

Gly Ala Val Ile Leu Asp Pro Ser Thr Gly Glu Val Ile Ala Thr Ala
        35                  40                  45

Gly Asn Gly Pro Ile Ala Ala His Asp Pro Thr Ala His Ala Glu Ile
    50                  55                  60
```

```
Ala Ala Met Arg Ala Ala Ala Lys Leu Gly Asn Tyr Arg Leu Thr
 65                  70                  75                  80

Asp Leu Thr Leu Val Val Thr Leu Glu Pro Cys Ala Met Cys Ala Gly
                 85                  90                  95

Ala Ile Ser His Ala Arg Ile Gly Arg Val Val Phe Gly Ala Asp Asp
            100                 105                 110

Pro Lys Gly Gly Ala Val Val His Gly Pro Lys Phe Phe Ala Gln Pro
        115                 120                 125

Thr Cys His Trp Arg Pro Glu Val Thr Gly Gly Val Leu Ala Asp Glu
    130                 135                 140

Ser Ala Asp Leu Leu Arg Gly Phe Phe Arg Ala Arg Lys Ala Lys
145                 150                 155                 160

Ile
```

<210> SEQ ID NO 46
<211> LENGTH: 179
<212> TYPE: PRT
<213> ORGANISM: Artificial Sequence
<220> FEATURE:
<223> OTHER INFORMATION: Synthetic sequence

<400> SEQUENCE: 46

```
Met Ser Ser Leu Lys Lys Thr Pro Ile Arg Asp Asp Ala Tyr Trp Met
  1               5                  10                  15

Gly Lys Ala Ile Arg Glu Ala Ala Lys Ala Ala Ala Arg Asp Glu Val
             20                  25                  30

Pro Ile Gly Ala Val Ile Val Arg Asp Gly Ala Val Ile Gly Arg Gly
         35                  40                  45

His Asn Leu Arg Glu Gly Ser Asn Asp Pro Ser Ala His Ala Glu Met
     50                  55                  60

Ile Ala Ile Arg Gln Ala Ala Arg Arg Ser Ala Asn Trp Arg Leu Thr
 65                  70                  75                  80

Gly Ala Thr Leu Tyr Val Thr Leu Glu Pro Cys Leu Met Cys Met Gly
                 85                  90                  95

Ala Ile Ile Leu Ala Arg Leu Glu Arg Val Val Phe Gly Cys Tyr Asp
            100                 105                 110

Pro Lys Gly Gly Ala Ala Gly Ser Leu Tyr Asp Leu Ser Ala Asp Pro
        115                 120                 125

Arg Leu Asn His Gln Val Arg Leu Ser Pro Gly Val Cys Gln Glu Glu
    130                 135                 140

Cys Gly Thr Met Leu Ser Asp Phe Phe Arg Asp Leu Arg Arg Arg Lys
145                 150                 155                 160

Lys Ala Lys Ala Thr Pro Ala Leu Phe Ile Asp Glu Arg Lys Val Pro
                165                 170                 175

Pro Glu Pro
```

<210> SEQ ID NO 47
<211> LENGTH: 198
<212> TYPE: PRT
<213> ORGANISM: Artificial Sequence
<220> FEATURE:
<223> OTHER INFORMATION: Synthetic sequence

<400> SEQUENCE: 47

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
        130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
                195
```

<210> SEQ ID NO 48
<211> LENGTH: 188
<212> TYPE: PRT
<213> ORGANISM: Artificial Sequence
<220> FEATURE:
<223> OTHER INFORMATION: Synthetic sequence

<400> SEQUENCE: 48

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Glu Asn
        130                 135                 140
```

```
His Glu Arg Thr Phe Lys Ala Trp Glu Gly Leu His Glu Asn Ser Val
145                 150                 155                 160

Arg Leu Ser Arg Gln Leu Arg Arg Ile Leu Leu Pro Leu Tyr Glu Val
                165                 170                 175

Asp Asp Leu Arg Asp Ala Phe Arg Thr Leu Gly Leu
            180                 185
```

<210> SEQ ID NO 49
<211> LENGTH: 7
<212> TYPE: PRT
<213> ORGANISM: Artificial Sequence
<220> FEATURE:
<223> OTHER INFORMATION: Synthetic sequence

<400> SEQUENCE: 49

```
Pro Lys Lys Lys Arg Lys Val
1               5
```

<210> SEQ ID NO 50
<211> LENGTH: 16
<212> TYPE: PRT
<213> ORGANISM: Artificial Sequence
<220> FEATURE:
<223> OTHER INFORMATION: Synthetic sequence

<400> SEQUENCE: 50

```
Lys Arg Pro Ala Ala Thr Lys Lys Ala Gly Gln Ala Lys Lys Lys Lys
1               5                   10                  15
```

<210> SEQ ID NO 51
<211> LENGTH: 9
<212> TYPE: PRT
<213> ORGANISM: Artificial Sequence
<220> FEATURE:
<223> OTHER INFORMATION: Synthetic sequence

<400> SEQUENCE: 51

```
Pro Ala Ala Lys Arg Val Lys Leu Asp
1               5
```

<210> SEQ ID NO 52
<211> LENGTH: 11
<212> TYPE: PRT
<213> ORGANISM: Artificial Sequence
<220> FEATURE:
<223> OTHER INFORMATION: Synthetic sequence

<400> SEQUENCE: 52

```
Arg Gln Arg Arg Asn Glu Leu Lys Arg Ser Pro
1               5                   10
```

<210> SEQ ID NO 53
<211> LENGTH: 38
<212> TYPE: PRT
<213> ORGANISM: Artificial Sequence
<220> FEATURE:
<223> OTHER INFORMATION: Synthetic sequence

<400> SEQUENCE: 53

```
Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35
```

<210> SEQ ID NO 54
<211> LENGTH: 42
<212> TYPE: PRT
<213> ORGANISM: Artificial Sequence
<220> FEATURE:
<223> OTHER INFORMATION: Synthetic sequence

<400> SEQUENCE: 54

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 55
<211> LENGTH: 8
<212> TYPE: PRT
<213> ORGANISM: Artificial Sequence
<220> FEATURE:
<223> OTHER INFORMATION: Synthetic sequence

<400> SEQUENCE: 55

Val Ser Arg Lys Arg Pro Arg Pro
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic sequence

<400> SEQUENCE: 56

Pro Gln Pro Lys Lys Lys Pro Leu
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic sequence

<400> SEQUENCE: 57

Ser Ala Leu Ile Lys Lys Lys Lys Lys Met Ala Pro
1               5                   10

<210> SEQ ID NO 58
<211> LENGTH: 5
<212> TYPE: PRT
<213> ORGANISM: Artificial Sequence
<220> FEATURE:
<223> OTHER INFORMATION: Synthetic sequence

<400> SEQUENCE: 58

Asp Arg Leu Arg Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic sequence

```
<400> SEQUENCE: 59

Pro Lys Gln Lys Lys Arg Lys
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic sequence

<400> SEQUENCE: 60

Arg Lys Leu Lys Lys Lys Ile Lys Lys Leu
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic sequence

<400> SEQUENCE: 61

Arg Glu Lys Lys Lys Phe Leu Lys Arg Arg
1               5                   10

<210> SEQ ID NO 62
<211> LENGTH: 20
<212> TYPE: PRT
<213> ORGANISM: Artificial Sequence
<220> FEATURE:
<223> OTHER INFORMATION: Synthetic sequence

<400> SEQUENCE: 62

Lys Arg Lys Gly Asp Glu Val Asp Gly Val Asp Glu Val Ala Lys Lys
1               5                   10                  15

Lys Ser Lys Lys
            20

<210> SEQ ID NO 63
<211> LENGTH: 17
<212> TYPE: PRT
<213> ORGANISM: Artificial Sequence
<220> FEATURE:
<223> OTHER INFORMATION: Synthetic sequence

<400> SEQUENCE: 63

Arg Lys Cys Leu Gln Ala Gly Met Asn Leu Glu Ala Arg Lys Thr Lys
1               5                   10                  15

Lys

<210> SEQ ID NO 64
<211> LENGTH: 11
<212> TYPE: PRT
<213> ORGANISM: Artificial Sequence
<220> FEATURE:
<223> OTHER INFORMATION: Synthetic sequence

<400> SEQUENCE: 64

Tyr Gly Arg Lys Lys Arg Arg Gln Arg Arg
1               5                   10
```

```
<210> SEQ ID NO 65
<211> LENGTH: 12
<212> TYPE: PRT
<213> ORGANISM: Artificial Sequence
<220> FEATURE:
<223> OTHER INFORMATION: Synthetic sequence

<400> SEQUENCE: 65

Arg Arg Gln Arg Arg Thr Ser Lys Leu Met Lys Arg
1               5                   10

<210> SEQ ID NO 66
<211> LENGTH: 27
<212> TYPE: PRT
<213> ORGANISM: Artificial Sequence
<220> FEATURE:
<223> OTHER INFORMATION: Synthetic sequence

<400> SEQUENCE: 66

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 67
<211> LENGTH: 33
<212> TYPE: PRT
<213> ORGANISM: Artificial Sequence
<220> FEATURE:
<223> OTHER INFORMATION: Synthetic sequence

<400> SEQUENCE: 67

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 68
<211> LENGTH: 16
<212> TYPE: PRT
<213> ORGANISM: Artificial Sequence
<220> FEATURE:
<223> OTHER INFORMATION: Synthetic sequence

<400> SEQUENCE: 68

Arg Gln Ile Lys Ile Trp Phe Gln Asn Arg Arg Met Lys Trp Lys Lys
1               5                   10                  15

<210> SEQ ID NO 69
<211> LENGTH: 9
<212> TYPE: PRT
<213> ORGANISM: Artificial Sequence
<220> FEATURE:
<223> OTHER INFORMATION: Synthetic sequence

<400> SEQUENCE: 69

Arg Lys Lys Arg Arg Gln Arg Arg Arg
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic sequence
```

```
<400> SEQUENCE: 70

Arg Lys Lys Arg Arg Gln Arg Arg
1               5

<210> SEQ ID NO 71
<211> LENGTH: 11
<212> TYPE: PRT
<213> ORGANISM: Artificial Sequence
<220> FEATURE:
<223> OTHER INFORMATION: Synthetic sequence

<400> SEQUENCE: 71

Tyr Ala Arg Ala Ala Ala Arg Gln Ala Arg Ala
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic sequence

<400> SEQUENCE: 72

Thr His Arg Leu Pro Arg Arg Arg Arg Arg Arg
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic sequence

<400> SEQUENCE: 73

Gly Gly Arg Arg Ala Arg Arg Arg Arg Arg Arg
1               5                   10

<210> SEQ ID NO 74
<211> LENGTH: 5
<212> TYPE: PRT
<213> ORGANISM: Artificial Sequence
<220> FEATURE:
<223> OTHER INFORMATION: Synthetic sequence

<400> SEQUENCE: 74

Gly Ser Gly Gly Ser
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic sequence

<400> SEQUENCE: 75

Gly Gly Ser Gly Gly Ser
1               5

<210> SEQ ID NO 76
<211> LENGTH: 4
<212> TYPE: PRT
<213> ORGANISM: Artificial Sequence
<220> FEATURE:
<223> OTHER INFORMATION: Synthetic sequence
```

```
<400> SEQUENCE: 76

Gly Gly Gly Ser
1

<210> SEQ ID NO 77
<211> LENGTH: 4
<212> TYPE: PRT
<213> ORGANISM: Artificial Sequence
<220> FEATURE:
<223> OTHER INFORMATION: Synthetic sequence

<400> SEQUENCE: 77

Gly Gly Ser Gly
1

<210> SEQ ID NO 78
<211> LENGTH: 5
<212> TYPE: PRT
<213> ORGANISM: Artificial Sequence
<220> FEATURE:
<223> OTHER INFORMATION: Synthetic sequence

<400> SEQUENCE: 78

Gly Gly Ser Gly Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic sequence

<400> SEQUENCE: 79

Gly Ser Gly Ser Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic sequence

<400> SEQUENCE: 80

Gly Ser Gly Gly Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic sequence

<400> SEQUENCE: 81

Gly Gly Gly Ser Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic sequence
```

<400> SEQUENCE: 82

Gly Ser Ser Ser Gly
1               5

<210> SEQ ID NO 83
<211> LENGTH: 36
<212> TYPE: RNA
<213> ORGANISM: Artificial Sequence
<220> FEATURE:
<223> OTHER INFORMATION: Synthetic sequence

<400> SEQUENCE: 83
gucucgacua aucgagcaau cguuugagau cucucc                             36

<210> SEQ ID NO 84
<211> LENGTH: 36
<212> TYPE: RNA
<213> ORGANISM: Artificial Sequence
<220> FEATURE:
<223> OTHER INFORMATION: Synthetic sequence

<400> SEQUENCE: 84
gucggaacgc ucaacgauug ccccucacga ggggac                             36

<210> SEQ ID NO 85
<211> LENGTH: 35
<212> TYPE: RNA
<213> ORGANISM: Artificial Sequence
<220> FEATURE:
<223> OTHER INFORMATION: Synthetic sequence

<400> SEQUENCE: 85
gucccagcgu acugggcaau caauagcguu uggu                               35

<210> SEQ ID NO 86
<211> LENGTH: 40
<212> TYPE: RNA
<213> ORGANISM: Artificial Sequence
<220> FEATURE:
<223> OTHER INFORMATION: Synthetic sequence

<400> SEQUENCE: 86
cacaggagag aucucaaacg auugcucgau uagucgagac                         40

<210> SEQ ID NO 87
<211> LENGTH: 40
<212> TYPE: RNA
<213> ORGANISM: Artificial Sequence
<220> FEATURE:
<223> OTHER INFORMATION: Synthetic sequence

<400> SEQUENCE: 87
uaaugucgga acgcucaacg auugccccuc acgagggac                          40

<210> SEQ ID NO 88
<211> LENGTH: 40
<212> TYPE: RNA
<213> ORGANISM: Artificial Sequence
<220> FEATURE:
<223> OTHER INFORMATION: Synthetic sequence

<400> SEQUENCE: 88
auuaaccaaa acgacuauug auugcccagu acgcugggac                         40

```
<210> SEQ ID NO 89
<211> LENGTH: 71
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(35)
<223> OTHER INFORMATION: n is a, c, g, or u

<400> SEQUENCE: 89
nnnnnnnnnn nnnnnnnnnn nnnnnnnnnn nnnnngucuc gacuaaucga gcaaucguuu    60
gagaucucuc c                                                         71

<210> SEQ ID NO 90
<211> LENGTH: 71
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(35)
<223> OTHER INFORMATION: n is a, c, g, or u

<400> SEQUENCE: 90
nnnnnnnnnn nnnnnnnnnn nnnnnnnnnn nnnnngucgg aacgcucaac gauugcccu    60 cacgagggga c                                                         71

<210> SEQ ID NO 91
<211> LENGTH: 71
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (37)..(71)
<223> OTHER INFORMATION: n is a, c, g, or u

<400> SEQUENCE: 91
gucucgacua aucgagcaau cguuugagau cucuccnnnn nnnnnnnnnn nnnnnnnnnn    60
nnnnnnnnnn n                                                         71

<210> SEQ ID NO 92
<211> LENGTH: 71
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (37)..(71)
<223> OTHER INFORMATION: n is a, c, g, or u

<400> SEQUENCE: 92
ggagagaucu caaacgauug cucgauuagu cgagacnnnn nnnnnnnnnn nnnnnnnnnn    60
nnnnnnnnnn n                                                         71

<210> SEQ ID NO 93
<211> LENGTH: 71
<212> TYPE: RNA
<213> ORGANISM: Artificial Sequence
<220> FEATURE:
<223> OTHER INFORMATION: Synthetic sequence
```

```
<220> FEATURE:
<221> NAME/KEY: misc_feature
<222> LOCATION: (37)..(71)
<223> OTHER INFORMATION: n is a, c, g, or u

<400> SEQUENCE: 93
gucggaacgc ucaacgauug ccccucacga ggggacnnnn nnnnnnnnnn nnnnnnnnnn    60
nnnnnnnnnn n                                                        71

<210> SEQ ID NO 94
<211> LENGTH: 71
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (37)..(71)
<223> OTHER INFORMATION: n is a, c, g, or u

<400> SEQUENCE: 94
guccccucgu gaggggcaau cguugagcgu uccgacnnnn nnnnnnnnnn nnnnnnnnnn    60
nnnnnnnnnn n                                                        71

<210> SEQ ID NO 95
<211> LENGTH: 75
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (41)..(75)
<223> OTHER INFORMATION: n is a, c, g, or u

<400> SEQUENCE: 95
cacaggagag aucucaaacg auugcucgau uagucgagac nnnnnnnnnn nnnnnnnnnn    60
nnnnnnnnnn nnnnn                                                    75

<210> SEQ ID NO 96
<211> LENGTH: 75
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (41)..(75)
<223> OTHER INFORMATION: n is a, c, g, or u

<400> SEQUENCE: 96
uaaugucgga acgcucaacg auugccccuc acgagggggac nnnnnnnnnn nnnnnnnnnn   60
nnnnnnnnnn nnnnn                                                    75

<210> SEQ ID NO 97
<211> LENGTH: 75
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (41)..(75)
<223> OTHER INFORMATION: n is a, c, g, or u
```

-continued

<400> SEQUENCE: 97
auuaaccaaa acgacuauug auugcccagu acgcugggac nnnnnnnnnn nnnnnnnnnn    60
nnnnnnnnnn nnnnn                                                    75

<210> SEQ ID NO 98
<211> LENGTH: 8
<212> TYPE: PRT
<213> ORGANISM: Artificial Sequence
<220> FEATURE:
<223> OTHER INFORMATION: Synthetic sequence

<400> SEQUENCE: 98

Pro Pro Lys Lys Ala Arg Glu Asp
1               5

<210> SEQ ID NO 99
<211> LENGTH: 60
<212> TYPE: RNA
<213> ORGANISM: Artificial Sequence
<220> FEATURE:
<223> OTHER INFORMATION: Synthetic sequence

<400> SEQUENCE: 99
cacaggagag aucucaaacg auugcucgau uagucgagac agcugguaau gggauaccuu    60

<210> SEQ ID NO 100
<211> LENGTH: 60
<212> TYPE: RNA
<213> ORGANISM: Artificial Sequence
<220> FEATURE:
<223> OTHER INFORMATION: Synthetic sequence

<400> SEQUENCE: 100
uaaugucgga acgcucaacg auugccccuc acgaggggac ugccgccucc gcgacgccca    60

<210> SEQ ID NO 101
<211> LENGTH: 60
<212> TYPE: RNA
<213> ORGANISM: Artificial Sequence
<220> FEATURE:
<223> OTHER INFORMATION: Synthetic sequence

<400> SEQUENCE: 101
auuaaccaaa acgacuauug auugcccagu acgcugggac uaugagcuua uguacaucaa    60

<210> SEQ ID NO 102
<211> LENGTH: 1895
<212> TYPE: DNA
<213> ORGANISM: Artificial Sequence
<220> FEATURE:
<223> OTHER INFORMATION: Synthetic sequence

<400> SEQUENCE: 102
gctcttgccc ggcgtcaata cgggataata ccgcgccaca tagcagaact taaaagtgc     60 tcatcattgg aaaacgttct cggggcgaaa actctcaag gatcttaccg ctgttgagat    120
ccagttcgat gtaacccact cgtgcaccca actgatcttc agcatctttt actttcacca   180
gcgtttctgg gtgagcaaaa acaggaaggc aaaatgccgc aaaaaaggga ataagggcga   240
cacggaaatg ttgaatactc atactcttcc tttttcaata ttattgaagc atttatcagg   300
gttattgtct catgagcgga tacatatttg aatgtattta gaaaaataaa caaataggg    360 ttccgcgcac atttccccga aaagtgccac ctgtcatgac caaaatccct taacgtgagt   420

| | |
|---|---|
| tttcgttcca ctgagcgtca gacccgtag aaaagatcaa aggatcttct tgagatcctt | 480 |
| tttttctgcg cgtaatctgc tgcttgcaaa caaaaaaacc accgctacca gcggtggttt | 540 |
| gtttgccgga tcaagagcta ccaactcttt ttccgaaggt aactggcttc agcagagcgc | 600 |
| agataccaaa tactgttctt ctagtgtagc cgtagttagg ccaccacttc aagaactctg | 660 |
| tagcaccgcc tacatacctc gctctgctaa tcctgttacc agtggctgct gccagtggcg | 720 |
| ataagtcgtg tcttaccggg ttggactcaa gacgatagtt accggataag gcgcagcggt | 780 |
| cgggctgaac gggggggttcg tgcacacagc ccagcttgga gcgaacgacc tacaccgaac | 840 |
| tgagatacct acagcgtgag ctatgagaaa gcgccacgct tcccgaaggg agaaaggcgg | 900 |
| acaggtatcc ggtaagcggc agggtcggaa caggagagcg cacgagggag cttccagggg | 960 |
| gaaacgcctg gtatctttat agtcctgtcg ggtttcgcca cctctgactt gagcgtcgat | 1020 |
| ttttgtgatg ctcgtcaggg gggcggagcc tatggaaaaa cgccagcaac gcggcctttt | 1080 |
| tacggttcct ggccttttgc tggccttttg ctcacatgtt ctttcctgcg ttatcccctg | 1140 |
| attctgtgga taaccgtgcg gccgccccctt gtagttaagc tggtaatggg ataccttata | 1200 |
| cagcggccgc gattatcaaa aaggatcttc acctagatcc tttttaaatta aaaatgaagt | 1260 |
| tttaaatcaa tctaaagtat atatgagtaa acttggtctg acagttacca atgcttaatc | 1320 |
| agtgaggcac ctatctcagc gatctgtcta tttcgttcat ccatagttgc ctgactcccc | 1380 |
| gtcgtgtaga taactacgat acgggagggc ttaccatctg gccccagtgc tgcaatgata | 1440 |
| ccgcgggacc cacgctcacc ggctccagat ttatcagcaa taaaccagcc agccggaagg | 1500 |
| gccgagcgca gaagtggtcc tgcaacttta tccgcctcca tccagtctat taattgttgc | 1560 |
| cgggaagcta gagtaagtag ttcgccagtt aatagtttgc gcaacgttgt tgccattgct | 1620 |
| acaggcatcg tggtgtcacg ctcgtcgttt ggtatggctt cattcagctc cggttcccaa | 1680 |
| cgatcaaggc gagttacatg atcccccatg ttgtgcaaaa aagcggttag ctccttcggt | 1740 |
| cctccgatcg ttgtcagaag taagttggcc gcagtgttat cactcatggt tatggcagca | 1800 |
| ctgcataatt ctcttactgt catgccatcc gtaagatgct tttctgtgac tggtgagtac | 1860 |
| tcaaccaagt cattctgaga atagtgtatg cggcg | 1895 |

<210> SEQ ID NO 103
<211> LENGTH: 1895
<212> TYPE: DNA
<213> ORGANISM: Artificial Sequence
<220> FEATURE:
<223> OTHER INFORMATION: Synthetic sequence

<400> SEQUENCE: 103

| | |
|---|---|
| gctcttgccc ggcgtcaata cgggataata ccgcgccaca tagcagaact ttaaaagtgc | 60 |
| tcatcattgg aaaacgttct cgggggcgaa aactctcaag gatcttaccg ctgttgagat | 120 |
| ccagttcgat gtaacccact cgtgcaccca actgatcttc agcatctttt actttcacca | 180 |
| gcgtttctgg gtgagcaaaa acaggaaggc aaaatgccgc aaaaaaggga ataagggcga | 240 |
| cacggaaatg ttgaatactc atactcttcc ttttcaata ttattgaagc atttatcagg | 300 |
| gttattgtct catgagcgga tacatatttg aatgtattta gaaaaataaa caaataggggg | 360 |
| ttccgcgcac atttccccga aaagtgccac ctgtcatgac caaaatccct taacgtgagt | 420 |
| tttcgttcca ctgagcgtca gacccgtag aaaagatcaa aggatcttct tgagatcctt | 480 |
| tttttctgcg cgtaatctgc tgcttgcaaa caaaaaaacc accgctacca gcggtggttt | 540 |
| gtttgccgga tcaagagcta ccaactcttt ttccgaaggt aactggcttc agcagagcgc | 600 |

| | | |
|---|---|---|
| agataccaaa tactgttctt ctagtgtagc cgtagttagg ccaccacttc aagaactctg | 660 | |
| tagcaccgcc tacatacctc gctctgctaa tcctgttacc agtggctgct gccagtggcg | 720 | |
| ataagtcgtg tcttaccggg ttggactcaa gacgatagtt accggataag gcgcagcggt | 780 | |
| cgggctgaac gggggttcg tgcacacagc ccagcttgga gcgaacgacc tacaccgaac | 840 | |
| tgagatacct acagcgtgag ctatgagaaa gcgccacgct tcccgaaggg agaaaggcgg | 900 | |
| acaggtatcc ggtaagcggc agggtcggaa caggagagcg cacgagggag cttccagggg | 960 | |
| gaaacgcctg gtatctttat agtcctgtcg ggtttcgcca cctctgactt gagcgtcgat | 1020 | |
| ttttgtgatg ctcgtcaggg gggcggagcc tatggaaaaa cgccagcaac gcggcctttt | 1080 | |
| tacggttcct ggccttttgc tggccttttg ctcacatgtt ctttcctgcg ttatcccctg | 1140 | |
| attctgtgga taaccgtgcg ccgcccctt gtatttctgc cgcctccgcg acgcccaata | 1200 | |
| cagcggccgc gattatcaaa aaggatcttc acctagatcc ttttaaatta aaatgaagt | 1260 | |
| tttaaatcaa tctaaagtat atatgagtaa acttggtctg acagttacca atgcttaatc | 1320 | |
| agtgaggcac ctatctcagc gatctgtcta tttcgttcat ccatagttgc ctgactcccc | 1380 | |
| gtcgtgtaga taactacgat acgggagggc ttaccatctg gccccagtgc tgcaatgata | 1440 | |
| ccgcgggacc cacgctcacc ggctccagat ttatcagcaa taaaccagcc agccggaagg | 1500 | |
| gccgagcgca gaagtggtcc tgcaacttta tccgcctcca tccagtctat taattgttgc | 1560 | |
| cgggaagcta gagtaagtag ttcgccagtt aatagtttgc gcaacgttgt tgccattgct | 1620 | |
| acaggcatcg tggtgtcacg ctcgtcgttt ggtatggctt cattcagctc cggttcccaa | 1680 | |
| cgatcaaggc gagttacatg atcccccatg ttgtgcaaaa aagcggttag ctccttcggt | 1740 | |
| cctccgatcg ttgtcagaag taagttggcc gcagtgttat cactcatggt tatggcagca | 1800 | |
| ctgcataatt ctcttactgt catgccatcc gtaagatgct tttctgtgac tggtgagtac | 1860 | |
| tcaaccaagt cattctgaga atagtgtatg cggcg | 1895 | |

<210> SEQ ID NO 104
<211> LENGTH: 1895
<212> TYPE: DNA
<213> ORGANISM: Artificial Sequence
<220> FEATURE:
<223> OTHER INFORMATION: Synthetic sequence

<400> SEQUENCE: 104

| | | |
|---|---|---|
| gctcttgccc ggcgtcaata cgggataata ccgcgccaca tagcagaact ttaaaagtgc | 60 | |
| tcatcattgg aaaacgttct cggggcgaa aactctcaag gatcttaccg ctgttgagat | 120 | |
| ccagttcgat gtaacccact cgtgcaccca actgatcttc agcatctttt actttcacca | 180 | |
| gcgtttctgg gtgagcaaaa acaggaaggc aaaatgccgc aaaaaaggga ataagggcga | 240 | |
| cacggaaatg ttgaatactc atactcttcc ttttcaata ttattgaagc atttatcagg | 300 | |
| gttattgtct catgagcgga tacatatttg aatgtattta gaaaaataaa caaataggg | 360 | |
| ttccgcgcac atttccccga aaagtgccac ctgtcatgac caaaatccct aacgtgagt | 420 | |
| tttcgttcca ctgagcgtca gaccccgtag aaaagatcaa aggatcttct tgagatcctt | 480 | |
| ttttttctgcg cgtaatctgc tgcttgcaaa caaaaaaacc accgctacca gcggtggttt | 540 | |
| gtttgccgga tcaagagcta ccaactcttt ttccgaaggt aactggcttc agcagagcgc | 600 | |
| agataccaaa tactgttctt ctagtgtagc cgtagttagg ccaccacttc aagaactctg | 660 | |
| tagcaccgcc tacatacctc gctctgctaa tcctgttacc agtggctgct gccagtggcg | 720 | |
| ataagtcgtg tcttaccggg ttggactcaa gacgatagtt accggataag gcgcagcggt | 780 | |

```
cgggctgaac ggggggttcg tgcacacagc ccagcttgga gcgaacgacc tacaccgaac    840
tgagatacct acagcgtgag ctatgagaaa gcgccacgct tcccgaaggg agaaaggcgg    900
acaggtatcc ggtaagcggc agggtcggaa caggagagcg cacgagggag cttccagggg    960
gaaacgcctg gtatctttat agtcctgtcg ggtttcgcca cctctgactt gagcgtcgat   1020
ttttgtgatg ctcgtcaggg gggcggagcc tatggaaaaa cgccagcaac gcggcctttt   1080
tacggttcct ggccttttgc tggccttttg ctcacatgtt ctttcctgcg ttatcccctg   1140
attctgtgga taaccgtgcg gccgccccTT gtaattctat gagcttatgt acatcaaata   1200
cagcggccgc gattatcaaa aaggatcttc acctagatcc tttTAAatta aaaatgaagt   1260
tttaaatcaa tctaaagtat atatgagtaa acttggtctg acagttacca atgcttaatc   1320
agtgaggcac ctatctcagc gatctgtcta tttcgttcat ccatagttgc ctgactcccc   1380
gtcgtgtaga taactacgat acgggagggc ttaccatctg gccccagtgc tgcaatgata   1440
ccgcgggacc cacgctcacc ggctccagat ttatcagcaa taaaccagcc agccggaagg   1500
gccgagcgca gaagtggtcc tgcaacttta tccgcctcca tccagtctat taattgttgc   1560
cgggaagcta gagtaagtag ttcgccagtt aatagtttgc gcaacgttgt tgccattgct   1620
acaggcatcg tggtgtcacg ctcgtcgttt ggtatggctt cattcagctc cggttcccaa   1680
cgatcaaggc gagttacatg atcccccatg ttgtgcaaaa aagcggttag ctccttcggt   1740
cctccgatcg ttgtcagaag taagttggcc gcagtgttat cactcatggt tatggcagca   1800
ctgcataatt ctcttactgt catgccatcc gtaagatgct tttctgtgac tggtgagtac   1860
tcaaccaagt cattctgaga atagtgtatg cggcg                              1895
```

<210> SEQ ID NO 105
<211> LENGTH: 20
<212> TYPE: DNA
<213> ORGANISM: Artificial Sequence
<220> FEATURE:
<223> OTHER INFORMATION: Synthetic sequence

<400> SEQUENCE: 105
cgtgatggtc tcgattgagt                                                 20

<210> SEQ ID NO 106
<211> LENGTH: 20
<212> TYPE: DNA
<213> ORGANISM: Artificial Sequence
<220> FEATURE:
<223> OTHER INFORMATION: Synthetic sequence

<400> SEQUENCE: 106
accggggtgg tgcccatcct                                                 20

<210> SEQ ID NO 107
<211> LENGTH: 20
<212> TYPE: DNA
<213> ORGANISM: Artificial Sequence
<220> FEATURE:
<223> OTHER INFORMATION: Synthetic sequence

<400> SEQUENCE: 107
atctgcacca ccggcaagct                                                 20

<210> SEQ ID NO 108
<211> LENGTH: 20
<212> TYPE: DNA
<213> ORGANISM: Artificial Sequence -continued
<220> FEATURE:
<223> OTHER INFORMATION: Synthetic sequence

<400> SEQUENCE: 108
gagggcgaca ccctggtgaa                                               20

<210> SEQ ID NO 109
<211> LENGTH: 707
<212> TYPE: PRT
<213> ORGANISM: Artificial Sequence
<220> FEATURE:
<223> OTHER INFORMATION: Synthetic sequence

<400> SEQUENCE: 109

```
Met Ala Asp Thr Pro Thr Leu Phe Thr Gln Phe Leu Arg His His Leu
1               5                   10                  15

Pro Gly Gln Arg Phe Arg Lys Asp Ile Leu Lys Gln Ala Gly Arg Ile
            20                  25                  30

Leu Ala Asn Lys Gly Glu Asp Ala Thr Ile Ala Phe Leu Arg Gly Lys
        35                  40                  45

Ser Glu Glu Ser Pro Pro Asp Phe Gln Pro Val Lys Cys Pro Ile
    50                  55                  60

Ile Ala Cys Ser Arg Pro Leu Thr Glu Trp Pro Ile Tyr Gln Ala Ser
65                  70                  75                  80

Val Ala Ile Gln Gly Tyr Val Tyr Gly Gln Ser Leu Ala Glu Phe Glu
                85                  90                  95

Ala Ser Asp Pro Gly Cys Ser Lys Asp Gly Leu Leu Gly Trp Phe Asp
            100                 105                 110

Lys Thr Gly Val Cys Thr Asp Tyr Phe Ser Val Gln Gly Leu Asn Leu
        115                 120                 125

Ile Phe Gln Asn Ala Arg Lys Arg Tyr Ile Gly Val Gln Thr Lys Val
    130                 135                 140

Thr Asn Arg Asn Glu Lys Arg His Lys Lys Leu Lys Arg Ile Asn Ala
145                 150                 155                 160

Lys Arg Ile Ala Glu Gly Leu Pro Glu Leu Thr Ser Asp Glu Pro Glu
                165                 170                 175

Ser Ala Leu Asp Glu Thr Gly His Leu Ile Asp Pro Pro Gly Leu Asn
            180                 185                 190

Thr Asn Ile Tyr Cys Tyr Gln Gln Val Ser Pro Lys Pro Leu Ala Leu
        195                 200                 205

Ser Glu Val Asn Gln Leu Pro Thr Ala Tyr Ala Gly Tyr Ser Thr Ser
    210                 215                 220

Gly Asp Asp Pro Ile Gln Pro Met Val Thr Lys Asp Arg Leu Ser Ile
225                 230                 235                 240

Ser Lys Gly Gln Pro Gly Tyr Ile Pro Glu His Gln Arg Ala Leu Leu
                245                 250                 255

Ser Gln Lys Lys His Arg Arg Met Arg Gly Tyr Gly Leu Lys Ala Arg
            260                 265                 270

Ala Leu Leu Val Ile Val Arg Ile Gln Asp Asp Trp Ala Val Ile Asp
        275                 280                 285

Leu Arg Ser Leu Leu Arg Asn Ala Tyr Trp Arg Ile Val Gln Thr
    290                 295                 300

Lys Glu Pro Ser Thr Ile Thr Lys Leu Leu Lys Leu Val Thr Gly Asp
305                 310                 315                 320

Pro Val Leu Asp Ala Thr Arg Met Val Ala Thr Phe Thr Tyr Lys Pro
                325                 330                 335
```

-continued

Gly Ile Val Gln Val Arg Ser Ala Lys Cys Leu Lys Asn Lys Gln Gly
            340                 345                 350

Ser Lys Leu Phe Ser Glu Arg Tyr Leu Asn Glu Thr Val Ser Val Thr
355                 360                 365

Ser Ile Asp Leu Gly Ser Asn Asn Leu Val Ala Val Ala Thr Tyr Arg
        370                 375                 380

Leu Val Asn Gly Asn Thr Pro Glu Leu Leu Gln Arg Phe Thr Leu Pro
385                 390                 395                 400

Ser His Leu Val Lys Asp Phe Glu Arg Tyr Lys Gln Ala His Asp Thr
                405                 410                 415

Leu Glu Asp Ser Ile Gln Lys Thr Ala Val Ala Ser Leu Pro Gln Gly
            420                 425                 430

Gln Gln Thr Glu Ile Arg Met Trp Ser Met Tyr Gly Phe Arg Glu Ala
        435                 440                 445

Gln Glu Arg Val Cys Gln Glu Leu Gly Leu Ala Asp Gly Ser Ile Pro
    450                 455                 460

Trp Asn Val Met Thr Ala Thr Ser Thr Ile Leu Thr Asp Leu Phe Leu
465                 470                 475                 480

Ala Arg Gly Gly Asp Pro Lys Lys Cys Met Phe Thr Ser Glu Pro Lys
                485                 490                 495

Lys Lys Lys Asn Ser Lys Gln Val Leu Tyr Lys Ile Arg Asp Arg Ala
            500                 505                 510

Trp Ala Lys Met Tyr Arg Thr Leu Leu Ser Lys Glu Thr Arg Glu Ala
        515                 520                 525

Trp Asn Lys Ala Leu Trp Gly Leu Lys Arg Gly Ser Pro Asp Tyr Ala
    530                 535                 540

Arg Leu Ser Lys Arg Lys Glu Glu Leu Ala Arg Arg Cys Val Asn Tyr
545                 550                 555                 560

Thr Ile Ser Thr Ala Glu Lys Arg Ala Gln Cys Gly Arg Thr Ile Val
                565                 570                 575

Ala Leu Glu Asp Leu Asn Ile Gly Phe Phe His Gly Arg Gly Lys Gln
            580                 585                 590

Glu Pro Gly Trp Val Gly Leu Phe Thr Arg Lys Lys Glu Asn Arg Trp
        595                 600                 605

Leu Met Gln Ala Leu His Lys Ala Phe Leu Glu Leu Ala His His Arg
    610                 615                 620

Gly Tyr His Val Ile Glu Val Asn Pro Ala Tyr Thr Ser Gln Thr Cys
625                 630                 635                 640

Pro Val Cys Arg His Cys Asp Pro Asp Asn Arg Asp Gln His Asn Arg
                645                 650                 655

Glu Ala Phe His Cys Ile Gly Cys Gly Phe Arg Gly Asn Ala Asp Leu
            660                 665                 670

Asp Val Ala Thr His Asn Ile Ala Met Val Ala Ile Thr Gly Glu Ser
        675                 680                 685

Leu Lys Arg Ala Arg Gly Ser Val Ala Ser Lys Thr Pro Gln Pro Leu
    690                 695                 700

Ala Ala Glu
705

<210> SEQ ID NO 110
<211> LENGTH: 757
<212> TYPE: PRT
<213> ORGANISM: Artificial Sequence
<220> FEATURE:
<223> OTHER INFORMATION: Synthetic sequence

<400> SEQUENCE: 110

```
Met Pro Lys Pro Ala Val Glu Ser Glu Phe Ser Lys Val Leu Lys Lys
1               5                   10                  15

His Phe Pro Gly Glu Arg Phe Arg Ser Ser Tyr Met Lys Arg Gly Gly
            20                  25                  30

Lys Ile Leu Ala Ala Gln Gly Glu Glu Ala Val Val Ala Tyr Leu Gln
        35                  40                  45

Gly Lys Ser Glu Glu Gly Pro Pro Asn Phe Gln Pro Pro Ala Lys Cys
    50                  55                  60

His Val Thr Lys Ser Arg Asp Phe Ala Glu Trp Pro Ile Met Lys
65                  70                  75                  80

Ala Ser Glu Ala Ile Gln Arg Tyr Ile Tyr Ala Leu Ser Thr Thr Glu
                85                  90                  95

Arg Ala Ala Cys Lys Pro Gly Lys Ser Ser Glu Ser His Ala Ala Trp
            100                 105                 110

Phe Ala Ala Thr Gly Val Ser Asn His Gly Tyr Ser His Val Gln Gly
        115                 120                 125

Leu Asn Leu Ile Phe Asp His Thr Leu Gly Arg Tyr Asp Gly Val Leu
    130                 135                 140

Lys Lys Val Gln Leu Arg Asn Glu Lys Ala Arg Ala Arg Leu Glu Ser
145                 150                 155                 160

Ile Asn Ala Ser Arg Ala Asp Glu Gly Leu Pro Glu Ile Lys Ala Glu
                165                 170                 175

Glu Glu Glu Val Ala Thr Asn Glu Thr Gly His Leu Leu Gln Pro Pro
            180                 185                 190

Gly Ile Asn Pro Ser Phe Tyr Val Tyr Gln Thr Ile Ser Pro Gln Ala
        195                 200                 205

Tyr Arg Pro Arg Asp Glu Ile Val Leu Pro Pro Glu Tyr Ala Gly Tyr
    210                 215                 220

Val Arg Asp Pro Asn Ala Pro Ile Pro Leu Gly Val Val Arg Asn Arg
225                 230                 235                 240

Cys Asp Ile Gln Lys Gly Cys Pro Gly Tyr Ile Pro Glu Trp Gln Arg
                245                 250                 255

Glu Ala Gly Thr Ala Ile Ser Pro Lys Thr Gly Lys Ala Val Thr Val
            260                 265                 270

Pro Gly Leu Ser Pro Lys Lys Asn Lys Arg Met Arg Arg Tyr Trp Arg
        275                 280                 285

Ser Glu Lys Glu Lys Ala Gln Asp Ala Leu Leu Val Thr Val Arg Ile
    290                 295                 300

Gly Thr Asp Trp Val Val Ile Asp Val Arg Gly Leu Leu Arg Asn Ala
305                 310                 315                 320

Arg Trp Arg Thr Ile Ala Pro Lys Asp Ile Ser Leu Asn Ala Leu Leu
                325                 330                 335

Asp Leu Phe Thr Gly Asp Pro Val Ile Asp Val Arg Arg Asn Ile Val
            340                 345                 350

Thr Phe Thr Tyr Thr Leu Asp Ala Cys Gly Thr Tyr Ala Arg Lys Trp
        355                 360                 365

Thr Leu Lys Gly Lys Gln Thr Lys Ala Thr Leu Asp Lys Leu Thr Ala
    370                 375                 380

Thr Gln Thr Val Ala Leu Val Ala Ile Asp Leu Gly Gln Thr Asn Pro
385                 390                 395                 400

Ile Ser Ala Gly Ile Ser Arg Val Thr Gln Glu Asn Gly Ala Leu Gln
                405                 410                 415
```

Cys Glu Pro Leu Asp Arg Phe Thr Leu Pro Asp Leu Leu Lys Asp
            420                 425                 430

Ile Ser Ala Tyr Arg Ile Ala Trp Asp Arg Asn Glu Glu Glu Leu Arg
        435                 440                 445

Ala Arg Ser Val Glu Ala Leu Pro Glu Ala Gln Gln Ala Glu Val Arg
    450                 455                 460

Ala Leu Asp Gly Val Ser Lys Glu Thr Ala Arg Thr Gln Leu Cys Ala
465                 470                 475                 480

Asp Phe Gly Leu Asp Pro Lys Arg Leu Pro Trp Asp Lys Met Ser Ser
                485                 490                 495

Asn Thr Thr Phe Ile Ser Glu Ala Leu Leu Ser Asn Ser Val Ser Arg
            500                 505                 510

Asp Gln Val Phe Phe Thr Pro Ala Pro Lys Lys Gly Ala Lys Lys Lys
        515                 520                 525

Ala Pro Val Glu Val Met Arg Lys Asp Arg Thr Trp Ala Arg Ala Tyr
    530                 535                 540

Lys Pro Arg Leu Ser Val Glu Ala Gln Lys Leu Lys Asn Glu Ala Leu
545                 550                 555                 560

Trp Ala Leu Lys Arg Thr Ser Pro Glu Tyr Leu Lys Leu Ser Arg Arg
                565                 570                 575

Lys Glu Glu Leu Cys Arg Arg Ser Ile Asn Tyr Val Ile Glu Lys Thr
            580                 585                 590

Arg Arg Arg Thr Gln Cys Gln Ile Val Ile Pro Val Ile Glu Asp Leu
        595                 600                 605

Asn Val Arg Phe Phe His Gly Ser Gly Lys Arg Leu Pro Gly Trp Asp
    610                 615                 620

Asn Phe Phe Thr Ala Lys Lys Glu Asn Arg Trp Phe Ile Gln Gly Leu
625                 630                 635                 640

His Lys Ala Phe Ser Asp Leu Arg Thr His Arg Ser Phe Tyr Val Phe
                645                 650                 655

Glu Val Arg Pro Glu Arg Thr Ser Ile Thr Cys Pro Lys Cys Gly His
            660                 665                 670

Cys Glu Val Gly Asn Arg Asp Gly Glu Ala Phe Gln Cys Leu Ser Cys
        675                 680                 685

Gly Lys Thr Cys Asn Ala Asp Leu Asp Val Ala Thr His Asn Leu Thr
    690                 695                 700

Gln Val Ala Leu Thr Gly Lys Thr Met Pro Lys Arg Glu Glu Pro Arg
705                 710                 715                 720

Asp Ala Gln Gly Thr Ala Pro Ala Arg Lys Thr Lys Lys Ala Ser Lys
                725                 730                 735

Ser Lys Ala Pro Pro Ala Glu Arg Glu Asp Gln Thr Pro Ala Gln Glu
            740                 745                 750

Pro Ser Gln Thr Ser
        755

<210> SEQ ID NO 111
<211> LENGTH: 765
<212> TYPE: PRT
<213> ORGANISM: Artificial Sequence
<220> FEATURE:
<223> OTHER INFORMATION: Synthetic sequence

<400> SEQUENCE: 111

```
Met Tyr Ile Leu Glu Met Ala Asp Leu Lys Ser Glu Pro Ser Leu Leu
1               5                   10                  15

Ala Lys Leu Leu Arg Asp Arg Phe Pro Gly Lys Tyr Trp Leu Pro Lys
            20                  25                  30

Tyr Trp Lys Leu Ala Glu Lys Lys Arg Leu Thr Gly Glu Glu Ala
        35                  40                  45

Ala Cys Glu Tyr Met Ala Asp Lys Gln Leu Asp Ser Pro Pro Pro Asn
    50                  55                  60

Phe Arg Pro Pro Ala Arg Cys Val Ile Leu Ala Lys Ser Arg Pro Phe
65                  70                  75                  80

Glu Asp Trp Pro Val His Arg Val Ala Ser Lys Ala Gln Ser Phe Val
                85                  90                  95

Ile Gly Leu Ser Glu Gln Gly Phe Ala Ala Leu Arg Ala Ala Pro Pro
            100                 105                 110

Ser Thr Ala Asp Ala Arg Arg Asp Trp Leu Arg Ser His Gly Ala Ser
            115                 120                 125

Glu Asp Asp Leu Met Ala Leu Glu Ala Gln Leu Leu Glu Thr Ile Met
130                 135                 140

Gly Asn Ala Ile Ser Leu His Gly Gly Val Leu Lys Lys Ile Asp Asn
145                 150                 155                 160

Ala Asn Val Lys Ala Ala Lys Arg Leu Ser Gly Arg Asn Glu Ala Arg
                165                 170                 175

Leu Asn Lys Gly Leu Gln Glu Leu Pro Pro Glu Gln Glu Gly Ser Ala
            180                 185                 190

Tyr Gly Ala Asp Gly Leu Leu Val Asn Pro Pro Gly Leu Asn Leu Asn
        195                 200                 205

Ile Tyr Cys Arg Lys Ser Cys Cys Pro Lys Pro Val Lys Asn Thr Ala
210                 215                 220

Arg Phe Val Gly His Tyr Pro Gly Tyr Leu Arg Asp Ser Asp Ser Ile
225                 230                 235                 240

Leu Ile Ser Gly Thr Met Asp Arg Leu Thr Ile Ile Glu Gly Met Pro
                245                 250                 255

Gly His Ile Pro Ala Trp Gln Arg Glu Gln Gly Leu Val Lys Pro Gly
            260                 265                 270

Gly Arg Arg Arg Leu Ser Gly Ser Glu Ser Asn Met Arg Gln Lys
        275                 280                 285

Val Asp Pro Ser Thr Gly Pro Arg Arg Ser Thr Arg Ser Gly Thr Val
    290                 295                 300

Asn Arg Ser Asn Gln Arg Thr Gly Arg Asn Gly Asp Pro Leu Leu Val
305                 310                 315                 320

Glu Ile Arg Met Lys Glu Asp Trp Val Leu Leu Asp Ala Arg Gly Leu
                325                 330                 335

Leu Arg Asn Leu Arg Trp Arg Glu Ser Lys Arg Gly Leu Ser Cys Asp
            340                 345                 350

His Glu Asp Leu Ser Leu Ser Gly Leu Leu Ala Leu Phe Ser Gly Asp
        355                 360                 365

Pro Val Ile Asp Pro Val Arg Asn Glu Val Phe Leu Tyr Gly Glu
    370                 375                 380

Gly Ile Ile Pro Val Arg Ser Thr Lys Pro Val Gly Thr Arg Gln Ser
385                 390                 395                 400

Lys Lys Leu Leu Glu Arg Gln Ala Ser Met Gly Pro Leu Thr Leu Ile
                405                 410                 415
```

```
Ser Cys Asp Leu Gly Gln Thr Asn Leu Ile Ala Gly Arg Ala Ser Ala
            420                 425                 430

Ile Ser Leu Thr His Gly Ser Leu Gly Val Arg Ser Ser Val Arg Ile
            435                 440                 445

Glu Leu Asp Pro Glu Ile Ile Lys Ser Phe Glu Arg Leu Arg Lys Asp
            450                 455                 460

Ala Asp Arg Leu Glu Thr Glu Ile Leu Thr Ala Ala Lys Glu Thr Leu
465                 470                 475                 480

Ser Asp Glu Gln Arg Gly Glu Val Asn Ser His Glu Lys Asp Ser Pro
            485                 490                 495

Gln Thr Ala Lys Ala Ser Leu Cys Arg Glu Leu Gly Leu His Pro Pro
            500                 505                 510

Ser Leu Pro Trp Gly Gln Met Gly Pro Ser Thr Thr Phe Ile Ala Asp
            515                 520                 525

Met Leu Ile Ser His Gly Arg Asp Asp Ala Phe Leu Ser His Gly
            530                 535                 540

Glu Phe Pro Thr Leu Glu Lys Arg Lys Phe Asp Lys Arg Phe Cys
545                 550                 555                 560

Leu Glu Ser Arg Pro Leu Leu Ser Ser Glu Thr Arg Lys Ala Leu Asn
            565                 570                 575

Glu Ser Leu Trp Glu Val Lys Arg Thr Ser Ser Glu Tyr Ala Arg Leu
            580                 585                 590

Ser Gln Arg Lys Lys Glu Met Ala Arg Arg Ala Val Asn Phe Val Val
            595                 600                 605

Glu Ile Ser Arg Arg Lys Thr Gly Leu Ser Asn Val Ile Val Asn Ile
            610                 615                 620

Glu Asp Leu Asn Val Arg Ile Phe His Gly Gly Lys Gln Ala Pro
625                 630                 635                 640

Gly Trp Asp Gly Phe Phe Arg Pro Lys Ser Glu Asn Arg Trp Phe Ile
            645                 650                 655

Gln Ala Ile His Lys Ala Phe Ser Asp Leu Ala Ala His His Gly Ile
            660                 665                 670

Pro Val Ile Glu Ser Asp Pro Gln Arg Thr Ser Met Thr Cys Pro Glu
            675                 680                 685

Cys Gly His Cys Asp Ser Lys Asn Arg Asn Gly Val Arg Phe Leu Cys
            690                 695                 700

Lys Gly Cys Gly Ala Ser Met Asp Ala Asp Phe Asp Ala Ala Cys Arg
705                 710                 715                 720

Asn Leu Glu Arg Val Ala Leu Thr Gly Lys Pro Met Pro Lys Pro Ser
            725                 730                 735

Thr Ser Cys Glu Arg Leu Leu Ser Ala Thr Thr Gly Lys Val Cys Ser
            740                 745                 750

Asp His Ser Leu Ser His Asp Ala Ile Glu Lys Ala Ser
            755                 760                 765

<210> SEQ ID NO 112
<211> LENGTH: 766
<212> TYPE: PRT
<213> ORGANISM: Artificial Sequence
<220> FEATURE:
<223> OTHER INFORMATION: Synthetic sequence
```

<400> SEQUENCE: 112

```
Met Glu Lys Glu Ile Thr Glu Leu Thr Lys Ile Arg Arg Glu Phe Pro
1               5                   10                  15

Asn Lys Lys Phe Ser Ser Thr Asp Met Lys Lys Ala Gly Lys Leu Leu
            20                  25                  30

Lys Ala Glu Gly Pro Asp Ala Val Arg Asp Phe Leu Asn Ser Cys Gln
        35                  40                  45

Glu Ile Ile Gly Asp Phe Lys Pro Pro Val Lys Thr Asn Ile Val Ser
    50                  55                  60

Ile Ser Arg Pro Phe Glu Glu Trp Pro Val Ser Met Val Gly Arg Ala
65                  70                  75                  80

Ile Gln Glu Tyr Tyr Phe Ser Leu Thr Lys Glu Leu Glu Ser Val
                85                  90                  95

His Pro Gly Thr Ser Ser Glu Asp His Lys Ser Phe Phe Asn Ile Thr
            100                 105                 110

Gly Leu Ser Asn Tyr Asn Tyr Thr Ser Val Gln Gly Leu Asn Leu Ile
        115                 120                 125

Phe Lys Asn Ala Lys Ala Ile Tyr Asp Gly Thr Leu Val Lys Ala Asn
    130                 135                 140

Asn Lys Asn Lys Lys Leu Glu Lys Lys Phe Asn Glu Ile Asn His Lys
145                 150                 155                 160

Arg Ser Leu Glu Gly Leu Pro Ile Ile Thr Pro Asp Phe Glu Glu Pro
                165                 170                 175

Phe Asp Glu Asn Gly His Leu Asn Asn Pro Pro Gly Ile Asn Arg Asn
            180                 185                 190

Ile Tyr Gly Tyr Gln Gly Cys Ala Ala Lys Val Phe Val Pro Ser Lys
        195                 200                 205

His Lys Met Val Ser Leu Pro Lys Glu Tyr Gly Tyr Asn Arg Asp
    210                 215                 220

Pro Asn Leu Ser Leu Ala Gly Phe Arg Asn Arg Leu Glu Ile Pro Glu
225                 230                 235                 240

Gly Glu Pro Gly His Val Pro Trp Phe Gln Arg Met Asp Ile Pro Glu
                245                 250                 255

Gly Gln Ile Gly His Val Asn Lys Ile Gln Arg Phe Asn Phe Val His
            260                 265                 270

Gly Lys Asn Ser Gly Lys Val Lys Phe Ser Asp Lys Thr Gly Arg Val
        275                 280                 285

Lys Arg Tyr His His Ser Lys Tyr Lys Asp Ala Thr Lys Pro Tyr Lys
    290                 295                 300

Phe Leu Glu Glu Ser Lys Lys Val Ser Ala Leu Asp Ser Ile Leu Ala
305                 310                 315                 320

Ile Ile Thr Ile Gly Asp Asp Trp Val Val Phe Asp Ile Arg Gly Leu
                325                 330                 335

Tyr Arg Asn Val Phe Tyr Arg Glu Leu Ala Gln Lys Gly Leu Thr Ala
            340                 345                 350

Val Gln Leu Leu Asp Leu Phe Thr Gly Asp Pro Val Ile Asp Pro Lys
        355                 360                 365

Lys Gly Val Val Thr Phe Ser Tyr Lys Glu Gly Val Pro Val Phe
    370                 375                 380

Ser Gln Lys Ile Val Pro Arg Phe Lys Ser Arg Asp Thr Leu Glu Lys
385                 390                 395                 400

Leu Thr Ser Gln Gly Pro Val Ala Leu Leu Ser Val Asp Leu Gly Gln
                405                 410                 415
```

-continued

```
Asn Glu Pro Val Ala Ala Arg Val Cys Ser Leu Lys Asn Ile Asn Asp
            420                 425                 430

Lys Ile Thr Leu Asp Asn Ser Cys Arg Ile Ser Phe Leu Asp Asp Tyr
        435                 440                 445

Lys Lys Gln Ile Lys Asp Tyr Arg Asp Ser Leu Asp Glu Leu Glu Ile
450                 455                 460

Lys Ile Arg Leu Glu Ala Ile Asn Ser Leu Glu Thr Asn Gln Gln Val
465                 470                 475                 480

Glu Ile Arg Asp Leu Asp Val Phe Ser Ala Asp Arg Ala Lys Ala Asn
                485                 490                 495

Thr Val Asp Met Phe Asp Ile Asp Pro Asn Leu Ile Ser Trp Asp Ser
            500                 505                 510

Met Ser Asp Ala Arg Val Ser Thr Gln Ile Ser Asp Leu Tyr Leu Lys
        515                 520                 525

Asn Gly Gly Asp Glu Ser Arg Val Tyr Phe Glu Ile Asn Asn Lys Arg
530                 535                 540

Ile Lys Arg Ser Asp Tyr Asn Ile Ser Gln Leu Val Arg Pro Lys Leu
545                 550                 555                 560

Ser Asp Ser Thr Arg Lys Asn Leu Asn Asp Ser Ile Trp Lys Leu Lys
                565                 570                 575

Arg Thr Ser Glu Glu Tyr Leu Lys Leu Ser Arg Lys Leu Glu Leu
            580                 585                 590

Ser Arg Ala Val Val Asn Tyr Thr Ile Arg Gln Ser Lys Leu Leu Ser
        595                 600                 605

Gly Ile Asn Asp Ile Val Ile Leu Glu Asp Leu Asp Val Lys Lys
610                 615                 620

Lys Phe Asn Gly Arg Gly Ile Arg Asp Ile Gly Trp Asp Asn Phe Phe
625                 630                 635                 640

Ser Ser Arg Lys Glu Asn Arg Trp Phe Ile Pro Ala Phe His Lys Ala
                645                 650                 655

Phe Ser Glu Leu Ser Ser Asn Arg Gly Leu Cys Val Ile Glu Val Asn
            660                 665                 670

Pro Ala Trp Thr Ser Ala Thr Cys Pro Asp Cys Gly Phe Cys Ser Lys
        675                 680                 685

Glu Asn Arg Asp Gly Ile Asn Phe Thr Cys Arg Lys Cys Gly Val Ser
690                 695                 700

Tyr His Ala Asp Ile Asp Val Ala Thr Leu Asn Ile Ala Arg Val Ala
705                 710                 715                 720

Val Leu Gly Lys Pro Met Ser Gly Pro Ala Asp Arg Glu Arg Leu Gly
                725                 730                 735

Asp Thr Lys Lys Pro Arg Val Ala Arg Ser Lys Thr Met Lys Arg
            740                 745                 750

Lys Asp Ile Ser Asn Ser Thr Val Glu Ala Met Val Thr Ala
        755                 760                 765
```

<210> SEQ ID NO 113
<211> LENGTH: 812
<212> TYPE: PRT
<213> ORGANISM: Artificial Sequence
<220> FEATURE:
<223> OTHER INFORMATION: Synthetic sequence

<400> SEQUENCE: 113

```
Met Asp Met Leu Asp Thr Glu Thr Asn Tyr Ala Thr Glu Thr Pro Ala
1               5                   10                  15

Gln Gln Gln Asp Tyr Ser Pro Lys Pro Lys Lys Ala Gln Arg Ala
            20                  25                  30

Pro Lys Gly Phe Ser Lys Lys Ala Arg Pro Glu Lys Lys Pro Pro Lys
            35                  40                  45

Pro Ile Thr Leu Phe Thr Gln Lys His Phe Ser Gly Val Arg Phe Leu
    50                  55                  60

Lys Arg Val Ile Arg Asp Ala Ser Lys Ile Leu Lys Leu Ser Glu Ser
65                  70                  75                  80

Arg Thr Ile Thr Phe Leu Glu Gln Ala Ile Glu Arg Asp Gly Ser Ala
                85                  90                  95

Pro Pro Asp Val Thr Pro Pro Val His Asn Thr Ile Met Ala Val Thr
            100                 105                 110

Arg Pro Phe Glu Glu Trp Pro Glu Val Ile Leu Ser Lys Ala Leu Gln
            115                 120                 125

Lys His Cys Tyr Ala Leu Thr Lys Lys Ile Lys Ile Lys Thr Trp Pro
130                 135                 140

Lys Lys Gly Pro Gly Lys Lys Cys Leu Ala Ala Trp Ser Ala Arg Thr
145                 150                 155                 160

Lys Ile Pro Leu Ile Pro Gly Gln Val Gln Ala Thr Asn Gly Leu Phe
                165                 170                 175

Asp Arg Ile Gly Ser Ile Tyr Asp Gly Val Glu Lys Lys Val Thr Asn
            180                 185                 190

Arg Asn Ala Asn Lys Lys Leu Glu Tyr Asp Glu Ala Ile Lys Glu Gly
            195                 200                 205

Arg Asn Pro Ala Val Pro Glu Tyr Glu Thr Ala Tyr Asn Ile Asp Gly
    210                 215                 220

Thr Leu Ile Asn Lys Pro Gly Tyr Asn Pro Asn Leu Tyr Ile Thr Gln
225                 230                 235                 240

Ser Arg Thr Pro Arg Leu Ile Thr Glu Ala Asp Arg Pro Leu Val Glu
                245                 250                 255

Lys Ile Leu Trp Gln Met Val Glu Lys Lys Thr Gln Ser Arg Asn Gln
            260                 265                 270

Ala Arg Arg Ala Arg Leu Glu Lys Ala Ala His Leu Gln Gly Leu Pro
            275                 280                 285

Val Pro Lys Phe Val Pro Glu Lys Val Asp Arg Ser Gln Lys Ile Glu
    290                 295                 300

Ile Arg Ile Ile Asp Pro Leu Asp Lys Ile Glu Pro Tyr Met Pro Gln
305                 310                 315                 320

Asp Arg Met Ala Ile Lys Ala Ser Gln Asp Gly His Val Pro Tyr Trp
                325                 330                 335

Gln Arg Pro Phe Leu Ser Lys Arg Arg Asn Arg Arg Val Arg Ala Gly
            340                 345                 350

Trp Gly Lys Gln Val Ser Ser Ile Gln Ala Trp Leu Thr Gly Ala Leu
            355                 360                 365

Leu Val Ile Val Arg Leu Gly Asn Glu Ala Phe Leu Ala Asp Ile Arg
    370                 375                 380

Gly Ala Leu Arg Asn Ala Gln Trp Arg Lys Leu Leu Lys Pro Asp Ala
385                 390                 395                 400

Thr Tyr Gln Ser Leu Phe Asn Leu Phe Thr Gly Asp Pro Val Val Asn
                405                 410                 415
```

```
Thr Arg Thr Asn His Leu Thr Met Ala Tyr Arg Glu Gly Val Val Asn
            420                 425                 430

Ile Val Lys Ser Arg Ser Phe Lys Gly Arg Gln Thr Arg Glu His Leu
        435                 440                 445

Leu Thr Leu Leu Gly Gln Gly Lys Thr Val Ala Gly Val Ser Phe Asp
    450                 455                 460

Leu Gly Gln Lys His Ala Ala Gly Leu Ala Ala His Phe Gly Leu
465                 470                 475                 480

Gly Glu Asp Gly Asn Pro Val Phe Thr Pro Ile Gln Ala Cys Phe Leu
                485                 490                 495

Pro Gln Arg Tyr Leu Asp Ser Leu Thr Asn Tyr Arg Asn Arg Tyr Asp
            500                 505                 510

Ala Leu Thr Leu Asp Met Arg Arg Gln Ser Leu Leu Ala Leu Thr Pro
        515                 520                 525

Ala Gln Gln Gln Glu Phe Ala Asp Ala Gln Arg Asp Pro Gly Gly Gln
    530                 535                 540

Ala Lys Arg Ala Cys Cys Leu Lys Leu Asn Leu Asn Pro Asp Glu Ile
545                 550                 555                 560

Arg Trp Asp Leu Val Ser Gly Ile Ser Thr Met Ile Ser Asp Leu Tyr
                565                 570                 575

Ile Glu Arg Gly Gly Asp Pro Arg Asp Val His Gln Val Glu Thr
            580                 585                 590

Lys Pro Lys Gly Lys Arg Lys Ser Glu Ile Arg Ile Leu Lys Ile Arg
        595                 600                 605

Asp Gly Lys Trp Ala Tyr Asp Phe Arg Pro Lys Ile Ala Asp Glu Thr
    610                 615                 620

Arg Lys Ala Gln Arg Glu Gln Leu Trp Lys Leu Gln Lys Ala Ser Ser
625                 630                 635                 640

Glu Phe Glu Arg Leu Ser Arg Tyr Lys Ile Asn Ile Ala Arg Ala Ile
                645                 650                 655

Ala Asn Trp Ala Leu Gln Trp Gly Arg Glu Leu Ser Gly Cys Asp Ile
            660                 665                 670

Val Ile Pro Val Leu Glu Asp Leu Asn Val Gly Ser Lys Phe Phe Asp
        675                 680                 685

Gly Lys Gly Lys Trp Leu Leu Gly Trp Asp Asn Arg Phe Thr Pro Lys
    690                 695                 700

Lys Glu Asn Arg Trp Phe Ile Lys Val Leu His Lys Ala Val Ala Glu
705                 710                 715                 720

Leu Ala Pro His Arg Gly Val Pro Val Tyr Glu Val Met Pro His Arg
                725                 730                 735

Thr Ser Met Thr Cys Pro Ala Cys His Tyr Cys His Pro Thr Asn Arg
            740                 745                 750

Glu Gly Asp Arg Phe Glu Cys Gln Ser Cys His Val Val Lys Asn Thr
        755                 760                 765

Asp Arg Asp Val Ala Pro Tyr Asn Ile Leu Arg Val Ala Val Glu Gly
    770                 775                 780

Lys Thr Leu Asp Arg Trp Gln Ala Glu Lys Lys Pro Gln Ala Glu Pro
785                 790                 795                 800

Asp Arg Pro Met Ile Leu Ile Asp Asn Gln Glu Ser
                805                 810
```

-continued

```
<210> SEQ ID NO 114
<211> LENGTH: 812
<212> TYPE: PRT
<213> ORGANISM: Artificial Sequence
<220> FEATURE:
<223> OTHER INFORMATION: Synthetic sequence

<400> SEQUENCE: 114

Met Asp Met Leu Asp Thr Glu Thr Asn Tyr Ala Thr Glu Thr Pro Ala
1               5                   10                  15

Gln Gln Gln Asp Tyr Ser Pro Lys Pro Lys Lys Ala Gln Arg Ala
            20                  25                  30

Pro Lys Gly Phe Ser Lys Lys Ala Arg Pro Glu Lys Lys Pro Pro Lys
        35                  40                  45

Pro Ile Thr Leu Phe Thr Gln Lys His Phe Ser Gly Val Arg Phe Leu
    50                  55                  60

Lys Arg Val Ile Arg Asp Ala Ser Lys Ile Leu Lys Leu Ser Glu Ser
65                  70                  75                  80

Arg Thr Ile Thr Phe Leu Glu Gln Ala Ile Glu Arg Asp Gly Ser Ala
                85                  90                  95

Pro Pro Asp Val Thr Pro Pro Val His Asn Thr Ile Met Ala Val Thr
            100                 105                 110

Arg Pro Phe Glu Glu Trp Pro Glu Val Ile Leu Ser Lys Ala Leu Gln
        115                 120                 125

Lys His Cys Tyr Ala Leu Thr Lys Lys Ile Lys Ile Lys Thr Trp Pro
    130                 135                 140

Lys Lys Gly Pro Gly Lys Lys Cys Leu Ala Ala Trp Ser Ala Arg Thr
145                 150                 155                 160

Lys Ile Pro Leu Ile Pro Gly Gln Val Gln Ala Thr Asn Gly Leu Phe
                165                 170                 175

Asp Arg Ile Gly Ser Ile Tyr Asp Gly Val Glu Lys Lys Val Thr Asn
            180                 185                 190

Arg Asn Ala Asn Lys Lys Leu Glu Tyr Asp Glu Ala Ile Lys Glu Gly
        195                 200                 205

Arg Asn Pro Ala Val Pro Glu Tyr Glu Thr Ala Tyr Asn Ile Asp Gly
    210                 215                 220

Thr Leu Ile Asn Lys Pro Gly Tyr Asn Pro Asn Leu Tyr Ile Thr Gln
225                 230                 235                 240

Ser Arg Thr Pro Arg Leu Ile Thr Glu Ala Asp Arg Pro Leu Val Glu
                245                 250                 255

Lys Ile Leu Trp Gln Met Val Glu Lys Lys Thr Gln Ser Arg Asn Gln
            260                 265                 270

Ala Arg Arg Ala Arg Leu Glu Lys Ala Ala His Leu Gln Gly Leu Pro
        275                 280                 285

Val Pro Lys Phe Val Pro Glu Lys Val Asp Arg Ser Gln Lys Ile Glu
    290                 295                 300

Ile Arg Ile Ile Asp Pro Leu Asp Lys Ile Glu Pro Tyr Met Pro Gln
305                 310                 315                 320

Asp Arg Met Ala Ile Lys Ala Ser Gln Asp Gly His Val Pro Tyr Trp
                325                 330                 335

Gln Arg Pro Phe Leu Ser Lys Arg Arg Asn Arg Val Arg Ala Gly
        340                 345                 350

Trp Gly Lys Gln Val Ser Ser Ile Gln Ala Trp Leu Thr Gly Ala Leu
    355                 360                 365
```

```
Leu Val Ile Val Arg Leu Gly Asn Glu Ala Phe Leu Ala Asp Ile Arg
370                 375                 380
Gly Ala Leu Arg Asn Ala Gln Trp Arg Lys Leu Leu Lys Pro Asp Ala
385                 390                 395                 400
Thr Tyr Gln Ser Leu Phe Asn Leu Phe Thr Gly Asp Pro Val Val Asn
                405                 410                 415
Thr Arg Thr Asn His Leu Thr Met Ala Tyr Arg Glu Gly Val Val Asp
                420                 425                 430
Ile Val Lys Ser Arg Ser Phe Lys Gly Arg Gln Thr Arg Glu His Leu
                435                 440                 445
Leu Thr Leu Leu Gly Gln Gly Lys Thr Val Ala Gly Val Ser Phe Asp
450                 455                 460
Leu Gly Gln Lys His Ala Ala Gly Leu Leu Ala Ala His Phe Gly Leu
465                 470                 475                 480
Gly Glu Asp Gly Asn Pro Val Phe Thr Pro Ile Gln Ala Cys Phe Leu
                485                 490                 495
Pro Gln Arg Tyr Leu Asp Ser Leu Thr Asn Tyr Arg Asn Arg Tyr Asp
                500                 505                 510
Ala Leu Thr Leu Asp Met Arg Arg Gln Ser Leu Leu Ala Leu Thr Pro
                515                 520                 525
Ala Gln Gln Gln Glu Phe Ala Asp Ala Gln Arg Asp Pro Gly Gly Gln
530                 535                 540
Ala Lys Arg Ala Cys Cys Leu Lys Leu Asn Leu Asn Pro Asp Glu Ile
545                 550                 555                 560
Arg Trp Asp Leu Val Ser Gly Ile Ser Thr Met Ile Ser Asp Leu Tyr
                565                 570                 575
Ile Glu Arg Gly Gly Asp Pro Arg Asp Val His Gln Gln Val Glu Thr
                580                 585                 590
Lys Pro Lys Gly Lys Arg Lys Ser Glu Ile Arg Ile Leu Lys Ile Arg
                595                 600                 605
Asp Gly Lys Trp Ala Tyr Asp Phe Arg Pro Lys Ile Ala Asp Glu Thr
                610                 615                 620
Arg Lys Ala Gln Arg Glu Gln Leu Trp Lys Leu Gln Lys Ala Ser Ser
625                 630                 635                 640
Glu Phe Glu Arg Leu Ser Arg Tyr Lys Ile Asn Ile Ala Arg Ala Ile
                645                 650                 655
Ala Asn Trp Ala Leu Gln Trp Gly Arg Glu Leu Ser Gly Cys Asp Ile
                660                 665                 670
Val Ile Pro Val Leu Glu Asp Leu Asn Val Gly Ser Lys Phe Phe Asp
                675                 680                 685
Gly Lys Gly Lys Trp Leu Leu Gly Trp Asp Asn Arg Phe Thr Pro Lys
                690                 695                 700
Lys Glu Asn Arg Trp Phe Ile Lys Val Leu His Lys Ala Val Ala Glu
705                 710                 715                 720
Leu Ala Pro His Lys Gly Val Pro Val Tyr Glu Val Met Pro His Arg
                725                 730                 735
Thr Ser Met Thr Cys Pro Ala Cys His Tyr Cys His Pro Thr Asn Arg
                740                 745                 750
Glu Gly Asp Arg Phe Glu Cys Gln Ser Cys His Val Val Lys Asn Thr
                755                 760                 765
Asp Arg Asp Val Ala Pro Tyr Asn Ile Leu Arg Val Ala Val Glu Gly
770                 775                 780
```

Lys Thr Leu Asp Arg Trp Gln Ala Glu Lys Lys Pro Gln Ala Glu Pro
785                 790                 795                 800

Asp Arg Pro Met Ile Leu Ile Asp Asn Gln Glu Ser
            805                 810

<210> SEQ ID NO 115
<211> LENGTH: 793
<212> TYPE: PRT
<213> ORGANISM: Artificial Sequence
<220> FEATURE:
<223> OTHER INFORMATION: Synthetic sequence

<400> SEQUENCE: 115

Met Ser Ser Leu Pro Thr Pro Leu Glu Leu Leu Lys Gln Lys His Ala
1               5                   10                  15

Asp Leu Phe Lys Gly Leu Gln Phe Ser Ser Lys Asp Asn Lys Met Ala
            20                  25                  30

Gly Lys Val Leu Lys Lys Asp Gly Glu Glu Ala Ala Leu Ala Phe Leu
        35                  40                  45

Ser Glu Arg Gly Val Ser Arg Gly Leu Pro Asn Phe Arg Pro Pro
    50                  55                  60

Ala Lys Thr Leu Val Val Ala Gln Ser Arg Pro Phe Glu Glu Phe Pro
65                  70                  75                  80

Ile Tyr Arg Val Ser Glu Ala Ile Gln Leu Tyr Val Tyr Ser Leu Ser
                85                  90                  95

Val Lys Glu Leu Glu Thr Val Pro Ser Gly Ser Ser Thr Lys Lys Glu
            100                 105                 110

His Gln Arg Phe Phe Gln Asp Ser Ser Val Pro Asp Phe Gly Tyr Thr
        115                 120                 125

Ser Val Gln Gly Leu Asn Lys Ile Phe Gly Leu Ala Arg Gly Ile Tyr
    130                 135                 140

Leu Gly Val Ile Thr Arg Gly Glu Asn Gln Leu Gln Lys Ala Lys Ser
145                 150                 155                 160

Lys His Glu Ala Leu Asn Lys Lys Arg Arg Ala Ser Gly Glu Ala Glu
                165                 170                 175

Thr Glu Phe Asp Pro Thr Pro Tyr Glu Tyr Met Thr Pro Glu Arg Lys
            180                 185                 190

Leu Ala Lys Pro Pro Gly Val Asn His Ser Ile Met Cys Tyr Val Asp
        195                 200                 205

Ile Ser Val Asp Glu Phe Asp Phe Arg Asn Pro Asp Gly Ile Val Leu
    210                 215                 220

Pro Ser Glu Tyr Ala Gly Tyr Cys Arg Glu Ile Asn Thr Ala Ile Glu
225                 230                 235                 240

Lys Gly Thr Val Asp Arg Leu Gly His Leu Lys Gly Pro Gly Tyr
                245                 250                 255

Ile Pro Gly His Gln Arg Lys Glu Ser Thr Thr Glu Gly Pro Lys Ile
            260                 265                 270

Asn Phe Arg Lys Gly Arg Ile Arg Arg Ser Tyr Thr Ala Leu Tyr Ala
        275                 280                 285

Lys Arg Asp Ser Arg Arg Val Arg Gln Gly Lys Leu Ala Leu Pro Ser
    290                 295                 300

Tyr Arg His His Met Met Arg Leu Asn Ser Asn Ala Glu Ser Ala Ile
305                 310                 315                 320

Leu Ala Val Ile Phe Phe Gly Lys Asp Trp Val Phe Asp Leu Arg
                325                 330                 335

```
Gly Leu Leu Arg Asn Val Arg Trp Arg Asn Leu Phe Val Asp Gly Ser
                340                 345                 350

Thr Pro Ser Thr Leu Leu Gly Met Phe Gly Asp Pro Val Ile Asp Pro
            355                 360                 365

Lys Arg Gly Val Val Ala Phe Cys Tyr Lys Glu Gln Ile Val Pro Val
        370                 375                 380

Val Ser Lys Ser Ile Thr Lys Met Val Lys Ala Pro Glu Leu Leu Asn
385                 390                 395                 400

Lys Leu Tyr Leu Lys Ser Glu Asp Pro Leu Val Leu Val Ala Ile Asp
                405                 410                 415

Leu Gly Gln Thr Asn Pro Val Gly Val Gly Val Tyr Arg Val Met Asn
            420                 425                 430

Ala Ser Leu Asp Tyr Glu Val Val Thr Arg Phe Ala Leu Glu Ser Glu
        435                 440                 445

Leu Leu Arg Glu Ile Glu Ser Tyr Arg Gln Arg Thr Asn Ala Phe Glu
450                 455                 460

Ala Gln Ile Arg Ala Glu Thr Phe Asp Ala Met Thr Ser Glu Glu Gln
465                 470                 475                 480

Glu Glu Ile Thr Arg Val Arg Ala Phe Ser Ala Ser Lys Ala Lys Glu
                485                 490                 495

Asn Val Cys His Arg Phe Gly Met Pro Val Asp Ala Val Asp Trp Ala
            500                 505                 510

Thr Met Gly Ser Asn Thr Ile His Ile Ala Lys Trp Val Met Arg His
        515                 520                 525

Gly Asp Pro Ser Leu Val Glu Val Leu Glu Tyr Arg Lys Asp Asn Glu
530                 535                 540

Ile Lys Leu Asp Lys Asn Gly Val Pro Lys Lys Val Lys Leu Thr Asp
545                 550                 555                 560

Lys Arg Ile Ala Asn Leu Thr Ser Ile Arg Leu Arg Phe Ser Gln Glu
                565                 570                 575

Thr Ser Lys His Tyr Asn Asp Thr Met Trp Glu Leu Arg Arg Lys His
            580                 585                 590

Pro Val Tyr Gln Lys Leu Ser Lys Ser Lys Ala Asp Phe Ser Arg Arg
        595                 600                 605

Val Val Asn Ser Ile Ile Arg Arg Val Asn His Leu Val Pro Arg Ala
610                 615                 620

Arg Ile Val Phe Ile Ile Glu Asp Leu Lys Asn Leu Gly Lys Val Phe
625                 630                 635                 640

His Gly Ser Gly Lys Arg Glu Leu Gly Trp Asp Ser Tyr Phe Glu Pro
                645                 650                 655

Lys Ser Glu Asn Arg Trp Phe Ile Gln Val Leu His Lys Ala Phe Ser
            660                 665                 670

Glu Thr Gly Lys His Lys Gly Tyr Tyr Ile Ile Glu Cys Trp Pro Asn
        675                 680                 685

Trp Thr Ser Cys Thr Cys Pro Lys Cys Ser Cys Cys Asp Ser Glu Asn
690                 695                 700

Arg His Gly Glu Val Phe Arg Cys Leu Ala Cys Gly Tyr Thr Cys Asn
705                 710                 715                 720

Thr Asp Phe Gly Thr Ala Pro Asp Asn Leu Val Lys Ile Ala Thr Thr
                725                 730                 735

Gly Lys Gly Leu Pro Gly Pro Lys Arg Cys Lys Gly Ser Ser Lys
            740                 745                 750
```

```
Gly Lys Asn Pro Lys Ile Ala Arg Ser Ser Glu Thr Gly Val Ser Val
            755                 760                 765

Thr Glu Ser Gly Ala Pro Lys Val Lys Lys Ser Pro Thr Gln Thr
770                 775                 780

Ser Gln Ser Ser Gln Ser Ala Pro
785                 790

<210> SEQ ID NO 116
<211> LENGTH: 441
<212> TYPE: PRT
<213> ORGANISM: Artificial Sequence
<220> FEATURE:
<223> OTHER INFORMATION: Synthetic sequence

<400> SEQUENCE: 116

Met Asn Lys Ile Glu Lys Glu Lys Thr Pro Leu Ala Lys Leu Met Asn
1               5                   10                  15

Glu Asn Phe Ala Gly Leu Arg Phe Pro Phe Ala Ile Ile Lys Gln Ala
            20                  25                  30

Gly Lys Lys Leu Leu Lys Glu Gly Glu Leu Lys Thr Ile Glu Tyr Met
        35                  40                  45

Thr Gly Lys Gly Ser Ile Glu Pro Leu Pro Asn Phe Lys Pro Pro Val
    50                  55                  60

Lys Cys Leu Ile Val Ala Lys Arg Arg Asp Leu Lys Tyr Phe Pro Ile
65                  70                  75                  80

Cys Lys Ala Ser Cys Glu Ile Gln Ser Tyr Val Tyr Ser Leu Asn Tyr
                85                  90                  95

Lys Asp Phe Met Asp Tyr Phe Ser Thr Pro Met Thr Ser Gln Lys Gln
            100                 105                 110

His Glu Glu Phe Phe Lys Lys Ser Gly Leu Asn Ile Glu Tyr Gln Asn
        115                 120                 125

Val Ala Gly Leu Asn Leu Ile Phe Asn Asn Val Lys Asn Thr Tyr Asn
    130                 135                 140

Gly Val Ile Leu Lys Val Lys Asn Arg Asn Glu Lys Leu Lys Lys Lys
145                 150                 155                 160

Ala Ile Lys Asn Asn Tyr Glu Phe Glu Glu Ile Lys Thr Phe Asn Asp
                165                 170                 175

Asp Gly Cys Leu Ile Asn Lys Pro Gly Ile Asn Asn Val Ile Tyr Cys
            180                 185                 190

Phe Gln Ser Ile Ser Pro Lys Ile Leu Lys Asn Ile Thr His Leu Pro
        195                 200                 205

Lys Glu Tyr Asn Asp Tyr Asp Cys Ser Val Asp Arg Asn Ile Ile Gln
    210                 215                 220

Lys Tyr Val Ser Arg Leu Asp Ile Pro Glu Ser Gln Pro Gly His Val
225                 230                 235                 240

Pro Glu Trp Gln Arg Lys Leu Pro Glu Phe Asn Asn Thr Asn Asn Pro
                245                 250                 255

Arg Arg Arg Arg Lys Trp Tyr Ser Asn Gly Arg Asn Ile Ser Lys Gly
            260                 265                 270

Tyr Ser Val Asp Gln Val Asn Gln Ala Lys Ile Glu Asp Ser Leu Leu
        275                 280                 285

Ala Gln Ile Lys Ile Gly Glu Asp Trp Ile Ile Leu Asp Ile Arg Gly
    290                 295                 300

Leu Leu Arg Asp Leu Asn Arg Arg Glu Leu Ile Ser Tyr Lys Asn Lys
305                 310                 315                 320
```

```
Leu Thr Ile Lys Asp Val Leu Gly Phe Phe Ser Asp Tyr Pro Ile Ile
                325                 330                 335

Asp Ile Lys Lys Asn Leu Val Thr Phe Cys Tyr Lys Glu Gly Val Ile
            340                 345                 350

Gln Val Val Ser Gln Lys Ser Ile Gly Asn Lys Lys Ser Lys Gln Leu
        355                 360                 365

Leu Glu Lys Leu Ile Glu Asn Lys Pro Ile Ala Leu Val Ser Ile Asp
    370                 375                 380

Leu Gly Gln Thr Asn Pro Val Ser Val Lys Ile Ser Lys Leu Asn Lys
385                 390                 395                 400

Ile Asn Asn Lys Ile Ser Ile Glu Ser Phe Thr Tyr Arg Phe Leu Asn
                405                 410                 415

Glu Glu Ile Leu Lys Glu Ile Glu Lys Tyr Arg Lys Asp Tyr Asp Lys
            420                 425                 430

Leu Glu Leu Lys Leu Ile Asn Glu Ala
        435                 440

<210> SEQ ID NO 117
<211> LENGTH: 812
<212> TYPE: PRT
<213> ORGANISM: Artificial Sequence
<220> FEATURE:
<223> OTHER INFORMATION: Synthetic sequence

<400> SEQUENCE: 117

Met Asp Met Leu Asp Thr Glu Thr Asn Tyr Ala Thr Glu Thr Pro Ser
1               5                   10                  15

Gln Gln Gln Asp Tyr Ser Pro Lys Pro Pro Lys Asp Arg Arg Ala
            20                  25                  30

Pro Lys Gly Phe Ser Lys Lys Ala Arg Pro Glu Lys Lys Pro Pro Lys
        35                  40                  45

Pro Ile Thr Leu Phe Thr Gln Lys His Phe Ser Gly Val Arg Phe Leu
    50                  55                  60

Lys Arg Val Ile Arg Asp Ala Ser Lys Ile Leu Lys Leu Ser Glu Ser
65                  70                  75                  80

Arg Thr Ile Thr Phe Leu Glu Gln Ala Ile Glu Arg Asp Gly Ser Ala
                85                  90                  95

Pro Pro Asp Val Thr Pro Val His Asn Thr Ile Met Ala Val Thr
            100                 105                 110

Arg Pro Phe Glu Glu Trp Pro Glu Val Ile Leu Ser Lys Ala Leu Gln
        115                 120                 125

Lys His Cys Tyr Ala Leu Thr Lys Lys Ile Lys Ile Lys Thr Trp Pro
    130                 135                 140

Lys Lys Gly Pro Gly Lys Lys Cys Leu Ala Ala Trp Ser Ala Arg Thr
145                 150                 155                 160

Lys Ile Pro Leu Ile Pro Gly Gln Val Gln Ala Thr Asn Gly Leu Phe
                165                 170                 175

Asp Arg Ile Gly Ser Ile Tyr Asp Gly Val Glu Lys Val Thr Asn
            180                 185                 190

Arg Asn Ala Asn Lys Leu Glu Tyr Asp Ala Ile Lys Glu Gly
        195                 200                 205

Arg Asn Pro Ala Val Pro Glu Tyr Glu Thr Ala Tyr Asn Ile Asp Gly
    210                 215                 220

Thr Leu Ile Asn Lys Pro Gly Tyr Asn Pro Asn Leu Tyr Ile Thr Gln
225                 230                 235                 240
```

```
Ser Arg Thr Pro Arg Leu Ile Thr Glu Ala Asp Arg Pro Leu Val Glu
            245                 250                 255

Lys Ile Leu Trp Gln Met Val Glu Lys Lys Thr Gln Ser Arg Asn Gln
        260                 265                 270

Ala Arg Arg Ala Arg Leu Glu Lys Ala Ala His Leu Gln Gly Leu Pro
        275                 280                 285

Val Pro Lys Phe Val Pro Glu Lys Val Asp Arg Ser Gln Lys Ile Glu
        290                 295                 300

Ile Arg Ile Ile Asp Pro Leu Asp Lys Ile Glu Pro Tyr Met Pro Gln
305                 310                 315                 320

Asp Arg Met Ala Ile Lys Ala Ser Gln Asp Gly His Val Pro Tyr Trp
                325                 330                 335

Gln Arg Pro Phe Leu Ser Lys Arg Arg Asn Arg Arg Val Arg Ala Gly
            340                 345                 350

Trp Gly Lys Gln Val Ser Ser Ile Gln Ala Trp Leu Thr Gly Ala Leu
        355                 360                 365

Leu Val Ile Val Arg Leu Gly Asn Glu Ala Phe Leu Ala Asp Ile Arg
        370                 375                 380

Gly Ala Leu Arg Asn Ala Gln Trp Arg Lys Leu Leu Lys Pro Asp Ala
385                 390                 395                 400

Thr Tyr Gln Ser Leu Phe Asn Leu Phe Thr Gly Asp Pro Val Val Asn
                405                 410                 415

Thr Arg Thr Asn His Leu Thr Met Ala Tyr Arg Glu Gly Val Val Asp
                420                 425                 430

Ile Val Lys Ser Arg Ser Phe Lys Gly Arg Gln Thr Arg Glu His Leu
            435                 440                 445

Leu Thr Leu Leu Gly Gln Gly Lys Thr Val Ala Gly Val Ser Phe Asp
        450                 455                 460

Leu Gly Gln Lys His Ala Ala Gly Leu Leu Ala Ala His Phe Gly Leu
465                 470                 475                 480

Gly Glu Asp Gly Asn Pro Val Phe Thr Pro Ile Gln Ala Cys Phe Leu
                485                 490                 495

Pro Gln Arg Tyr Leu Asp Ser Leu Thr Asn Tyr Arg Asn Arg Tyr Asp
            500                 505                 510

Ala Leu Thr Leu Asp Met Arg Arg Gln Ser Leu Leu Ala Leu Thr Pro
        515                 520                 525

Ala Gln Gln Gln Glu Phe Ala Asp Ala Gln Arg Asp Pro Gly Gly Gln
        530                 535                 540

Ala Lys Arg Ala Cys Cys Leu Lys Leu Asn Leu Asn Pro Asp Glu Ile
545                 550                 555                 560

Arg Trp Asp Leu Val Ser Gly Ile Ser Thr Met Ile Ser Asp Leu Tyr
                565                 570                 575

Ile Glu Arg Gly Gly Asp Pro Arg Asp Val His Gln Gln Val Glu Thr
            580                 585                 590

Lys Pro Lys Gly Lys Arg Lys Ser Glu Ile Arg Ile Leu Lys Ile Arg
        595                 600                 605

Asp Gly Lys Trp Ala Tyr Asp Phe Arg Pro Lys Ile Ala Asp Glu Thr
        610                 615                 620

Arg Lys Ala Gln Arg Glu Gln Leu Trp Lys Leu Gln Lys Ala Ser Ser
625                 630                 635                 640

Glu Phe Glu Arg Leu Ser Arg Tyr Lys Ile Asn Ile Ala Arg Ala Ile
                645                 650                 655
```

```
Ala Asn Trp Ala Leu Gln Trp Gly Arg Glu Leu Ser Gly Cys Asp Ile
            660                 665                 670

Val Ile Pro Val Leu Glu Asp Leu Asn Val Gly Ser Lys Phe Phe Asp
        675                 680                 685

Gly Lys Gly Lys Trp Leu Leu Gly Trp Asp Asn Arg Phe Thr Pro Lys
    690                 695                 700

Lys Glu Asn Arg Trp Phe Ile Lys Val Leu His Lys Ala Val Ala Glu
705                 710                 715                 720

Leu Ala Pro His Arg Gly Val Pro Val Tyr Glu Val Met Pro His Arg
                725                 730                 735

Thr Ser Met Thr Cys Pro Ala Cys His Tyr Cys His Pro Thr Asn Arg
            740                 745                 750

Glu Gly Asp Arg Phe Glu Cys Gln Ser Cys His Val Val Lys Asn Thr
        755                 760                 765

Asp Arg Asp Val Ala Pro Tyr Asn Ile Leu Arg Val Ala Val Glu Gly
    770                 775                 780

Lys Thr Leu Asp Arg Trp Gln Ala Glu Lys Lys Pro Gln Ala Glu Pro
785                 790                 795                 800

Asp Arg Pro Met Ile Leu Ile Asp Asn Gln Glu Ser
                805                 810
```

<210> SEQ ID NO 118
<211> LENGTH: 812
<212> TYPE: PRT
<213> ORGANISM: Artificial Sequence
<220> FEATURE:
<223> OTHER INFORMATION: Synthetic sequence

<400> SEQUENCE: 118

```
Met Asp Met Leu Asp Thr Glu Thr Asn Tyr Ala Thr Glu Thr Pro Ser
1               5                   10                  15

Gln Gln Gln Asp Tyr Ser Pro Lys Pro Lys Lys Asp Arg Arg Ala
                20                  25                  30

Pro Lys Gly Phe Ser Lys Lys Ala Arg Pro Glu Lys Lys Pro Pro Lys
            35                  40                  45

Pro Ile Thr Leu Phe Thr Gln Lys His Phe Ser Gly Val Arg Phe Leu
        50                  55                  60

Lys Arg Val Ile Arg Asp Ala Ser Lys Ile Leu Lys Leu Ser Glu Ser
65                  70                  75                  80

Arg Thr Ile Thr Phe Leu Glu Gln Ala Ile Glu Arg Asp Gly Ser Ala
                85                  90                  95

Pro Pro Asp Val Thr Pro Val His Asn Thr Ile Met Ala Val Thr
            100                 105                 110

Arg Pro Phe Glu Glu Trp Pro Glu Val Ile Leu Ser Lys Ala Leu Gln
        115                 120                 125

Lys His Cys Tyr Ala Leu Thr Lys Lys Ile Lys Ile Lys Thr Trp Pro
    130                 135                 140

Lys Lys Gly Pro Gly Lys Lys Cys Leu Ala Ala Trp Ser Ala Arg Thr
145                 150                 155                 160

Lys Ile Pro Leu Ile Pro Gly Gln Val Gln Ala Thr Asn Gly Leu Phe
                165                 170                 175

Asp Arg Ile Gly Ser Ile Tyr Asp Gly Val Glu Lys Lys Val Thr Asn
            180                 185                 190

Arg Asn Ala Asn Lys Lys Leu Glu Tyr Asp Glu Ala Ile Lys Glu Gly
        195                 200                 205
```

```
Arg Asn Pro Ala Val Pro Glu Tyr Glu Thr Ala Tyr Asn Ile Asp Gly
    210                 215                 220

Thr Leu Ile Asn Lys Pro Gly Tyr Asn Pro Asn Leu Tyr Ile Thr Gln
225                 230                 235                 240

Ser Arg Thr Pro Arg Leu Ile Thr Glu Ala Asp Arg Pro Leu Val Glu
                245                 250                 255

Lys Ile Leu Trp Gln Met Val Glu Lys Thr Gln Ser Arg Asn Gln
            260                 265                 270

Ala Arg Ala Arg Leu Glu Lys Ala His Leu Gln Gly Leu Pro
        275                 280                 285

Val Pro Lys Phe Val Pro Glu Lys Val Asp Arg Ser Gln Lys Ile Glu
290                 295                 300

Ile Arg Ile Ile Asp Pro Leu Asp Lys Ile Glu Pro Tyr Met Pro Gln
305                 310                 315                 320

Asp Arg Met Ala Ile Lys Ala Ser Gln Asp Gly His Val Pro Tyr Trp
                325                 330                 335

Gln Arg Pro Phe Leu Ser Lys Arg Arg Asn Arg Val Arg Ala Gly
            340                 345                 350

Trp Gly Lys Gln Val Ser Ser Ile Gln Ala Trp Leu Thr Gly Ala Leu
        355                 360                 365

Leu Val Ile Val Arg Leu Gly Asn Glu Ala Phe Leu Ala Asp Ile Arg
    370                 375                 380

Gly Ala Leu Arg Asn Ala Gln Trp Arg Lys Leu Leu Lys Pro Asp Ala
385                 390                 395                 400

Thr Tyr Gln Ser Leu Phe Asn Leu Phe Thr Gly Asp Pro Val Val Asn
                405                 410                 415

Thr Arg Thr Asn His Leu Thr Met Ala Tyr Arg Glu Gly Val Val Asn
                420                 425                 430

Ile Val Lys Ser Arg Ser Phe Lys Gly Arg Gln Thr Arg Glu His Leu
            435                 440                 445

Leu Thr Leu Leu Gly Gln Gly Lys Thr Val Ala Gly Val Ser Phe Asp
450                 455                 460

Leu Gly Gln Lys His Ala Ala Gly Leu Leu Ala Ala His Phe Gly Leu
465                 470                 475                 480

Gly Glu Asp Gly Asn Pro Val Phe Thr Pro Ile Gln Ala Cys Phe Leu
                485                 490                 495

Pro Gln Arg Tyr Leu Asp Ser Leu Thr Asn Tyr Arg Asn Arg Tyr Asp
            500                 505                 510

Ala Leu Thr Leu Asp Met Arg Arg Gln Ser Leu Leu Ala Leu Thr Pro
            515                 520                 525

Ala Gln Gln Gln Glu Phe Ala Asp Ala Gln Arg Asp Pro Gly Gly Gln
530                 535                 540

Ala Lys Arg Ala Cys Cys Leu Lys Leu Asn Leu Asn Pro Asp Glu Ile
545                 550                 555                 560

Arg Trp Asp Leu Val Ser Gly Ile Ser Thr Met Ile Ser Asp Leu Tyr
                565                 570                 575

Ile Glu Arg Gly Gly Asp Pro Arg Asp Val His Gln Val Glu Thr
            580                 585                 590

Lys Pro Lys Gly Lys Arg Lys Ser Glu Ile Arg Ile Leu Lys Ile Arg
            595                 600                 605

Asp Gly Lys Trp Ala Tyr Asp Phe Arg Pro Lys Ile Ala Asp Glu Thr
610                 615                 620
```

```
Arg Lys Ala Gln Arg Glu Gln Leu Trp Lys Leu Gln Lys Ala Ser Ser
625                 630                 635                 640

Glu Phe Glu Arg Leu Ser Arg Tyr Lys Ile Asn Ile Ala Arg Ala Ile
            645                 650                 655

Ala Asn Trp Ala Leu Gln Trp Gly Arg Glu Leu Ser Gly Cys Asp Ile
        660                 665                 670

Val Ile Pro Val Leu Glu Asp Leu Asn Val Gly Ser Lys Phe Phe Asp
    675                 680                 685

Gly Lys Gly Lys Trp Leu Leu Gly Trp Asp Asn Arg Phe Thr Pro Lys
690                 695                 700

Lys Glu Asn Arg Trp Phe Ile Lys Val Leu His Lys Ala Val Ala Glu
705                 710                 715                 720

Leu Ala Pro His Arg Gly Val Pro Val Tyr Glu Val Met Pro His Arg
            725                 730                 735

Thr Ser Met Thr Cys Pro Ala Cys His Tyr Cys His Pro Thr Asn Arg
        740                 745                 750

Glu Gly Asp Arg Phe Glu Cys Gln Ser Cys His Val Val Lys Asn Thr
    755                 760                 765

Asp Arg Asp Val Ala Pro Tyr Asn Ile Leu Arg Val Ala Val Glu Gly
770                 775                 780

Lys Thr Leu Asp Arg Trp Gln Ala Glu Lys Lys Pro Gln Ala Glu Pro
785                 790                 795                 800

Asp Arg Pro Met Ile Leu Ile Asp Asn Gln Glu Ser
            805                 810
```

<210> SEQ ID NO 119
<211> LENGTH: 772
<212> TYPE: PRT
<213> ORGANISM: Artificial Sequence
<220> FEATURE:
<223> OTHER INFORMATION: Synthetic sequence

<400> SEQUENCE: 119

```
Met Ser Asn Thr Ala Val Ser Thr Arg Glu His Met Ser Asn Lys Thr
1               5                   10                  15

Thr Pro Pro Ser Pro Leu Ser Leu Leu Leu Arg Ala His Phe Pro Gly
            20                  25                  30

Leu Lys Phe Glu Ser Gln Asp Tyr Lys Ile Ala Gly Lys Lys Leu Arg
        35                  40                  45

Asp Gly Gly Pro Glu Ala Val Ile Ser Tyr Leu Thr Gly Lys Gly Gln
    50                  55                  60

Ala Lys Leu Lys Asp Val Lys Pro Pro Ala Lys Ala Phe Val Ile Ala
65                  70                  75                  80

Gln Ser Arg Pro Phe Ile Glu Trp Asp Leu Val Arg Val Ser Arg Gln
            85                  90                  95

Ile Gln Glu Lys Ile Phe Gly Ile Pro Ala Thr Lys Gly Arg Pro Lys
        100                 105                 110

Gln Asp Gly Leu Ser Glu Thr Ala Phe Asn Glu Ala Val Ala Ser Leu
    115                 120                 125

Glu Val Asp Gly Lys Ser Lys Leu Asn Glu Glu Thr Arg Ala Ala Phe
130                 135                 140

Tyr Glu Val Leu Gly Leu Asp Ala Pro Ser Leu His Ala Gln Ala Gln
145                 150                 155                 160

Asn Ala Leu Ile Lys Ser Ala Ile Ser Ile Arg Glu Gly Val Leu Lys
            165                 170                 175
```

-continued

Lys Val Glu Asn Arg Asn Glu Lys Asn Leu Ser Lys Thr Lys Arg Arg
              180                 185                 190

Lys Glu Ala Gly Glu Ala Thr Phe Val Glu Lys Ala His Asp
        195                 200                 205

Glu Arg Gly Tyr Leu Ile His Pro Pro Gly Val Asn Gln Thr Ile Pro
    210                 215                 220

Gly Tyr Gln Ala Val Val Ile Lys Ser Cys Pro Ser Asp Phe Ile Gly
225                 230                 235                 240

Leu Pro Ser Gly Cys Leu Ala Lys Glu Ser Ala Glu Ala Leu Thr Asp
                245                 250                 255

Tyr Leu Pro His Asp Arg Met Thr Ile Pro Lys Gly Gln Pro Gly Tyr
            260                 265                 270

Val Pro Glu Trp Gln His Pro Leu Leu Asn Arg Arg Lys Asn Arg Arg
        275                 280                 285

Arg Arg Asp Trp Tyr Ser Ala Ser Leu Asn Lys Pro Lys Ala Thr Cys
    290                 295                 300

Ser Lys Arg Ser Gly Thr Pro Asn Arg Lys Asn Ser Arg Thr Asp Gln
305                 310                 315                 320

Ile Gln Ser Gly Arg Phe Lys Gly Ala Ile Pro Val Leu Met Arg Phe
                325                 330                 335

Gln Asp Glu Trp Val Ile Ile Asp Ile Arg Gly Leu Leu Arg Asn Ala
            340                 345                 350

Arg Tyr Arg Lys Leu Leu Lys Glu Lys Ser Thr Ile Pro Asp Leu Leu
        355                 360                 365

Ser Leu Phe Thr Gly Asp Pro Ser Ile Asp Met Arg Gln Gly Val Cys
    370                 375                 380

Thr Phe Ile Tyr Lys Ala Gly Gln Ala Cys Ser Ala Lys Met Val Lys
385                 390                 395                 400

Thr Lys Asn Ala Pro Glu Ile Leu Ser Glu Leu Thr Lys Ser Gly Pro
                405                 410                 415

Val Val Leu Val Ser Ile Asp Leu Gly Gln Thr Asn Pro Ile Ala Ala
            420                 425                 430

Lys Val Ser Arg Val Thr Gln Leu Ser Asp Gly Gln Leu Ser His Glu
        435                 440                 445

Thr Leu Leu Arg Glu Leu Leu Ser Asn Asp Ser Ser Asp Gly Lys Glu
    450                 455                 460

Ile Ala Arg Tyr Arg Val Ala Ser Asp Arg Leu Arg Asp Lys Leu Ala
465                 470                 475                 480

Asn Leu Ala Val Glu Arg Leu Ser Pro Glu His Lys Ser Glu Ile Leu
                485                 490                 495

Arg Ala Lys Asn Asp Thr Pro Ala Leu Cys Lys Ala Arg Val Cys Ala
            500                 505                 510

Ala Leu Gly Leu Asn Pro Glu Met Ile Ala Trp Asp Lys Met Thr Pro
        515                 520                 525

Tyr Thr Glu Phe Leu Ala Thr Ala Tyr Leu Glu Lys Gly Gly Asp Arg
    530                 535                 540

Lys Val Ala Thr Leu Lys Pro Lys Asn Arg Pro Glu Met Leu Arg Arg
545                 550                 555                 560

Asp Ile Lys Phe Lys Gly Thr Glu Gly Val Arg Ile Glu Val Ser Pro
                565                 570                 575

Glu Ala Ala Glu Ala Tyr Arg Glu Ala Gln Trp Asp Leu Gln Arg Thr
            580                 585                 590

Ser Pro Glu Tyr Leu Arg Leu Ser Thr Trp Lys Gln Glu Leu Thr Lys
            595                 600                 605

Arg Ile Leu Asn Gln Leu Arg His Lys Ala Ala Lys Ser Ser Gln Cys
        610                 615                 620

Glu Val Val Met Ala Phe Glu Asp Leu Asn Ile Lys Met Met His
625                 630                 635                 640

Gly Asn Gly Lys Trp Ala Asp Gly Gly Trp Asp Ala Phe Phe Ile Lys
                645                 650                 655

Lys Arg Glu Asn Arg Trp Phe Met Gln Ala Phe His Lys Ser Leu Thr
                660                 665                 670

Glu Leu Gly Ala His Lys Gly Val Pro Thr Ile Glu Val Thr Pro His
            675                 680                 685

Arg Thr Ser Ile Thr Cys Thr Lys Cys Gly His Cys Asp Lys Ala Asn
        690                 695                 700

Arg Asp Gly Glu Arg Phe Ala Cys Gln Lys Cys Gly Phe Val Ala His
705                 710                 715                 720

Ala Asp Leu Glu Ile Ala Thr Asp Asn Ile Glu Arg Val Ala Leu Thr
                725                 730                 735

Gly Lys Pro Met Pro Lys Pro Glu Ser Glu Arg Ser Gly Asp Ala Lys
            740                 745                 750

Lys Ser Val Gly Ala Arg Lys Ala Ala Phe Lys Pro Glu Glu Asp Ala
        755                 760                 765

Glu Ala Ala Glu
    770

<210> SEQ ID NO 120
<211> LENGTH: 717
<212> TYPE: PRT
<213> ORGANISM: Artificial Sequence
<220> FEATURE:
<223> OTHER INFORMATION: Synthetic sequence

<400> SEQUENCE: 120

Met Ile Lys Pro Thr Val Ser Gln Phe Leu Thr Pro Gly Phe Lys Leu
1               5                   10                  15

Ile Arg Asn His Ser Arg Thr Ala Gly Leu Lys Leu Lys Asn Glu Gly
            20                  25                  30

Glu Glu Ala Cys Lys Lys Phe Val Arg Glu Asn Glu Ile Pro Lys Asp
        35                  40                  45

Glu Cys Pro Asn Phe Gln Gly Gly Pro Ala Ile Ala Asn Ile Ile Ala
    50                  55                  60

Lys Ser Arg Glu Phe Thr Glu Trp Glu Ile Tyr Gln Ser Ser Leu Ala
65                  70                  75                  80

Ile Gln Glu Val Ile Phe Thr Leu Pro Lys Asp Lys Leu Pro Glu Pro
                85                  90                  95

Ile Leu Lys Glu Glu Trp Arg Ala Gln Trp Leu Ser Glu His Gly Leu
            100                 105                 110

Asp Thr Val Pro Tyr Lys Glu Ala Ala Gly Leu Asn Leu Ile Ile Lys
        115                 120                 125

Asn Ala Val Asn Thr Tyr Lys Gly Val Gln Val Lys Val Asp Asn Lys
    130                 135                 140

Asn Lys Asn Asn Leu Ala Lys Ile Asn Arg Lys Asn Glu Ile Ala Lys
145                 150                 155                 160

Leu Asn Gly Glu Gln Glu Ile Ser Phe Glu Glu Ile Lys Ala Phe Asp
                165                 170                 175

```
Asp Lys Gly Tyr Leu Leu Gln Lys Pro Ser Pro Asn Lys Ser Ile Tyr
            180                 185                 190
Cys Tyr Gln Ser Val Ser Pro Lys Pro Phe Ile Thr Ser Lys Tyr His
        195                 200                 205
Asn Val Asn Leu Pro Glu Glu Tyr Ile Gly Tyr Tyr Arg Lys Ser Asn
    210                 215                 220
Glu Pro Ile Val Ser Pro Tyr Gln Phe Asp Arg Leu Arg Ile Pro Ile
225                 230                 235                 240
Gly Glu Pro Gly Tyr Val Pro Lys Trp Gln Tyr Thr Phe Leu Ser Lys
                245                 250                 255
Lys Glu Asn Lys Arg Arg Lys Leu Ser Lys Arg Ile Lys Asn Val Ser
            260                 265                 270
Pro Ile Leu Gly Ile Ile Cys Ile Lys Lys Asp Trp Cys Val Phe Asp
        275                 280                 285
Met Arg Gly Leu Leu Arg Thr Asn His Trp Lys Lys Tyr His Lys Pro
    290                 295                 300
Thr Asp Ser Ile Asn Asp Leu Phe Asp Tyr Phe Thr Gly Asp Pro Val
305                 310                 315                 320
Ile Asp Thr Lys Ala Asn Val Val Arg Phe Arg Tyr Lys Met Glu Asn
                325                 330                 335
Gly Ile Val Asn Tyr Lys Pro Val Arg Glu Lys Lys Gly Lys Glu Leu
            340                 345                 350
Leu Glu Asn Ile Cys Asp Gln Asn Gly Ser Cys Lys Leu Ala Thr Val
        355                 360                 365
Asp Val Gly Gln Asn Asn Pro Val Ala Ile Gly Leu Phe Glu Leu Lys
    370                 375                 380
Lys Val Asn Gly Glu Leu Thr Lys Thr Leu Ile Ser Arg His Pro Thr
385                 390                 395                 400
Pro Ile Asp Phe Cys Asn Lys Ile Thr Ala Tyr Arg Glu Arg Tyr Asp
                405                 410                 415
Lys Leu Glu Ser Ser Ile Lys Leu Asp Ala Ile Lys Gln Leu Thr Ser
            420                 425                 430
Glu Gln Lys Ile Glu Val Asp Asn Tyr Asn Asn Asn Phe Thr Pro Gln
        435                 440                 445
Asn Thr Lys Gln Ile Val Cys Ser Lys Leu Asn Ile Asn Pro Asn Asp
    450                 455                 460
Leu Pro Trp Asp Lys Met Ile Ser Gly Thr His Phe Ile Ser Glu Lys
465                 470                 475                 480
Ala Gln Val Ser Asn Lys Ser Glu Ile Tyr Phe Thr Ser Thr Asp Lys
                485                 490                 495
Gly Lys Thr Lys Asp Val Met Lys Ser Asp Tyr Lys Trp Phe Gln Asp
            500                 505                 510
Tyr Lys Pro Lys Leu Ser Lys Glu Val Arg Asp Ala Leu Ser Asp Ile
        515                 520                 525
Glu Trp Arg Leu Arg Arg Glu Ser Leu Glu Phe Asn Lys Leu Ser Lys
    530                 535                 540
Ser Arg Glu Gln Asp Ala Arg Gln Leu Ala Asn Trp Ile Ser Ser Met
545                 550                 555                 560
Cys Asp Val Ile Gly Ile Glu Asn Leu Val Lys Lys Asn Asn Phe Phe
                565                 570                 575
Gly Gly Ser Gly Lys Arg Glu Pro Gly Trp Asp Asn Phe Tyr Lys Pro
            580                 585                 590
```

```
Lys Lys Glu Asn Arg Trp Trp Ile Asn Ala Ile His Lys Ala Leu Thr
            595                 600                 605
Glu Leu Ser Gln Asn Lys Gly Lys Arg Val Ile Leu Leu Pro Ala Met
610                 615                 620
Arg Thr Ser Ile Thr Cys Pro Lys Cys Lys Tyr Cys Asp Ser Lys Asn
625                 630                 635                 640
Arg Asn Gly Glu Lys Phe Asn Cys Leu Lys Cys Gly Ile Glu Leu Asn
                645                 650                 655
Ala Asp Ile Asp Val Ala Thr Glu Asn Leu Ala Thr Val Ala Ile Thr
                660                 665                 670
Ala Gln Ser Met Pro Lys Pro Thr Cys Glu Arg Ser Gly Asp Ala Lys
                675                 680                 685
Lys Pro Val Arg Ala Arg Lys Ala Lys Ala Pro Glu Phe His Asp Lys
            690                 695                 700
Leu Ala Pro Ser Tyr Thr Val Val Leu Arg Glu Ala Val
705                 710                 715
```

<210> SEQ ID NO 121
<211> LENGTH: 793
<212> TYPE: PRT
<213> ORGANISM: Artificial Sequence
<220> FEATURE:
<223> OTHER INFORMATION: Synthetic sequence

<400> SEQUENCE: 121

```
Met Arg Ser Ser Arg Glu Ile Gly Asp Lys Ile Leu Met Arg Gln Pro
1               5                   10                  15
Ala Glu Lys Thr Ala Phe Gln Val Phe Arg Gln Glu Val Ile Gly Thr
                20                  25                  30
Gln Lys Leu Ser Gly Gly Asp Ala Lys Thr Ala Gly Arg Leu Tyr Lys
            35                  40                  45
Gln Gly Lys Met Glu Ala Ala Arg Glu Trp Leu Leu Lys Gly Ala Arg
        50                  55                  60
Asp Asp Val Pro Pro Asn Phe Gln Pro Pro Ala Lys Cys Leu Val Val
65                  70                  75                  80
Ala Val Ser His Pro Phe Glu Glu Trp Asp Ile Ser Thr Asn His
                85                  90                  95
Asp Val Gln Ala Tyr Ile Tyr Ala Gln Pro Leu Gln Ala Glu Gly His
                100                 105                 110
Leu Asn Gly Leu Ser Glu Lys Trp Glu Asp Thr Ser Ala Asp Gln His
            115                 120                 125
Lys Leu Trp Phe Glu Lys Thr Gly Val Pro Asp Arg Gly Leu Pro Val
        130                 135                 140
Gln Ala Ile Asn Lys Ile Ala Lys Ala Ala Val Asn Arg Ala Phe Gly
145                 150                 155                 160
Val Val Arg Lys Val Glu Asn Arg Asn Glu Lys Arg Arg Ser Arg Asp
                165                 170                 175
Asn Arg Ile Ala Glu His Asn Arg Glu Asn Gly Leu Thr Glu Val Val
                180                 185                 190
Arg Glu Ala Pro Glu Val Ala Thr Asn Ala Asp Gly Phe Leu Leu His
            195                 200                 205
Pro Pro Gly Ile Asp Pro Ser Ile Leu Ser Tyr Ala Ser Val Ser Pro
        210                 215                 220
Val Pro Tyr Asn Ser Ser Lys His Ser Phe Val Arg Leu Pro Glu Glu
225                 230                 235                 240
```

```
Tyr Gln Ala Tyr Asn Val Glu Pro Asp Ala Pro Ile Pro Gln Phe Val
                245                 250                 255
Val Glu Asp Arg Phe Ala Ile Pro Pro Gly Gln Pro Gly Tyr Val Pro
            260                 265                 270
Glu Trp Gln Arg Leu Lys Cys Ser Thr Asn Lys His Arg Arg Met Arg
        275                 280                 285
Gln Trp Ser Asn Gln Asp Tyr Lys Pro Lys Ala Gly Arg Arg Ala Lys
    290                 295                 300
Pro Leu Glu Phe Gln Ala His Leu Thr Arg Glu Arg Ala Lys Gly Ala
305                 310                 315                 320
Leu Leu Val Val Met Arg Ile Lys Glu Asp Trp Val Val Phe Asp Val
                325                 330                 335
Arg Gly Leu Leu Arg Asn Val Glu Trp Arg Lys Val Leu Ser Glu Glu
            340                 345                 350
Ala Arg Glu Lys Leu Thr Leu Lys Gly Leu Leu Asp Leu Phe Thr Gly
        355                 360                 365
Asp Pro Val Ile Asp Thr Lys Arg Gly Ile Val Thr Phe Leu Tyr Lys
    370                 375                 380
Ala Glu Ile Thr Lys Ile Leu Ser Lys Arg Thr Val Lys Thr Lys Asn
385                 390                 395                 400
Ala Arg Asp Leu Leu Leu Arg Leu Thr Glu Pro Gly Glu Asp Gly Leu
                405                 410                 415
Arg Arg Glu Val Gly Leu Val Ala Val Asp Leu Gly Gln Thr His Pro
            420                 425                 430
Ile Ala Ala Ala Ile Tyr Arg Ile Gly Arg Thr Ser Ala Gly Ala Leu
        435                 440                 445
Glu Ser Thr Val Leu His Arg Gln Gly Leu Arg Glu Asp Gln Lys Glu
    450                 455                 460
Lys Leu Lys Glu Tyr Arg Lys Arg His Thr Ala Leu Asp Ser Arg Leu
465                 470                 475                 480
Arg Lys Glu Ala Phe Glu Thr Leu Ser Val Glu Gln Lys Glu Ile
                485                 490                 495
Val Thr Val Ser Gly Ser Gly Ala Gln Ile Thr Lys Asp Lys Val Cys
            500                 505                 510
Asn Tyr Leu Gly Val Asp Pro Ser Thr Leu Pro Trp Glu Lys Met Gly
        515                 520                 525
Ser Tyr Thr His Phe Ile Ser Asp Asp Phe Leu Arg Arg Gly Gly Asp
    530                 535                 540
Pro Asn Ile Val His Phe Asp Arg Gln Pro Lys Lys Gly Lys Val Ser
545                 550                 555                 560
Lys Lys Ser Gln Arg Ile Lys Arg Ser Asp Ser Gln Trp Val Gly Arg
                565                 570                 575
Met Arg Pro Arg Leu Ser Gln Glu Thr Ala Lys Ala Arg Met Glu Ala
            580                 585                 590
Asp Trp Ala Ala Gln Asn Glu Asn Glu Glu Tyr Lys Arg Leu Ala Arg
        595                 600                 605
Ser Lys Gln Glu Leu Ala Arg Trp Cys Val Asn Thr Leu Leu Gln Asn
    610                 615                 620
Thr Arg Cys Ile Thr Gln Cys Asp Glu Ile Val Val Ile Glu Asp
625                 630                 635                 640
Leu Asn Val Lys Ser Leu His Gly Lys Gly Ala Arg Glu Pro Gly Trp
                645                 650                 655
```

-continued

```
Asp Asn Phe Phe Thr Pro Lys Thr Glu Asn Arg Trp Phe Ile Gln Ile
            660                 665                 670

Leu His Lys Thr Phe Ser Glu Leu Pro Lys His Arg Gly Glu His Val
        675                 680                 685

Ile Glu Gly Cys Pro Leu Arg Thr Ser Ile Thr Cys Pro Ala Cys Ser
    690                 695                 700

Tyr Cys Asp Lys Asn Ser Arg Asn Gly Glu Lys Phe Val Cys Val Ala
705                 710                 715                 720

Cys Gly Ala Thr Phe His Ala Asp Phe Glu Val Ala Thr Tyr Asn Leu
            725                 730                 735

Val Arg Leu Ala Thr Thr Gly Met Pro Met Pro Lys Ser Leu Glu Arg
        740                 745                 750

Gln Gly Gly Gly Glu Lys Ala Gly Gly Ala Arg Lys Ala Arg Lys Lys
    755                 760                 765

Ala Lys Gln Val Glu Lys Ile Val Val Gln Ala Asn Ala Asn Val Thr
770                 775                 780

Met Asn Gly Ala Ser Leu His Ser Pro
785                 790
```

<210> SEQ ID NO 122
<211> LENGTH: 793
<212> TYPE: PRT
<213> ORGANISM: Artificial Sequence
<220> FEATURE:
<223> OTHER INFORMATION: Synthetic sequence

<400> SEQUENCE: 122

```
Met Ser Ser Leu Pro Thr Pro Leu Glu Leu Leu Lys Gln Lys His Ala
1               5                   10                  15

Asp Leu Phe Lys Gly Leu Gln Phe Ser Ser Lys Asp Asn Lys Met Ala
            20                  25                  30

Gly Lys Val Leu Lys Lys Asp Gly Glu Glu Ala Ala Leu Ala Phe Leu
        35                  40                  45

Ser Glu Arg Gly Val Ser Arg Gly Glu Leu Pro Asn Phe Arg Pro Pro
    50                  55                  60

Ala Lys Thr Leu Val Val Ala Gln Ser Arg Pro Phe Glu Glu Phe Pro
65                  70                  75                  80

Ile Tyr Arg Val Ser Glu Ala Ile Gln Leu Tyr Val Tyr Ser Leu Ser
                85                  90                  95

Val Lys Glu Leu Glu Thr Val Pro Ser Gly Ser Ser Thr Lys Lys Glu
            100                 105                 110

His Gln Arg Phe Phe Gln Asp Ser Ser Val Pro Asp Phe Gly Tyr Thr
        115                 120                 125

Ser Val Gln Gly Leu Asn Lys Ile Phe Gly Leu Ala Arg Gly Ile Tyr
    130                 135                 140

Leu Gly Val Ile Thr Arg Gly Glu Asn Gln Leu Gln Lys Ala Lys Ser
145                 150                 155                 160

Lys His Glu Ala Leu Asn Lys Lys Arg Arg Ala Ser Gly Glu Ala Glu
                165                 170                 175

Thr Glu Phe Asp Pro Thr Pro Tyr Glu Tyr Met Thr Pro Glu Arg Lys
            180                 185                 190

Leu Ala Lys Pro Pro Gly Val Asn His Ser Ile Met Cys Tyr Val Asp
        195                 200                 205

Ile Ser Val Asp Glu Phe Asp Phe Arg Asn Pro Asp Gly Ile Val Leu
    210                 215                 220
```

```
Pro Ser Glu Tyr Ala Gly Tyr Cys Arg Glu Ile Asn Thr Ala Ile Glu
225                 230                 235                 240

Lys Gly Thr Val Asp Arg Leu Gly His Leu Lys Gly Gly Pro Gly Tyr
            245                 250                 255

Ile Pro Gly His Gln Arg Lys Glu Ser Thr Thr Glu Gly Pro Lys Ile
        260                 265                 270

Asn Phe Arg Lys Gly Arg Ile Arg Arg Ser Tyr Thr Ala Leu Tyr Ala
    275                 280                 285

Lys Arg Asp Ser Arg Arg Val Arg Gln Gly Lys Leu Ala Leu Pro Ser
290                 295                 300

Tyr Arg His His Met Met Arg Leu Asn Ser Asn Ala Glu Ser Ala Ile
305                 310                 315                 320

Leu Ala Val Ile Phe Phe Gly Lys Asp Trp Val Val Phe Asp Leu Arg
                325                 330                 335

Gly Leu Leu Arg Asn Val Arg Trp Arg Asn Leu Phe Val Asp Gly Ser
            340                 345                 350

Thr Pro Ser Thr Leu Leu Gly Met Phe Gly Asp Pro Val Ile Asp Pro
        355                 360                 365

Lys Arg Gly Val Val Ala Phe Cys Tyr Lys Glu Gln Ile Val Pro Val
370                 375                 380

Val Ser Lys Ser Ile Thr Lys Met Val Lys Ala Pro Glu Leu Leu Asn
385                 390                 395                 400

Lys Leu Tyr Leu Lys Ser Glu Asp Pro Leu Val Leu Val Ala Ile Asp
                405                 410                 415

Leu Gly Gln Thr Asn Pro Val Gly Val Gly Val Tyr Arg Val Met Asn
            420                 425                 430

Ala Ser Leu Asp Tyr Glu Val Thr Arg Phe Ala Leu Glu Ser Glu
                435                 440                 445

Leu Leu Arg Glu Ile Glu Ser Tyr Arg Gln Arg Thr Asn Ala Phe Glu
            450                 455                 460

Ala Gln Ile Arg Ala Glu Thr Phe Asp Ala Met Thr Ser Glu Glu Gln
465                 470                 475                 480

Glu Glu Ile Thr Arg Val Arg Ala Phe Ser Ala Ser Lys Ala Lys Glu
                485                 490                 495

Asn Val Cys His Arg Phe Gly Met Pro Val Asp Ala Val Asp Trp Ala
            500                 505                 510

Thr Met Gly Ser Asn Thr Ile His Ile Ala Lys Trp Val Met Arg His
            515                 520                 525

Gly Asp Pro Ser Leu Val Glu Val Leu Glu Tyr Arg Lys Asp Asn Glu
530                 535                 540

Ile Lys Leu Asp Lys Asn Gly Val Pro Lys Lys Val Lys Leu Thr Asp
545                 550                 555                 560

Lys Arg Ile Ala Asn Leu Thr Ser Ile Arg Leu Arg Phe Ser Gln Glu
            565                 570                 575

Thr Ser Lys His Tyr Asn Asp Thr Met Trp Glu Leu Arg Arg Lys His
            580                 585                 590

Pro Val Tyr Gln Lys Leu Ser Lys Ser Lys Ala Asp Phe Ser Arg Arg
            595                 600                 605

Val Val Asn Ser Ile Ile Arg Arg Val Asn His Leu Val Pro Arg Ala
        610                 615                 620

Arg Ile Val Phe Ile Ile Glu Asp Leu Lys Asn Leu Gly Lys Val Phe
625                 630                 635                 640
```

His Gly Ser Gly Lys Arg Glu Leu Gly Trp Asp Ser Tyr Phe Glu Pro
              645                 650                 655

Lys Ser Glu Asn Arg Trp Phe Ile Gln Val Leu His Lys Ala Phe Ser
          660                 665                 670

Glu Thr Gly Lys His Lys Gly Tyr Tyr Ile Ile Glu Cys Trp Pro Asn
          675                 680                 685

Trp Thr Ser Cys Thr Cys Pro Lys Cys Ser Cys Cys Asp Ser Glu Asn
690                 695                 700

Arg His Gly Glu Val Phe Arg Cys Leu Ala Cys Gly Tyr Thr Cys Asn
705                 710                 715                 720

Thr Asp Phe Gly Thr Ala Pro Asp Asn Leu Val Lys Ile Ala Thr Thr
              725                 730                 735

Gly Lys Gly Leu Pro Gly Pro Lys Lys Arg Cys Lys Gly Ser Ser Lys
              740                 745                 750

Gly Lys Asn Pro Lys Ile Ala Arg Ser Ser Glu Thr Gly Val Ser Val
          755                 760                 765

Thr Glu Ser Gly Ala Pro Lys Val Lys Lys Ser Ser Pro Thr Gln Thr
770                 775                 780

Ser Gln Ser Ser Gln Ser Ala Pro
785                 790

<210> SEQ ID NO 123
<211> LENGTH: 717
<212> TYPE: PRT
<213> ORGANISM: Artificial Sequence
<220> FEATURE:
<223> OTHER INFORMATION: Synthetic sequence

<400> SEQUENCE: 123

Met Ile Lys Pro Thr Val Ser Gln Phe Leu Thr Pro Gly Phe Lys Leu
1               5                   10                  15

Ile Arg Asn His Ser Arg Thr Ala Gly Leu Lys Leu Lys Asn Glu Gly
              20                  25                  30

Glu Glu Ala Cys Lys Lys Phe Val Arg Glu Asn Glu Ile Pro Lys Asp
          35                  40                  45

Glu Cys Pro Asn Phe Gln Gly Gly Pro Ala Ile Ala Asn Ile Ile Ala
      50                  55                  60

Lys Ser Arg Glu Phe Thr Glu Trp Glu Ile Tyr Gln Ser Ser Leu Ala
65                  70                  75                  80

Ile Gln Glu Val Ile Phe Thr Leu Pro Lys Asp Lys Leu Pro Glu Pro
              85                  90                  95

Ile Leu Lys Glu Glu Trp Arg Ala Gln Trp Leu Ser Glu His Gly Leu
          100                 105                 110

Asp Thr Val Pro Tyr Lys Glu Ala Ala Gly Leu Asn Leu Ile Ile Lys
      115                 120                 125

Asn Ala Val Asn Thr Tyr Lys Gly Val Gln Val Lys Val Asp Asn Lys
130                 135                 140

Asn Lys Asn Asn Leu Ala Lys Ile Asn Arg Lys Asn Glu Ile Ala Lys
145                 150                 155                 160

Leu Asn Gly Glu Gln Glu Ile Ser Phe Glu Glu Ile Lys Ala Phe Asp
              165                 170                 175

Asp Lys Gly Tyr Leu Leu Gln Lys Pro Ser Pro Asn Lys Ser Ile Tyr
          180                 185                 190

Cys Tyr Gln Ser Val Ser Pro Lys Pro Phe Ile Thr Ser Lys Tyr His
      195                 200                 205

Asn Val Asn Leu Pro Glu Glu Tyr Ile Gly Tyr Tyr Arg Lys Ser Asn
210                 215                 220

Glu Pro Ile Val Ser Pro Tyr Gln Phe Asp Arg Leu Arg Ile Pro Ile
225                 230                 235                 240

Gly Glu Pro Gly Tyr Val Pro Lys Trp Gln Tyr Thr Phe Leu Ser Lys
            245                 250                 255

Lys Glu Asn Lys Arg Lys Leu Ser Lys Arg Ile Lys Asn Val Ser
            260                 265                 270

Pro Ile Leu Gly Ile Ile Cys Ile Lys Lys Asp Trp Cys Val Phe Asp
            275                 280                 285

Met Arg Gly Leu Leu Arg Thr Asn His Trp Lys Lys Tyr His Lys Pro
290                 295                 300

Thr Asp Ser Ile Asn Asp Leu Phe Asp Tyr Phe Thr Gly Asp Pro Val
305                 310                 315                 320

Ile Asp Thr Lys Ala Asn Val Val Arg Phe Arg Tyr Lys Met Glu Asn
            325                 330                 335

Gly Ile Val Asn Tyr Lys Pro Val Arg Glu Lys Gly Lys Glu Leu
            340                 345                 350

Leu Glu Asn Ile Cys Asp Gln Asn Gly Ser Cys Lys Leu Ala Thr Val
            355                 360                 365

Asp Val Gly Gln Asn Pro Val Ala Ile Gly Leu Phe Glu Leu Lys
370                 375                 380

Lys Val Asn Gly Glu Leu Thr Lys Thr Leu Ile Ser Arg His Pro Thr
385                 390                 395                 400

Pro Ile Asp Phe Cys Asn Lys Ile Thr Ala Tyr Arg Glu Arg Tyr Asp
            405                 410                 415

Lys Leu Glu Ser Ser Ile Lys Leu Asp Ala Ile Lys Gln Leu Thr Ser
            420                 425                 430

Glu Gln Lys Ile Glu Val Asp Asn Tyr Asn Asn Phe Thr Pro Gln
            435                 440                 445

Asn Thr Lys Gln Ile Val Cys Ser Lys Leu Asn Ile Asn Pro Asn Asp
450                 455                 460

Leu Pro Trp Asp Lys Met Ile Ser Gly Thr His Phe Ile Ser Glu Lys
465                 470                 475                 480

Ala Gln Val Ser Asn Lys Ser Glu Ile Tyr Phe Thr Ser Thr Asp Lys
            485                 490                 495

Gly Lys Thr Lys Asp Val Met Lys Ser Asp Tyr Lys Trp Phe Gln Asp
            500                 505                 510

Tyr Lys Pro Lys Leu Ser Lys Glu Val Arg Asp Ala Leu Ser Asp Ile
            515                 520                 525

Glu Trp Arg Leu Arg Arg Glu Ser Leu Glu Phe Asn Lys Leu Ser Lys
530                 535                 540

Ser Arg Glu Gln Asp Ala Arg Gln Leu Ala Asn Trp Ile Ser Ser Met
545                 550                 555                 560

Cys Asp Val Ile Gly Ile Glu Asn Leu Val Lys Lys Asn Asn Phe Phe
            565                 570                 575

Gly Gly Ser Gly Lys Arg Glu Pro Gly Trp Asp Asn Phe Tyr Lys Pro
            580                 585                 590

Lys Lys Glu Asn Arg Trp Trp Ile Asn Ala Ile His Lys Ala Leu Thr
            595                 600                 605

Glu Leu Ser Gln Asn Lys Gly Lys Arg Val Ile Leu Leu Pro Ala Met
610                 615                 620

Arg Thr Ser Ile Thr Cys Pro Lys Cys Lys Tyr Cys Asp Ser Lys Asn
625                 630                 635                 640

Arg Asn Gly Glu Lys Phe Asn Cys Leu Lys Cys Gly Ile Glu Leu Asn
            645                 650                 655

Ala Asp Ile Asp Val Ala Thr Glu Asn Leu Ala Thr Val Ala Ile Thr
        660                 665                 670

Ala Gln Ser Met Pro Lys Pro Thr Cys Glu Arg Ser Gly Asp Ala Lys
    675                 680                 685

Lys Pro Val Arg Ala Arg Lys Ala Lys Ala Pro Glu Phe His Asp Lys
690                 695                 700

Leu Ala Pro Ser Tyr Thr Val Val Leu Arg Glu Ala Val
705                 710                 715

<210> SEQ ID NO 124
<211> LENGTH: 772
<212> TYPE: PRT
<213> ORGANISM: Artificial Sequence
<220> FEATURE:
<223> OTHER INFORMATION: Synthetic sequence

<400> SEQUENCE: 124

Met Ser Asn Thr Ala Val Ser Thr Arg Glu His Met Ser Asn Lys Thr
1               5                   10                  15

Thr Pro Pro Ser Pro Leu Ser Leu Leu Arg Ala His Phe Pro Gly
            20                  25                  30

Leu Lys Phe Glu Ser Gln Asp Tyr Lys Ile Ala Gly Lys Lys Leu Arg
        35                  40                  45

Asp Gly Gly Pro Glu Ala Val Ile Ser Tyr Leu Thr Gly Lys Gly Gln
    50                  55                  60

Ala Lys Leu Lys Asp Val Lys Pro Pro Ala Lys Ala Phe Val Ile Ala
65                  70                  75                  80

Gln Ser Arg Pro Phe Ile Glu Trp Asp Leu Val Arg Val Ser Arg Gln
                85                  90                  95

Ile Gln Glu Lys Ile Phe Gly Ile Pro Ala Thr Lys Gly Arg Pro Lys
            100                 105                 110

Gln Asp Gly Leu Ser Glu Thr Ala Phe Asn Glu Ala Val Ala Ser Leu
        115                 120                 125

Glu Val Asp Gly Lys Ser Lys Leu Asn Glu Glu Thr Arg Ala Ala Phe
    130                 135                 140

Tyr Glu Val Leu Gly Leu Asp Ala Pro Ser Leu His Ala Gln Ala Gln
145                 150                 155                 160

Asn Ala Leu Ile Lys Ser Ala Ile Ser Ile Arg Glu Gly Val Leu Lys
                165                 170                 175

Lys Val Glu Asn Arg Asn Glu Lys Asn Leu Ser Lys Thr Lys Arg Arg
            180                 185                 190

Lys Glu Ala Gly Glu Glu Ala Thr Phe Val Glu Glu Lys Ala His Asp
        195                 200                 205

Glu Arg Gly Tyr Leu Ile His Pro Pro Gly Val Asn Gln Thr Ile Pro
    210                 215                 220

Gly Tyr Gln Ala Val Val Ile Lys Ser Cys Pro Ser Asp Phe Ile Gly
225                 230                 235                 240

Leu Pro Ser Gly Cys Leu Ala Lys Glu Ser Ala Glu Ala Leu Thr Asp
                245                 250                 255

Tyr Leu Pro His Asp Arg Met Thr Ile Pro Lys Gly Gln Pro Gly Tyr
            260                 265                 270

```
Val Pro Glu Trp Gln His Pro Leu Leu Asn Arg Arg Lys Asn Arg Arg
        275                 280                 285

Arg Arg Asp Trp Tyr Ser Ala Ser Leu Asn Lys Pro Lys Ala Thr Cys
290                 295                 300

Ser Lys Arg Ser Gly Thr Pro Asn Arg Lys Asn Ser Arg Thr Asp Gln
305                 310                 315                 320

Ile Gln Ser Gly Arg Phe Lys Gly Ala Ile Pro Val Leu Met Arg Phe
                    325                 330                 335

Gln Asp Glu Trp Val Ile Ile Asp Ile Arg Gly Leu Leu Arg Asn Ala
            340                 345                 350

Arg Tyr Arg Lys Leu Leu Lys Glu Lys Ser Thr Ile Pro Asp Leu Leu
        355                 360                 365

Ser Leu Phe Thr Gly Asp Pro Ser Ile Asp Met Arg Gln Gly Val Cys
370                 375                 380

Thr Phe Ile Tyr Lys Ala Gly Gln Ala Cys Ser Ala Lys Met Val Lys
385                 390                 395                 400

Thr Lys Asn Ala Pro Glu Ile Leu Ser Glu Leu Thr Lys Ser Gly Pro
                    405                 410                 415

Val Val Leu Val Ser Ile Asp Leu Gly Gln Thr Asn Pro Ile Ala Ala
            420                 425                 430

Lys Val Ser Arg Val Thr Gln Leu Ser Asp Gly Gln Leu Ser His Glu
        435                 440                 445

Thr Leu Leu Arg Glu Leu Leu Ser Asn Asp Ser Ser Asp Gly Lys Glu
450                 455                 460

Ile Ala Arg Tyr Arg Val Ala Ser Asp Arg Leu Arg Asp Lys Leu Ala
465                 470                 475                 480

Asn Leu Ala Val Glu Arg Leu Ser Pro Glu His Lys Ser Glu Ile Leu
                    485                 490                 495

Arg Ala Lys Asn Asp Thr Pro Ala Leu Cys Lys Ala Arg Val Cys Ala
            500                 505                 510

Ala Leu Gly Leu Asn Pro Glu Met Ile Ala Trp Asp Lys Met Thr Pro
        515                 520                 525

Tyr Thr Glu Phe Leu Ala Thr Ala Tyr Leu Lys Gly Gly Asp Arg
530                 535                 540

Lys Val Ala Thr Leu Lys Pro Lys Asn Arg Pro Glu Met Leu Arg Arg
545                 550                 555                 560

Asp Ile Lys Phe Lys Gly Thr Glu Gly Val Arg Ile Glu Val Ser Pro
                    565                 570                 575

Glu Ala Ala Glu Ala Tyr Arg Glu Ala Gln Trp Asp Leu Gln Arg Thr
            580                 585                 590

Ser Pro Glu Tyr Leu Arg Leu Ser Thr Trp Lys Gln Glu Leu Thr Lys
        595                 600                 605

Arg Ile Leu Asn Gln Leu Arg His Lys Ala Ala Lys Ser Ser Gln Cys
610                 615                 620

Glu Val Val Val Met Ala Phe Glu Asp Leu Asn Ile Lys Met Met His
625                 630                 635                 640

Gly Asn Gly Lys Trp Ala Asp Gly Gly Trp Asp Ala Phe Phe Ile Lys
                    645                 650                 655

Lys Arg Glu Asn Arg Trp Phe Met Gln Ala Phe His Lys Ser Leu Thr
            660                 665                 670

Glu Leu Gly Ala His Lys Gly Val Pro Thr Ile Glu Val Thr Pro His
        675                 680                 685
```

```
Arg Thr Ser Ile Thr Cys Thr Lys Cys Gly His Cys Asp Lys Ala Asn
        690                 695                 700
Arg Asp Gly Glu Arg Phe Ala Cys Gln Lys Cys Gly Phe Val Ala His
705                 710                 715                 720
Ala Asp Leu Glu Ile Ala Thr Asp Asn Ile Glu Arg Val Ala Leu Thr
                725                 730                 735
Gly Lys Pro Met Pro Lys Pro Glu Ser Glu Arg Ser Gly Asp Ala Lys
            740                 745                 750
Lys Ser Val Gly Ala Arg Lys Ala Phe Lys Pro Glu Glu Asp Ala
        755                 760                 765
Glu Ala Ala Glu
    770

<210> SEQ ID NO 125
<211> LENGTH: 765
<212> TYPE: PRT
<213> ORGANISM: Artificial Sequence
<220> FEATURE:
<223> OTHER INFORMATION: Synthetic sequence

<400> SEQUENCE: 125

Met Tyr Ser Leu Glu Met Ala Asp Leu Lys Ser Glu Pro Ser Leu Leu
1               5                   10                  15
Ala Lys Leu Leu Arg Asp Arg Phe Pro Gly Lys Tyr Trp Leu Pro Lys
            20                  25                  30
Tyr Trp Lys Leu Ala Glu Lys Lys Arg Leu Thr Gly Gly Glu Glu Ala
        35                  40                  45
Ala Cys Glu Tyr Met Ala Asp Lys Gln Leu Asp Ser Pro Pro Pro Asn
    50                  55                  60
Phe Arg Pro Pro Ala Arg Cys Val Ile Leu Ala Lys Ser Arg Pro Phe
65                  70                  75                  80
Glu Asp Trp Pro Val His Arg Val Ala Ser Lys Ala Gln Ser Phe Val
                85                  90                  95
Ile Gly Leu Ser Glu Gln Gly Phe Ala Ala Leu Arg Ala Ala Pro Pro
            100                 105                 110
Ser Thr Ala Asp Ala Arg Arg Asp Trp Leu Arg Ser His Gly Ala Ser
        115                 120                 125
Glu Asp Asp Leu Met Ala Leu Glu Ala Gln Leu Leu Glu Thr Ile Met
    130                 135                 140
Gly Asn Ala Ile Ser Leu His Gly Gly Val Leu Lys Lys Ile Asp Asn
145                 150                 155                 160
Ala Asn Val Lys Ala Ala Lys Arg Leu Ser Gly Arg Asn Glu Ala Arg
                165                 170                 175
Leu Asn Lys Gly Leu Gln Glu Leu Pro Pro Glu Gln Glu Gly Ser Ala
            180                 185                 190
Tyr Gly Ala Asp Gly Leu Leu Val Asn Pro Gly Leu Asn Leu Asn
        195                 200                 205
Ile Tyr Cys Arg Lys Ser Cys Cys Pro Lys Pro Val Lys Asn Thr Ala
    210                 215                 220
Arg Phe Val Gly His Tyr Pro Gly Tyr Leu Arg Asp Ser Asp Ser Ile
225                 230                 235                 240
Leu Ile Ser Gly Thr Met Asp Arg Leu Thr Ile Ile Glu Gly Met Pro
                245                 250                 255
Gly His Ile Pro Ala Trp Gln Arg Glu Gln Gly Leu Val Lys Pro Gly
            260                 265                 270
```

```
Gly Arg Arg Arg Arg Leu Ser Gly Ser Glu Ser Asn Met Arg Gln Lys
            275                 280                 285

Val Asp Pro Ser Thr Gly Pro Arg Arg Ser Thr Arg Ser Gly Thr Val
290                 295                 300

Asn Arg Ser Asn Gln Arg Thr Gly Arg Asn Gly Asp Pro Leu Leu Val
305                 310                 315                 320

Glu Ile Arg Met Lys Glu Asp Trp Val Leu Leu Asp Ala Arg Gly Leu
                325                 330                 335

Leu Arg Asn Leu Arg Trp Arg Glu Ser Lys Arg Gly Leu Ser Cys Asp
            340                 345                 350

His Glu Asp Leu Ser Leu Ser Gly Leu Leu Ala Leu Phe Ser Gly Asp
            355                 360                 365

Pro Val Ile Asp Pro Val Arg Asn Glu Val Val Phe Leu Tyr Gly Glu
            370                 375                 380

Gly Ile Ile Pro Val Arg Ser Thr Lys Pro Val Gly Thr Arg Gln Ser
385                 390                 395                 400

Lys Lys Leu Leu Glu Arg Gln Ala Ser Met Gly Pro Leu Thr Leu Ile
                405                 410                 415

Ser Cys Asp Leu Gly Gln Thr Asn Leu Ile Ala Gly Arg Ala Ser Ala
            420                 425                 430

Ile Ser Leu Thr His Gly Ser Leu Gly Val Arg Ser Val Arg Ile
            435                 440                 445

Glu Leu Asp Pro Glu Ile Ile Lys Ser Phe Glu Arg Leu Arg Lys Asp
            450                 455                 460

Ala Asp Arg Leu Glu Thr Glu Ile Leu Thr Ala Ala Lys Glu Thr Leu
465                 470                 475                 480

Ser Asp Glu Gln Arg Gly Glu Val Asn Ser His Glu Lys Asp Ser Pro
                485                 490                 495

Gln Thr Ala Lys Ala Ser Leu Cys Arg Glu Leu Gly Leu His Pro Pro
            500                 505                 510

Ser Leu Pro Trp Gly Gln Met Gly Pro Ser Thr Thr Phe Ile Ala Asp
            515                 520                 525

Met Leu Ile Ser His Gly Arg Asp Asp Ala Phe Leu Ser His Gly
            530                 535                 540

Glu Phe Pro Thr Leu Glu Lys Arg Lys Lys Phe Asp Lys Arg Phe Cys
545                 550                 555                 560

Leu Glu Ser Arg Pro Leu Leu Ser Glu Thr Arg Lys Ala Leu Asn
                565                 570                 575

Glu Ser Leu Trp Glu Val Lys Arg Thr Ser Ser Glu Tyr Ala Arg Leu
            580                 585                 590

Ser Gln Arg Lys Lys Glu Met Ala Arg Ala Val Asn Phe Val Val
            595                 600                 605

Glu Ile Ser Arg Arg Lys Thr Gly Leu Ser Asn Val Ile Val Asn Ile
            610                 615                 620

Glu Asp Leu Asn Val Arg Ile Phe His Gly Gly Lys Gln Ala Pro
625                 630                 635                 640

Gly Trp Asp Gly Phe Phe Arg Pro Lys Ser Glu Asn Arg Trp Phe Ile
                645                 650                 655

Gln Ala Ile His Lys Ala Phe Ser Asp Leu Ala Ala His His Gly Ile
            660                 665                 670

Pro Val Ile Glu Ser Asp Pro Gln Arg Thr Ser Met Thr Cys Pro Glu
            675                 680                 685
```

Cys Gly His Cys Asp Ser Lys Asn Arg Asn Gly Val Arg Phe Leu Cys
    690                 695                 700

Lys Gly Cys Gly Ala Ser Met Asp Ala Asp Phe Asp Ala Ala Cys Arg
705                 710                 715                 720

Asn Leu Glu Arg Val Ala Leu Thr Gly Lys Pro Met Pro Lys Pro Ser
                725                 730                 735

Thr Ser Cys Glu Arg Leu Leu Ser Ala Thr Thr Gly Lys Val Cys Ser
            740                 745                 750

Asp His Ser Leu Ser His Asp Ala Ile Glu Lys Ala Ser
        755                 760                 765

<210> SEQ ID NO 126
<211> LENGTH: 766
<212> TYPE: PRT
<213> ORGANISM: Artificial Sequence
<220> FEATURE:
<223> OTHER INFORMATION: Synthetic sequence

<400> SEQUENCE: 126

Met Glu Lys Glu Ile Thr Glu Leu Thr Lys Ile Arg Arg Glu Phe Pro
1               5                   10                  15

Asn Lys Lys Phe Ser Ser Thr Asp Met Lys Lys Ala Gly Lys Leu Leu
            20                  25                  30

Lys Ala Glu Gly Pro Asp Ala Val Arg Asp Phe Leu Asn Ser Cys Gln
        35                  40                  45

Glu Ile Ile Gly Asp Phe Lys Pro Pro Val Lys Thr Asn Ile Val Ser
    50                  55                  60

Ile Ser Arg Pro Phe Glu Trp Pro Val Ser Met Val Gly Arg Ala
65                  70                  75                  80

Ile Gln Glu Tyr Tyr Phe Ser Leu Thr Lys Glu Glu Leu Glu Ser Val
                85                  90                  95

His Pro Gly Thr Ser Ser Glu Asp His Lys Ser Phe Phe Asn Ile Thr
            100                 105                 110

Gly Leu Ser Asn Tyr Asn Tyr Thr Ser Val Gln Gly Leu Asn Leu Ile
        115                 120                 125

Phe Lys Asn Ala Lys Ala Ile Tyr Asp Gly Thr Leu Val Lys Ala Asn
    130                 135                 140

Asn Lys Asn Lys Lys Leu Glu Lys Lys Phe Asn Glu Ile Asn His Lys
145                 150                 155                 160

Arg Ser Leu Glu Gly Leu Pro Ile Ile Thr Pro Asp Phe Glu Glu Pro
                165                 170                 175

Phe Asp Glu Asn Gly His Leu Asn Asn Pro Pro Gly Ile Asn Arg Asn
            180                 185                 190

Ile Tyr Gly Tyr Gln Gly Cys Ala Ala Lys Val Phe Val Pro Ser Lys
        195                 200                 205

His Lys Met Val Ser Leu Pro Lys Glu Tyr Glu Gly Tyr Asn Arg Asp
    210                 215                 220

Pro Asn Leu Ser Leu Ala Gly Phe Arg Asn Arg Leu Glu Ile Pro Glu
225                 230                 235                 240

Gly Glu Pro Gly His Val Pro Trp Phe Gln Arg Met Asp Ile Pro Glu
                245                 250                 255

Gly Gln Ile Gly His Val Asn Lys Ile Gln Arg Phe Asn Phe Val His
            260                 265                 270

Gly Lys Asn Ser Gly Lys Val Lys Phe Ser Asp Lys Thr Gly Arg Val
        275                 280                 285

```
Lys Arg Tyr His His Ser Lys Tyr Lys Asp Ala Thr Lys Pro Tyr Lys
            290                 295                 300

Phe Leu Glu Glu Ser Lys Lys Val Ser Ala Leu Asp Ser Ile Leu Ala
305                 310                 315                 320

Ile Ile Thr Ile Gly Asp Asp Trp Val Val Phe Asp Ile Arg Gly Leu
                325                 330                 335

Tyr Arg Asn Val Phe Tyr Arg Glu Leu Ala Gln Lys Gly Leu Thr Ala
            340                 345                 350

Val Gln Leu Leu Asp Leu Phe Thr Gly Asp Pro Val Ile Asp Pro Lys
            355                 360                 365

Lys Gly Val Val Thr Phe Ser Tyr Lys Glu Gly Val Val Pro Val Phe
370                 375                 380

Ser Gln Lys Ile Val Pro Arg Phe Lys Ser Arg Asp Thr Leu Glu Lys
385                 390                 395                 400

Leu Thr Ser Gln Gly Pro Val Ala Leu Leu Ser Val Asp Leu Gly Gln
                405                 410                 415

Asn Glu Pro Val Ala Ala Arg Val Cys Ser Leu Lys Asn Ile Asn Asp
            420                 425                 430

Lys Ile Thr Leu Asp Asn Ser Cys Arg Ile Ser Phe Leu Asp Asp Tyr
            435                 440                 445

Lys Lys Gln Ile Lys Asp Tyr Arg Asp Ser Leu Asp Glu Leu Glu Ile
450                 455                 460

Lys Ile Arg Leu Glu Ala Ile Asn Ser Leu Thr Asn Gln Gln Val
465                 470                 475                 480

Glu Ile Arg Asp Leu Asp Val Phe Ser Ala Asp Arg Ala Lys Ala Asn
            485                 490                 495

Thr Val Asp Met Phe Asp Ile Asp Pro Asn Leu Ile Ser Trp Asp Ser
            500                 505                 510

Met Ser Asp Ala Arg Val Ser Thr Gln Ile Ser Asp Leu Tyr Leu Lys
            515                 520                 525

Asn Gly Gly Asp Glu Ser Arg Val Tyr Phe Glu Ile Asn Asn Lys Arg
530                 535                 540

Ile Lys Arg Ser Asp Tyr Asn Ile Ser Gln Leu Val Arg Pro Lys Leu
545                 550                 555                 560

Ser Asp Ser Thr Arg Lys Asn Leu Asn Asp Ser Ile Trp Lys Leu Lys
            565                 570                 575

Arg Thr Ser Glu Glu Tyr Leu Lys Leu Ser Lys Arg Lys Leu Glu Leu
            580                 585                 590

Ser Arg Ala Val Val Asn Tyr Thr Ile Arg Gln Ser Lys Leu Leu Ser
            595                 600                 605

Gly Ile Asn Asp Ile Val Ile Ile Leu Glu Asp Leu Asp Val Lys Lys
            610                 615                 620

Lys Phe Asn Gly Arg Gly Ile Arg Asp Ile Gly Trp Asp Asn Phe Phe
625                 630                 635                 640

Ser Ser Arg Lys Glu Asn Arg Trp Phe Ile Pro Ala Phe His Lys Thr
            645                 650                 655

Phe Ser Glu Leu Ser Ser Asn Arg Gly Leu Cys Val Ile Glu Val Asn
            660                 665                 670

Pro Ala Trp Thr Ser Ala Thr Cys Pro Asp Cys Gly Phe Cys Ser Lys
            675                 680                 685

Glu Asn Arg Asp Gly Ile Asn Phe Thr Cys Arg Lys Cys Gly Val Ser
690                 695                 700
```

Tyr His Ala Asp Ile Asp Val Ala Thr Leu Asn Ile Ala Arg Val Ala
705                 710                 715                 720

Val Leu Gly Lys Pro Met Ser Gly Pro Ala Asp Arg Glu Arg Leu Gly
            725                 730                 735

Asp Thr Lys Lys Pro Arg Val Ala Arg Ser Arg Lys Thr Met Lys Arg
            740                 745                 750

Lys Asp Ile Ser Asn Ser Thr Val Glu Ala Met Val Thr Ala
            755                 760                 765

<210> SEQ ID NO 127
<211> LENGTH: 36
<212> TYPE: DNA
<213> ORGANISM: Artificial Sequence
<220> FEATURE:
<223> OTHER INFORMATION: Synthetic sequence

<400> SEQUENCE: 127
gtctcgacta atcgagcaat cgtttgagat ctctcc                          36

<210> SEQ ID NO 128
<211> LENGTH: 36
<212> TYPE: DNA
<213> ORGANISM: Artificial Sequence
<220> FEATURE:
<223> OTHER INFORMATION: Synthetic sequence

<400> SEQUENCE: 128
ggagagatct caaacgattg ctcgattagt cgagac                          36

<210> SEQ ID NO 129
<211> LENGTH: 36
<212> TYPE: DNA
<213> ORGANISM: Artificial Sequence
<220> FEATURE:
<223> OTHER INFORMATION: Synthetic sequence

<400> SEQUENCE: 129
gtcggaacgc tcaacgattg cccctcacga ggggac                          36

<210> SEQ ID NO 130
<211> LENGTH: 36
<212> TYPE: DNA
<213> ORGANISM: Artificial Sequence
<220> FEATURE:
<223> OTHER INFORMATION: Synthetic sequence

<400> SEQUENCE: 130
gtcccctcgt gagggcaat cgttgagcgt tccgac                           36

<210> SEQ ID NO 131
<211> LENGTH: 36
<212> TYPE: DNA
<213> ORGANISM: Artificial Sequence
<220> FEATURE:
<223> OTHER INFORMATION: Synthetic sequence

<400> SEQUENCE: 131
gtcccagcgt actgggcaat caatagtcgt tttggt                          36

<210> SEQ ID NO 132
<211> LENGTH: 36
<212> TYPE: DNA
<213> ORGANISM: Artificial Sequence
<220> FEATURE:
<223> OTHER INFORMATION: Synthetic sequence

<400> SEQUENCE: 132
accaaaacga ctattgattg cccagtacgc tgggac    36

<210> SEQ ID NO 133
<211> LENGTH: 37
<212> TYPE: DNA
<213> ORGANISM: Artificial Sequence
<220> FEATURE:
<223> OTHER INFORMATION: Synthetic sequence

<400> SEQUENCE: 133
ggatccaatc cttttttgatt gcccaattcg ttgggac    37

<210> SEQ ID NO 134
<211> LENGTH: 36
<212> TYPE: DNA
<213> ORGANISM: Artificial Sequence
<220> FEATURE:
<223> OTHER INFORMATION: Synthetic sequence

<400> SEQUENCE: 134
ggatctgagg atcattattg ctcgttacga cgagac    36

<210> SEQ ID NO 135
<211> LENGTH: 36
<212> TYPE: DNA
<213> ORGANISM: Artificial Sequence
<220> FEATURE:
<223> OTHER INFORMATION: Synthetic sequence

<400> SEQUENCE: 135
gtctcgtcgt aacgagcaat aatgatcctc agatcc    36

<210> SEQ ID NO 136
<211> LENGTH: 36
<212> TYPE: DNA
<213> ORGANISM: Artificial Sequence
<220> FEATURE:
<223> OTHER INFORMATION: Synthetic sequence

<400> SEQUENCE: 136
gtctcagcgt actgagcaat caaaaggttt cgcagg    36

<210> SEQ ID NO 137
<211> LENGTH: 36
<212> TYPE: DNA
<213> ORGANISM: Artificial Sequence
<220> FEATURE:
<223> OTHER INFORMATION: Synthetic sequence

<400> SEQUENCE: 137
cctgcgaaac cttttgattg ctcagtacgc tgagac    36

<210> SEQ ID NO 138
<211> LENGTH: 36
<212> TYPE: DNA
<213> ORGANISM: Artificial Sequence
<220> FEATURE:
<223> OTHER INFORMATION: Synthetic sequence

<400> SEQUENCE: 138
gtctcctcgt aaggagcaat ctattagtct tgaaag    36

```
<210> SEQ ID NO 139
<211> LENGTH: 36
<212> TYPE: DNA
<213> ORGANISM: Artificial Sequence
<220> FEATURE:
<223> OTHER INFORMATION: Synthetic sequence

<400> SEQUENCE: 139
ctttcaagac taatagattg ctccttacga ggagac                                 36

<210> SEQ ID NO 140
<211> LENGTH: 36
<212> TYPE: DNA
<213> ORGANISM: Artificial Sequence
<220> FEATURE:
<223> OTHER INFORMATION: Synthetic sequence

<400> SEQUENCE: 140
gtctcggcgc accgagcaat cagcgaggtc ttctac                                 36

<210> SEQ ID NO 141
<211> LENGTH: 36
<212> TYPE: DNA
<213> ORGANISM: Artificial Sequence
<220> FEATURE:
<223> OTHER INFORMATION: Synthetic sequence

<400> SEQUENCE: 141
gtagaagacc tcgctgattg ctcggtgcgc cgagac                                 36

<210> SEQ ID NO 142
<211> LENGTH: 36
<212> TYPE: DNA
<213> ORGANISM: Artificial Sequence
<220> FEATURE:
<223> OTHER INFORMATION: Synthetic sequence

<400> SEQUENCE: 142
gtctcctcgt aaggagcaat ctattagtct tgaaag                                 36

<210> SEQ ID NO 143
<211> LENGTH: 36
<212> TYPE: DNA
<213> ORGANISM: Artificial Sequence
<220> FEATURE:
<223> OTHER INFORMATION: Synthetic sequence

<400> SEQUENCE: 143
ctttcaagac taatagattg ctccttacga ggagac                                 36

<210> SEQ ID NO 144
<211> LENGTH: 36
<212> TYPE: DNA
<213> ORGANISM: Artificial Sequence
<220> FEATURE:
<223> OTHER INFORMATION: Synthetic sequence

<400> SEQUENCE: 144
gtctcagcgt actgagcaat caaaaggttt cgcagg                                 36

<210> SEQ ID NO 145
<211> LENGTH: 36
<212> TYPE: DNA
<213> ORGANISM: Artificial Sequence
<220> FEATURE:
<223> OTHER INFORMATION: Synthetic sequence
```

```
<400> SEQUENCE: 145
cctgcgaaac cttttgattg ctcagtacgc tgagac                                  36

<210> SEQ ID NO 146
<211> LENGTH: 36
<212> TYPE: DNA
<213> ORGANISM: Artificial Sequence
<220> FEATURE:
<223> OTHER INFORMATION: Synthetic sequence

<400> SEQUENCE: 146
accaaaacga ctattgattg cccagtacgc tgggac                                  36

<210> SEQ ID NO 147
<211> LENGTH: 37
<212> TYPE: DNA
<213> ORGANISM: Artificial Sequence
<220> FEATURE:
<223> OTHER INFORMATION: Synthetic sequence

<400> SEQUENCE: 147
gtcccaacga attgggcaat caaaaaggat tggatcc                                 37

<210> SEQ ID NO 148
<211> LENGTH: 37
<212> TYPE: DNA
<213> ORGANISM: Artificial Sequence
<220> FEATURE:
<223> OTHER INFORMATION: Synthetic sequence

<400> SEQUENCE: 148
ggatccaatc cttttgatt gcccaattcg ttgggac                                  37

<210> SEQ ID NO 149
<211> LENGTH: 36
<212> TYPE: DNA
<213> ORGANISM: Artificial Sequence
<220> FEATURE:
<223> OTHER INFORMATION: Synthetic sequence

<400> SEQUENCE: 149
gtctcagcgt actgagcaat caaaaggttt cgcagg                                  36

<210> SEQ ID NO 150
<211> LENGTH: 36
<212> TYPE: DNA
<213> ORGANISM: Artificial Sequence
<220> FEATURE:
<223> OTHER INFORMATION: Synthetic sequence

<400> SEQUENCE: 150
cctgcgaaac cttttgattg ctcagtacgc tgagac                                  36

<210> SEQ ID NO 151
<211> LENGTH: 36
<212> TYPE: DNA
<213> ORGANISM: Artificial Sequence
<220> FEATURE:
<223> OTHER INFORMATION: Synthetic sequence

<400> SEQUENCE: 151
gtctcgacta atcgagcaat cgtttgagat ctctcc                                  36
```

```
<210> SEQ ID NO 152
<211> LENGTH: 36
<212> TYPE: DNA
<213> ORGANISM: Artificial Sequence
<220> FEATURE:
<223> OTHER INFORMATION: Synthetic sequence

<400> SEQUENCE: 152
ggagagatct caaacgattg ctcgattagt cgagac                                  36

<210> SEQ ID NO 153
<211> LENGTH: 36
<212> TYPE: DNA
<213> ORGANISM: Artificial Sequence
<220> FEATURE:
<223> OTHER INFORMATION: Synthetic sequence

<400> SEQUENCE: 153
gtcggaacgc tcaacgattg cccctcacga ggggac                                  36

<210> SEQ ID NO 154
<211> LENGTH: 36
<212> TYPE: DNA
<213> ORGANISM: Artificial Sequence
<220> FEATURE:
<223> OTHER INFORMATION: Synthetic sequence

<400> SEQUENCE: 154
gtcccctcgt gagggcaat cgttgagcgt tccgac                                   36

<210> SEQ ID NO 155
<211> LENGTH: 36
<212> TYPE: DNA
<213> ORGANISM: Artificial Sequence
<220> FEATURE:
<223> OTHER INFORMATION: Synthetic sequence

<400> SEQUENCE: 155
gtcgcggcgt accgcgcaat gagagtctgt tgccat                                  36

<210> SEQ ID NO 156
<211> LENGTH: 36
<212> TYPE: DNA
<213> ORGANISM: Artificial Sequence
<220> FEATURE:
<223> OTHER INFORMATION: Synthetic sequence

<400> SEQUENCE: 156
atggcaacag actctcattg cgcggtacgc cgcgac                                  36

<210> SEQ ID NO 157
<211> LENGTH: 36
<212> TYPE: DNA
<213> ORGANISM: Artificial Sequence
<220> FEATURE:
<223> OTHER INFORMATION: Synthetic sequence

<400> SEQUENCE: 157
gtctcctcgt aaggagcaat ctattagtct tgaaag                                  36

<210> SEQ ID NO 158
<211> LENGTH: 36
<212> TYPE: DNA
<213> ORGANISM: Artificial Sequence
<220> FEATURE:
<223> OTHER INFORMATION: Synthetic sequence
```

<400> SEQUENCE: 158
ctttcaagac taatagattg ctccttacga ggagac                          36

<210> SEQ ID NO 159
<211> LENGTH: 36
<212> TYPE: DNA
<213> ORGANISM: Artificial Sequence
<220> FEATURE:
<223> OTHER INFORMATION: Synthetic sequence

<400> SEQUENCE: 159
gtctcggcgc accgagcaat cagcgaggtc ttctac                          36

<210> SEQ ID NO 160
<211> LENGTH: 36
<212> TYPE: DNA
<213> ORGANISM: Artificial Sequence
<220> FEATURE:
<223> OTHER INFORMATION: Synthetic sequence

<400> SEQUENCE: 160
gtagaagacc tcgctgattg ctcggtgcgc cgagac                          36

<210> SEQ ID NO 161
<211> LENGTH: 7180
<212> TYPE: DNA
<213> ORGANISM: Artificial Sequence
<220> FEATURE:
<223> OTHER INFORMATION: Synthetic sequence

<400> SEQUENCE: 161
atgccaaagc cagccgtgga gtctgagttt tctaaggtac tcaagaagca ctttccgggc      60
gagcgattta ggtctagcta catgaagcgg ggtggtaaaa tcttggcagc ccagggtgaa     120
gaagcggtcg tcgcgtatct gcaaggcaag tccgaggagg aaccccgaa ttttcagccg      180 ccggcgaaat gtcatgttgt tacgaaatca cgagatttcg ccgagtggcc aattatgaag     240
gcctccgaag caatccaaag gtatatctat gcgctctcta cgacggaacg ggcagcttgc     300
aagcctggca atcttcaga gtcccacgcg gcctggttcg cggcaactgg cgtgtcaaac      360
cacggttata gccatgttca aggcctcaat cttatcttcg accacacgct gggaagatac     420
gatggtgttc tgaaaaaggt gcagctgaga atgagaaag cccgcgcccg gctgaaaagt      480
atcaacgcct ctcgagccga cgaaggactt ccagaaataa aggcagagga ggaagaggtc     540
gctacaaatg aaaccggaca ccttttgcag cctccgggga tcaacccaag tttctacgtt     600
taccagacta tttctccgca ggcttacagg ccgcgagatg agattgtact gccgcccgag     660
tatgccggct acgtccgaga tccgaacgcc cctatccccc ttggcgtggt tcggaatcgg     720
tgcgatattc agaagggatg ccctggatac atccccgaat ggcaaagaga ggcaggtact     780
gcaatttccc ctaagacggg taaagccgtc accgttcccg gcctcagtcc aaaaaaaaat     840
aaacgaatgc gacgatactg gaggtccgag aaagagaagg cccaagatgc actgctcgtt     900
actgtgagaa tcggcactga ctgggtcgta atcgacgttc gaggtttgct gcggaatgcg     960
cggtggcgca ccattgcgcc caaggatata tccttgaatg ccctcttgga tctctttaca    1020
ggcgacccgg tcatagatgt tcggagaaac attgtgactt tcacctacac tctggacgct    1080
tgcggtacat atgctcgcaa atggactctc aaagggaaac agactaaggc aaccctcgat    1140
aagttgaccg caacccagac cgtggccctg gtagcaatag accttggaca aaccaatccc    1200
ataagtgcgg gtatcagtag ggtcacgcaa gaaaacgggg cacttcaatg tgaacctctg    1260

```
gatcggttca ctctccctga tgatctgctc aaggatatct ccgcgtaccg aatcgcttgg      1320
gatcgcaacg aggaggaact gagggctagg tccgtcgaag cgctcccaga agctcaacaa      1380
gctgaagtga gggctctgga cggcgtttct aaagaaaccg ccaggaccca gctctgcgcg      1440
gacttcggcc ttgatcccaa acggctgcct tgggataaaa tgagcagcaa caccactttc      1500
atcagtgaag cgttgcttag taattctgtg tctagagatc aggttttttt tactcctgcg      1560
cctaaaaagg gagcaaagaa aaagccccc gttgaagtta tgcggaagga taggacctgg      1620
gcgagggcct ataaaccacg gctcagtgtg gaagcccaaa gctgaaaaa tgaggccttg      1680 tgggctctca gcgcacttc tccagaatac ctcaagctga gtcggagaaa agaggagctt      1740
tgtaggcgaa gtattaacta cgtcattgaa aaaacaagac ggaggacaca atgtcagatc      1800
gtgatacctg tcatagagga cttgaatgtg cgattctttc acggttcagg gaagcgcctg      1860
cctggctggg ataatttttt cactgcgaag aaggagaaca ggtggtttat acagggcctc      1920
cacaaagcat tcagcgactt gcgaactcat cgctccttct acgtattcga agtccgcccg      1980
gagcggactt caataacgtg cccaaaatgc gggcactgcg aggttgggaa ccggatgggg      2040
gaggcttttc agtgccttag ttgcggcaaa acgtgcaatg ccgaccttga cgtggctacc      2100
cataatctga ctcaagtcgc ccttacagga aaaacaatgc cgaaacgcga ggaacctaga      2160
gatgcccagg gcacagctcc agcccgaaaa acaaagaagg cgtcaaagag caaggctccg      2220
ccagccgaac gagaggacca aactccagca caggaaccgt cccagacttc cggaagcgga      2280
cccaagaaaa aacgcaaggt ggaagatcct aagaaaaagc ggaaagtgag cctgggcagc      2340
ggctccgatt acaagatga cgatgacaaa gactacaagg atgatgatga taagggatcc      2400
ggcgcaacaa acttctctct gctgaaacaa gccggagatg tcgaagagaa tcctggaccg      2460
accgagtaca gcccacggt gcgcctcgcc acccgcgacg acgtcccag gccgtacgc      2520 accctcgccg ccgcgttcgc cgactacccc gccacgcgcc acaccgtcga tccggaccgc      2580
cacatcgagc gggtcaccga gctgcaagaa ctcttcctca cgcgcgtcgg gctcgacatc      2640
ggcaaggtgt gggtcgcgga cgacggcgcc gcggtggcgg tctggaccac gccggagagc      2700
gtcgaagcgg gggcggtgtt cgccgagatc ggcccgcgca tggccgagtt gagcggttcc      2760
cggctggccg cgcagcaaca gatggaaggc ctcctggcgc cgcaccggcc caaggagccc      2820
gcgtggttcc tggccaccgt cggagtctcg cccgaccacc agggcaaggg tctgggcagc      2880
gccgtcgtgc tccccggagt ggaggcggcc gagcgcgccg gggtgccgc cttcctggag      2940 acctccgcgc cccgcaacct ccccttctac gagcggctcg gcttcaccgt caccgccgac      3000
gtcgaggtgc ccgaaggacc gcgcacctgg tgcatgaccc gcaagcccgg tgcctgaacg      3060
cgttaagaat tcctagagct cgctgatcag cctcgactgt gccttctagt tgccagccat      3120
ctgttgtttg cccctccccc gtgccttcct tgaccctgga aggtgccact cccactgtcc      3180
tttcctaata aaatgaggaa attgcatcgc attgtctgag taggtgtcat tctattctgg      3240
ggggtggggt ggggcaggac agcaaggggg aggattggga agagaatagc aggcatgctg      3300
gggagcggcc gcaggaaccc ctagtgatgg agttggccac tccctctctg cgcgctcgct      3360
cgctcactga ggccgggcga ccaaaggtcg cccgacgccc gggctttgcc cggcggcct      3420 cagtgagcga gcgagcgcgc agctgcctgc aggggcgcct gatgcggtat tttctcctta      3480
cgcatctgtg cggtatttca caccgcatac gtcaaagcaa ccatagtacg cgccctgtag      3540
cggcgcatta agcgcggcgg gtgtggtggt tacgcgcagc gtgaccgcta cacttgccag      3600
cgccttagcg cccgctcctt tcgctttctt cccttccttt ctcgccacgt tcgccggctt      3660
```

-continued

```
tccccgtcaa gctctaaatc gggggctccc tttagggttc cgatttagtg ctttacggca      3720
cctcgacccc aaaaaacttg atttgggtga tggttcacgt agtgggccat cgccctgata      3780
gacggttttt cgcccttga cgttggagtc cacgttcttt aatagtggac tcttgttcca       3840
aactggaaca acactcaact ctatctcggg ctattctttt gatttataag ggattttgcc      3900
gatttcggtc tattggttaa aaatgagct gatttaacaa aaatttaacg cgaattttaa       3960
caaaatatta acgtttacaa ttttatggtg cactctcagt acaatctgct ctgatgccgc      4020
atagttaagc cagccccgac acccgccaac acccgctgac gcgccctgac gggcttgtct      4080
gctcccggca tccgcttaca gacaagctgt gaccgtctcc gggagctgca tgtgtcagag      4140
gttttcaccg tcatcaccga aacgcgcgag acgaaagggc ctcgtgatac gcctattttt      4200
ataggttaat gtcatgataa taatggtttc ttagacgtca ggtggcactt ttcggggaaa      4260
tgtgcgcgga acccctattt gtttattttt ctaaatacat tcaaatatgt atccgctcat      4320
gagacaataa ccctgataaa tgcttcaata atattgaaaa aggaagagta tgagtattca      4380
acatttccgt gtcgccctta ttcccttttt tgcggcattt tgccttcctg tttttgctca      4440
cccagaaacg ctggtgaaag taaaagatgc tgaagatcag ttgggtgcac gagtgggtta      4500
catcgaactg gatctcaaca gcggtaagat ccttgagagt tttcgccccg aagaacgttt      4560
tccaatgatg agcactttta aagttctgct atgtggcgcg gtattatccc gtattgacgc      4620
cgggcaagag caactcggtc gccgcataca ctattctcag aatgacttgg ttgagtactc      4680
accagtcaca gaaaagcatc ttacggatgg catgacagta agagaattat gcagtgctgc      4740
cataaccatg agtgataaca ctgcggccaa cttacttctg acaacgatcg gaggaccgaa      4800
ggagctaacc gcttttttgc acaacatggg ggatcatgta actcgccttg atcgttggga      4860
accggagctg aatgaagcca taccaaacga cgagcgtgac accacgatgc ctgtagcaat      4920
ggcaacaacg ttgcgcaaac tattaactgg cgaactactt actctagctt cccggcaaca      4980
attaatagac tggatggagg cggataaagt tgcaggacca cttctgcgct cggcccttcc      5040
ggctggctgg tttattgctg ataaatctgg agccggtgag cgtggaagcc gcggtatcat      5100
tgcagcactg gggccagatg gtaagccctc ccgtatcgta gttatctaca cgacggggag      5160
tcaggcaact atggatgaac gaaatagaca gatcgctgag ataggtgcct cactgattaa      5220
gcattggtaa ctgtcagacc aagtttactc atatatactt tagattgatt taaaacttca      5280
tttttaattt aaaaggatct aggtgaagat cctttttgat aatctcatga ccaaaatccc      5340
ttaacgtgag ttttcgttcc actgagcgtc agaccccgta gaaaagatca aaggatcttc      5400
ttgagatcct ttttttctgc gcgtaatctg ctgcttgcaa acaaaaaaac caccgctacc      5460
agcggtggtt tgtttgccgg atcaagagct accaactctt ttccgaagg taactggctt       5520
cagcagagcg cagataccaa atactgttct tctagtgtag ccgtagttag gccaccactt      5580
caagaactct gtagcaccgc ctacatacct cgctctgcta atcctgttac cagtggctgc      5640
tgccagtggc gataagtcgt gtcttaccgg gttggactca agacgatagt taccggataa      5700
ggcgcagcgg tcgggctgaa cggggggttc gtgcacacag cccagcttgg agcgaacgac      5760
ctacaccgaa ctgagatacc tacagcgtga gctatgagaa agcgccacgc ttcccgaagg      5820
gagaaaggcg gacaggtatc cggtaagcgg cagggtcgga acaggagagc gcacgaggga      5880
gcttccaggg ggaaacgcct ggtatcttta tagtcctgtc gggtttcgcc acctctgact      5940
tgagcgtcga tttttgtgat gctcgtcagg ggggcggagc ctatggaaaa acgccagcaa      6000
cgcggccttt ttacggttcc tggccttttg ctggccttt gctcacatgt gagggcctat      6060
```

```
ttcccatgat tccttcatat ttgcatatac gatacaaggc tgttagagag ataattggaa    6120
ttaatttgac tgtaaacaca aagatattag tacaaaatac gtgacgtaga aagtaataat    6180
ttcttgggta gtttgcagtt ttaaaattat gttttaaaat ggactatcat atgcttaccg    6240
taacttgaaa gtatttcgat ttcttggctt tatatatctt gtggaaagga cgaaacaccg    6300
gtcggaacgc tcaacgattg cccctcacga ggggacagaa gagctaatgc tcttcatttt    6360
ttttggtacc cgttacataa cttacggtaa atggcccgcc tggctgaccg cccaacgacc    6420
cccgcccatt gacgtcaata gtaacgccaa tagggacttt ccattgacgt caatgggtgg    6480
agtatttacg gtaaactgcc cacttggcag tacatcaagt gtatcatatg ccaagtacgc    6540
cccctattga cgtcaatgac ggtaaatggc ccgcctggca ttgtgcccag tacatgacct    6600
tatgggactt tcctacttgg cagtacatct acgtattagt catcgctatt accatggtcg    6660
aggtgagccc cacgttctgc ttcactctcc ccatctcccc cccctcccca ccccaatttt    6720
tgtatttatt tattttttaa ttattttgtg cagcgatggg ggcggggggg ggggggggc    6780 gcgcgccagg cggggcgggg sggggsgrgg ggsggggsgg ggsgrggcgg agaggtgcgg    6840
cggcagccaa tcagagcggc gcgctccgaa agtttccttt tatggcgagg cggcggcggc    6900
ggcggcccta taaaagcga agcgcgcggc gggcgggagt cgctgcgcgc tgccttcgcc    6960
ccgtgccccg ctccgccgcc gcctcgcgcc gcccgccccg gctctgactg accgcgttac    7020
tcccacaggt gagcgggcgg gacggccctt ctcctccggg ctgtaattag ctgagcaaga    7080
ggtaagggtt taagggatgg ttggttggtg gggtattaat gtttaattac ctggagcacc    7140
tgcctgaaat cacttttttt caggttggac cggtgccacc                          7180

<210> SEQ ID NO 162
<211> LENGTH: 7207
<212> TYPE: DNA
<213> ORGANISM: Artificial Sequence
<220> FEATURE:
<223> OTHER INFORMATION: Synthetic sequence

<400> SEQUENCE: 162
atggaaaaag aaataactga gctcaccaag attaggcgcg agtttccgaa taaaaagttc      60
agcagcactg atatgaagaa ggcaggtaag ttgttgaagg cagaaggtcc tgatgctgtt     120
agagacttcc tgaactcctg ccaggagatt atcgggggatt ttaagccgcc tgtaaagaca    180
aacatagtca gcatatcacg acccttgag gagtggcctg ttagtatggt ggggcgcgcc     240
atccaggaat attactttag tttgacaaaa gaggaattgg agtccgtcca tcccggaact    300
tccagcgagg atcacaagtc cttctttaac ataactggcc tgagcaatta caattatacg    360
tcagtccaag gcttgaatct catcttcaaa aatgcgaagg ccatatacga cgggactctg    420
gttaaagcaa acaataaaaa taagaagttg gaaaaaaagt tcaatgagat taaccacaag    480
cgaagccttg aggggcttcc tataattacg ccggatttcg aggaacccctt tgatgagaat    540 ggccatctga ataatccgcc aggtattaat cgaaatatttt acggctacca aggatgtgcc    600
gctaaagtat tcgttccttc caagcataaa atggtatccc tccctaaaga atacgaaggg    660
tacaaccggg atccgaacct gtccttggcg ggcttccgaa atcggctcga gataccggag    720
ggggagcccg gtcacgtgcc atggtttcag cgcatggata tcccggaagg ccagatcggg    780
cacgtaaata agattcaacg attcaatttc gttcatggca agaattcagg aaaagtcaaa    840
ttcagcgata agacaggacg ggtaaaaacgc taccatcatt ccaagtataa agatgccact    900
aagccttaca aatttcttga agaatccaag aaagtcagtg ctctggactc catccttgcc    960
```

```
attatcacaa tcggtgatga ctgggtagtg tttgacattc gcggtctgta tagaaatgtt    1020
ttttatcgcg aactggcaca gaagggcctg acagcagtgc agctgctgga tctgtttacg    1080
ggggatccgg tgattgaccc gaagaagggc gttgtgacat tcagctataa ggaaggcgtg    1140
gttccagtat tttcacagaa gatcgttcca aggttcaaga gtcgagacac gctcgagaaa    1200
ttgaccagtc aaggacctgt ggcgctgctc tcagtcgacc tcggccaaaa tgaaccagtg    1260
gcggcaaggg tttgtagctt gaagaacata aatgataaga tcacattgga taattccttgc   1320 agaatctcct tcctggatga ctacaaaaaa caaatcaaag actacagaga ttccctggac    1380
gaacttgaaa tcaagatacg actggaagca atcaattctc tggaaactaa ccaacaagta    1440
gaaattcgcg acctggatgt attcagtgct gatcgggcaa aggcaaacac tgtagatatg    1500
ttcgacatcg acccaaattt gatatcctgg gattcaatga gcgacgcgag ggtgagcacg    1560
caaataagcg atctttatct gaagaatggg ggtgacgaat ctcgagtata tttcgaaatt    1620
aacaacaaac ggataaagcg atctgattat aacattagtc agctggtgag gccaaagctt    1680
tccgacagca ctcggaagaa tctgaacgat tctatatgga gttgaaaag aactagtgaa     1740 gaatatttga aattgtccaa acgaaagttg gaactgagca gagctgttgt gaactacact    1800
atccgccaga gcaagctcct ctccggaatt aacgacattg ttataatact tgaggacctg    1860
gatgtaaaaa aaaaattcaa tggcaggggc attcgagata tcggatggga caacttcttc    1920
agctccagga aagagaacag gtggttcatt ccggcattcc ataaggcttt ctcagagctt    1980
tcaagcaacc ggggcctctg tgtcatcgaa gtcaacccgg catggacatc tgccacctgt    2040
cccgactgcg ggttctgtag taaagagaac agagatggca ttaattttac ctgtcgcaag    2100
tgcggtgtct cttaccacgc ggacatagat gttgccactc ttaatatagc ccgggtggcc    2160
gttctcggca agcctatgtc cggacccgcc gaccgcgaga gactgggcga tactaagaaa    2220
ccccgggtag caaggagccg aaagactatg aaacggaaag atattagcaa tagcaccgtt    2280
gaggctatgg ttacagccgg aagcggaccc aagaaaaaac gcaaggtgga agatcctaag    2340
aaaaagcgga aagtgagcct gggcagcggc tccgattaca agatgacga tgacaaagac     2400 tacaaggatg atgatgataa gggatccggc gcaacaaact ctctctgct gaaacaagcc     2460 ggagatgtcg aagagaatcc tggaccgacc gagtacaagc ccacggtgcg cctcgccacc    2520
cgcgacgacg tccccagggc cgtacgcacc ctcgccgccg cgttcgccga ctacccgcc     2580 acgcgccaca ccgtcgatcc ggaccgccac atcgagcggg tcaccgagct gcaagaactc    2640
ttcctcacgc gcgtcgggct cgacatcggc aaggtgtggg tcgcggacga cggcgccgcg    2700
gtggcggtct ggaccacgcc ggagagcgtc gaagcggggg cggtgttcgc cgagatcggc    2760
ccgcgcatgg ccgagttgag cggttcccgg ctggccgcgc agcaacagat ggaaggcctc    2820
ctggcgccgc accggcccaa ggagcccgcg tggttcctgg ccaccgtcgg agtctcgccc    2880
gaccaccagg gcaagggtct gggcagcgcc gtcgtgctcc ccggagtgga ggcggccgag    2940
cgcgccgggg tgcccgcctt cctggagacc tccgcgcccc gcaacctccc cttctacgag    3000
cggctcggct tcaccgtcac cgccgacgtc gaggtgcccg aaggaccgcg cacctggtgc    3060
atgaccgcag agcccggtgc ctgaacgcgt taagaattcc tagagctcgc tgatcagcct    3120
cgactgtgcc ttctagttgc cagccatctg ttgtttgccc ctcccccgtg ccttccttga    3180
ccctggaagg tgccactccc actgtccttt cctaataaaa tgaggaaatt gcatcgcatt    3240
gtctgagtag tgtcattct attctggggg gtggggtggg gcaggacagc aagggggagg    3300
attgggaaga gaatagcagg catgctgggg agcggccgca ggaacccta gtgatggagt     3360
```

```
tggccactcc ctctctgcgc gctcgctcgc tcactgaggc cgggcgacca aaggtcgccc    3420
gacgcccggg ctttgcccgg gcggcctcag tgagcgagcg agcgcgcagc tgcctgcagg    3480
ggcgcctgat gcggtatttt ctccttacgc atctgtgcgg tatttcacac cgcatacgtc    3540
aaagcaacca tagtacgcgc cctgtagcgg cgcattaagc gcggcgggtg tggtggttac    3600
gcgcagcgtg accgctacac ttgccagcgc cttagcgccc gctcctttcg ctttcttccc    3660
ttcctttctc gccacgttcg ccggctttcc ccgtcaagct ctaaatcggg gctcccttt     3720 agggttccga tttagtgctt tacggcacct cgaccccaaa aaacttgatt tgggtgatgg    3780
ttcacgtagt gggccatcgc cctgatagac ggttttttcgc cctttgacgt tggagtccac   3840
gttctttaat agtggactct tgttccaaac tggaacaaca ctcaactcta tctcgggcta    3900
ttcttttgat ttataaggga ttttgccgat ttcggtctat tggttaaaaa atgagctgat    3960
ttaacaaaaa tttaacgcga attttaacaa aatattaacg tttacaattt tatggtgcac    4020
tctcagtaca atctgctctg atgccgcata gttaagccag ccccgacacc cgccaacacc    4080
cgctgacgcg ccctgacggg cttgtctgct cccggcatcc gcttacagac aagctgtgac    4140
cgtctccggg agctgcatgt gtcagaggtt ttcaccgtca tcaccgaaac gcgcgagacg    4200
aaagggcctc gtgatacgcc tatttttata ggttaatgtc atgataataa tggtttctta    4260
gacgtcaggt ggcacttttc ggggaaatgt gcgcggaacc cctatttgtt tatttttcta    4320
aatacattca aatatgtatc cgctcatgag acaataaccc tgataaatgc ttcaataata    4380
ttgaaaaagg aagagtatga gtattcaaca tttccgtgtc gcccttattc ccttttttgc    4440 ggcatttttgc cttcctgttt ttgctcaccc agaaacgctg gtgaaagtaa agatgctga    4500 agatcagttg ggtgcacgag tgggttacat cgaactggat ctcaacagcg gtaagatcct    4560
tgagagtttt cgccccgaag aacgttttcc aatgatgagc acttttaaag ttctgctatg    4620
tggcgcggta ttatcccgta ttgacgccgg gcaagagcaa ctcggtcgcc gcatacacta    4680
ttctcagaat gacttggttg agtactcacc agtcacagaa aagcatctta cggatggcat    4740
gacagtaaga gaattatgca gtgctgccat aaccatgagt gataacactg cggccaactt    4800
acttctgaca acgatcggag gaccgaagga gctaaccgct ttttttgcaca acatggggga    4860 tcatgtaact cgccttgatc gttgggaacc ggagctgaat gaagccatac caaacgacga    4920
gcgtgacacc acgatgcctg tagcaatggc aacaacgttg cgcaaactat taactggcga    4980
actacttact ctagcttccc ggcaacaatt aatagactgg atggaggcgg ataaagttgc    5040
aggaccactt ctgcgctcgg cccttccggc tggctggttt attgctgata atctggagc     5100 cggtgagcgt ggaagccgcg gtatcattgc agcactgggg ccagatggta agccctcccg    5160
tatcgtagtt atctacacga cggggagtca ggcaactatg gatgaacgaa atagacagat    5220
cgctgagata ggtgcctcac tgattaagca ttggtaactg tcagaccaag tttactcata    5280
tatactttag attgatttaa aacttcattt ttaatttaaa aggatctagg tgaagatcct    5340
ttttgataat ctcatgacca aaatccctta acgtgagttt cgttccact gagcgtcaga    5400 ccccgtagaa aagatcaaag gatcttcttg agatcctttt tttctgcgcg taatctgctg    5460
cttgcaaaca aaaaaaccac cgctaccagc ggtggttttgt tgccggatc aagagctacc    5520 aactcttttt ccgaaggtaa ctggcttcag cagagcgcag ataccaaata ctgttcttct    5580
agtgtagccg tagttaggcc accacttcaa gaactctgta gcaccgccta catacctcgc    5640
tctgctaatc ctgttaccag tggctgctgc cagtggcgat aagtcgtgtc ttaccgggtt    5700
ggactcaaga cgatagttac cggataaggc gcagcggtcg ggctgaacgg ggggttcgtg    5760
```

```
cacacagccc agcttggagc gaacgaccta caccgaactg agatacctac agcgtgagct    5820
atgagaaagc gccacgcttc ccgaagggag aaaggcggac aggtatccgg taagcggcag    5880
ggtcggaaca ggagagcgca cgagggagct tccagggga aacgcctggt atctttatag     5940
tcctgtcggg tttcgccacc tctgacttga gcgtcgattt ttgtgatgct cgtcagggg     6000 gcggagccta tggaaaaacg ccagcaacgc ggcctttta cggttcctgg ccttttgctg     6060
gccttttgct cacatgtgag ggcctatttc ccatgattcc ttcatatttg catatacgat    6120
acaaggctgt tagagagata attggaatta atttgactgt aaacacaaag atattagtac    6180
aaaatacgtg acgtagaaag taataatttc ttgggtagtt tgcagtttta aaattatgtt    6240
ttaaaatgga ctatcatatg cttaccgtaa cttgaaagta tttcgatttc ttggctttat    6300
atatcttgtg gaaaggacga acaccgacc aaaacgacta ttgattgccc agtacgctgg     6360
gacagaagag ctaatgctct tcatttttt tggtacccgt tacataactt acggtaaatg     6420
gcccgcctgg ctgaccgccc aacgacccc gcccattgac gtcaatagta acgccaatag     6480
ggactttcca ttgacgtcaa tgggtggagt atttacggta aactgcccac ttggcagtac    6540
atcaagtgta tcatatgcca agtacgcccc ctattgacgt caatgacggt aaatggcccg    6600
cctggcattg tgcccagtac atgaccttat gggactttcc tacttggcag tacatctacg    6660
tattagtcat cgctattacc atggtcgagg tgagccccac gttctgcttc actctcccca    6720
tctccccccc ctccccaccc caattttgt atttatttat tttttaatta ttttgtgcag     6780 cgatggggc gggggggg ggggggcgcg cgccaggcgg ggcggggsgg ggsgrgggs        6840 ggggsgggs grggcggaga ggtgcggcgg cagccaatca gagcggcgcg ctccgaaagt     6900 ttcctttat ggcgaggcgg cggcggcggc ggccctataa aaagcgaagc gcgcggcggg     6960
cgggagtcgc tgccgcgctgc cttcgccccg tgccccgctc cgccgccgcc tcgcgccgcc    7020
cgccccggct ctgactgacc gcgttactcc cacaggtgag cgggcgggac ggcccttctc    7080
ctccgggctg taattagctg agcaagaggt aaggtttaa gggatggttg ttggtgggg      7140 tattaatgtt taattacctg gagcacctgc ctgaaatcac ttttttttcag gttggaccgg   7200 tgccacc                                                              7207

<210> SEQ ID NO 163
<211> LENGTH: 28
<212> TYPE: DNA
<213> ORGANISM: Artificial Sequence
<220> FEATURE:
<223> OTHER INFORMATION: Synthetic sequence

<400> SEQUENCE: 163
gttaactgcc gcataggcag cttagaaa                                         28

<210> SEQ ID NO 164
<211> LENGTH: 28
<212> TYPE: DNA
<213> ORGANISM: Artificial Sequence
<220> FEATURE:
<223> OTHER INFORMATION: Synthetic sequence

<400> SEQUENCE: 164
gtgaaccgcc gtataggcag cttagaaa                                         28

<210> SEQ ID NO 165
<211> LENGTH: 36
<212> TYPE: RNA
<213> ORGANISM: Artificial Sequence
```

-continued

```
<220> FEATURE:
<223> OTHER INFORMATION: Synthetic sequence
<220> FEATURE:
<221> NAME/KEY: misc_feature
<222> LOCATION: (4)..(4)
<223> OTHER INFORMATION: y is c or u
<220> FEATURE:
<221> NAME/KEY: misc_feature
<222> LOCATION: (6)..(6)
<223> OTHER INFORMATION: r is a or g
<220> FEATURE:
<221> NAME/KEY: misc_feature
<222> LOCATION: (7)..(7)
<223> OTHER INFORMATION: d is a, g, or u
<220> FEATURE:
<221> NAME/KEY: misc_feature
<222> LOCATION: (10)..(10)
<223> OTHER INFORMATION: w is a or u
<220> FEATURE:
<221> NAME/KEY: misc_feature
<222> LOCATION: (12)..(12)
<223> OTHER INFORMATION: h is a, c, or u
<220> FEATURE:
<221> NAME/KEY: misc_feature
<222> LOCATION: (13)..(13)
<223> OTHER INFORMATION: y is c or u
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature
<222> LOCATION: (22)..(22)
<223> OTHER INFORMATION: r is a or g
<220> FEATURE:
<221> NAME/KEY: misc_feature
<222> LOCATION: (23)..(23)
<223> OTHER INFORMATION: d is a, g or u
<220> FEATURE:
<221> NAME/KEY: misc_feature
<222> LOCATION: (24)..(24)
<223> OTHER INFORMATION: w is a or u
<220> FEATURE:
<221> NAME/KEY: misc_feature
<222> LOCATION: (25)..(26)
<223> OTHER INFORMATION: r is a or g
<220> FEATURE:
<221> NAME/KEY: misc_feature
<222> LOCATION: (27)..(27)
<223> OTHER INFORMATION: n is a, c, g, or u
<220> FEATURE:
<221> NAME/KEY: misc_feature
<222> LOCATION: (28)..(28)
<223> OTHER INFORMATION: k is g or u
<220> FEATURE:
<221> NAME/KEY: misc_feature
<222> LOCATION: (29)..(29)
<223> OTHER INFORMATION: d is a, g, or u
<220> FEATURE:
<221> NAME/KEY: misc_feature
<222> LOCATION: (32)..(32)
<223> OTHER INFORMATION: k is g or u
<220> FEATURE:
<221> NAME/KEY: misc_feature
<222> LOCATION: (33)..(33)
<223> OTHER INFORMATION: n is a, c, g, or u
<220> FEATURE:
<221> NAME/KEY: misc_feature
<222> LOCATION: (34)..(34)
<223> OTHER INFORMATION: d is a, g, or u
<220> FEATURE:
<221> NAME/KEY: misc_feature
<222> LOCATION: (35)..(35)
<223> OTHER INFORMATION: r is a or g
<220> FEATURE:
<221> NAME/KEY: misc_feature
<222> LOCATION: (36)..(36)
<223> OTHER INFORMATION: b is c, g, or u
```

-continued

```
<400> SEQUENCE: 165
gucycrdcgw ahygrgcaau crdwrrnkdu ukndrb                        36

<210> SEQ ID NO 166
<211> LENGTH: 36
<212> TYPE: RNA
<213> ORGANISM: Artificial Sequence
<220> FEATURE:
<223> OTHER INFORMATION: Synthetic sequence

<400> SEQUENCE: 166
gucccaacga auugggcaau caaaaaggau uggauc                        36

<210> SEQ ID NO 167
<211> LENGTH: 36
<212> TYPE: RNA
<213> ORGANISM: Artificial Sequence
<220> FEATURE:
<223> OTHER INFORMATION: Synthetic sequence

<400> SEQUENCE: 167
gucucagcgu acugagcaau caaaagguuu cgcagg                        36

<210> SEQ ID NO 168
<211> LENGTH: 36
<212> TYPE: RNA
<213> ORGANISM: Artificial Sequence
<220> FEATURE:
<223> OTHER INFORMATION: Synthetic sequence

<400> SEQUENCE: 168
gucucgacua aucgagcaau cguuugagau cucucc                        36

<210> SEQ ID NO 169
<211> LENGTH: 36
<212> TYPE: RNA
<213> ORGANISM: Artificial Sequence
<220> FEATURE:
<223> OTHER INFORMATION: Synthetic sequence

<400> SEQUENCE: 169
guccccucgu gagggcaau cguugagcgu uccgac                         36

<210> SEQ ID NO 170
<211> LENGTH: 36
<212> TYPE: RNA
<213> ORGANISM: Artificial Sequence
<220> FEATURE:
<223> OTHER INFORMATION: Synthetic sequence

<400> SEQUENCE: 170
gucccagcgu acugggcaau caauagucgu uuuggu                        36

<210> SEQ ID NO 171
<211> LENGTH: 36
<212> TYPE: RNA
<213> ORGANISM: Artificial Sequence
<220> FEATURE:
<223> OTHER INFORMATION: Synthetic sequence

<400> SEQUENCE: 171
gucgcggcgu accgcgcaau gagagucugu ugccau                        36
```

-continued

```
<210> SEQ ID NO 172
<211> LENGTH: 36
<212> TYPE: RNA
<213> ORGANISM: Artificial Sequence
<220> FEATURE:
<223> OTHER INFORMATION: Synthetic sequence

<400> SEQUENCE: 172
gucuccucgu aaggagcaau cuauuagucu ugaaag            36

<210> SEQ ID NO 173
<211> LENGTH: 36
<212> TYPE: RNA
<213> ORGANISM: Artificial Sequence
<220> FEATURE:
<223> OTHER INFORMATION: Synthetic sequence

<400> SEQUENCE: 173
gucucggcgc accgagcaau cagcgagguc uucuac            36

<210> SEQ ID NO 174
<211> LENGTH: 36
<212> TYPE: RNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: v is a, c, or g
<220> FEATURE:
<221> NAME/KEY: misc_feature
<222> LOCATION: (2)..(2)
<223> OTHER INFORMATION: y is c or u
<220> FEATURE:
<221> NAME/KEY: misc_feature
<222> LOCATION: (3)..(3)
<223> OTHER INFORMATION: h is a, c, or u
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (5)..(5)
<223> OTHER INFORMATION: m is a or c
<220> FEATURE:
<221> NAME/KEY: misc_feature
<222> LOCATION: (8)..(8)
<223> OTHER INFORMATION: h is a, c, or u
<220> FEATURE:
<221> NAME/KEY: misc_feature
<222> LOCATION: (9)..(9)
<223> OTHER INFORMATION: m is a or c
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (11)..(12)
<223> OTHER INFORMATION: y is c or u
<220> FEATURE:
<221> NAME/KEY: misc_feature
<222> LOCATION: (13)..(13)
<223> OTHER INFORMATION: w is a or u
<220> FEATURE:
<221> NAME/KEY: misc_feature
<222> LOCATION: (13)..(13)
<223> OTHER INFORMATION: w is a or u
<220> FEATURE:
<221> NAME/KEY: misc_feature
<222> LOCATION: (14)..(14)
<223> OTHER INFORMATION: h is a, c, or u
```

```
<220> FEATURE:
<221> NAME/KEY: misc_feature
<222> LOCATION: (15)..(15)
<223> OTHER INFORMATION: y is c or u
<220> FEATURE:
<221> NAME/KEY: misc_feature
<222> LOCATION: (21)..(21)
<223> OTHER INFORMATION: y is c or u
<220> FEATURE:
<221> NAME/KEY: misc_feature
<222> LOCATION: (24)..(24)
<223> OTHER INFORMATION: r is a or g
<220> FEATURE:
<221> NAME/KEY: misc_feature
<222> LOCATION: (25)..(25)
<223> OTHER INFORMATION: d is a, g or u
<220> FEATURE:
<221> NAME/KEY: misc_feature
<222> LOCATION: (27)..(27)
<223> OTHER INFORMATION: w is a or u
<220> FEATURE:
<221> NAME/KEY: misc_feature
<222> LOCATION: (30)..(30)
<223> OTHER INFORMATION: h is a, c, or u
<220> FEATURE:
<221> NAME/KEY: misc_feature
<222> LOCATION: (31)..(31)
<223> OTHER INFORMATION: y is c or u
<220> FEATURE:
<221> NAME/KEY: misc_feature
<222> LOCATION: (33)..(33)
<223> OTHER INFORMATION: r is a or g

<400> SEQUENCE: 174
vyhnmaahmn yywhygauug cycrduwcgh ygrgac                            36

<210> SEQ ID NO 175
<211> LENGTH: 36
<212> TYPE: RNA
<213> ORGANISM: Artificial Sequence
<220> FEATURE:
<223> OTHER INFORMATION: Synthetic sequence

<400> SEQUENCE: 175
gauccaaucc uuuuugauug cccaauucgu ugggac                            36

<210> SEQ ID NO 176
<211> LENGTH: 36
<212> TYPE: RNA
<213> ORGANISM: Artificial Sequence
<220> FEATURE:
<223> OTHER INFORMATION: Synthetic sequence

<400> SEQUENCE: 176
ccugcgaaac cuuuugauug cucaguacgc ugagac                            36

<210> SEQ ID NO 177
<211> LENGTH: 36
<212> TYPE: RNA
<213> ORGANISM: Artificial Sequence
<220> FEATURE:
<223> OTHER INFORMATION: Synthetic sequence

<400> SEQUENCE: 177
ggagagaucu caaacgauug cucgauuagu cgagac                            36

<210> SEQ ID NO 178
<211> LENGTH: 36
<212> TYPE: RNA
<213> ORGANISM: Artificial Sequence
```

```
<220> FEATURE:
<223> OTHER INFORMATION: Synthetic sequence

<400> SEQUENCE: 178
gucggaacgc ucaacgauug ccccucacga ggggac                              36

<210> SEQ ID NO 179
<211> LENGTH: 36
<212> TYPE: RNA
<213> ORGANISM: Artificial Sequence
<220> FEATURE:
<223> OTHER INFORMATION: Synthetic sequence

<400> SEQUENCE: 179
accaaaacga cuauugauug cccaguacgc ugggac                              36

<210> SEQ ID NO 180
<211> LENGTH: 36
<212> TYPE: RNA
<213> ORGANISM: Artificial Sequence
<220> FEATURE:
<223> OTHER INFORMATION: Synthetic sequence

<400> SEQUENCE: 180
auggcaacag acucucauug cgcgguacgc cgcgac                              36

<210> SEQ ID NO 181
<211> LENGTH: 36
<212> TYPE: RNA
<213> ORGANISM: Artificial Sequence
<220> FEATURE:
<223> OTHER INFORMATION: Synthetic sequence

<400> SEQUENCE: 181
cuuucaagac uaauagauug cuccuuacga ggagac                              36

<210> SEQ ID NO 182
<211> LENGTH: 36
<212> TYPE: RNA
<213> ORGANISM: Artificial Sequence
<220> FEATURE:
<223> OTHER INFORMATION: Synthetic sequence

<400> SEQUENCE: 182
guagaagacc ucgcugauug cucggugcgc cgagac                              36

<210> SEQ ID NO 183
<211> LENGTH: 49
<212> TYPE: RNA
<213> ORGANISM: Artificial Sequence
<220> FEATURE:
<223> OTHER INFORMATION: Synthetic sequence

<400> SEQUENCE: 183
caacgauugc cccuacagag gggacagcug guaaugggau accuugugc                49

<210> SEQ ID NO 184
<211> LENGTH: 36
<212> TYPE: RNA
<213> ORGANISM: Artificial Sequence
<220> FEATURE:
<223> OTHER INFORMATION: Synthetic sequence

<400> SEQUENCE: 184
ugccccuaca gaggggacag cugguaaugg gauacc                              36
```

```
<210> SEQ ID NO 185
<211> LENGTH: 29
<212> TYPE: DNA
<213> ORGANISM: Artificial Sequence
<220> FEATURE:
<223> OTHER INFORMATION: Synthetic sequence

<400> SEQUENCE: 185
caattcgacc attaccctat ggaacacga                                    29

<210> SEQ ID NO 186
<211> LENGTH: 29
<212> TYPE: DNA
<213> ORGANISM: Artificial Sequence
<220> FEATURE:
<223> OTHER INFORMATION: Synthetic sequence

<400> SEQUENCE: 186
gttaagctgg taatgggata ccttgtgct                                    29

<210> SEQ ID NO 187
<211> LENGTH: 36
<212> TYPE: RNA
<213> ORGANISM: Artificial Sequence
<220> FEATURE:
<223> OTHER INFORMATION: Synthetic sequence

<400> SEQUENCE: 187
ugcucgauua gucgagacag cugguaaugg gauacc                            36

<210> SEQ ID NO 188
<211> LENGTH: 29
<212> TYPE: DNA
<213> ORGANISM: Artificial Sequence
<220> FEATURE:
<223> OTHER INFORMATION: Synthetic sequence

<400> SEQUENCE: 188
caattcgacc attaccctat ggaacacga                                    29

<210> SEQ ID NO 189
<211> LENGTH: 28
<212> TYPE: DNA
<213> ORGANISM: Artificial Sequence
<220> FEATURE:
<223> OTHER INFORMATION: Synthetic sequence

<400> SEQUENCE: 189
gttagctggt aatgggatac cttgtgct                                     28

<210> SEQ ID NO 190
<211> LENGTH: 36
<212> TYPE: RNA
<213> ORGANISM: Artificial Sequence
<220> FEATURE:
<223> OTHER INFORMATION: Synthetic sequence

<400> SEQUENCE: 190
ugccccuaca gagggacag cugguaaugg gauacc                             36

<210> SEQ ID NO 191
<211> LENGTH: 29
<212> TYPE: DNA
<213> ORGANISM: Artificial Sequence
<220> FEATURE:
<223> OTHER INFORMATION: Synthetic sequence
```

```
<400> SEQUENCE: 191
caattcgacc attaccctat ggaacacga                                    29

<210> SEQ ID NO 192
<211> LENGTH: 29
<212> TYPE: DNA
<213> ORGANISM: Artificial Sequence
<220> FEATURE:
<223> OTHER INFORMATION: Synthetic sequence

<400> SEQUENCE: 192
gttaagctgg taatgggata ccttgtgct                                    29

<210> SEQ ID NO 193
<211> LENGTH: 36
<212> TYPE: RNA
<213> ORGANISM: Artificial Sequence
<220> FEATURE:
<223> OTHER INFORMATION: Synthetic sequence

<400> SEQUENCE: 193
ugcccaguac gcugggacag cugguaaugg gauacc                            36

<210> SEQ ID NO 194
<211> LENGTH: 29
<212> TYPE: DNA
<213> ORGANISM: Artificial Sequence
<220> FEATURE:
<223> OTHER INFORMATION: Synthetic sequence

<400> SEQUENCE: 194
taagtcgacc attaccctat ggaacacga                                    29

<210> SEQ ID NO 195
<211> LENGTH: 29
<212> TYPE: DNA
<213> ORGANISM: Artificial Sequence
<220> FEATURE:
<223> OTHER INFORMATION: Synthetic sequence

<400> SEQUENCE: 195
attcagctgg taatgggata ccttgtgct                                    29

<210> SEQ ID NO 196
<211> LENGTH: 60
<212> TYPE: RNA
<213> ORGANISM: Artificial Sequence
<220> FEATURE:
<223> OTHER INFORMATION: Synthetic sequence

<400> SEQUENCE: 196
cacaggagag aucucaaacg auugcucgau uagucgagac agcugguaau gggauaccuu   60

<210> SEQ ID NO 197
<211> LENGTH: 60
<212> TYPE: RNA
<213> ORGANISM: Artificial Sequence
<220> FEATURE:
<223> OTHER INFORMATION: Synthetic sequence

<400> SEQUENCE: 197
uaaugucgga acgcucaacg auugcccuua cagaggggac ugccgccucc gcgacgccca   60
```

-continued

```
<210> SEQ ID NO 198
<211> LENGTH: 35
<212> TYPE: DNA
<213> ORGANISM: Artificial Sequence
<220> FEATURE:
<223> OTHER INFORMATION: Synthetic sequence

<400> SEQUENCE: 198
ctggagttgt cccaattctt gttgaattag atggt                          35

<210> SEQ ID NO 199
<211> LENGTH: 35
<212> TYPE: DNA
<213> ORGANISM: Artificial Sequence
<220> FEATURE:
<223> OTHER INFORMATION: Synthetic sequence

<400> SEQUENCE: 199
aacatttccg tgtcgccctt attccctttt ttgcg                          35

<210> SEQ ID NO 200
<211> LENGTH: 20
<212> TYPE: DNA
<213> ORGANISM: Artificial Sequence
<220> FEATURE:
<223> OTHER INFORMATION: Synthetic sequence

<400> SEQUENCE: 200
ggcgagggcg atgccaccta                                           20

<210> SEQ ID NO 201
<211> LENGTH: 20
<212> TYPE: DNA
<213> ORGANISM: Artificial Sequence
<220> FEATURE:
<223> OTHER INFORMATION: Synthetic sequence

<400> SEQUENCE: 201
ttcaagtccg ccatgcccga                                           20

<210> SEQ ID NO 202
<211> LENGTH: 20
<212> TYPE: DNA
<213> ORGANISM: Artificial Sequence
<220> FEATURE:
<223> OTHER INFORMATION: Synthetic sequence

<400> SEQUENCE: 202
ggtgaaccgc atcgagctga                                           20

<210> SEQ ID NO 203
<211> LENGTH: 20
<212> TYPE: DNA
<213> ORGANISM: Artificial Sequence
<220> FEATURE:
<223> OTHER INFORMATION: Synthetic sequence

<400> SEQUENCE: 203
cttgtacagc tcgtccatgc                                           20

<210> SEQ ID NO 204
<211> LENGTH: 20
<212> TYPE: DNA
<213> ORGANISM: Artificial Sequence
<220> FEATURE:
<223> OTHER INFORMATION: Synthetic sequence
```

<400> SEQUENCE: 204
tcgggcagca gcacggggcc                                               20

<210> SEQ ID NO 205
<211> LENGTH: 20
<212> TYPE: DNA
<213> ORGANISM: Artificial Sequence
<220> FEATURE:
<223> OTHER INFORMATION: Synthetic sequence

<400> SEQUENCE: 205
tagttgtact ccagcttgtg                                               20

<210> SEQ ID NO 206
<211> LENGTH: 20
<212> TYPE: DNA
<213> ORGANISM: Artificial Sequence
<220> FEATURE:
<223> OTHER INFORMATION: Synthetic sequence

<400> SEQUENCE: 206
tggccgttta cgtcgccgtc                                               20

<210> SEQ ID NO 207
<211> LENGTH: 20
<212> TYPE: DNA
<213> ORGANISM: Artificial Sequence
<220> FEATURE:
<223> OTHER INFORMATION: Synthetic sequence

<400> SEQUENCE: 207
aagaagtcgt gctgcttcat                                               20

<210> SEQ ID NO 208
<211> LENGTH: 20
<212> TYPE: DNA
<213> ORGANISM: Artificial Sequence
<220> FEATURE:
<223> OTHER INFORMATION: Synthetic sequence

<400> SEQUENCE: 208
accggggtgg tgcccatcct                                               20

<210> SEQ ID NO 209
<211> LENGTH: 20
<212> TYPE: DNA
<213> ORGANISM: Artificial Sequence
<220> FEATURE:
<223> OTHER INFORMATION: Synthetic sequence

<400> SEQUENCE: 209
agcgtgtccg gcgagggcga                                               20

<210> SEQ ID NO 210
<211> LENGTH: 20
<212> TYPE: DNA
<213> ORGANISM: Artificial Sequence
<220> FEATURE:
<223> OTHER INFORMATION: Synthetic sequence

<400> SEQUENCE: 210
atctgcacca ccggcaagct                                               20

```
<210> SEQ ID NO 211
<211> LENGTH: 20
<212> TYPE: DNA
<213> ORGANISM: Artificial Sequence
<220> FEATURE:
<223> OTHER INFORMATION: Synthetic sequence

<400> SEQUENCE: 211
gagggcgaca ccctggtgaa                                               20

<210> SEQ ID NO 212
<211> LENGTH: 20
<212> TYPE: DNA
<213> ORGANISM: Artificial Sequence
<220> FEATURE:
<223> OTHER INFORMATION: Synthetic sequence

<400> SEQUENCE: 212
accagggtgt cgccctcgaa                                               20

<210> SEQ ID NO 213
<211> LENGTH: 20
<212> TYPE: DNA
<213> ORGANISM: Artificial Sequence
<220> FEATURE:
<223> OTHER INFORMATION: Synthetic sequence

<400> SEQUENCE: 213
ttctgcttgt cggccatgat                                               20

<210> SEQ ID NO 214
<211> LENGTH: 20
<212> TYPE: DNA
<213> ORGANISM: Artificial Sequence
<220> FEATURE:
<223> OTHER INFORMATION: Synthetic sequence

<400> SEQUENCE: 214
accttgatgc cgttcttctg                                               20

<210> SEQ ID NO 215
<211> LENGTH: 20
<212> TYPE: DNA
<213> ORGANISM: Artificial Sequence
<220> FEATURE:
<223> OTHER INFORMATION: Synthetic sequence

<400> SEQUENCE: 215
tgctggtagt ggtcggcgag                                               20

<210> SEQ ID NO 216
<211> LENGTH: 20
<212> TYPE: DNA
<213> ORGANISM: Artificial Sequence
<220> FEATURE:
<223> OTHER INFORMATION: Synthetic sequence

<400> SEQUENCE: 216
gtgaccgccg ccgggatcac                                               20

<210> SEQ ID NO 217
<211> LENGTH: 20
<212> TYPE: DNA
<213> ORGANISM: Artificial Sequence
<220> FEATURE:
<223> OTHER INFORMATION: Synthetic sequence
```

-continued

<400> SEQUENCE: 217
gggtctttgc tcagcttgga					20

<210> SEQ ID NO 218
<211> LENGTH: 20
<212> TYPE: DNA
<213> ORGANISM: Artificial Sequence
<220> FEATURE:
<223> OTHER INFORMATION: Synthetic sequence

<400> SEQUENCE: 218
tggcggatct tgaagttcac					20

<210> SEQ ID NO 219
<211> LENGTH: 20
<212> TYPE: DNA
<213> ORGANISM: Artificial Sequence
<220> FEATURE:
<223> OTHER INFORMATION: Synthetic sequence

<400> SEQUENCE: 219
tggctgttgt agttgtactc					20

<210> SEQ ID NO 220
<211> LENGTH: 20
<212> TYPE: DNA
<213> ORGANISM: Artificial Sequence
<220> FEATURE:
<223> OTHER INFORMATION: Synthetic sequence

<400> SEQUENCE: 220
tactccagct tgtgccccag					20

<210> SEQ ID NO 221
<211> LENGTH: 20
<212> TYPE: DNA
<213> ORGANISM: Artificial Sequence
<220> FEATURE:
<223> OTHER INFORMATION: Synthetic sequence

<400> SEQUENCE: 221
ccgtcctcct tgaagtcgat					20

<210> SEQ ID NO 222
<211> LENGTH: 20
<212> TYPE: DNA
<213> ORGANISM: Artificial Sequence
<220> FEATURE:
<223> OTHER INFORMATION: Synthetic sequence

<400> SEQUENCE: 222
ccgtcgtcct tgaagaagat					20

<210> SEQ ID NO 223
<211> LENGTH: 20
<212> TYPE: DNA
<213> ORGANISM: Artificial Sequence
<220> FEATURE:
<223> OTHER INFORMATION: Synthetic sequence

<400> SEQUENCE: 223
ccgtaggtgg catcgccctc					20

```
<210> SEQ ID NO 224
<211> LENGTH: 20
<212> TYPE: DNA
<213> ORGANISM: Artificial Sequence
<220> FEATURE:
<223> OTHER INFORMATION: Synthetic sequence

<400> SEQUENCE: 224
ccggtggtgc agatgaactt                                          20

<210> SEQ ID NO 225
<211> LENGTH: 20
<212> TYPE: DNA
<213> ORGANISM: Artificial Sequence
<220> FEATURE:
<223> OTHER INFORMATION: Synthetic sequence

<400> SEQUENCE: 225
aagaagatgg tgcgctcctg                                          20

<210> SEQ ID NO 226
<211> LENGTH: 20
<212> TYPE: DNA
<213> ORGANISM: Artificial Sequence
<220> FEATURE:
<223> OTHER INFORMATION: Synthetic sequence

<400> SEQUENCE: 226
cgtgatggtc tcgattgagt                                          20

<210> SEQ ID NO 227
<211> LENGTH: 60
<212> TYPE: RNA
<213> ORGANISM: Artificial Sequence
<220> FEATURE:
<223> OTHER INFORMATION: Synthetic sequence

<400> SEQUENCE: 227
cacaggagag aucucaaacg auugcucgau uagucgagac agcugguaau gggauaccuu      60

<210> SEQ ID NO 228
<211> LENGTH: 60
<212> TYPE: RNA
<213> ORGANISM: Artificial Sequence
<220> FEATURE:
<223> OTHER INFORMATION: Synthetic sequence

<400> SEQUENCE: 228
uaaugucgga acgcucaacg auugccccuc acgagggac ugccgccucc gcgacgccca       60

<210> SEQ ID NO 229
<211> LENGTH: 60
<212> TYPE: RNA
<213> ORGANISM: Artificial Sequence
<220> FEATURE:
<223> OTHER INFORMATION: Synthetic sequence

<400> SEQUENCE: 229
auuaaccaaa acgacuauug auugcccagu acgcugggac uaugagcuua uguacaucaa      60

<210> SEQ ID NO 230
<211> LENGTH: 52
<212> TYPE: RNA
<213> ORGANISM: Artificial Sequence
<220> FEATURE:
<223> OTHER INFORMATION: Synthetic sequence
```

<400> SEQUENCE: 230
gaccuuuuua auucuacuc uuguagauaa agugcucauc auuggaaaac gu    52

<210> SEQ ID NO 231
<211> LENGTH: 1906
<212> TYPE: DNA
<213> ORGANISM: Artificial Sequence
<220> FEATURE:
<223> OTHER INFORMATION: Synthetic sequence

<400> SEQUENCE: 231

| | |
|---|---:|
| ccaatgctta atcagtgagg cacctatctc agcgatctgt ctatttcgtt catccatagt | 60 |
| tgcctgactc cccgtcgtgt agataactac gatacgggag ggcttaccat ctggccccag | 120 |
| tgctgcaatg ataccgcggg acccacgctc accggctcca gatttatcag caataaacca | 180 |
| gccagccgga agggccgagc gcagaagtgg tcctgcaact ttatccgcct ccatccagtc | 240 |
| tattaattgt tgccgggaag ctagagtaag tagttcgcca gttaatagtt tgcgcaacgt | 300 |
| tgttgccatt gctacaggca tcgtggtgtc acgctcgtcg tttggtatgg cttcattcag | 360 |
| ctccggttcc caacgatcaa ggcgagttac atgatccccc atgttgtgca aaaaagcggt | 420 |
| tagctccttc ggtcctccga tcgttgtcag aagtaagttg gccgcagtgt tatcactcat | 480 |
| ggttatggca gcactgcata attctcttac tgtcatgcca tccgtaagat gcttttctgt | 540 |
| gactggtgag tactcaacca agtcattctg agaatagtgt atgcggcgac cgagttgctc | 600 |
| ttgcccggcg tcaatacggg ataataccgc gccacatagc agaactttaa aagtgctcat | 660 |
| cattggaaaa cgttcttcgg ggcgaaaact ctcaaggatc ttaccgctgt tgagatccag | 720 |
| ttcgatgtaa cccactcgtg cacccaactg atcttcagca tctttactt tcaccagcgt | 780 |
| ttctgggtga gcaaaaacag gaaggcaaaa tgccgcaaaa aagggaataa gggcgacacg | 840 |
| gaaatgttga atactcatac tcttcctttt tcaatattat tgaagcattt atcagggtta | 900 |
| ttgtctcatg agcggataca tatttgaatg tatttagaaa aataaacaaa tagggggttcc | 960 |
| gcgcacattt ccccgaaaag tgccacctgt catgaccaaa atcccttaac gtgagttttc | 1020 |
| gttccactga gcgtcagacc ccgtagaaaa gatcaaagga tcttcttgag atcctttttt | 1080 |
| tctgcgcgta atctgctgct tgcaaacaaa aaaaccaccg ctaccagcgg tggtttgttt | 1140 |
| gccggatcaa gagctaccaa ctcttttttcc gaaggtaact ggcttcagca gagcgcagat | 1200 |
| accaaatact gttcttctag tgtagccgta gttaggccac cacttcaaga actctgtagc | 1260 |
| accgcctaca tacctcgctc tgctaatcct gttaccagtg gctgctgcca gtggcgataa | 1320 |
| gtcgtgtctt accgggttgg actcaagacg atagttaccg gataaggcgc agcggtcggg | 1380 |
| ctgaacgggg ggttcgtgca cacagcccag cttggagcga acgacctaca ccgaactgag | 1440 |
| atacctacag cgtgagctat gagaaagcgc cacgcttccc gaaggagaa aggcggacag | 1500 |
| gtatccggta agcggcaggg tcggaacagg agagcgcacg agggagcttc caggggggaaa | 1560 |
| cgcctggtat ctttatagtc ctgtcgggtt tcgccacctc tgacttgagc gtcgattttt | 1620 |
| gtgatgctcg tcaggggggc ggagcctatg gaaaaacgcc agcaacgcgg cctttttacg | 1680 |
| gttcctggcc ttttgctggc cttttgctca catgttcttt cctgcgttat cccctgattc | 1740 |
| tgtggataac cgtgcggccg ccccttgtag ttaagctggt aatgggatac cttgtgctac | 1800 |
| agcggccgcg attatcaaaa aggatcttca cctagatcct tttaaattaa aaatgaagtt | 1860 |
| ttaaatcaat ctaaagtata tatgagtaaa cttggtctga cagtta | 1906 |

<210> SEQ ID NO 232
<211> LENGTH: 1898
<212> TYPE: DNA
<213> ORGANISM: Artificial Sequence
<220> FEATURE:
<223> OTHER INFORMATION: Synthetic sequence

<400> SEQUENCE: 232

| | | | | | |
|---|---|---|---|---|---|
| gctcttgccc | ggcgtcaata | cgggataata | ccgcgccaca | tagcagaact | ttaaaagtgc | 60 |
| tcatcattgg | aaaacgttct | tcggggcgaa | aactctcaag | gatcttaccg | ctgttgagat | 120 |
| ccagttcgat | gtaacccact | cgtgcaccca | actgatcttc | agcatctttt | actttcacca | 180 |
| gcgtttctgg | gtgagcaaaa | acaggaaggc | aaaatgccgc | aaaaaaggga | ataagggcga | 240 |
| cacggaaatg | ttgaatactc | atactcttcc | tttttcaata | ttattgaagc | atttatcagg | 300 |
| gttattgtct | catgagcgga | tacatatttg | aatgtattta | gaaaaataaa | caaatagggg | 360 |
| ttccgcgcac | atttccccga | aaagtgccac | ctgtcatgac | caaaatccct | taacgtgagt | 420 |
| tttcgttcca | ctgagcgtca | gacccccgtag | aaaagatcaa | aggatcttct | tgagatcctt | 480 |
| tttttctgcg | cgtaatctgc | tgcttgcaaa | caaaaaaacc | accgctacca | gcggtggttt | 540 |
| gtttgccgga | tcaagagcta | ccaactcttt | ttccgaaggt | aactggcttc | agcagagcgc | 600 |
| agataccaaa | tactgttctt | ctagtgtagc | cgtagttagg | ccaccacttc | aagaactctg | 660 |
| tagcaccgcc | tacatacctc | gctctgctaa | tcctgttacc | agtggctgct | gccagtggcg | 720 |
| ataagtcgtg | tcttaccggg | ttggactcaa | gacgatagtt | accggataag | gcgcagcggt | 780 |
| cgggctgaac | ggggggttcg | tgcacacagc | ccagcttgga | gcgaacgacc | tacaccgaac | 840 |
| tgagatacct | acagcgtgag | ctatgagaaa | gcgccacgct | tcccgaaggg | agaaaggcgg | 900 |
| acaggtatcc | ggtaagcggc | agggtcggaa | caggagagcg | cacgagggag | cttccagggg | 960 |
| gaaacgcctg | gtatctttat | agtcctgtcg | ggtttcgcca | cctctgactt | gagcgtcgat | 1020 |
| ttttgtgatg | ctcgtcaggg | gggcggagcc | tatggaaaaa | cgccagcaac | gcggcctttt | 1080 |
| tacggttcct | ggccttttgc | tggccttttg | ctcacatgtt | ctttcctgcg | ttatcccctg | 1140 |
| attctgtgga | taaccgtgcg | gccgcccctt | gtagttaagc | tggtaatggg | ataccttgtg | 1200 |
| ctacagcggc | cgcgattatc | aaaaaggatc | ttcacctaga | tcctttaaa | ttaaaaatga | 1260 |
| agttttaaat | caatctaaag | tatatatgag | taaacttggt | ctgacagtta | ccaatgctta | 1320 |
| atcagtgagg | cacctatctc | agcgatctgt | ctatttcgtt | catccatagt | tgcctgactc | 1380 |
| cccgtcgtgt | agataactac | gatacgggag | ggcttaccat | ctggccccag | tgctgcaatg | 1440 |
| ataccgcggg | acccacgctc | accggctcca | gatttatcag | caataaacca | gccagccgga | 1500 |
| agggccgagc | gcagaagtgg | tcctgcaact | ttatccgcct | ccatccagtc | tattaattgt | 1560 |
| tgccgggaag | ctagagtaag | tagttcgcca | gttaatagtt | tgcgcaacgt | tgttgccatt | 1620 |
| gctacaggca | tcgtggtgtc | acgctcgtcg | tttggtatgg | cttcattcag | ctccggttcc | 1680 |
| caacgatcaa | ggcgagttac | atgatccccc | atgttgtgca | aaaaagcggt | tagctccttc | 1740 |
| ggtcctccga | tcgttgtcag | aagtaagttg | gccgcagtgt | tatcactcat | ggttatggca | 1800 |
| gcactgcata | attctcttac | tgtcatgcca | tccgtaagat | gcttttctgt | gactggtgag | 1860 |
| tactcaacca | agtcattctg | agaatagtgt | atgcggcg | | | 1898 |

<210> SEQ ID NO 233
<211> LENGTH: 1898
<212> TYPE: DNA
<213> ORGANISM: Artificial Sequence
<220> FEATURE:
<223> OTHER INFORMATION: Synthetic sequence

<400> SEQUENCE: 233

```
gctcttgccc ggcgtcaata cgggataata ccgcgccaca tagcagaact ttaaaagtgc      60
tcatcattgg aaaacgttct tcggggcgaa aactctcaag gatcttaccg ctgttgagat     120
ccagttcgat gtaacccact cgtgcaccca actgatcttc agcatctttt actttcacca     180
gcgtttctgg gtgagcaaaa acaggaaggc aaaatgccgc aaaaaaggga ataagggcga     240
cacggaaatg ttgaatactc atactcttcc ttttcaata ttattgaagc atttatcagg     300
gttattgtct catgagcgga tacatatttg aatgtattta gaaaaataaa caatagggg      360
ttccgcgcac atttccccga aaagtgccac ctgtcatgac caaaatccct taacgtgagt     420
tttcgttcca ctgagcgtca gaccccgtag aaaagatcaa aggatcttct tgagatcctt     480
ttttttctgcg cgtaatctgc tgcttgcaaa caaaaaaacc accgctacca gcggtggttt     540
gtttgccgga tcaagagcta ccaactcttt ttccgaaggt aactggcttc agcagagcgc     600
agataccaaa tactgttctt ctagtgtagc cgtagttagg ccaccacttc aagaactctg     660
tagcaccgcc tacatacctc gctctgctaa tcctgttacc agtggctgct gccagtggcg     720
ataagtcgtg tcttaccggg ttggactcaa gacgatagtt accggataag gcgcagcggt     780
cgggctgaac ggggggttcg tgcacacagc ccagcttgga gcgaacgacc tacaccgaac     840
tgagatacct acagcgtgag ctatgagaaa gcgccacgct cccgaaggg agaaaggcgg      900
acaggtatcc ggtaagcggc agggtcggaa caggagagcg cacgagggag cttccagggg     960
gaaacgcctg gtatctttat agtcctgtcg ggtttcgcca cctctgactt gagcgtcgat    1020
ttttgtgatg ctcgtcaggg gggcggagcc tatggaaaaa cgccagcaac gcggccttt     1080
tacggttcct ggccttttgc tggccttttg ctcacatgtt ctttcctgcg ttatcccctg    1140
attctgtgga taaccgtgcg gccgcccctt gtagccaagc tggtaatggg ataccttgtg    1200
ctacagcggc cgcgattatc aaaaaggatc ttcacctaga tcctttaaa ttaaaaatga    1260
agttttaaat caatctaaag tatatatgag taaacttggt ctgacagtta ccaatgctta    1320
atcagtgagg cacctatctc agcgatctgt ctatttcgtt catccatagt tgcctgactc    1380
cccgtcgtgt agataactac gatacgggag ggcttaccat ctggcccag tgctgcaatg    1440
ataccgcggg acccacgctc accggctcca gatttatcag caataaacca gccagccgga    1500
agggccgagc gcagaagtgg tcctgcaact ttatccgcct ccatccagtc tattaattgt    1560
tgccgggaag ctagagtaag tagttcgcca gttaatagtt tgcgcaacgt tgttgccatt    1620
gctacaggca tcgtggtgtc acgctcgtcg tttggtatgg cttcattcag ctccggttcc    1680
caacgatcaa ggcgagttac atgatccccc atgttgtgca aaaagcggt tagctccttc     1740
ggtcctccga tcgttgtcag aagtaagttg gccgcagtgt tatcactcat ggttatggca    1800
gcactgcata attctcttac tgtcatgcca tccgtaagat gcttttctgt gactggtgag    1860
tactcaacca agtcattctg agaatagtgt atgcggcg                           1898
```

<210> SEQ ID NO 234
<211> LENGTH: 56
<212> TYPE: DNA
<213> ORGANISM: Artificial Sequence
<220> FEATURE:
<223> OTHER INFORMATION: Synthetic sequence

<400> SEQUENCE: 234
cggccgcccc ttgtagttaa gctggtaatg ggataccttg tgctacagcg gccgcg        56

<210> SEQ ID NO 235
<211> LENGTH: 56
<212> TYPE: DNA
<213> ORGANISM: Artificial Sequence
<220> FEATURE:
<223> OTHER INFORMATION: Synthetic sequence

<400> SEQUENCE: 235
cgcggccgct gtagcacaag gtatcccatt accagcttaa ctacaagggg cggccg        56

<210> SEQ ID NO 236
<211> LENGTH: 56
<212> TYPE: DNA
<213> ORGANISM: Artificial Sequence
<220> FEATURE:
<223> OTHER INFORMATION: Synthetic sequence

<400> SEQUENCE: 236
cggccgcccc ttgtaattca gctggtaatg ggataccttg tgctacagcg gccgcg        56

<210> SEQ ID NO 237
<211> LENGTH: 56
<212> TYPE: DNA
<213> ORGANISM: Artificial Sequence
<220> FEATURE:
<223> OTHER INFORMATION: Synthetic sequence

<400> SEQUENCE: 237
cgcggccgct gtagcacaag gtatcccatt accagctgaa ttacaagggg cggccg        56

<210> SEQ ID NO 238
<211> LENGTH: 41
<212> TYPE: RNA
<213> ORGANISM: Artificial Sequence
<220> FEATURE:
<223> OTHER INFORMATION: Synthetic sequence

<400> SEQUENCE: 238
cgcuguagca caagguaucc cauuaccagc uuaacuacaa g                          41

<210> SEQ ID NO 239
<211> LENGTH: 48
<212> TYPE: DNA
<213> ORGANISM: Artificial Sequence
<220> FEATURE:
<223> OTHER INFORMATION: Synthetic sequence

<400> SEQUENCE: 239
gtggccgttt aaaagtgctc atcattggaa aacgtaggat gggcacca                  48

<210> SEQ ID NO 240
<211> LENGTH: 32
<212> TYPE: RNA
<213> ORGANISM: Artificial Sequence
<220> FEATURE:
<223> OTHER INFORMATION: Synthetic sequence

<400> SEQUENCE: 240
aguauuuaau cguugcaaga ggcgcugcgu uu                                    32

```
<210> SEQ ID NO 241
<211> LENGTH: 25
<212> TYPE: RNA
<213> ORGANISM: Artificial Sequence
<220> FEATURE:
<223> OTHER INFORMATION: Synthetic sequence

<400> SEQUENCE: 241
caacgauugc cccucacgag gggac                                  25

<210> SEQ ID NO 242
<211> LENGTH: 37
<212> TYPE: RNA
<213> ORGANISM: Artificial Sequence
<220> FEATURE:
<223> OTHER INFORMATION: Synthetic sequence

<400> SEQUENCE: 242
caacgauugc cccucacgag gggacagcug guaaugg                     37

<210> SEQ ID NO 243
<211> LENGTH: 39
<212> TYPE: RNA
<213> ORGANISM: Artificial Sequence
<220> FEATURE:
<223> OTHER INFORMATION: Synthetic sequence

<400> SEQUENCE: 243
caacgauugc cccucacgag gggacagcug guaauggga                   39

<210> SEQ ID NO 244
<211> LENGTH: 41
<212> TYPE: RNA
<213> ORGANISM: Artificial Sequence
<220> FEATURE:
<223> OTHER INFORMATION: Synthetic sequence

<400> SEQUENCE: 244
caacgauugc cccucacgag gggacagcug guaaugggau a                41

<210> SEQ ID NO 245
<211> LENGTH: 43
<212> TYPE: RNA
<213> ORGANISM: Artificial Sequence
<220> FEATURE:
<223> OTHER INFORMATION: Synthetic sequence

<400> SEQUENCE: 245
caacgauugc cccucacgag gggacagcug guaaugggau acc              43

<210> SEQ ID NO 246
<211> LENGTH: 45
<212> TYPE: RNA
<213> ORGANISM: Artificial Sequence
<220> FEATURE:
<223> OTHER INFORMATION: Synthetic sequence

<400> SEQUENCE: 246
caacgauugc cccucacgag gggacagcug guaaugggau accuu            45

<210> SEQ ID NO 247
<211> LENGTH: 47
<212> TYPE: RNA
<213> ORGANISM: Artificial Sequence
<220> FEATURE:
<223> OTHER INFORMATION: Synthetic sequence
```

```
<400> SEQUENCE: 247
caacgauugc cccucacgag gggacagcug guaaugggau accuugu                47

<210> SEQ ID NO 248
<211> LENGTH: 49
<212> TYPE: RNA
<213> ORGANISM: Artificial Sequence
<220> FEATURE:
<223> OTHER INFORMATION: Synthetic sequence

<400> SEQUENCE: 248
caacgauugc cccucacgag gggacagcug guaaugggau accuugugc              49

<210> SEQ ID NO 249
<211> LENGTH: 43
<212> TYPE: RNA
<213> ORGANISM: Artificial Sequence
<220> FEATURE:
<223> OTHER INFORMATION: Synthetic sequence

<400> SEQUENCE: 249
aaacgauugc ucgauuaguc gagacagcug guaaugggau acc                    43

<210> SEQ ID NO 250
<211> LENGTH: 43
<212> TYPE: RNA
<213> ORGANISM: Artificial Sequence
<220> FEATURE:
<223> OTHER INFORMATION: Synthetic sequence

<400> SEQUENCE: 250
uauugauugc ccaguacgcu gggacagcug guaaugggau acc                    43
```

…

CRISPR-CAS12J EFFECTOR POLYPEPTIDES AND METHODS OF USE THEREOF

CROSS-REFERENCE

This application is a continuation of Ser. No. 17/225,866, filed, Apr. 8, 2021, which is a continuation of PCT/US2020/021213, filed Mar. 5, 2020, which claims the benefit of U.S. Provisional Patent Application No. 62/815,173, filed Mar. 7, 2019, U.S. Provisional Patent Application No. 62/855,739, filed May 31, 2019, U.S. Provisional Patent Application No. 62/907,422, filed Sep. 27, 2019, and U.S. Provisional Patent Application No. 62/948,470, filed Dec. 16, 2019, each of which applications is incorporated herein by reference in its entirety.

INTRODUCTION

CRISPR-Cas systems include Cas proteins, which are involved in acquisition, targeting and cleavage of foreign DNA or RNA, and a guide RNA(s), which includes a segment that binds Cas proteins and a segment that binds to a target nucleic acid. For example, Class 2 CRISPR-Cas systems comprise a single Cas protein bound to a guide RNA, where the Cas protein binds to and cleaves a targeted nucleic acid. The programmable nature of these systems has facilitated their use as a versatile technology for use in modification of target nucleic acid.

INCORPORATION BY REFERENCE OF SEQUENCE LISTING PROVIDED AS A TEXT FILE

A Sequence Listing is provided herewith as a text file, "09_BERK-403CON8_SeqList_(rev January 2023)_ST25.txt" created on Jan. 26, 2023 and having a size of 227,001 bytes. The contents of the text file are incorporated by reference herein in their entirety.

SUMMARY

The present disclosure provides RNA-guided CRISPR-Cas effector proteins, nucleic acids encoding same, and compositions comprising same. The present disclosure provides ribonucleoprotein complexes comprising: an RNA-guided CRISPR-Cas effector protein of the present disclosure; and a guide RNA. The present disclosure provides methods of modifying a target nucleic acid, using an RNA-guided CRISPR-Cas effector protein of the present disclosure and a guide RNA. The present disclosure provides methods of modulating transcription of a target nucleic acid.

BRIEF DESCRIPTION OF THE DRAWINGS

FIG. 6A-6R provide amino acid sequences of examples of Cas12J polypeptides of the present disclosure.

FIG. 7 provides nucleotide sequences of constant region portions of Cas12J guide RNAs (Depicted as the DNA encoding the RNA). Sequences in bold are the orientation used and/or extrapolated from the working examples (see, e.g., the crRNA 'sequences used' in Example 3). Sequences separated by an "or" are the reverse complement of one another.

FIG. 9 provides the positions of amino acids in RuvC-I, RuvC-II, and RuvC-III domains of Cas12J polypeptides that, when substituted, results in a Cas12J polypeptide that binds, but does not cleave, a target nucleic acid in the presence of a Cas12J guide RNA.

FIG. 11A-11C shows the efficiency of transformation plasmid interference assay.

FIG. 17A-17G present Table 1, which provides nucleotide sequences of the pCas12J-2-hs and pCas12J-3-hs constructs (from top to bottom: SEQ ID NOs: 161-162).

FIG. 31A-31B depict formation of ribonucleoprotein (RNP) complexes with: a) pre-crRNA FIG. 32A-32C depict CasΦ-mediated enhanced green fluorescent protein (EGFP) disruption in HEK293 cells.

FIG. 34 presents Table 3, which provides a description of some of the plasmids used in Example 7.

FIG. 35 presents Table 4, which provides guide sequences for experiments described in Example 7.

FIG. 36 presents Table 5, which provides substrate sequences for in vitro experiments described in Example 7.

FIG. 37 presents Table 6, which provides crRNA sequences for in vitro experiments described in Example 7 (from top to bottom SEQ ID NOs:241-250).

DEFINITIONS

Figure 1A:
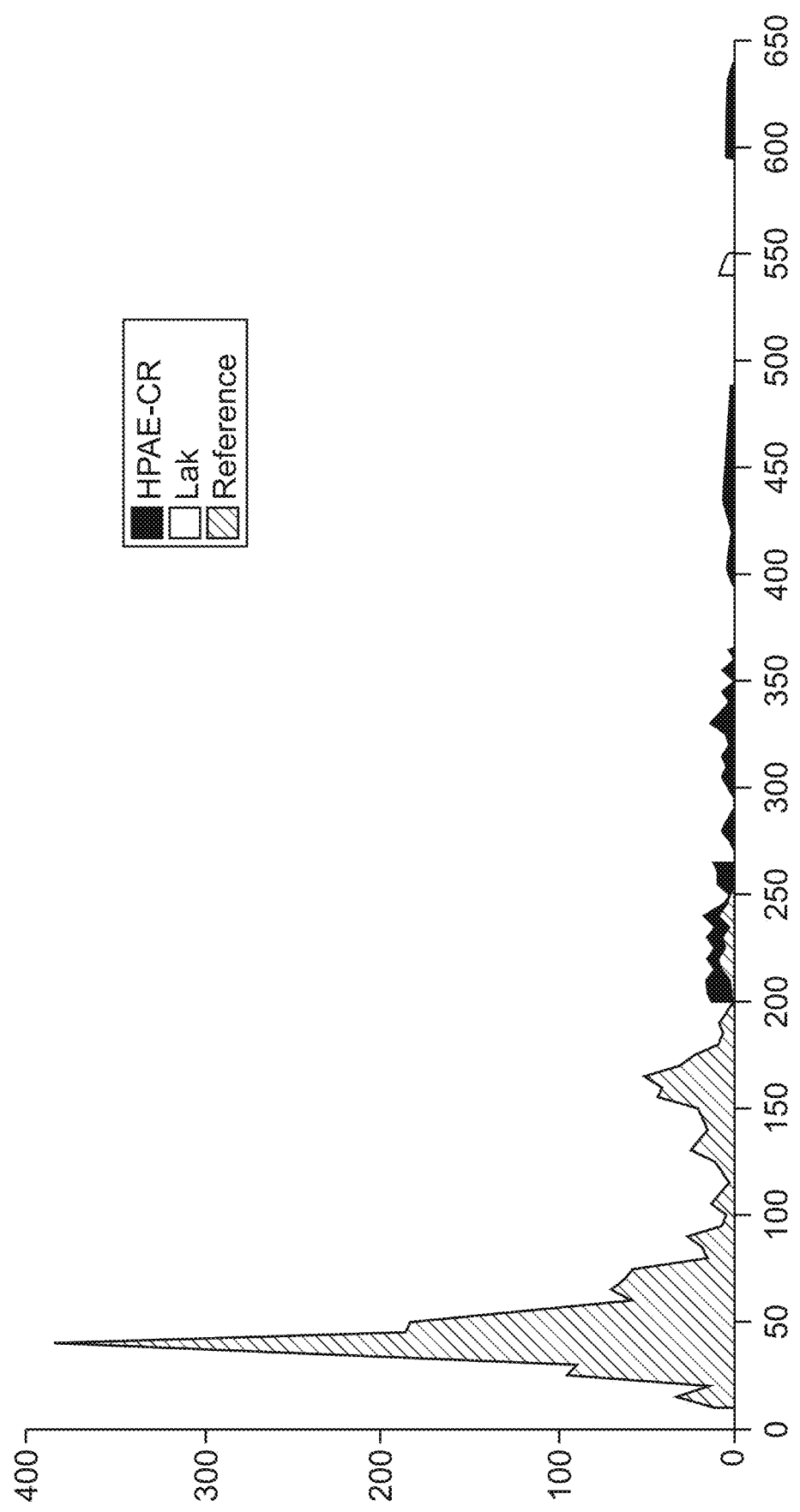
FIG. 1A shows the size distribution of complete bacteriophage genomes from this study, Lak phage reported recently from a subset of the same samples and reference sources (all dsDNA genomes from RefSeq v92 and non-artifactual assemblies >200 kb from (Paez-Espino et al. (2016) Nature 536: 425).

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is at least partially responsible for the degeneracy (i.e., redundancy) of the genetic code in the context of tRNA anti-codon base-pairing with codons in mRNA. Thus, in the context of this disclosure, a guanine (G) (e.g., of dsRNA duplex of a guide RNA molecule; of a guide RNA base pairing with a target nucleic acid, etc.) is considered complementary to both a uracil (U) and to an adenine (A). For example, when a G/U base-pair can be made at a given nucleotide position of a dsRNA duplex of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656), the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489), and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a Cas12J polypeptide/guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain) In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleotide sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

A "protein coding sequence" or a sequence that encodes a particular protein or polypeptide, is a nucleotide sequence that is transcribed into mRNA (in the case of DNA) and is translated (in the case of mRNA) into a polypeptide in vitro or in vivo when placed under the control of appropriate regulatory sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., RNA-guided endonuclease, GeoCas9 polypeptide, GeoCas9 fusion polypeptide, and the like) and/or regulate translation of an encoded polypeptide.

As used herein, a "promoter" or a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive expression by the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism that can be isolated from a source in nature is naturally occurring.

The term "fusion" as used herein as applied to a nucleic acid or polypeptide refers to two components that are defined by structures derived from different sources. For example, where "fusion" is used in the context of a fusion polypeptide (e.g., a fusion Cas12J protein), the fusion polypeptide includes amino acid sequences that are derived from different polypeptides. A fusion polypeptide may comprise either modified or naturally-occurring polypeptide sequences (e.g., a first amino acid sequence from a modified or unmodified Cas12J protein; and a second amino acid sequence from a modified or unmodified protein other than a Cas12J protein, etc.). Similarly, "fusion" in the context of a polynucleotide encoding a fusion polypeptide includes nucleotide sequences derived from different coding regions (e.g., a first nucleotide sequence encoding a modified or unmodified Cas12J protein; and a second nucleotide sequence encoding a polypeptide other than a Cas12J protein).

The term "fusion polypeptide" refers to a polypeptide which is made by the combination (i.e., "fusion") of two otherwise separated segments of amino acid sequence, usually through human intervention.

"Heterologous," as used herein, means a nucleotide or polypeptide sequence that is not found in the native nucleic acid or protein, respectively. For example, in some cases, in a variant Cas12J protein of the present disclosure, a portion of naturally-occurring Cas12J polypeptide (or a variant thereof) may be fused to a heterologous polypeptide (i.e. an amino acid sequence from a protein other than a Cas12J polypeptide or an amino acid sequence from another organism). As another example, a fusion Cas12J polypeptide can comprise all or a portion of a naturally-occurring Cas12J polypeptide (or variant thereof) fused to a heterologous polypeptide, i.e., a polypeptide from a protein other than a Cas12J polypeptide, or a polypeptide from another organism. The heterologous polypeptide may exhibit an activity (e.g., enzymatic activity) that will also be exhibited by the variant Cas12J protein or the fusion Cas12J protein (e.g., biotin ligase activity; nuclear localization; etc.). A heterologous nucleic acid sequence may be linked to a naturally-occurring nucleic acid sequence (or a variant thereof) (e.g., by genetic engineering) to generate a nucleotide sequence encoding a fusion polypeptide (a fusion protein).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences"). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. An example of such a case is a DNA (a recombinant) encoding a wild-type protein where the DNA sequence is codon optimized for expression of the protein in a cell (e.g., a eukaryotic cell) in which the protein is not naturally found (e.g., expression of a CRISPR/Cas RNA-guided polypeptide such as Cas12J (e.g., wild-type Cas12J; variant Cas12J; fusion Cas12J; etc.) in a eukaryotic cell). A codon-optimized DNA can therefore be recombinant and non-naturally occurring while the protein encoded by the DNA may have a wild type amino acid sequence.

Thus, the term "recombinant" polypeptide does not necessarily refer to a polypeptide whose amino acid sequence does not naturally occur. Instead, a "recombinant" polypeptide is encoded by a recombinant non-naturally occurring DNA sequence, but the amino acid sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, artificial chromosome, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression.

The terms "recombinant expression vector," or "DNA construct" are used interchangeably herein to refer to a DNA molecule comprising a vector and an insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA or exogenous RNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., DNA such as genomic DNA) that includes a site ("target site" or "target sequence") targeted by an RNA-guided endonuclease polypeptide (e.g., wild-type Cas12J; variant Cas12J; fusion Cas12J; etc.). The target sequence is the sequence to which the guide sequence of a subject Cas12J guide RNA (e.g., a dual Cas12J guide RNA or a single-molecule Cas12J guide RNA) will hybridize. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand."

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events.

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

In some instances, a component (e.g., a nucleic acid component (e.g., a Cas12J guide RNA); a protein component (e.g., wild-type Cas12J polypeptide; variant Cas12J polypeptide; fusion Cas12J polypeptide; etc.); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels; e.g., a fluorescent label) and indirectly detectable labels (indirect labels; e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^{3}$H, $^{125}$I, $^{35}$S, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle &

Griffiths, John Wiley & Sons 1998), the disclosures of which are incorporated herein by reference.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, non-human primates, ungulates, felines, canines, bovines, ovines, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Cas12J CRISPR-Cas effector polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided CRISPR-Cas effector proteins, referred to herein as "Cas12J" polypeptides, "CasΦ" polypeptides, or "CasXS" polypeptides"; nucleic acids encoding same; and compositions comprising same. The present disclosure provides ribonucleoprotein complexes comprising: a Cas12J polypeptide of the present disclosure; and a guide RNA. The present disclosure provides methods of modifying a target nucleic acid, using a Cas12J polypeptide of the present disclosure and a guide RNA. The present disclosure provides methods of modulating transcription of a target nucleic acid.

The present disclosure provides guide RNAs (referred to herein as "Cas12J guide RNAs") that bind to and provide sequence specificity to the Cas12J proteins; nucleic acids encoding the Cas12J guide RNAs; and modified host cells comprising the Cas12J guide RNAs and/or nucleic acids encoding same. Cas12J guide RNAs are useful in a variety of applications, which are provided.

COMPOSITIONS

Crispr/Cas12J Proteins and Guide RNAs

A Cas12J CRISPR/Cas effector polypeptide (e.g., a Cas12J protein; also referred to as a "CasXS polypeptide" or a "CasΦ polypeptide") interacts with (binds to) a corresponding guide RNA (e.g., a Cas12J guide RNA) to form a ribonucleoprotein (RNP) complex that is targeted to a particular site in a target nucleic acid (e.g. a target DNA) via base pairing between the guide RNA and a target sequence within the target nucleic acid molecule. A guide RNA includes a nucleotide sequence (a guide sequence) that is complementary to a sequence (the target site) of a target nucleic acid. Thus, a Cas12J protein forms a complex with a Cas12J guide RNA and the guide RNA provides sequence specificity to the RNP complex via the guide sequence. The Cas12J protein of the complex provides the site-specific activity. In other words, the Cas12J protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

In some cases, a Cas12J CRISPR/Cas effector polypeptide of the present disclosure, when complexed with a guide RNA, cleaves double-stranded DNA or single-stranded DNA, but not single-stranded RNA.

In some cases, a Cas12J CRISPR/Cas effector polypeptide of the present disclosure catalyzes processing of pre-crRNA in a magnesium-dependent manner.

The present disclosure provides compositions comprising a Cas12J polypeptide (and/or a nucleic acid comprising a nucleotide sequence encoding the Cas12J polypeptide) (e.g., where the Cas12J polypeptide can be a naturally existing protein, a nickase Cas12J protein, a catalytically inactive ("dead" Cas12J; also referred to herein as a "dCas12J protein"), a fusion Cas12J protein, etc.). The present disclosure provides compositions comprising a Cas12J guide RNA (and/or a nucleic acid comprising a nucleotide sequence encoding the Cas12J guide RNA). The present disclosure provides compositions comprising (a) a Cas12J polypeptide (and/or a nucleic acid encoding the Cas12J polypeptide) (e.g., where the Cas12J polypeptide can be a naturally existing protein, a nickase Cas12J protein, a dCas12J protein, a fusion Cas12J protein, etc.) and (b) a Cas12J guide RNA (and/or a nucleic acid encoding the Cas12J guide RNA). The present disclosure provides a nucleic acid/protein complex (RNP complex) comprising: (a) a Cas12J polypeptide of the present disclosure (e.g., where the Cas12J polypeptide can be a naturally existing protein, a nickase Cas12J protein, a Cdas12J protein, a fusion Cas12J protein, etc.); and (b) a Cas12J guide RNA.

Cas12J Protein

A Cas12J polypeptide (this term is used interchangeably with the term "Cas12J protein", "CasΦ polypeptide", and "CasΦ protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases, the Cas12J protein includes a fusion partner with an activity, and in some cases, the Cas12J protein provides nuclease activity). In some cases, the Cas12J protein is a naturally-occurring protein (e.g., naturally occurs in bacteriophage). In other cases, the Cas12J protein is not a naturally-occurring polypeptide (e.g., the Cas12J protein is a variant Cas12J protein (e.g., a catalytically inactive Cas12J protein, a fusion Cas12J protein, and the like).

A Cas12J polypeptide (e.g., not fused to any heterologous fusion partner) can have a molecular weight of from about 65 kiloDaltons (kDa) to about 85 kDa. For example, a Cas12J polypeptide can have a molecular weight of from about 65 kDa to about 70 kDa, from about 70 kDa to about 75 kDa, or from about 75 kDa to about 80 kDa. For example, a Cas12J polypeptide can have a molecular weight of from about 70 kDa to about 80 kDa.

Assays to determine whether given protein interacts with a Cas12J guide RNA can be any convenient binding assay that tests for binding between a protein and a nucleic acid. Suitable binding assays (e.g., gel shift assays) will be known to one of ordinary skill in the art (e.g., assays that include adding a Cas12J guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring Cas12J protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring Cas12J guide RNA is a crRNA, where the crRNA includes (i) a guide sequence that hybridizes to a target sequence in the target DNA and (ii) a protein binding segment which includes a stem-loop (hairpin—dsRNA duplex) that binds to the Cas12J protein.

In some cases, a C12J polypeptide of the present disclosure, when complexed with a Cas12J guide RNA, generates a product nucleic acid comprising 5' overhang following site specific cleavage of a target nucleic acid. The 5' overhang can be an 8 to 12 nucleotide (nt) overhang. For example, the 5' overhang can be 8 nt, 9 nt, 10 nt, 11 nt, or 12 nt in length.

In some embodiments, the Cas12J protein of the subject methods and/or compositions is (or is derived from) a naturally occurring (wild type) protein. Examples of naturally occurring Cas12J proteins are depicted in FIG. 6A-6R. In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the Cas12J amino acid sequences depicted in FIG. 6 (e.g., any one of FIG. 6A-6R). In some cases, a Cas12J protein (of the subject compositions and/or methods) includes an amino acid sequence depicted in FIG. 6 (e.g., any one of FIG. 6A-6R).

In some cases, a Cas12J protein (of the subject compositions and/or methods) has more sequence identity to an amino acid sequence depicted in FIG. 6 (e.g., any of the Cas12J amino acid sequences depicted in FIG. 6) than to any of the following: Cas12a proteins, Cas12b proteins, Cas12c proteins, Cas12d proteins, Cas12e proteins, Cas12 g proteins, Cas12h proteins, and Cas12i proteins. In some cases, a Cas12J protein (of the subject compositions and/or methods) includes an amino acid sequence having a RuvC domain (which includes the RuvC-I, RuvC-II, and RuvC-III domains) that has more sequence identity to the RuvC domain of an amino acid sequence depicted in FIG. 6 (e.g., the RuvC domain of any of the Cas12J amino acid sequences depicted in FIG. 6) than to the RuvC domain of any of the following: Cas12a proteins, Cas12b proteins, Cas12c proteins, Cas12d proteins, Cas12e proteins, Cas12 g proteins, Cas12h proteins, and Cas12i proteins.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the RuvC domain (which includes the RuvC-I, RuvC-II, and RuvC-III domains) of any one of the Cas12J amino acid sequences depicted in FIG. 6 (e.g., any one of FIG. 6A-6R). In some cases, a Cas12J protein (of the subject compositions and/or methods) includes an amino acid sequence having 70% or more sequence identity (e.g., 75% or more, 80% or more, 85% or more, 90% or more, 95% or more, 97% or more, 98% or more, 99% or more, or 100% sequence identity) with the RuvC domain (which includes the RuvC-I, RuvC-II, and RuvC-III domains) of any one of the Cas12J amino acid sequences depicted in FIG. 6 (e.g., any one of FIG. 6A-6R). In some cases, a Cas12J protein (of the subject compositions and/or methods) includes the RuvC domain (which includes the RuvC-I, RuvC-II, and RuvC-III domains) of any one of the Cas12J amino acid sequences depicted in FIG. 6 (e.g., any one of FIG. 6A-6R).

In some cases, a guide RNA that binds a Cas12J polypeptide includes a nucleotide sequence depicted in FIG. 7 (or in some cases the reverse complement of same). In some cases, the guide RNA comprises the nucleotide sequence (N)nX or the reverse complement of same, where N is any nucleotide, n is an integer from 15 to 30 (e.g., from 15 to 20, from 17 to 25, from 17 to 22, from 18 to 22, from 18 to 20, from 20 to 25, or from 25 to 30), and X is any one of the nucleotide sequences depicted in FIG. 7 (or in some cases the reverse complement of same).

In some cases, a guide RNA that binds a Cas12J polypeptide includes a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 7 (or in some cases the reverse complement of same). In some cases, the guide RNA comprises the nucleotide sequence (N)nX or the reverse complement of same, where N is any nucleotide, n is an integer from 15 to 30 (e.g., from 15 to 20, from 17 to 25, from 17 to 22, from 18 to 22, from 18 to 20, from 20 to 25, or from 25 to 30), and X a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 7.

In some cases, a guide RNA that binds a Cas12J polypeptide includes a nucleotide sequence having 85% or more sequence identity (e.g., 90% or more, 95% or more, 97% or more, 98% or more, 99% or more, or 100% sequence identity) with any one of the sequences depicted in FIG. 7 (or in some cases the reverse complement of same). In some cases, the guide RNA comprises the nucleotide sequence (N)nX or the reverse complement of same, where N is any nucleotide, n is an integer from 15 to 30 (e.g., from 15 to 20, from 17 to 25, from 17 to 22, from 18 to 22, from 18 to 20, from 20 to 25, or from 25 to 30), and X a nucleotide sequence having 85% or more sequence identity (e.g., 90% or more, 95% or more, 97% or more, 98% or more, 99% or more, or 100% sequence identity) with any one of the sequences depicted in FIG. 7.

In some cases, a guide RNA that binds a Cas12J polypeptide includes a nucleotide sequence depicted in FIG. 7 (or in some cases the reverse complement of same). In some cases, the guide RNA comprises the nucleotide sequence X(N)n, where N is any nucleotide, n is an integer from 15 to 30 (e.g., from 15 to 20, from 17 to 25, from 17 to 22, from 18 to 22, from 18 to 20, from 20 to 25, or from 25 to 30), and X is any one of the nucleotide sequences depicted in FIG. 7 (or in some cases the reverse complement of same).

In some cases, a guide RNA that binds a Cas12J polypeptide includes a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 7 (or in some cases the reverse complement of same). In some cases, the guide RNA comprises the nucleotide sequence X(N)n, where N is any nucleotide, n is an integer from 15 to 30 (e.g., from 15 to 20, from 17 to 25, from 17 to 22, from 18 to 22, from 18 to 20, from 20 to 25, or from 25 to 30), and X a nucleotide sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the sequences depicted in FIG. 7.

Examples of Cas12J proteins are depicted in FIG. 6A-6R. As noted above, a Cas12J polypeptide is also referred to herein as a "CasΦ polypeptide." For example:

1) the Cas12J polypeptide designated "Cas12J_1947455" (or "Cas12J_1947455_11" in FIG. 9) and depicted in FIG. 6A is also referred to herein as "CasΦ-1";

2) the Cas12J polypeptide designated "Cas12J_2071242" and depicted in FIG. 6B is also referred to herein as "CasΦ-2"

3) the Cas12J polypeptide designated "Cas12J_3339380 (or "Cas12J_3339380_12" in FIG. 9) and depicted in FIG. 6D is also referred to herein as "CasΦ-3";

4) the Cas12J polypeptide designated "Cas12J_3877103_16" and depicted in FIG. 6Q is also referred to herein as "CasΦ-4";

5) the Cas12J polypeptide designated "Cas12J_10000002_47" or "Cas12J_1000002_112" and depicted in FIG. 6G is also referred to herein as "CasΦ-5";

6) the Cas12J polypeptide designated "Cas12J_10100763_4" and depicted in FIG. 6H is also referred to herein as "CasΦ-6";

7) the Cas12J polypeptide designated "Cas12J_1000007_143" or "Cas12J_1000001_267" and depicted in FIG. 6P is also referred to herein as "CasΦ-7";

8) the Cas12J polypeptide designated "Cas12J_10000286_53" and depicted in FIG. 6L (or "Cas12J_10000506_8" and depicted in FIG. 6O) is also referred to herein as "CasΦ-8";

9) the Cas12J polypeptide designated "Cas12J_10001283_7" and depicted in FIG. 6M is also referred to herein as "CasΦ-9";

10) the Cas12J polypeptide designated "Cas12J_10037042_3" and depicted in FIG. 6E is also referred to herein as "CasΦ-10".

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6A and designated "Cas12J_1947455." For example, in some cases, a Cas12J protein includes an amino acid sequence having 50% or more sequence identity (e.g., 60% or more, 70% or more, 80% or more, 85% or more, 90% or more, 95% or amino acid sequence depicted in FIG. 6A. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6A. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6A. In some cases, a Cas12J protein includes an amino acid sequence having the Cas12J protein sequence depicted in FIG. 6A. In some cases, a Cas12J protein includes an amino acid sequence having the Cas12J protein sequence depicted in FIG. 6A, with the exception that the sequence includes an amino acid substitution (e.g., 1, 2, or 3 amino acid substitutions) that reduces the naturally occurring catalytic activity of the protein. In some cases, the Cas12J polypeptide has a length of from 680 amino acids (aa) to 720 aa, e.g., from 680 aa to 690 aa, from 690 aa to 700 aa, from 700 aa to 710 aa, or from 710 aa to 720 aa). In some cases, the Cas12J polypeptide has a length of 707 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6A.) includes the following nucleotide sequence: GTCTCGACTAATCGAGCAATCGTTTGAGATCTCTCC (SEQ ID NO: 1) or the reverse complement of same. In some cases, the guide RNA comprises the nucleotide sequence (N)nGTCTCGACTAATCGAGCAATCGTTT-GAGATCTCTCC (SEQ ID NO: 2) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30). The Cas12J protein designated Cas12J_1947455 (or Cas12J_1947455_11 in FIG. 9), and depicted in FIG. 6A, is also referred to herein as "ortholog #1" or "Cas12Φ-1."

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6B and designated "Cas12J_071242." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6B. In some cases, a Cas12J protein includes an amino acid sequence having 80% or more sequence identity (e.g., 85% or more, 90% or more, 95% or amino acid sequence depicted in FIG. 6B. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6B. In some cases, a Cas12J protein includes an amino acid sequence having the Cas12J protein sequence depicted in FIG. 6B. In some cases, a Cas12J protein includes an amino acid sequence having the Cas12J protein sequence depicted in FIG. 6B, with the exception that the sequence includes an amino acid substitution (e.g., 1, 2, or 3 amino acid substitutions) that reduces the naturally occurring catalytic activity of the protein. In some cases, the Cas12J polypeptide has a length of from 740 amino acids (aa) to 780 aa, e.g., from 740 aa to 750 aa, from 750 aa to 760 aa, from 760 aa to 770 aa, or from 770 aa to 780 aa). In some cases, the Cas12J polypeptide has a length of 757 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6B) includes the following nucleotide sequence: GTCG-GAACGCTCAACGATTGCCCCTCACGAGGGGAC (SEQ ID NO: 3) or the reverse complement of same. In some cases, the guide RNA comprises the nucleotide sequence (N)nGTCGGAACGCTCAACGATTGCCCCT-CACGAGGGGAC (SEQ ID NO: 4) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30). The Cas12J protein designated Cas12J_2071242, and depicted in FIG. 6B, is also referred to herein as "ortholog #2" or "Cas12Φ-2."

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6C and designated "Cas12J_1973640." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6C. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6C. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6C. In some cases, a Cas12J protein includes an amino acid sequence having the Cas12J protein sequence depicted in FIG. 6C. In some cases, a Cas12J protein includes an amino acid sequence having the Cas12J protein sequence depicted in FIG. 6C, with the exception that the sequence includes an amino acid substitution (e.g., 1, 2, or 3 amino acid substitutions) that reduces the naturally occurring catalytic activity of the protein. In some cases, the Cas12J polypeptide has a length of from 740 amino acids (aa) to 780 aa, e.g., from 740 aa to 750 aa, from 750 aa to 760 aa, from 760 aa to 770 aa, or from 770 aa to 780 aa). In some cases, the Cas12J polypeptide has a length of 765 amino acids.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6D and designated "Cas12J_3339380." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6D. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6D. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6D. In some cases, a Cas12J protein includes an amino acid sequence having the Cas12J protein sequence depicted in FIG. 6D. In some cases, a Cas12J protein includes an amino acid sequence having the Cas12J protein sequence depicted in FIG. 6D, with the exception that the sequence includes an amino acid substitution (e.g., 1, 2, or 3 amino acid substitutions) that reduces the naturally occurring catalytic activity of the protein. In some cases, the Cas12J polypeptide has a length of from 740 amino acids (aa) to 780 aa, e.g., from 740 aa to 750 aa, from 750 aa to 760 aa, from 760 aa to 770 aa, or from 770 aa to 780 aa). In some cases, the Cas12J polypeptide has a length of 766 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6D) includes the following nucleotide sequence: GTCCCAGCGTACTGGGCAATCAATAGTCGTTTTGGT (SEQ ID NO: 5) or the reverse complement of same. In some cases, the guide RNA comprises the nucleotide sequence (N)nGTCCCAGCGTACTGGGCAAT-CAATAGTCGTTTTGGT (SEQ ID NO: 6) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30). The Cas12J protein designated Cas12J_3339380, and depicted in FIG. 6D, is also referred to herein as "ortholog #3" or "Cas12Φ-3."

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6E and designated "Cas12J_10037042_3." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6E. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6E. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6E. In some cases, a Cas12J protein includes an amino acid sequence having the Cas12J protein sequence depicted in FIG. 6E. In some cases, a Cas12J protein includes an amino acid sequence having the Cas12J protein sequence depicted in FIG. 6E, with the exception that the sequence includes an amino acid substitution (e.g., 1, 2, or 3 amino acid substitutions) that reduces the naturally occurring catalytic activity of the protein. In some cases, the Cas12J polypeptide has a length of from 780 amino acids (aa) to 820 aa, e.g., from 780 aa to 790 aa, from 790 aa to 800 aa, from 800 aa to 810 aa, or from 810 aa to 820 aa). In some cases, the Cas12J polypeptide has a length of 812 amino acids.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6F and designated "Cas12J_10020921_9." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6F. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6F. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6F. In some cases, a Cas12J protein includes an amino acid sequence having the Cas12J protein sequence depicted in FIG. 6F. In some cases, a Cas12J protein includes an amino acid sequence having the Cas12J protein sequence depicted in FIG. 6F, with the exception that the sequence includes an amino acid substitution (e.g., 1, 2, or 3 amino acid substitutions) that reduces the naturally occurring catalytic activity of the protein. In some cases, the Cas12J polypeptide has a length of from 780 amino acids (aa) to 820 aa, e.g., from 780 aa to 790 aa, from 790 aa to 800 aa, from 800 aa to 810 aa, or from 810 aa to 820 aa). In some cases, the Cas12J polypeptide has a length of 812 amino acids.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6G and designated "Cas12J_10000002_47." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6G. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6G. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6G. In some cases, a Cas12J protein includes an amino acid sequence having the Cas12J protein sequence depicted in FIG. 6G. In some cases, a Cas12J protein includes an amino acid sequence having the Cas12J protein sequence depicted in FIG. 6G, with the exception that the sequence includes an amino acid substitution (e.g., 1, 2, or 3 amino acid substitutions) that reduces the naturally occurring catalytic activity of the protein. In some cases, the Cas12J polypeptide has a length of from 770 amino acids (aa) to 810 aa, e.g., from 770 aa to 780 aa, from 780 aa to 790 aa, from 790 aa to 800 aa, or from 800 aa to 810 aa). In some cases, the Cas12J polypeptide has a length of 793 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6G) includes the following nucleotide sequence: GGATCCAATCCTTTTT-GATTGCCCAATTCGTTGGGAC (SEQ ID NO: 7) or the reverse complement of same. In some cases, the guide RNA comprises the nucleotide sequence (N)nGGATC-CAATCCTTTTTGATTGCCCAATTCGTTGGGAC (SEQ ID NO: 8) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6H and designated "Cas12J_10100763_4." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6H. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6H. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6H. In some cases, a Cas12J protein includes an amino acid sequence having the Cas12J protein sequence depicted in FIG. 6H. In some cases, a Cas12J protein includes an amino acid sequence having the Cas12J protein sequence depicted in FIG. 6H, with the exception that the sequence includes an amino acid substitution (e.g., 1, 2, or 3 amino acid substitutions) that reduces the naturally occurring catalytic activity of the protein. In some cases, the Cas12J polypeptide has a length of from 420 amino acids (aa) to 460 aa, e.g., from 420 aa to 430 aa, from 430 aa to 440 aa, from 440 aa to 450 aa, or from 450 aa to 460 aa). In some cases, the Cas12J polypeptide has a length of 441 amino acids.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6I and designated "Cas12J_10004149_10." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6I. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6I. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6I. In some cases, a Cas12J protein includes an amino acid sequence having the Cas12J protein sequence depicted in FIG. 6I. In some cases, a Cas12J protein includes an amino acid sequence having the Cas12J protein sequence depicted in FIG. 6I, with the exception that the sequence includes an amino acid substitution (e.g., 1, 2, or 3 amino acid substitutions) that reduces the naturally occurring catalytic activity of the protein. In some cases, the Cas12J polypeptide has a length of from 790 amino acids (aa) to 830 aa, e.g., from 790 aa to 800 aa, from 800 aa to 810 aa, from 810 aa to 820 aa, or from 820 aa to 830 aa). In some cases, the Cas12J polypeptide has a length of 812 amino acids.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6J and designated "Cas12J_10000724_71." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6J. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6J. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6J. In some cases, a Cas12J protein includes an amino acid sequence having the Cas12J protein sequence depicted in FIG. 6J. In some cases, a Cas12J protein includes an amino acid sequence having the Cas12J protein sequence depicted in FIG. 6J, with the exception that the sequence includes an amino acid substitution (e.g., 1, 2, or 3 amino acid substitutions) that reduces the naturally occurring catalytic activity of the protein. In some cases, the Cas12J polypeptide has a length of from 790 amino acids (aa) to 830 aa, e.g., from 790 aa to 800 aa, from 800 aa to 810 aa, from 810 aa to 820 aa, or from 820 aa to 830 aa). In some cases, the Cas12J polypeptide has a length of 812 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6J) includes the following nucleotide sequence: GGATCTGAGGATCATT-ATTGCTCGTTACGACGAGAC (SEQ ID NO: 9) or the reverse complement of same. In some cases, the guide RNA comprises the nucleotide sequence (N)nGGATCTGAG-GATCATTATTGCTCGTTACGACGAGAC (SEQ ID NO: 10) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6J) includes the following nucleotide sequence: GTCTCGTCGTAACGAGCAATAATGATCCTCAGATCC (SEQ ID NO: 11) or the reverse complement of same. In some cases, the guide RNA comprises the nucleotide sequence (N)n GTCTCGTCGTAACGAGCAATAAT-GATCCTCAGATCC (SEQ ID NO: 12) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6K and designated "Cas12J_1000001_267." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6K. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6K. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6K. In some cases, a Cas12J protein includes an amino acid sequence having the Cas12J protein sequence depicted in FIG. 6K. In some cases, a Cas12J protein includes an amino acid sequence having the Cas12J protein sequence depicted in FIG. 6K, with the exception that the sequence includes an amino acid substitution (e.g., 1, 2, or 3 amino acid substitutions) that reduces the naturally occurring catalytic activity of the protein. In some cases, the Cas12J polypeptide has a length of from 750 amino acids (aa) to 790 aa, e.g., from 750 aa to 760 aa, from 760 aa to 770 aa, from 770 aa to 780 aa, or from 780 aa to 790 aa). In some cases, the Cas12J polypeptide has a length of 772 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6K) includes the following nucleotide sequence: GTCTCAGCGTACT-GAGCAATCAAAAGGTTTCGCAGG (SEQ ID NO: 13) or the reverse complement of same. In some cases, the guide RNA comprises the nucleotide sequence (N)nGTCTCAGCGTACTGAGCAAT-CAAAAGGTTTCGCAGG (SEQ ID NO: 14) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6L and designated "Cas12J_10000286_53." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6L. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6L. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6L. In some cases, a Cas12J protein includes an amino acid sequence having the Cas12J protein sequence depicted in FIG. 6L. In some cases, a Cas12J protein includes an amino acid sequence having the Cas12J protein sequence depicted in FIG. 6L, with the exception that the sequence includes an amino acid substitution (e.g., 1, 2, or 3 amino acid substitutions) that reduces the naturally occurring catalytic activity of the protein. In some cases, the Cas12J polypeptide has a length of from 700 amino acids (aa) to 740 aa, e.g., from 700 aa to 710 aa, from 710 aa to 720 aa, from 720 aa to 730 aa, or from 730 aa to 740 aa). In some cases, the Cas12J polypeptide has a length of 717 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6L) includes the following nucleotide sequence: GTCTCCTCGTAAGGAGCAATCTATTAGTCTTGAAAG (SEQ ID NO: 15) or the reverse complement of same. In some cases, the guide RNA comprises the nucleotide sequence (N)nGTCTCCTCGTAAGGAGCAATCTATT-AGTCTTGAAAG (SEQ ID NO: 16) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6M and designated "Cas12J_10001283_7." For example, in some cases, a Cas12J protein includes an amino acid sequence having 50% or more sequence identity (e.g., 60% or more, 70% or more, 80% or more, 85% or more, 90% or more, 95% or amino acid sequence depicted in FIG. 6M. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6M. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6M. In some cases, a Cas12J protein includes an amino acid sequence having the Cas12J protein sequence depicted in FIG. 6M. In some cases, a Cas12J protein includes an amino acid sequence having the Cas12J protein sequence depicted in FIG. 6M, with the exception that the sequence includes an amino acid substitution (e.g., 1, 2, or 3 amino acid substitutions) that reduces the naturally occurring catalytic activity of the protein. In some cases, the Cas12J polypeptide has a length of from 770 amino acids (aa) to 810 aa, e.g., from 770 aa to 780 aa, from 780 aa to 790 aa, from 790 aa to 800 aa, or from 800 aa to 810 aa). In some cases, the Cas12J polypeptide has a length of 793 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6M) includes the following nucleotide sequence: GTCTCGGCGCACCGAGCAATCAGCGAGGTCTTCTAC (SEQ ID NO: 17) or the reverse complement of same. In some cases, the guide RNA comprises the nucleotide sequence (N)nGTCTCGGCGCACCGAGCAATCAGCGAGGTCTTCTAC (SEQ ID NO: 18) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6N and designated "Cas12J_1000002_112." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6N. In some cases, a Cas12J protein includes an amino acid sequence having 80% or more sequence identity (e.g., 85% or more, 90% or more, 95% or amino acid sequence depicted in FIG. 6N. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6N. In some cases, a Cas12J protein includes an amino acid sequence having the Cas12J protein sequence depicted in FIG. 6N. In some cases, a Cas12J protein includes an amino acid sequence having the Cas12J protein sequence depicted in FIG. 6N, with the exception that the sequence includes an amino acid substitution (e.g., 1, 2, or 3 amino acid substitutions) that reduces the naturally occurring catalytic activity of the protein. In some cases, the Cas12J polypeptide has a length of from 770 amino acids (aa) to 810 aa, e.g., from 770 aa to 780 aa, from 780 aa to 790 aa, from 790 aa to 800 aa, or from 800 aa to 810 aa). In some cases, the Cas12J polypeptide has a length of 793 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6N) includes the following nucleotide sequence: GTCCCAACGAATTGGGCAATCAAAAAGGATTGGATCC (SEQ ID NO: 19) or the reverse complement of same. In some cases, the guide RNA comprises the nucleotide sequence (N)nGTCCCAACGAATTGGGCAATCAAAAAGGATTGGATCC (SEQ ID NO: 20) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6O and designated "Cas12J_10000506_8." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6O. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6O. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6O. In some cases, a Cas12J protein includes an amino acid sequence having the Cas12J protein sequence depicted in FIG. 6O. In some cases, a Cas12J protein includes an amino acid sequence having the Cas12J protein sequence depicted in FIG. 6O, with the exception that the sequence includes an amino acid substitution (e.g., 1, 2, or 3 amino acid substitutions) that reduces the naturally occurring catalytic activity of the protein. In some cases, the Cas12J polypeptide has a length of from 700 amino acids (aa) to 740 aa, e.g., from 700 aa to 710 aa, from 710 aa to 720 aa, from 720 aa to 730 aa, or from 730 aa to 740 aa). In some cases, the Cas12J polypeptide has a length of 717 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6O) includes the following nucleotide sequence: GTCTCCTCGTAAGGAGCAATCTATTAGTCTTGAAAG (SEQ ID NO: 15) or the reverse complement of same. In some cases, the guide RNA comprises the nucleotide sequence (N)nGTCTCCTCGTAAGGAGCAATCTATT-AGTCTTGAAAG (SEQ ID NO: 16) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6P and designated "Cas12J_1000007_143." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6P. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6P. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6P. In some cases, a Cas12J protein includes an amino acid sequence having the Cas12J protein sequence depicted in FIG. 6P. In some cases, a Cas12J protein includes an amino acid sequence having the Cas12J protein sequence depicted in FIG. 6P, with the exception that the sequence includes an amino acid substitution (e.g., 1, 2, or 3 amino acid substitutions) that reduces the naturally occurring catalytic activity of the protein. In some cases, the Cas12J polypeptide has a length of from 750 amino acids (aa) to 790 aa, e.g., from 750 aa to 760 aa, from 760 aa to 770 aa, from 770 aa to 780 aa, or from 780 aa to 790 aa). In some cases, the Cas12J polypeptide has a length of 772 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6P) includes the following nucleotide sequence: GTCTCAGCGTACT-GAGCAATCAAAAGGTTTCGCAGG (SEQ ID NO: 13) or the reverse complement of same. In some cases, the guide RNA comprises the nucleotide sequence (N)nGTCTCAGCGTACTGAGCAAT-CAAAAGGTTTCGCAGG (SEQ ID NO: 14) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6Q and designated "Cas12J_3877103_16." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6Q. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6Q. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6Q. In some cases, a Cas12J protein includes an amino acid sequence having the Cas12J protein sequence depicted in FIG. 6Q. In some cases, a Cas12J protein includes an amino acid sequence having the Cas12J protein sequence depicted in FIG. 6Q, with the exception that the sequence includes an amino acid substitution (e.g., 1, 2, or 3 amino acid substitutions) that reduces the naturally occurring catalytic activity of the protein. In some cases, the Cas12J polypeptide has a length of from 750 amino acids (aa) to 790 aa, e.g., from 750 aa to 760 aa, from 760 aa to 770 aa, from 770 aa to 780 aa, or from 780 aa to 790 aa). In some cases, the Cas12J polypeptide has a length of 765 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6Q) includes the following nucleotide sequence: GTCGCGGCGTACCGCGCAATGAGAGTCTGTTGC-CAT (SEQ ID NO: 21) or the reverse complement of same. In some cases, the guide RNA comprises the nucleotide sequence (N)n GTCGCGGCGTACCGCGCAAT-GAGAGTCTGTTGCCAT (SEQ ID NO: 22) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

In some cases, a Cas12J protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the Cas12J amino acid sequence depicted in FIG. 6R and designated "Cas12J_877636_12." For example, in some cases, a Cas12J protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the Cas12J amino acid sequence depicted in FIG. 6R. In some cases, a Cas12J protein includes an amino acid sequence having 80% or more sequence identity (e.g., 85% or more, 90% or more, 95% or more, 97% or more, 98% or more, 99% or more, or 100% sequence identity) with the Cas12J amino acid sequence depicted in FIG. 6R. In some cases, a Cas12J protein includes an amino acid sequence having 90% or more sequence identity (e.g., 95% or more, 97% or more, 98% or more, 99% or more, or 100% sequence identity) with the Cas12J amino acid sequence depicted in FIG. 6R. In some cases, a Cas12J protein includes an amino acid sequence having the Cas12J protein sequence depicted in FIG. 6R. In some cases, a Cas12J protein includes an amino acid sequence having the Cas12J protein sequence depicted in FIG. 6R, with the exception that the sequence includes an amino acid substitution (e.g., 1, 2, or 3 amino acid substitutions) that reduces the naturally occurring catalytic activity of the protein. In some cases, the Cas12J polypeptide has a length of from 750 amino acids (aa) to 790 aa, e.g., from 750 aa to 760 aa, from 760 aa to 770 aa, from 770 aa to 780 aa, or from 780 aa to 790 aa). In some cases, the Cas12J polypeptide has a length of 766 amino acids. In some cases, a guide RNA that binds a Cas12J polypeptide (e.g., a Cas12J polypeptide comprising an amino acid sequence having 20% or more, 30% or more, 40% or more, 50% or more, 60% or more, 70% or more, 80% or more, 85% or more, 90% or more, 95% or more, 97% or more, 98% or more, 99% or more, or 100%, amino acid sequence identity to the Cas12J amino acid sequence depicted in FIG. 6R) includes the following nucleotide sequence: ACCAAAACGACTATTGATTGCCCAGTACGCTGGGAC (SEQ ID NO: 23) or the reverse complement of same. In some cases, the guide RNA comprises the nucleotide sequence (N)n ACCAAAACGACTATTGATTGCCCAGTACGCTGGGAC (SEQ ID NO: 24) or the reverse complement of same, where N is any nucleotide and n is an integer from 15 to 30, e.g., from 15 to 20, from 17 to 25, from 17 to 22, from 18 to 22, from 18 to 20, from 20 to 25, or from 25 to 30.

Cas12J Variants

A variant Cas12J protein has an amino acid sequence that is different by at least one amino acid (e.g., has a deletion, insertion, substitution, fusion) when compared to the amino acid sequence of the corresponding wild type Cas12J protein, e.g., when compared to the Cas12J amino acid sequence depicted in any one of FIG. 6A-6R. In some cases, a Cas12J variant comprises from 1 amino acid substitution to 10 amino acid substitutions compared to the Cas12J amino acid sequence depicted in any one of FIG. 6A-6R. In some cases, a Cas12J variant comprises from 1 amino acid substitution to 10 amino acid substitutions in the RuvC domain, compared to the Cas12J amino acid sequence depicted in any one of FIG. 6A-6R.

Variants—Catalytic Activity

In some cases, the Cas12J protein is a variant Cas12J protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant Cas12J protein is a catalytically 'dead' protein (has substantially no cleavage activity) and can be referred to as a 'dCas12J.' In some cases, the variant Cas12J protein is a nickase (cleaves only one strand of a double stranded target nucleic acid, e.g., a double stranded target DNA). As described in more detail herein, in some cases, a Cas12J protein (in some case a Cas12J protein with wild type cleavage activity and in some cases a variant Cas12J with reduced cleavage activity, e.g., a dCas12J or a nickase Cas12J) is fused (conjugated) to a heterologous polypeptide that has an activity of interest (e.g., a catalytic activity of interest) to form a fusion protein (a fusion Cas12J protein).

Amino acid substitutions that result in a Cas12J polypeptide that, when complexed with a Cas12J guide RNA, binds, but does not cleave, a target nucleic acid are depicted in FIG. 9. For example, a substitution of the Asp at position 464 of Cas12J_10037042_3, or a corresponding position in another Cas12J, results in a dCas12J. As another example, a substitution of the Glu at position 678 of Cas12J_10037042_3, or a corresponding position in another Cas12J, results in a dCas12J. As another example, a substation of the Asp at position 769 of Cas12J_10037042_3, or a corresponding position in another Cas12J, results in a dCas12J.

An amino acid substitution that results in a dCas12J polypeptide (i.e., a Cas12J polypeptide that binds, but does not cleave, a target nucleic acid when complexed with a guide RNA) includes a substitution of the Asp at position 413 of Cas12J_3339380 (FIG. 6D), or a corresponding position in another Cas12J, with an amino acid other than Asp. As an example, an amino acid substitution that results in a dCas12J polypeptide (i.e., a Cas12J polypeptide that binds, but does not cleave, a target nucleic acid when complexed with a guide RNA) includes a D413A substitution at position 413 of Cas12J_3339380 (FIG. 6D), or a corresponding position in another Cas12J.

An amino acid substitution that results in a dCas12J polypeptide (i.e., a Cas12J polypeptide that binds, but does not cleave, a target nucleic acid when complexed with a guide RNA) includes a substitution of the Asp at position 371 of Cas12J_1947455 (FIG. 6A), or a corresponding position in another Cas12J, with an amino acid other than Asp. As an example, an amino acid substitution that results in a dCas12J polypeptide (i.e., a Cas12J polypeptide that binds, but does not cleave, a target nucleic acid when complexed with a guide RNA) includes a D371A substitution at position 371 of Cas12J_1947455 (FIG. 6A), or a corresponding position in another Cas12J.

An amino acid substitution that results in a dCas12J polypeptide (i.e., a Cas12J polypeptide that binds, but does not cleave, a target nucleic acid when complexed with a guide RNA) includes a substitution of the Asp at position 394 of Cas12J_2071242 (FIG. 6B), or a corresponding position in another Cas12J, with an amino acid other than Asp. As an example, an amino acid substitution that results in a dCas12J polypeptide (i.e., a Cas12J polypeptide that binds, but does not cleave, a target nucleic acid when complexed with a guide RNA) includes a D394A substitution at position 394 of Cas12J_2071242 (FIG. 6B), or a corresponding position in another Cas12J.

Amino acid positions corresponding to the Asp at position 413 of Cas12J_3339380 (FIG. 6D) (CasΦ-3), the Asp at position 371 of Cas12J_1947455 (FIG. 6A) (CasΦ-1), and the Asp at position 394 of Cas12J_2071242 (FIG. 6B) (CasΦ-2), can be readily determined by, e.g., aligning the amino acid sequences of the Cas12J polypeptides depicted in FIG. 6A-6R. For example, amino acid positions corresponding to the Asp at position 413 of Cas12J_3339380 (FIG. 6D), the Asp at position 371 of Cas12J_1947455 (FIG. 6A), and the Asp at position 394 of Cas12J_2071242 (FIG. 6B), are depicted in FIG. 9. For example, the Asp in Ruv-CI that, when substituted with an amino acid other than Asp, can in a dCas12J polypeptide includes:

1) Asp-371 of the Cas12J polypeptide designated "Cas12J_1947455" (or "Cas12J_1947455_11" in FIG. 9) and depicted in FIG. 6A ("CasΦ-1");

2) Asp-394 of the Cas12J polypeptide designated "Cas12J_2071242" and depicted in FIG. 6B ("CasΦ-2");

3) Asp-413 of the Cas12J polypeptide designated "Cas12J_3339380 (or "Cas12J_3339380_12" in FIG. 9) and depicted in FIG. 6D ("CasΦ-3");

4) Asp-419 of the Cas12J polypeptide designated "Cas12J_3877103_16" and depicted in FIG. 6Q ("CasΦ-4");

5) Asp-416 of the Cas12J polypeptide designated "Cas12J_10000002_47" or "Cas12J_1000002_112" and depicted in FIG. 6G ("CasΦ-5");

6) Asp-384 of the Cas12J polypeptide designated "Cas12J_10100763_4" and depicted in FIG. 6H ("CasΦ-6");

7) Asp-423 of the Cas12J polypeptide designated "Cas12J_1000007_143" or "Cas12J_1000001_267" and depicted in FIG. 6P ("CasΦ-7");

8) Asp-369 of the Cas12J polypeptide designated "Cas12J_10000286_53" and depicted in FIG. 6L (or "Cas12J_10000506_8" and depicted in FIG. 6O) ("CasΦ-8");

9) Asp-426 of the Cas12J polypeptide designated "Cas12J_10001283_7" and depicted in FIG. 6M ("CasΦ-9");

10) Asp-464 of the Cas12J polypeptide designated "Cas12J_10037042_3" and depicted in FIG. 6E ("CasΦ-10").

Variants—Fusion Cas12J Polypeptides

As noted above, in some cases, a Cas12J protein (in some cases a Cas12J protein with wild type cleavage activity and in some cases a variant Cas12J with reduced cleavage activity, e.g., a dCas12J or a nickase Cas12J) is fused (conjugated) to a heterologous polypeptide (i.e., one or more heterologous polypeptides) that has an activity of interest (e.g., a catalytic activity of interest) to form a fusion protein. A heterologous polypeptide to which a Cas12J protein can be fused is referred to herein as a "fusion partner."

In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases, the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like). In some cases, the fusion partner is a reverse transcriptase. In some cases, the fusion partner is a base editor. In some cases, the fusion partner is a deaminase.

In some cases, a fusion Cas12J protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, or glycosylase activity).

In some cases, a fusion Cas12J protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/

SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/ JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of a suitable fusion partners are dihydrofolate reductase (DHFR) destabilization domain (e.g., to generate a chemically controllable fusion Cas12J protein), and a chloroplast transit peptide. Suitable chloroplast transit peptides include, but are not limited to:

```
                                        (SEQ ID NO: 25)
MASMISSSAVTTVSRASRGQSAAMAPFGGLKSMTGFPVRKVN

TDITSITSNGGRVKCMQVWPPIGKKKFETLSYLPPLTRDSRA;

(SEQ ID NO: 26)
MASMISSSAVTTVSRASRGQSAAMAPFGGLKSMTGFPVRKVN

TDITSITSNGGRVKS;

(SEQ ID NO: 27)
MASSMLSSATMVASPAQATMVAPFNGLKSSAAFPATRKANND

ITSITSNGGRVNCMQVWPPIEKKKFETLSYLPDLTDSGGRVN

C;

(SEQ ID NO: 28)
MAQVSRICNGVQNPSLISNLSKSSQRKSPLSVSLKTQQHPRA

YPISSSWGLKKSGMTLIGSELRPLKVMSSVSTAC;

(SEQ ID NO: 29)
MAQVSRICNGVWNPSLISNLSKSSQRKSPLSVSLKTQQHPRA

YPISSSWGLKKSGMTLIGSELRPLKVMSSVSTAC;

(SEQ ID NO: 30)
MAQINNMAQGIQTLNPNSNFHKPQVPKSSSFLVFGSKKLKNS

ANSMLVLKKDSIFMQLFCSFRISASVATAC;

(SEQ ID NO: 31)
MAALVTSQLATSGTVLSVTDRFRRPGFQGLRPRNPADAALGM

RTVGASAAPKQSRKPHRFDRRCLSMVV;

(SEQ ID NO: 32)
MAALTTSQLATSATGFGIADRSAPSSLLRHGFQGLKPRSPAG

GDATSLSVTTSARATPKQQRSVQRGSRRFPSVVVC;

(SEQ ID NO: 33)
MASSVLSSAAVATRSNVAQANMVAPFTGLKSAASFPVSRKQN

LDITSIASNGGRVQC;
```

```
-continued
                                        (SEQ ID NO: 34)
MESLAATSVFAPSRVAVPAARALVRAGTVVPTRRTSSTSGTS GVKCSAAVTPQASPVISRSAAAA;
and (SEQ ID NO: 35)
MGAAATSMQSLKFSNRLVPPSRRLSPVPNNVTCNNLPKSAAP

VRTVKCCASSWNSTINGAAATTNGASAASS.
```

In some case, a Cas12J fusion polypeptide of the present disclosure comprises: a) a Cas12J polypeptide of the present disclosure; and b) a chloroplast transit peptide. Thus, for example, a Cas12J polypeptide/guide RNA complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the amino terminus ($NH_2$ terminus) of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a Cas12J fusion polypeptide of the present disclosure can comprise: a) a Cas12J polypeptide of the present disclosure; and b) an endosomal escape peptide. In some cases, an endosomal escape polypeptide comprises the amino acid sequence GLFXALLXLLXSLWXLLLXA (SEQ ID NO: 36), wherein each X is independently selected from lysine, histidine, and arginine. In some cases, an endosomal escape polypeptide comprises the amino acid sequence GLFHALLHLLHSLWHLLLHA (SEQ ID NO: 37).

For examples of some of the above fusion partners (and more) used in the context of fusions with Cas9, Zinc Finger, and/or TALE proteins (for site specific target nucleic modification, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et al., Cell. 2013 Jul. 18; 154(2):442-51; Kearns et al., Nat Methods. 2015 May; 12(5):401-3; Mendenhall et al., Nat Biotechnol. 2013 December; 31(12):1133-6; Hilton et al., Nat Biotechnol. 2015 May; 33(5):510-7; Gordley et al., Proc Natl Acad Sci USA. 2009 Mar. 31; 106(13):5053-8; Akopian et al., Proc Natl Acad Sci USA. 2003 Jul. 22; 100(15):8688-91; Tan et., al., J Virol. 2006 February; 80(4):1939-48; Tan et al., Proc Natl Acad Sci USA. 2003 Oct. 14; 100(21):11997-2002; Papworth et al., Proc Natl Acad Sci USA. 2003 Feb. 18; 100(4):1621-6; Sanjana et al., Nat Protoc. 2012 Jan. 5; 7(1):171-92; Beerli et al., Proc Natl Acad Sci USA. 1998 Dec. 8; 95(25):14628-33; Snowden et al., Curr Biol. 2002 Dec. 23; 12(24):2159-66; Xu et. al., Xu et al., Cell Discov. 2016 May 3; 2:16009; Komor et al., Nature. 2016 Apr. 20;

533(7603):420-4; Chaikind et al., Nucleic Acids Res. 2016 Aug. 11; Choudhury at. al., Oncotarget. 2016 Jun. 23; Du et al., Cold Spring Harb Protoc. 2016 Jan. 4; Pham et al., Methods Mol Biol. 2016; 1358:43-57; Balboa et al., Stem Cell Reports. 2015 Sep. 8; 5(3):448-59; Hara et al., Sci Rep. 2015 Jun. 9; 5:11221; Piatek et al., Plant Biotechnol J. 2015 May; 13(4):578-89; Hu et al., Nucleic Acids Res. 2014 April; 42(7):4375-90; Cheng et al., Cell Res. 2013 October; 23(10):1163-71; and Maeder et al., Nat Methods. 2013 October; 10(10):977-9.

Additional suitable heterologous polypeptides include, but are not limited to, a polypeptide that directly and/or indirectly provides for increased or decreased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a fusion Cas12J polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain)

The heterologous polypeptide of a subject fusion Cas12J polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a fusion Cas12J polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to, proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Nucleases

In some cases, a subject fusion Cas12J polypeptide comprises: i) a Cas12J polypeptide of the present disclosure; and ii) a heterologous polypeptide (a "fusion partner"), where the heterologous polypeptide is a nuclease. Suitable nucleases include, but are not limited to, a homing nuclease polypeptide; a FokI polypeptide; a transcription activator-like effector nuclease (TALEN) polypeptide; a MegaTAL polypeptide; a meganuclease polypeptide; a zinc finger nuclease (ZFN); an ARCUS nuclease; and the like. The meganuclease can be engineered from an LADLIDADG homing endonuclease (LHE). A megaTAL polypeptide can comprise a TALE DNA binding domain and an engineered meganuclease. See, e.g., WO 2004/067736 (homing endonuclease); Urnov et al. (2005) Nature 435:646 (ZFN); Mussolino et al. (2011) *Nucle. Acids Res.* 39:9283 (TALE nuclease); Boissel et al. (2013) *Nucl. Acids Res.* 42:2591 (MegaTAL).

Reverse Transcriptases

In some cases, a subject fusion Cas12J polypeptide comprises: i) a Cas12J polypeptide of the present disclosure; and ii) a heterologous polypeptide (a "fusion partner"), where the heterologous polypeptide is a reverse transcriptase polypeptide. In some cases, the Cas12J polypeptide is catalytically inactive. Suitable reverse transcriptases include, e.g., a murine leukemia virus reverse transcriptase; a Rous sarcoma virus reverse transcriptase; a human immunodeficiency virus type I reverse transcriptase; a Moloney murine leukemia virus reverse transcriptase; and the like.

Base Editors

In some cases, a Cas12J fusion polypeptide of the present disclosure comprises: i) a Cas12J polypeptide of the present disclosure; and ii) a heterologous polypeptide (a "fusion partner"), where the heterologous polypeptide is a base editor. Suitable base editors include, e.g., an adenosine deaminase; a cytidine deaminase (e.g., an activation-induced cytidine deaminase (AID)); APOBEC3G; and the like; and the like.

A suitable adenosine deaminase is any enzyme that is capable of deaminating adenosine in DNA. In some cases, the deaminase is a TadA deaminase.

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                       (SEQ ID NO: 38)
MSEVEFSHEYWMRHALTLAKRAWDEREVPVGAVLVHNNRVIG

EGWNRPIGRHDPTAHAEIMALRQGGLVMQNYRLIDATLYVTL

EPCVMCAGAMIHSRIGRVVFGARDAKTGAAGSLMDVLHHPGM

NHRVEITEGILADECAALLSDFFRMRRQEIKAQKKAQSSTD
```

In some cases, a suitable adenosine deaminase comprises an amino acid sequence having at least 80%, at least 85%, at least 90%, at least 95%, at least 98%, at least 99%, or 100%, amino acid sequence identity to the following amino acid sequence:

```
                                       (SEQ ID NO: 39)
MRRAFITGVFFLSEVEFSHEYWMRHALTLAKRAWDEREVPVG

AVLVHNNRVIGEGWNRPIGRHDPTAHAEIMALRQGGLVMQNY

RLIDATLYVTLEPCVMCAGAMIHSRIGRVVFGARDAKTGAAG

SLMDVLHHPGMNHRVEITEGILADECAALLSDFFRMRRQEIK

AQKKAQSSTD.
```

In some cases, a suitable adenosine deaminase comprises an amino acid sequence having at least 80%, at least 85%, at least 90%, at least 95%, at least 98%, at least 99%, or 100%, amino acid sequence identity to the following *Staphylococcus aureus* TadA amino acid sequence:

```
                                       (SEQ ID NO: 40)
MGSHMTNDIYFMTLAIEEAKKAAQLGEVPIGAIITKDDEVIA

RAHNLRETLQQPTAHAEHIAIERAAKVLGSWRLEGCTLYVTL

EPCVMCAGTIVMSRIPRVVYGADDPKGGCSGSLMNLLQQSNF

NHRAIVDKGVLKEACSTLLTTFFKNLRANKKSTN;
```

In some cases, a suitable adenosine deaminase comprises an amino acid sequence having at least 80%, at least 85%, at least 90%, at least 95%, at least 98%, at least 99%, or 100%, amino acid sequence identity to the following *Bacillus subtilis* TadA amino acid sequence:

```
                                       (SEQ ID NO: 41)
MTQDELYMKEAIKEAKKAEEKGEVPIGAVLVINGEIIARAHN

LRETEQRSIAHAEMLVIDEACKALGTWRLEGATLYVTLEPCP

MCAGAVVLSRVEKVVFGAFDPKGGCSGTLMNLLQEERFNHQA

EVVSGVLEEECGGMLSAFFRELRKKKAARKNLSE
```

In some cases, a suitable adenosine deaminase comprises an amino acid sequence having at least 80%, at least 85%, at least 90%, at least 95%, at least 98%, at least 99%, or 100%, amino acid sequence identity to the following *Salmonella typhimurium* TadA:

```
                                       (SEQ ID NO: 42)
MPPAFITGVTSLSDVELDHEYWMRHALTLAKRAWDEREVPVG

AVLVHNHRVIGEGWNRPIGRHDPTAHAEIMALRQGGLVLQNY

RLLDTTLYVTLEPCVMCAGAMVHSRIGRVVFGARDAKTGAAG

SLIDVLHHPGMNHRVEIIEGVLRDECATLLSDFFRMRRQEIK

ALKKADRAEGAGPAV
```

In some cases, a suitable adenosine deaminase comprises an amino acid sequence having at least 80%, at least 85%, at least 90%, at least 95%, at least 98%, at least 99%, or 100%, amino acid sequence identity to the following *Shewanella putrefaciens* TadA amino acid sequence:

```
                                      (SEQ ID NO: 43)
MDEYWMQVAMQMAEKAEAAGEVPVGAVLVKDGQQIATGYNLS

ISQHDPTAHAEILCLRSAGKKLENYRLLDATLYITLEPCAMC

AGAMVHSRIARVVYGARDEKTGAAGTVVNLLQHPAFNHQVEV

TSGVLAEACSAQLSRFFKRRRDEKKALKLAQRAQQGIE
```

In some cases, a suitable adenosine deaminase comprises an amino acid sequence having at least 80%, at least 85%, at least 90%, at least 95%, at least 98%, at least 99%, or 100%, amino acid sequence identity to the following *Haemophilus influenzae* F3031 TadA amino acid sequence:

```
                                      (SEQ ID NO: 44)
MDAAKVRSEFDEKMMRYALELADKAEALGEIPVGAVLVDDAR

NIIGEGWNLSIVQSDPTAHAEIIALRNGAKNIQNYRLLNSTL

YVTLEPCTMCAGAILHSRIKRLVFGASDYKTGAIGSRFHFFD

DYKMNHTLEITSGVLAEECSQKLS TFFQKRREEKKIEKALL

KSLSDK
```

In some cases, a suitable adenosine deaminase comprises an amino acid sequence having at least 80%, at least 85%, at least 90%, at least 95%, at least 98%, at least 99%, or 100%, amino acid sequence identity to the following *Caulobacter crescentus* TadA amino acid sequence:

```
                                      (SEQ ID NO: 45)
MRTDESEDQDHRMMRLALDAARAAAEAGETPVGAVILDPSTG

EVIATAGNGPIAAHDPTAHAEIAAMRAAAAKLGNYRLTDLTL

VVTLEPCAMCAGAISHARIGRVVFGADDPKGGAVVHGPKFFA

QPTCHWRPEVTGGVLADESADLLRGFFRARRKAKI
```

In some cases, a suitable adenosine deaminase comprises an amino acid sequence having at least 80%, at least 85%, at least 90%, at least 95%, at least 98%, at least 99%, or 100%, amino acid sequence identity to the following Geobacter sulfurreducens TadA amino acid sequence:

```
                                      (SEQ ID NO: 46)
MSSLKKTPIRDDAYWMGKAIREAAKAAARDEVPIGAVIVRDG

AVIGRGHNLREGSNDPSAHAEMIAIRQAARRSANWRLTGATL

YVTLEPCLMCMGAIILARLERVVFGCYDPKGGAAGSLYDLSA

DPRLNHQVRLSPGVCQEECGTMLSDFFRDLRRRKKAKATPAL

FIDERKVPPEP
```

Cytidine deaminases suitable for inclusion in a CRISPR/Cas effector polypeptide fusion polypeptide include any enzyme that is capable of deaminating cytidine in DNA.

In some cases, the cytidine deaminase is a deaminase from the apolipoprotein B mRNA-editing complex (APOBEC) family of deaminases. In some cases, the APOBEC family deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In some cases, the cytidine deaminase is an activation induced deaminase (AID).

In some cases, a suitable cytidine deaminase comprises an amino acid sequence having at least 80%, at least 85%, at least 90%, at least 95%, at least 98%, at least 99%, or 100%, amino acid sequence identity to the following amino acid sequence:

```
                                      (SEQ ID NO: 47)
MDSLLMNRRKFLYQFKNVRWAKGRRETYLCYVVKRRDSATS

FSLDFGYLRNKNGCHVELLFLRYISDWDLDPGRCYRVTWFT

SWSPCYDCARHVADFLRGNPNLSLRIFTARLYFCEDRKAEP

EGLRRLHRAGVQIAIMTFKDYFYCWNTFVENHERTFKAWEG

LHENSVRLSRQLRRILLPLYEVDDLRDAFRTLGL
```

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

```
                                      (SEQ ID NO: 48)
MDSLLMNRRK FLYQFKNVRW AKGRRETYLC

YVVKRRDSAT SFSLDFGYLR NKNGCHVELL

FLRYISDWDL DPGRCYRVTW FTSWSPCYDC

ARHVADFLRG NPNLSLRIFT ARLYFCEDRK

AEPEGLRRLH RAGVQIAIMT FKENHERTFK

AWEGLHENSV RLSRQLRRIL LPLYEVDDLR

DAFRTLGL.
```

In some cases, a suitable cytidine deaminase is an AID and comprises an amino acid sequence having at least 80%, at least 85%, at least 90%, at least 95%, at least 98%, at least 99%, or 100%, amino acid sequence identity to the following amino acid sequence:

```
                                      (SEQ ID NO: 47)
MDSLLMNRRK FLYQFKNVRW AKGRRETYLC

YVVKRRDSAT SFSLDFGYLR NKNGCHVELL

FLRYISDWDL DPGRCYRVTW FTSWSPCYDC

ARHVADFLRG NPNLSLRIFT ARLYFCEDRK

AEPEGLRRLH RAGVQIAIMT FKDYFYCWNT

FVENHERTFK AWEGLHENSV RLSRQLRRIL

LPLYEVDDLR DAFRTLGL.
```

Transcription Factors

In some cases, a Cas12J fusion polypeptide of the present disclosure comprises: i) a Cas12J polypeptide of the present disclosure; and ii) a heterologous polypeptide (a "fusion partner"), where the heterologous polypeptide is a transcription factor. A transcription factor can include: i) a DNA binding domain; and ii) a transcription activator. A transcription factor can include: i) a DNA binding domain; and ii) a transcription repressor. Suitable transcription factors include polypeptides that include a transcription activator or a transcription repressor domain (e.g., the Kruppel associated box (KRAB or SKD); the Mad mSIN3 interaction domain (SID); the ERF repressor domain (ERD), etc.); zinc-finger-based artificial transcription factors (see, e.g., Sera (2009) *Adv. Drug Deliv.* 61:513); TALE-based artificial transcription factors (see, e.g., Liu et al. (2013) *Nat. Rev. Genetics* 14:781); and the like. In some cases, the transcription factor comprises a VP64 polypeptide (transcriptional activation). In some cases, the transcription factor comprises a Kruppel-associated box (KRAB) polypeptide (transcriptional repression). In some cases, the transcription factor comprises a Mad mSIN3 interaction domain (SID) polypeptide (transcriptional repression). In some cases, the transcription factor comprises an ERF repressor domain (ERD) polypeptide (transcriptional repression). For example, in some cases, the transcription factor is a transcriptional activator, where the transcriptional activator is GAL4-VP16.

Recombinases

In some cases, a Cas12J fusion polypeptide of the present disclosure comprises: i) a Cas12J polypeptide of the present disclosure; and ii) a heterologous polypeptide (a "fusion partner"), where the heterologous polypeptide is a recombinase. Suitable recombinases include, e.g., a Cre recombinase; a Hin recombinase; a Tre recombinase; a FLP recombinase; and the like.

Examples of various additional suitable heterologous polypeptide (or fragments thereof) for a subject fusion Cas12J polypeptide include, but are not limited to, those described in the following applications (which publications are related to other CRISPR endonucleases such as Cas9, but the described fusion partners can also be used with Cas12J instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256606; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some cases, a Cas12J fusion polypeptide does not include an NLS so that the protein is not targeted to the nucleus (which can be advantageous, e.g., when the target nucleic acid is an RNA that is present in the cytosol). In some cases, the heterologous polypeptide can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6×His tag; a hemagglutinin (HA) tag; a FLAG tag; a Myc tag; and the like).

In some cases, a Cas12J protein (e.g., a wild type Cas12J protein, a variant Cas12J protein, a fusion Cas12J protein, a dCas12J protein, and the like) includes (is fused to) a nuclear localization signal (NLS) (e.g., in some cases 2 or more, 3 or more, 4 or more, or 5 or more NLSs). Thus, in some cases, a Cas12J polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases, a Cas12J protein (e.g., a wild type Cas12J protein, a variant Cas12J protein, a fusion Cas12J protein, a dCas12J protein, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a Cas12J protein (e.g., a wild type Cas12J protein, a variant Cas12J protein, a fusion Cas12J protein, a dCas12J protein, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 49); the NLS from nucleoplasmin (e.g., the nucleoplasmin bipartite NLS with the sequence KRPAATKKAGQAKKKK (SEQ ID NO: 50)); the c-myc NLS having the amino acid sequence PAAKRVKLD (SEQ ID NO: 51) or RQRRNELKRSP (SEQ ID NO: 52); the hRNPA1 M9 NLS having the sequence NQSSNFGPMKGGNFGGRSSGPYGGGGQYFAKPRNQGGY (SEQ ID NO: 53); the sequence RMRIZFKNKGKDTAELRRRRVEVSVELRKAKKDEQILKRRNV (SEQ ID NO: 54) of the IBB domain from importin-alpha; the sequences VSRKRPRP (SEQ ID NO: 55) and PPKKARED (SEQ ID NO: 98) of the myoma T protein; the sequence PQPKKKPL (SEQ ID NO: 56) of human p53; the sequence SALIKKKKMAP (SEQ ID NO: 57) of mouse c-abl IV; the sequences DRLRR (SEQ ID NO: 58) and PKQKKRK (SEQ ID NO: 59) of the influenza virus NS1; the sequence RKLKKKIKKL (SEQ ID NO: 60) of the Hepatitis virus delta antigen; the sequence REKKKFLKRR (SEQ ID NO: 61) of the mouse Mx1 protein; the sequence KRKGDEVDGVDEVAKKKSKK (SEQ ID NO: 62) of the human poly(ADP-ribose) polymerase; and the sequence RKCLQAGMNLEARKTKK (SEQ ID NO: 63) of the steroid hormone receptors (human) glucocorticoid. In general, NLS (or multiple NLSs) are of sufficient strength to drive accumulation of the Cas12J protein in a detectable amount in the nucleus of a eukaryotic cell. Detection of accumulation in the nucleus may be performed by any suitable technique. For example, a detectable marker may be fused to the Cas12J protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some cases, a Cas12J fusion polypeptide includes a "Protein Transduction Domain" or PTD (also known as a CPP—cell penetrating peptide), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus a polypeptide (e.g., linked to a wild type Cas12J to generate a fusion protein, or linked to a variant Cas12J protein such as a dCas12J, nickase Cas12J, or fusion Cas12J protein, to generate a fusion protein). In some embodiments, a PTD is covalently linked to the carboxyl terminus of a polypeptide (e.g., linked to a wild type Cas12J to generate a fusion protein, or linked to a variant Cas12J protein such as a dCas12J, nickase Cas12J, or fusion Cas12J protein to generate a fusion protein). In some cases, the PTD is inserted internally in the Cas12J fusion polypeptide (i.e., is not at the N- or C-terminus of the Cas12J fusion polypeptide) at a suitable insertion site. In some cases, a subject Cas12J fusion polypeptide includes (is conjugated to, is fused to) one or more PTDs (e.g., two or more, three or more, four or more PTDs). In some cases, a PTD includes a nuclear localization signal (NLS) (e.g., in some cases 2 or more, 3 or more, 4 or more, or 5 or more NLSs). Thus, in some cases, a Cas12J fusion polypeptide includes one or more NLSs (e.g., 2 or more, 3 or more, 4 or more, or 5 or more NLSs). In some embodiments, a PTD is covalently linked to a nucleic acid (e.g., a Cas12J guide nucleic acid, a polynucleotide encoding a Cas12J guide nucleic acid, a polynucleotide encoding a Cas12J fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO: 64); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 65); Transportan GWTLNSAGYLLGKINLKA-LAALAKKIL (SEQ ID NO: 66); KALAWEAKLAKA-LAKALAKHLAKALAKALKCEA (SEQ ID NO: 67); and RQIKIWFQNRRMKWKK (SEQ ID NO: 68). Exemplary PTDs include but are not limited to, YGRKKRRQRRR (SEQ ID NO: 64), RKKRRQRRR (SEQ ID NO: 70); an arginine homopolymer of from 3 arginine residues to 50 arginine residues; Exemplary PTD domain amino acid sequences include, but are not limited to, any of the following: YGRKKRRQRRR (SEQ ID NO: 64); RKKRRQRRR (SEQ ID NO: 70); YARAAARQARA (SEQ ID NO: 71); THRLPRRRRRR (SEQ ID NO: 72); and GGRRARRRRRR (SEQ ID NO: 73). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Linkers (e.g., for Fusion Partners)

In some embodiments, a subject Cas12J protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Examples of linker polypeptides include glycine polymers $(G)_n$, glycine-serine polymers (including, for example, $(GS)_n$, $GSGGS_n$ (SEQ ID NO: 74), $GGSGGS_n$ (SEQ ID NO: 75), and $GGGS_n$ (SEQ ID NO: 76), where n is an integer of at least one), glycine-alanine polymers, alanine-serine polymers. Exemplary linkers can comprise amino acid sequences including, but not limited to, GGSG (SEQ ID NO: 77), GGSGG (SEQ ID NO: 78), GSGSG (SEQ ID NO: 79), GSGGG (SEQ ID NO: 80), GGGSG (SEQ ID NO: 81), GSSSG (SEQ ID NO: 82), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a Cas12J polypeptide of the present disclosure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin.

Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A Cas12J protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some embodiments, the PAM for a Cas12J protein is immediately 5' of the target sequence of the non-complementary strand of the target DNA (the complementary strand: (i) hybridizes to the guide sequence of the guide RNA, while the non-complementary strand does not directly hybridize with the guide RNA; and (ii) is the reverse complement of the non-complementary strand).

In some cases (e.g., when Cas12J-1947455—also referred to herein as "ortholog #1"—as described herein is used), the PAM sequence of the non-complementary strand is 5'-VTTR-3' (where V is G, A, or C and R is A or G)—see, e.g., FIG. 13A. Thus, in some cases, suitable PAMs can include GTTA, GTTG, ATTA, ATTG, CTTA, and CTTG.

In some cases (e.g., when Cas12J-2071242—also referred to herein as "ortholog #2"—as described herein is used), the PAM sequence of the non-complementary strand is 5'-TBN-3' (where B is T, C, or G)—see, e.g., FIG. 13A. Thus, in some cases, suitable PAMs can include TTA, TTC, TTT, TTG, TCA, TCC, TCT, TCG, TGA, TGC, TGT, and TGG. In some embodiments (e.g., when Cas12J-2071242—also referred to herein as "ortholog #2"—as described herein is used), the PAM sequence of the non-complementary strand is 5'-TNN-3'.

In some cases (e.g., when Cas12J-3339380—also referred to herein as "ortholog #3"- as described herein is used), the PAM sequence of the non-complementary strand is 5'-VTTB-3' (where V is G, A, or C and where B is T, C, or G)—see, e.g., FIG. 13A. Thus, in some cases, suitable PAMs can include GTTT, GTTC, GTTG, ATTT, ATTC, ATTG, CTTT, CTTC, CTTG. In some cases (e.g., when Cas12J-3339380—also referred to herein as "ortholog #3"- as described herein is used), the PAM sequence of the non-complementary strand is 5'-NTTN-3'. In some cases (e.g., when Cas12J-3339380—also referred to herein as "ortholog #3"- as described herein is used), the PAM sequence of the non-complementary strand is 5'-VTTN-3' (where V is G, A, or C). In some embodiments (e.g., when Cas12J-3339380— also referred to herein as "ortholog #3"—as described herein is used), the PAM sequence of the non-complementary strand is 5'-VTTC-3'.

In some cases, different Cas12J proteins (i.e., Cas12J proteins from various species) may be advantageous to use in the various provided methods in order to capitalize on various enzymatic characteristics of the different Cas12J proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). Cas12J proteins from different species may require different PAM sequences in the target DNA. Thus, for a particular Cas12J protein of choice, the PAM sequence preference may be different than the sequences described above. Various methods (including in silico and/or wet lab methods) for identification of the appropriate PAM sequence are known in the art and are routine, and any convenient method can be used. For example, PAM sequences described herein were identified using a PAM depletion assay (e.g., see working examples below), but could also have been identified using a variety of different methods (including computational analysis of sequencing data—as known in the art).

Cas12J Guide RNA

A nucleic acid that binds to a Cas12J protein, forming a ribonucleoprotein complex (RNP), and targets the complex to a specific location within a target nucleic acid (e.g., a target DNA) is referred to herein as a "Cas12J guide RNA" or simply as a "guide RNA." It is to be understood that in some cases, a hybrid DNA/RNA can be made such that a Cas12J guide RNA includes DNA bases in addition to RNA bases, but the term "Cas12J guide RNA" is still used to encompass such a molecule herein.

A Cas12J guide RNA can be said to include two segments, a targeting segment and a protein-binding segment. The protein-binding segment is also referred to herein as the "constant region" of the guide RNA. The targeting segment of a Cas12J guide RNA includes a nucleotide sequence (a guide sequence) that is complementary to (and therefore hybridizes with) a specific sequence (a target site) within a target nucleic acid (e.g., a target dsDNA, a target ssRNA, a target ssDNA, the complementary strand of a double stranded target DNA, etc.). The protein-binding segment (or "protein-binding sequence") interacts with (binds to) a Cas12J polypeptide. The protein-binding segment of a subject Cas12J guide RNA can include two complementary stretches of nucleotides that hybridize to one another to form a double stranded RNA duplex (dsRNA duplex). Site-specific binding and/or cleavage of a target nucleic acid (e.g., genomic DNA, ds DNA, RNA, etc.) can occur at locations (e.g., target sequence of a target locus) determined by base-pairing complementarity between the Cas12J guide RNA (the guide sequence of the Cas12J guide RNA) and the target nucleic acid.

A Cas12J guide RNA and a Cas12J protein (e.g., a wild-type Cas12J protein; a variant Cas12J protein; a fusion Cas12J polypeptide; etc.) form a complex (e.g., bind via non-covalent interactions). The Cas12J guide RNA provides target specificity to the complex by including a targeting segment, which includes a guide sequence (a nucleotide sequence that is complementary to a sequence of a target nucleic acid). The Cas12J protein of the complex provides the site-specific activity (e.g., cleavage activity provided by the Cas12J protein and/or an activity provided by the fusion partner in the case of a fusion Cas12J protein). In other words, the Cas12J protein is guided to a target nucleic acid sequence (e.g. a target sequence) by virtue of its association with the Cas12J guide RNA.

The "guide sequence" also referred to as the "targeting sequence" of a Cas12J guide RNA can be modified so that the Cas12J guide RNA can target a Cas12J protein (e.g., a naturally occurring Cas12J protein, a fusion Cas12J polypeptide, and the like) to any desired sequence of any desired target nucleic acid, with the exception (e.g., as described herein) that the PAM sequence can be taken into account. Thus, for example, a Cas12J guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

Guide Sequence of a Cas12J Guide RNA

A subject Cas12J guide RNA includes a guide sequence (i.e., a targeting sequence), which is a nucleotide sequence that is complementary to a sequence (a target site) in a target nucleic acid. In other words, the guide sequence of a Cas12J guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a Cas12J guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some cases, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%.

In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, or 20-22 nt). In some cases, the guide sequence has a length of 17 or more nt (e.g., 18 or more, 19 or more, 20 or more, 21 or more, or 22 or more nt; 19 nt, 20 nt, 21 nt, 22 nt, 23 nt, 24 nt, 25 nt, etc.). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt.

In some cases, the guide sequence (also referred to as a "spacer sequence") has a length of from 15 to 50 nucleotides (e.g., from 15 nucleotides (nt) to 20 nt, from 20 nt to 25 nt, from 25 nt to 30 nt, from 30 nt to 35 nt, from 35 nt to 40 nt, from 40 nt to 45 nt, or from 45 nt to 50 nt).

Protein-Binding Segment of a Cas12J Guide RNA

The protein-binding segment (the "constant region") of a subject Cas12J guide RNA interacts with a Cas12J protein. The Cas12J guide RNA guides the bound Cas12J protein to a specific nucleotide sequence within target nucleic acid via the above-mentioned guide sequence. The protein-binding segment of a Cas12J guide RNA can include two stretches of nucleotides that are complementary to one another and hybridize to form a double stranded RNA duplex (dsRNA duplex). Thus, in some cases, the protein-binding segment includes a dsRNA duplex.

In some cases, the dsRNA duplex region includes a range of from 5-25 base pairs (bp) (e.g., from 5-22, 5-20, 5-18, 5-15, 5-12, 5-10, 5-8, 8-25, 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 5 bp, 6 bp, 7 bp, 8 bp, 9 bp, 10 bp, etc.). In some cases, the dsRNA duplex region includes a range of from 6-15 base pairs (bp) (e.g., from 6-12, 6-10, or 6-8 bp, e.g., 6 bp, 7 bp, 8 bp, 9 bp, 10 bp, etc.). In some cases, the duplex region includes 5 or more bp (e.g., 6 or more, 7 or more, or 8 or more bp). In some cases, the duplex region includes 6 or more bp (e.g., 7 or more, or 8 or more bp). In some cases, not all nucleotides of the duplex region are paired, and therefore the duplex forming region can include a bulge. The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA includes 1 or more bulges (e.g., 2 or more, 3 or more, 4 or more bulges). In some cases, the dsRNA duplex includes 2 or more bulges (e.g., 3 or more, 4 or more bulges). In some cases, the dsRNA duplex includes 1-5 bulges (e.g., 1-4, 1-3, 2-5, 2-4, or 2-3 bulges).

Thus, in some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 70%-100% complementarity (e.g., 75%-100%, 80%-10%, 85%-100%, 90%-100%, 95%-100% complementarity) with one another. In some cases, the stretches of nucleotides that hybridize to one another to form the dsRNA duplex have 85%-100% complementarity (e.g., 90%-100%, 95%-100% complementarity) with one another. In some cases, the stretches of nucleotides that hybridize to one another to form the dsRNA duplex have 70%-95% complementarity (e.g., 75%-95%, 80%-95%, 85%-95%, 90%-95% complementarity) with one another.

In other words, in some embodiments, the dsRNA duplex includes two stretches of nucleotides that have 70%-100% complementarity (e.g., 75%-100%, 80%-10%, 85%-100%, 90%-100%, 95%-100% complementarity) with one another. In some cases, the dsRNA duplex includes two stretches of nucleotides that have 85%-100% complementarity (e.g., 90%-100%, 95%-100% complementarity) with one another. In some cases, the dsRNA duplex includes two stretches of nucleotides that have 70%-95% complementarity (e.g., 75%-95%, 80%-95%, 85%-95%, 90%-95% complementarity) with one another.

The duplex region of a subject Cas12J guide RNA can include one or more (1, 2, 3, 4, 5, etc.) mutations relative to a naturally occurring duplex region. For example, in some cases a base pair can be maintained while the nucleotides contributing to the base pair from each segment can be different. In some cases, the duplex region of a subject Cas12J guide RNA includes more paired bases, less paired bases, a smaller bulge, a larger bulge, fewer bulges, more bulges, or any convenient combination thereof, as compared to a naturally occurring duplex region (of a naturally occurring Cas12J guide RNA).

Examples of various Cas9 guide RNAs can be found in the art, and in some cases variations similar to those introduced into Cas9 guide RNAs can also be introduced into Cas12J guide RNAs of the present disclosure (e.g., mutations to the dsRNA duplex region, extension of the 5' or 3' end for added stability for to provide for interaction with another protein, and the like). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et. al, Nucleic Acids Res. 2013 Nov. 1; 41(20):e187; Hu et al., Cell Res. 2013 November; 23(11): 1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889, 418; 8,889,356; 8,871,445; 8,865,406; 8,795,965; 8,771, 945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Examples of constant regions suitable for inclusion in a Cas12J guide RNA are provided in FIG. 7 (e.g., where T is substituted with U). A Cas12J guide RNA can include a constant region having from 1 to 5 nucleotide substitutions compared to any one of the nucleotide sequences depicted in FIG. 7. As one example, the constant region of a Cas12J guide RNA can comprise the nucleotide sequence: GUCUCGACUAAUCGAGCAAUCGUUUGAGAUCUCUCC (SEQ ID NO: 83). As another example, the constant region of a Cas12J guide RNA can comprise the nucleotide sequence: GUCGGAACGCUCAACGAUUGCCCCUCACGAGGGGAC (SEQ ID NO: 84). As another example, the constant region of a Cas12J guide RNA can comprise the nucleotide sequence: GUCCCAGCGUACUGGGCAAUCAAUAGTCGUUUUGGU (SEQ ID NO: 85). As another example, the constant region of a Cas12J guide RNA can comprise the nucleotide sequence: CACAGGAGAGAUCUCAAACGAUUGCUCGAUUAGUCGAGAC (SEQ ID NO: 86). As another example, the constant region of a Cas12J guide RNA can comprise the nucleotide sequence: UAAUGUCGGAACGCUCAACGAUUGCCCUCACGAGGGGAC (SEQ ID NO: 87). As another example, the constant region of a Cas12J guide RNA can comprise the nucleotide sequence: AUUAACCAAAACGACUAUUGAUUGCCCAGUACGCUGGGAC (SEQ ID NO: 88).

Figure 8:
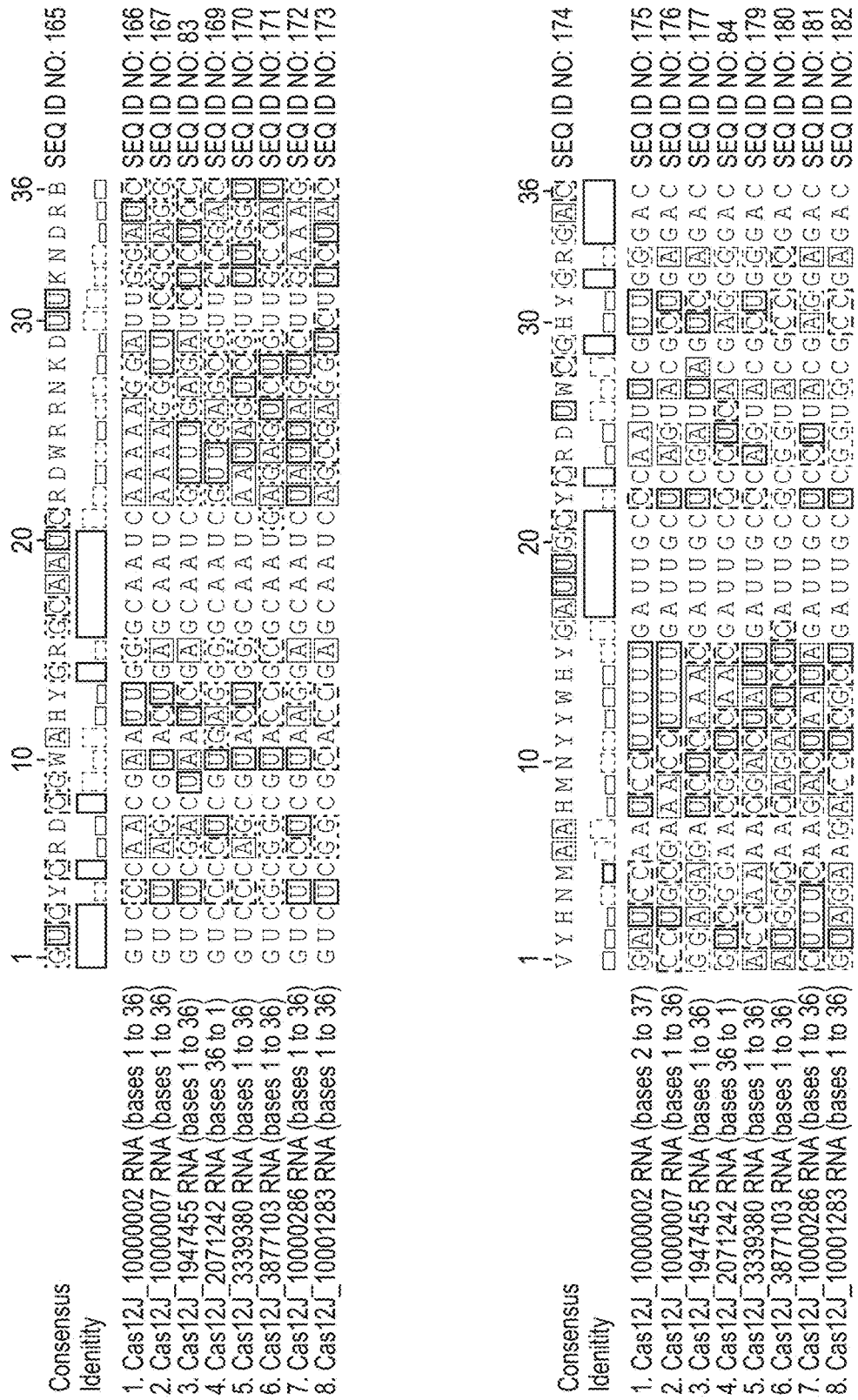
FIG. 8 depicts consensus sequences for Cas12J guide RNAs.
Figure 8:
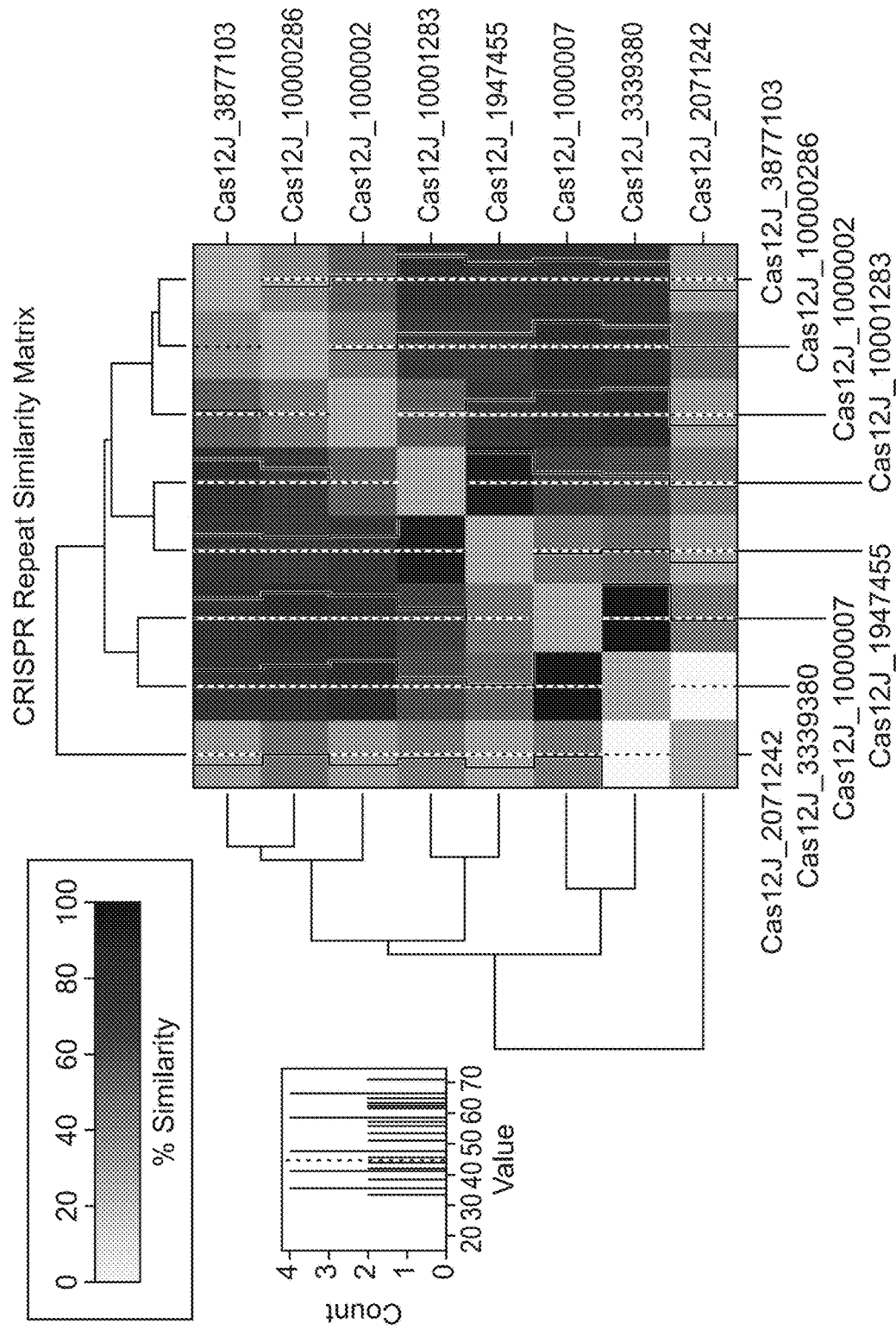
Figure 10:
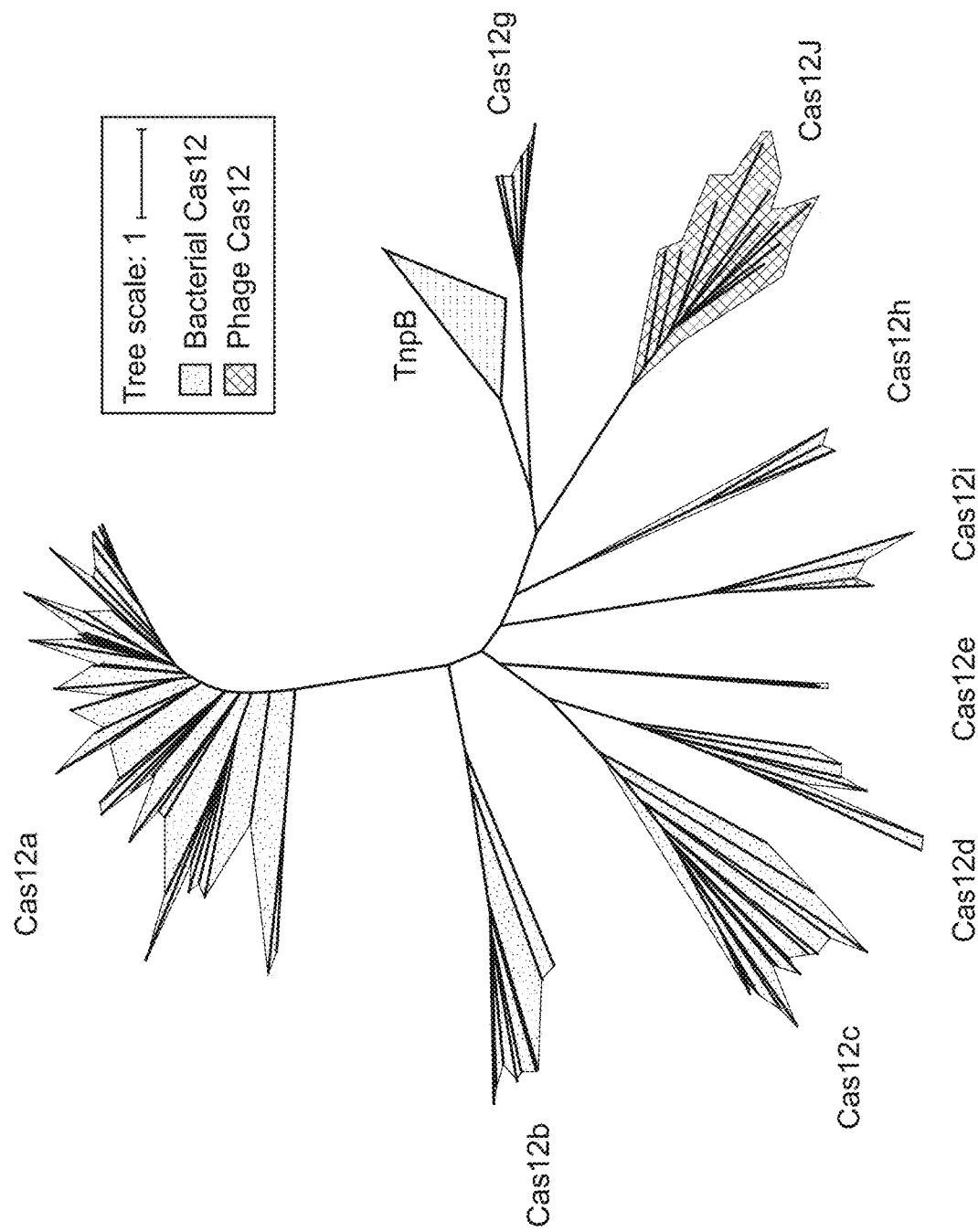
FIG. 10 provides a tree showing various CRISPR-Cas effector protein families.

A Cas12J guide RNA constant region can include any one of the nucleotide sequences depicted in FIG. 8. A Cas12J guide RNA constant region can include a nucleotide sequence within the consensus sequence(s) depicted in FIG. 8.

The nucleotide sequences (with T substituted with U) can be combined with a spacer sequence (where the spacer sequence comprises a target nucleic acid-binding sequence ("guide sequence")) of choice that is from 15 to 50 nucleotides (e.g., from 15 nucleotides (nt) to 20 nt, from 20 nt to 25 nt, from 25 nt to 30 nt, from 30 nt to 35 nt, from 35 nt to 40 nt, from 40 nt to 45 nt, or from 45 nt to 50 nt in length). In some cases, the spacer sequence is 35-38 nucleotides in length. For example, any one of the nucleotide sequences (with T substituted with U) depicted in FIG. 7 can be included in a guide RNA comprising (N)n-constant region, where N is any nucleotide and n is an integer from 15 to 50 (e.g., from 15 to 20, from 20 to 25, from 25 to 30, from 30 to 35, from 35 to 38, from 35 to 40, from 40 to 45, or from 45 to 50). The reverse complement of any one of the nucleotide sequences depicted in FIG. 7 (but with T substituted with U) can be included in a guide RNA comprising constant region-(N)n, where N is any nucleotide and n is an integer from 15 to 50 (e.g., from 15 to 20, from 20 to 25, from 25 to 30, from 30 to 35, from 35 to 38, from 35 to 40, from 40 to 45, or from 45 to 50).

As one example, a guide RNA can have the following nucleotide sequence: NNNNNNNNNNNNNNNNNNNNNNNNNNNNNNNNNNNGUCUCGACUAAUCGAGCAAUCGUUUGAGAUCUCUCC (SEQ ID NO: 89) or in some cases the reverse complement, where N is any nucleotide, e.g., where the stretch of Ns includes a target nucleic acid-binding sequence. As another example, a guide RNA can have the following nucleotide sequence: NNNNNNNNNNNNNNNNNNNNNNNNNNNNNNNNNNNGUCGGAACGCUCAACGAUUGCCCCUCACGAGGGGAC (SEQ ID NO: 90) or in some cases the reverse complement, where N is any nucleotide, e.g., where the stretch of Ns includes a target nucleic acid-binding sequence.

As one example, a guide RNA can have the following nucleotide sequence: GUCUCGACUAAUCGAGCAAUCGUUUGAGAUCUCUCC (SEQ ID NO: 83)-'guide sequence' (e.g., GUCUCGACUAAUCGAGCAAUCGUUUGAGAUCUCUCCNNNNNNNNNNNNNNNNNNNNNNNNNNNNNNNNNNNN (SEQ ID NO: 91), where the stretch of Ns represents the guide sequence/targeting sequence and N is any nucleotide). As another example, a guide RNA can have the following nucleotide sequence: GGAGAGAUCUCAAACGAUUGCUCGAUUAGUCGAGAC (SEQ ID NO: 177)-'guide sequence' (e.g., GGAGAGAUCUCAAACGAUUGCUCGAUUAGUCGAGACNNNNNNNNNNNNNNNNNNNNNNNNNNNNNNNNNNNN (SEQ ID NO: 92), where the stretch of Ns represents the guide sequence/targeting sequence and N is any nucleotide).

As another example, a guide RNA can have the following nucleotide sequence: GUCGGAACGCUCAACGAUUGCCCCUCACGAGGGGAC (SEQ ID NO: 84)-'guide sequence' (e.g., GUCGGAACGCUCAACGAUUGCCCCUCACGAGGGGACNNNNNNNNNNNNNNNNNNNNNNNNNNNNNNNNNNNN (SEQ ID NO: 93), where the stretch of Ns represents the guide sequence/targeting sequence and N is any nucleotide). As another example, a guide RNA can have the following nucleotide sequence: GUCCCCUCGUGAGGGGCAAUCGUUGAGCGUUCCGAC (SEQ ID NO: 169)-'guide sequence' (e.g., GUCCCUCGUGAGGGGCAAUCGUUGAGCGUUCCGACNNNNNNNNNNNNNNNNNNNNNNNNNNNNNNNNNNN (SEQ ID NO: 94), where the stretch of Ns represents the guide sequence/targeting sequence and N is any nucleotide).

As another example, a guide RNA can have the following nucleotide sequence: CACAGGAGAGAUCUCAAACGAUUGCUCGAUUAGUCGAGAC (SEQ ID NO: 86)-'guide sequence' (e.g., CACAGGAGAGAUCUCAAACGAUUGCUCGAUUAGUCGAGACNNNNNNNNNNNNNNNNNNNNNNNNNNNNNNNNNNNN (SEQ ID NO: 95), where the stretch of Ns represents the guide sequence/targeting sequence and N is any nucleotide). As another example, a guide RNA can have the following nucleotide sequence: UAAUGUCGGAACGCUCAACGAUUGCCCCUCACGAGGGGAC (SEQ ID NO: 87)-'guide sequence' (e.g., UAAUGUCGGAACGCUCAACGAUUGCCCCUCACGAGGGGACNNNNNNNNNNNNNNNNNNNNNNNNNNNNNNNNNNNN (SEQ ID NO: 96), where the stretch of Ns represents the guide sequence/targeting sequence and N is any nucleotide). As another example, a guide RNA can have the following nucleotide sequence:
AUUAACCAAAACGACUAUUGAUUGCCCAGUACGCUGGGAC (SEQ ID NO: 88)-'guide sequence' (e.g., AUUAACCAAAACGACUAUUGAUUGCCCAGUACGCUGGGACNNNNNNNNNNNNNNNNNNNNNNNNNNNNNNNNNNNN (SEQ ID NO: 97), where the stretch of Ns represents the guide sequence/targeting sequence and N is any nucleotide).

Cas12J Guide Polynucleotides

In some cases, a nucleic acid that binds to a Cas12J protein, forming a nucleic acid/Cas12J polypeptide complex, and that targets the complex to a specific location within a target nucleic acid (e.g., a target DNA) comprises ribonucleotides only, deoxyribonucleotides only, or a mixture of ribonucleotides and deoxyribonucleotides. In some cases, a guide polynucleotide comprises ribonucleotides only, and is referred to herein as a "guide RNA." In some cases, a guide polynucleotide comprises deoxyribonucleotides only, and is referred to herein as a "guide DNA." In some cases, a guide polynucleotide comprises both ribonucleotides and deoxyribonucleotides. A guide polynucleotide can comprise combinations of ribonucleotide bases, deoxyribonucleotide bases, nucleotide analogs, modified nucleotides, and the like; and may further include naturally-occurring backbone residues and/or linkages and/or non-naturally-occurring backbone residues and/or linkages.

Cas12J Systems

The present disclosure provides a Cas12J system. A Cas12J system of the present disclosure can comprise: a) a Cas12J polypeptide of the present disclosure and a Cas12J guide RNA; b) a Cas12J polypeptide of the present disclosure, a Cas12J guide RNA, and a donor template nucleic acid; c) a Cas12J fusion polypeptide of the present disclosure and a Cas12J guide RNA; d) a Cas12J fusion polypeptide of the present disclosure, a Cas12J guide RNA, and a donor template nucleic acid; e) an mRNA encoding a Cas12J polypeptide of the present disclosure; and a Cas12J guide RNA; f) an mRNA encoding a Cas12J polypeptide of the present disclosure, a Cas12J guide RNA, and a donor template nucleic acid; g) an mRNA encoding a Cas12J fusion polypeptide of the present disclosure; and a Cas12J guide RNA; h) an mRNA encoding a Cas12J fusion polypeptide of the present disclosure, a Cas12J guide RNA, and a donor template nucleic acid; i) a recombinant expression vector comprising a nucleotide sequence encoding a Cas12J polypeptide of the present disclosure and a nucleotide sequence encoding a Cas12J guide RNA; j) a recombinant expression vector comprising a nucleotide sequence encoding a Cas12J polypeptide of the present disclosure, a nucleotide sequence encoding a Cas12J guide RNA, and a nucleotide sequence encoding a donor template nucleic acid; k) a recombinant expression vector comprising a nucleotide sequence encoding a Cas12J fusion polypeptide of the present disclosure and a nucleotide sequence encoding a Cas12J guide RNA; l) a recombinant expression vector comprising a nucleotide sequence encoding a Cas12J fusion polypeptide of the present disclosure, a nucleotide sequence encoding a Cas12J guide RNA, and a nucleotide sequence encoding a donor template nucleic acid; m) a first recombinant expression vector comprising a nucleotide sequence encoding a Cas12J polypeptide of the present disclosure, and a second recombinant expression vector comprising a nucleotide sequence encoding a Cas12J guide RNA; n) a first recombinant expression vector comprising a nucleotide sequence encoding a Cas12J polypeptide of the present disclosure, and a second recombinant expression vector comprising a nucleotide sequence encoding a Cas12J guide RNA; and a donor template nucleic acid; o) a first recombinant expression vector comprising a nucleotide sequence encoding a Cas12J fusion polypeptide of the present disclosure, and a second recombinant expression vector comprising a nucleotide sequence encoding a Cas12J guide RNA; p) a first recombinant expression vector comprising a nucleotide sequence encoding a Cas12J fusion polypeptide of the present disclosure, and a second recombinant expression vector comprising a nucleotide sequence encoding a Cas12J guide RNA; and a donor template nucleic acid; q) a recombinant expression vector comprising a nucleotide sequence encoding a Cas12J polypeptide of the present disclosure, a nucleotide sequence encoding a first Cas12J guide RNA, and a nucleotide sequence encoding a second Cas12J guide RNA; or r) a recombinant expression vector comprising a nucleotide sequence encoding a Cas12J fusion polypeptide of the present disclosure, a nucleotide sequence encoding a first Cas12J guide RNA, and a nucleotide sequence encoding a second Cas12J guide RNA; or some variation of one of (a) through (r).

Nucleic Acids

The present disclosure provides one or more nucleic acids comprising one or more of: a donor polynucleotide sequence, a nucleotide sequence encoding a Cas12J polypeptide (e.g., a wild type Cas12J protein, a nickase Cas12J protein, a dCas12J protein, fusion Cas12J protein, and the like), a Cas12J guide RNA, and a nucleotide sequence encoding a Cas12J guide RNA. The present disclosure provides a nucleic acid comprising a nucleotide sequence encoding a Cas12J fusion polypeptide. The present disclosure provides a recombinant expression vector that comprises a nucleotide sequence encoding a Cas12J polypeptide. The present disclosure provides a recombinant expression vector that comprises a nucleotide sequence encoding a Cas12J fusion polypeptide. The present disclosure provides a recombinant expression vector that comprises: a) a nucleotide sequence encoding a Cas12J polypeptide; and b) a nucleotide sequence encoding a Cas12J guide RNA(s). The present disclosure provides a recombinant expression vector that comprises: a) a nucleotide sequence encoding a Cas12J fusion polypeptide; and b) a nucleotide sequence encoding a Cas12J guide RNA(s). In some cases, the nucleotide sequence encoding the Cas12J protein and/or the nucleotide sequence encoding the Cas12J guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a Cas12J polypeptide of the present disclosure is codon optimized. This type of optimization can entail a mutation of a Cas12J-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized Cas12J-encoding nucleotide sequence could be used. As another non-limiting example, if the intended host cell were a mouse cell, then a mouse codon-optimized Cas12J-encoding nucleotide sequence could be generated. As another non-limiting example, if the intended host cell were a plant cell, then a plant codon-optimized Cas12J-encoding nucleotide sequence could be generated. As another non-limiting example, if the intended host cell were an insect cell, then an insect codon-optimized Cas12J-encoding nucleotide sequence could be generated.

Codon usage tables are readily available, for example, at the "Codon Usage Database" available at www[dot]kazusa [dot]or[dot]jp[forwardslash]codon. In some cases, a nucleic acid of the present disclosure comprises a Cas12J polypeptide-encoding nucleotide sequence that is codon optimized for expression in a eukaryotic cell. In some cases, a nucleic acid of the present disclosure comprises a Cas12J polypeptide-encoding nucleotide sequence that is codon optimized for expression in an animal cell. In some cases, a nucleic acid of the present disclosure comprises a Cas12J polypeptide-encoding nucleotide sequence that is codon optimized for expression in a fungus cell. In some cases, a nucleic acid of the present disclosure comprises a Cas12J polypeptide-encoding nucleotide sequence that is codon optimized for expression in a plant cell. In some cases, a nucleic acid of the present disclosure comprises a Cas12J polypeptide-encoding nucleotide sequence that is codon optimized for expression in a monocotyledonous plant species. In some cases, a nucleic acid of the present disclosure comprises a Cas12J polypeptide-encoding nucleotide sequence that is codon optimized for expression in a dicotyledonous plant species.

In some cases, a nucleic acid of the present disclosure comprises a Cas12J polypeptide-encoding nucleotide sequence that is codon optimized for expression in a gymnosperm plant species. In some cases, a nucleic acid of the present disclosure comprises a Cas12J polypeptide-encoding nucleotide sequence that is codon optimized for expression in an angiosperm plant species. In some cases, a nucleic acid of the present disclosure comprises a Cas12J polypeptide-encoding nucleotide sequence that is codon optimized for expression in a corn cell. In some cases, a nucleic acid of the present disclosure comprises a Cas12J polypeptide-encoding nucleotide sequence that is codon optimized for expression in a soybean cell. In some cases, a nucleic acid of the present disclosure comprises a Cas12J polypeptide-encoding nucleotide sequence that is codon optimized for expression in a rice cell. In some cases, a nucleic acid of the present disclosure comprises a Cas12J polypeptide-encoding nucleotide sequence that is codon optimized for expression in a wheat cell. In some cases, a nucleic acid of the present disclosure comprises a Cas12J polypeptide-encoding nucleotide sequence that is codon optimized for expression in a cotton cell. In some cases, a nucleic acid of the present disclosure comprises a Cas12J polypeptide-encoding nucleotide sequence that is codon optimized for expression in a sorghum cell. In some cases, a nucleic acid of the present disclosure comprises a Cas12J polypeptide-encoding nucleotide sequence that is codon optimized for expression in an alfalfa cell. In some cases, a nucleic acid of the present disclosure comprises a Cas12J polypeptide-encoding nucleotide sequence that is codon optimized for expression in a sugar cane cell. In some cases, a nucleic acid of the present disclosure comprises a Cas12J polypeptide-encoding nucleotide sequence that is codon optimized for expression in an *Arabidopsis* cell. In some cases, a nucleic acid of the present disclosure comprises a Cas12J polypeptide-encoding nucleotide sequence that is codon optimized for expression in a tomato cell. In some cases, a nucleic acid of the present disclosure comprises a Cas12J polypeptide-encoding nucleotide sequence that is codon optimized for expression in a cucumber cell. In some cases, a nucleic acid of the present disclosure comprises a Cas12J polypeptide-encoding nucleotide sequence that is codon optimized for expression in a potato cell. In some cases, a nucleic acid of the present disclosure comprises a Cas12J polypeptide-encoding nucleotide sequence that is codon optimized for expression in an algae cell.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a Cas12J guide RNA that hybridizes to a target sequence of the target locus of the targeted genome (e.g., operably linked to a promoter that is operable in a target cell such as a eukaryotic cell); and (iii) a nucleotide sequence encoding a Cas12J protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a Cas12J guide RNA that hybridizes to a target sequence of the target locus of the targeted genome (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a Cas12J guide RNA that hybridizes to a target sequence of the target locus of the targeted genome (e.g., operably linked to a promoter that is operable in a target cell such as a eukaryotic cell); and (ii) a nucleotide sequence encoding a Cas12J protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

For plant applications, viral vectors based on Tobamoviruses, Potexviruses, Potyviruses, Tobraviruses, Tombusviruses, Geminiviruses, Bromoviruses, Carmoviruses, Alfamoviruses, or Cucumoviruses can be used. See, e.g., Peyret and Lomonossoff (2015) *Plant Biotechnol. J.* 13:1121. Suitable Tobamovirus vectors include, for example, a tomato mosaic virus (ToMV) vector, a tobacco mosaic virus (TMV) vector, a tobacco mild green mosaic virus (TMGMV) vector, a pepper mild mottle virus (PMMoV) vector, a paprika mild mottle virus (PaMMV) vector, a cucumber green mottle mosaic virus (CGMMV) vector, a kyuri green mottle mosaic virus (KGMMV) vector, a hibiscus latent fort pierce virus (HLFPV) vector, an odontoglossum ringspot virus (ORSV) vector, a rehmannia mosaic virus (ReMV) vector, a Sammon's opuntia virus (SOV) vector, a wasabi mottle virus (WMoV) vector, a youcai mosaic virus (YoMV) vector, a sunn-hemp mosaic virus (SHMV) vector, and the like. Suitable Potexvirus vectors include, for example, a potato virus X (PVX) vector, a potato aucubamosaicvirus (PAMV) vector, an Alstroemeria virus X (AlsVX) vector, a cactus virus X (CVX) vector, a Cymbidium mosaic virus (CymMV) vector, a hosta virus X (HVX) vector, a lily virus X (LVX) vector, a *Narcissus* mosaic virus (NMV) vector, a Nerine virus X (NVX) vector, a *Plantago asiatica* mosaic virus (P1AMV) vector, a strawberry mild yellow edge virus (SMYEV) vector, a tulip virus X (TVX) vector, a white clover mosaic virus (WC1MV) vector, a bamboo mosaic virus (BaMV) vector, and the like. Suitable Potyvirus vectors include, for example, a potato virus Y (PVY) vector, a bean common mosaic virus (BCMV) vector, a clover yellow vein virus (C1YVV) vector, an East Asian *Passiflora* virus (EAPV) vector, a Freesia mosaic virus (FreMV) vector, a Japanese yam mosaic virus (JYMV) vector, a lettuce mosaic virus (LMV) vector, a Maize dwarf mosaic virus (MDMV) vector, an onion yellow dwarf virus (OYDV) vector, a papaya ringspot virus (PRSV) vector, a pepper mottle virus (PepMoV) vector, a *Perilla* mottle virus (PerMoV) vector, a plum pox virus (PPV) vector, a potato virus A (PVA) vector, a sorghum mosaic virus (SrMV) vector, a soybean mosaic virus (SMV) vector, a sugarcane mosaic virus (SCMV) vector, a tulip mosaic virus (TulMV) vector, a turnip mosaic virus (TuMV) vector, a watermelon mosaic virus (WMV) vector, a zucchini yellow mosaic virus (ZYMV) vector, a tobacco etch virus (TEV) vector, and the like. Suitable Tobravirus vectors include, for example, a tobacco rattle virus (TRV) vector and the like. Suitable Tombusvirus vectors include, for example, a tomato bushy stunt virus (TBSV) vector, an eggplant mottled crinkle virus (EMCV) vector, a grapevine Algerian latent virus (GALV) vector, and the like. Suitable Cucumovirus vectors include, for example, a cucumber mosaic virus (CMV) vector, a peanut stunt virus (PSV) vector, a tomato aspermy virus (TAV) vector, and the like. Suitable Bromovirus vectors include, for example, a brome mosaic virus (BMV) vector, a cowpea chlorotic mottle virus (CCMV) vector, and the like. Suitable Carmovirus vectors include, for example, a carnation mottle virus (CarMV) vector, a melon necrotic spot virus (MNSV) vector, a pea stem necrotic virus (PSNV) vector, a turnip crinkle virus (TCV) vector, and the like. Suitable Alfamovirus vectors include, for example, an alfalfa mosaic virus (AMV) vector, and the like.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a Cas12J guide RNA is operably linked to a control element, e.g., a transcriptional control element, such as a promoter. In some embodiments, a nucleotide sequence encoding a Cas12J protein or a Cas12J fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the Cas12J protein, thus resulting in a fusion Cas12J polypeptide.

In some embodiments, a nucleotide sequence encoding a Cas12J guide RNA and/or a Cas12J fusion polypeptide is operably linked to an inducible promoter. In some embodiments, a nucleotide sequence encoding a Cas12J guide RNA and/or a Cas12J fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a Cas12J guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA in a eukaryotic cell it may sometimes be necessary to modify the sequence encoding the guide RNA to eliminate runs of Ts. In some cases, a nucleotide sequence encoding a Cas12J protein (e.g., a wild type Cas12J protein, a nickase Cas12J protein, a dCas12J protein, a fusion Cas12J protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

RNA polymerase III (Pol III) promoters can be used to drive the expression of non-protein coding RNA molecules (e.g., guide RNAs). In some cases, a suitable promoter is a Pol III promoter. In some cases, a Pol III promoter is operably linked to a nucleotide sequence encoding a guide RNA (gRNA). In some cases, a Pol III promoter is operably linked to a nucleotide sequence encoding a single-guide RNA (sgRNA). In some cases, a Pol III promoter is operably linked to a nucleotide sequence encoding a CRISPR RNA (crRNA). In some cases, a Pol III promoter is operably linked to a nucleotide sequence encoding a encoding a tracrRNA.

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez (2002) Genes & Development 16:2593-2620. In some cases, a Pol III promoter is selected from the group consisting of a U6 promoter, an H1 promoter, a 5S promoter, an Adenovirus 2 (Ad2) VAI promoter, a tRNA promoter, and a 7SK promoter. In some cases, a guide RNA-encoding nucleotide sequence is operably linked to a promoter selected from the group consisting of a U6 promoter, an H1 promoter, a 5S promoter, an Adenovirus 2 (Ad2) VAI promoter, a tRNA promoter, and a 7SK promoter. In some cases, a single-guide RNA-encoding nucleotide sequence is operably linked to a promoter selected from the group consisting of a U6 promoter, an H1 promoter, a 5S promoter, an Adenovirus 2 (Ad2) VAI promoter, a tRNA promoter, and a 7SK promoter.

Examples describing a promoter that can be used herein in connection with expression in plants, plant tissues, and plant cells include, but are not limited to, promoters described in: U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use include a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al. Plant Molecular Biology (1987) 9: 315-324), the CaMV 35S promoter (Odell et al., Nature (1985) 313: 810-812), the figwort mosaic virus 35S-promoter (U.S. Pat. Nos. 6,051,753; 5,378,619), the sucrose synthase promoter (Yang and Russell, Proceedings of the National Academy of Sciences, USA (1990) 87: 4144-4148), the R gene complex promoter (Chandler et al., Plant Cell (1989) 1:1175-1183), and the chlorophyll a/b binding protein gene promoter, PC1SV (U.S. Pat. No. 5,850,019), and AGRtu.nos (GenBank Accession V00087; Depicker et al., Journal of Molecular and Applied Genetics (1982) 1: 561-573; Bevan et al., 1983) promoters.

Methods of introducing a nucleic acid (e.g., a nucleic acid comprising a donor polynucleotide sequence, one or more nucleic acids encoding a Cas12J protein and/or a Cas12J guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a Cas12J protein can be provided as RNA. The RNA can be provided by direct chemical synthesis or may be transcribed in vitro from a DNA (e.g., encoding the Cas12J protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Minis Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the Cas12J guide RNA; recombinant expression vectors encoding the Cas12J protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding Cas12J guide RNA and/or a Cas12J polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a Cas12J guide RNA and/or a Cas12J protein to a cell may include nucleic acid sequences that encode for selectable markers in the target cells, so as to identify cells that have taken up the Cas12J guide RNA and/or Cas12J protein.

A nucleic acid comprising a nucleotide sequence encoding a Cas12J polypeptide, or a Cas12J fusion polypeptide, is in some cases an RNA. Thus, a Cas12J fusion protein can be introduced into cells as RNA. Methods of introducing RNA into cells are known in the art and may include, for example, direct injection, transfection, or any other method used for the introduction of DNA. A Cas12J protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a Cas12J polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 68). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The site at which the fusion is made may be selected in order to optimize the biological activity, secretion or binding characteristics of the polypeptide. The optimal site will be determined by routine experimentation.

As noted above, in some cases, the target cell is a plant cell. Numerous methods for transforming chromosomes or plastids in a plant cell with a recombinant nucleic acid are known in the art, which can be used according to methods of the present application to produce a transgenic plant cell and/or a transgenic plant. Any suitable method or technique for transformation of a plant cell known in the art can be used. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958. Additional methods for transforming plants can be found in, for example, Compendium of Transgenic Crop Plants (2009) Blackwell Publishing. Any appropriate method known to those skilled in the art can be used to transform a plant cell with any of the nucleic acids provided herein.

A Cas12J polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a Cas12J guide RNA, encoding a Cas12J fusion protein, etc.) and proteins (e.g., a Cas12J fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A Cas12J polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus, e.g., cysteines can be used to make thioethers, histidines for linking to a metal ion complex, carboxyl groups for forming amides or esters, amino groups for forming amides, and the like.

A Cas12J polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a Cas12J polypeptide, or a Cas12J fusion polypeptide, of the present disclosure is at least 80% pure, at least 85% pure, at least 90% pure, at least 95% pure, at least 98% pure, or at least 99% pure (e.g., free of contaminants, non-Cas12J proteins or other macromolecules, etc.).

To induce cleavage or any desired modification to a target nucleic acid (e.g., genomic DNA), or any desired modification to a polypeptide associated with target nucleic acid, the Cas12J guide RNA and/or the Cas12J polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different Cas12J guide RNAs that are complementary to different sequences within the same or different target nucleic acid), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also, as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a Cas12J guide RNA that does not change when the guide sequence is changed to hybridized to a desired target sequence (e.g., sequences that contribute to the Cas12J binding aspect of the guide RNA, e.g., the sequences that contribute to the dsRNA duplex(es) of the Cas12J guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a Cas12J guide RNA, except that the portion encoding the guide sequence portion of the guide RNA is an insertion sequence (an insertion site). An insertion site is any nucleotide sequence used for the insertion of the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a Cas12J guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a Cas12J guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; fonnacetyl and thioformacetyl backbones; methylene fonnacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., *Chem. Commun.*, 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.*, 2000, 97, 5633-5638, the disclosure of which is incorporated herein by reference in its entirety).

The synthesis and preparation of the LNA monomers adenine, cytosine, guanine, 5-methyl-cytosine, thymine and uracil, along with their oligomerization, and nucleic acid recognition properties have been described (e.g., Koshkin et al., *Tetrahedron*, 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_nCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, $OCN$, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504, the disclosure of which is incorporated herein by reference in its entirety) i.e., an alkoxyalkoxy group. A further suitable modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2CH_2NH_2$), allyl (—$CH_2$—CH=$CH_2$), —O-allyl (—O—$CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, Antisense Research and Applications, pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications*, CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO: 64); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO: 65); Transportan GWTLNSAGYLLGKINLKALAALAKKIL SEQ ID NO: 66); KALAWEAKLAKALAKA-LAKHLAKALAKALKCEA SEQ ID NO: 67); and RQIKIWFQNRRMKWKK SEQ ID NO: 68). Exemplary PTDs include but are not limited to, YGRKKRRQRRR SEQ ID NO: 64), RKKRRQRRR SEQ ID NO: 69); an arginine homopolymer of from 3 arginine residues to 50 arginine residues; Exemplary PTD domain amino acid sequences include, but are not limited to, any of the following: YGRKKRRQRRR SEQ ID NO: 64); RKKRRQRR SEQ ID NO: 69); YARAAARQARA SEQ ID NO: 71); THRL-PRRRRRR SEQ ID NO: 72); and GGRRARRRRRR SEQ ID NO: 73). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A Cas12J guide RNA (or a nucleic acid comprising a nucleotide sequence encoding same) and/or a Cas12J polypeptide of the present disclosure (or a nucleic acid comprising a nucleotide sequence encoding same) and/or a Cas12J fusion polypeptide of the present disclosure (or a nucleic acid that includes a nucleotide sequence encoding a Cas12J fusion polypeptide of the present disclosure) and/or a donor polynucleotide (donor template) can be introduced into a host cell by any of a variety of well-known methods.

Any of a variety of compounds and methods can be used to deliver to a target cell a Cas12J system of the present disclosure (e.g., where a Cas12J system comprises: a) a Cas12J polypeptide of the present disclosure and a Cas12J guide RNA; b) a Cas12J polypeptide of the present disclosure, a Cas12J guide RNA, and a donor template nucleic acid; c) a Cas12J fusion polypeptide of the present disclosure and a Cas12J guide RNA; d) a Cas12J fusion polypeptide of the present disclosure, a Cas12J guide RNA, and a donor template nucleic acid; e) an mRNA encoding a Cas12J polypeptide of the present disclosure; and a Cas12J guide RNA; f) an mRNA encoding a Cas12J polypeptide of the present disclosure, a Cas12J guide RNA, and a donor template nucleic acid; g) an mRNA encoding a Cas12J fusion polypeptide of the present disclosure; and a Cas12J guide RNA; h) an mRNA encoding a Cas12J fusion polypeptide of the present disclosure, a Cas12J guide RNA, and a donor template nucleic acid; i) a recombinant expression vector comprising a nucleotide sequence encoding a Cas12J polypeptide of the present disclosure and a nucleotide sequence encoding a Cas12J guide RNA; j) a recombinant expression vector comprising a nucleotide sequence encoding a Cas12J polypeptide of the present disclosure, a nucleotide sequence encoding a Cas12J guide RNA, and a nucleotide sequence encoding a donor template nucleic acid; k) a recombinant expression vector comprising a nucleotide sequence encoding a Cas12J fusion polypeptide of the present disclosure and a nucleotide sequence encoding a Cas12J guide RNA; l) a recombinant expression vector comprising a nucleotide sequence encoding a Cas12J fusion polypeptide of the present disclosure, a nucleotide sequence encoding a Cas12J guide RNA, and a nucleotide sequence encoding a donor template nucleic acid; m) a first recombinant expression vector comprising a nucleotide sequence encoding a Cas12J polypeptide of the present disclosure, and a second recombinant expression vector comprising a nucleotide sequence encoding a Cas12J guide RNA); n) a first recombinant expression vector comprising a nucleotide sequence encoding a Cas12J polypeptide of the present disclosure, and a second recombinant expression vector comprising a nucleotide sequence encoding a Cas12J guide RNA; and a donor template nucleic acid; o) a first recombinant expression vector comprising a nucleotide sequence encoding a Cas12J fusion polypeptide of the present disclosure, and a second recombinant expression vector comprising a nucleotide sequence encoding a Cas12J guide RNA; p) a first recombinant expression vector comprising a nucleotide sequence encoding a Cas12J fusion polypeptide of the present disclosure, and a second recombinant expression vector comprising a nucleotide sequence encoding a Cas12J guide RNA; and a donor template nucleic acid; q) a recombinant expression vector comprising a nucleotide sequence encoding a Cas12J polypeptide of the present disclosure, a nucleotide sequence encoding a first Cas12J guide RNA, and a nucleotide sequence encoding a second Cas12J guide RNA; or r) a recombinant expression vector comprising a nucleotide sequence encoding a Cas12J fusion polypeptide of the present disclosure, a nucleotide sequence encoding a first Cas12J guide RNA, and a nucleotide sequence encoding a second Cas12J guide RNA; or some variation of one of (a) through (r). As a non-limiting example, a Cas12J system of the present disclosure can be combined with a lipid. As another non-limiting example, a Cas12J system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a Cas12J polypeptide of the present disclosure is provided as a nucleic acid (e.g., an mRNA, a DNA, a plasmid, an expression vector, a viral vector, etc.) that encodes the Cas12J polypeptide. In some cases, the Cas12J polypeptide of the present disclosure is provided directly as a protein (e.g., without an associated guide RNA or with an associate guide RNA, i.e., as a ribonucleoprotein complex). A Cas12J polypeptide of the present disclosure can be introduced into a cell (provided to the cell) by any convenient method; such methods are known to those of ordinary skill in the art. As an illustrative example, a Cas12J polypeptide of the present disclosure can be injected directly into a cell (e.g., with or without a Cas12J guide RNA or nucleic acid encoding a Cas12J guide RNA, and with or without a donor polynucleotide). As another example, a preformed complex of a Cas12J polypeptide of the present disclosure and a Cas12J guide RNA (an RNP) can be introduced into a cell (e.g., eukaryotic cell) (e.g., via injection, via nucleofection; via a protein transduction domain (PTD) conjugated to one or more components, e.g., conjugated to the Cas12J protein, conjugated to a guide RNA, conjugated to a Cas12J polypeptide of the present disclosure and a guide RNA; etc.).

In some cases, a Cas12J fusion polypeptide (e.g., dCas12J fused to a fusion partner, nickase Cas12J fused to a fusion partner, etc.) of the present disclosure is provided as a nucleic acid (e.g., an mRNA, a DNA, a plasmid, an expression vector, a viral vector, etc.) that encodes the Cas12J fusion polypeptide. In some cases, the Cas12J fusion polypeptide of the present disclosure is provided directly as a protein (e.g., without an associated guide RNA or with an associate guide RNA, i.e., as a ribonucleoprotein complex). A Cas12J fusion polypeptide of the present disclosure can be introduced into a cell (provided to the cell) by any convenient method; such methods are known to those of ordinary skill in the art. As an illustrative example, a Cas12J fusion polypeptide of the present disclosure can be injected directly into a cell (e.g., with or without nucleic acid encoding a Cas12J guide RNA and with or without a donor polynucleotide). As another example, a preformed complex of a Cas12J fusion polypeptide of the present disclosure and a Cas12J guide RNA (an RNP) can be introduced into a cell (e.g., via injection, via nucleofection; via a protein transduction domain (PTD) conjugated to one or more components, e.g., conjugated to the Cas12J fusion protein, conjugated to a guide RNA, conjugated to a Cas12J fusion polypeptide of the present disclosure and a guide RNA; etc.).

In some cases, a nucleic acid (e.g., a Cas12J guide RNA; a nucleic acid comprising a nucleotide sequence encoding a Cas12J polypeptide of the present disclosure; etc.) is delivered to a cell (e.g., a target host cell) and/or a polypeptide (e.g., a Cas12J polypeptide; a Cas12J fusion polypeptide) in a particle, or associated with a particle. In some cases, a Cas12J system of the present disclosure is delivered to a cell in a particle, or associated with a particle. The terms "particle" and nanoparticle" can be used interchangeable, as appropriate. A recombinant expression vector comprising a nucleotide sequence encoding a Cas12J polypeptide of the present disclosure and/or a Cas12J guide RNA, an mRNA comprising a nucleotide sequence encoding a Cas12J polypeptide of the present disclosure, and guide RNA may be delivered simultaneously using particles or lipid envelopes; for instance, a Cas12J polypeptide and a Cas12J guide RNA, e.g., as a complex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a Cas12J polypepide and a Cas12J guideRNA are mixed together, e.g., at a 1:1 molar ratio, e.g., at room temperature, e.g., for 30 minutes, e.g., in sterile, nuclease free 1×phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A Cas12J polypeptide of the present disclosure (or an mRNA comprising a nucleotide sequence encoding a Cas12J polypeptide of the present disclosure; or a recombinant expression vector comprising a nucleotide sequence encoding a Cas12J polypeptide of the present disclosure) and/or Cas12J guide RNA (or a nucleic acid such as one or more expression vectors encoding the Cas12J guide RNA) may be delivered simultaneously using particles or lipid envelopes. For example, a biodegradable core-shell structured nanoparticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engineered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administration of polynucleotides, and can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure (e.g., where a Cas12J system comprises: a) a Cas12J polypeptide of the present disclosure and a Cas12J guide RNA; b) a Cas12J polypeptide of the present disclosure, a Cas12J guide RNA, and a donor template nucleic acid; c) a Cas12J fusion polypeptide of the present disclosure and a Cas12J guide RNA; d) a Cas12J fusion polypeptide of the present disclosure, a Cas12J guide RNA, and a donor template nucleic acid; e) an mRNA encoding a Cas12J polypeptide of the present disclosure; and a Cas12J guide RNA; f) an mRNA encoding a Cas12J polypeptide of the present disclosure, a Cas12J guide RNA, and a donor template nucleic acid; g) an mRNA encoding a Cas12J fusion polypeptide of the present disclosure; and a Cas12J guide RNA; h) an mRNA encoding a Cas12J fusion polypeptide of the present disclosure, a Cas12J guide RNA, and a donor template nucleic acid; i) a recombinant expression vector comprising a nucleotide sequence encoding a Cas12J polypeptide of the present disclosure and a nucleotide sequence encoding a Cas12J guide RNA; j) a recombinant expression vector comprising a nucleotide sequence encoding a Cas12J polypeptide of the present disclosure, a nucleotide sequence encoding a Cas12J guide RNA, and a nucleotide sequence encoding a donor template nucleic acid; k) a recombinant expression vector comprising a nucleotide sequence encoding a Cas12J fusion polypeptide of the present disclosure and a nucleotide sequence encoding a Cas12J guide RNA; l) a recombinant expression vector comprising a nucleotide sequence encoding a Cas12J fusion polypeptide of the present disclosure, a nucleotide sequence encoding a Cas12J guide RNA, and a nucleotide sequence encoding a donor template nucleic acid; m) a first recombinant expression vector comprising a nucleotide sequence encoding a Cas12J polypeptide of the present disclosure, and a second recombinant expression vector comprising a nucleotide sequence encoding a Cas12J guide RNA; n) a first recombinant expression vector comprising a nucleotide sequence encoding a Cas12J polypeptide of the present disclosure, and a second recombinant expression vector comprising a nucleotide sequence encoding a Cas12J guide RNA; and a donor template nucleic acid; o) a first recombinant expression vector comprising a nucleotide sequence encoding a Cas12J fusion polypeptide of the present disclosure, and a second recombinant expression vector comprising a nucleotide sequence encoding a Cas12J guide RNA; p) a first recombinant expression vector comprising a nucleotide sequence encoding a Cas12J fusion polypeptide of the present disclosure, and a second recombinant expression vector comprising a nucleotide sequence encoding a Cas12J guide RNA; and a donor template nucleic acid; q) a recombinant expression vector comprising a nucleotide sequence encoding a Cas12J polypeptide of the present disclosure, a nucleotide sequence encoding a first Cas12J guide RNA, and a nucleotide sequence encoding a second Cas12J guide RNA; or r) a recombinant expression vector comprising a nucleotide sequence encoding a Cas12J fusion polypeptide of the present disclosure, a nucleotide sequence encoding a first Cas12J guide RNA, and a nucleotide sequence encoding a second Cas12J guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell.

In some cases, lipid nanoparticles (LNPs) are used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-C-DOMG) may be used. A nucleic acid (e.g., a Cas12J guide RNA; a nucleic acid of the present disclosure; etc.) may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. See, e.g., Cutler et al., J. Am. Chem. Soc. 2011 133:9254-9257, Hao et al., Small 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell have a diameter of from 25 nm to 200 nm. In some cases, nanoparticles suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell have a diameter of 100 nm or less In some cases, nanoparticles suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell have a diameter of from 35 nm to 60 nm.

Nanoparticles suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. A prototype nanoparticle of semi-solid nature is the liposome.

In some cases, an exosome is used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. Exosomes are endogenous nano-vesicles that transport RNAs and proteins, and which can deliver RNA to the brain and other target organs.

In some cases, a liposome is used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. Liposomes are spherical vesicle structures composed of a uni- or multilamellar lipid bilayer surrounding internal aqueous compartments and a relatively impermeable outer lipophilic phospholipid bilayer. Liposomes can be made from several different types of lipids; however, phospholipids are most commonly used to generate liposomes. Although liposome formation is spontaneous when a lipid film is mixed with an aqueous solution, it can also be expedited by applying force in the form of shaking by using a homogenizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N; N-dimethyl)aminopropane (DLinDMA).

Other cationic lipids, such as amino lipid 2,2-dilinoleyl-4-dimethylaminoethyl-[1,3]-dioxolane (DLin-KC2-DMA) can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Lipids may be formulated with a Cas12J system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl choline, cholesterol, and PEG-DMG may be formulated with a Cas12J system, or component thereof, of the present disclosure, using a spontaneous vesicle formation procedure. The component molar ratio may be about 50/10/38.5/1.5 (DLin-KC2-DMA or C12-200/disteroylphosphatidyl choline/cholesterol/PEG-DMG).

A Cas12J system of the present disclosure, or a component thereof, may be delivered encapsulated in PLGA microspheres such as that further described in US published applications 20130252281 and 20130245107 and 20130244279.

Supercharged proteins can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. Supercharged proteins are a class of engineered or naturally occurring proteins with unusually high positive or negative net theoretical charge. Both supernegatively and superpositively charged proteins exhibit the ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo.

Cell Penetrating Peptides (CPPs) can be used to deliver a Cas12J polypeptide of the present disclosure, a Cas12J fusion polypeptide of the present disclosure, an RNP of the present disclosure, a nucleic acid of the present disclosure, or a Cas12J system of the present disclosure, to a target cell. CPPs typically have an amino acid composition that either contains a high relative abundance of positively charged amino acids such as lysine or arginine or has sequences that contain an alternating pattern of polar/charged amino acids and non-polar, hydrophobic amino acids.

An implantable device can be used to deliver a Cas12J polypeptide of the present disclosure, a Cas12J fusion polypeptide of the present disclosure, an RNP of the present disclosure, a nucleic acid of the present disclosure (e.g., a Cas12J guide RNA, a nucleic acid encoding a Cas12J guide RNA, a nucleic acid encoding Cas12J polypeptide, a donor template, and the like), or a Cas12J system of the present disclosure, to a target cell (e.g., a target cell in vivo, where the target cell is a target cell in circulation, a target cell in a tissue, a target cell in an organ, etc.). An implantable device suitable for use in delivering a Cas12J polypeptide of the present disclosure, a Cas12J fusion polypeptide of the present disclosure, an RNP of the present disclosure, a nucleic acid of the present disclosure, or a Cas12J system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the Cas12J polypeptide, the Cas12J fusion polypeptide, the RNP, or the Cas12J system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear-auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a Cas12J polypeptide of the present disclosure and/or a nucleic acid comprising a nucleotide sequence encoding a Cas12J polypeptide of the present disclosure. The present disclosure provides a modified cell comprising a Cas12J polypeptide of the present disclosure, where the modified cell is a cell that does not normally comprise a Cas12J polypeptide of the present disclosure. The present disclosure provides a modified cell (e.g., a genetically modified cell) comprising nucleic acid comprising a nucleotide sequence encoding a Cas12J polypeptide of the present disclosure. The present disclosure provides a genetically modified cell that is genetically modified with an mRNA comprising a nucleotide sequence encoding a Cas12J polypeptide of the present disclosure. The present disclosure provides a genetically modified cell that is genetically modified with a recombinant expression vector comprising a nucleotide sequence encoding a Cas12J polypeptide of the present disclosure. The present disclosure provides a genetically modified cell that is genetically modified with a recombinant expression vector comprising: a) a nucleotide sequence encoding a Cas12J polypeptide of the present disclosure; and b) a nucleotide sequence encoding a Cas12J guide RNA of the present disclosure. The present disclosure provides a genetically modified cell that is genetically modified with a recombinant expression vector comprising: a) a nucleotide sequence encoding a Cas12J polypeptide of the present disclosure; b) a nucleotide sequence encoding a Cas12J guide RNA of the present disclosure; and c) a nucleotide sequence encoding a donor template.

A cell that serves as a recipient for a Cas12J polypeptide of the present disclosure and/or a nucleic acid comprising a nucleotide sequence encoding a Cas12J polypeptide of the present disclosure and/or a Cas12J guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a Cas12J polypeptide of the present disclosure and/or a nucleic acid comprising a nucleotide sequence encoding a Cas12J polypeptide of the present disclosure and/or a Cas12J guide RNA of the present disclosure is referred to as a "host cell" or a "target cell." A host cell or a target cell can be a recipient of a Cas12J system of the present disclosure. A host cell or a target cell can be a recipient of a Cas12J RNP of the present disclosure. A host cell or a target cell can be a recipient of a single component of a Cas12J system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatos, rice, cassava, sugarcane, pumpkin, hay, potatos, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf-green), lettuce (oak leaf-red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

In some cases, the plant cell is a cell of a plant component such as a leaf, a stem, a root, a seed, a flower, pollen, an anther, an ovule, a pedicel, a fruit, a meristem, a cotyledon, a hypocotyl, a pod, an embryo, endosperm, an explant, a callus, or a shoot.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera,* or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a Cas12J system of the present disclosure, or a component of a Cas12J system of the present disclosure.

A kit of the present disclosure can comprise: a) a Cas12J polypeptide of the present disclosure and a Cas12J guide RNA; b) a Cas12J polypeptide of the present disclosure, a Cas12J guide RNA, and a donor template nucleic acid; c) a Cas12J fusion polypeptide of the present disclosure and a Cas12J guide RNA; d) a Cas12J fusion polypeptide of the present disclosure, a Cas12J guide RNA, and a donor template nucleic acid; e) an mRNA encoding a Cas12J polypeptide of the present disclosure; and a Cas12J guide RNA; f) an mRNA encoding a Cas12J polypeptide of the present disclosure, a Cas12J guide RNA, and a donor template nucleic acid; g) an mRNA encoding a Cas12J fusion polypeptide of the present disclosure; and a Cas12J guide RNA; h) an mRNA encoding a Cas12J fusion polypeptide of the present disclosure, a Cas12J guide RNA, and a donor template nucleic acid; i) a recombinant expression vector comprising a nucleotide sequence encoding a Cas12J polypeptide of the present disclosure and a nucleotide sequence encoding a Cas12J guide RNA; j) a recombinant expression vector comprising a nucleotide sequence encoding a Cas12J polypeptide of the present disclosure, a nucleotide sequence encoding a Cas12J guide RNA, and a nucleotide sequence encoding a donor template nucleic acid; k) a recombinant expression vector comprising a nucleotide sequence encoding a Cas12J fusion polypeptide of the present disclosure and a nucleotide sequence encoding a Cas12J guide RNA; l) a recombinant expression vector comprising a nucleotide sequence encoding a Cas12J fusion polypeptide of the present disclosure, a nucleotide sequence encoding a Cas12J guide RNA, and a nucleotide sequence encoding a donor template nucleic acid; m) a first recombinant expression vector comprising a nucleotide sequence encoding a Cas12J polypeptide of the present disclosure, and a second recombinant expression vector comprising a nucleotide sequence encoding a Cas12J guide RNA; n) a first recombinant expression vector comprising a nucleotide sequence encoding a Cas12J polypeptide of the present disclosure, and a second recombinant expression vector comprising a nucleotide sequence encoding a Cas12J guide RNA; and a donor template nucleic acid; o) a first recombinant expression vector comprising a nucleotide sequence encoding a Cas12J fusion polypeptide of the present disclosure, and a second recombinant expression vector comprising a nucleotide sequence encoding a Cas12J guide RNA; p) a first recombinant expression vector comprising a nucleotide sequence encoding a Cas12J fusion polypeptide of the present disclosure, and a second recombinant expression vector comprising a nucleotide sequence encoding a Cas12J guide RNA; and a donor template nucleic acid; q) a recombinant expression vector comprising a nucleotide sequence encoding a Cas12J polypeptide of the present disclosure, a nucleotide sequence encoding a first Cas12J guide RNA, and a nucleotide sequence encoding a second Cas12J guide RNA; or r) a recombinant expression vector comprising a nucleotide sequence encoding a Cas12J fusion polypeptide of the present disclosure, a nucleotide sequence encoding a first Cas12J guide RNA, and a nucleotide sequence encoding a second Cas12J guide RNA; or some variation of one of (a) through (r).

A kit of the present disclosure can comprise: a) a component, as described above, of a Cas12J system of the present disclosure, or can comprise a Cas12J system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control Cas12J guide RNA; and the like. A kit of the present disclosure can comprise: a) a component, as described above, of a Cas12J system of the present disclosure, or can comprise a Cas12J system of the present disclosure; and b) a therapeutic agent.

A kit of the present disclosure can comprise a recombinant expression vector comprising: a) an insertion site for inserting a nucleic acid comprising a nucleotide sequence encoding a portion of a Cas12J guide RNA that hybridizes to a target nucleotide sequence in a target nucleic acid; and b) a nucleotide sequence encoding the Cas12J-binding portion of a Cas12J guide RNA. A kit of the present disclosure can comprise a recombinant expression vector comprising: a) an insertion site for inserting a nucleic acid comprising a nucleotide sequence encoding a portion of a Cas12J guide RNA that hybridizes to a target nucleotide sequence in a target nucleic acid; b) a nucleotide sequence encoding the Cas12J-binding portion of a Cas12J guide RNA; and c) a nucleotide sequence encoding a Cas12J polypeptide of the present disclosure.

Utility

A Cas12J polypeptide of the present disclosure, or a Cas12J fusion polypeptide of the present disclosure, finds use in a variety of methods (e.g., in combination with a Cas12J guide RNA and in some cases further in combination with a donor template). For example, a Cas12J polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a Cas12J polypeptide of the present disclosure; and b) one or more (e.g., two) Cas12J guide RNAs. In some cases, a method of the present disclosure for modifying a target nucleic acid comprises contacting the target nucleic acid with: a) a Cas12J polypeptide of the present disclosure; b) a Cas12J guide RNA; and c) a donor nucleic acid (e.g., a donor template). In some cases, the contacting step is carried out in a cell in vitro. In some cases, the contacting step is carried out in a cell in vivo. In some cases, the contacting step is carried out in a cell ex vivo.

Because a method that uses a Cas12J polypeptide includes binding of the Cas12J polypeptide to a particular region in a target nucleic acid (by virtue of being targeted there by an associated Cas12J guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci U.S.A. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a Cas12J polypeptide or with a Cas12J fusion polypeptide, etc., encompass all methods for contacting the target nucleic acid. For example, a Cas12J polypeptide can be provided to a cell as protein, RNA (encoding the Cas12J polypeptide), or DNA (encoding the Cas12J polypeptide); while a Cas12J guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for Cas12J polypeptide; in the form of a protein for a Cas12J fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a Cas12J polypeptide or a Cas12J fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises introducing into a target cell a Cas12J locus, e.g., a nucleic acid comprising a nucleotide sequence encoding a Cas12J polypeptide as well as nucleotide sequences of about 1 kilobase (kb) to 5 kb in length surrounding the Cas12J-encoding nucleotide sequence from a cell (e.g., in some cases a cell that in its natural state (the state in which it occurs in nature) comprises a Cas12J locus) comprising a Cas12J locus, where the target cell does not normally (in its natural state) comprise a Cas12J locus. However, one or more spacer sequences, encoding guide sequences for the encoded crRNA(s), can be modified such that one or more target sequences of interest are targeted. Thus, for example, in some cases, a method of the present disclosure for modifying a target nucleic acid comprises introducing into a target cell a Cas12J locus, e.g., a nucleic acid obtained from a source cell (e.g., in some cases a cell that in its natural state (the state in which it occurs in nature) comprises a Cas12J locus), where the nucleic acid has a length of from 100 nucleotides (nt) to 5 kb in length (e.g., from 100 nt to 500 nt, from 500 nt to 1 kb, from 1 kb to 1.5 kb, from 1.5 kb to 2 kb, from 2 kb to 2.5 kb, from 2.5 kb to 3 kb, from 3 kb to 3.5 kb, from 3.5 kb to 4 kb, or from 4 kb to 5 kb in length) and comprises a nucleotide sequence encoding a Cas12J polypeptide. As noted above, in some such cases, one or more spacer sequences, encoding guide sequences for the encoded crRNA(s), can be modified such that one or more target sequences of interest are targeted. In some cases, the method comprises introducing into a target cell: i) a Cas12J locus; and ii) a donor DNA template. In some cases, the target nucleic acid is in a cell-free composition in vitro. In some cases, the target nucleic acid is present in a target cell. In some cases, the target nucleic acid is present in a target cell, where the target cell is a prokaryotic cell. In some cases, the target nucleic acid is present in a target cell, where the target cell is a eukaryotic cell. In some cases, the target nucleic acid is present in a target cell, where the target cell is a mammalian cell. In some cases, the target nucleic acid is present in a target cell, where the target cell is a plant cell.

In some cases, a method of the present disclosure for modifying a target nucleic acid comprises contacting a target nucleic acid with a Cas12J polypeptide of the present disclosure, or with a Cas12J fusion polypeptide of the present disclosure. In some cases, a method of the present disclosure for modifying a target nucleic acid comprises contacting a target nucleic acid with a Cas12J polypeptide and a Cas12J guide RNA. In some cases, a method of the present disclosure for modifying a target nucleic acid comprises contacting a target nucleic acid with a Cas12J polypeptide, a first Cas12J guide RNA, and a second Cas12J guide RNA In some cases, a method of the present disclosure for modifying a target nucleic acid comprises contacting a target nucleic acid with a Cas12J polypeptide of the present disclosure and a Cas12J guide RNA and a donor DNA template.

Target Nucleic Acids and Target Cells of Interest

A Cas12J polypeptide of the present disclosure, or a Cas12J fusion polypeptide of the present disclosure, when bound to a Cas12J guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the Cas12J guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuña, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to genetically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject Cas12J protein (and/or nucleic acid encoding the protein such as DNA and/or RNA), and/or Cas12J guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some cases, the stem cell is a hematopoietic stem cell (HSC). HSCs are mesoderm-derived cells that can be isolated from bone marrow, blood, cord blood, fetal liver and yolk sac. HSCs are characterized as $CD34^+$ and $CD3^-$. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf-green), lettuce (oak leaf-red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams, yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera,* or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A Cas12J guide RNA (or a nucleic acid comprising a nucleotide sequence encoding same), and/or a Cas12J fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a target cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like. Any or all of the components can be introduced into a cell as a composition (e.g., including any convenient combination of: a a Cas12J polypeptide, a Cas12J guide RNA, a donor polynucleotide, etc.) using known methods, e.g., such as nucleofection.

Donor Polynucleotide (Donor Template)

Guided by a Cas12J guide RNA, a Cas12J protein in some cases generates site-specific double strand breaks (DSBs) or single strand breaks (SSBs) (e.g., when the Cas12J protein is a nickase variant) within double-stranded DNA (dsDNA)

target nucleic acids, which are repaired either by non-homologous end joining (NHEJ) or homology-directed recombination (HDR).

In some cases, contacting a target DNA (with a Cas12J protein and a Cas12J guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, Cas12J guide RNA (or DNA encoding same) and a Cas12J protein (or a nucleic acid encoding same, such as an RNA or a DNA, e.g., one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a Cas12J guide RNA and Cas12J protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the Cas12J protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair to a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a Cas12J guide RNA and/or a Cas12J fusion polypeptide and/or donor polynucleotide.

Detection Methods

A Cas12J polypeptide of the present disclosure can promiscuously cleave non-targeted single stranded DNA (ssDNA) once activated by detection of a target DNA (double or single stranded). Once a Cas12J polypeptide of the present disclosure is activated by a guide RNA, which occurs when the guide RNA hybridizes to a target sequence of a target DNA (i.e., the sample includes the targeted DNA), the Cas12J polypeptide becomes a nuclease that promiscuously cleaves ssDNAs (i.e., the nuclease cleaves non-target ssDNAs, i.e., ssDNAs to which the guide sequence of the guide RNA does not hybridize). Thus, when the target DNA is present in the sample (e.g., in some cases above a threshold amount), the result is cleavage of ssDNAs in the sample, which can be detected using any convenient detection method (e.g., using a labeled single stranded detector DNA). Cleavage of non-target nucleic acid is referred to as "trans cleavage." In some cases, a Cas12J effector polypeptide of the present disclosure mediates trans cleavage of ssDNA, but not ssRNA.

Provided are compositions and methods for detecting a target DNA (double stranded or single stranded) in a sample. In some cases, a detector DNA is used that is single stranded (ssDNA) and does not hybridize with the guide sequence of the guide RNA (i.e., the detector ssDNA is a non-target ssDNA). Such methods can include (a) contacting the sample with: (i) a Cas12J polypeptide of the present disclosure; (ii) a guide RNA comprising: a region that binds to the Cas12J polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the Cas12J polypeptide, thereby detecting the target DNA. As noted above, once a Cas12J polypeptide of the present disclosure is activated by a guide RNA, which occurs when the sample includes a target DNA to which the guide RNA hybridizes (i.e., the sample includes the targeted target DNA), the Cas12J polypeptide is activated and functions as an endoribonuclease that non-specifically cleaves ssDNAs (including non-target ssDNAs) present in the sample. Thus, when the targeted target DNA is present in the sample (e.g., in some cases above a threshold amount), the result is cleavage of ssDNA (including non-target ssDNA) in the sample, which can be detected using any convenient detection method (e.g., using a labeled detector ssDNA).

Also provided are compositions and methods for cleaving single stranded DNAs (ssDNAs) (e.g., non-target ssDNAs). Such methods can include contacting a population of nucleic acids, wherein said population comprises a target DNA and a plurality of non-target ssDNAs, with: (i) a Cas12J polypeptide of the present disclosure; and (ii) a guide RNA comprising: a region that binds to the Cas12J polypeptide and a guide sequence that hybridizes with the target DNA, wherein the Cas12J polypeptide cleaves non-target ssDNAs of said plurality. Such a method can be used, e.g., to cleave foreign ssDNAs (e.g., viral DNAs) in a cell.

The contacting step of a subject method can be carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

The guide RNA can be provided as RNA or as a nucleic acid encoding the guide RNA (e.g., a DNA such as a recombinant expression vector). The Cas12J polypeptide can be provided as a protein or as a nucleic acid encoding the protein (e.g., an mRNA, a DNA such as a recombinant expression vector). In some cases, two or more (e.g., 3 or more, 4 or more, 5 or more, or 6 or more) guide RNAs can be provided by (e.g., using a precursor guide RNA array, which can be cleaved by the Cas12J effector protein into individual ("mature") guide RNAs).

In some cases (e.g., when contacting with a guide RNA and a Cas12J polypeptide of the present disclosure, the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases, the sample is contacted for 20 minutes or less prior to the measuring step. In some cases, the sample is contacted for 10 minutes or less prior to the measuring step. In some cases, the sample is contacted for 5 minutes or less prior to the measuring step. In some cases, the sample is contacted for 1 minute or less prior to the measuring step. In some cases, the sample is contacted for from 50 seconds to 60 seconds prior to the measuring step. In some cases, the sample is contacted for from 40 seconds to 50 seconds prior to the measuring step. In some cases, the sample is contacted for from 30 seconds to 40 seconds prior to the measuring step. In some cases, the sample is contacted for from 20 seconds to 30 seconds prior to the measuring step. In some cases, the sample is contacted for from 10 seconds to 20 seconds prior to the measuring step.

A method of the present disclosure for detecting a target DNA (single-stranded or double-stranded) in a sample can detect a target DNA with a high degree of sensitivity. In some cases, a method of the present disclosure can be used to detect a target DNA present in a sample comprising a plurality of DNAs (including the target DNA and a plurality of non-target DNAs), where the target DNA is present at one or more copies per $10^7$ non-target DNAs (e.g., one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs). In some cases, a method of the present disclosure can be used to detect a target DNA present in a sample comprising a plurality of DNAs (including the target DNA and a plurality of non-target DNAs), where the target DNA is present at one or more copies per $10^{18}$ non-target DNAs (e.g., one or more copies per $10^{15}$ non-target DNAs, one or more copies per $10^{12}$ non-target DNAs, one or more copies per $10^9$ non-target DNAs, one or more copies per $10^6$ non-target DNAs, one or more copies per $10^5$ non-target DNAs, one or more copies per $10^4$ non-target DNAs, one or more copies per $10^3$ non-target DNAs, one or more copies per $10^2$ non-target DNAs, one or more copies per 50 non-target DNAs, one or more copies per 20 non-target DNAs, one or more copies per 10 non-target DNAs, or one or more copies per 5 non-target DNAs).

In some cases, a method of the present disclosure can detect a target DNA present in a sample, where the target DNA is present at from one copy per $10^7$ non-target DNAs to one copy per 10 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^{18}$ non-target DNAs to one copy per 10 non-target DNAs (e.g., from 1 copy per $10^{18}$ non-target DNAs to 1 copy per $10^2$ non-target DNAs, from 1 copy per $10^{15}$ non-target DNAs to 1 copy per $10^2$ non-target DNAs, from 1 copy per $10^{12}$ non-target DNAs to 1 copy per $10^2$ non-target DNAs, from 1 copy per $10^9$ non-target DNAs to 1 copy per $10^2$ non-target DNAs, from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 10 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 10 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, a method of the present disclosure can detect a target DNA present in a sample, where the target DNA is present at from one copy per $10^7$ non-target DNAs to one copy per 100 non-target DNAs (e.g., from 1 copy per $10^7$ non-target DNAs to 1 copy per $10^2$ non-target DNAs, from 1 copy per $10^7$ non-target DNAs to 1 copy per $10^3$ non-target DNAs, from 1 copy per $10^7$ non-target DNAs to 1 copy per $10^4$ non-target DNAs, from 1 copy per $10^7$ non-target DNAs to 1 copy per $10^5$ non-target DNAs, from 1 copy per $10^7$ non-target DNAs to 1 copy per $10^6$ non-target DNAs, from 1 copy per $10^6$ non-target DNAs to 1 copy per 100 non-target DNAs, from 1 copy per $10^6$ non-target DNAs to 1 copy per $10^2$ non-target DNAs, from 1 copy per $10^6$ non-target DNAs to 1 copy per $10^3$ non-target DNAs, from 1 copy per $10^6$ non-target DNAs to 1 copy per $10^4$ non-target DNAs, from 1 copy per $10^6$ non-target DNAs to 1 copy per $10^5$ non-target DNAs, from 1 copy per $10^5$ non-target DNAs to 1 copy per 100 non-target DNAs, from 1 copy per $10^5$ non-target DNAs to 1 copy per $10^2$ non-target DNAs, from 1 copy per $10^5$ non-target DNAs to 1 copy per $10^3$ non-target DNAs, or from 1 copy per $10^5$ non-target DNAs to 1 copy per $10^4$ non-target DNAs).

In some cases, the threshold of detection, for a subject method of detecting a target DNA in a sample, is 10 nM or less. The term "threshold of detection" is used herein to describe the minimal amount of target DNA that must be present in a sample in order for detection to occur. Thus, as an illustrative example, when a threshold of detection is 10 nM, then a signal can be detected when a target DNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less. In some cases, a method of the present disclosure has a threshold of detection of 500 aM (attomolar) or less. In some cases, a method of the present disclosure has a threshold of detection of 250 aM or less. In some cases, a method of the present disclosure has a threshold of detection of 100 aM or less. In some cases, a method of the present disclosure has a threshold of detection of 50 aM or less. In some cases, a method of the present disclosure has a threshold of detection of 10 aM or less. In some cases, a method of the present disclosure has a threshold of detection of 1 aM or less.

In some cases, the threshold of detection (for detecting the target DNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a target DNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 800 fM to 100 pM. In some cases, the minimum concentration at which a target DNA can be detected in a sample is in a range of from 1 pM to 10 pM.

In some cases, the threshold of detection (for detecting the target DNA in a subject method), is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target DNA at which the target DNA can be detected). In some cases, a method of the present disclosure has a threshold of detection in a range of from 1 aM to 800 aM. In some cases, a method of the present disclosure has a threshold of detection in a range of from 50 aM to 1 pM. In some cases, a method of the present disclosure has a threshold of detection in a range of from 50 aM to 500 fM.

In some cases, the minimum concentration at which a target DNA can be detected in a sample is in a range of from 1 aM to 1 nM (e.g., from 1 aM to 500 pM, from 1 aM to 200 pM, from 1 aM to 100 pM, from 1 aM to 10 pM, from 1 aM to 1 pM, from 100 aM to 1 nM, from 100 aM to 500 pM, from 100 aM to 200 pM, from 100 aM to 100 pM, from 100 aM to 10 pM, from 100 aM to 1 pM, from 250 aM to 1 nM, from 250 aM to 500 pM, from 250 aM to 200 pM, from 250 aM to 100 pM, from 250 aM to 10 pM, from 250 aM to 1 pM, from 500 aM to 1 nM, from 500 aM to 500 pM, from 500 aM to 200 pM, from 500 aM to 100 pM, from 500 aM to 10 pM, from 500 aM to 1 pM, from 750 aM to 1 nM, from 750 aM to 500 pM, from 750 aM to 200 pM, from 750 aM to 100 pM, from 750 aM to 10 pM, from 750 aM to 1 pM, from 1 fM to 1 nM, from 1 fM to 500 pM, from 1 fM to 200 pM, from 1 fM to 100 pM, from 1 fM to 10 pM, from 1 fM to 1 pM, from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a target DNA can be detected in a sample is in a range of from 1 aM to 500 pM. In some cases, the minimum concentration at which a target DNA can be detected in a sample is in a range of from 100 aM to 500 pM.

In some cases, a subject composition or method exhibits an attomolar (aM) sensitivity of detection. In some cases, a subject composition or method exhibits a femtomolar (fM) sensitivity of detection. In some cases, a subject composition or method exhibits a picomolar (pM) sensitivity of detection. In some cases, a subject composition or method exhibits a nanomolar (nM) sensitivity of detection.

Target DNA

A target DNA can be single stranded (ssDNA) or double stranded (dsDNA). When the target DNA is single stranded, there is no preference or requirement for a PAM sequence in the target DNA. However, when the target DNA is dsDNA, a PAM is usually present adjacent to the target sequence of the target DNA (e.g., see discussion of the PAM elsewhere herein). The source of the target DNA can be the same as the source of the sample, e.g., as described below.

The source of the target DNA can be any source. In some cases, the target DNA is a viral DNA (e.g., a genomic DNA of a DNA virus). As such, subject method can be for detecting the presence of a viral DNA amongst a population of nucleic acids (e.g., in a sample). A subject method can also be used for the cleavage of non-target ssDNAs in the present of a target DNA. For example, if a method takes place in a cell, a subject method can be used to promiscuously cleave non-target ssDNAs in the cell (ssDNAs that do not hybridize with the guide sequence of the guide RNA) when a particular target DNA is present in the cell (e.g., when the cell is infected with a virus and viral target DNA is detected).

Examples of possible target DNAs include, but are not limited to, viral DNAs such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), epstein-barr virus (EBV), cytomegalovirus (CMV), herpes lymphotropic virus, Pityriasis Rosea, kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. In some cases, the target DNA is parasite DNA. In some cases, the target DNA is bacterial DNA, e.g., DNA of a pathogenic bacterium.

Samples

A subject sample includes nucleic acid (e.g., a plurality of nucleic acids). The term "plurality" is used herein to mean two or more. Thus, in some cases, a sample includes two or more (e.g., 3 or more, 5 or more, 10 or more, 20 or more, 50 or more, 100 or more, 500 or more, 1,000 or more, or 5,000 or more) nucleic acids (e.g., DNAs). A subject method can be used as a very sensitive way to detect a target DNA present in a sample (e.g., in a complex mixture of nucleic acids such as DNAs). In some cases, the sample includes 5 or more DNAs (e.g., 10 or more, 20 or more, 50 or more, 100 or more, 500 or more, 1,000 or more, or 5,000 or more DNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, DNAs. In some cases, the sample comprises from 10 to 20, from 20 to 50, from 50 to 100, from 100 to 500, from 500 to $10^3$, from $10^3$ to $5 \times 10^3$, from $5 \times 10^3$ to $10^4$, from $10^4$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, DNAs. In some cases, the sample comprises from 5 to $10^7$ DNAs (e.g., that differ from one another in sequence)(e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 DNAs). In some cases, the sample includes 20 or more DNAs that differ from one another in sequence. In some cases, the sample includes DNAs from a cell lysate (e.g., a eukaryotic cell lysate, a mammalian cell lysate, a human cell lysate, a prokaryotic cell lysate, a plant cell lysate, and the like). For example, in some cases the sample includes DNA from a cell such as a eukaryotic cell, e.g., a mammalian cell such as a human cell.

The term "sample" is used herein to mean any sample that includes DNA (e.g., in order to determine whether a target DNA is present among a population of DNAs). The sample can be derived from any source, e.g., the sample can be a synthetic combination of purified DNAs; the sample can be a cell lysate, an DNA-enriched cell lysate, or DNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a target DNA and a plurality of non-target DNAs. In some cases, the target DNA is present in the sample at one copy per 10 non-target DNAs, one copy per 20 non-target DNAs, one copy per 25 non-target DNAs, one copy per 50 non-target DNAs, one copy per 100 non-target DNAs, one copy per 500 non-target DNAs, one copy per $10^3$ non-target DNAs, one copy per $5 \times 10^3$ non-target DNAs, one copy per $10^4$ non-target DNAs, one copy per $5 \times 10^4$ non-target DNAs, one copy per $10^5$ non-target DNAs, one copy per $5 \times 10^5$ non-target DNAs, one copy per $10^6$ non-target DNAs, or less than one copy per $10^6$ non-target DNAs. In some cases, the target DNA is present in the sample at from one copy per 10 non-target DNAs to 1 copy per 20 non-target DNAs, from 1 copy per 20 non-target DNAs to 1 copy per 50 non-target DNAs, from 1 copy per 50 non-target DNAs to 1 copy per 100 non-target DNAs, from 1 copy per 100 non-target DNAs to 1 copy per 500 non-target DNAs, from 1 copy per 500 non-target DNAs to 1 copy per $10^3$ non-target DNAs, from 1 copy per $10^3$ non-target DNAs to 1 copy per $5 \times 10^3$ non-target DNAs, from 1 copy per $5 \times 10^3$ non-target DNAs to 1 copy per $10^4$ non-target DNAs, from 1 copy per $10^4$ non-target DNAs to 1 copy per $10^5$ non-target DNAs, from 1 copy per $10^5$ non-target DNAs to 1 copy per $10^6$ non-target DNAs, or from 1 copy per $10^6$ non-target DNAs to 1 copy per $10^7$ non-target DNAs.

Suitable samples include but are not limited to saliva, blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., DNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising DNAs that is obtained from such cells (e.g., a cell lysate or other cell extract comprising DNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., *flagellates* (e.g., *Euglena*), amoeboids (e.g., amoeba), sporozoans (e.g, Apicomplexa, Myxozoa, Microsporidia), and ciliates (e.g., Paramecium). Suitable sample sources include include members of the kingdom Fungi, including, but not limited to, members of any of the phyla: Basidiomycota (club fungi; e.g., members of *Agaricus, Amanita, Boletus*, Cantherellus, etc.); Ascomycota (sac fungi, including, e.g., *Saccharomyces*); Mycophycophyta (lichens); Zygomycota (conjugation fungi); and Deuteromycota. Suitable sample sources include include members of the kingdom Plantae, including, but not limited to, members of any of the following divisions: Bryophyta (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, hill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Ayes (birds); and Mammalian (mammals) Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a (or is suspected of being a diseased cell, fluid, tissue, or organ. In some cases, the source of the sample is a normal (non-diseased) cell, fluid, tissue, or organ. In some cases, the source of the sample is a (or is suspected of being) a pathogen-infected cell, tissue, or organ. For example, the source of a sample can be an individual who may or may not be infected—and the sample could be any biological sample (e.g., blood, saliva, biopsy, plasma, serum, bronchoalveolar lavage, sputum, a fecal sample, cerebrospinal fluid, a fine needle aspirate, a swab sample (e.g., a buccal swab, a cervical swab, a nasal swab), interstitial fluid, synovial fluid, nasal discharge, tears, buffy coat, a mucous membrane sample, an epithelial cell sample (e.g., epithelial cell scraping), etc.) collected from the individual. In some cases, the sample is a cell-free liquid sample. In some cases, the sample is a liquid sample that can comprise cells. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from Giardia spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis,* and *Candida albicans*. Pathogenic viruses include, e.g., human immunodeficiency virus (e.g., HIV); influenza virus; dengue; West Nile virus; herpes virus; yellow fever virus; Hepatitis C Virus; Hepatitis A Virus; Hepatitis B Virus; papillomavirus; and the like. Pathogenic viruses can include DNA viruses such as: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, *Pityriasis Rosea*, Kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like. Pathogens can include, e.g., DNAviruses (e.g.: a papovavirus (e.g., human papillomavirus (HPV), polyomavirus); a hepadnavirus (e.g., Hepatitis B Virus (HBV)); a herpesvirus (e.g., herpes simplex virus (HSV), varicella zoster virus (VZV), Epstein-Barr virus (EBV), cytomegalovirus (CMV), herpes lymphotropic virus, *Pityriasis Rosea*, Kaposi's sarcoma-associated herpesvirus); an adenovirus (e.g., atadenovirus, aviadenovirus, ichtadenovirus, mastadenovirus, siadenovirus); a poxvirus (e.g., smallpox, vaccinia virus, cowpox virus, monkeypox virus, orf virus, pseudocowpox, bovine papular stomatitis virus; tanapox virus, yaba monkey tumor virus; molluscum contagiosum virus (MCV)); a parvovirus (e.g., adeno-associated virus (AAV), Parvovirus B19, human bocavirus, bufavirus, human parv4 G1); Geminiviridae; Nanoviridae; Phycodnaviridae; and the like], *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis,* Pneumococcus, *Cryptococcus neoformans, Histoplasma capsulatum, Hemophilus influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma* rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium and M. pneumoniae.

Measuring a Detectable Signal

In some cases, a subject method includes a step of measuring (e.g., measuring a detectable signal produced by Cas12J-mediated ssDNA cleavage). Because a Cas12J polypeptide of the present disclosure cleaves non-targeted ssDNA once activated, which occurs when a guide RNA hybridizes with a target DNA in the presence of a Cas12J effector protein, a detectable signal can be any signal that is produced when ssDNA is cleaved. For example, in some cases, the step of measuring can include one or more of: gold nanoparticle based detection (e.g., see Xu et al., Angew Chem Int Ed Engl. 2007; 46(19):3468-70; and Xia et al., Proc Natl Acad Sci USA. 2010 Jun. 15; 107(24):10837-41), fluorescence polarization, colloid phase transition/dispersion (e.g., Baksh et al., Nature. 2004 Jan. 8; 427(6970):139-41), electrochemical detection, semiconductor-based sensing (e.g., Rothberg et al., Nature. 2011 Jul. 20; 475(7356): 348-52; e.g., one could use a phosphatase to generate a pH change after ssDNA cleavage reactions, by opening 2'-3' cyclic phosphates, and by releasing inorganic phosphate into solution), and detection of a labeled detector ssDNA (see elsewhere herein for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target DNA present in the sample. The measuring can in some cases be qualitative, e.g., in the sense that the presence or absence of detectable signal can indicate the presence or absence of targeted DNA (e.g., virus, SNP, etc.). In some cases, a detectable signal will not be present (e.g., above a given threshold level) unless the targeted DNA(s) (e.g., virus, SNP, etc.) is present above a particular threshold concentration. In some cases, the threshold of detection can be titrated by modifying the amount of Cas12J effector, guide RNA, sample volume, and/or detector ssDNA (if one is used). As such, for example, as would be understood by one of ordinary skill in the art, a number of controls can be used if desired in order to set up one or more reactions, each set up to detect a different threshold level of target DNA, and thus such a series of reactions could be used to determine the amount of target DNA present in a sample (e.g., one could use such a series of reactions to determine that a target DNA is present in the sample 'at a concentration of at least X').

Examples of uses of a detection method of the present disclosure include, e.g., single nucleotide polymorphism (SNP) detection, cancer screening, detection of bacterial infection, detection of antibiotic resistance, detection of viral infection, and the like. The compositions and methods of this disclosure can be used to detect any DNA target. For example, any virus that integrates nucleic acid material into the genome can be detected because a subject sample can include cellular genomic DNA—and the guide RNA can be designed to detect integrated nucleotide sequence.

In some cases, a method of the present disclosure can be used to determine the amount of a target DNA in a sample (e.g., a sample comprising the target DNA and a plurality of non-target DNAs). Determining the amount of a target DNA in a sample can comprise comparing the amount of detectable signal generated from a test sample to the amount of detectable signal generated from a reference sample. Determining the amount of a target DNA in a sample can comprise: measuring the detectable signal to generate a test measurement; measuring a detectable signal produced by a reference sample to generate a reference measurement; and comparing the test measurement to the reference measurement to determine an amount of target DNA present in the sample.

For example, in some cases, a method of the present disclosure for determining the amount of a target DNA in a sample comprises: a) contacting the sample (e.g., a sample comprising the target DNA and a plurality of non-target DNAs) with: (i) a guide RNA that hybridizes with the target DNA, (ii) a Cas12J polypeptide of the present disclosure that cleaves RNAs present in the sample, and (iii) a detector ssDNA; b) measuring a detectable signal produced by Cas12J-mediated ssDNA cleavage (e.g., cleavage of the detector ssDNA), generating a test measurement; c) measuring a detectable signal produced by a reference sample to generate a reference measurement; and d) comparing the test measurement to the reference measurement to determine an amount of target DNA present in the sample.

As another example, in some cases, a method of the present disclosure for determining the amount of a target DNA in a sample comprises: a) contacting the sample (e.g., a sample comprising the target DNA and a plurality of non-target DNAs) with: i) a precursor guide RNA array comprising two or more guide RNAs each of which has a different guide sequence; (ii) a Cas12J polypeptide of the present disclosure that cleaves the precursor guide RNA array into individual guide RNAs, and also cleaves RNAs of the sample; and (iii) a detector ssDNA; b) measuring a detectable signal produced by Cas12J- mediated ssDNA cleavage (e.g., cleavage of the detector ssDNA), generating a test measurement; c) measuring a detectable signal produced by each of two or more reference samples to generate two or more reference measurements; and d) comparing the test measurement to the reference measurements to determine an amount of target DNA present in the sample.

Amplification of Nucleic Acids in the Sample

In some embodiments, sensitivity of a subject composition and/or method (e.g., for detecting the presence of a target DNA, such as viral DNA or a SNP, in cellular genomic DNA) can be increased by coupling detection with nucleic acid amplification. In some cases, the nucleic acids in a sample are amplified prior to contact with a Cas12J polypeptide of the present disclosure that cleaved ssDNA (e.g., amplification of nucleic acids in the sample can begin prior to contact with a Cas12J polypeptide of the present disclosure). In some cases, the nucleic acids in a sample are amplified simultaneously with contact with a Cas12J polypeptide of the present disclosure. For example, in some cases, a subject method includes amplifying nucleic acids of a sample (e.g., by contacting the sample with amplification components) prior to contacting the amplified sample with a Cas12J polypeptide of the present disclosure. In some cases, a subject method includes contacting a sample with amplification components at the same time (simultaneous with)

that the sample is contacted with a Cas12J polypeptide of the present disclosure. If all components are added simultaneously (amplification components and detection components such as a Cas12J polypeptide of the present disclosure, a guide RNA, and a detector DNA), it is possible that the trans-cleavage activity of the Cas12J will begin to degrade the nucleic acids of the sample at the same time the nucleic acids are undergoing amplification. However, even if this is the case, amplifying and detecting simultaneously can still increase sensitivity compared to performing the method without amplification.

In some cases, specific sequences (e.g., sequences of a virus, sequences that include a SNP of interest) are amplified from the sample, e.g., using primers. As such, a sequence to which the guide RNA will hybridize can be amplified in order to increase sensitivity of a subject detection method—this could achieve biased amplification of a desired sequence in order to increase the number of copies of the sequence of interest present in the sample relative to other sequences present in the sample. As one illustrative example, if a subject method is being used to determine whether a given sample includes a particular virus (or a particular SNP), a desired region of viral sequence (or non-viral genomic sequence) can be amplified, and the region amplified will include the sequence that would hybridize to the guide RNA if the viral sequence (or SNP) were in fact present in the sample.

As noted, in some cases the nucleic acids are amplified (e.g., by contact with amplification components) prior to contacting the amplified nucleic acids with a Cas12J polypeptide of the present disclosure. In some cases, amplification occurs for 10 seconds or more, (e.g., 30 seconds or more, 45 seconds or more, 1 minute or more, 2 minutes or more, 3 minutes or more, 4 minutes or more, 5 minutes or more, 7.5 minutes or more, 10 minutes or more, etc.) prior to contact with a Cas12J polypeptide of the present disclosure. In some cases, amplification occurs for 2 minutes or more (e.g., 3 minutes or more, 4 minutes or more, 5 minutes or more, 7.5 minutes or more, 10 minutes or more, etc.) prior to contact with a Cas12J polypeptide of the present disclosure. In some cases, amplification occurs for a period of time in a range of from 10 seconds to 60 minutes (e.g., 10 seconds to 40 minutes, 10 seconds to 30 minutes, 10 seconds to 20 minutes, 10 seconds to 15 minutes, 10 seconds to 10 minutes, 10 seconds to 5 minutes, 30 seconds to 40 minutes, 30 seconds to 30 minutes, 30 seconds to 20 minutes, 30 seconds to 15 minutes, 30 seconds to 10 minutes, 30 seconds to 5 minutes, 1 minute to 40 minutes, 1 minute to 30 minutes, 1 minute to 20 minutes, 1 minute to 15 minutes, 1 minute to 10 minutes, 1 minute to 5 minutes, 2 minutes to 40 minutes, 2 minutes to 30 minutes, 2 minutes to 20 minutes, 2 minutes to 15 minutes, 2 minutes to 10 minutes, 2 minutes to 5 minutes, 5 minutes to 40 minutes, 5 minutes to 30 minutes, 5 minutes to 20 minutes, 5 minutes to 15 minutes, or 5 minutes to 10 minutes). In some cases, amplification occurs for a period of time in a range of from 5 minutes to 15 minutes. In some cases, amplification occurs for a period of time in a range of from 7 minutes to 12 minutes.

In some cases, a sample is contacted with amplification components at the same time as contact with a Cas12J polypeptide of the present disclosure. In some such cases, the Cas12J protein is inactive at the time of contact and is activated once nucleic acids in the sample have been amplified.

Various amplification methods and components will be known to one of ordinary skill in the art and any convenient method can be used (see, e.g., Zanoli and Spoto, Biosensors (Basel). 2013 March; 3(1): 18-43; Gill and Ghaemi, Nucleosides, Nucleotides, and Nucleic Acids, 2008, 27: 224-243; Craw and Balachandrana, Lab Chip, 2012, 12, 2469-2486; which are herein incorporated by reference in their entirety). Nucleic acid amplification can comprise polymerase chain reaction (PCR), reverse transcription PCR (RT-PCR), quantitative PCR (qPCR), reverse transcription qPCR (RT-qPCR), nested PCR, multiplex PCR, asymmetric PCR, touchdown PCR, random primer PCR, hemi-nested PCR, polymerase cycling assembly (PCA), colony PCR, ligase chain reaction (LCR), digital PCR, methylation specific-PCR (MSP), co-amplification at lower denaturation temperature-PCR (COLD-PCR), allele-specific PCR, intersequence-specific PCR (ISS-PCR), whole genome amplification (WGA), inverse PCR, and thermal asymmetric interlaced PCR (TAIL-PCR).

In some cases, the amplification is isothermal amplification. The term "isothermal amplification" indicates a method of nucleic acid (e.g., DNA) amplification (e.g., using enzymatic chain reaction) that can use a single temperature incubation thereby obviating the need for a thermal cycler. Isothermal amplification is a form of nucleic acid amplification which does not rely on the thermal denaturation of the target nucleic acid during the amplification reaction and hence may not require multiple rapid changes in temperature. Isothermal nucleic acid amplification methods can therefore be carried out inside or outside of a laboratory environment. By combining with a reverse transcription step, these amplification methods can be used to isothermally amplify RNA.

Examples of isothermal amplification methods include but are not limited to: loop-mediated isothermal Amplification (LAMP), helicase-dependent Amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR) and isothermal multiple displacement amplification (IMDA).

In some cases, the amplification is recombinase polymerase amplification (RPA) (see, e.g., U.S. Pat. Nos. 8,030,000; 8,426,134; 8,945,845; 9,309,502; and 9,663,820, which are hereby incorporated by reference in their entirety). Recombinase polymerase amplification (RPA) uses two opposing primers (much like PCR) and employs three enzymes—a recombinase, a single-stranded DNA-binding protein (SSB) and a strand-displacing polymerase. The recombinase pairs oligonucleotide primers with homologous sequence in duplex DNA, SSB binds to displaced strands of DNA to prevent the primers from being displaced, and the strand displacing polymerase begins DNA synthesis where the primer has bound to the target DNA. Adding a reverse transcriptase enzyme to an RPA reaction can facilitate detection RNA as well as DNA, without the need for a separate step to produce cDNA. One example of components for an RPA reaction is as follows (see, e.g., U.S. Pat. Nos. 8,030,000; 8,426,134; 8,945,845; 9,309,502; 9,663,820): 50 mM Tris pH 8.4, 80 mM Potassium actetate, 10 mM Magnesium acetate, 2 mM dithiothreitol (DTT), 5% PEG compound (Carbowax-20M), 3 mM ATP, 30 mM Phosphocreatine, 100 ng/µl creatine kinase, 420 ng/µl gp32, 140 ng/µd UvsX, 35 ng/µl UvsY, 2000M dNTPs, 300 nM each oligonucleotide, 35 ng/µd Bsu polymerase, and a nucleic acid-containing sample).

In a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is similar to Self-Sustained Sequence Replication (3SR) and Nucleic Acid Sequence Based Amplification (NASBA), but varies in the enzymes employed. For another example, helicase-dependent amplification (HDA) utilizes a thermostable helicase (Tte-UvrD) rather than heat to unwind dsDNA to create single-strands that are then available for hybridization and extension of primers by polymerase. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand.

Detector DNA

In some cases, a subject method includes contacting a sample (e.g., a sample comprising a target DNA and a plurality of non-target ssDNAs) with: i) a Cas12J polypeptide of the present disclosure; ii) a guide RNA (or precursor guide RNA array); and iii) a detector DNA that is single stranded and does not hybridize with the guide sequence of the guide RNA. For example, in some cases, a subject method includes contacting a sample with a labeled single stranded detector DNA (detector ssDNA) that includes a fluorescence-emitting dye pair; the Cas12J polypeptide cleaves the labeled detector ssDNA after it is activated (by binding to the guide RNA in the context of the guide RNA hybridizing to a target DNA); and the detectable signal that is measured is produced by the fluorescence-emitting dye pair. For example, in some cases, a subject method includes contacting a sample with a labeled detector ssDNA comprising a fluorescence resonance energy transfer (FRET) pair or a quencher/fluor pair, or both. In some cases, a subject method includes contacting a sample with a labeled detector ssDNA comprising a FRET pair. In some cases, a subject method includes contacting a sample with a labeled detector ssDNA comprising a fluor/quencher pair.

Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector ssDNA includes a FRET pair) the labeled detector ssDNA produces an amount of detectable signal prior to being cleaved, and the amount of detectable signal that is measured is reduced when the labeled detector ssDNA is cleaved. In some cases, the labeled detector ssDNA produces a first detectable signal prior to being cleaved (e.g., from a FRET pair) and a second detectable signal when the labeled detector ssDNA is cleaved (e.g., from a quencher/fluor pair). As such, in some cases, the labeled detector ssDNA comprises a FRET pair and a quencher/fluor pair.

In some cases, the labeled detector ssDNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector ssDNA includes two signal partners (a signal pair), when one signal partner is a FRET donor moiety and the other signal partner is a FRET acceptor moiety. A subject labeled detector ssDNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a Cas12J polypeptide of the present disclosure).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14; 16(9); and Abraham et al. PLoS One. 2015 Aug. 3; 10(8):e0134436.

TABLE 1

Examples of FRET pairs
(donor and acceptor FRET moieties)

| Donor | Acceptor |
|---|---|
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |

TABLE 1-continued

Examples of FRET pairs
(donor and acceptor FRET moieties)

| Donor | Acceptor |
|---|---|
| Cy3 | Cy5 |
| GFP | Yellow fluorescent protein (YFP) |
| BODIPY FL (4) | BODIPY FL (4) |
| Rhodamine 110 | Cy3 |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector ssDNA is cleaved (e.g., in some cases, the labeled detector ssDNA comprises a quencher/fluor pair). One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector ssDNA is cleaved. For example, in some cases, the signal exhibited by one signal partner (a signal moiety) is quenched by the other signal partner (a quencher signal moiety), e.g., when both are present on the same ssDNA molecule prior to cleavage by a Cas12J polypeptide of the present disclosure). Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector ssDNA by a Cas12J polypeptide of the present disclosure), but the signal will be quenched when the partners are in close proximity (e.g., prior to cleavage of the detector ssDNA by a Cas12J polypeptide of the present disclosure).

A quencher moiety can quench a signal from the signal moiety (e.g., prior to cleave of the detector ssDNA by a Cas12J polypeptide of the present disclosure) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases, the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qx1 quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611,20130323851, 20130224871,20110223677,20110190486,20110172420, 20060179585 and 20030003486; and international patent applications: WO200142505 and WO200186001, all of which are hereby incorporated by reference in their entirety.

In some cases, cleavage of a labeled detector ssDNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector ssDNA can be detected by a color-shift. Such a shift can be expressed as a loss of an amount of signal of one color (wavelength), a gain in the amount of another color, a change in the ration of one color to another, and the like.

Transgenic, Non-Human Organisms

As described above, in some cases, a nucleic acid (e.g., a recombinant expression vector) of the present disclosure (e.g., a nucleic acid comprising a nucleotide sequence encoding a Cas12J polypeptide of the present disclosure; a nucleic acid comprising a nucleotide sequence encoding a Cas12J fusion polypeptide of the present disclosure; etc.), is used as a transgene to generate a transgenic non-human organism that produces a Cas12J polypeptide, or a Cas12J fusion polypeptide, of the present disclosure. The present disclosure provides a transgenic-non-human organism comprising a nucleotide sequence encoding a Cas12J polypeptide, or a Cas12J fusion polypeptide, of the present disclosure.

Transgenic, Non-Human Animals

The present disclosure provides a transgenic non-human animal, which animal comprises a transgene comprising a nucleic acid comprising a nucleotide sequence encoding a Cas12J polypeptide or a Cas12J fusion polypeptide. In some embodiments, the genome of the transgenic non-human animal comprises a nucleotide sequence encoding a Cas12J polypeptide or a Cas12J fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a a Cas12J polypeptide, or a Cas12J fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a Cas12J polypeptide of the present disclosure; a nucleic acid comprising a nucleotide sequence encoding a Cas12J fusion polypeptide of the present disclosure; etc.), is used as a transgene to generate a transgenic plant that produces a Cas12J polypeptide, or a Cas12J fusion polypeptide, of the present disclosure. The present disclosure provides a transgenic plant comprising a nucleotide sequence encoding a Cas12J polypeptide, or a Cas12J fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a Cas12J polypeptide, or a Cas12J fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a Cas12J polypeptide, or a Cas12J fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a Cas12J polypeptide, or a Cas12J fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-149 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A composition comprising: a) a Cas12J polypeptide, or a nucleic acid molecule encoding the Cas12J polypeptide; and b) a Cas12J guide RNA, or one or more DNA molecules encoding the Cas12J guide RNA.

Aspect 2. The composition of aspect 1, wherein the Cas12J polypeptide comprises an amino acid sequence having 50% or more amino acid sequence identity to the amino acid sequence depicted in any one of FIG. 6A-6R.

Aspect 3. The composition of aspect 1 or aspect 2, wherein the Cas12J guide RNA comprises a nucleotide sequence having 80%, 90%, 95%, 98%, 99%, or 100%, nucleotide sequence identity with any one of the crRNA sequences depicted in FIG. 7.

Aspect 4. The composition of aspect 1 or aspect 2, wherein the Cas12J polypeptide is fused to a nuclear localization signal (NLS).

Aspect 5. The composition of any one of aspects 1-4, wherein the composition comprises a lipid.

Aspect 6. The composition of any one of aspects 1-4, wherein a) and b) are within a liposome.

Aspect 7. The composition of any one of aspects 1-4, wherein a) and b) are within a particle.

Aspect 8. The composition of any one of aspects 1-7, comprising one or more of: a buffer, a nuclease inhibitor, and a protease inhibitor.

Aspect 9. The composition of any one of aspects 1-8, wherein the Cas12J polypeptide comprises an amino acid sequence having 85% or more identity to the amino acid sequence depicted in any one of FIG. 6A-6R.

Aspect 10. The composition of any one of aspects 1-9, wherein the Cas12J polypeptide is a nickase that can cleave only one strand of a double-stranded target nucleic acid molecule.

Aspect 11. The composition of any one of aspects 1-9, wherein the Cas12J polypeptide is a catalytically inactive Cas12J polypeptide (dCas12J).

Aspect 12. The composition of aspect 10 or aspect 11, wherein the Cas12J polypeptide comprises one or more mutations at a position corresponding to those selected from: D464, E678, and D769 of Cas12J_10037042_3.

Aspect 13. The composition of any one of aspects 1-12, further comprising a DNA donor template.

Aspect 14. A Cas12J fusion polypeptide comprising: a Cas12J polypeptide fused to a heterologous polypeptide.

Aspect 15. The Cas12J fusion polypeptide of Aspect 14, wherein the Cas12J polypeptide comprises an amino acid sequence having 50% or more identity to the amino acid sequence depicted in any one of FIG. 6A-6R.

Aspect 16. The Cas12J fusion polypeptide of Aspect 14, wherein the Cas12J polypeptide comprises an amino acid sequence having 85% or more identity to the amino acid sequence depicted in any one of FIG. 6A-6R.

Aspect 17. The Cas12J fusion polypeptide of any one of aspects 14-16, wherein the Cas12J polypeptide is a nickase that can cleave only one strand of a double-stranded target nucleic acid molecule.

Aspect 18. The Cas12J fusion polypeptide of any one of aspects 14-17, wherein the Cas12J polypeptide is a catalytically inactive Cas12J polypeptide (dCas12J).

Aspect 19. The Cas12J fusion polypeptide of aspect 17 or aspect 18, wherein the Cas12J polypeptide comprises one or more mutations at a position corresponding to those selected from: D464, E678, and D769 of Cas12J_10037042_3.

Aspect 20. The Cas12J fusion polypeptide of any one of aspects 14-19, wherein the heterologous polypeptide is fused to the N-terminus and/or the C-terminus of the Cas12J polypeptide.

Aspect 21. The Cas12J fusion polypeptide of any one of aspects 14-20, comprising a nuclear localization signal (NLS).

Aspect 22. The Cas12J fusion polypeptide of any one of aspects 14-21, wherein the heterologous polypeptide is a targeting polypeptide that provides for binding to a cell surface moiety on a target cell or target cell type.

Aspect 23. The Cas12J fusion polypeptide of any one of aspects 14-21, wherein the heterologous polypeptide exhibits an enzymatic activity that modifies target DNA.

Aspect 24. The Cas12J fusion polypeptide of aspect 23, wherein the heterologous polypeptide exhibits one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 25. The Cas12J fusion polypeptide of aspect 24, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 26. The Cas12J fusion polypeptide of any one of aspects 14-21, wherein the heterologous polypeptide exhibits an enzymatic activity that modifies a target polypeptide associated with a target nucleic acid.

Aspect 27. The Cas12J fusion polypeptide of aspect 26, wherein the heterologous polypeptide exhibits histone modification activity.

Aspect 28. The Cas12J fusion polypeptide of aspect 26 or aspect 27, wherein the heterologous polypeptide exhibits one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

Aspect 29. The Cas12J fusion polypeptide of aspect 28, wherein the heterologous polypeptide exhibits one or more enzymatic activities selected from: methyltransferase activity, demethylase activity, acetyltransferase activity, and deacetylase activity.

Aspect 30. The Cas12J fusion polypeptide of any one of aspects 14-21, wherein the heterologous polypeptide is an endosomal escape polypeptide.

Aspect 31. The Cas12J fusion polypeptide of aspect 30, wherein the endosomal escape polypeptide comprises an amino acid sequence selected from: GLFX-ALLXLLXSLWXLLLXA (SEQ ID NO: 36), and GLF-HALLHLLHSLWHLLLHA (SEQ ID NO: 37), wherein each X is independently selected from lysine, histidine, and arginine.

Aspect 32. The Cas12J fusion polypeptide of any one of aspects 14-21, wherein the heterologous polypeptide is a chloroplast transit peptide.

Aspect 33. The Cas12J fusion polypeptide of any one of aspects 14-21, wherein the heterologous polypeptide comprises a protein transduction domain.

Aspect 34. The Cas12J fusion polypeptide of any one of aspects 14-21, wherein the heterologous polypeptide is a protein that increases or decreases transcription.

Aspect 35. The Cas12J fusion polypeptide of aspect 34, wherein the heterologous polypeptide is a transcriptional repressor domain Aspect 36. The Cas12J fusion polypeptide of aspect 34, wherein the heterologous polypeptide is a transcriptional activation domain Aspect 37. The Cas12J fusion polypeptide of any one of aspects 14-21, wherein the heterologous polypeptide is a protein binding domain.

Aspect 38. A nucleic acid comprising a nucleotide sequence encoding the Cas12J fusion polypeptide of any one of aspects 14-37.

Aspect 39. The nucleic acid of Aspect 38, wherein the nucleotide sequence encoding the Cas12J fusion polypeptide is operably linked to a promoter.

Aspect 40. The nucleic acid of Aspect 39, wherein the promoter is functional in a eukaryotic cell.

Aspect 41. The nucleic acid of Aspect 40, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 43. The nucleic acid of any one of Aspects 39-41, wherein the promoter is one or more of: a constitutive promoter, an inducible promoter, a cell type-specific promoter, and a tissue-specific promoter.

Aspect 43. The nucleic acid of any one of Aspects 38-42, wherein the nucleic acid is a recombinant expression vector.

Aspect 44. The nucleic acid of Aspect 43, wherein the recombinant expression vector is a recombinant adenoassociated viral vector, a recombinant retroviral vector, or a recombinant lentiviral vector.

Aspect 45. The nucleic acid of Aspect 39, wherein the promoter is functional in a prokaryotic cell.

Aspect 46. The nucleic acid of Aspect 38, wherein the nucleic acid molecule is an mRNA.

Aspect 47. One or more nucleic acids comprising: (a) a nucleotide sequence encoding a Cas12J guide RNA; and (b) a nucleotide sequence encoding a Cas12J polypeptide.

Aspect 48. The one or more nucleic acids of aspect 47, wherein the Cas12J polypeptide comprises an amino acid sequence having 50% or more identity to the amino acid sequence depicted in any one of FIG. 6A-6R.

Aspect 49. The one or more nucleic acids of aspect 47, wherein the Cas12J polypeptide comprises an amino acid sequence having 85% or more identity to the amino acid sequence depicted in any one of FIG. 6A-6R.

Aspect 50. The one or more nucleic acids of any one of aspects 47-49, wherein the Cas12J guide RNA comprises a nucleotide sequence having 80% or more nucleotide sequence identity with any one of the crRNA sequences set forth in FIG. 7.

Aspect 51. The one or more nucleic acids of any one of aspects 47-50, wherein the Cas12J polypeptide is fused to a nuclear localization signal (NLS).

Aspect 52. The one or more nucleic acids of any one of aspects 47-51, wherein the nucleotide sequence encoding the Cas12J guide RNA is operably linked to a promoter.

Aspect 53. The one or more nucleic acids of any one of aspects 47-52, wherein the nucleotide sequence encoding the Cas12J polypeptide is operably linked to a promoter.

Aspect 54. The one or more nucleic acids of Aspect 52 or Aspect 53, wherein the promoter operably linked to the nucleotide sequence encoding the Cas12J guide RNA, and/or the promoter operably linked to the nucleotide sequence encoding the Cas12J polypeptide, is functional in a eukaryotic cell.

Aspect 55. The one or more nucleic acids of Aspect 54, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

Aspect 56. The one or more nucleic acids of any one of Aspects 53-55, wherein the promoter is one or more of: a constitutive promoter, an inducible promoter, a cell type-specific promoter, and a tissue-specific promoter.

Aspect 57. The one or more nucleic acids of any one of Aspects 47-56, wherein the one or more nucleic acids is one or more recombinant expression vectors.

Aspect 58. The one or more nucleic acids of Aspect 57, wherein the one or more recombinant expression vectors are selected from: one or more adenoassociated viral vectors, one or more recombinant retroviral vectors, or one or more recombinant lentiviral vectors.

Aspect 59. The one or more nucleic acids of Aspect 53, wherein the promoter is functional in a prokaryotic cell.

Aspect 60. A eukaryotic cell comprising one or more of: a) a Cas12J polypeptide, or a nucleic acid comprising a nucleotide sequence encoding the Cas12J polypeptide, b) a Cas12J fusion polypeptide, or a nucleic acid comprising a nucleotide sequence encoding the Cas12J fusion polypeptide, and c) a Cas12J guide RNA, or a nucleic acid comprising a nucleotide sequence encoding the Cas12J guide RNA.

Aspect 61. The eukaryotic cell of aspect 60, comprising the nucleic acid encoding the Cas12J polypeptide, wherein said nucleic acid is integrated into the genomic DNA of the cell.

Aspect 62. The eukaryotic cell of aspect 60 or aspect 61, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

Aspect 63. A cell comprising a comprising a Cas12J fusion polypeptide, or a nucleic acid comprising a nucleotide sequence encoding the Cas12J fusion polypeptide.

Aspect 64. The cell of aspect 63, wherein the cell is a prokaryotic cell.

Aspect 65. The cell of aspect 63 or aspect 64, comprising the nucleic acid comprising a nucleotide sequence encoding the Cas12J fusion polypeptide, wherein said nucleic acid molecule is integrated into the genomic DNA of the cell.

Aspect 66. A method of modifying a target nucleic acid, the method comprising contacting the target nucleic acid with: a) a Cas12J polypeptide; and b) a Cas12J guide RNA comprising a guide sequence that hybridizes to a target sequence of the target nucleic acid, wherein said contacting results in modification of the target nucleic acid by the Cas12J polypeptide.

Aspect 67. The method of aspect 66, wherein said modification is cleavage of the target nucleic acid.

Aspect 68. The method of aspect 66 or aspect 67, wherein the target nucleic acid is selected from: double stranded DNA, single stranded DNA, RNA, genomic DNA, and extrachromosomal DNA.

Aspect 69. The method of any of aspects 66-68, wherein said contacting takes place in vitro outside of a cell.

Aspect 70. The method of any of aspects 66-68, wherein said contacting takes place inside of a cell in culture.

Aspect 71. The method of any of aspects 66-68, wherein said contacting takes place inside of a cell in vivo.

Aspect 72. The method of aspect 70 or aspect 71, wherein the cell is a eukaryotic cell.

Aspect 73. The method of aspect 72, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 74. The method of aspect 70 or aspect 71, wherein the cell is a prokaryotic cell.

Aspect 75. The method of any one of aspects 66-74, wherein said contacting results in genome editing.

Aspect 76. The method of any one of aspects 66-75, wherein said contacting comprises: introducing into a cell: (a) the Cas12J polypeptide, or a nucleic acid comprising a nucleotide sequence encoding the Cas12J polypeptide, and (b) the Cas12J guide RNA, or a nucleic acid comprising a nucleotide sequence encoding the Cas12J guide RNA.

Aspect 77. The method of aspect 76, wherein said contacting further comprises: introducing a DNA donor template into the cell.

Aspect 78. The method of any one of aspects 66-77, wherein the Cas12J guide RNA comprises a nucleotide sequence having 80% or more nucleotide sequence identity with any one of the crRNA sequences set forth in FIG. 7.

Aspect 79. The method of any one of aspects 66-78, wherein the Cas12J polypeptide is fused to a nuclear localization signal.

Aspect 80. A method of modulating transcription from a target DNA, modifying a target nucleic acid, or modifying a protein associated with a target nucleic acid, the method comprising contacting the target nucleic acid with: a) a Cas12J fusion polypeptide comprising a Cas12J polypeptide fused to a heterologous polypeptide; and b) a Cas12J guide RNA comprising a guide sequence that hybridizes to a target sequence of the target nucleic acid.

Aspect 81. The method of aspect 80, wherein the Cas12J guide RNA comprises a nucleotide sequence having 80% or more nucleotide sequence identity with any one of the crRNA sequences set forth in FIG. 7.

Aspect 82. The method of aspect 80 or aspect 81, wherein the Cas12J fusion polypeptide comprises nuclear localization signal.

Aspect 83. The method of any of aspects 80-82, wherein said modification is not cleavage of the target nucleic acid.

Aspect 84. The method of any of aspects 80-83, wherein the target nucleic acid is selected from: double stranded DNA, single stranded DNA, RNA, genomic DNA, and extrachromosomal DNA.

Aspect 85. The method of any of aspects 80-84, wherein said contacting takes place in vitro outside of a cell.

Aspect 86. The method of any of aspects 80-84, wherein said contacting takes place inside of a cell in culture.

Aspect 87. The method of any of aspects 80-84, wherein said contacting takes place inside of a cell in vivo.

Aspect 88. The method of aspect 86 or aspect 87, wherein the cell is a eukaryotic cell.

Aspect 89. The method of aspect 88, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Aspect 90. The method of aspect 86 or aspect 87, wherein the cell is a prokaryotic cell.

Aspect 91. The method of any one of aspects 80-90, wherein said contacting comprises: introducing into a cell: (a) the Cas12J fusion polypeptide, or a nucleic acid comprising a nucleotide sequence encoding the Cas12J fusion polypeptide, and (b) the Cas12J guide RNA, or a nucleic acid comprising a nucleotide sequence encoding the Cas12J guide RNA.

Aspect 92. The method of any one of aspects 80-91, wherein the Cas12J polypeptide is a catalytically inactive Cas12J polypeptide (dCas12J).

Aspect 93. The method of any one of aspects 80-92, wherein the Cas12J polypeptide comprises one or more amino acid substitutions at a position corresponding to those selected from: D464, E678, and D769 of Cas12J_10037042_3.

Aspect 94. The method of any one of aspects 80-93, wherein the heterologous polypeptide exhibits an enzymatic activity that modifies target DNA.

Aspect 95. The method of aspect 94, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

Aspect 96. The method of aspect 95, wherein the heterologous polypeptide exhibits one or more enzymatic activities selected from: nuclease activity, methyltransferase activity, demethylase activity, deamination activity, depurination activity, integrase activity, transposase activity, and recombinase activity.

Aspect 97. The method of any one of aspects 80-93, wherein the heterologous polypeptide exhibits an enzymatic activity that modifies a target polypeptide associated with a target nucleic acid.

Aspect 98. The method of aspect 97, wherein the heterologous polypeptide exhibits histone modification activity.

Aspect 99. The method of aspect 97 or aspect 98, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from 0-GlcNAc transferase) and deglycosylation activity.

Aspect 100. The method of aspect 99, wherein the heterologous polypeptide exhibits one or more enzymatic activities selected from: methyltransferase activity, demethylase activity, acetyltransferase activity, and deacetylase activity.

Aspect 101. The method of any one of aspects 80-93, wherein the heterologous polypeptide is protein that increases or decreases transcription.

Aspect 102. The method of aspect 101, wherein the heterologous polypeptide is a transcriptional repressor domain Aspect 103. The method of aspect 101, wherein the heterologous polypeptide is a transcriptional activation domain Aspect 104. The method of any one of aspects 80-93, wherein the heterologous polypeptide is a protein binding domain Aspect 105. A transgenic, multicellular, non-human organism whose genome comprises a transgene comprising a nucleotide sequence encoding one or more of: a) a Cas12J polypeptide; b) a Cas12J fusion polypeptide; and c) a Cas12J guide RNA Aspect 106. The transgenic, multicellular, non-human organism of aspect 105, wherein the Cas12J polypeptide comprises an amino acid sequence having 50% or more amino acid sequence identity to the amino acid sequence set forth in any one of FIG. 6A-6R.

Aspect 107. The transgenic, multicellular, non-human organism of aspect 105, wherein the Cas12J polypeptide comprises an amino acid sequence having 85% or more amino acid sequence identity to the amino acid sequence set forth in any one of FIG. 6A-6R.

Aspect 108. The transgenic, multicellular, non-human organism of any one of aspects 105-107, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

Aspect 109. A system comprising one of:
  a) a Cas12J polypeptide and a Cas12J guide RNA;
  b) a Cas12J polypeptide, a Cas12J guide RNA, and a DNA donor template;
  c) a Cas12J fusion polypeptide and a Cas12J guide RNA;
  d) a Cas12J fusion polypeptide, a Cas12J guide RNA, and a DNA donor template;
  e) an mRNA encoding a Cas12J polypeptide, and a Cas12J guide RNA;
  f) an mRNA encoding a Cas12J polypeptide; a Cas12J guide RNA, and a DNA donor template;
  g) an mRNA encoding a Cas12J fusion polypeptide, and a Cas12J guide RNA;
  h) an mRNA encoding a Cas12J fusion polypeptide, a Cas12J guide RNA, and a DNA donor template;
  i) one or more recombinant expression vectors comprising: i) a nucleotide sequence encoding a Cas12J polypeptide; and ii) a nucleotide sequence encoding a Cas12J guide RNA;
  j) one or more recombinant expression vectors comprising: i) a nucleotide sequence encoding a Cas12J polypeptide; ii) a nucleotide sequence encoding a Cas12J guide RNA; and iii) a DNA donor template;
  k) one or more recombinant expression vectors comprising: i) a nucleotide sequence encoding a Cas12J fusion polypeptide; and ii) a nucleotide sequence encoding a Cas12J guide RNA; and
  l) one or more recombinant expression vectors comprising: i) a nucleotide sequence encoding a Cas12J fusion polypeptide; ii) a nucleotide sequence encoding a Cas12J guide RNA; and a DNA donor template.

Aspect 110. The Cas12J system of aspect 109, wherein the Cas12J polypeptide comprises an amino acid sequence having 50% or more amino acid sequence identity to the amino acid sequence depicted in any one of FIG. 6A-6R.

Aspect 111. The Cas12J system of aspect 109, wherein the Cas12J polypeptide comprises an amino acid sequence having 85% or more amino acid sequence identity to the amino acid sequence depicted in any one of FIG. 6A-6R.

Aspect 112. The Cas12J system of any of aspects 109-111, wherein the donor template nucleic acid has a length of from 8 nucleotides to 1000 nucleotides.

Aspect 113. The Cas12J system of any of aspects 109-111, wherein the donor template nucleic acid has a length of from 25 nucleotides to 500 nucleotides.

Aspect 114. A kit comprising the Cas12J system of any one of aspects 109-113.

Aspect 115. The kit of aspect 114, wherein the components of the kit are in the same container.

Aspect 116. The kit of aspect 114, wherein the components of the kit are in separate containers.

Aspect 117. A sterile container comprising the Cas12J system of any one of aspects 109-116.

Aspect 118. The sterile container of aspect 117, wherein the container is a syringe.

Aspect 119. An implantable device comprising the Cas12J system of any one of aspects 109-116.

Aspect 120. The implantable device of aspect 119, wherein the Cas12J system is within a matrix.

Aspect 121. The implantable device of aspect 119, wherein the Cas12J system is in a reservoir.

Aspect 122. A method of detecting a target DNA in a sample, the method comprising: (a) contacting the sample with: (i) a Cas12L polypeptide; (ii) a guide RNA comprising: a region that binds to the Cas12L polypeptide, and a guide sequence that hybridizes with the target DNA; and (iii) a detector DNA that is single stranded and does not hybridize with the guide sequence of the guide RNA; and (b) measuring a detectable signal produced by cleavage of the single stranded detector DNA by the Cas12L polypeptide, thereby detecting the target DNA.

Aspect 123. The method of aspect 122, wherein the target DNA is single stranded.

Aspect 124. The method of aspect 122, wherein the target DNA is double stranded.

Aspect 125. The method of any one of aspects 122-124, wherein the target DNA is bacterial DNA.

Aspect 126. The method of any one of aspects 122-124, wherein the target DNA is viral DNA.

Aspect 127. The method of aspect 126, wherein the target DNA is papovavirus, human papillomavirus (HPV), hepadnavirus, Hepatitis B Virus (HBV), herpesvirus, varicella zoster virus (VZV), Epstein-Barr virus (EBV), Kaposi's sarcoma-associated herpesvirus, adenovirus, poxvirus, or parvovirus DNA.

Aspect 128. The method of aspect 122, wherein the target DNA is from a human cell.

Aspect 129. The method of aspect 122, wherein the target DNA is human fetal or cancer cell DNA.

Aspect 130. The method of any one of aspects 122-129, wherein the Cas12J polypeptide comprises an amino acid sequence having 50% or more amino acid sequence identity to the amino acid sequence depicted in any one of FIG. 6A-6R.

Aspect 131. The method of aspect 122, wherein the sample comprises DNA from a cell lysate.

Aspect 132. The method of aspect 122, wherein the sample comprises cells.

Aspect 133. The method of aspect 122, wherein the sample is a blood, serum, plasma, urine, aspirate, or biopsy sample.

Aspect 134. The method of any one of aspects 122-133, further comprising determining an amount of the target DNA present in the sample.

Aspect 135. The method of aspect 122, wherein said measuring a detectable signal comprises one or more of: visual based detection, sensor-based detection, color detection, gold nanoparticle based detection, fluorescence polarization, colloid phase transition/dispersion, electrochemical detection, and semiconductor-based sensing.

Aspect 136. The method of any one of aspects 122-135, wherein the labeled detector DNA comprises a modified nucleobase, a modified sugar moiety, and/or a modified nucleic acid linkage.

Aspect 137. The method of any one of aspects 122-135, further comprising detecting a positive control target DNA in a positive control sample, the detecting comprising: (c) contacting the positive control sample with: (i) the Cas12J polypeptide; (ii) a positive control guide RNA comprising: a region that binds to the Cas12J polypeptide, and a positive control guide sequence that hybridizes with the positive control target DNA; and (iii) a labeled detector DNA that is single stranded and does not hybridize with the positive control guide sequence of the positive control guide RNA; and (d) measuring a detectable signal produced by cleavage of the labeled detector DNA by the Cas12J polypeptide, thereby detecting the positive control target DNA Aspect 138. The method of any one of aspects 122-136, wherein the detectable signal is detectable in less than 45 minutes.

Aspect 139. The method of any one of aspects 122-136, wherein the detectable signal is detectable in less than 30 minutes.

Aspect 140. The method of any one of aspects 122-139, further comprising amplifying the target DNA in the sample by loop-mediated isothermal amplification (LAMP), helicase-dependent amplification (HDA), recombinase polymerase amplification (RPA), strand displacement amplification (SDA), nucleic acid sequence-based amplification (NASBA), transcription mediated amplification (TMA), nicking enzyme amplification reaction (NEAR), rolling circle amplification (RCA), multiple displacement amplification (MDA), Ramification (RAM), circular helicase-dependent amplification (cHDA), single primer isothermal amplification (SPIA), signal mediated amplification of RNA technology (SMART), self-sustained sequence replication (3SR), genome exponential amplification reaction (GEAR), or isothermal multiple displacement amplification (IMDA).

Aspect 141. The method of any one of aspects 122-140, wherein target DNA in the sample is present at a concentration of less than 10 aM.

Aspect 142. The method according to any one of aspect 122-141, wherein the single stranded detector DNA comprises a fluorescence-emitting dye pair.

Aspect 143. The method according to aspect 142, wherein the fluorescence-emitting dye pair produces an amount of detectable signal prior to cleavage of the single stranded detector DNA, and the amount of detectable signal is reduced after cleavage of the single stranded detector DNA.

Aspect 144. The method according to aspect 142, wherein the single stranded detector DNA produces a first detectable signal prior to being cleaved and a second detectable signal after cleavage of the single stranded detector DNA.

Aspect 145. The method according to any one of aspects 142-144, wherein the fluorescence-emitting dye pair is a fluorescence resonance energy transfer (FRET) pair.

Aspect 146. The method according to aspect 142, wherein an amount of detectable signal increases after cleavage of the single stranded detector DNA.

Aspect 147. The method according to any one of aspects 142-146, wherein the fluorescence-emitting dye pair is a quencher/fluor pair.

Aspect 148. The method according to any one of aspects 142-147, wherein the single stranded detector DNA comprises two or more fluorescence-emitting dye pairs.

Aspect 149. The method according to aspect 148, wherein said two or more fluorescence-emitting dye pairs include a fluorescence resonance energy transfer (FRET) pair and a quencher/fluor pair.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Metagenomic datasets from many diverse ecosystems were generated and hundreds of huge phage genomes, between 200 kbp and 716 kbp in length, were reconstructed. Thirty-four genomes were manually curated to completion, including the largest phage genomes yet reported. Expanded genetic repertoires include diverse and new CRISPR-Cas systems, tRNAs, tRNA synthetases, tRNA modification enzymes, initiation and elongation factors and ribosomal proteins. Phage CRISPR have the capacity to silence host transcription factors and translational genes, potentially as part of a larger interaction network that intercepts translation to redirect biosynthesis to phage-encoded functions. Some phage repurpose bacterial systems for phage-defense to eliminate competing phage. Seven major clades of huge phage from human and other animal microbiomes, oceans, lakes, sediments, soils and the built environment were phylogenetically defined. It is concluded that large gene inventories reflect a conserved biological strategy, observed across a broad bacterial host range and resulting in the distribution of huge phage across Earth's ecosystems.

Hundreds of phage sequences >200 kbp in length that were reconstructed from microbiome datasets generated from a wide variety of ecosystems were presented. The three largest complete genomes for phage known to date, ranging up to 642 kbp in length, were reconstructed. A graphical abstract provides an overview of the approach and main findings. The research expands the understanding of phage biodiversity and brings to light the variety of ecosystems in which phage have genome sizes that rival those of small celled bacteria.

Ecosystem sampling

Figure 5:
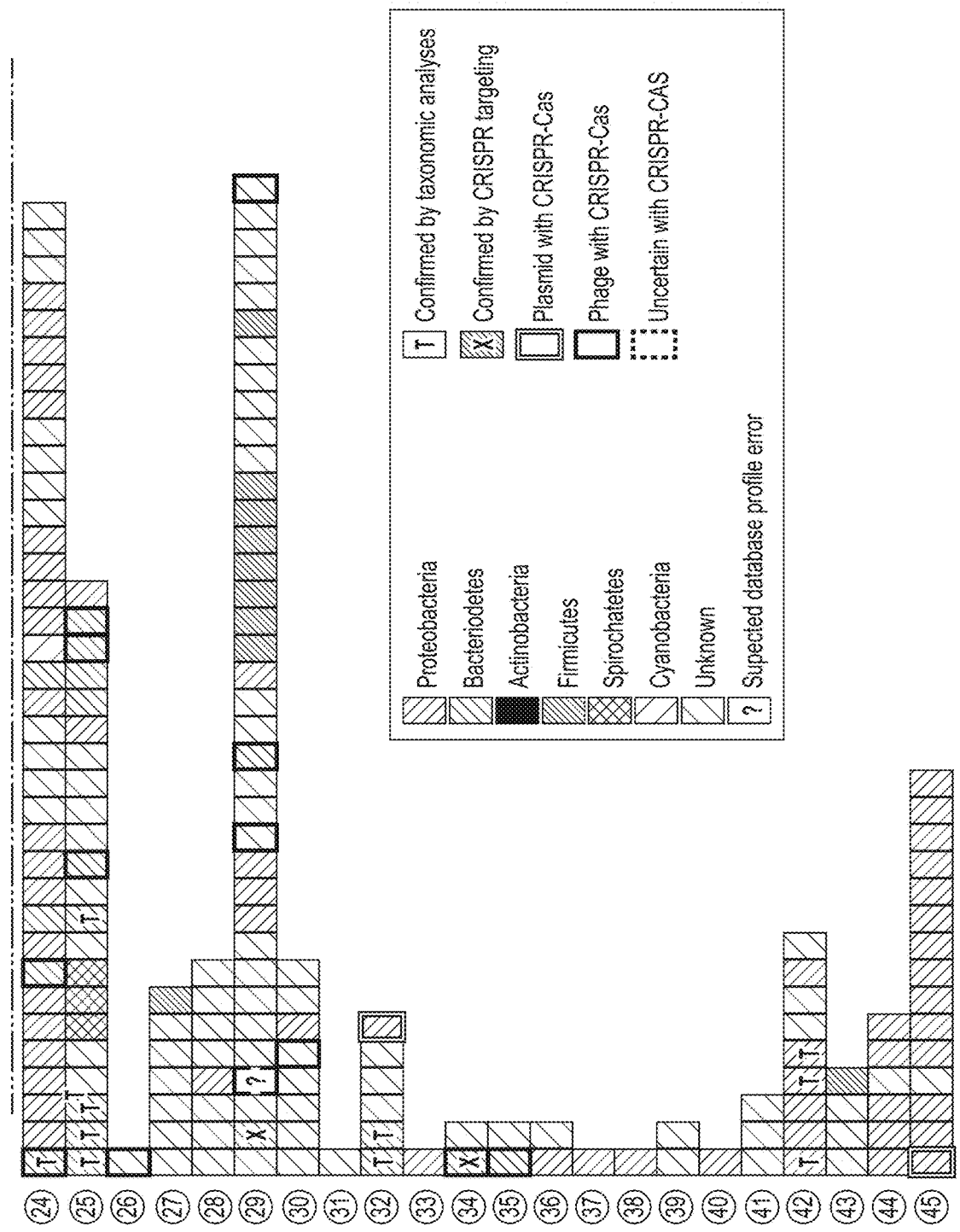
FIG. 5 shows ecosystems with phage and some plasmids with >200 kbp genomes, grouped by sampling site type. Each box represents a phage genome, and boxes are arranged in order of decreasing genome size; size range for each site type is listed to the right. Putative host phylum is indicated based on genome phylogenetic profile, with confirmation by CRISPR targeting (X) or information system gene phylogenetic analyses (T).

Metagenomic datasets were acquired from human fecal and oral samples, fecal samples from other animals, freshwater lakes and rivers, marine ecosystems, sediments, hot springs, soils, deep subsurface habitats and the built environment (FIG. 5). For a subset of these, analyses of bacterial, archaeal and eukaryotic organisms were published previously. Genome sequences that were clearly not bacterial, archaeal, archaeal virus, eukaryotic or eukaryotic virus were classified as either phage or plasmid-like based on their gene inventories. De novo assembled fragments of close to or >200 kbp in length were tested for circularization and a subset selected for manual verification and curation to completion (see Methods).

Figure 1B:
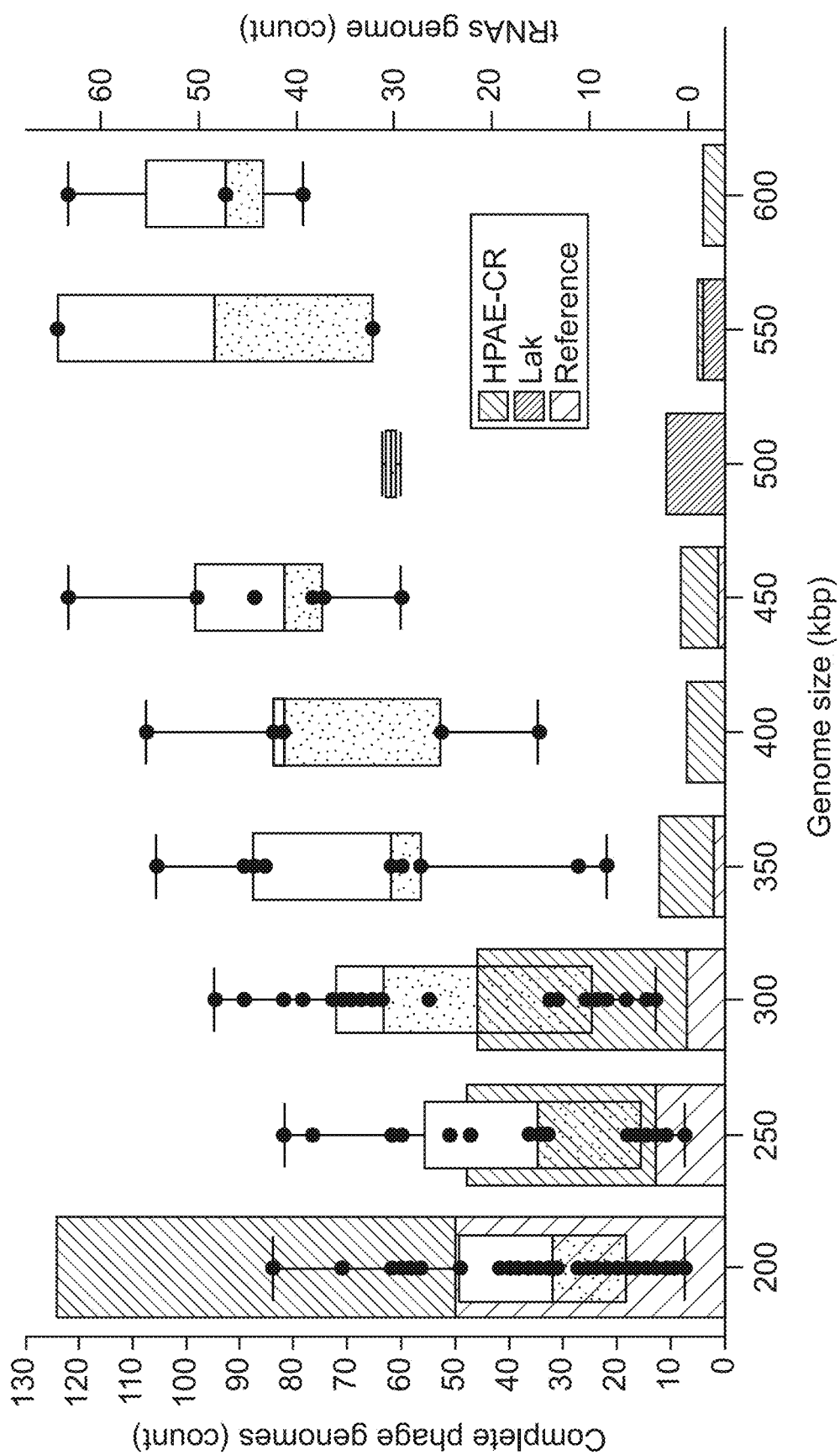
FIG. 1B shows a histogram of the genome size distribution of phage with genomes >200 kb from this study, Lak, and reference genomes. Box and whisker plots of tRNA counts per genome as a function of genome size.

Genome Sizes and Basic Features 358 phage, 3 plasmid and 4 phage-plasmid sequences were reconstructed (FIG. 5). Additional sequences inferred to be plasmids were excluded (see Methods), and only those encoding CRISPR-Cas loci were retained (see below). Consistent with classification as phage, a wide variety of phage-relevant genes were identified, including those involved in lysis and encoding structural proteins, and other expected phage genomic features were documented. Some phage predicted proteins are large, up to 7694 amino acids in length. Many of these were tentatively annotated as structural proteins. 180 phage sequences were circularized and 34 were manually curated to completion, in some cases by resolving complex repeat regions and their encoded proteins (see Methods). Some genomes show a clear GC skew signal for bi-directional replication, information that constrains their replication origin. The three largest complete, manually curated and circularized phage genomes are 634, 636 and 643 kbp in length and represent the largest phage genomes reported to date. Previously, the largest circularized phage genome was 596 kbp in length (Paez-Espino et al. (2016) supra). The same study reported a circularized genome of 630 kbp in length, but this is an artifact. The problem of concatenated sequences was sufficiently prominent in IMG-VR that these data were not included in further analyses. The complete and circularized genomes from the study, Refseq and published research were used to depict a current view of the distribution of phage genome sizes (Methods). The median genome size for complete phage is ~52 kbp (FIG. 1A), similar to the average size of ~54 kbp reported previously (Paez-Espino et al. (2016) supra). Thus, sequences reported here substantially expand the inventory of phage with unusually large genomes (FIG. 1B).

Intriguingly, two related sequences of 712 and >716 kbp in length were identified and manually curated (FIG. 5). These were classified as phage based on their overall genome content and the presence of terminase genes. The assemblies are confounded by few kb-long complex regions comprised of small repeats at both genome ends. It is anticipated that these genomes could be closed if the repeat regions could be rationalized Some genomes have very low coding density (nine <75%) due to use of a genetic code different from that used for gene prediction. A similar phenomenon was reported for Lak phage (Devoto et al. (2019) *Nat Microbiol*, and Ivanova et al. (2014) *Science* 344: 909-913). Distinct from prior studies, the genomes appear to use genetic code 16, in which TAG, normally a stop codon, codes for an amino acid.

In only one case, a sequence of >200 kbp that was classified as a prophage based on transition into flanking bacterial genome sequence was identified. However, around half the genomes were not circularized, so their derivation from prophage cannot be ruled out. The presence of integrases in some genomes is suggestive of a lysogenic lifestyle under some conditions.

Hosts, Diversity and Distribution

Figure 2:
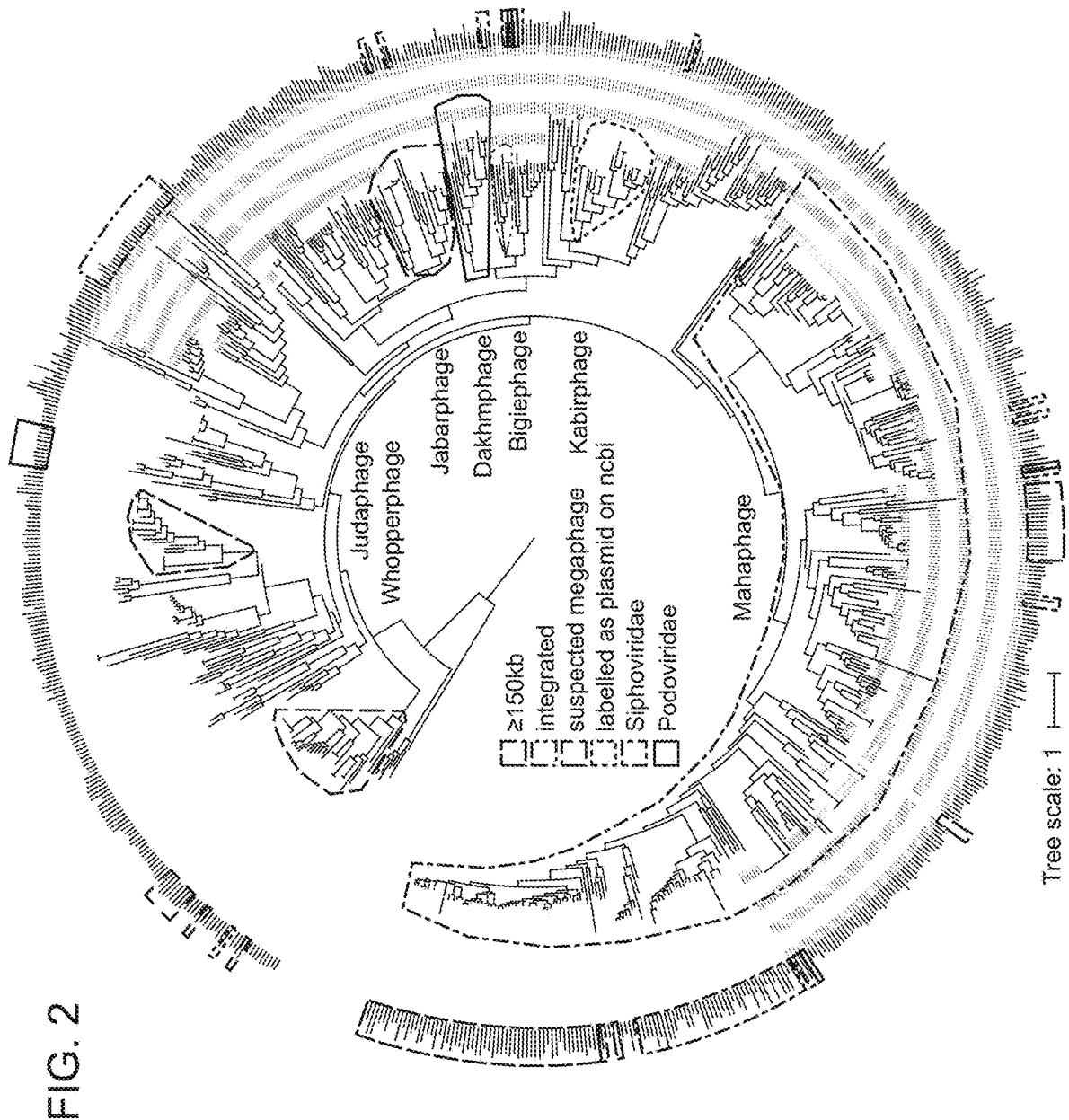
FIG. 2 shows a phylogenetic tree constructed using terminase sequences from huge phage genomes of this study and related database sequences.

An intriguing question relates to the evolutionary history of phage with huge genomes. Are they the result of recent genome expansion within clades of normal sized phage or is a large inventory of genes an established, persistent strategy? To investigate this, phylogenetic trees for the large terminase subunit (FIG. 2) and major capsid proteins using as context sequences in public databases for phage of all sizes were constructed (Methods). Many of the sequences from the large phage genomes cluster together, defining clades. Analysis of the genome size information for database sequences shows that the public sequences that fall into these clades are from phage with genomes of at least 120 kbp in length. The largest clade, referred to here as Mahaphage (Maha being Sanskrit for huge), includes all of the present study's largest genomes as well as the Lak genomes from human and animal microbiomes (Devoto et al. (2019) supra). Six other clearly defined clusters of large phage were identified, and they were named using the word for "huge" in a variety of languages. The existence of these clades establishes that large genome size is a relatively stable trait. Within the seven clades, phage were sampled from a wide variety of environment types, indicating diversification of these large phage and their hosts across ecosystems. The environmental distribution of phage that are closely enough related that their genomes largely can be aligned was also examined. In 17 cases, these phage occur in at least two biotope types.

To determine the extent to which bacterial host phylogeny correlates with phage clades, phage hosts were identified using CRISPR spacer targeting from bacteria in the same or related samples and phylogeny of normally host-associated genes that occur on phage (see below). The predictive value of bacterial affiliations of the phage gene inventories was also tested (Methods) and it was found that in every case, CRISPR spacer targeting and phylum-level phylogenetic profiling agreed with gene inventory characterizations. Consequently, this method was used to predict the phylum-level affiliations of hosts for many phage. The results establish the importance of firmicute and proteobacterial hosts, and indicate the higher prevalence of firmicute phage in the human and animal gut compared to other environments (FIG. 5). Notably, the four largest genomes (634-716 kbp in length) are all for phage predicted to replicate in Bacteroidetes, as do Lak phage with 540-552 kbp genomes (Devoto et al. (2019) supra), and all cluster within Mahaphage. Overall, phage grouped together phylogenetically are predicted to replicate in bacteria of the same phylum.

Metabolism, Transcription, Translation

The phage genomes encode proteins predicted to localize to the bacterial membrane or cell surface. These may impact the susceptibility of the host to infection by other phage. Almost all previously reported categories of genes suggested to augment host metabolism during infection were identified. Many phage have genes involved in steps of de novo biosynthesis of purines and pyrimidines and multiple steps that interconvert nucleic and ribonucleic acids and nucleotide phosphorylation states. These gene sets are intriguingly similar to those of bacteria with very small cells and putative symbiotic lifestyles (Castelle and Banfield (2018) *Cell* 172: 1181-1197).

Figure 3:
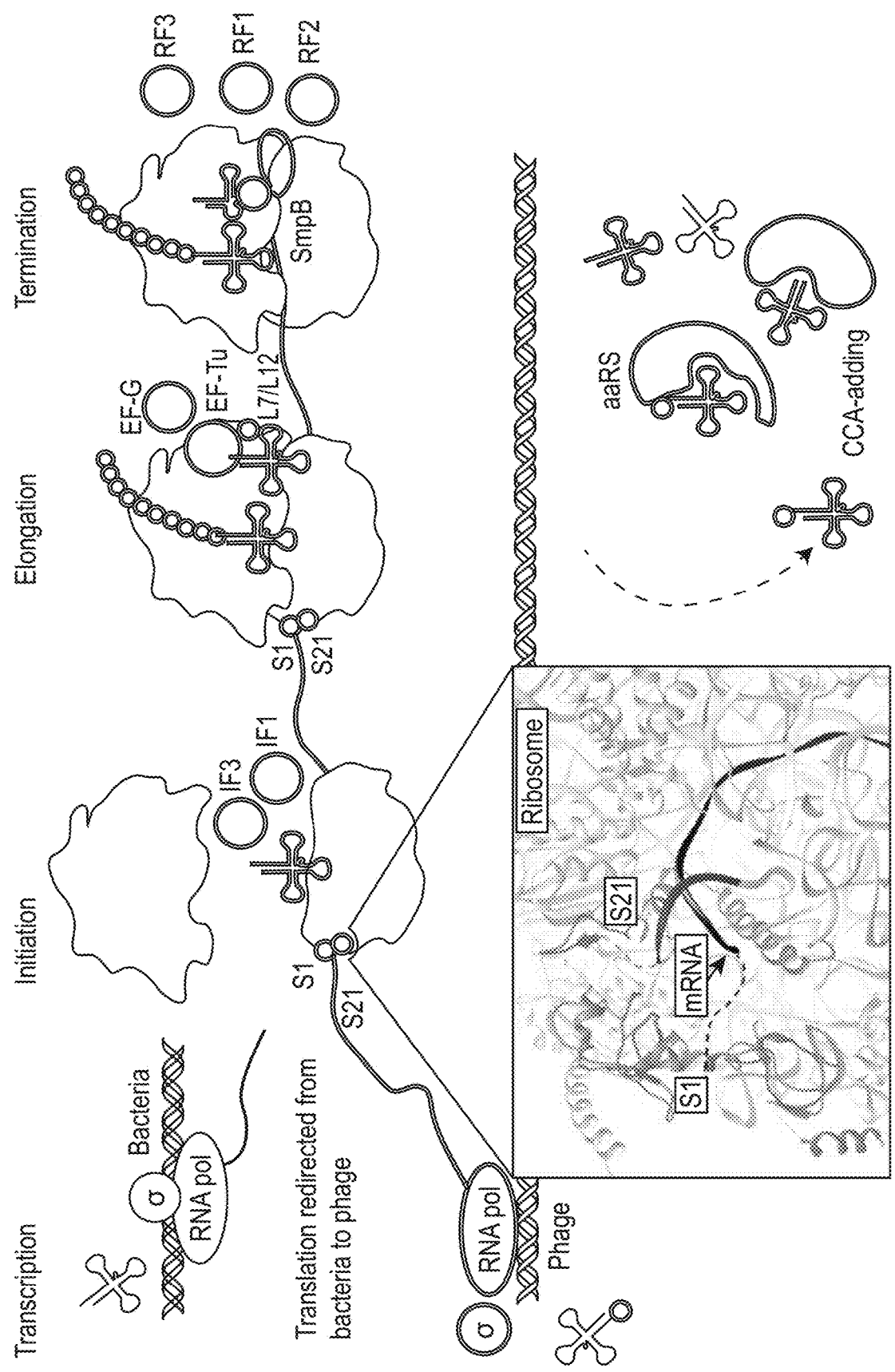
FIG. 3 shows a model for how phage-encoded capacities could function to redirect the host's translational system to produce phage proteins. No huge phage has all of these genes, but many have tRNAs (clover leaf shapes) and tRNA synthetases (aaRS). Phage proteins with up to 6 ribosomal protein S1 domains occur in a few genomes. The S1 binds mRNA to bring it into the site on the ribosome where it is decoded. Ribosomal protein S21 (S21) might selectively initiate translation of phage mRNAs, and many sequences have N-terminal extensions that may be involved in binding RNA (dashed line in ribosome insert, which is based on PDB code 6bu8 and pmid: 29247757 for ribosome and S1 structural model). Some phage have initiation factors (IF) and elongation factor G (EF G) and some have rpL7/L12, which could mediate efficient ribosome binding. Abbreviation: RNA pol, RNA polymerase.
Figure 4A:
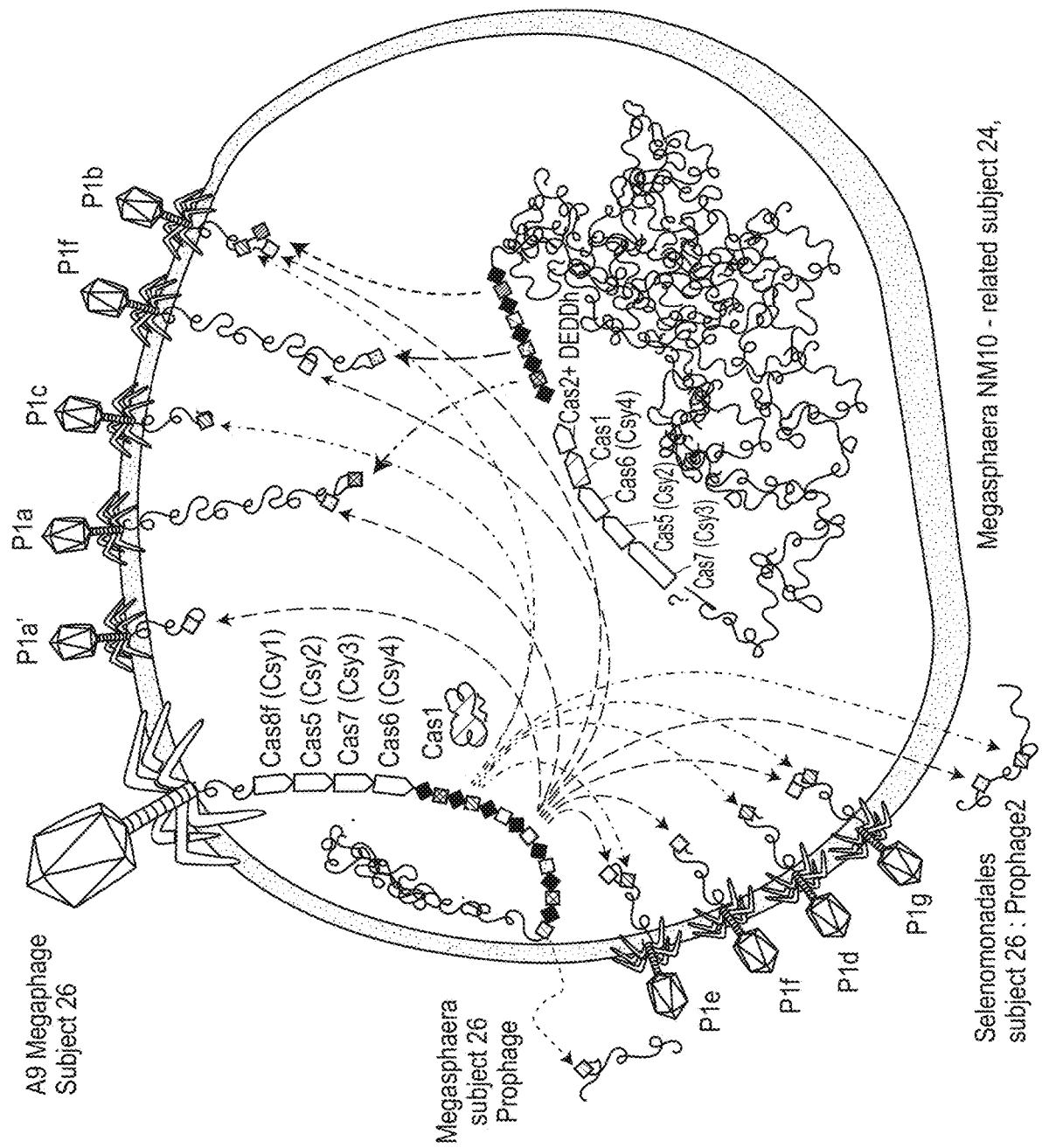
FIG. 4A shows a bacterium-phage interaction involving CRISPR targeting (cell diagram).
Figure 4B:
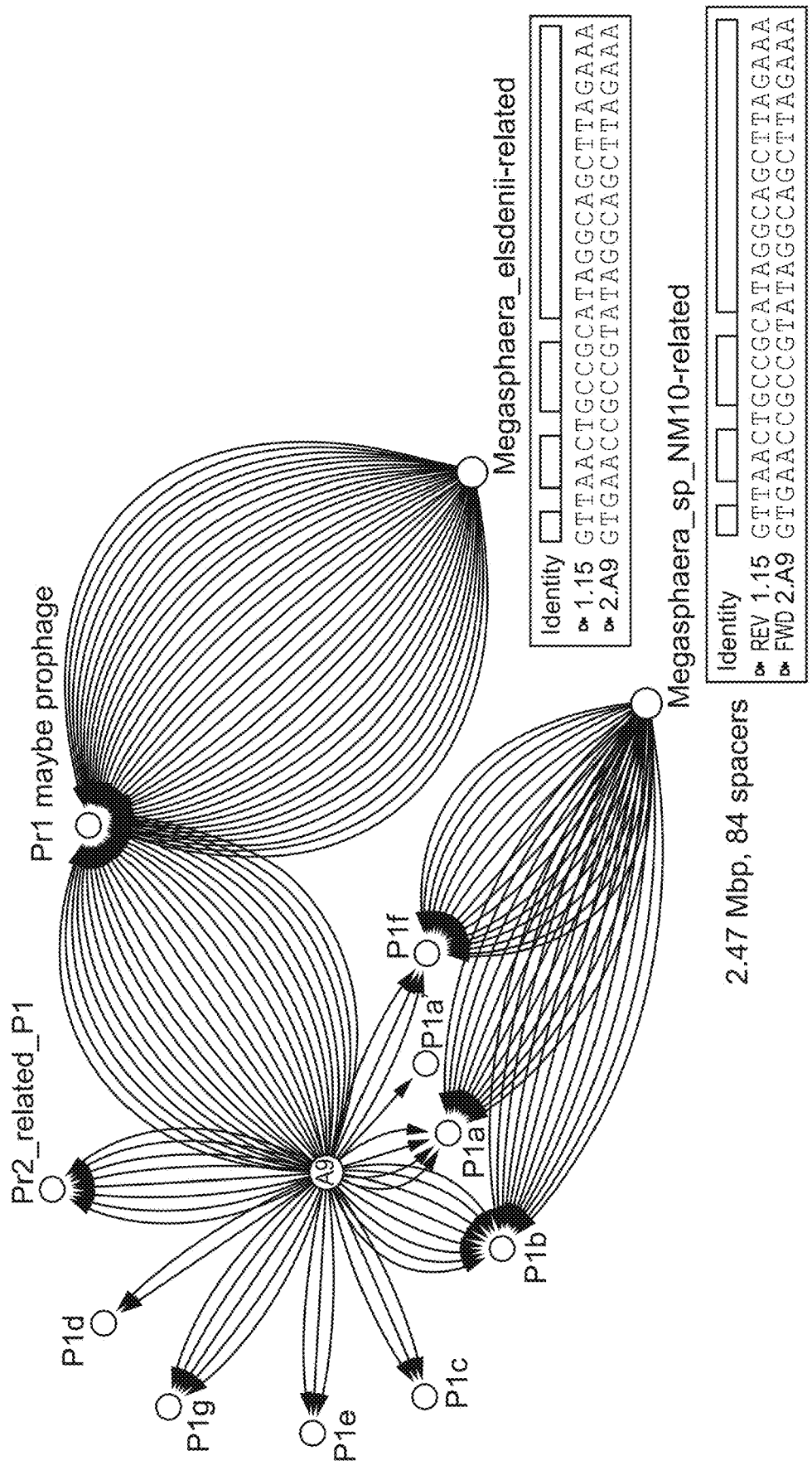
FIG. 4B shows the interaction network showing targeting of bacterial (from top to bottom: SEQ ID NOs: 163-164) and phage-encoded (from top to bottom: SEQ ID NOs: 163-164) CRISPR spacers.

Notably, many phage have genes whose predicted functions are in transcription and translation. Phage encode up to 64 tRNAs per genome, with sequences distinct from those of their hosts. Generally, the number of tRNAs per genome increases with genome length (FIG. 1). They often have up to 16 tRNA synthetases per genome, that are related to, but distinct from, those of their hosts. Phage may use these proteins to charge their own tRNA variants with host-derived amino acids. A subset of genomes have genes for tRNA modification and to repair tRNAs cleaved as part of host defense against phage infection. Also identified are up to three probable ribosomal proteins per genome, the most common of which is rpS21 (a phenomenon only recently reported in phage) (Mizuno et al. (2019) *Nat. Commun.* 10: 752); FIG. 3). Intriguingly, it is noted that the phage rpS21 sequences have N-terminal extensions rich in arginine, lysine, and phenylalanine: residues that bind nucleic acids. It is predicted that these phage ribosomal proteins substitute for host proteins in the ribosome (Mizuno et al. (2019) supra), and that the extensions protrude from the ribosome surface near the site of translation initiation to localize the phage mRNAs.

Some phage have genes predicted to function in other protein synthesis steps, including to ensure efficient translation. Several encode either initiation factor 1 or 3 or both, sometimes as well as elongation factors G, Tu, Ts and release factors. Also identified are genes that encode ribosome recycling factors, along with tmRNAs and small protein B (SmpB) that rescue ribosomes stalled on damaged transcripts and trigger the degradation of aberrant proteins. tmRNAs are also used by phages to sense the physiological state of host cells and can induce lysis when the number of stalled ribosomes in the host is high.

These observations suggest many ways in which some large phage can substantially intercept and redirect ribosome function. As phage mRNA sequences need to engage with the 3' end of the host 16S rRNA to initiate translation, their mRNA ribosomal binding sites were predicted. In the majority of cases, phage mRNAs have canonical Shine Dalgarno (SD) sequences, and an additional ~15% have non-standard SD binding sites. Interestingly, however, phage whose genomes encode a probable or possible rpS1 rarely have identifiable or canonical SD sequences. Thus, phage-encoded rpS1 may selectively initiate translation of phage mRNAs. Overall, phage genes appear to redirect the host's protein production capacity to favor phage genes by intercepting the earliest steps of translation. These inferences are aligned with findings for some eukaryotic viruses, which control every phase of protein synthesis (Jaafar and Kieft (2019) *Nat. Rev. Microbiol.* 17:110-123). Interestingly, some large putative plasmids also have analogous suites of translation relevant genes.

About half of the phage genomes have one to fifty sequences >25 nt in length that fold into perfect hairpins. The palindromes (sequences with dyad symmetry) are almost exclusively intergenic and each is unique within a genome. Some, but not all, are predicted to be rho-independent terminators, thus provide clues regarding genes that function as independently regulated units (Methods). However, some palindromes are up to 74 bp in length, and 34 genomes have examples of ≥40 nt in length, seemingly larger than normal terminators. These occur almost exclusively in Mahaphage and may have alternative or additional functions, such as modulation of the movement of the mRNA through the ribosome.

CRISPR-Cas Mediated Interactions

Almost all major types of CRISPR-Cas systems on phage, including Cas9, the recently described Type V-I (Yan et al. (2019) *Science* 363: 88-91), and new subtypes of Type V-F systems were identified (Harrington et al. (2018) *Science* 362: 839-842.). The Class II systems (types II and V) are reported in phage for the first time. Most effector nucleases (for interference) have conserved catalytic residues, implying that they may be functional.

Unlike the previously well described case of a phage with a CRISPR system (Seed et al. (2013) *Nature* 494: 489-491), almost all phage CRISPR systems lack spacer acquisition machinery (Cas1, Cas2, and Cas4) and many lack recognizable genes for interference. For example, two related phage have both a Type I-C variant system lacking Cas1 and Cas2 and a helicase protein in lieu of Cas3. They also harbor a second system containing a new candidate ~750 aa Type V effector protein that occurs proximal to CRISPR arrays. In some cases, phage lacking genes for interference and spacer integration have similar CRISPR repeats as their hosts, thus may use Cas proteins synthesized by their host for these functions. Alternatively the systems lacking an effector nuclease may repress transcription of the target sequences without cleavage (Luo et al. (2015) *Nucleic Acids Res.* 43:674-681; Stachler and Marchfelder (2016) *J. Biol. Chem.* 291:15226-15242).

The phage-encoded CRISPR arrays are often compact (3-55 repeats; median 6 per array. This range is substantially smaller than typically found in bacterial genomes (Toms and Barrangou (2017) *Biol. Direct* 12:20). Some phage spacers target core structural and regulatory genes of other phage. Thus, phage apparently augment their hosts' immune arsenal to prevent infection by competing phage.

Several large plasmid or plasmid-like genomes that encode a variety of types of CRISPR-Cas systems were identified. Some of these systems also lack Cas1 and Cas2. Most commonly, the spacers target the mobilization and conjugation-related genes of other plasmids, as well as nucleases and structural proteins of phage.

Some phage-encoded CRISPR loci have spacers that target bacteria in the same sample or in a sample from the same study. It is supposed that the targeted bacteria are the hosts for these phage, an inference supported by other host prediction analyses. Some loci with bacterial chromosome-targeting spacers encode Cas proteins that could cleave the host chromosome, and some do not. Targeting of host genes could disable or alter their regulation, which may be advantageous during the phage infection cycle. Some phage CRISPR spacers target bacterial intergenic regions, possibly interfering with genome regulation by blocking promoters or silencing non-coding RNAs.

Among the most interesting examples of CRISPR targeting of bacterial chromosomes are genes involved in transcription and translation. For instance, one phage targets a $\sigma^{70}$ transcription factor in its host's genome, while encoding the gene for $\sigma^{70}$. There are previous reports of $\sigma^{70}$ hijacking by phage with anti-sigma factors. This may also occur with some huge phage whose genomes encode anti-sigma factors. In another example, a phage spacer targets the host Glycyl tRNA synthetase.

Interestingly, no evidence was found of targeting of any CRISPR-bearing phage by a host-encoded spacer, hinting at yet to be revealed components in phage-host-CRISPR interactions. However, phage CRISPR targeting of other phage that are also targeted by bacterial CRISPR (FOG/4) suggested phage-host associations that were broadly confirmed by the phage phylogenetic profile.

Some large *Pseudomonas* phage encode Anti-CRISPRs (Acr) (Bondy-Denomy et al. (2015) *Nature* 526:136-139; Pawluk et al. (2016) *Nat Microbiol* 1: 16085) and proteins that assemble a nucleus-like compartment segregating their replicating genomes from host defense and other bacterial systems. Proteins encoded in huge phage genomes that cluster with AcrVA5, AcrVA2, and AcrIIA7 that may function as Acrs were identified. Also identified were tubulin-homologs (PhuZ) that position the "phage nucleus", and proteins related to components of the proteinaceous barrier. Thus, phage 'nuclei' may be a relatively common feature in large phage.

METHODS

Phage and Plasmid Genome Identification

Datasets generated in the current study, those from prior research, the Tara Oceans microbiomes (Karsenti et al. (2011) *PLoS Biol.* 9:e1001177), and the Global Oceans Virome (GOV; (Roux et al. (2016) *Nature* 537:689-693) were searched for sequence assemblies that could have derived from phage with genomes of >200 kbp in length. Read assembly, gene prediction, and initial gene annotation followed standard methods reported previously (Wrighton et al. (2014) *ISME J.* 8:1452-1463).

Phage candidates were initially found by retrieving sequences that were not assigned to a genome and had no clear taxonomic profile at the domain level. Taxonomic profiles were determined through a voting scheme, where there had to be a winner taxonomy >50% votes at each taxonomic rank based on Uniprot and ggKbase (ggkbase.berkeley.edu) database annotations. Phages were further narrowed down by identifying sequences with a high number of hypothetical protein annotations and/or the presence of phage structural genes, e.g. capsid, tail, holin. All candidate phage sequences were checked throughout to distinguish putative prophage from phage. Prophage were identified based on a clear transition into genome with a high fraction of confident functional predictions, often associated with core metabolic functions, and much higher similarity to bacterial genomes. Plasmids were distinguished from phage based on matches to plasmid marker genes (e.g. parA). Three sequence assemblies could not unambiguously be distinguished between phage and plasmid, and were assigned as "phage-plasmid".

Phage and Plasmid Genome Manual Curation

All scaffolds classified as phage or phage-like were tested for end overlaps using a custom script and checked manually for overlap. Assembled sequences that could be perfectly circularized were considered potentially "complete". Erroneous concatenated sequence assemblies were initially flagged by searching for direct repeats >5 kb using Vmatch (Kurtz (2003) *Ref Type: Computer Program* 412:297). Potentially concatenated sequence assemblies were manually checked for multiple large repeating sequences using the dotplot and RepeatFinder features in Geneious v9. Sequences were corrected and removed from further analysis if the corrected length was <200 kbp.

A subset of the phage sequences was selected for manual curation, with the goal of finishing (replacing all N's at scaffolding gaps or local misassemblies by the correct nucleotide sequences and circularization). Curation generally followed methods described previously (Devoto et al. (2019) supra). In brief, reads from the appropriate dataset were mapped using Bowtie2 (Langmead and Salzberg (2012) *Nat. Methods* 9:357-359) to the de novo assembled sequences. Unplaced mate pairs of mapped reads were retained with shrinksam (github.com/bcthomas/shrinksam). Mappings were manually checked throughout to identify local misassemblies using Geneious v9. N-filled gaps or misassembly corrections made use of unplaced paired reads, in some cases using reads relocated from sites where they were mis-mapped. In such cases, mis-mappings were identified based on much larger than expected paired read distances, high polymorphism densities, backwards mapping of one read pair, or any combination of the aforementioned.

Similarly, ends were extended using unplaced or incorrectly placed paired reads until circularization could be established. In some cases, extended ends were used to recruit new scaffolds that were then added to the assembly. The accuracy of all extensions and local assembly changes were verified in a subsequent phase of read mapping. In many cases, assemblies were terminated or internally corrupted by the presence of repeated sequences. In these cases, blocks of repeated sequence as well as unique flanking sequence were identified. Reads were then manually relocated, respecting paired read placement rules and unique flanking sequences. After gap closure, circularization, and verification of accuracy throughout, end overlap was eliminated, genes were predicted and throughout, and the start moved to an intergenic region, in some cases suspected to be origin based on a combination of coverage trends and GC skew (Brown et al. (2016) *Nat. Biotechnol.* 34:1256-1263). Finally, the sequences were checked to identify any repeated sequences that could have led to an incorrect path choice because the repeated regions were larger than the distance spanned by paired reads. This step also ruled out artifactual long phage sequences generated by end to end repeats of smaller phage, which occur in previously described datasets.

Structural and Functional Annotation

Following identification and curation of phage genomes, coding sequences (CDS) were predicted with prodigal (-m -c -g 11 -p single) with genetic code 11. The resulting CDS were annotated as previously described by searching against UniProt, UniRef, and KEGG (Wrighton et al. (2014) supra). Functional annotations were further assigned by searching proteins against Pfam r32 (Finn et al. (2014) *Nucleic Acids Res.* 42:D222-30), TIGRFAMS r15 (Haft et al. (2013) *Nucleic Acids Res.* 41:D387-95), and Virus Orthologous Groups r90 (vogdb.org). tRNAs were identified with tRNA-scan-SE 2.0 (Lowe and Eddy, (1997) *Nucleic Acids Res.* 25: 955-964) using the bacterial model. tmRNAs were assigned using ARAGORN v1.2.38 (Laslett and Canback, (2004) *Nucleic Acids Res.* 32: 11-16) with the bacterial/plant genetic code. Clustering of the protein sequences into families was achieved using a two-step procedure. A first protein clustering was done using the fast and sensitive protein sequence searching software MMseqs (Hauser et al. (2016) *Bioinformatics* 32: 1323-1330). An all-vs-all sequences search was performed using e-value: 0.001, sensitivity: 7.5 and coverage: 0.5. A sequence similarity network was built based on the pairwise similarities and the greedy set cover algorithm from MMseqs was performed to define protein subclusters. The resulting subclusters were defined as subfamilies. In order to test for distant homology, subfamilies were grouped into protein families using an HMM-HMM comparison. The proteins of each subfamily with at least two protein members were aligned using the result2msa parameter of mmseqs2, and from the multiple sequence alignments HMM profiles were built using the HHpred suite. The subfamilies were then compared to each other using HHblits (Remmert et al. (2011) *Nat. Methods* 9: 173-175 from the HHpred suite (with parameters -v 0 -p 50 -z 4 -Z 32000 -B 0 -b 0). For subfamilies with probability scores of ≥95% and coverage ≥0.50, a similarity score (probability×coverage) was used as weights of the input network in the final clustering using the Markov Clustering algorithm, with 2.0 as the inflation parameter. These clusters were defined as the protein families Hairpins (palindromes, based on identical overlapping repeats in the forward and reverse directions) were identified using the Geneious Repeat Finder and located dataset-wide using Vmatch (Kurtz (2003) supra). Repeats >25 bp with 100% similarity were tabulated.

Reference Genomes for Size Comparisons

RefSeq v92 genomes were recovered by using the NCBI Virus portal and selecting only complete dsDNA genomes with bacterial hosts. Genomes from (Paez-Espino et al. (2016) supra) were downloaded from IMG/VR and only sequence assemblies labeled "circular" with predicted bacterial hosts were retained. Many of the genomes were the result of erroneous concatenated repeating assemblies. Given the presence of sequences in IMG/VR that are based on erroneous concatenations, the study only considered sequences from this source that are >200 kb; a subset of these were removed as artifactual sequences.

Host Prediction

The phylum affiliations of bacterial hosts for phage were predicted by considering the Uniprot taxonomic profiles of every CDS for each phage genome. The phylum level matches for each phage genome were summed and the phylum with the most hits was considered as the potential host phylum. However, only cases where this phylum that had 3× as many counts as the next most counted phylum were assigned as the tentative phage host phylum. Phage hosts were further assigned and verified using CRISPR targeting. CRISPR arrays were predicted on sequence assemblies >1 kbp from the same environment that each phage genome was reconstructed. Spacers were extracted and searched against the genomes from the same site using BLASTN-short (Altschul et al. (1990) *J. Mol. Biol.* 215: 403-410). Sequence assemblies containing spacers with a match of length >24 bp and ≤1 mismatch or at least 90% sequence identity to a genome were considered targets. In the case of phage, the match was used to infer a phage-host relationship. In all cases, the predicted host phylum based on taxonomic profiling and CRISPR targeting were in complete agreement. Similarly, the phyla of hosts were predicted based on phylogenetic analysis of phage genes also found in host genomes (e.g., involved in translation and nucleotide reactions). Inferences based on computed taxonomic profiles and phylogenetic trees were also in complete agreement.

Alternative Genetic Codes

In cases where gene prediction using the standard bacterial code (code 11) resulted in seemingly anomalously low coding densities, potential alternative genetic codes were investigated. In addition to making a prediction using Fast and Accurate genetic Code Inference and Logo (FACIL; (Dutilh et al. (2011) *Bioinformatics* 27:1929-1933)), genes with well defined functions (e.g., polymerase, nuclease) were identified and the stop codons terminating genes that were shorter than expected were determined. Genes were then re-predicted using Glimmer and Prodigal set such that codon was not interpreted as a stop. Other combinations of repurposed stop codons were evaluated, and candidate codes (e.g., code 6, with only one stop codon) were ruled out due to unlikely gene fusion predictions.

Introns were identified in some longer than expected pseudo-tRNAs by re-predicting the tRNAs using eukaryotic settings (as tRNA scan does not expect introns in tRNA genes in bacteria and phage).

Terminase Phylogenetic Analysis

The large terminase phylogenetic tree was constructed by recovering large terminases from the aforementioned annotation pipeline. CDS that matched with >30 bitscore against PFAM, TIGRFAMS, and VOG were retained. Any CDS that had a hit to large terminase, regardless of bitscore, was searched using HHblits (Steinegger et al. Bioinformatics 21: 951-960) against the uniclust30_2018_08 database. The resulting alignment was then further searched against the PDB70 database. Remaining CDS that clustered in protein families with a large terminase HMM were also included after manual verification. Detected large terminases were manually verified using HHPred (Steinegger et al. supra) and jPred (Cole et al. (2008) Nucleic Acids Res. 36:W197-201). Large terminases from the >200 kb (Paez-Espino et al. (2016) supra) phage genomes and all >200 kb complete dsDNA phage genomes from RefSeq r92 were also included by protein family clustering with the phage CDS from this study. The resulting terminases were clustered at 95% amino acid identity (AAI) to reduce redundancy using cd-hit (Huang et al. (2010) *Bioinformatics* 26:680-682) Smaller phage genomes were included by searching the resulting CDS set against the Refseq protein database and retaining the top 10 best hits. Those hits that had no large terminase match against PFAM, TIGRFAMS, or VOG were removed from further consideration and the remaining set was clustered 90% AAI. The final set of large terminase CDS were aligned MAFFT v7.407 (-localpair -maxiterate 1000) and poorly aligned sequences were removed and the resulting set was realigned. The phylogenetic tree was inferred using IQTREE v1.6.9 (Nguyen et al. (2015) *Mol. Biol. Evol.* 32:268-274).

Phage Encoded tRNA Synthetase Trees

Phylogenetic trees were constructed for phage encoded tRNA synthetase, ribosomal and initiation factor protein sequences using a set of the closest set of reference from NCBI and bacterial genomes from the current study.

CRISPR-Cas Locus Detection and Host Identification

Phage-encoded CRISPR-Cas loci were identified using the same methods as used to identify bacterial CRISPR-Cas loci, spacers extracted from between repeats of the CRISPR locus using MinCED (github.com/ctSkennerton/minced) and CRISPRDetect (Biswas et al., 2016) were compared to sequences reconstructed from the same site and targets classified as bacterial, phage or other.

Because many phage hosts cannot be identified by CRISPR targeting (perhaps because phage had proliferated in samples containing sensitive hosts, or the targets are sufficiently mutated to avoid spacer detection) additional lines of evidence were used to propose host identities. Due to uncertainty in these methods, possible phage predictions were made only at the phylum level. In this analysis, the fraction of genes encoded on any genome with the best predicted protein match to each phylum was computed. Only in cases where the most highly represented phylum exceeded in frequency the next most common phylum by ≥3× was a tentative bacterial host proposed. This threshold was verified as conservative, based on confirmed host phylum information from CRISPR targeting or phylogenetic analysis.

Data Availability

Supplementary document "Genbank" includes the Genbank format files for the genome sequences reported in this study. All reads are being deposited in the short read archive (if not already lodged there) and genome sequences in NCBI.

Example 2

Cas12J represents the smallest known single-effector Cas protein with double-stranded DNA (dsDNA) targeting ability. Cas12J is capable of cleaving dsDNA without a requirement for an accessory RNA (e.g. such as a tracrRNA) to function. Additionally, the RuvC domain, which is the a highly conserved domain across Cas12 and Cas9, is highly divergent in Cas12J from known Cas proteins, and the domain architecture is different across members of the Cas12 protein superfamily.

Results

Figure 11A:
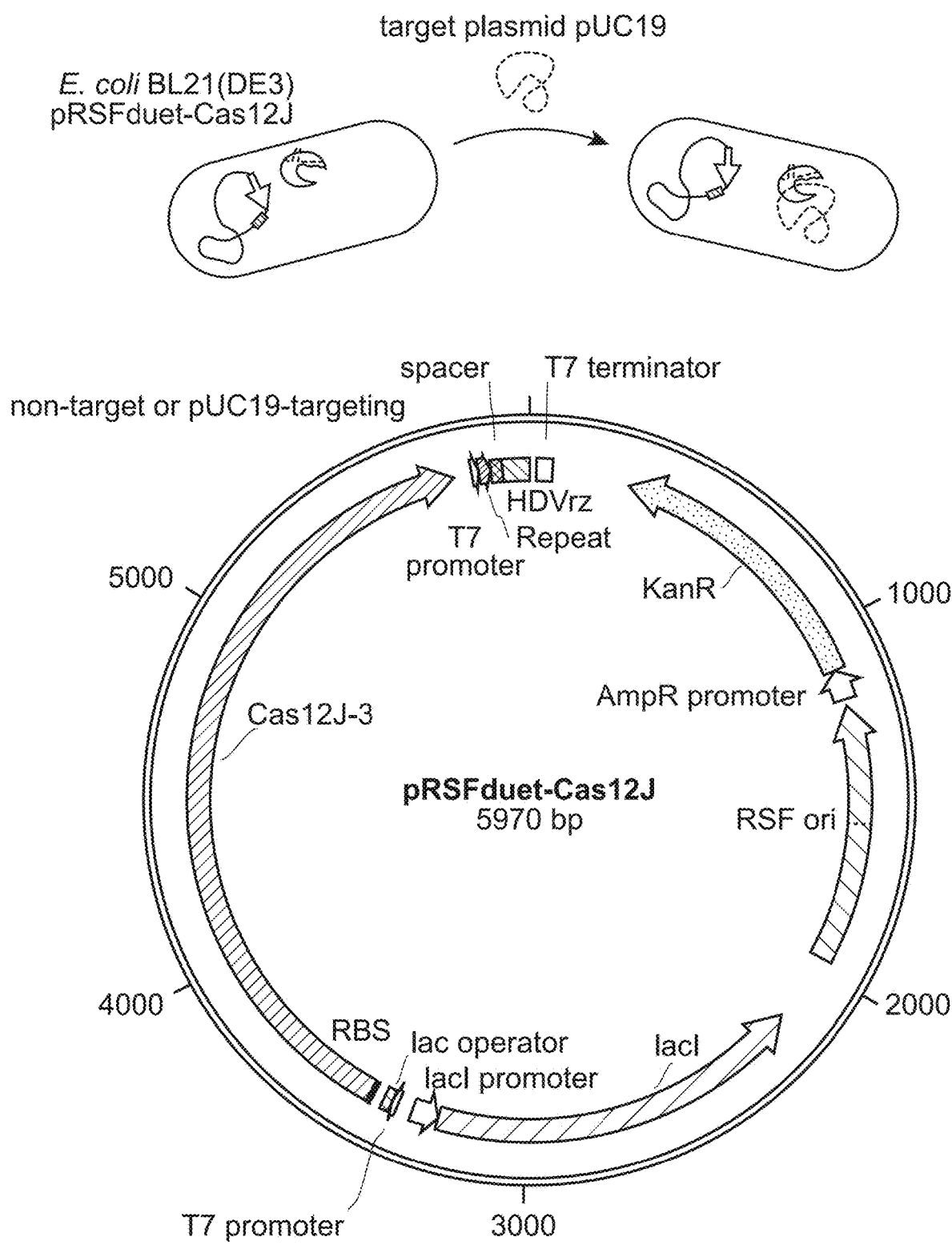
Figure 11B:
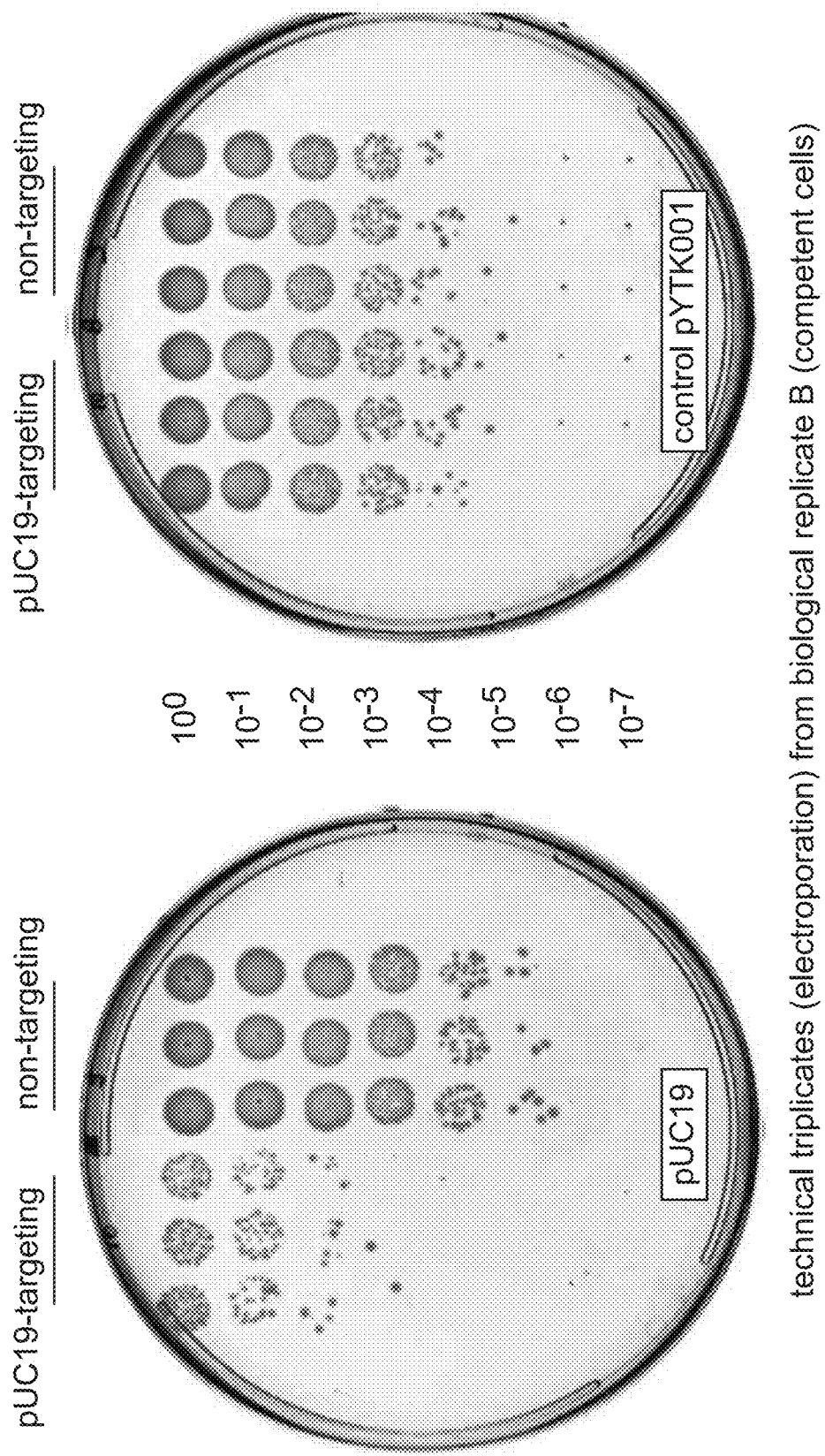

To investigate the functionality and DNA targeting capability of the Cas12J effector in a heterologous context, an efficiency of transformation (EOT) plasmid interference assay was set up (FIG. 11A). *Escherichia coli* BL21(DE3) expressing cas12J and a crRNA guide targeting the antisense strand of the bla gene, or a non-targeting guide, were transformed with pUC19 (FIG. 11B). The assay revealed that the pUC19 transformation efficiency is reduced by 2-3 orders of magnitude in strains producing Cas12J and the pUC19 targeting guide, compared to strains producing Cas12J and the non-targeting guide (FIG. 11C). This result is indicative of a robust and guide dependent double-stranded DNA interference activity of Cas12J. To assess the DNA interference unbiased relative transformation efficiency of each strain, the pYTK001 plasmid was transformed as a control (FIG. 11B). The transformation efficiency revealed that the strains are equally competent for transformation of a non-targeted plasmid (FIG. 11C).

Methods

Cloning of the expression plasmids

The gene sequence of cas12J from contig P0_An_GD2017L_S7_coassembly_k141_3339380 was ordered as a G-block from IDT and cloned into pRSFDuet-1 (Novagen) into MCSI using Golden Gate assembly. In the same reaction a T7 promotor, the respective consensus repeat sequence from the CRISPR-array located on contig P0_An_GD2017L_S7_coassembly_k141_3339380, together with a 35 bp spacer amenable to Golden Gate assembly mediated spacer exchange were introduced downstream of the cas12J ORF in place of MCSII. In the same reaction a hepatitis delta virus ribozyme (HDVrz) was introduced downstream of the spacer to facilitate homogeneous processing of the immature crRNA transcript at its 3'-terminus. To generate the pUC19 targeting Cas12J-vector, the non-targeting spacer was exchanged by Golden Gate assembly to a sequence matching base pairs 11-45 of the pUC19 bla gene downstream of the AGTATTC sequence, to allow for production of an antisense strand complementary crRNA guide.

Plasmid Interference Assay

The generated Cas12J vectors (non-targeting and pUC19-targeting) were transformed in chemically competent *E. coli* BL21(DE3) (NEB). Three individual colonies for each strain (A, B and C strains) were picked to inoculate three 5 mL (LB, Kanamycin 50 µg/mL) starter cultures to prepare electrocompetent cells the following day. 50 mL (LB, Kanamycin 50 µg/mL) main cultures were inoculated 1:100 and grown vigorously shaking at 37° C. to an $OD_{600}$ of 0.3. Subsequently, the cultures were cooled to room temperature and cas12J expression was induced with 0.2 mM IPTG. Cultures were grown to an $OD_{600}$ of 0.6-0.7 at 25° C. for 1 h, before preparation of electrocompetent cells by repeated ice-cold dd$H_2O$ and 10% glycerol washes. Cells were resuspended in 250 µL 10% glycerol. 90 µL aliquots were flash frozen in liquid nitrogen and stored at −80° C. The next day, 80 µL competent cells were combined with 3.2 µL plasmid (20 ng/µL pUC19 target plasmid, or 20 ng/µL pYTK001 control plasmid), incubated for 30 min on ice and split into three individual 25 µL transformation reactions. After electroporation in 0.1 mm electroporation cuvettes (Bio-Rad) on a Micropulser electroporator (Bio-Rad), cells were recovered in 1 mL recovery medium (Lucigen) supplemented with 0.2 mM IPTG, shaking at 37° C. for one hour. Subsequently, 10-fold dilution series were prepared and 5 µL of the respective dilution steps were spot-plated on LB-Agar containing the appropriate antibiotics. Plates were incubated over night at 37° C. and colonies were counted the following day to determine the transformation efficiency. To assess the transformation efficiency, the mean and standard deviations were calculated from the cell forming units per ng transformed plasmids for the electroporation triplicates.

FIG. 11A-11C shows the efficiency of transformation plasmid interference assay. FIG. 11A upper panel: experimental scheme. *E. coli* producing Cas12J are transformed with a targeted plasmid (pUC19). Lower panel: vector map of the effector expression plasmid. FIG. 11B, serial dilutions of *E. coli* producing Cas12J and either pUC19-targeting or non-targeting guides, transformed with pUC19 (left) or pYTK001 (right). FIG. 11C, calculated transformation efficiencies in cell forming units (cfu) per ng transformed plasmid. Mean and +/−s.d. (error bars) values were derived from triplicates.

Example 3

Results

Figure 12A:
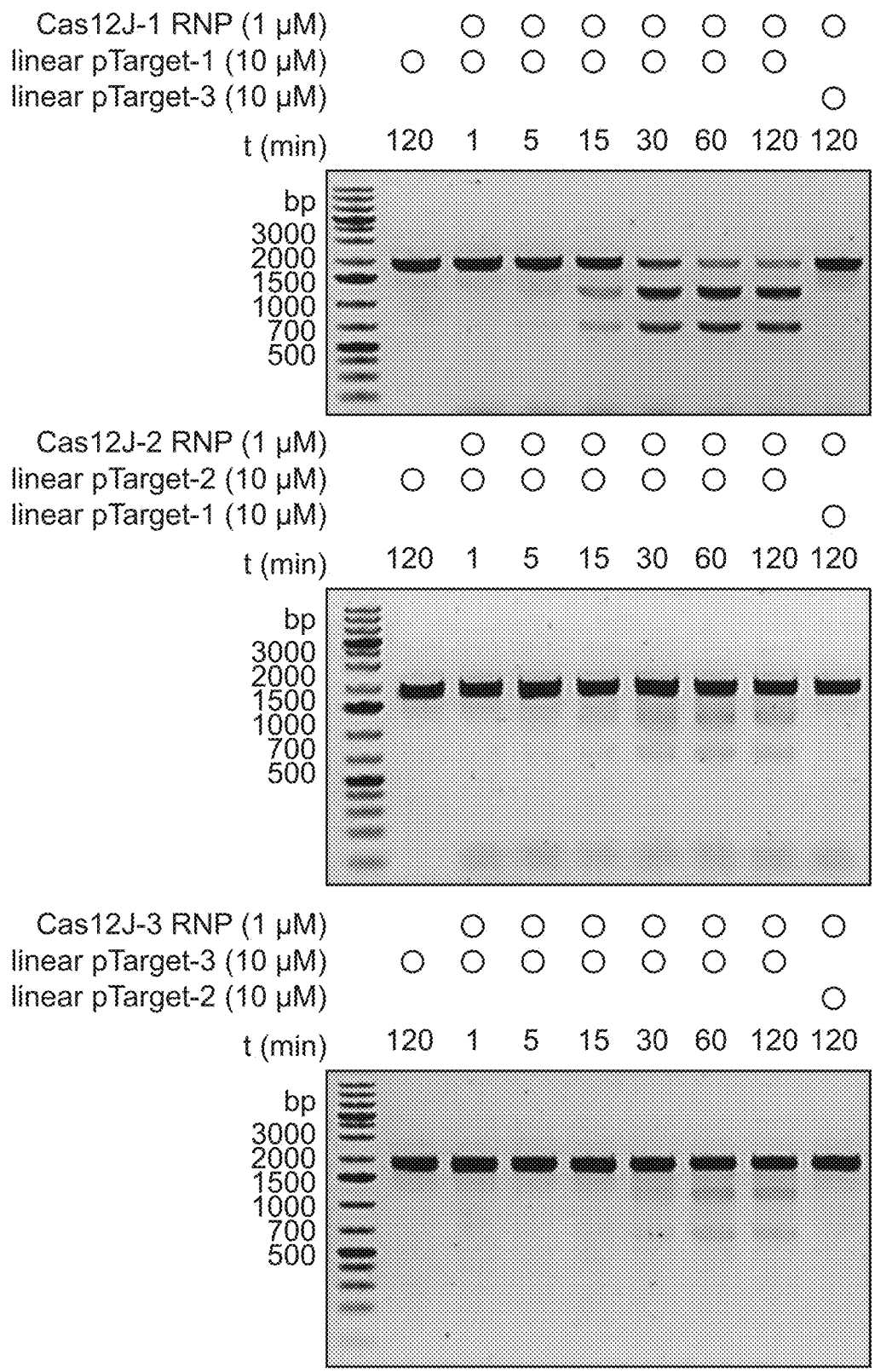
FIG. 12A-12B shows a demonstration that Cas12J (e.g., Cas12J-1947455, Cas12J-2071242 and Cas12J-3339380) can cleave linear dsDNA fragments guided by a crRNA spacer sequence.
Figure 12B:
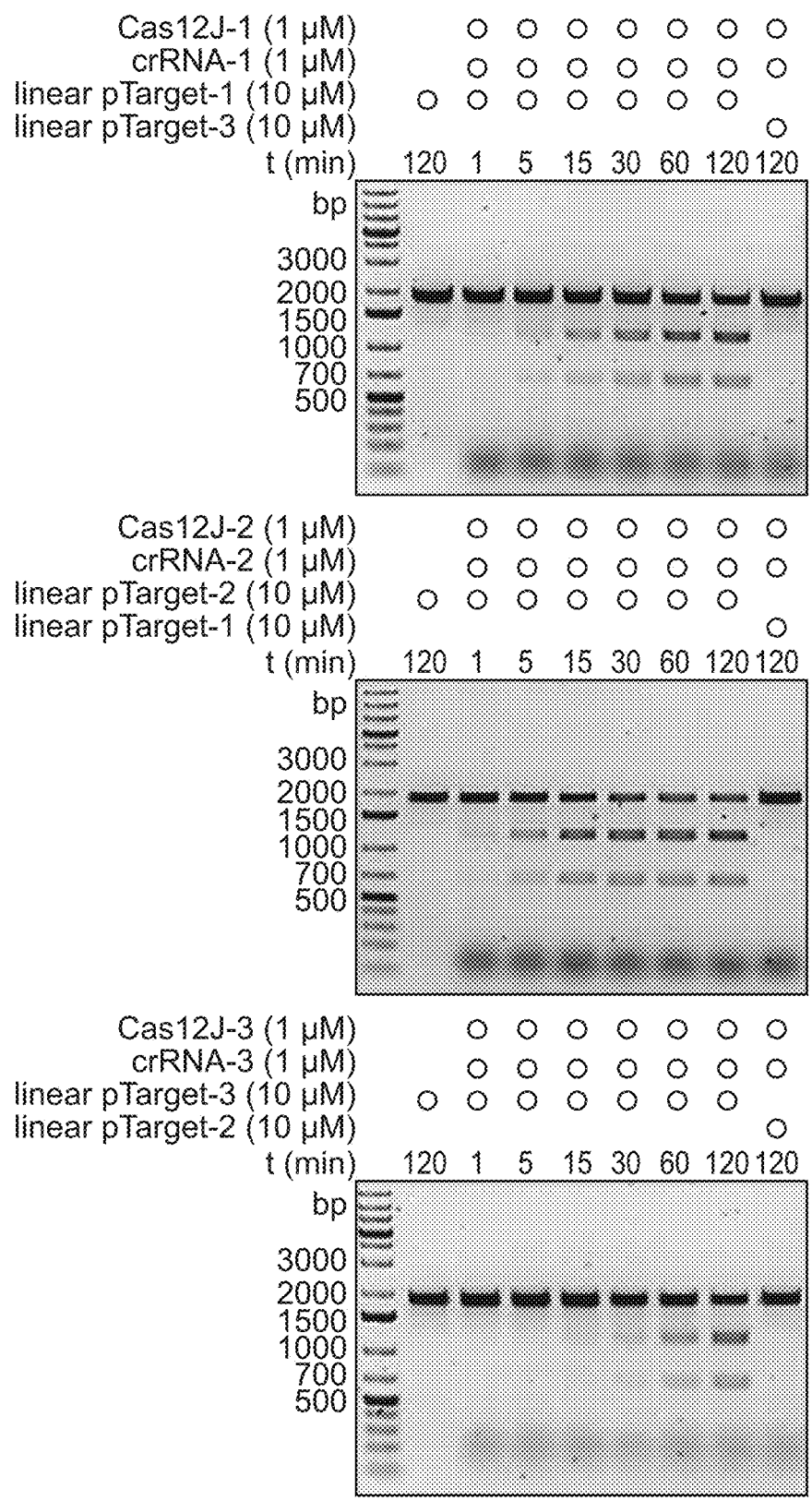

To demonstrate that Cas12J cuts dsDNA—in vitro experiments outside of cells (i.e., in a non-cellular context) were performed. Linear dsDNA was cleaved in the presence of Cas12J and a guide RNA designed to hybridize to a target sequence adjacent to a PAM motif. The Cas12J ribonucleoprotein (RNP) complex was either assembled inside of cells (*E. coli* in this case via the introduction of plasmid DNA encoding the protein and the guide RNA), or assembled in vitro outside of cells from apo protein and synthetic RNA oligonucleotides. The experiment revealed that RNPs with Cas12J-1947455 ("Ortholog #1"), Cas12J-2071242 ("Ortholog #2"), or Cas12J-3339380 ("Ortholog #3") assembled either inside or outside of cells cleaved linear dsDNA fragments guided by the crRNA spacer sequence of the guide RNA (FIG. 12A and FIG. 12B). The 1.9 kb linear DNA substrate was cleaved into 1.2 kb and a 0.7 kb fragment, indicative of an endonucleolytic DNA double strand cleavage event close to the site of guide complementarity. dsDNA cleavage was not observed in the absence of a guide complementary site on the DNA. This experiment demonstrated that Cas12J (e.g., Cas12J-1947455, Cas12J-2071242 and Cas12J-3339380) is a crRNA guided DNA-endonucleases capable of introducing double strand breaks into DNA. Furthermore, the experiment demonstrated that functional Cas12J RNPs can be assembled inside and/or outside of cells.

FIG. 12A-12B demonstrates that Cas12J (e.g., Cas12J-1947455, Cas12J-2071242 and Cas12J-3339380) cleave linear dsDNA fragments guided by a crRNA spacer sequence. FIG. 12A, Time dependent dsDNA cleavage assays for the RNPs that were assembled inside of cells. top: Cas12J-1947455 (Cas12J-1), middle: Cas12J-2071242 (Cas12J-2) and bottom: Cas12J-3339380 (Cas12J-3). The far right lanes are non-complementary DNA controls, which could not be identified by the respective crRNA guide. FIG. 12B, Time dependent dsDNA cleavage assays for the RNPs that were assembled in vitro outside of cells. top: Cas12J-1947455 (Cas12J-1), middle: Cas12J-2071242 (Cas12J-2) and bottom: Cas12J-3339380 (Cas12J-3). The far right lanes are non-complementary DNA controls, which could not be identified by the respective crRNA guide.

Figure 13:
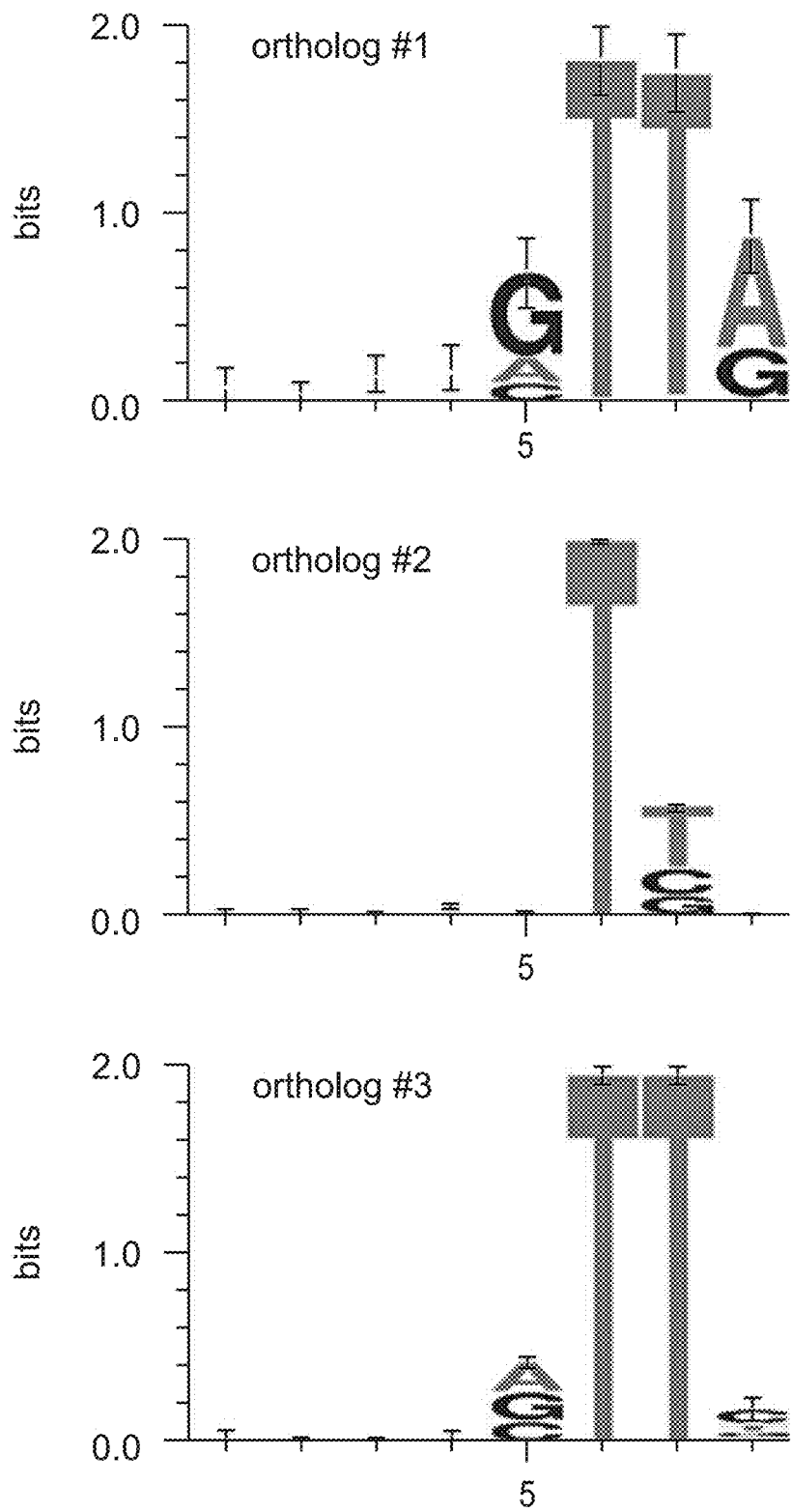
FIG. 13 shows results demonstrating the elucidation of PAM sequences.

PAM depletion assays were performed in *Escherichia coli*. In the assay, Cas12J targets a DNA sequence adjacent to a randomized sequence in a plasmid library. NGS sequencing revealed that Cas12J and crRNA were sufficient in bacteria to deplete plasmids with crRNA guide complementary target DNA sites, when a T-rich PAM sequence was adjacent to the protospacer (FIG. 13). The experiment also showed that no tracrRNA was required for the formation of functional effectors. Noteworthy, ortholog #2 features a minimal 5'-TBN-3' PAM sequence.

FIG. 13. PAM sequences depleted by the three different orthologs, demonstrating that PAMs are straightforward to identify for any desired Cas12J protein.

Methods

Cloning of the Expression Constructs

The gene sequences of Cas12J-1947455, Cas12J-2071242 and Cas12J-3339380 were ordered as G-blocks from IDT and cloned into pRSFDuet-1 (Novagen) into MCSI C-terminally fused to a hexa-histidine tags using Golden Gate assembly. For co-expression of cas12J with crRNA guides, CRISPR-arrays (36 bp repeat followed by a 35 bp spacer, six units thereof) were cloned under the control of a T7-promoter in high copy vectors (ColE1 origin), which contained bla genes for selection.

Production of the Cas12J-RNP In Vivo and Purification

The generated cas12J overexpression vectors and CRISPR array expression vectors were co-transformed in *E. coli* BLR(DE3) (Novagen) and incubated over night at 37° C. on LB-Kan-Carb agar plates (50 µg/mL Kanamycin, 50 µg/mL Carbenicillin).). Single colonies were picked to inoculate 80 mL (LB, Carbenicillin 50 µg/mL and Kanamycin 50 µg/mL) starter cultures which were incubated at 37° C. shaking vigorously overnight. The next day, 1.5 L TB-Kan-Carb medium (Carbenicillin 50 µg/mL and Kanamycin 50 µg/mL) were inoculated with the respective 40 mL starter culture and grown at 37° C. to an $OD_{600}$ of 0.6, cooled down on ice for 15 min and gene expression was subsequently induced with 0.5 mM IPTG followed by incubation over night at 16° C. Cells were harvested by centrifugation and resuspended in wash buffer (50 mM HEPES-Na (pH 7.5), 500 mM NaCl, 20 mM imidazole, 5% glycerol and 0.5 mM TCEP), subsequently lysed by sonication followed by lysate clarification by centrifugation. The soluble fraction was loaded on a 5 mL Ni-NTA Superflow Cartridge (Qiagen) pre-equilibrated in wash buffer. Bound proteins were washed with 20 column volumes (CV) wash buffer and subsequently eluted in 3 CV elution buffer (50 mM HEPES-Na (pH 7.5), 500 mM NaCl, 500 mM imidazole, 5% glycerol and 0.5 mM TCEP). Eluted proteins were dialyzed over night at 4° C. in slide-a-lyzer dialysis cassettes 10 k mwco (Thermo Fisher Scientific) against ion-exchange (IEX) loading buffer (20 mM Tris pH 9.0, 4° C., 125 mM NaCl, 5% glycerol and 0.5 mM TCEP). Proteins were loaded onto 2× 5 mL HiTrap Q HP anion exchange chromatography columns. Proteins were eluted in a gradient of IEX elution buffer (20 mM Tris pH 9.0, 4° C., 1 M NaCl, 5% glycerol and 0.5 mM TCEP). Elution fractions were analyzed by SDS-PAGE and Urea-PAGE and fraction containing RNP formed by Cas12J and crRNA were concentrated to 1 mL. Finally, proteins were injection into a HiLoad 16/600 Superdex® 200 pg column pre-equilibrated in size-exclusion buffer (10 mM HEPES-Na (pH 7.5), 150 mM NaCl and 0.5 mM TCEP). Peak fractions were concentrated to an absorption at 280 nm of 60 AU (NanoDrop® 8000 Spectrophotometer, Thermo Scientific), corresponding to an estimated concentration of 500 µM. Subsequently, proteins were snap frozen in liquid nitrogen and stored at −80° C.

Production and Purification of Apo Cas12J

The generated cas12J overexpression vectors were transformed in chemically competent *E. coli* BL21(DE3) (NEB) and incubated over night at 37° C. on LB-Kan agar plates (50 µg/mL Kanamycin). Single colonies were picked to inoculate 80 mL (LB, Kanamycin 50 µg/mL) starter cultures which were incubated at 37° C. shaking vigorously overnight. The next day, 1.5 L TB-Kan medium (50 µg/mL Kanamycin) were inoculated with the respective 40 mL starter culture and grown at 37° C. to an $OD_{600}$ of 0.6, cooled down on ice for 15 min and gene expression was subsequently induced with 0.5 mM IPTG followed by incubation over night at 16° C. Cells were harvested by centrifugation and resuspended in wash buffer (50 mM HEPES-Na (pH 7.5), 1 M NaCl, 20 mM imidazole, 5% glycerol and 0.5 mM TCEP), subsequently lysed by sonication followed by lysate clarification by centrifugation. The soluble fraction was loaded on a 5 mL Ni-NTA Superflow Cartridge (Qiagen) pre-equilibrated in wash buffer. Bound proteins were washed with 20 column volumes (CV) wash buffer and subsequently eluted in 5 CV elution buffer (50 mM HEPES-Na (pH 7.5), 500 mM NaCl, 500 mM imidazole, 5% glycerol and 0.5 mM TCEP). The eluted proteins were concentrated to 1 mL before injection into a HiLoad 16/600 Superdex® 200 pg column pre-equilibrated in size-exclusion buffer (20 mM HEPES-Na (pH 7.5), 500 mM NaCl, 5% glycerol and 0.5 mM TCEP). Peak fractions were concentrated to an absorption at 280 nm of 40 AU (NanoDrop® 8000 Spectrophotometer, Thermo Scientific), corresponding to an estimated concentration of 500 µM. Subsequently, proteins were snap frozen in liquid nitrogen and stored at −80° C.

Cas12J-crRNA RNP Reconstitution

Cas12J-crRNA RNP complexes were assembled at a concentration of 1.25 µM by mixing protein and synthetic crRNA (IDT) in a 1:1 molar ratio in reconstitution buffer (10 mM Hepes-K pH 7.5, 150 mM KCl, 5 mM $MgCl_2$, 0.5 mM TCEP) and incubation at 20° C. for 30 min. The synthetic crRNA was prior to the assembly reaction heated to 95° C. for 3 min and then cooled down to RT for proper folding.

DNA Cleavage Assay

DNA target substrates were generated by PCR from plasmid template DNA. Cleavage reactions were initiated by addition of DNA (10 nM) to preformed RNP (1 µM) in reaction buffer (10 mM Hepes-K pH 7.5, 150 mM KCl, 5 mM $MgCl_2$, 0.5 mM TCEP). The reactions were incubated at 37° C. and aliquots were removed at the indicated intervals, quenched with 50 mM EDTA and stored in liquid nitrogen. After completion of the time-series, samples were thawed and treated with 0.8 units proteinase K (NEB) for 20 min at 37° C. Loading dye was added (Gel Loading Dye Purple 6×, NEB) and samples were analyzed by electrophoresis on an 1% agarose gel.

Sequences Used
M1 crRNA guides:
>crRNA-1 (guide sequence/targeting sequence is in bold)
(SEQ ID NO: 99)
CACAGGAGAGAUCUCAAACGAUUGCUCGAUUAGUCGAGA

CAGCUGGUAAUGGGAUACCUU

>crRNA-2 (guide sequence/targeting
sequence is in bold)
(SEQ ID NO: 100)
UAAUGUCGGAACGCUCAACGAUUGCCCCUCACGAGGGGAC

UGCCGCCUCCGCGACGCCCA

>crRNA-3 (guide sequence/targeting
sequence is in bold)
(SEQ ID NO: 101)
AUUAACCAAAACGACUAUUGAUUGCCCAGUACGCUGGGAC

UAUGAGCUUAUGUACAUCAA

DNA targets (PAM motifs are underlined crRNA
spacer complementary sequences are bold):
>Linear pTarget1:
(SEQ ID NO: 102)
gctcttgcccggcgtcaatacgggataataccgcgccaca tagcagaactttaaaagtgctcatcattggaaaacgttct tcggggcgaaaactctcaaggatcttaccgctgttgagat ccagttcgatgtaacccactcgtgcacccaactgatcttc agcatcttttactttcaccagcgtttctgggtgagcaaaa acaggaaggcaaaatgccgcaaaaaagggaataagggcga cacggaaatgttgaatactcatactcttccttttcaata ttattgaagcatttatcagggttattgtctcatgagcgga tacatatttgaatgtatttagaaaaataaacaaatagggg ttccgcgcacatttccccgaaaagtgccacctgtcatgac caaaatcccttaacgtgagttttcgttccactgagcgtca gaccccgtagaaaagatcaaaggatcttcttgagatcctt ttttttctgcgcgtaatctgctgcttgcaaacaaaaaaacc accgctaccagcggtggtttgtttgccggatcaagagcta ccaactcttttttccgaaggtaactggcttcagcagagcgc agataccaaatactgttcttctagtgtagccgtagttagg ccaccacttcaagaactctgtagcaccgcctacatacctc gctctgctaatcctgttaccagtggctgctgccagtggcg ataagtcgtgtcttaccgggttggactcaagacgatagtt accggataaggcgcagcggtcgggctgaacggggggttcg tgcacacagcccagcttggagcgaacgacctacaccgaac tgagatacctacagcgtgagctatgagaaagcgccacgct tcccgaagggagaaaggcggacaggtatccggtaagcggc agggtcggaacaggagagcgcacgagggagcttccagggg gaaacgcctggtatctttatagtcctgtcgggtttcgcca cctctgacttgagcgtcgatttttgtgatgctcgtcaggg gggcggagcctatggaaaaacgccagcaacgcggccttt tacggttcctggccttttgctggccttttgctcacatgtt ctttcctgcgttatcccctgattctgtggataaccgtgcg gccgcccctgtaGTTAagctggtaatgggataccttAta cagcggccgcgattatcaaaaaggatcttcacctagatcc ttttaaattaaaaatgaagttttaaatcaatctaaagtat atatgagtaaacttggtctgacagttaccaatgcttaatc agtgaggcacctatctcagcgatctgtctatttcgttcat ccatagttgcctgactccccgtcgtgtagataactacgat acgggagggcttaccatctggccccagtgctgcaatgata ccgcgggacccacgctcaccggctccagatttatcagcaa taaaccagccagccggaagggccgagcgcagaagtggtcc tgcaactttatccgcctccatccagtctattaattgttgc cgggaagctagagtaagtagttcgccagttaatagtttgc gcaacgttgttgccattgctacaggcatcgtggtgtcacg ctcgtcgtttggtatggcttcattcagctccggttcccaa cgatcaaggcgagttacatgatcccccatgttgtgcaaaa aagcggttagctccttcggtcctccgatcgttgtcagaag taagttggccgcagtgttatcactcatggttatggcagca ctgcataattctcttactgtcatgccatccgtaagatgct tttctgtgactggtgagtactcaaccaagtcattctgaga atagtgtatgcggcg >linear pTarget2:
(SEQ ID NO: 103)
gctcttgcccggcgtcaatacgggataataccgcgccaca tagcagaactttaaaagtgctcatcattggaaaacgttct tcggggcgaaaactctcaaggatcttaccgctgttgagat ccagttcgatgtaacccactcgtgcacccaactgatcttc agcatcttttactttcaccagcgtttctgggtgagcaaaa acaggaaggcaaaatgccgcaaaaaagggaataagggcga cacggaaatgttgaatactcatactcttccttttcaata ttattgaagcatttatcagggttattgtctcatgagcgga tacatatttgaatgtatttagaaaaataaacaaatagggg ttccgcgcacatttccccgaaaagtgccacctgtcatgac caaaatcccttaacgtgagttttcgttccactgagcgtca gaccccgtagaaaagatcaaaggatcttcttgagatcctt ttttttctgcgcgtaatctgctgcttgcaaacaaaaaaacc accgctaccagcggtggtttgtttgccggatcaagagcta ccaactcttttttccgaaggtaactggcttcagcagagcgc agataccaaatactgttcttctagtgtagccgtagttagg ccaccacttcaagaactctgtagcaccgcctacatacctc gctctgctaatcctgttaccagtggctgctgccagtggcg ataagtcgtgtcttaccgggttggactcaagacgatagtt accggataaggcgcagcggtcgggctgaacggggggttcg tgcacacagcccagcttggagcgaacgacctacaccgaac tgagatacctacagcgtgagctatgagaaagcgccacgct tcccgaagggagaaaggcggacaggtatccggtaagcggc agggtcggaacaggagagcgcacgagggagcttccagggg -continued
```
gaaacgcctggtatctttatagtcctgtcgggtttcgcca cctctgacttgagcgtcgattttttgtgatgctcgtcaggg gggcggagcctatggaaaaacgccagcaacgcggccttt tacggttcctggccttttgctggccttttgctcacatgtt ctttcctgcgttatccctgattctgtggataaccgtgcg gccgcccttgtatTTCTGCCGCCTCCGCGACGCCCAata cagcggccgcgattatcaaaaaggatcttcacctagatcc ttttaaattaaaaatgaagttttaaatcaatctaaagtat atatgagtaaacttggtctgacagttaccaatgcttaatc agtgaggcacctatctcagcgatctgtctatttcgttcat ccatagttgcctgactccccgtcgtgtagataactacgat acgggagggcttaccatctggccccagtgctgcaatgata ccgcgggacccacgctcaccggctccagatttatcagcaa taaaccagccagccggaagggccgagcgcagaagtggtcc tgcaactttatccgcctccatccagtctattaattgttgc cgggaagctagagtaagtagttcgccagttaatagtttgc gcaacgttgttgccattgctacaggcatcgtggtgtcacg ctcgtcgtttggtatggcttcattcagctccggttcccaa cgatcaaggcgagttacatgatcccccatgttgtgcaaaa aagcggttagctccttcggtcctccgatcgttgtcagaag taagttggccgcagtgttatcactcatggttatggcagca ctgcataattctcttactgtcatgccatccgtaagatgct tttctgtgactggtgagtactcaaccaagtcattctgaga atagtgtatgcggcg >linear pTarget3:
                              (SEQ ID NO: 104)
gctcttgcccggcgtcaatacgggataataccgcgccaca tagcagaacttttaaaagtgctcatcattggaaaacgttct tcggggcgaaaactctcaaggatcttaccgctgttgagat ccagttcgatgtaacccactcgtgcacccaacigatcttc agcatcttttactttcaccagcgtttctgggtgagcaaaa acaggaaggcaaaatgccgcaaaaaagggaataagggcga cacggaaatgttgaatactcatactcttccttttttcaata ttattgaagcatttatcagggttattgtctcatgagcgga tacatatttgaatgtatttagaaaaataaacaaataggg ttccgcgcacatttccccgaaaagtgccacctgtcatgac caaaatcccttaacgtgagttttcgttccactgagcgtca gaccccgtagaaaagatcaaaggatcttcttgagatcctt tttttctgcgcgtaatctgctgcttgcaaacaaaaaacc accgctaccagcggtggtttgtttgccggatcaagagcta ccaactcttttccgaaggtaactggcttcagcagagcgc agataccaaatactgttcttctagtgtagccgtagttagg
```

```
ccaccacttcaagaactctgtagcaccgcctacatacctc gctctgctaatcctgttaccagtggctgctgccagtggcg ataagtcgtgtcttaccgggttggactcaagacgatagtt accggataaggcgcagcggtcgggctgaacggggggttcg tgcacacagcccagcttggagcgaacgacctacaccgaac tgagatacctacagcgtgagctatgagaaagcgccacgct tcccgaagggagaaaggcggacaggtatccggtaagcggc agggtcggaacaggagagcgcacgagggagcttccagggg gaaacgcctggtatctttatagtcctgtcgggtttcgcca cctctgacttgagcgtcgattttttgtgatgctcgtcaggg gggcggagcctatggaaaaacgccagcaacgcggccttt tacggttcctggccttttgctggccttttgcteacatgtt ctttcctgcgttatccctgattctgtggataaccgtgcg gccgcccttgtaATTCtatgagcttatgtacatcaaAta cagcggccgcgattatcaaaaaggatcttcacctagatcc ttttaaattaaaaatgaagttttaaatcaatctaaagtat atatgagtaaacttggtctgacagttaccaatgcttaatc agtgaggcacctatctcagcgatctgtctatttcgttcat ccatagttgcctgactccccgtcgtgtagataactacgat acgggagggcttaccatctggccccagtgctgcaatgata ccgcgggacccacgctcaccggctccagatttatcagcaa taaaccagccagccggaagggccgagcgcagaagtggtcc tgcaactttatccgcctccatccagtctattaattgttgc cgggaagctagagtaagtagttcgccagttaatagtttgc gcaacgttgttgccattgctacaggcatcgtggtgtcacg ctcgtcgtttggtatggcttcattcagctccggttcccaa cgatcaaggcgagttacatgatcccccatgttgtgcaaaa aagcggttagctccttcggtcctccgatcgttgtcagaag taagttggccgcagtgttatcactcatggttatggcagca ctgcataattctcttactgtcatgccatccgtaagatgct tttctgtgactggtgagtactcaaccaagtcattctgaga atagtgtatgcggcg
```

Example 4

Results

Transcriptomic mapping suggested that crRNA was expressed heterologously in *E. coli* cells and processed to include a 25 nucleotide-long repeat and a 14-20 nucleotide spacer. The data also suggested that Cas12J likely processes its own crRNA (see FIG. 14A-14C).

Figure 14A:
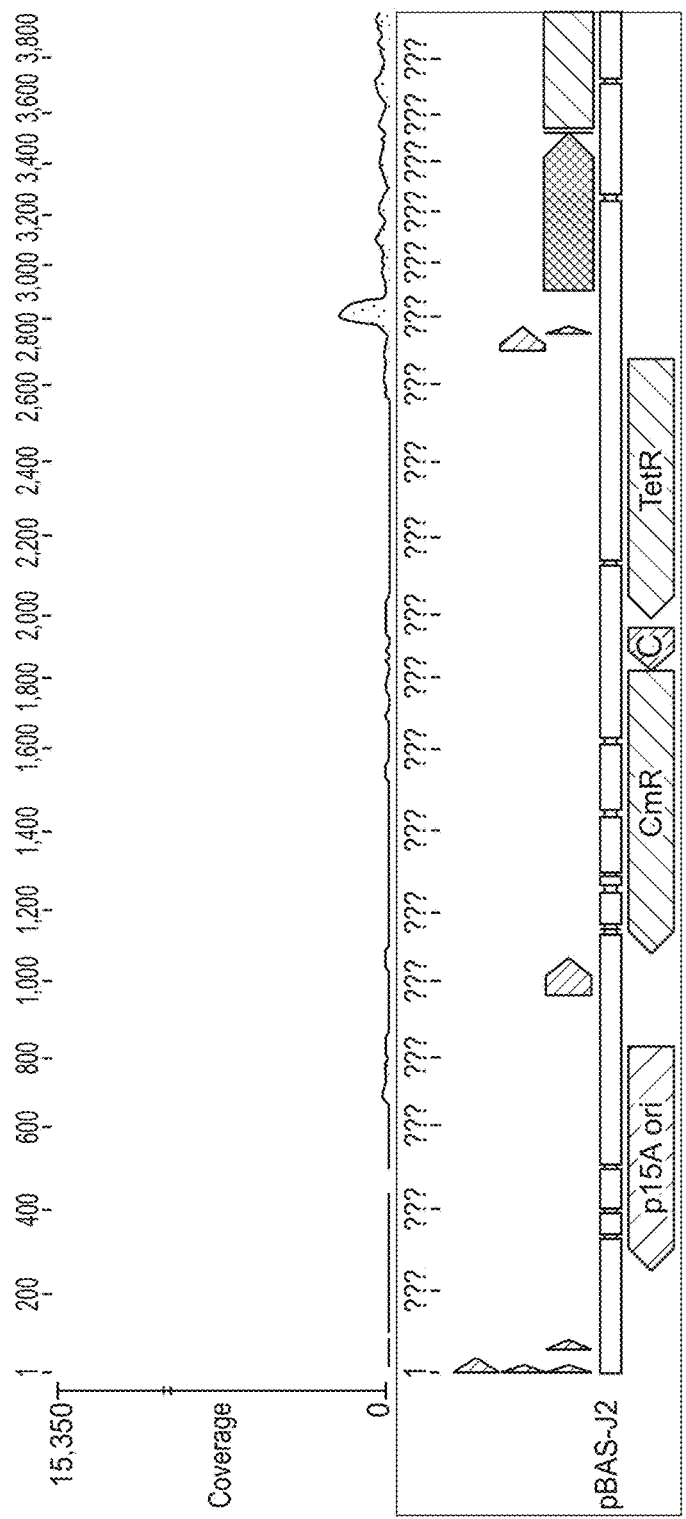
FIG. 14A-14C illustrates results from mapping RNA sequences to the Cas12J CRISPR loci from pBAS::Cas12J-1947455, pBAS::Cas12J-2071242, and pBAS::Cas12J-3339380.
Figure 14A:
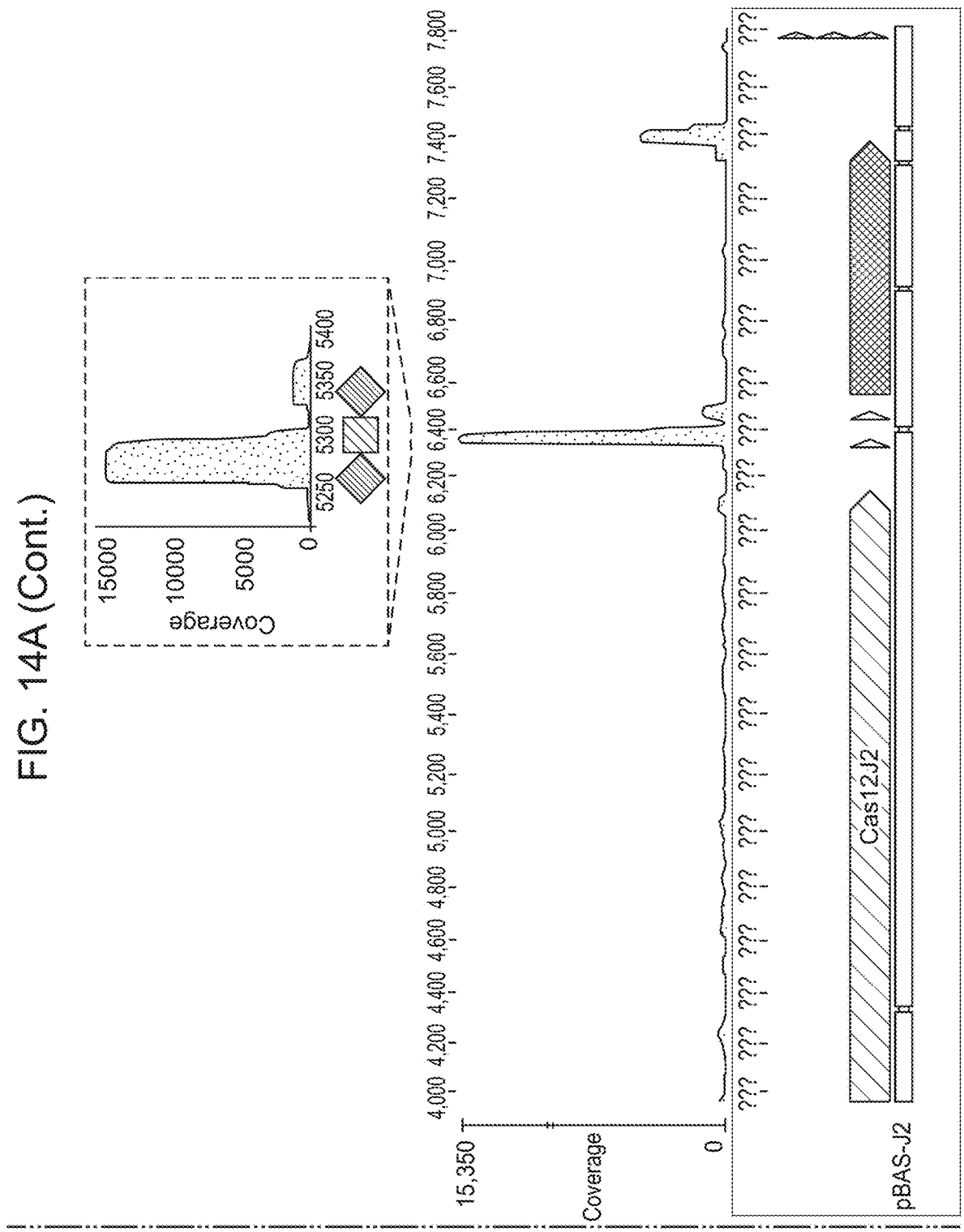
Figure 14B:
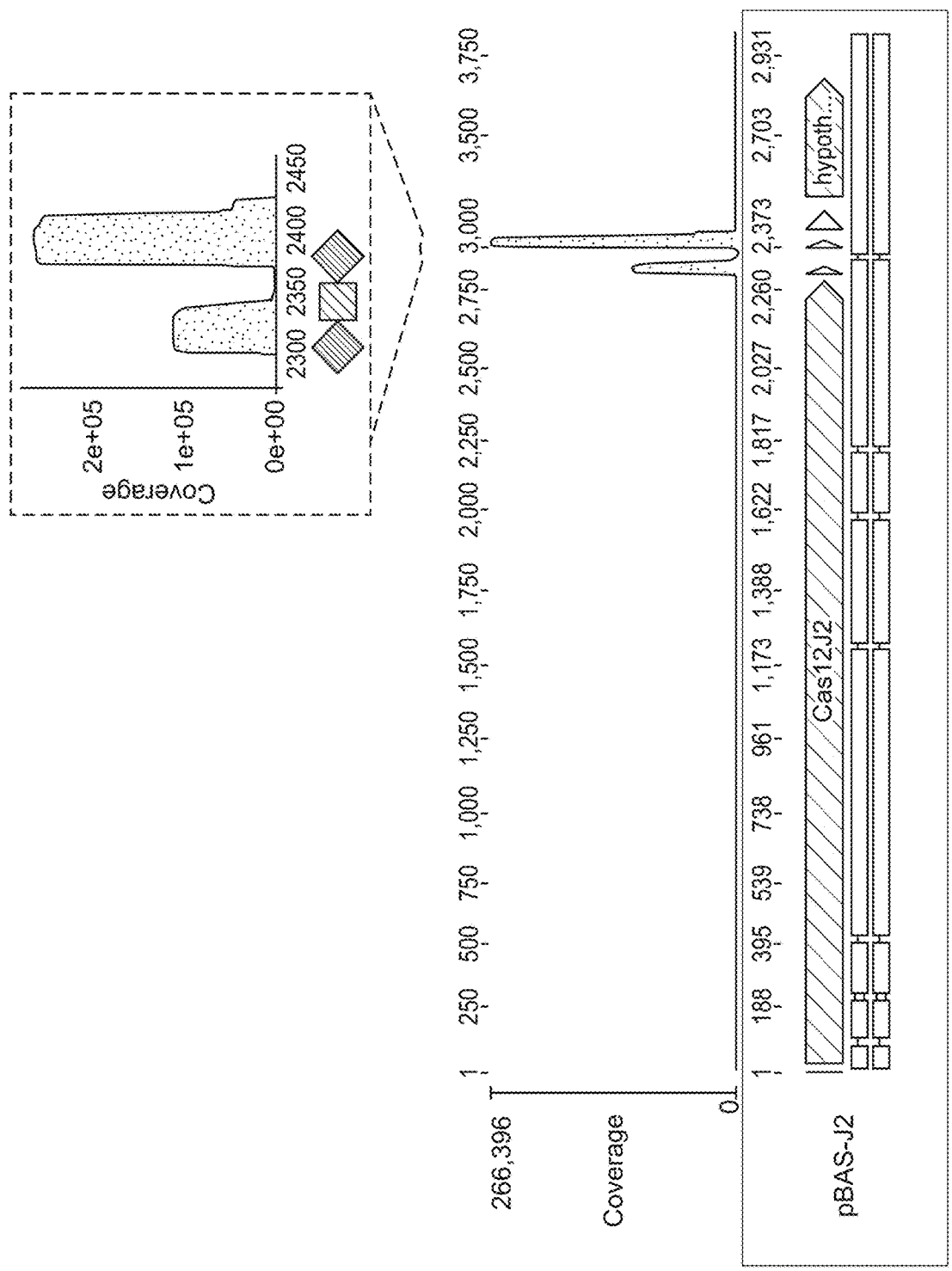
Figure 14B:
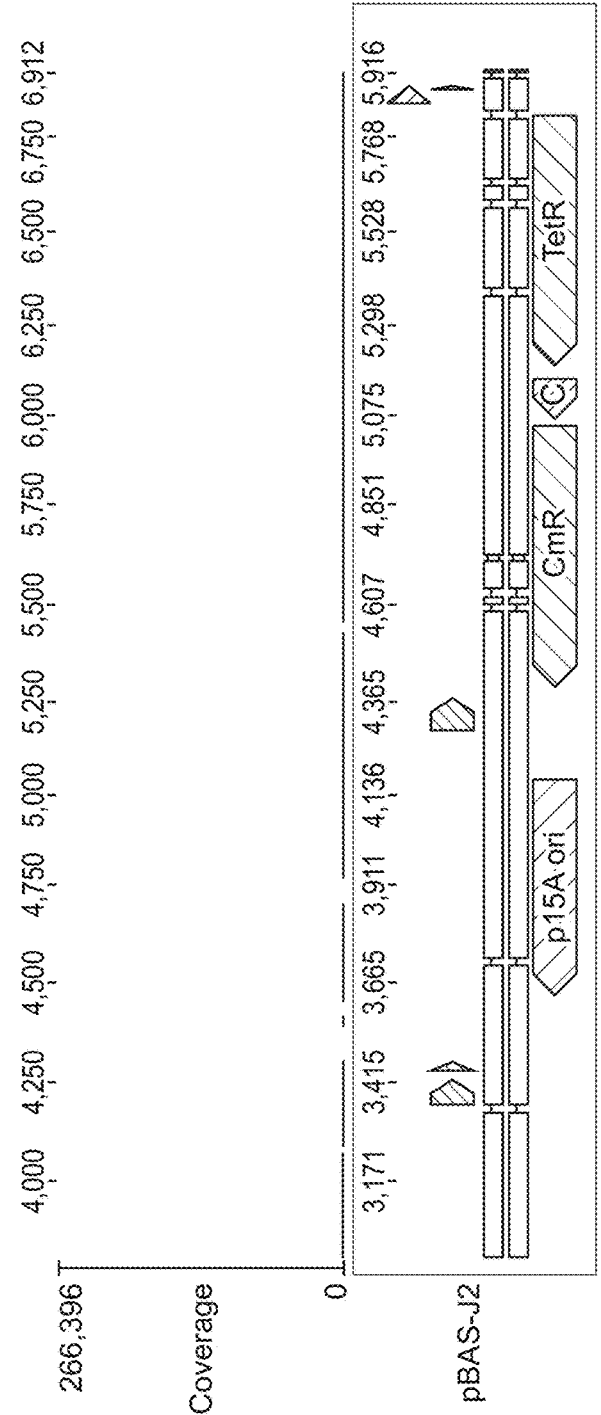
Figure 14C:
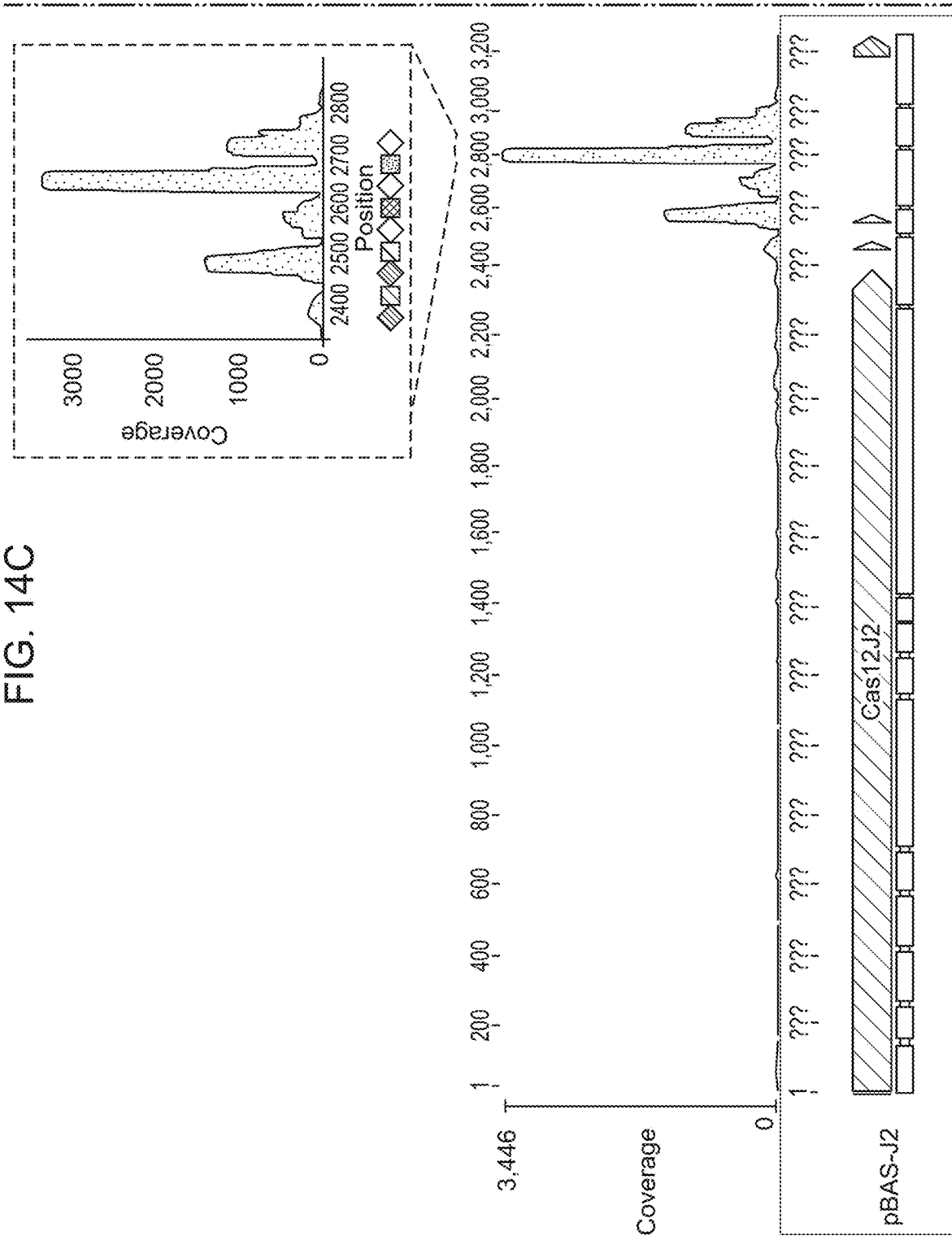
Figure 14C:
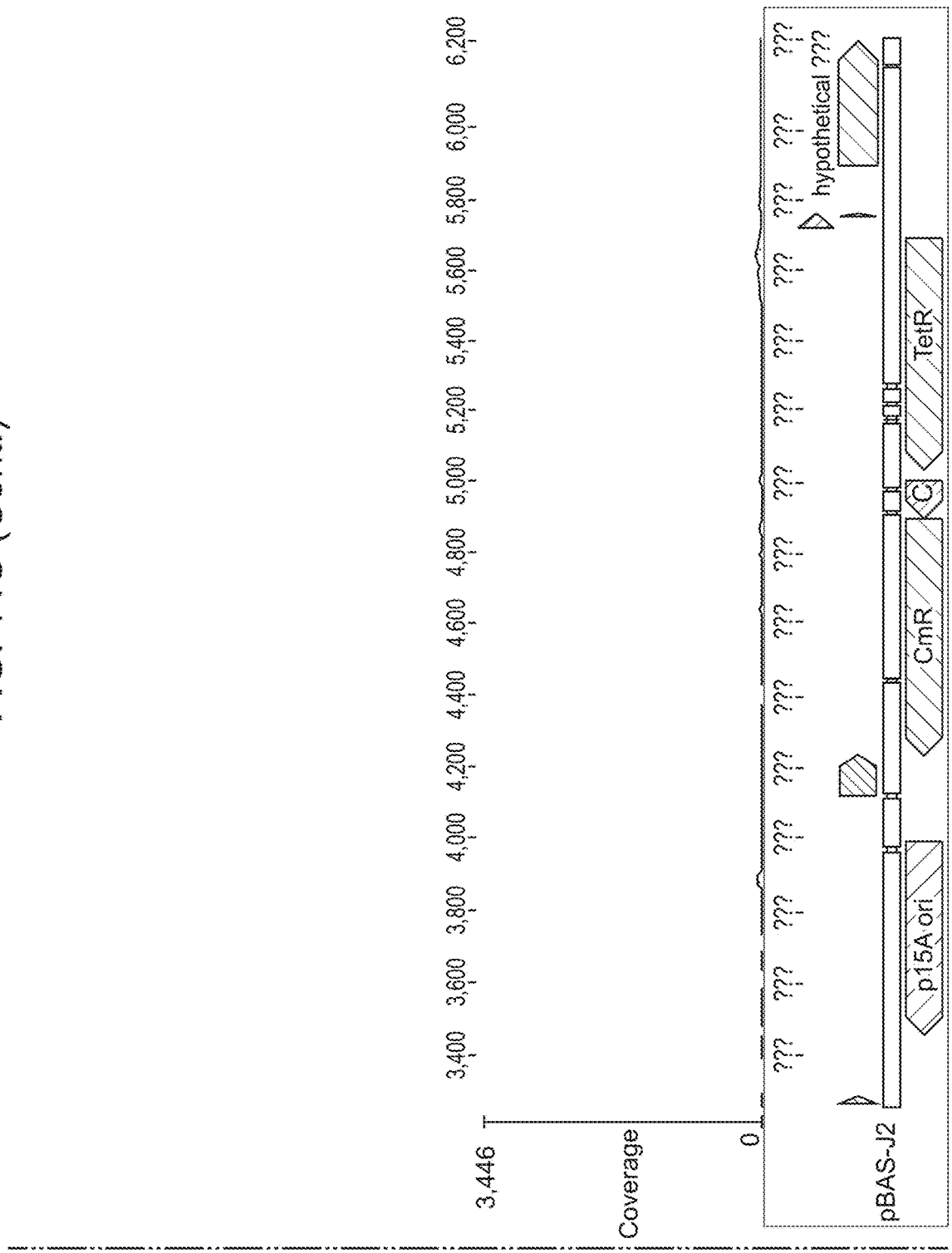

FIG. 14A-14C illustrates results from mapping RNA sequences to the Cas12J CRISPR locus from pBAS::Cas12J-1947455 (FIG. 14A), pBAS::Cas12J-2071242 (FIG. 14B), and pBAS::Cas12J-3339380 (FIG. 14C). Inset shows a detailed view of transcriptome mapping to the first repeat-spacer-repeat iteration in each locus. Black diamonds denote repeats; colored squares denote spacers; faded repeats and spacers denote the degenerate end of the array.

Methods

RNA-Seq pBAS::Cas12J-1947455, pBAS::Cas12J-2071242, and pBAS::Cas12J-3339380 constructs were transformed in chemically competent *E. coli* DH5a (QB3-Macrolab, UC Berkeley) and incubated over night at 37° C. on LB-Cm agar plates (34 µg/mL chloramphenicol). Single colonies were picked to inoculate 5 mL (LB, 34 µg/mL chloramphenicol) starter cultures which were incubated at 37° C. shaking vigorously overnight. The next morning, main cultures were inoculated 1:100 (LB, 34 µg/mL chloramphenicol) and locus expression was induced with 200 nM aTc for 24 h at 16° C. Cells were harvested by centrifugation, resuspended in lysis buffer (20 mM Hepes-Na pH 7.5, 200 mM NaCl) and lysed using glass beads (0.1 mm glass beads, 4×30 s vortex at 4° C., interspaced by 30 s cool-down on ice). 200 µL cell lysis supernatant were transferred into Trizol® for RNA extraction according to the manufacturers protocol (Ambion). 10 µg RNA were treated with 20 units of T4-PNK (NEB) for 6 h at 37° C. for dephosphorylation. Subsequently, 1 mM ATP was added and the sample was incubated for 1 h at 37° C. for 5'-phosphorylation before heat inactivation at 65° C. and subsequent Trizol® purification.

Next, cDNA libraries were prepared using the RealSeq®-AC miRNA library kit illumina sequencing (somagenics). cDNA libraries were subjected to Illumina MiSeq® sequencing, generating 50 nucleotide-long single reads. Raw sequencing data was processed to remove adapters and sequencing artifacts, and high-quality reads were maintained. The resulting reads were mapped to their respective plasmids to determine the CRISPR locus expression and crRNA processing.

Example 5

Results

Figure 15:
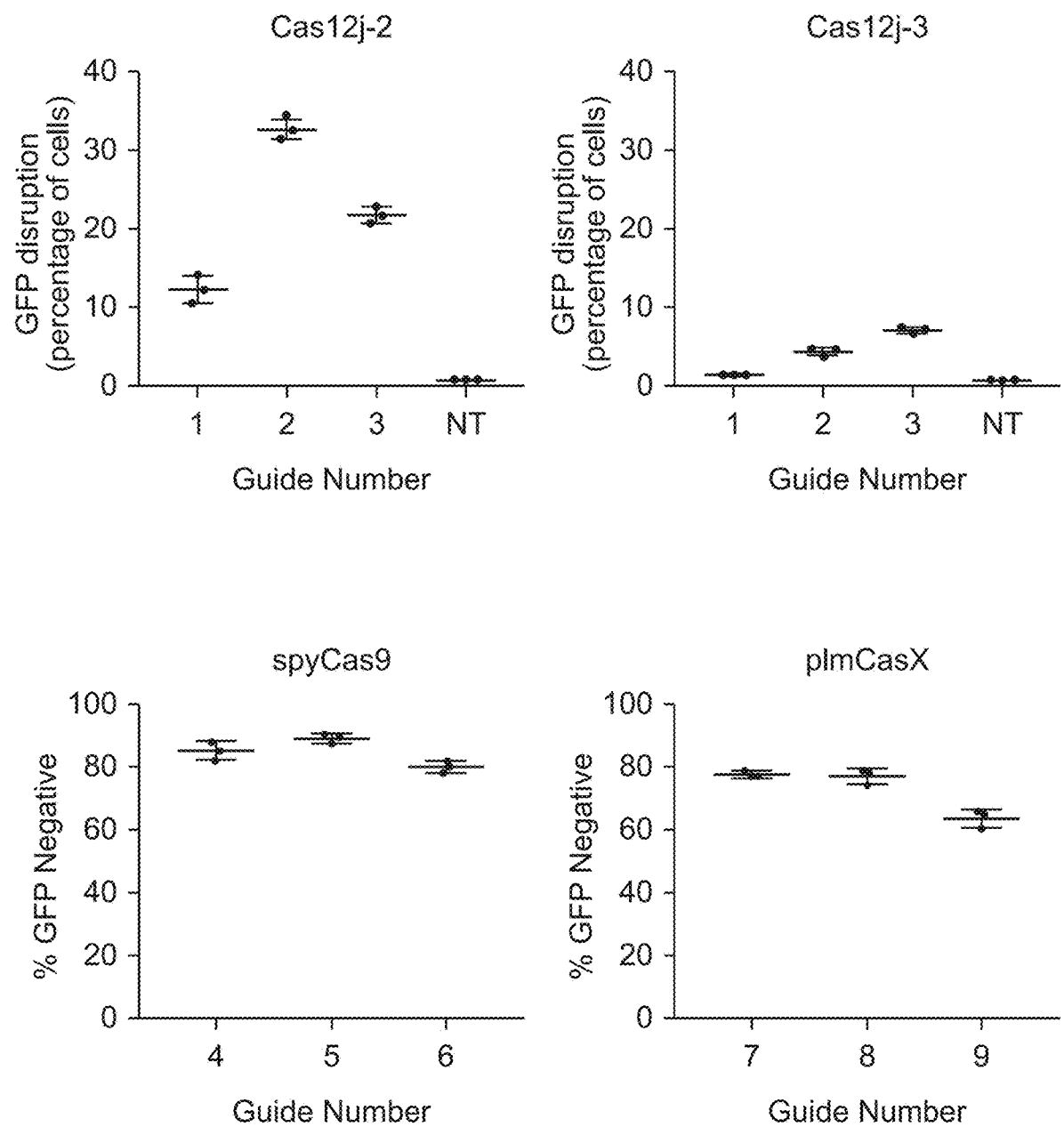
FIG. 15 depicts Cas12j-2- and Cas12j-3-mediated gene editing in human cells.

The data provided in FIG. 15 show that Cas12J can induce targeted GFP disruption, indicating successful Non-Homologous End Joining (NHEJ) and targeted genomic editing in human cells. In one case, an individual Cas12J/guide RNA was able to edit as high as 33% of cells (Cas12J-2 guide 2), comparable to levels reported for CRISPR-Cas9, CRISPR-Cas12a, and CRISPR-CasX (Coag et al. (2013) *Science* 339:819; Jinek et al (2013) eLife 2:e00471; Mali et al. (2013) *Science* 339:823; and Liu et al. (2019) *Nature* 566:7743).

Methods

Cloning of Cas12J Effector Plasmids for Expression in Human Cell

Figure 16A:
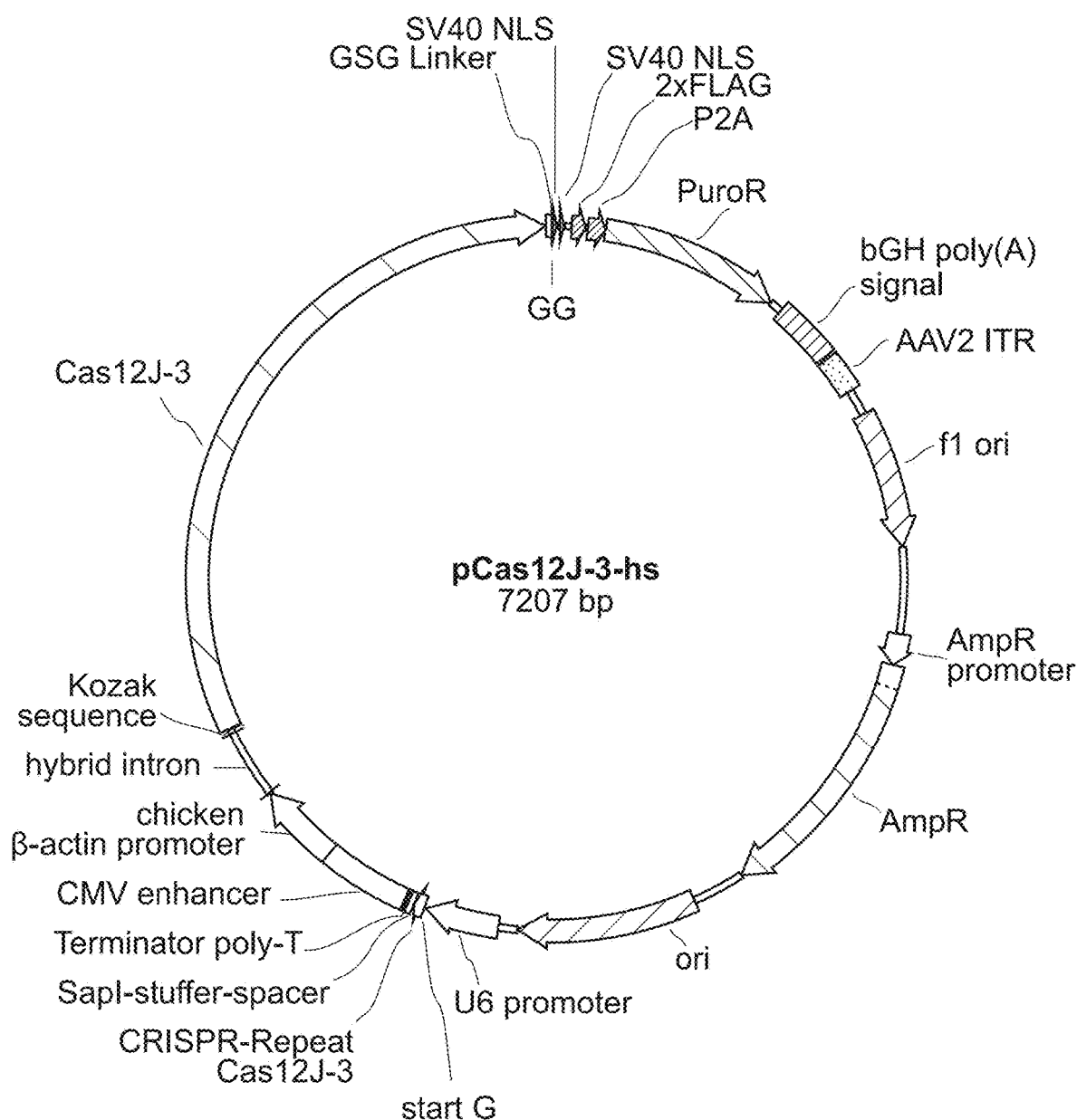
FIG. 16A-16B provide maps of the pCas12J-3-hs (FIG. 16A) and pCas12J-2-hs (FIG. 16B) constructs.
Figure 16B:
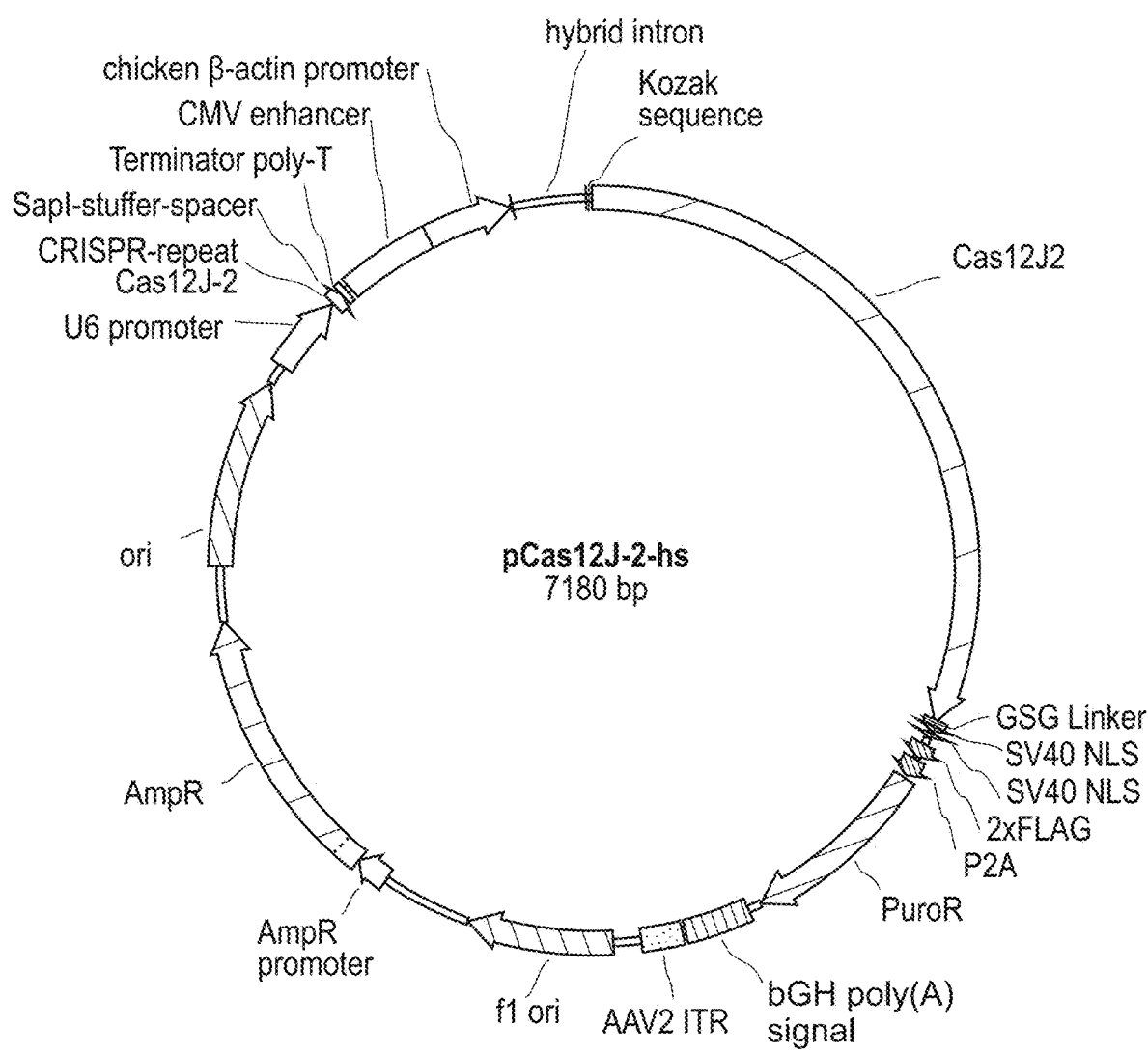

The gene sequence of cas12J-2 and cas12J-3 were ordered as G-blocks from Integrated DNA Technologies (IDT) encoding codon optimized genes for expression in human cells. G-blocks were cloned via Golden Gate assembly into the vector backbone of pBLO62.5, downstream fused to two SV40 NLSs via a GSG linker encoding sequence (FIG. 16A-16B, providing construct maps; and Table 1 (provided in FIG. 17A-17G), providing nucleotide sequences of the constructs). The guide encoding sequence of pBLO62.5 was exchanged to encode for a single CRISPR-repeat of the respective homologue, followed by a 20 bp stuffer spacer sequence amenable to Golden Gate exchange using the restriction enzyme SapI (FIG. 16A-16B; and Table 1 (provided in FIG. 17A-17G)). To generate EGFP targeting constructs, the stuffer was exchanged via Golden Gate assembly to encode the guide for the selected target site (Table 2).

TABLE 2

| Guide sequences | |
|---|---|
| Guide # | Spacer Sequence 5'->3' |
| NT | CGTGATGGTCTCGATTGAGT (SEQ ID NO: 105) |
| 1 | ACCGGGGTGGTGCCCATCCT (SEQ ID NO: 106) |
| 2 | ATCTGCACCACCGGCAAGCT (SEQ ID NO: 107) |
| 3 | GAGGGCGACACCCTGGTGAA (SEQ ID NO: 108) |

Human-Cell Targeted GFP Disruption

The GFP HEK293 reporter cells were previously generated via lentiviral integration as previously described. Antony et al. (2018) *Mol. Cell. Pediatrics* 5:9. Cells were routinely tested for mycoplasma using the MycoAlert Mycoplasma Detection Kit (Lonza), according to the manufacturer's protocol. GFP HEK293 reporter cells were seeded into 96-well plates and transfected the next day with Lipofectamine® 3000 (Life Technologies) and 200 ng of plasmid DNA encoding the Cas12J gRNA and Cas12J-P2A-puromycin fusion. 24 hours post-transfection, successfully transfected cells were selected for by adding 1.5 puromycin to the cell culture media for 72 hours. Cells were passaged to maintain sub-confluent conditions and then analyzed on an Attune N×T How Cytometer with an autosampler. Cells were analyzed on the flow cytometer after 7 days to allow for clearance of GFP from cells.

Example 6

Results

To test whether Cas12J features an unspecific trans-cleavage activity, once activated by cis-targeted nucleic acids, an in vitro cleavage assay was set up. In the assay, the Cas12J RNPs and trans cleavage ssDNA or ssRNA substrates were incubated in the presence of no cis-activator, ssDNA cis-activator, dsDNA cis-activator, or ssRNA cis-activator.

Figure 18:
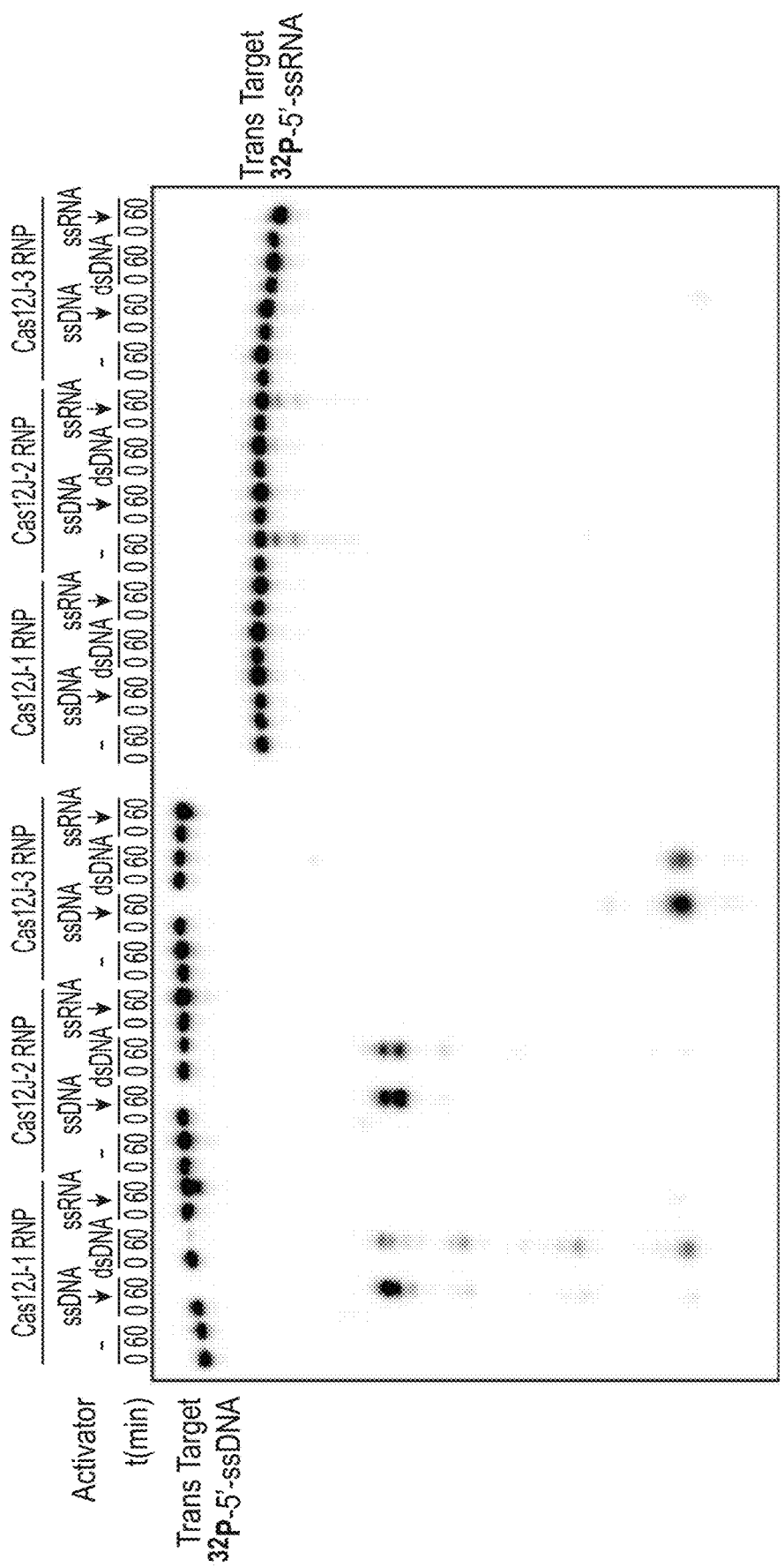
FIG. 18 depicts trans cleavage of ssDNA by Cas12J activated by binding to DNA.

As shown in FIG. 18, the three tested Cas12J homologs efficiently cleave ssDNA, but not ssRNA, when an activating DNA, but not RNA, is present in the reaction. This assay demonstrates that Cas12J can be activated by spacer complementary ssDNA, or dsDNA, to target ssDNA in trans. Furthermore, this DNA-activated ssDNA trans cleavage activity can be used for nucleic acid detection using a Fluorophore-quencher labeled reporter assay (East-Seletsky et al., Nature 538, 270-273 (2016)).

Methods ssDNA and ssRNA substrates for trans cleavage were designed to be non-complementary to the spacer of the Cas12J guide RNA. Substrates were 5'-end-labelled using T4-PNK (NEB) in the presence of $^{32}$P-γ-ATP. Active Cas12J RNP complexes were assembled by diluting Cas12J protein and guide crRNA to 4 µM in complex assembly buffer (20 mM HEPES-Na pH 7.5 RT, 300 mM KCl, 10 mM MgCl$_2$, 20% glycerol, 1 mM TCEP) and incubation for 30 min at RT. Spacer complementary activator substrates were diluted in oligonucleotide hybridization buffer (10 mM Tris pH 7.8 RT, 150 mM KCl) to a concentration of 4 µM, heated to 95° C. for 5 min, and subsequently cooled down at room temperature (RT) to allow duplex formation for double stranded activator substrates. Cleavage reactions were set up by combining 200 nM RNP with 400 nM activator substrate and incubation for 10 min at RT before addition of 2 nM ssDNA, or ssRNA, trans cleavage substrates. Reactions were conducted in reaction buffer (10 mM HEPES-Na pH 7.5 RT, 150 mM KCl, 5 mM $MgCl_2$, 10% glycerol, 0.5 mM TCEP) and incubated for 60 min at 37° C. Reactions were stopped by addition of two volumes formamide loading buffer (96% formamide, 100 µg/mL bromophenol blue, 50 µg/mL xylene cyanol, 10 mM EDTA, 50 µg/mL heparin), heated to 95° C. for 5 min, and cooled down on ice before separation on a 12.5% denaturing urea-polyacrylamide gel electrophoresis (PAGE). Gels were dried for 4 h at 80° C. before phosphor-imaging visualization using an Amersham Typhoon™ scanner (GE Healthcare).

Example 7

Materials and Methods
Metagenomic Assemblies, Genome Curation, and CRISPR-CasΦ (CRISPR-Cas12J) Detection Metagenomic sequencing data was assembled using previously described methods (Peng et al. *Bioinformatics*. 28, 1420-1428 (2012); and Nurk et al. *Genome Res*. 27, 824-834 (2017). Coding sequences (CDS) were predicted from sequence assemblies using prodigal with genetic code 11 (-m -g 11 -p single) and (-m -g 11 -p meta) and preliminary annotations were performed as previously described by searching against UniProt, UniRef100, and KEGG (Wrighton et al. *ISME J*. 8, 1452-1463 (2014)). Phage genome curation was performed as described above. Briefly, Bowtie2 v2.3.4.1 (Langmead and Salzberg *Nat. Methods*. 9, 357-359 (2012)) was used to map reads to the de novo assembled sequences, and unplaced mate pairs of mapped reads were retained with shrinksam (github.com/bcthomas/shrinksam). N-filled gaps and local misassemblies were identified and corrected, and unplaced or incorrectly placed paired reads allowed extension of contig ends. Local assembly changes and extensions were verified with further read mapping. A database of CasΦ sequences was generated using MAFFT v7.407 (Katoh and Standley *Mol. Biol. Evol*. 30, 772-780 (2013)) and hmmbuild. CDS from new assemblies were searched against the HMM database using hmmsearch with e-value <$1\times10^{-5}$ and added to the database upon verification.

Phylogenetic Analysis of Type V Systems

Cas protein sequences were collected as described above and representatives from the TnpB superfamily were collected from Makarova et al. (*Nat. Rev. Microbiol.,* 1-17 (2019)) and top BLAST hits from RefSeq. The resulting set was clustered at 90% amino acid identity using CD-HIT to reduce redundancy (Huang et al. *Bioinformatics*. 26, 680-682 (2010)). A new alignment of CasΦ with the resulting sequence set was generated using MAFFT LINSI with 1000 iterations and filtered to remove columns comprised of gaps in 95% of sequences. Poorly aligned sequences were removed and the resulting set was realigned. The phylogenetic tree was inferred using IQTREE v1.6.6 using automatic model selection (Nguyen et al. *Mol. Biol. Evol*. 32, 268-274 (2015)) and 1000 bootstraps.

crRNA Sequence Analysis

CRISPR-RNA (crRNA) repeats from Phage-encoded CRISPR loci were identified using MinCED (github.com/ctSkennerton/minced) and CRISPRDetect (Biswas et al. *BMC Genomics*. 17, 356 (2016)). The repeats were compared by generating pairwise similarity scores using the Needleman-Wunsch algorithm followed by EMBOSS Needle (McWilliam et al. *Nucleic Acids Res*. 41, W597-600 (2013)). A heatmap was built using the similarity score matrix and hierarchical clustering produced dendrograms that were overlaid onto the heatmap to delineate different clusters of repeats.

Generation of Plasmids

CasΦ loci, including an additional *E. coli* RBS upstream of casΦ, were ordered as G-blocks from Integrated DNA Technologies (IDT) and cloned using Golden Gate assembly (GG) under the control of a tetracycline-inducible promoter for RNA seq and PAM depletion plasmid interference experiments. Perfect repeat-spacer units of the CRISPR-arrays identified by metagenomics were reduced to a single repeat-spacer-repeat unit, amenable to stuffer-spacer exchange by GG-assembly (AarI-restriction sites). Subsequently, CasΦ gene sequences were subcloned by GG-assembly into pRSFDuet-1 (Novagen) within MCSI without tags for efficiency of transformation plasmid interference assays, or fused to a C-terminal hexa-histidine tag for protein purification. For plasmid interference assays, mini-CRISPR arrays (repeat-spacer-repeat, or repeat-spacer-HDV ribozyme) amenable to stuffer-spacer exchange by GG-assembly (AarI-restriction sites) were cloned into MCS II of pRSFDuet. For genome editing experiments in human cells, casΦ genes were ordered as G-blocks from IDT encoding codon optimized genes for expression in human cells. G-blocks were cloned via GG-assembly into the vector backbone of pBLO62.5, downstream fused to two SV40 NLSs via a GSG linker encoding sequence. The guide encoding sequence of pBLO62.5 was exchanged to encode for a single CRISPR-repeat of the respective homologue, followed by a 20 bp stuffer spacer sequence amenable to GG-assembly exchange using the restriction enzyme SapI. A list of plasmids and a brief description is given in FIG. 34 (providing Table 3). Plasmid sequences and maps will be made available on addgene. To reprogram the CasΦ vectors to target different loci, stuffer-spacer were exchanged via GG-assembly to encode the guide for the selected target site (guide spacer sequences are listed in FIG. 35 (providing Table 4)). Mutations in the casΦ genes were introduced by GG-assembly to create dcasΦ genes.

PAM Depletion DNA Interference Assay

PAM depletion assays were performed with both, CasΦ plasmids that either carried the whole CasΦ locus as derived from metagenomics (pPP049, pPP056 and pPP062), or with plasmids that contained only the casΦ gene and a mini CRISPR (pPP097, pPP102 and pPP107). Assays were performed as three individual biological replicates. Plasmids containing casΦ and mini CRISPRs were transformed into *E. coli* BL21(DE3) (NEB) and constructs containing CasΦ genomic loci were transformed into *E. coli* DH5a (QB3-Macrolab, UC Berkeley). Subsequently, electrocompetent cells were prepared by ice cold $H_2O$ and 10% glycerol washing. A plasmid library was constructed with 8 randomized nucleotides upstream (5') end of the target sequence. Competent cells were transformed in triplicate by electroporation with 200 ng library plasmids (0.1 mm electroporation cuvettes (Bio-Rad) on a Micropulser electroporator (Bio-Rad)). After a two-hour recovery period, cells were plated on selective media and colony forming units were determined to ensure appropriate coverage of all possible combinations of the randomized 5' PAM region. Strains were grown at 25° C. for 48 hours on media containing appropriate antibiotics (either 100 µg/mL carbenicillin and 34 µg/mL chloramphenicol, or 100 µg/mL carbenicillin and 50 µg/mL kanamycin) and 0.05 mM isopropyl-β-D-thiogalactopyranoside (IPTG), or 200 nM anhydrotetracycline (aTc), depending on the vector to ensure propagation of plasmids and CasΦ effector production. Subsequently, propagated plasmids were isolated using a QIAprep Spin Miniprep Kit (Qiagen).

PAM Depletion Sequencing Analysis

Amplicon sequencing of the targeted plasmid was used to identify PAM motifs that are preferentially depleted. Sequencing reads were mapped to the respective plasmids and PAM randomized regions were extracted. The abundance of each possible 8 nucleotide combination was counted from the aligned reads and normalized to the total reads for each sample. Enriched PAMs were computed by calculating the log ratio compared to the abundance in the control plasmids, and were used to produce sequence logos.

RNA Preparation for RNAseq

Plasmids containing CasΦ loci were transformed into chemically competent E. coli DH5α (QB3-Macrolab, UC Berkeley). Preparations were performed as three individual biological replicates. Single colonies were picked to inoculate 5 mL starter cultures (LB, 34 µg/mL chloramphenicol) which were incubated at 37° C. shaking vigorously overnight. The next morning, main cultures were inoculated 1:100 (LB, 34 µg/mL chloramphenicol) and locus expression was induced with 200 nM aTc for 24 h at 16° C. Cells were harvested by centrifugation, resuspended in lysis buffer (20 mM Hepes-Na pH 7.5 RT, 200 mM NaCl) and lysed using glass beads (0.1 mm glass beads, 4×30 s vortex at 4° C., interspaced by 30 s cool-down on ice). 200 µL cell lysis supernatant were transferred into Trizol® for RNA extraction according to the manufacturer's protocol (Ambion). 10 µg RNA were treated with 20 units of T4-PNK (NEB) for 6 h at 37° C. for 2'-3'-dephosphorylation. Subsequently, 1 mM ATP was added and the sample was incubated for 1 h at 37° C. for 5'-phosphorylation before heat inactivation at 65° C. for 20 min and subsequent Trizol® purification.

RNA Analysis by RNAseq cDNA libraries were prepared using the RealSeq®-AC miRNA library kit illumina sequencing (somagenics). cDNA libraries were subjected to Illumina MiSeq® sequencing, and raw sequencing data was processed to remove adapters and sequencing artifacts, and high-quality reads were maintained. The resulting reads were mapped to their respective plasmids to determine the CRISPR locus expression and crRNA processing, and coverage was calculated at each region.

Efficiency of transformation plasmid interference assay

CasΦ vectors were transformed into chemically competent E. coli BL21(DE3) (NEB). Individual colonies for biological replicates were picked to inoculate three 5 mL (LB, Kanamycin 50 µg/mL) starter cultures to prepare electrocompetent cells the following day. 50 mL (LB, Kanamycin 50 µg/mL) main cultures were inoculated 1:100 and grown vigorously shaking at 37° C. to an $OD_{600}$ of 0.3. Subsequently, the cultures were cooled to room temperature and casΦ expression was induced with 0.2 mM IPTG. Cultures were grown to an $OD_{600}$ of 0.6-0.7 at 25° C., before preparation of electrocompetent cells by repeated ice-cold $H_2O$ and 10% glycerol washes. Cells were resuspended in 250 µL 10% glycerol. 90 µL aliquots were flash frozen in liquid nitrogen and stored at −80° C. The next day, 80 µL competent cells were combined with 3.2 µt plasmid (20 ng/µL pUC19 target plasmid, or 20 ng/µL pYTK001 control plasmid), incubated for 30 min on ice and split into three individual 25 µL transformation reactions. After electroporation in 0.1 mm electroporation cuvettes (Bio-Rad) on a Micropulser electroporator (Bio-Rad), cells were recovered in 1 mL recovery medium (Lucigen) supplemented with 0.2 mM IPTG, shaking at 37° C. for one hour. Subsequently, 10-fold dilution series were prepared and 5 µL of the respective dilution steps were spot-plated on LB-Agar containing the appropriate antibiotics. Plates were incubated overnight at 37° C. and colonies were counted the following day to determine the transformation efficiency. To assess the transformation efficiency, the mean and standard deviations were calculated from the cell forming units per ng transformed plasmids for the electroporation triplicates.

Protein Production and Purification

CasΦ overexpression vectors were transformed into chemically competent E. coli BL21(DE3)-Star (QB3-Macrolab, UC Berkeley) and incubated overnight at 37° C. on LB-Kan agar plates (50 µg/mL Kanamycin). Single colonies were picked to inoculate 80 mL (LB, Kanamycin 50 µg/mL) starter cultures which were incubated at 37° C. shaking vigorously overnight. The next day, 1.5 L TB-Kan medium (50 µg/mL Kanamycin) were inoculated with 40 mL starter culture and grown at 37° C. to an $OD_{600}$ of 0.6, cooled down on ice for 15 min and gene expression was subsequently induced with 0.5 mM IPTG followed by incubation overnight at 16° C. Cells were harvested by centrifugation and resuspended in wash buffer (50 mM HEPES-Na pH 7.5 RT, 1 M NaCl, 20 mM imidazole, 5% glycerol and 0.5 mM TCEP), subsequently lysed by sonication, followed by lysate clarification by centrifugation. The soluble fraction was loaded on a 5 mL Ni-NTA Superflow Cartridge (Qiagen) pre-equilibrated in wash buffer. Bound proteins were washed with 20 column volumes (CV) wash buffer and subsequently eluted in 5 CV elution buffer (50 mM HEPES-Na pH 7.5 RT, 500 mM NaCl, 500 mM imidazole, 5% glycerol and 0.5 mM TCEP). The eluted proteins were concentrated to 1 mL before injection into a HiLoad 16/600 Superdex® 200 pg column (GE Healthcare) pre-equilibrated in size-exclusion chromatography buffer (20 mM HEPES-Na pH 7.5 RT, 500 mM NaCl, 5% glycerol and 0.5 mM TCEP). Peak fractions were concentrated to 1 mL and concentrations were determined using a NanoDrop® 8000 Spectrophotometer (Thermo Scientific). Proteins were purified at a constant temperature of 4° C. and concentrated proteins were kept on ice to prevent aggregation, snap frozen in liquid nitrogen and stored at −80° C. AsCas12a was purified as previously described (Knott et al. (2019) Nat. Struct. Mol. Biol. 26:315).

In Vitro Cleavage Assays—Spacer Tiling

Plasmid targets were cloned by GG-assembly of spacer 2, found in the CRISPR-array of CasΦ-1, downstream to a cognate 5'-TTA PAM, or non-cognate 5'-CCA PAM into pYTK095 (Target sequences are given in FIG. 36 (providing Table 5)). Supercoiled plasmids were prepared by propagation of the plasmid overnight at 37° C. in E. coli Mach1 (QB3-Macrolab, UC Berkeley) in LB and Carbenicillin (100 µg/mL) and subsequent preparation using a Qiagen Miniprep kit (Qiagen). Linear DNA targets were prepared by PCR from the plasmid target. crRNA guides were ordered as synthetic RNA oligos from IDT (FIG. 37 (providing Table 6)), dissolved in DEPC $H_2O$ and heated for 3 min at 95° C. before cool down at RT. Active RNP complexes were assembled at a concentration of 1.25 µM by mixing protein and crRNA (IDT) in a 1:1 molar ratio in cleavage buffer (10 mM Hepes-K pH 7.5 RT, 150 mM KCl, 5 mM $MgCl_2$, 0.5 mM TCEP) and incubation at RT for 30 min. Cleavage reactions were initiated by addition of DNA (10 nM) to preformed RNP (1 µM) in reaction buffer (10 mM Hepes-K pH 7.5 RT, 150 mM KCl, 5 mM $MgCl_2$, 0.5 mM TCEP). The reactions were incubated at 37° C., quenched with 50 mM EDTA and stored in liquid nitrogen. Samples were thawed and treated with 0.8 units proteinase K (NEB) for 20 min at 37° C. Loading dye was added (Gel Loading Dye Purple 6×, NEB) and samples were analyzed by electrophoresis on a 1% agarose gel and stained with SYBR Safe (Thermo Fisher Scientific). For comparison to cleavage products, supercoiled plasmids were digested with PciI (NEB) for linearization and Nt.BstNBI (NEB) for plasmid nicking and open circle formation. Comparable cleavage assays under varied conditions (n≥3) showed consistent results.

In Vitro Cleavage Assays—Radiolabeled Nucleic Acids

Active CasΦ RNP complexes were assembled in a 1:1.2 molar ratio by diluting CasΦ protein to 4 μM and crRNA (IDT) to 5 μM in RNP assembly buffer (20 mM HEPES-Na pH 7.5 RT, 300 mM KCl, 10 mM MgCl$_2$, 20% glycerol, 1 mM TCEP) and incubation for 30 min at RT. Substrates were 5'-end-labelled using T4-PNK (NEB) in the presence of $^{32}$P-γ-ATP (Substrate sequences are given in FIG. 36 (providing Table 5)). Oligo-duplex targets were generated by combining $^{32}$P-labelled and unlabelled complementary oligonucleotides in a 1:1.5 molar ratio. Oligos were hybridized to a DNA-duplex concentration of 50 nM in hybridization buffer (10 mM Tris-Cl pH 7.5 RT, 150 mM KCl), by heating for 5 min to 95° C. and a slow cool down to RT in a heating block. Cleavage reactions were initiated by combining 200 nM RNP with 2 nM substrate in reaction buffer (10 mM HEPES-Na pH 7.5 RT, 150 mM KCl, 5 mM MgCl$_2$, 10% glycerol, 0.5 mM TCEP) and subsequently incubated at 37° C. For trans-cleavage assays, guide complementary activator substrates were diluted in oligonucleotide hybridization buffer (10 mM Tris pH 7.8 RT, 150 mM KCl) to a concentration of 4 μM, heated to 95° C. for 5 min, and subsequently cooled down at RT to allow duplex formation for double stranded activator substrates. Cleavage reactions were set up by combining 200 nM RNP with 100 nM activator substrate and incubation for 10 min at RT before addition of 2 nM ssDNA, or ssRNA, trans cleavage substrates. Reactions were stopped by addition of two volumes formamide loading buffer (96% formamide, 100 μg/mL bromophenol blue, 50 μg/mL xylene cyanol, 10 mM EDTA, 50 μg/mL heparin), heated to 95° C. for 5 min, and cooled down on ice before separation on a 12.5% denaturing urea-PAGE. Gels were dried for 4 h at 80° C. before phosphor-imaging visualization using an Amersham Typhoon™ scanner (GE Healthcare). Technical replicates (n≥2) and comparable cleavage assays under varied conditions (n≥3) of biological replicates (n≥2) showed consistent results. Bands were quantified using ImageQuant™ TL (GE) and cleaved substrate was calculated from the intensity relative to the intensity observed at t=0 min. Curves were fit to a One-Phase-Decay model in Prism 8 (graphpad) to derive the rate of cleavage.

In Vitro Pre-crRNA Processing Assay

Pre-crRNA substrates were 5'-end-labelled using T4-PNK (NEB) in the presence of $^{32}$P-γ-ATP (Substrate sequences are given in FIG. 36 (providing Table 5)). Processing reactions were initiated by combining 50 nM CasΦ with 1 nM substrate in pre-crRNA processing buffer (10 mM Tris pH 8 RT, 200 mM KCl, 5 mM MgCl$_2$ or 25 mM EDTA, 10% glycerol, 1 mM DTT) and subsequently incubated at 37° C. Substrate hydrolysis ladders were prepared using the alkaline hydrolysis buffer according to the manufacturer's protocol (Ambion). 10 μL of the processing reaction products were treated with 10 units T4-PNK (NEB) for 1 h at 37° C. in the absence of ATP for termini chemistry analysis. Reactions were stopped by addition of two volumes formamide loading buffer (96% formamide, 100 μg/mL bromophenol blue, 50 μg/mL xylene cyanol, 10 mM EDTA, 50 μg/mL heparin), heated to 95° C. for 3 min, and cooled down on ice before separation on a 12.5%, or 20%, denaturing urea-PAGE. Gels were dried for 4 h at 80° C. before phosphor-imaging visualization using an Amersham Typhoon™ scanner (GE Healthcare). Technical replicates (n≥3) and comparable cleavage assays under varied conditions (n≥3) of biological replicates (n≥2) showed consistent results. Bands were quantified using ImageQuant™ TL (GE) and processed RNA was calculated from the intensity at t=60 min relative to the intensity observed at t=0 min.

Analytical Size Exclusion Chromatography

500 μL samples (5-10 μM protein, RNA, or reconstituted RNPs) were injected onto a S200 XK10/300 size exclusion chromatography (SEC) column (GE Healthcare) pre-equilibrated in SEC buffer (20 mM HEPES-Cl pH 7.5 RT, 250 mM KCl, 5 mM MgCl$_2$, 5% glycerol and 0.5 mM TCEP). Prior to SEC, CasΦ RNP complexes were assembled by incubating CasΦ protein and pre-crRNA for 1 h in 2× pre-crRNA processing buffer (20 mM Tris pH 7.8 RT, 400 mM KCl, 10 mM MgCl$_2$, 20% glycerol, 2 mM DTT).

Genome Editing in Human Cells

The GFP HEK293 reporter cells were generated via lentiviral integration as previously described. Richardson et al, (2016) Nat. Biotechnol. 34:339. Cells were routinely tested for absence of mycoplasma using the MycoAlert Mycoplasma Detection Kit (Lonza), according to the manufacturer's protocol. GFP HEK293 reporter cells were seeded into 96-well plates and transfected at 60-70% confluency the next day according to the manufacturer's protocol with Lipofectamine® 3000 (Life Technologies) and 200 ng of plasmid DNA encoding the CasΦ gRNA and CasΦ-P2A-PAC fusion. As a comparison control, 200 ng of plasmid DNA encoding the SpyCas9 sgRNA and SpyCas9-P2A-PAC fusion was transfected identically, with target sequences adjusted for PAM differences. 24 hours post-transfection, successfully transfected cells were selected for by adding 1.5 μg/mL puromycin to the cell culture media for 72 hours. Cells were passaged regularly to maintain sub-confluent conditions and then analyzed on an Attune NxT Flow Cytometer with an autosampler. Cells were analyzed on the flow cytometer after 10 days to allow for clearance of GFP from cells.

Results

Figure 19A:
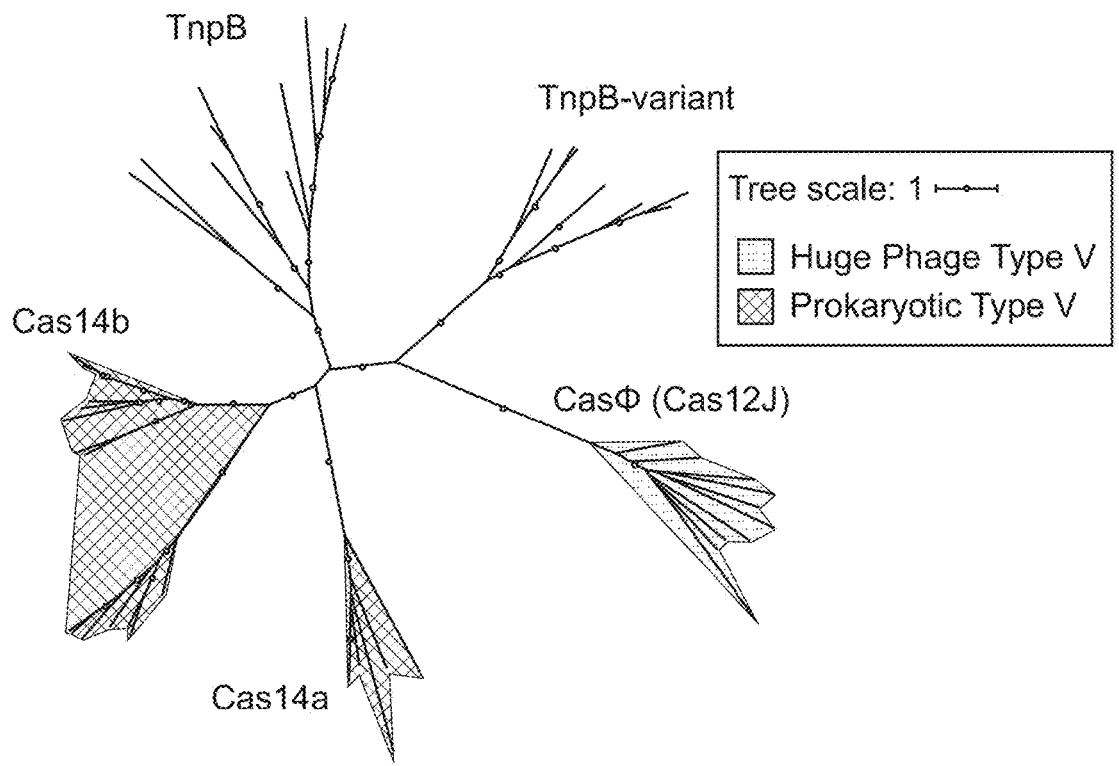
FIG. 19A-19F depict data showing that Cas12J (CasΦ) is a bona fide CRISPR-Cas system.
Figure 20:
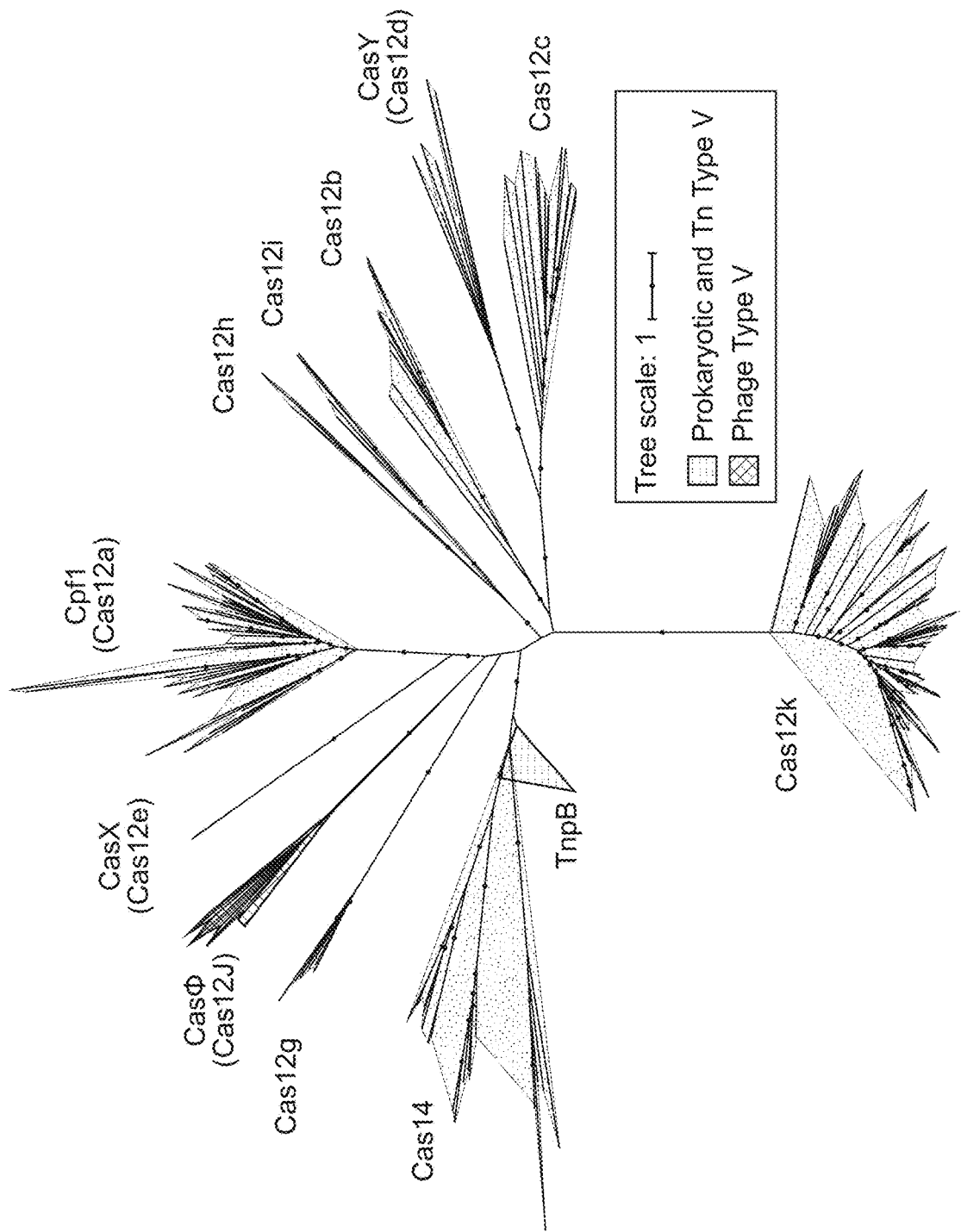
FIG. 20 presents a maximum likelihood phylogenetic tree of type V subtypes a-k.

Cas12J, or simply CasΦ as homage to its phage-restricted origin, is a previously unknown family of Cas proteins encoded in the Biggiephage clade. CasΦ contains a C-terminal RuvC domain with remote homology to that of the TnpB nuclease superfamily from which type V CRISPR-Cas proteins are thought to have evolved (FIG. 20). However, CasΦ shares <7% amino acid identity with other type V CRISPR-Cas proteins and is most closely related to a TnpB group distinct from miniature type V (Cas14) proteins (FIG. 19A).

Figure 19B:
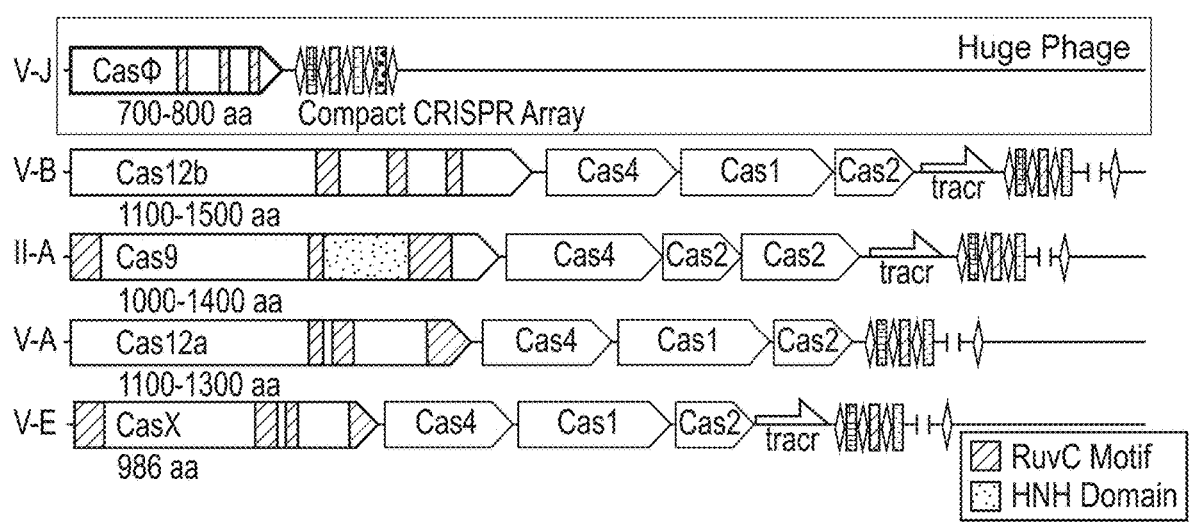

CasΦ's unusually small size of ~70-80 kDa, about half the size of the RNA-guided DNA cutting enzymes Cas9 and Cas12a (FIG. 19B), and its lack of co-occurring genes raised the question of whether CasΦ functions as a bona fide CRISPR-Cas system. Three different CasΦ orthologs from metagenomic assemblies were selected for study based on divergence of their protein and CRISPR repeat sequences (FIG. 21), referred to in FIG. 21 as CasΦ-1, CasΦ-2 and CasΦ-3. To investigate the ability of CasΦ to recognize and target DNA in bacterial cells, it was tested whether these systems could protect Escherichia coli from plasmid transformation. CRISPR-Cas systems are known to target DNA sequences following or preceding a 2-5 nucleotide Protospacer Adjacent Motif (PAM) for self-versus-non-self discrimination (Gleditzsch et al. (2019) RNA Biology 16:504).

Figure 19C:
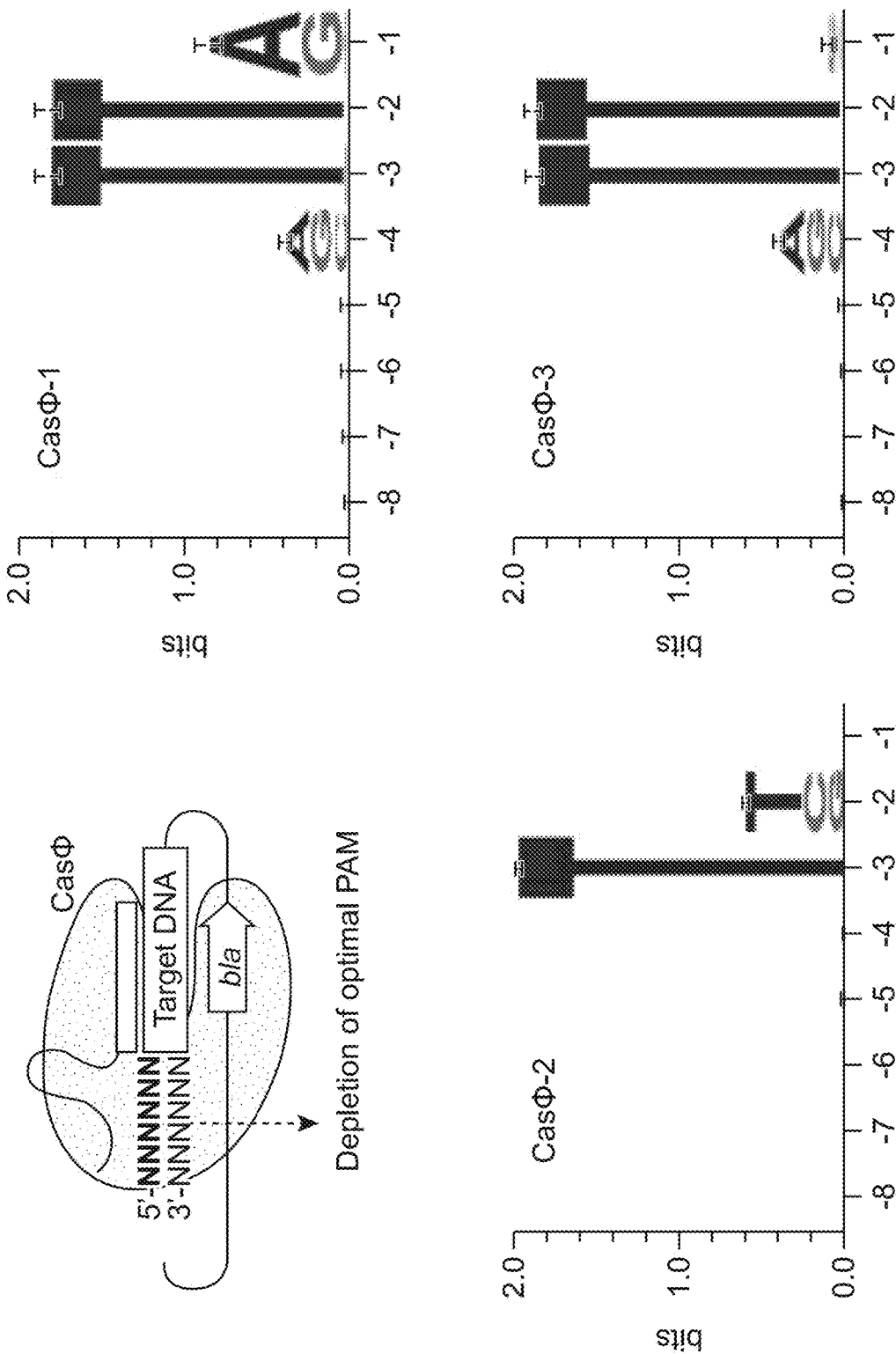

To determine whether CasΦ uses a PAM, a library of plasmids containing randomized regions adjacent to crRNA-complementary target sites was transformed into *E. coli*, thereby preferentially depleting plasmids including functional PAMs. This revealed the crRNA-guided double-strand DNA (dsDNA) targeting capability of CasΦ and distinct T-rich PAM sequences, including a minimal 5'-TBN-3' PAM observed for CasΦ-2 (FIG. 19C).

Figure 19D:
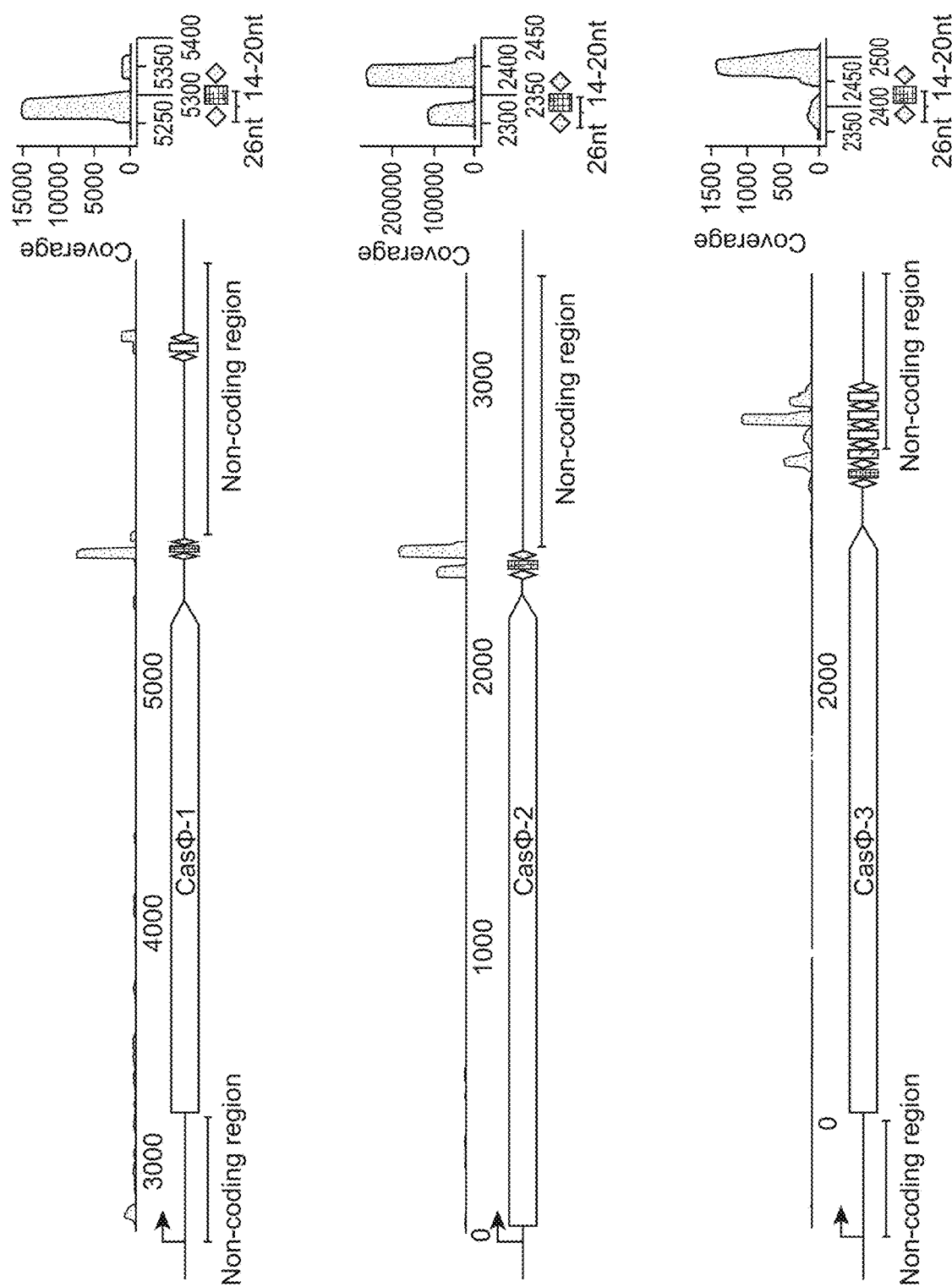
Figure 19E:
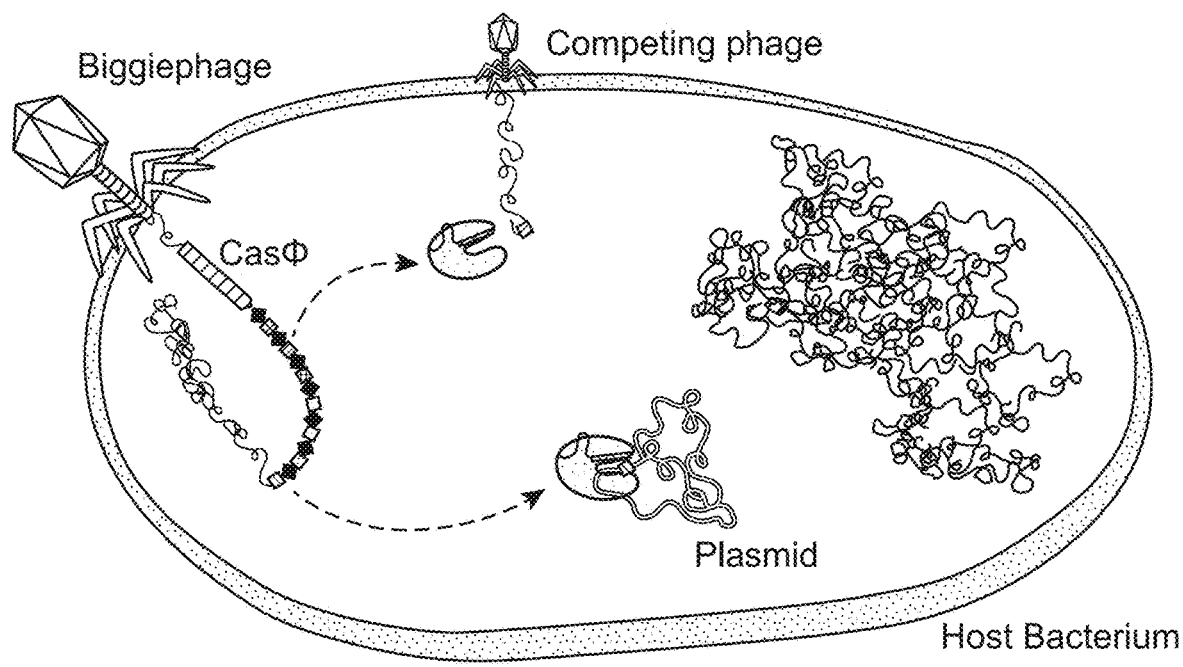
Figure 19F:
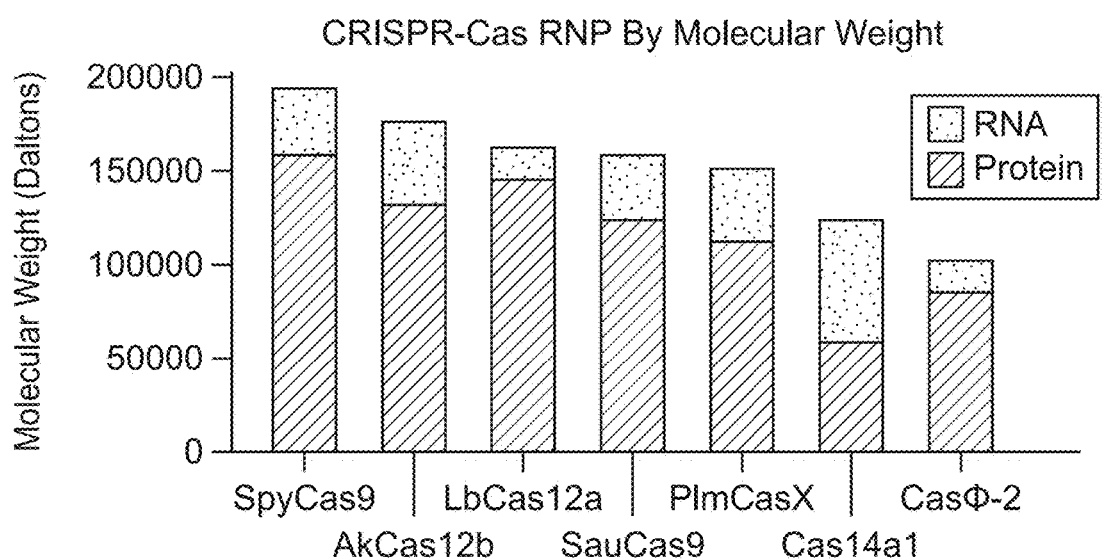
Figure 22A:
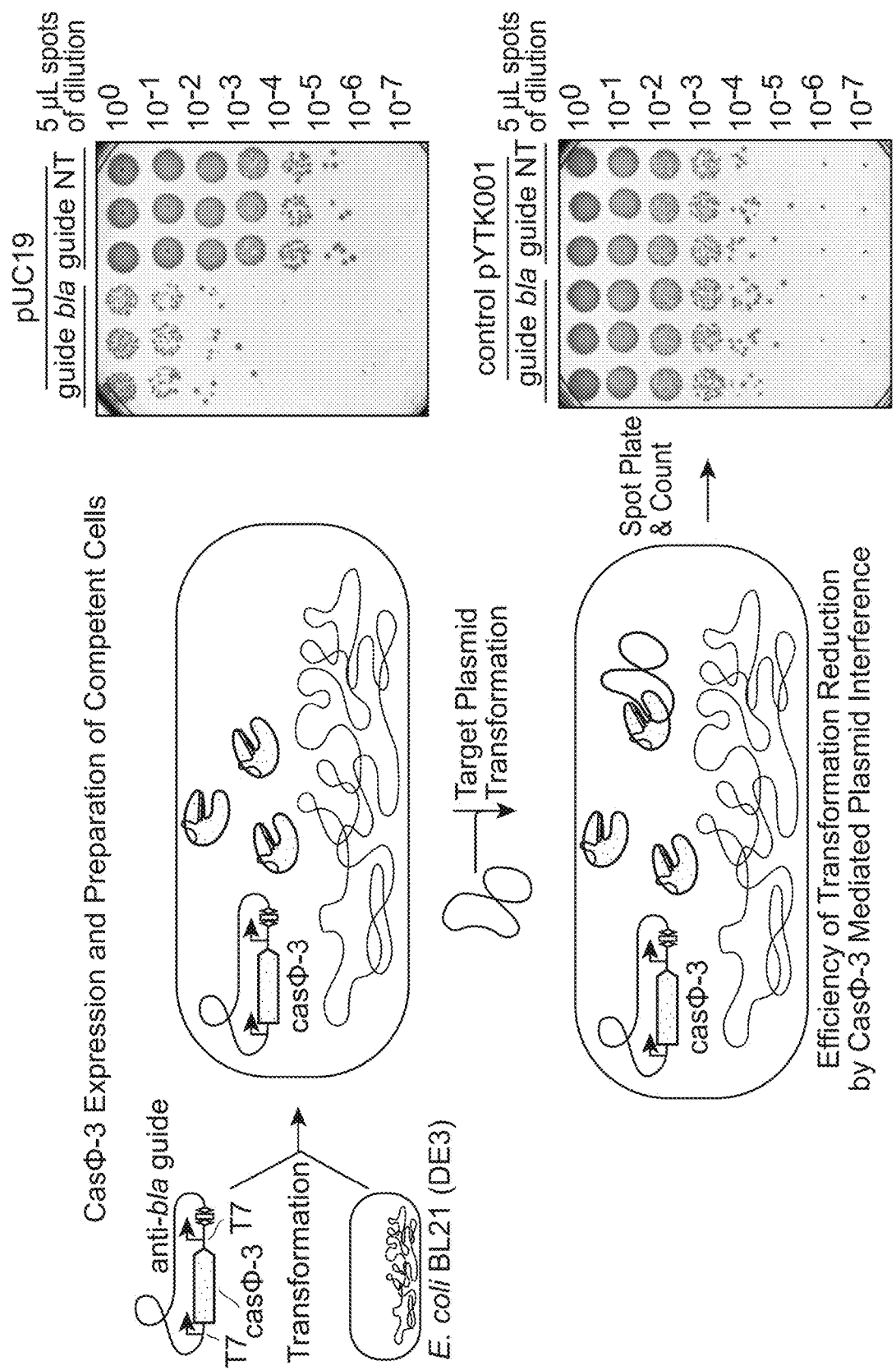
FIG. 22A-22C depict CasΦ-3-mediated protection against plasmid transformation.
Figure 22B:
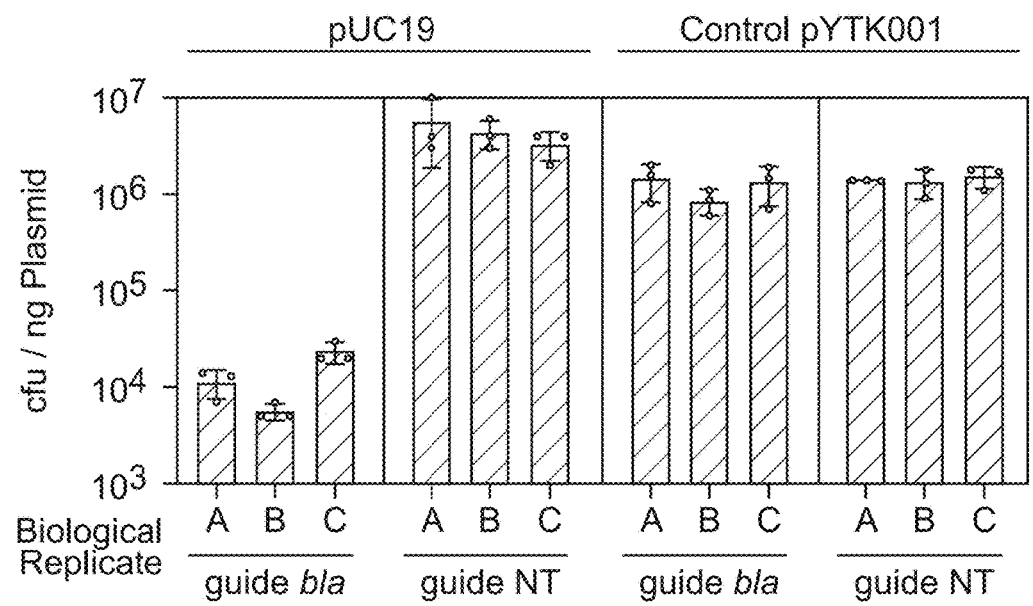
Figure 22C:
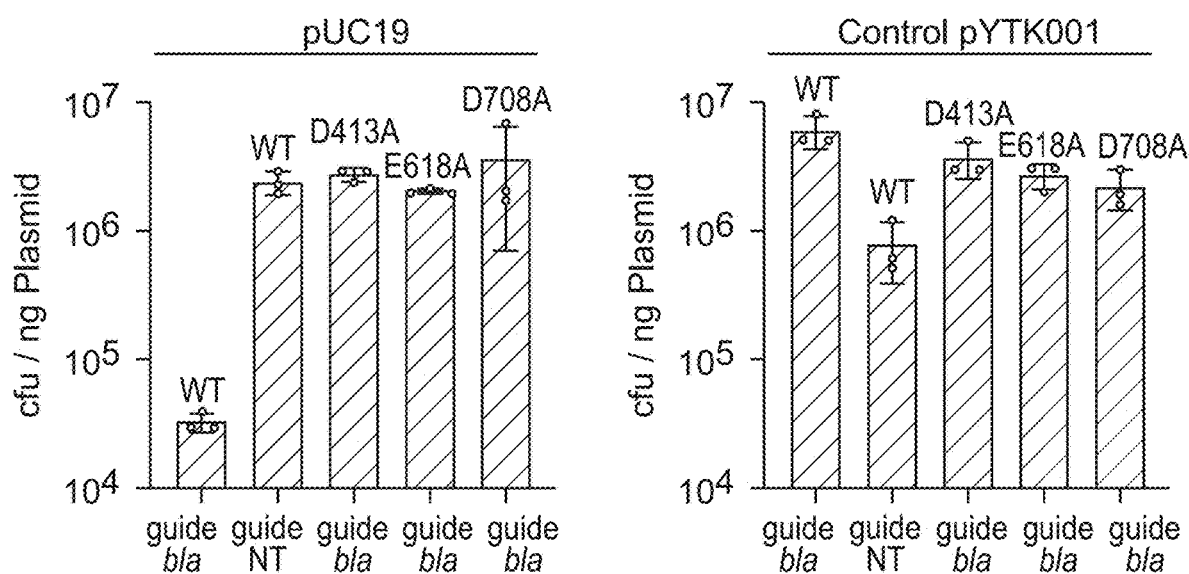

The *E. coli* expression system and plasmid interference assay was used to determine the components required for CRISPR-CasΦ system function. RNA-sequencing analysis revealed transcription of the casΦ gene and CRISPR array but no evidence of other non-coding RNA such as a trans-activating CRISPR RNA (tracrRNA) encoded in or near the locus (FIG. 19D). In addition, it was found that CasΦ activity could be readily directed against other plasmid sequences by altering the guide RNA, demonstrating the programmability of this system (FIG. 22A-22C). These findings suggest that in its native environment, CasΦ is a functional phage protein and bona fide CRISPR-Cas effector capable of cleaving DNA bearing complementarity to different crRNAs, likely other MGEs, to abrogate superinfection (FIG. 19E). Furthermore, these results demonstrate that this single-RNA system is much more compact than other active CRISPR-Cas systems (FIG. 19F).

Figure 23A:
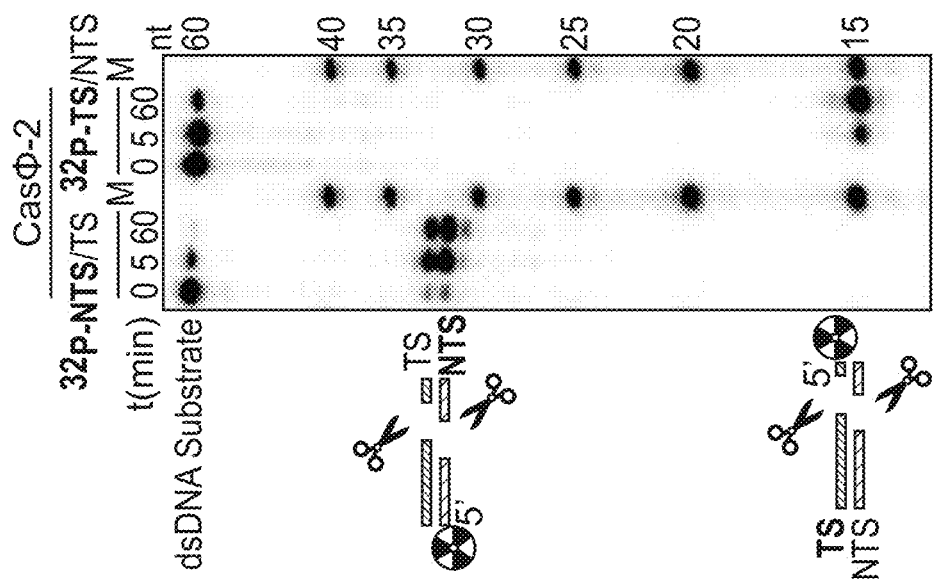
FIG. 23A-23D depict cleavage of DNA by CasΦ.
Figure 23B:
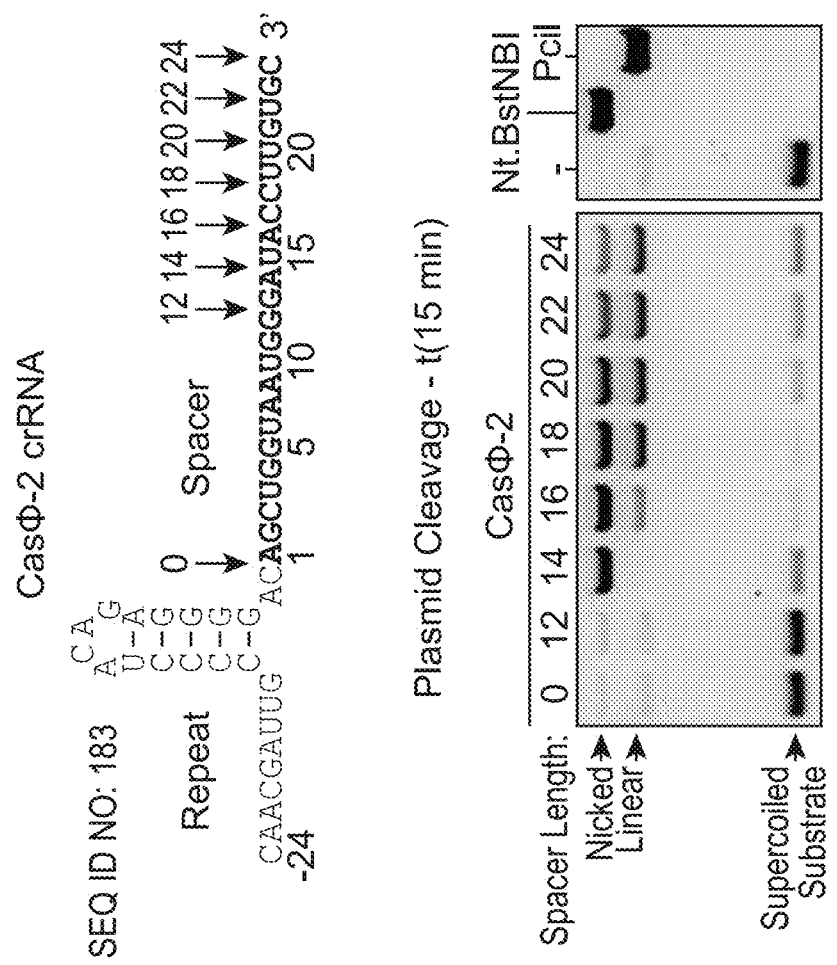
Figure 23C:
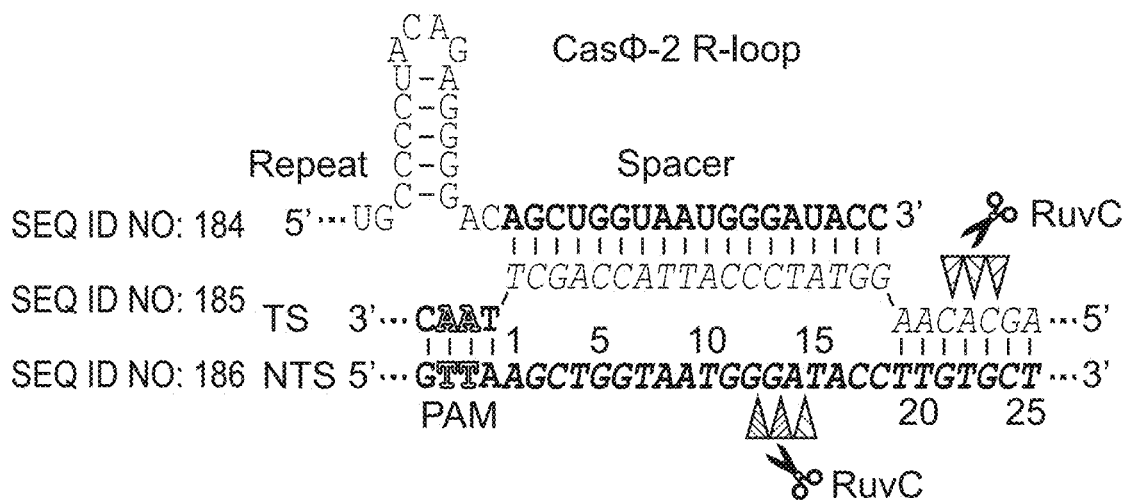
Figure 23D:
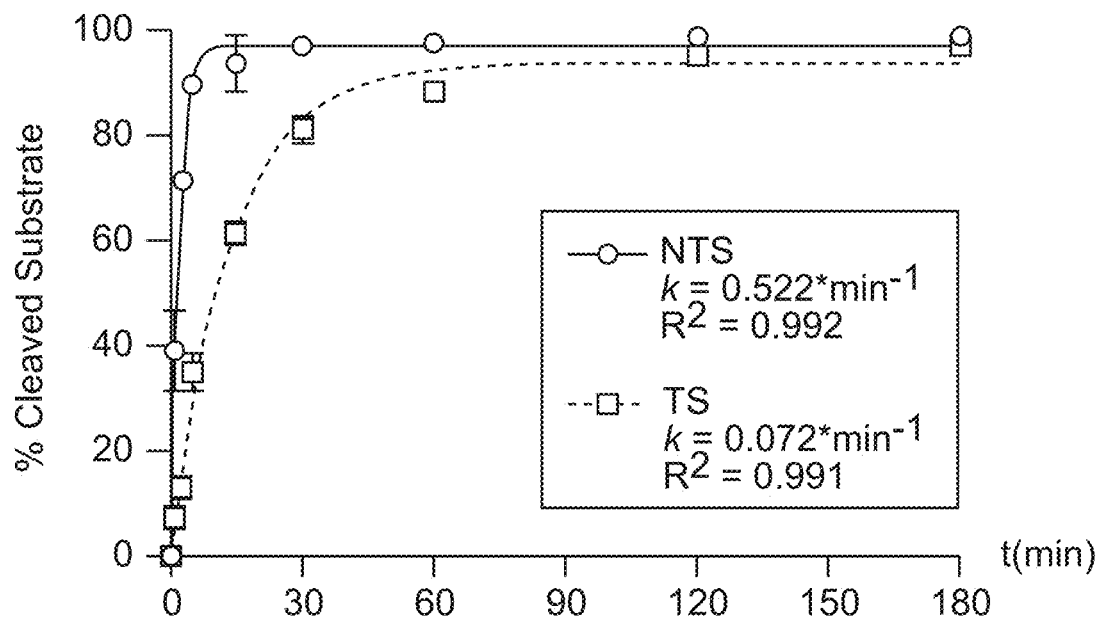
Figure 24A:
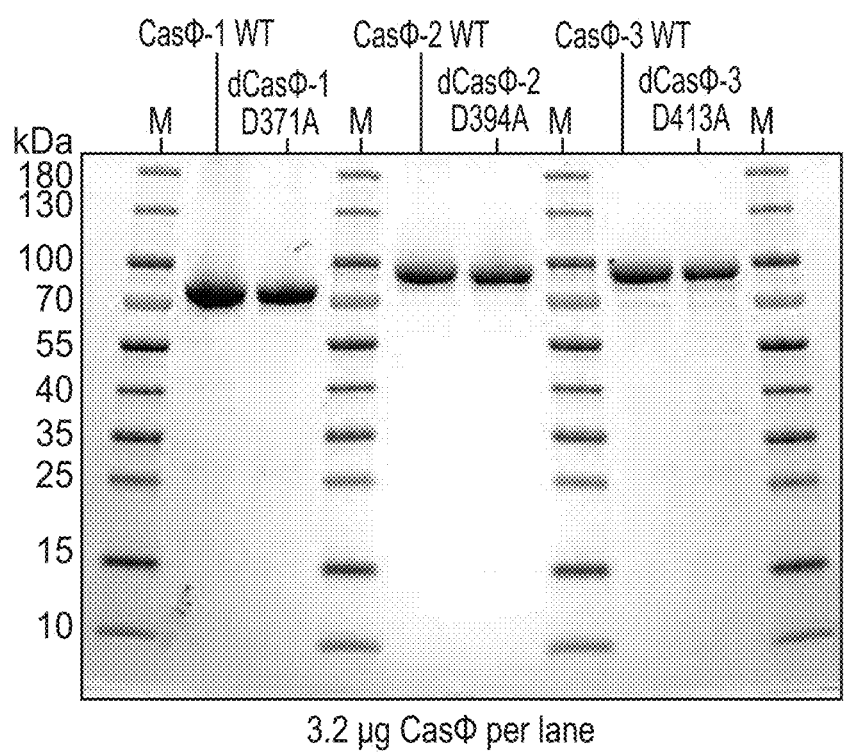
FIG. 24A-24D depict purification of apo CasΦ (CasΦ protein without guide RNA).
Figure 24B:
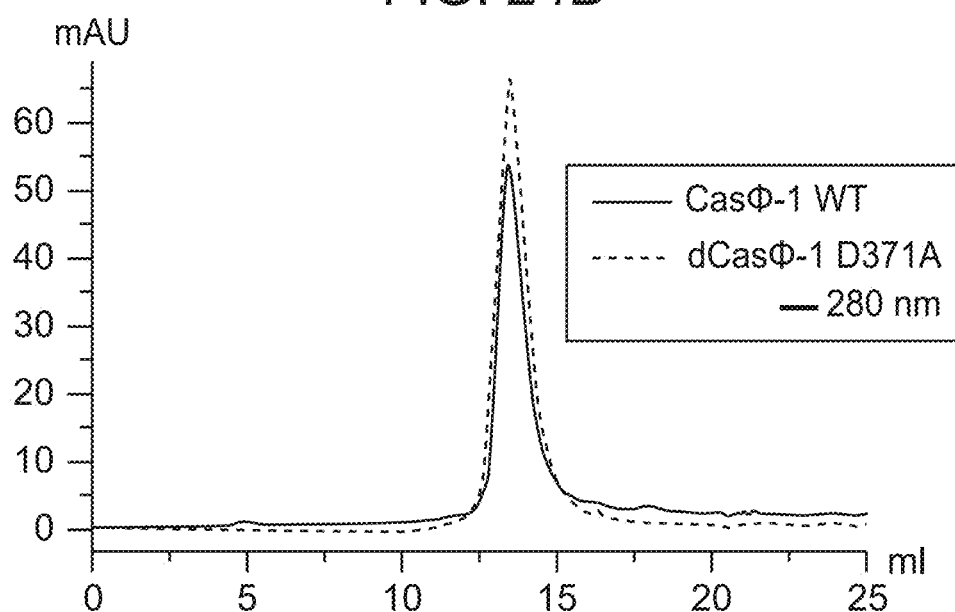
Figure 24C:
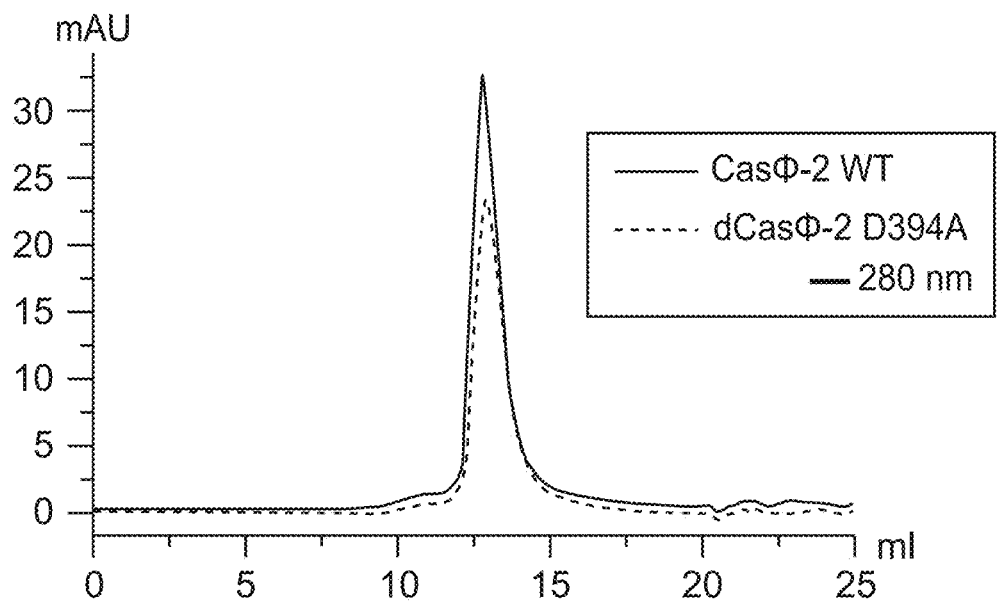
Figure 24D:
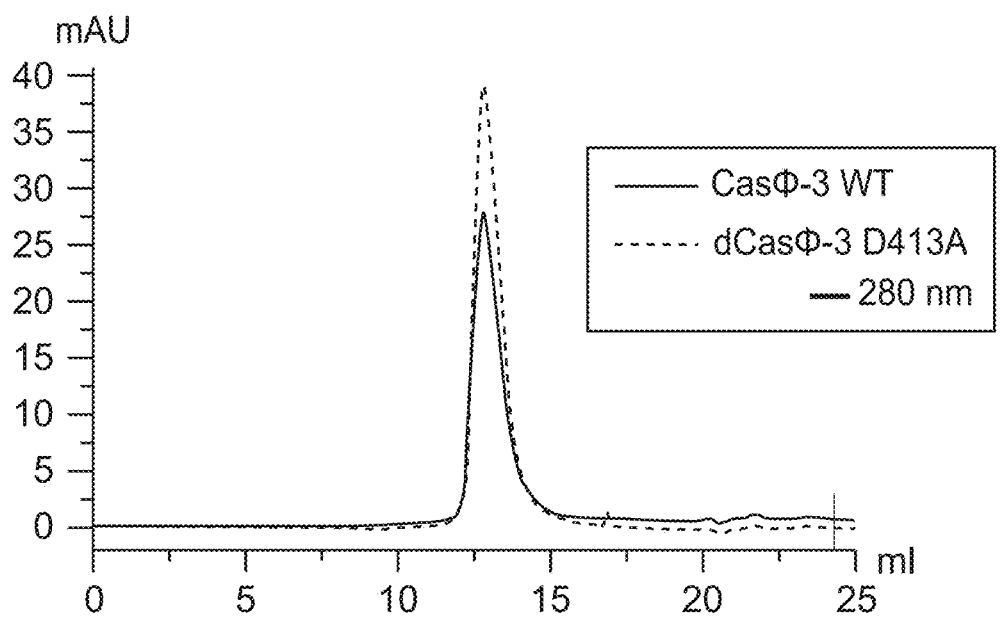
Figure 25A:
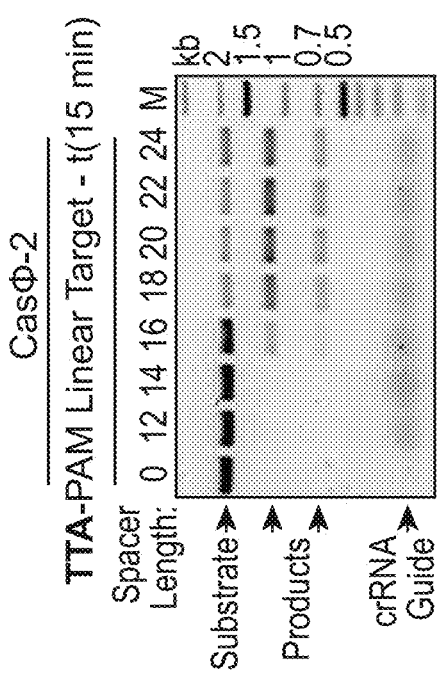
FIG. 25A-25C depict production of staggered cuts by CasΦ.
Figure 25B:
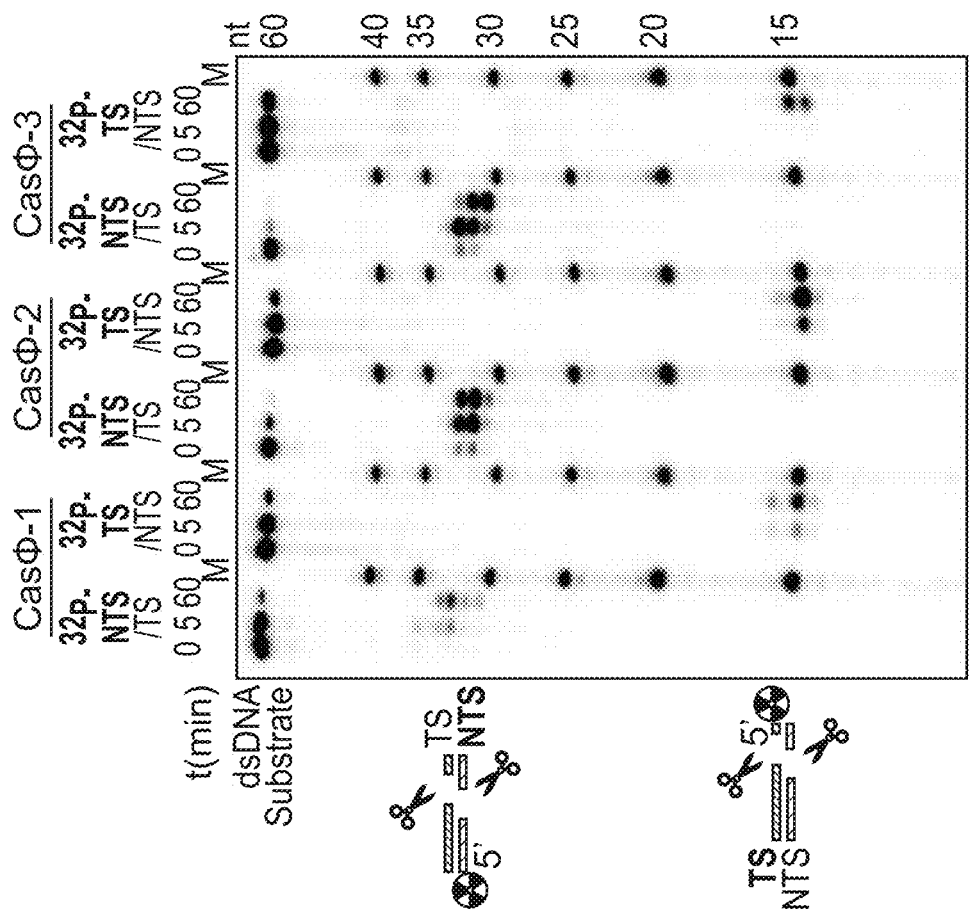
Figure 25C:
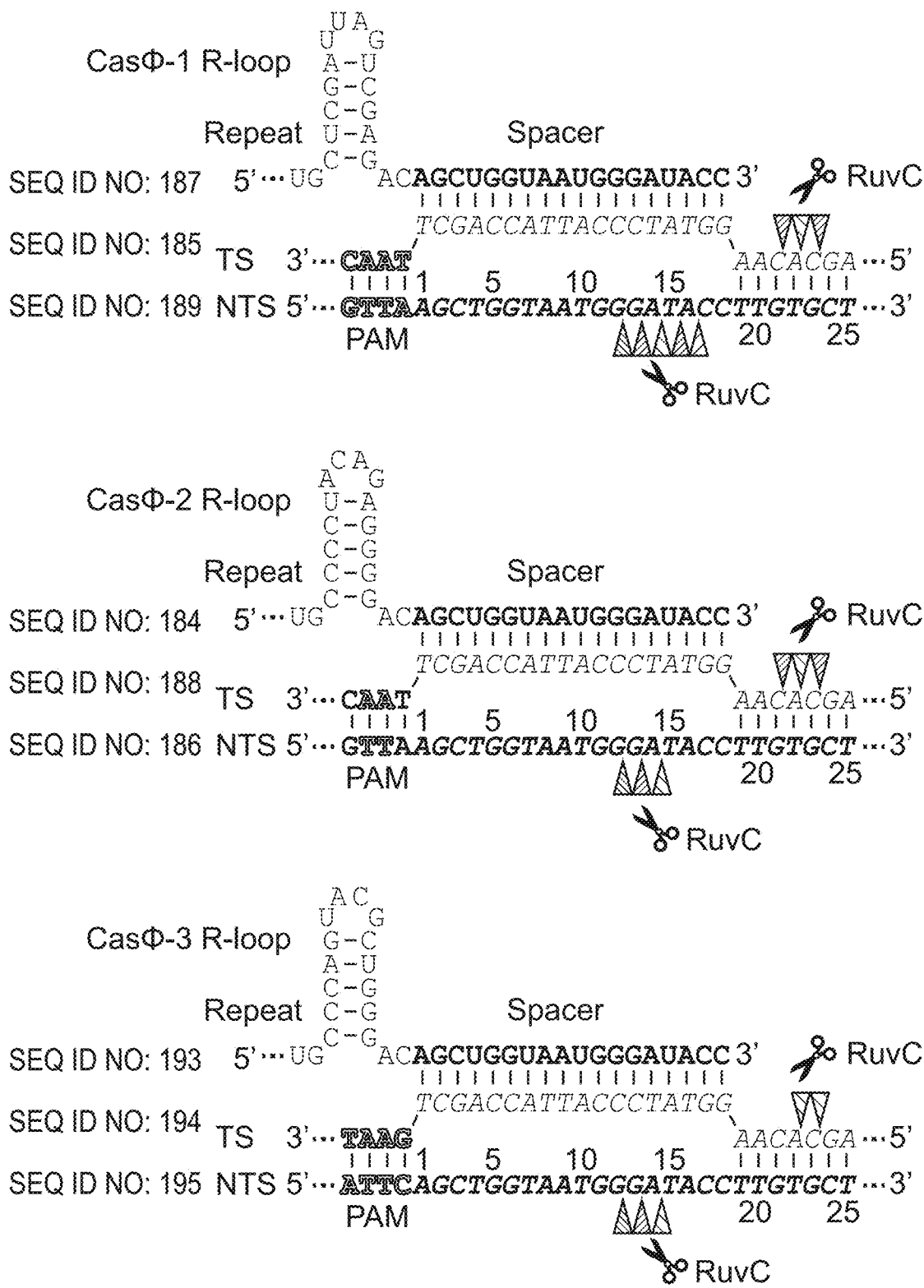
Figure 26A:
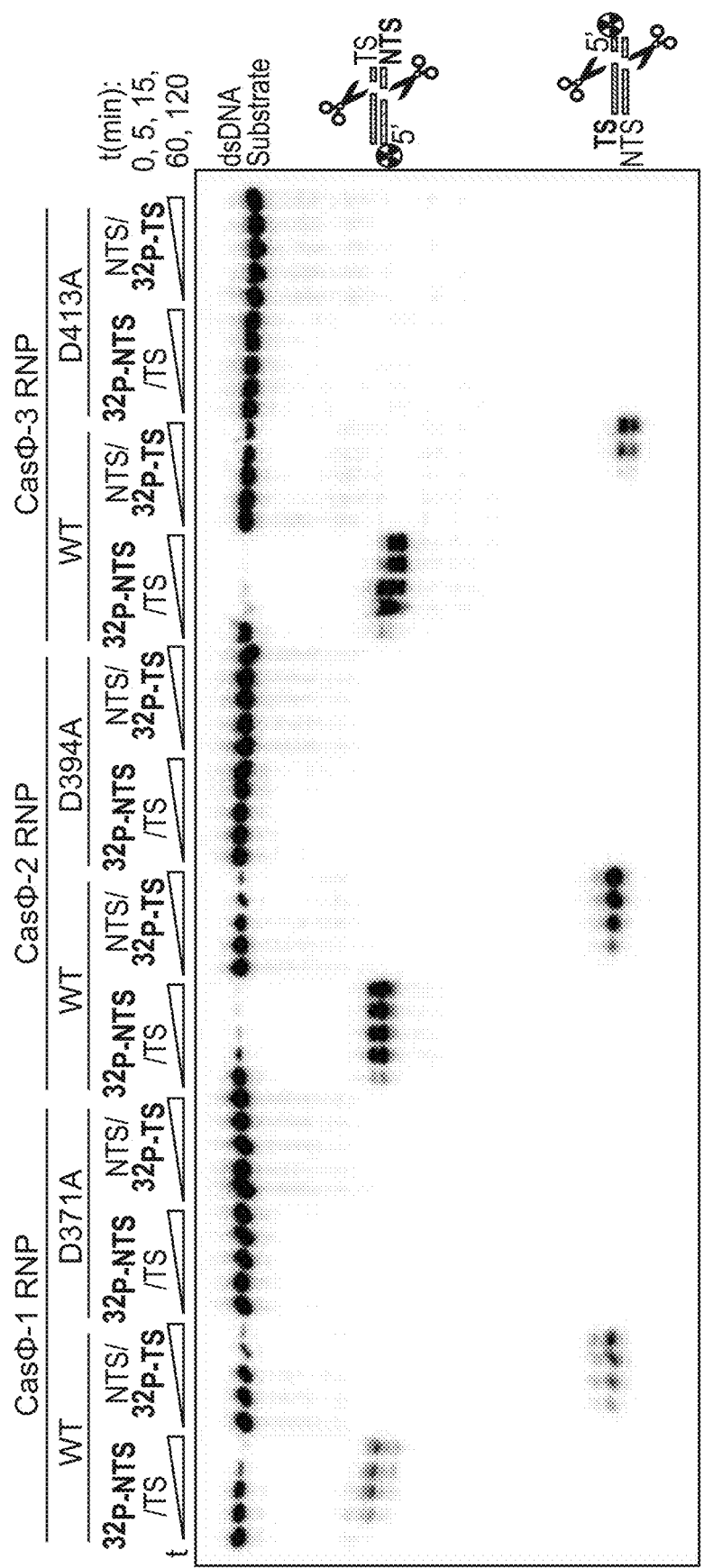
FIG. 26A-26B depict CasΦ-mediated cleavage of dsDNA and ssDNA.

CRISPR-Cas effector complexes identify and cleave foreign nucleic acids during the final stage of CRISPR-Cas mediated immunity against MGEs (Hille et al. (2018) *Cell* 172:1239). To determine how CasΦ achieves RNA-guided DNA targeting for Biggiephages, the recognition and cleavage requirements of CasΦ in vitro were investigated. RNA-seq revealed that the spacer sequence within the crRNA, which is complementary to DNA targets, is between 14-20 nucleotides (nt) long (FIG. 19D). Incubation of purified CasΦ (FIG. 24A-24D) with crRNAs of different spacer sizes along with supercoiled plasmid or linear dsDNA revealed that target DNA cleavage requires the presence of a cognate PAM and a spacer of ≥14 nt (FIG. 23A; FIG. 25A). Analysis of the cleavage products showed that CasΦ generates staggered 5'-overhangs of 8-12 nt (FIGS. 23B and 23C; FIGS. 25B and 25C), similar to the staggered DNA cuts observed for other type V CRISPR-Cas enzymes including Cas12a and CasX (Zetsche et al. (2015) *Cell* 163:759; Liu et al. (2019) *Nature* 566:218). It was observed that CasΦ-2 and CasΦ-3 were more active in vitro than CasΦ-1, and the non-target strand (NTS) was cleaved faster than the target-strand (TS) (FIG. 23D; FIG. 26A; FIGS. 27A and 27B). Furthermore, CasΦ was found to cleave ssDNA but not ssRNA targets (FIG. 26B), suggesting that CasΦ may also target ssDNA MGEs or ssDNA intermediates.

Figure 26B:
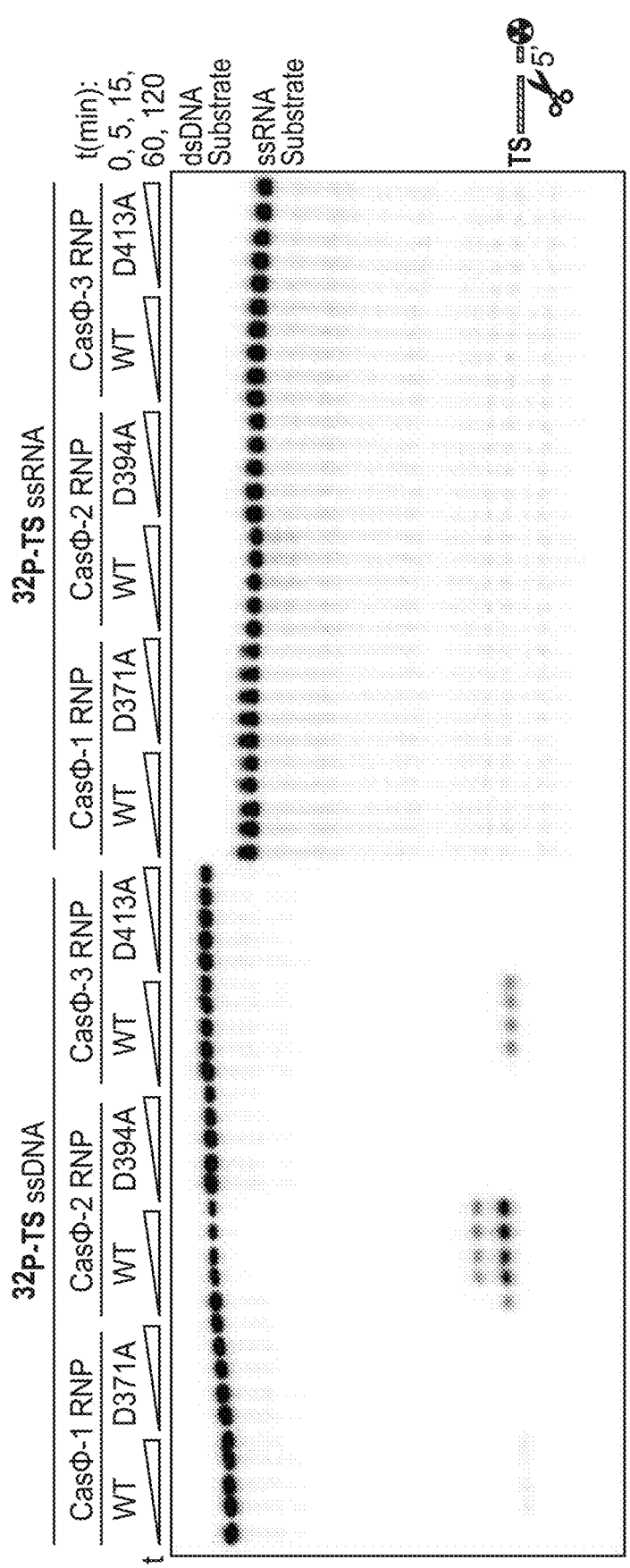
Figure 27A:
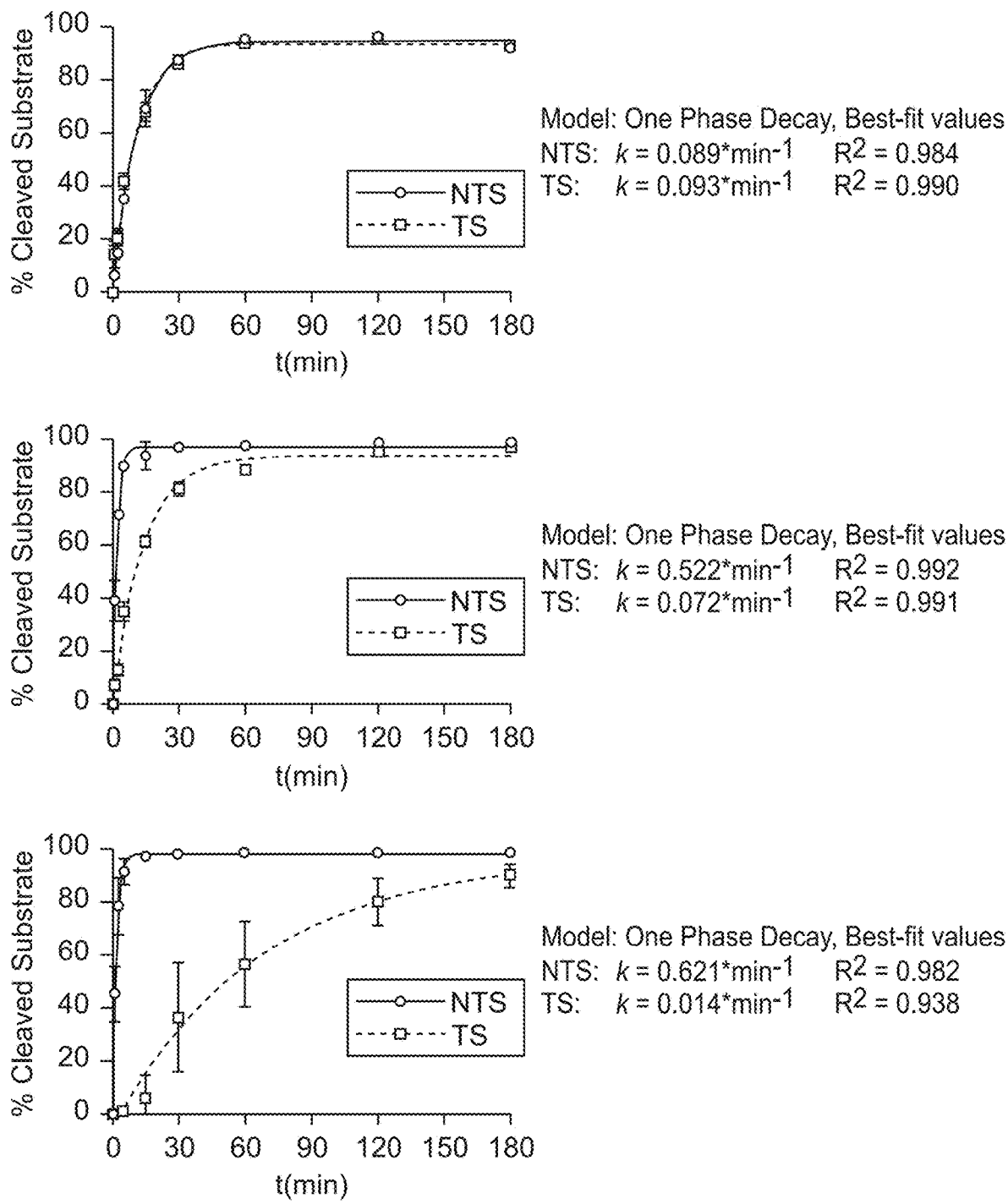
FIG. 27A-27B depict the results of a cleavage assay comparing target strand (TS) and non-target strand (NTS) cleavage efficiency by CasΦ.
Figure 27B:
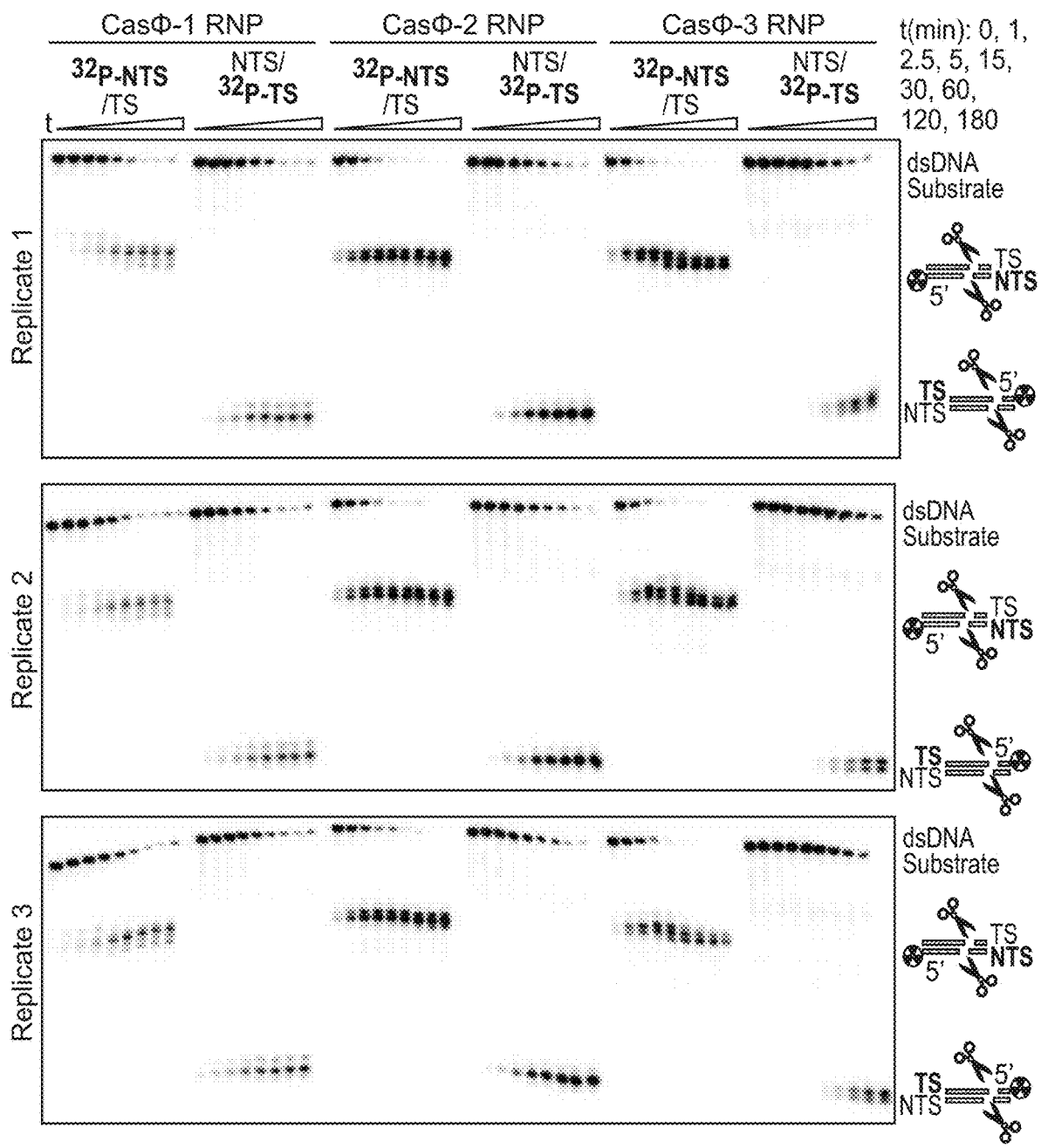

To assess the role of the RuvC domain in CasΦ-catalyzed DNA cleavage, the active site was mutated (D371A, D394A, or D413A) to produce a CasΦ variant (dCas0) that was found not to cleave dsDNA, ssDNA or ssRNA in vitro (FIGS. 26A and 26B). When expressed in *E. coli* along with the CRISPR array, dCasΦ could not prevent transformation of a crRNA-complementary plasmid, consistent with a requirement for RuvC-catalyzed DNA cutting (FIG. 22A-22B). This observation, together with the delayed cleavage of the target strand after non-target strand cleavage (FIG. 23D; FIGS. 27A and 27B), suggests that CasΦ cleaves each strand sequentially within the RuvC active site. Sequential dsDNA strand cleavage is consistent with the dsDNA cutting mechanism of the type V CRISPR-Cas proteins (10) that share closest evolutionary origin with CasΦ.

Figure 28A:
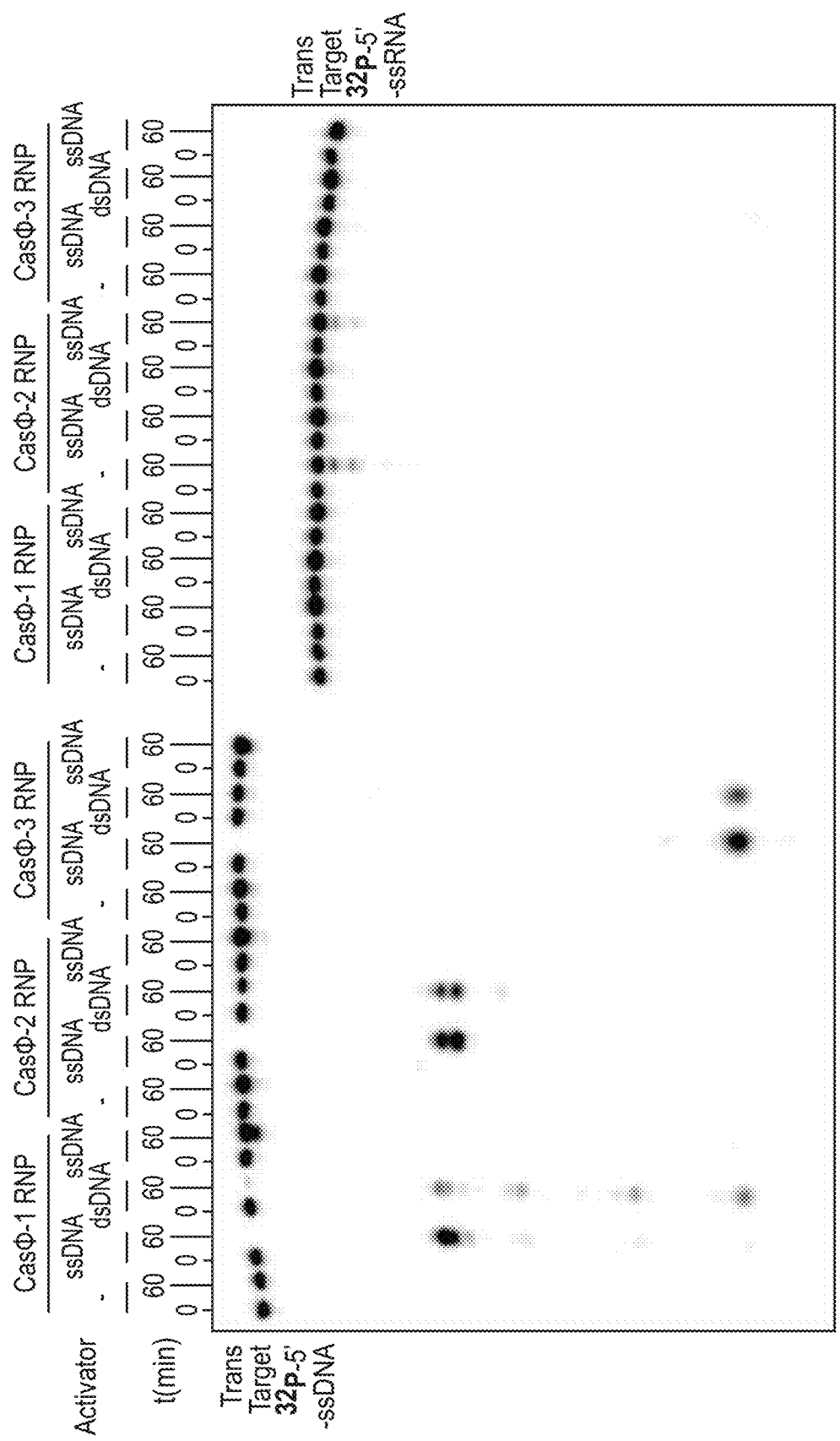
FIG. 28A-28B depict data showing that CasΦ cleaves ssDNA, but not RNA, in trans upon activation in cis.
Figure 28B:
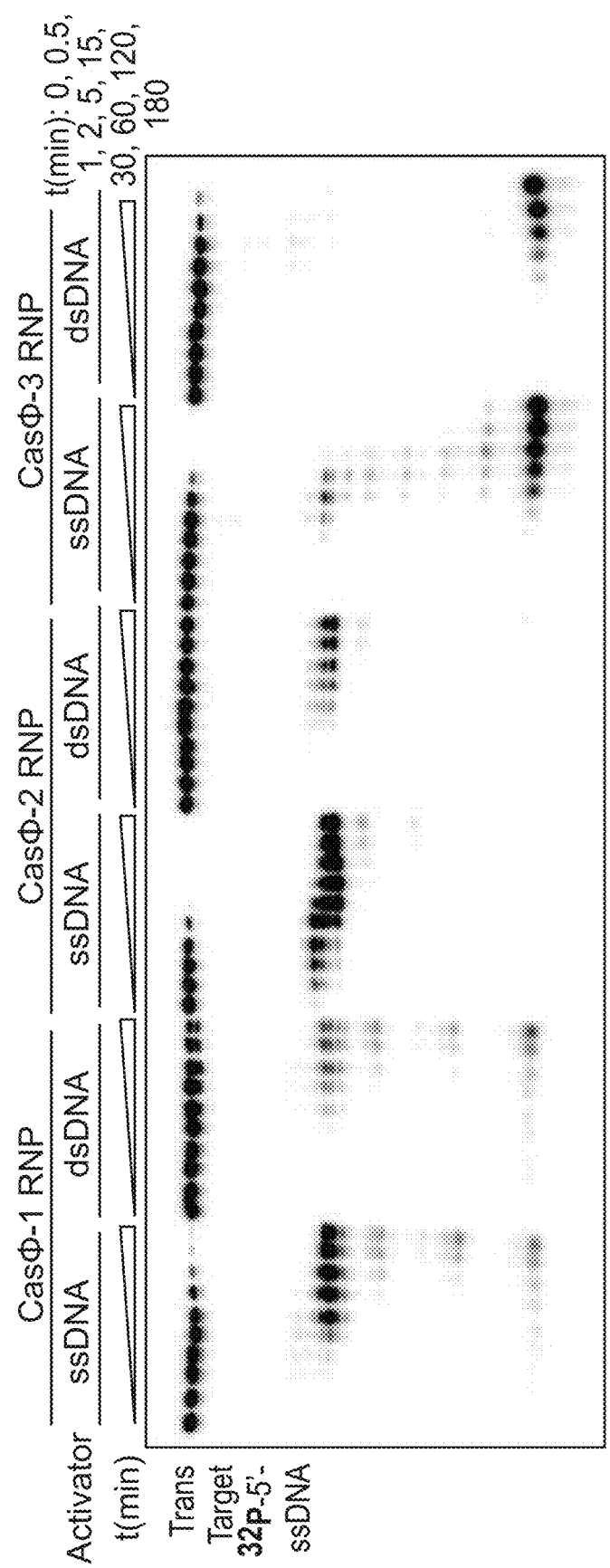

Furthermore, like other type V CRISPR-Cas effectors, CasΦ was found to degrade ssDNA in trans when activated by target dsDNA or ssDNA binding in cis. Trans single-stranded DNAse, but not RNAse, activity upon DNA target recognition in cis was observed (FIG. 28A-28B). This trans-cleavage activity, coupled with a minimal PAM requirement, may be useful for broader nucleic acid detection.

Figure 29A:
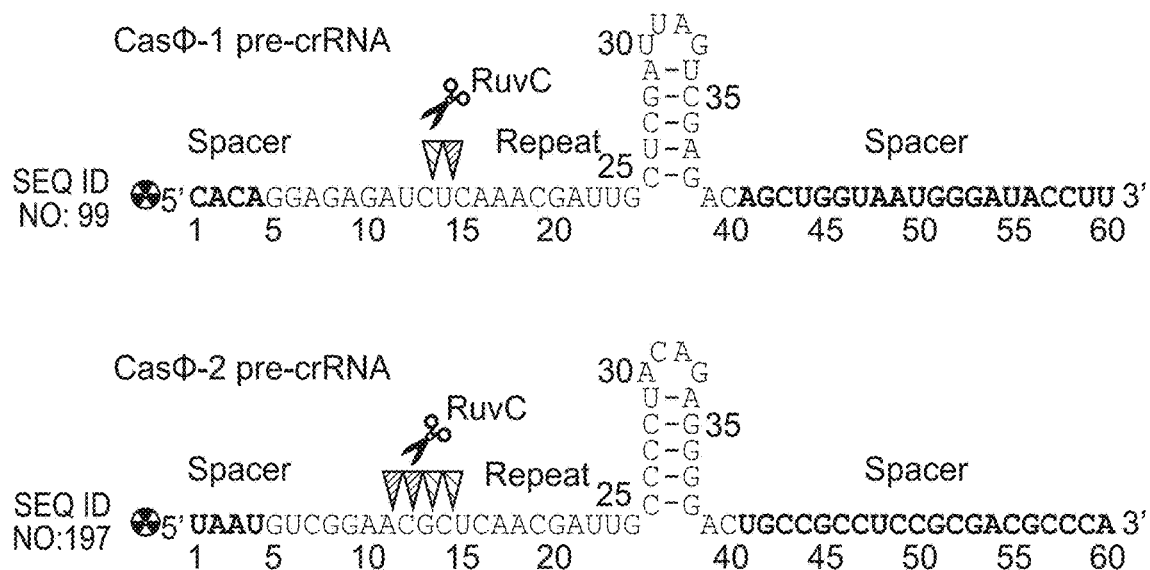
FIG. 29A-29D depict processing of pre-crRNA by CasΦ within the RuvC active site.
Figure 29B:
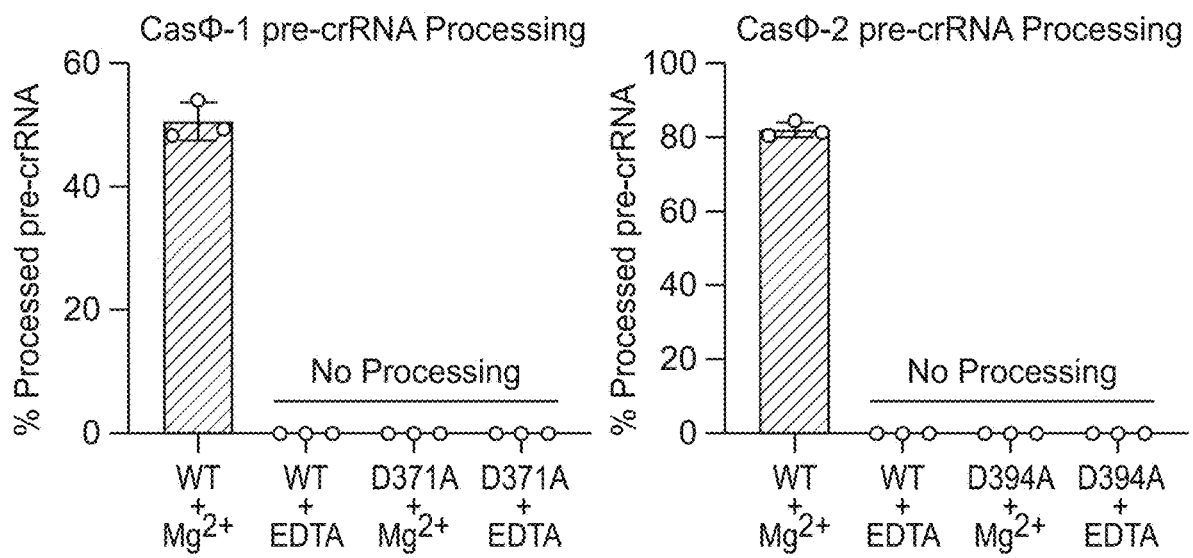
Figure 29C:
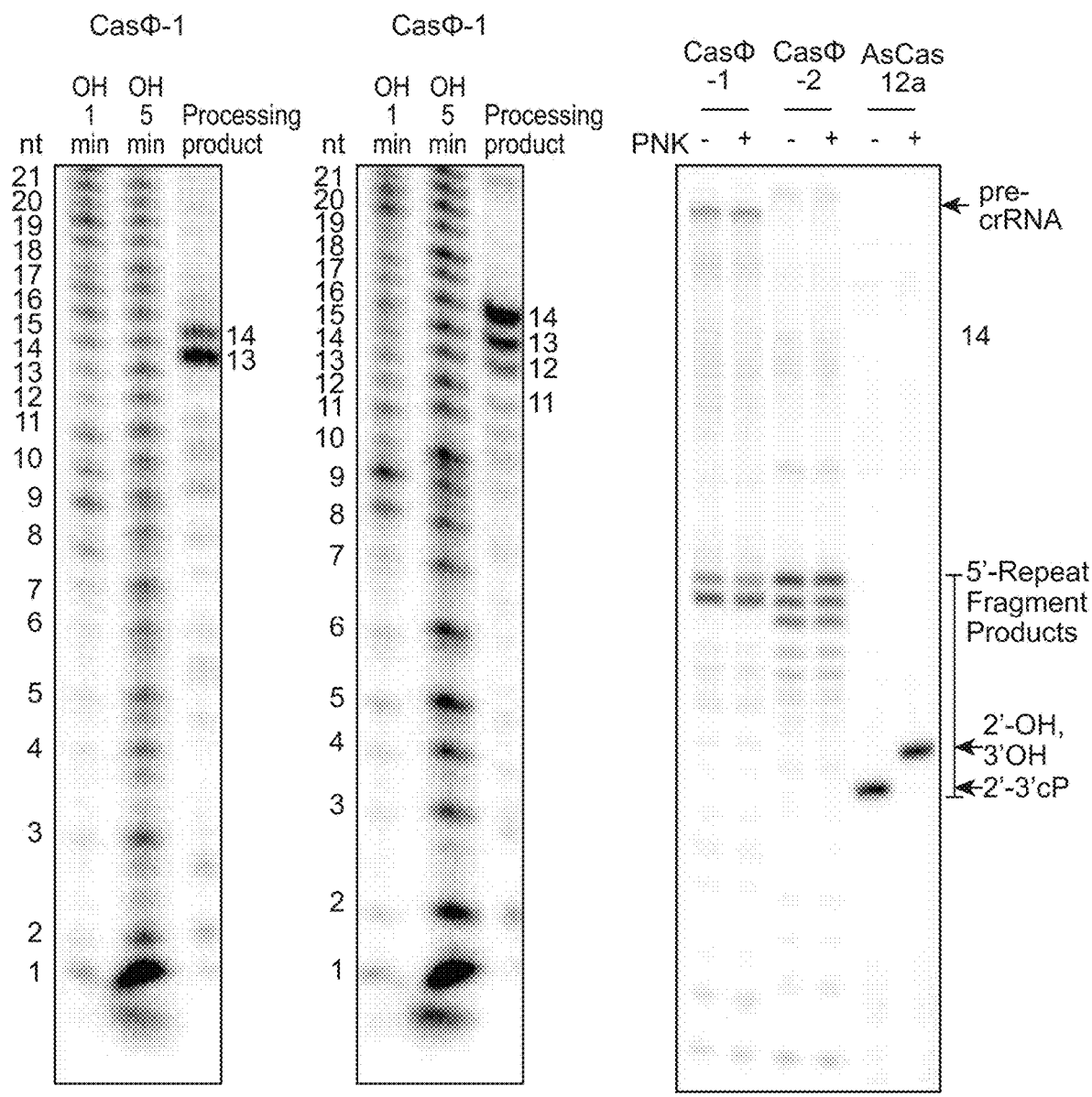
Figure 30A:
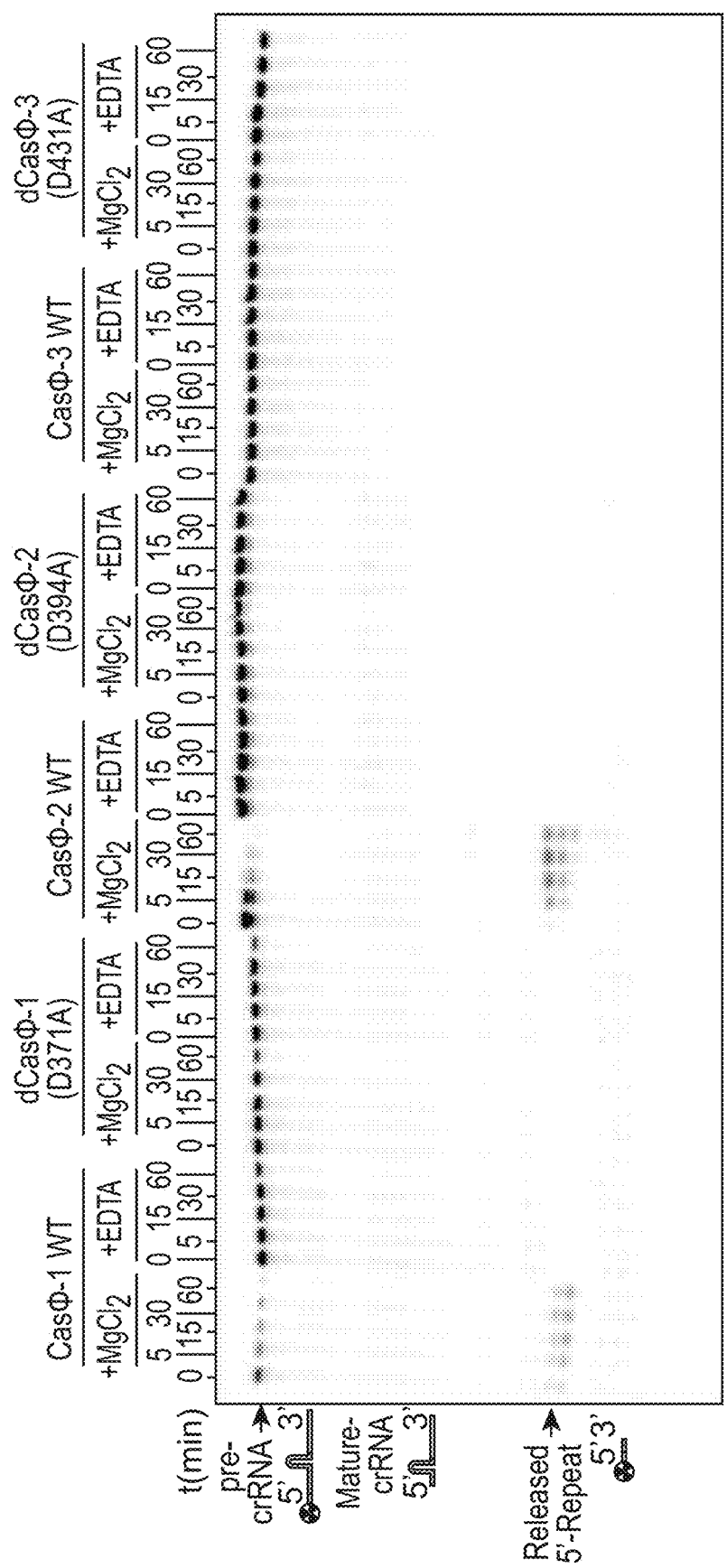
FIG. 30A-30C depict processing of pre-crRNA by CasΦ-1 and by CasΦ-2.
Figure 30B:
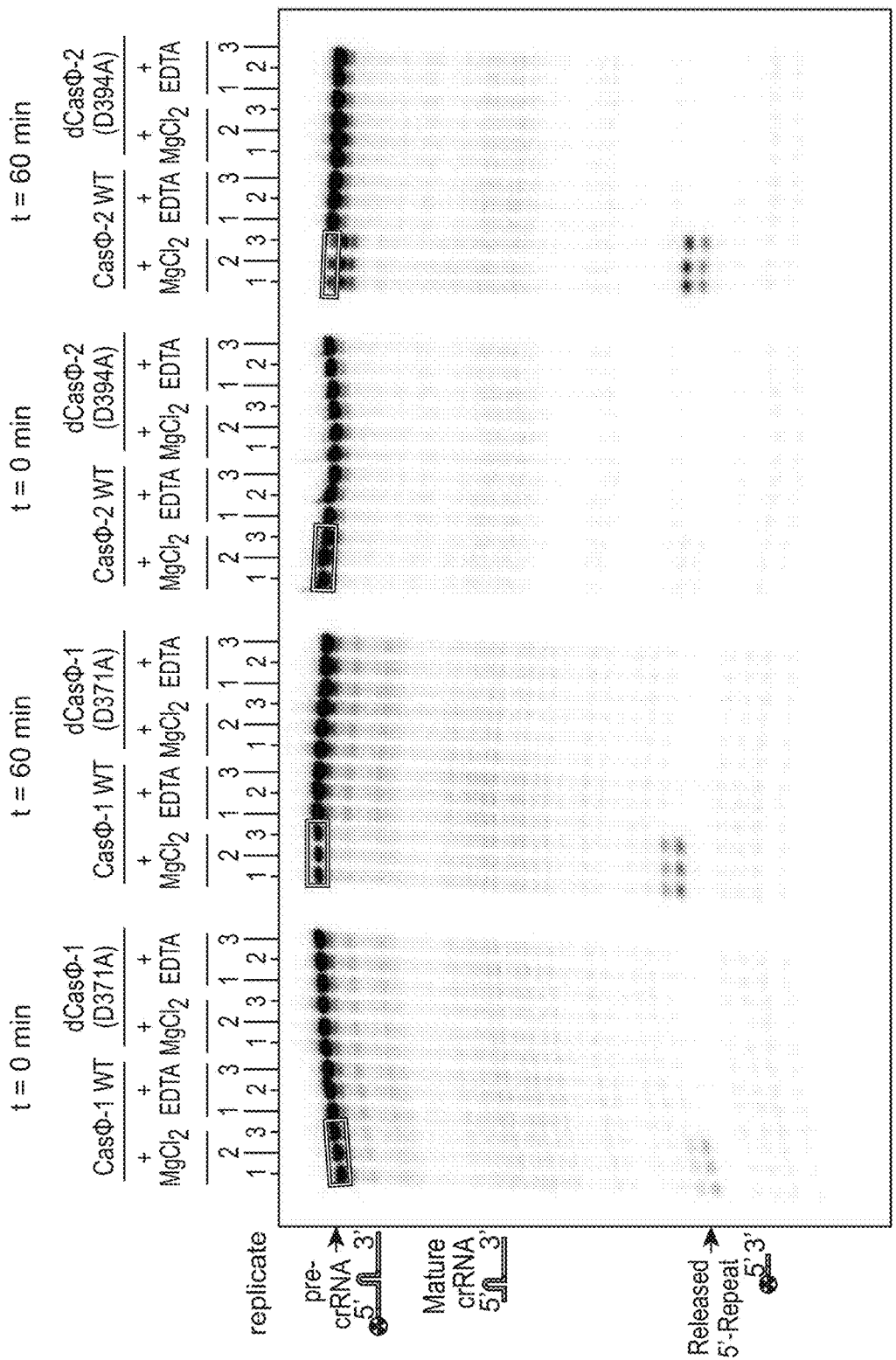
Figure 30C:
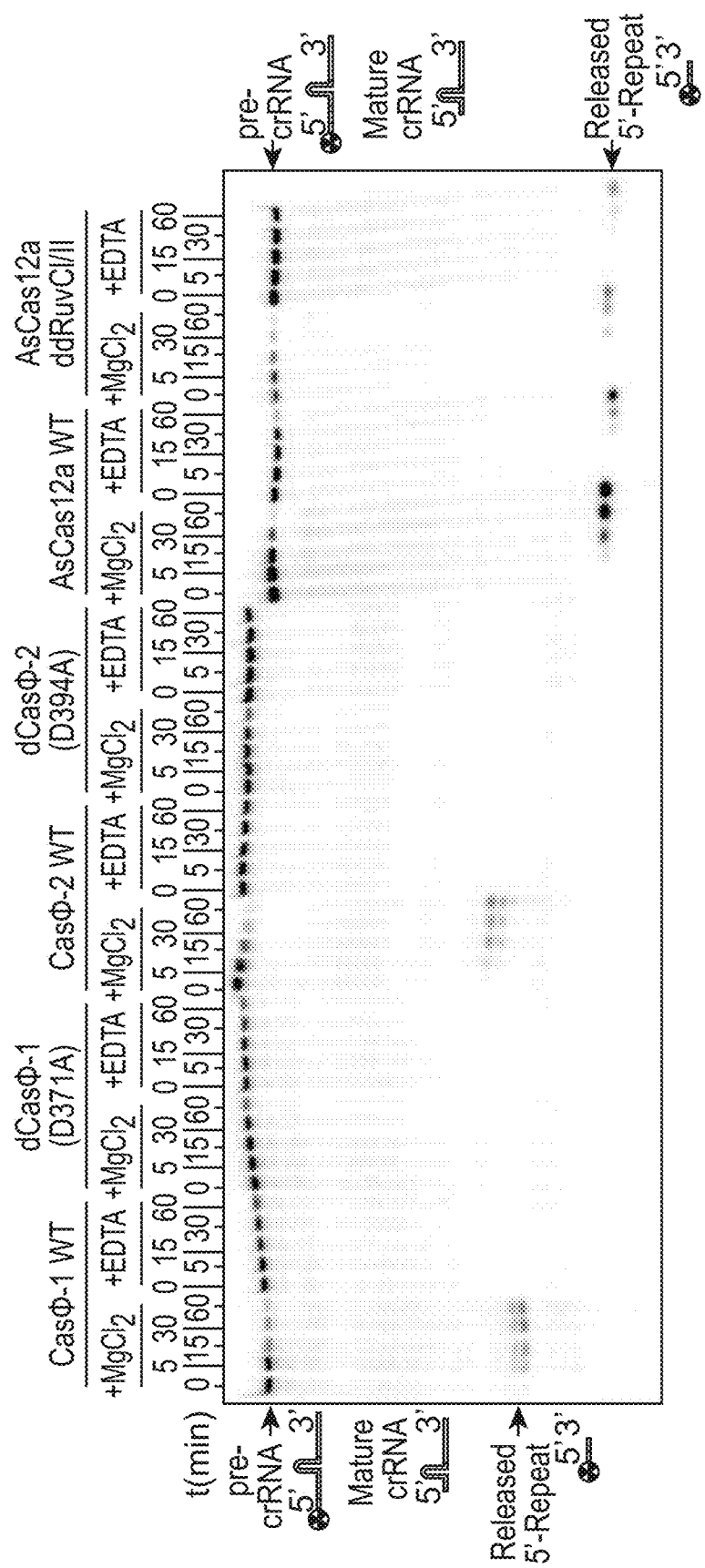
Figure 31B:
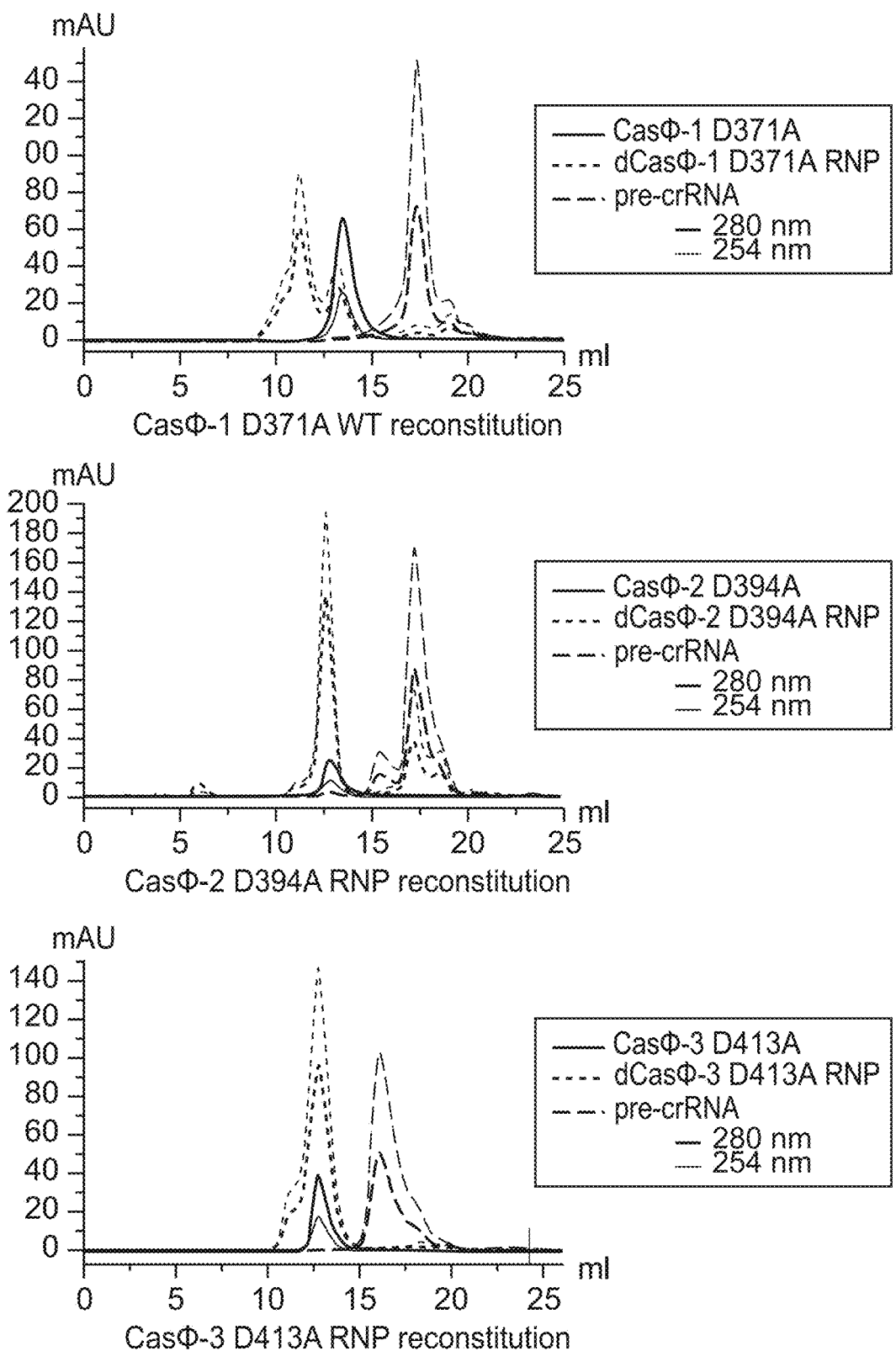

To provide genome defense, CRISPR-CasΦ systems must produce mature crRNA transcripts to guide foreign DNA cleavage. Other type V CRISPR-Cas proteins process their own pre-crRNAs using an internal active site distinct from the RuvC domain (Fonfara et al. *Nature.* 532, 517-521 (2016)) or by recruiting Ribonuclease III to cleave a duplex RNA substrate formed by pre-crRNA base pairing with a tracrRNA (Burstein et al. (2017) *Nature* 542:237; Harrington et al. (2018) *Science* 362:839; Yan et al. (2019) *Science* 363:88; Shmakov et al. (2015) *Mol. Cell.* 60:385). The absence of a detectable tracrRNA encoded in CRISPR-CasΦ genomic loci hinted that CasΦ may catalyze crRNA maturation on its own. To test this possibility, purified CasΦ was incubated with substrates designed to mimic the pre-crRNA structure (FIG. 29A). Reaction products corresponding to a 26-29 nucleotide-long repeat and 20 nucleotide guide sequence of the crRNA were observed only in the presence of wildtype CasΦ, corroborated by RNA-seq analysis of native loci (FIG. 19D; FIG. 29A; FIG. 29C; FIG. 30A-30C). In control experiments, it was found that CasΦ-catalyzed pre-crRNA processing is magnesium-dependent (FIG. 29B; FIG. 30A-30C), which is different from all other known CRISPR-Cas RNA processing reactions and suggested a distinct chemical mechanism of cleavage. Notably, the RuvC domain itself employs a magnesium-dependent mechanism to cleave DNA substrates (Nowotny et al. (2009) *EMBO Rep.* 10:144), and some RuvC domains have been reported to have endoribonucleolytic activity (Yan et al. (2019) *Science* 363:88). Based on these observations, a CasΦ containing a RuvC-inactivating mutation was tested; it was found to be incapable of processing pre-crRNAs (FIG. 29B; FIGS. 30A and 30B). Both wild-type and catalytically inactivated CasΦ proteins are capable of crRNA binding, and their reconstituted complexes with pre-crRNA have similar elution profiles from a size exclusion column, suggesting no pre-crRNA binding or protein stability defect resulting from the RuvC point mutation (FIG. 31A-31B).

Figure 29D:
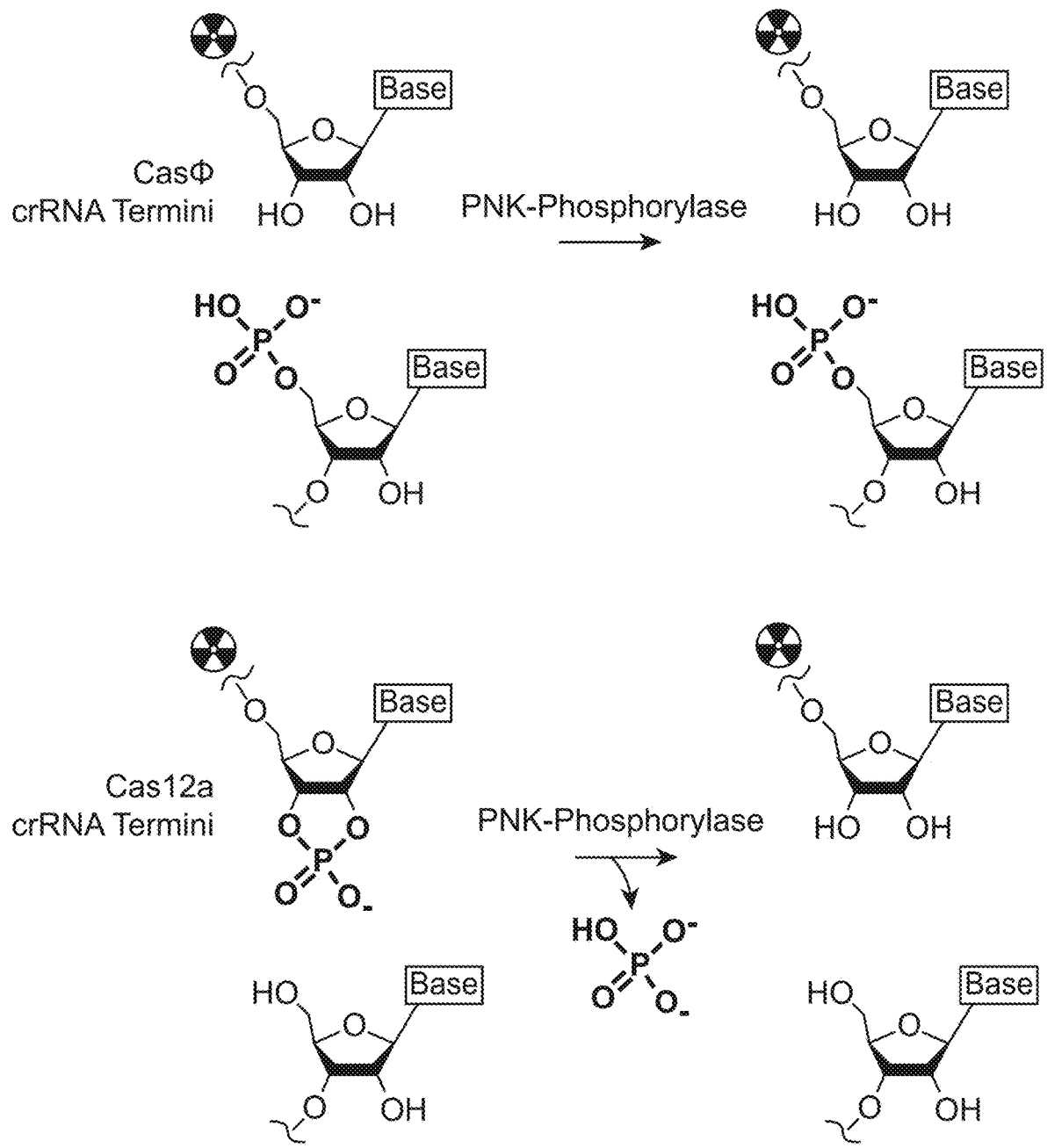

It was hypothesized that if the CasΦ RuvC domain is responsible for pre-crRNA cleavage, the products should contain 5'-phosphate and 2'- and 3'-hydroxyl moieties as observed in RNAs generated by the RuvC-related RNase HI enzymes (Nowotny et al. (2009) supra). In contrast, other type V CRISPR-Cas enzymes process pre-crRNA by a metal-independent acid-base catalysis mechanism in an active site distinct from the RuvC domain, generating 2'-3'-cyclic phosphate crRNA termini, as observed for Cas12a (Swarts et al. (2017) Mol. Cell. 66:221). PNK phosphatase treatment of CasΦ-generated crRNA followed by denaturing acrylamide gel analysis showed no change in the crRNA migration behavior, distinct from the change in mobility detected in a similar experiment conducted with crRNA generated by Cas12a (FIG. 29C; FIG. 30C). This result implies that no 2'-3'-cyclic phosphate was formed during the reaction catalyzed by CasΦ, in contrast to the RuvC-independent acid-base catalyzed pre-crRNA processing reaction by AsCas12a (FIGS. 29C and 29D). Together, these data demonstrate that CasΦ uses a single active site for both pre-crRNA processing and DNA cleavage, which is a previously unseen activity for a RuvC active site or a CRISPR-Cas enzyme.

The versatility and programmability of CRISPR-Cas systems have sparked a revolution in biotechnology and fundamental research, as they have been employed to manipulate genomes of virtually any organism. To investigate whether the DNA cleavage activity of CasΦ can be harnessed for programmed human genome editing, a gene disruption assay was performed (Liu et al. (2019) Nature 566:218; Oakes et al. (2016) Nat. Biotechnol. 34:646) using CasΦ co-expressed with a suitable crRNA in HEK293 cells (FIG. 32A). It was found that CasΦ-2 and CasΦ-3, but not CasΦ-1, can induce targeted disruption of a genomically integrated gene encoding enhanced green fluorescent protein (EGFP) (FIG. 33A; FIG. 32B). In one case, CasΦ-2 with an individual guide RNA was able to edit up to 33% of cells (FIG. 33A), comparable to levels initially reported for CRISPR-Cas9, CRISPR-Cas12a, and CRISPR-CasX (Zetsche et al. (2015) Cell 163:759; Liu et al. (2019) supra; Mali et al. (2013) Science 339:823). The small size of CasΦ in combination with its minimal PAM requirement is particularly advantageous for both vector-based delivery into cells and a wider range of targetable genomic sequences, providing a powerful addition to the CRISPR-Cas toolbox.

CasΦ represents a new family of CRISPR-Cas enzymes defined by its single active site for both RNA and DNA cutting. Three other well-characterized Cas enzymes Cas9, Cas12a, and CasX, use one (Cas12a and CasX) or two active sites (Cas9) for DNA cutting and rely on a separate active site (Cas12a) or additional factors (CasX and Cas9) for crRNA processing (FIG. 33B). The finding that in CasΦ a single RuvC active site is capable of both crRNA processing and DNA cutting suggests that size limitations of phage genomes, possibly in combination with large population sizes and higher mutation rates in phages compared to prokaryotes (24-26), led to a consolidation of chemistries within one catalytic center.

FIG. 19A-19F. CasΦ is a bona fide CRISPR-Cas system from huge phages. (A) Maximum Likelihood phylogenetic tree of reported type V effector proteins and respective predicted ancestral TnpB nucleases. Bootstrap and approximate likelihood-ratio test values ≥90 are denoted on the branches with black circles. (B) Illustrations of the genomic loci of CRISPR-Cas systems previously employed in genome editing applications. (C) Graphical representation of the PAM depletion assay and the resulting PAMs for three CasΦ orthologs. (D) RNA-sequencing results (left) mapped onto the native genomic loci of CasΦ orthologs and their upstream and downstream non-coding regions as cloned into their respective expression plasmids. Enlarged view of RNA mapped onto the first repeat-spacer pair (right). (E) Schematic of the hypothesized function of Biggiephage-encoded CasΦ in an instance of superinfection of its host. CasΦ may be used by the huge phage to eliminate competing mobile genetic elements. (F) Predicted molecular weights of the ribonucleoprotein (RNP) complexes of small CRISPR-Cas effectors and those functional in editing of mammalian cells.

FIG. 20. Maximum likelihood phylogenetic tree of type V subtypes a-k. Bootstrap and approximate likelihood ratio test values >90 are shown on the branches (circles).

Figure 21B:
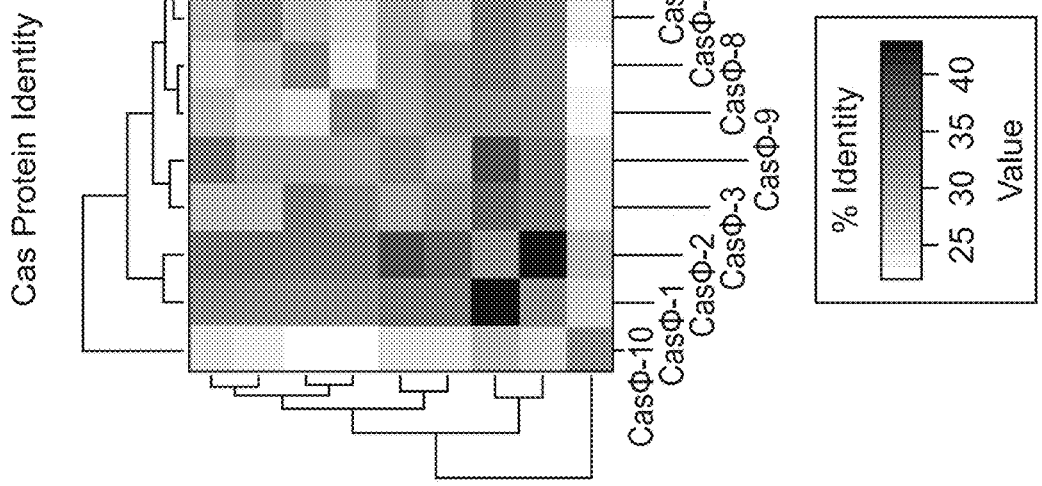
FIG. 21A-21B present crRNA repeat similarity (FIG. 21A) among various Cas12J crRNAs and Cas12J amino acid sequence identity (FIG. 21B) among various Cas12J proteins.
Figure 21A:
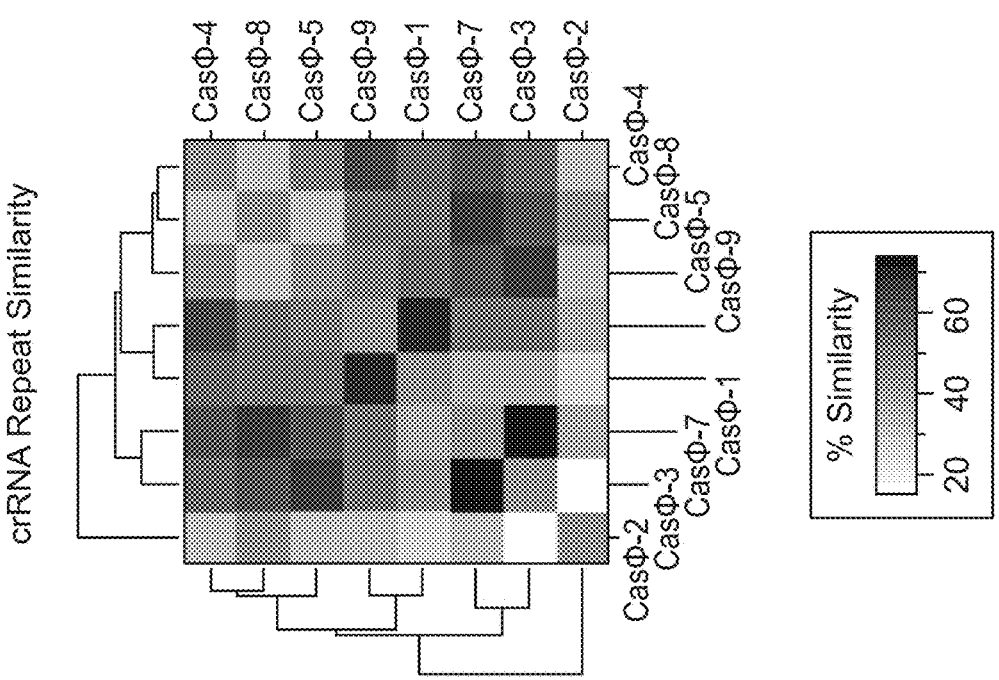

FIG. 21. CasΦ crRNA repeats are highly diverse. A similarity matrix was built and visualized using a heatmap and hierarchical clustering dendrogram. CasΦ-1, CasΦ-2, and CasΦ-3 repeats.

FIG. 22A-22C. CasΦ-3 protects against plasmid transformation. (A) Scheme illustrating the efficiency of transformation (EOT) assay. (B) EOT assay showing that CasΦ, programmed by a beta-lactamase (bla) gene targeting guide, reduces the efficiency of pUC19 transformation. Experiments were performed in three biological replicates and technical electroporation transformation triplicates (dots; n=3 each, mean±s.d.). Competent cells were tested for general transformation efficiency (grey bars) by transformation of pYTK095, which is not targeted by the tested bla and NT (non-targeting) guide. (C) EOT in dependence of CasΦ-3 RuvC active site residue variation (RuvCI: D413A; RuvCII: E618A; RuvCIII: D708A). N=3 each, mean±s.d. Competent cells were tested for general transformation efficiency (grey bars).

FIG. 23A-23D. CasΦ cleaves DNA. (A) Supercoiled plasmid cleavage assay in dependence of the guide spacer length. (B) Cleavage assay targeting dsDNA oligo-duplices for mapping of the cleavage structure. (C) Scheme illustrating the cleavage pattern. (D) NTS and TS DNA cleavage efficiency (n=3 each, mean±s.d.). Data is shown in FIG. 27B.

FIG. 24A-24D. Purification of apo CasΦ. (A) SDS-PAGE of the purified apo CasΦ orthologs and their dCasΦ variants. (B) Analytical size-exclusion chromatography (S200) of CasΦ-1 WT and dCasΦ-1. (C) Analytical size-exclusion chromatography (S200) of CasΦ-2 WT and dCasΦ-2. D) Analytical size-exclusion chromatography (S200) of CasΦ-3 WT and dCasΦ-3.

FIG. 25A-25C. CasΦ targets DNA in vitro to produce staggered cuts. (A) Linear PCR-fragment cleavage assay in dependence of the guide spacer length and presence of a cognate 5'-TTA-3' PAM (left), or non-cognate 5'-CCA-3' PAM (right). (B) Cleavage assay targeting dsDNA oligo-duplices for mapping of the cleavage structure. (C) Scheme illustrating the cleavage pattern of the staggered cuts. Shown are the proposed R-loop (replication loop) structures formed by CasΦ upon target DNA binding to the crRNA spacer.

FIG. 26A-26C. CasΦ targets dsDNA and ssDNA, but not RNA in vitro. (A) Cleavage assay assessing the ability of CasΦ and dCasΦ variant (D371A, D394A and D413A) RNPs to cleave the target strand (TS), and non-target strand (NTS), of a dsDNA oligo duplex. (B) Cleavage assay testing the ability of CasΦ and dCasΦ variant (D371A, D394A and D413A) RNPs to target and cleave a single stranded DNA, or RNA, target strand.

FIG. 27A-27B. Cleavage assay comparing TS and NTS cleavage efficiency by CasΦ. (A) Cleavage assay curves, fit to the One Phase Decay model using Prism 8 (GraphPad) (n=3 each, mean±s.d.). Cleaved fractions are calculated based on the substrate band intensities at t=(0 min) (panel B) relative to the respective time point. (B) Urea-Page gels of the three independent reaction replicates (Replicates 1, 2 and 3). This panel also relates to FIG. 23D for CasΦ-2.

FIG. 28A-28B. CasΦ targets ssDNA, but not RNA, in trans upon activation in cis. (A) Cleavage assay comparing the trans cleavage activities of CasΦ-1, CasΦ-2 and CasΦ-3 on ssDNA and ssRNA as targets in trans in dependence of either ssDNA, dsDNA, or ssRNA as activators in cis. (B) Cleavage assay comparing the trans cleavage activity of CasΦ-1, CasΦ-2 and CasΦ-3.

FIG. 29A-29D. CasΦ processes pre-crRNA within the RuvC active site. (A) pre-crRNA substrates and processing sites (triangles)-as derived from the OH-ladder in panel C. (B) Pre-crRNA processing assay for CasΦ-1 and CasΦ-2 in dependence of $Mg^{2+}$ and RuvC active site residue variation (D371A and D394A) (n=3 each, mean±s.d.; t=60 min). Data is shown in FIG. 30B. (C) Left and middle: Alkaline hydrolysis ladder (OH) of the pre-crRNA substrate. Right: PNK-phosphatase treatment of the CasΦ and Cas12a cleavage products. (D) Graphical representation of the mature crRNA termini chemistry of CasΦ and Cas12a and PNK-phosphorylase treatment outcomes.

FIG. 30A-30C. CasΦ-1 and CasΦ-2, but not CasΦ-3, process pre-crRNA. (A) Pre-crRNA processing assay for CasΦ-1, CasΦ-2 and CasΦ-3 in dependence of $Mg^{2+}$ and RuvC active site catalytic residues (dCasΦ variants). (A) Processing reaction replicates for CasΦ-1 and CasΦ-2 at t=0 min and t=60 min. Squares indicate quantified bands. This panel relates to FIG. 29B. (C) Pre-crRNA processing assay for CasΦ-1, CasΦ-2 and AsCas12a in dependence of $Mg^{2+}$ and RuvC active site catalytic residues (dCasΦ variants).

FIG. 31A-31B. CasΦ WT and dCasΦ proteins form RNPs with pre-crRNA. (A) Analytical size-exclusion chromatography (S200) of wild-type proteins, pre-crRNA, and their respective reconstituted RNP. (B) Analytical size-exclusion chromatography (S200) of dCasΦ variant proteins, pre-crRNA, and their respective reconstituted RNP.

Figure 32C:
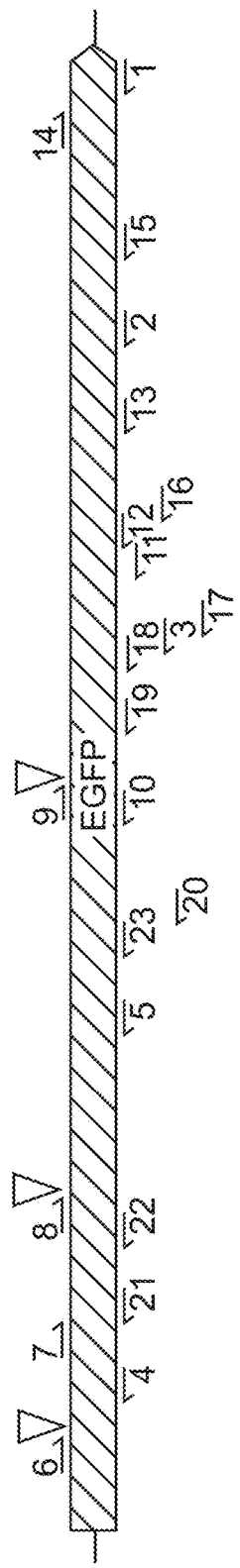

FIG. 32A-32C. CasΦ mediated EGFP gene disruption in HEK293 cells. (A) Schematic of the experimental workflow of the GFP disruption assay (left) and EGFP disruption by SpyCas9 (right) (B) CasΦ guides with GFP disruption below 5% (n=3 each, mean±s.d.). (C) EGFP map showing the target sites and orientation of guides (arrows and numbers). Yellow triangles indicate the best guides for gene disruption (relates to FIG. 34A). Guide sequences are listed in Table 4 (presented in FIG. 35).

Figure 33A:
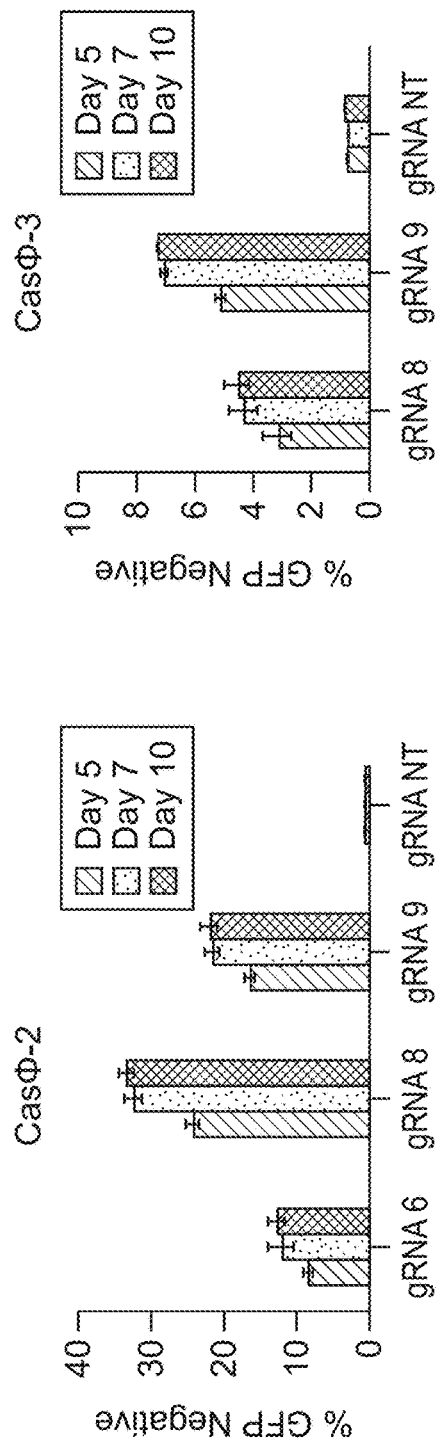
FIG. 33A-33B depict data showing CasΦ-mediate genome editing in human cells.
Figure 33B:
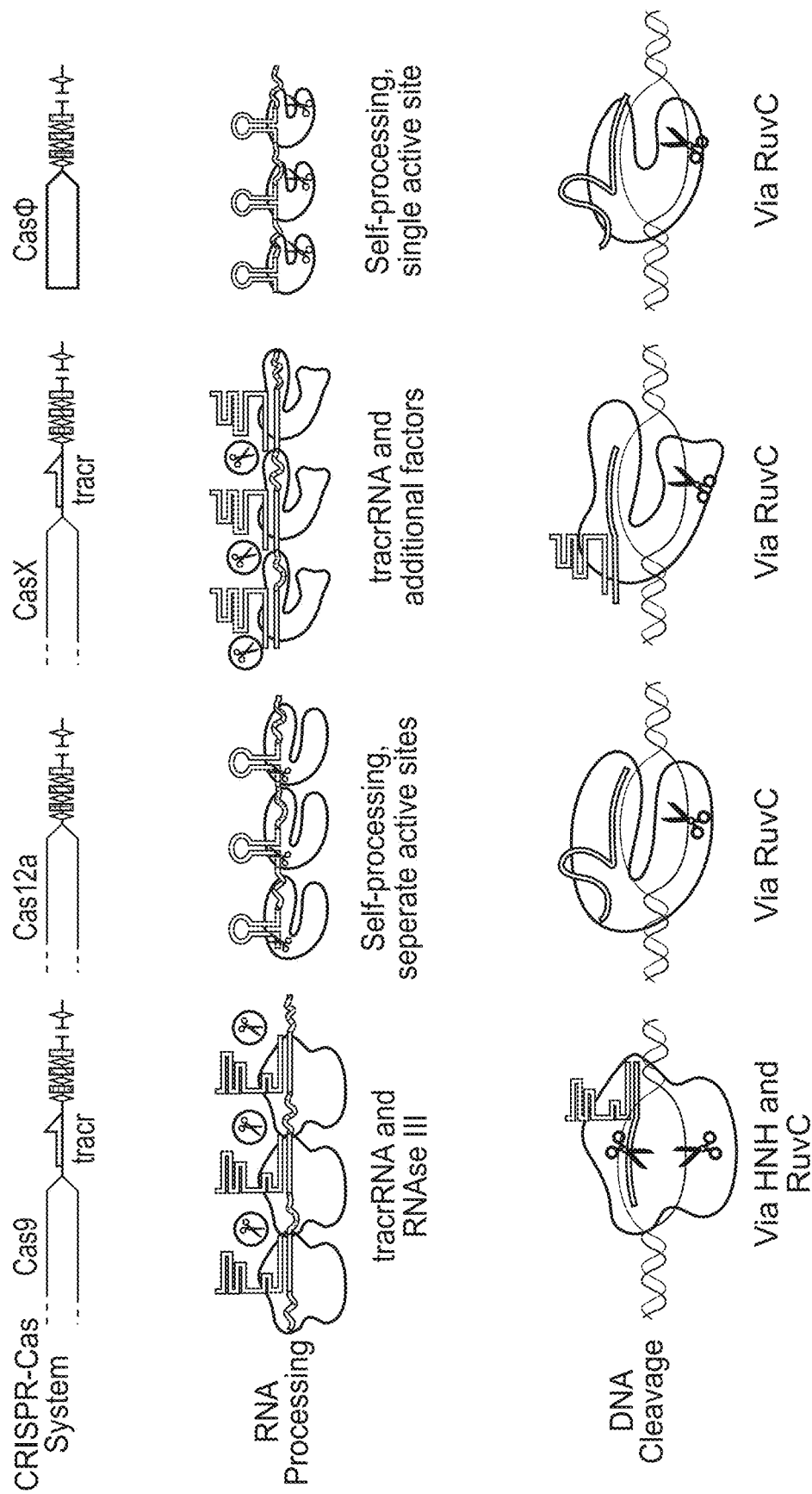

FIG. 33A-33B. CasΦ is functional for human genome editing. (A) GFP disruption using CasΦ-2 (left) and CasΦ-3 (right) and a non-targeting (NT) guide as a negative control (n=3 each, mean±s.d.). All tested guides and targeted regions within the EGFP gene are shown in FIG. 32A-32C. (B) Scheme illustrating the differences in RNA processing and DNA cutting for Cas9, Cas12a, CasX, and CasΦ.

FIG. 34 presents Table 3.
FIG. 35 presents Table 4.
FIG. 36 presents Table 5.
FIG. 37 presents Table 6.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of editing a target nucleic acid in a eukaryotic cell, wherein the target nucleic acid comprises double stranded DNA, the method comprising contacting the eukaryotic cell with:
   a) a polypeptide comprising an amino acid sequence that is at least 99% identical to the amino acid sequence set forth in SEQ ID NO:126, or a nucleic acid encoding the polypeptide; and
   b) a recombinant guide RNA, or a nucleic acid encoding the recombinant guide RNA, wherein the recombinant guide RNA comprises a guide sequence that hybridizes to a target sequence of a complementary strand of the target nucleic acid,
   wherein a protospacer adjacent motif (PAM) is immediately 5' of the target sequence of the non-complementary strand of the target nucleic acid, wherein the PAM is 5'-NTTN-3', wherein T is thymine and N is any nucleotide.

2. The method of claim 1, comprising contacting the eukaryotic cell ex vivo.

3. The method of claim 1, comprising contacting the eukaryotic cell in vivo.

4. The method of claim 1, wherein a nuclear localization signal (NLS) is fused to the N terminus of the polypeptide, the C terminus of the polypeptide, or both termini of the polypeptide.

5. The method of claim 1, wherein the polypeptide is fused to a base editor, and wherein the method comprises modifying at least one nucleobase of the target nucleic acid.

6. The method of claim 1, comprising inserting a DNA donor template into the target nucleic acid.

7. The method of claim 1, comprising contacting the cell with an additional recombinant guide RNA.

8. The method of claim 1, wherein the nucleic acid encoding the polypeptide is present in an expression vector.

9. The method of claim 8, wherein the expression vector comprises the nucleic acid encoding the recombinant guide RNA.

10. The method of claim 8, wherein the expression vector is an adenoviral associated viral vector.

11. The method of claim 1, comprising contacting the cell with a lipid or lipid nanoparticle.

12. The method of claim 1, wherein the nucleic acid encoding the polypeptide is a messenger RNA.

13. The method of claim 1, wherein the polypeptide is 100% identical to SEQ ID NO: 126.

14. The method of claim 1, wherein the eukaryotic cell is a human cell.

15. The method of claim 1, wherein the eukaryotic cell is a mammalian cell.

16. The method of claim 1, wherein the eukaryotic cell is a post-mitotic cell.

17. The method of claim 1, wherein the eukaryotic cell is selected from a myofibroblast, cardiomyocyte, myoblast, myocardial cell, cardiac myoblast, and a skeletal myoblast.

18. The method of claim 1, wherein the eukaryotic cell is a hematopoietic stem cell.

19. The method of claim 1, wherein the eukaryotic cell is selected from a monocyte, a macrophage, a T cell, a B cell, a natural killer cell, and a dendritic cell.

20. The method of claim 1, wherein the PAM is 5'-VTTN-3', wherein N is any nucleotide and V is selected from adenine, cytosine, and guanine.

21. The method of claim 1, wherein the recombinant guide RNA comprises a nucleotide sequence that is at least 80% identical to SEQ ID NO:179.

22. The method of claim 1, wherein the recombinant guide RNA comprises a nucleotide sequence that is at least 90% identical to SEQ ID NO: 179.

23. The method of claim 1, wherein the eukaryotic cell is a liver cell.

24. The method of claim 1, wherein the polypeptide is fused to a reverse transcriptase.

25. The method of claim 1, wherein the polypeptide is fused to a heterologous polypeptide.

* * * * *